(12) United States Patent
Zhang et al.

(10) Patent No.: US 11,365,239 B2
(45) Date of Patent: Jun. 21, 2022

(54) ANTI-SARS-COV-2 ANTIBODIES AND USES THEREOF

(71) Applicant: TSB THERAPEUTICS (BEIJING) CO., LTD., Beijing (CN)

(72) Inventors: Zheng Zhang, Shenzhen (CN); Linqi Zhang, Beijing (CN); Lei Liu, Shenzhen (CN); Qi Zhang, Beijing (CN); Bin Ju, Shenzhen (CN); Xuanling Shi, Beijing (CN); Qing Zhu, Beijing (CN)

(*) Notice: Subject to any disclaimer, the term of this patent is extended or adjusted under 35 U.S.C. 154(b) by 17 days.

(21) Appl. No.: 16/953,304

(22) Filed: Nov. 19, 2020

(65) Prior Publication Data
US 2021/0292392 A1  Sep. 23, 2021

(30) Foreign Application Priority Data

| Mar. 20, 2020 | (CN) | 202010203065.1 |
| Mar. 21, 2020 | (WO) | PCT/CN2020/080532 |
| Apr. 10, 2020 | (WO) | PCT/CN2020/084097 |
| Apr. 14, 2020 | (WO) | PCT/CN2020/084805 |
| Aug. 12, 2020 | (WO) | PCT/CN2020/108718 |

(51) Int. Cl.
*C07K 16/10* (2006.01)
*A61K 39/00* (2006.01)

(52) U.S. Cl.
CPC ........ *C07K 16/10* (2013.01); *A61K 2039/505* (2013.01); *A61K 2039/545* (2013.01); *C07K 2317/31* (2013.01); *C07K 2317/52* (2013.01); *C07K 2317/76* (2013.01); *C07K 2317/94* (2013.01)

(58) Field of Classification Search
CPC .................................................. C07K 16/10
USPC .......................................... 424/133.1, 138.1
See application file for complete search history.

(56) References Cited

U.S. PATENT DOCUMENTS

| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,571,894 A | 11/1996 | Wels et al. |
| 5,587,458 A | 12/1996 | King et al. |
| 5,624,821 A | 4/1997 | Winter et al. |
| 5,648,260 A | 7/1997 | Winter et al. |
| 5,731,168 A | 3/1998 | Carter et al. |
| 6,005,079 A | 12/1999 | Casterman et al. |
| 6,025,337 A | 12/2000 | Truong et al. |
| 6,194,551 B1 | 2/2001 | Idusogie et al. |
| 6,277,375 B1 | 8/2001 | Ward |
| 6,821,505 B2 | 11/2004 | Ward |
| 10,787,501 B1* | 9/2020 | Babb .............. A61K 39/15 |
| 10,954,289 B1* | 3/2021 | Babb .............. A61K 39/15 |
| 2005/0004063 A1 | 1/2005 | Kung et al. |

FOREIGN PATENT DOCUMENTS

| CN | 1648249 A | 8/2005 |
| CN | 101173275 A | 5/2008 |
| CN | 106414496 A | 2/2017 |
| CN | 111285933 A | 6/2020 |
| CN | 111303254 A | 6/2020 |
| CN | 111303279 A | 6/2020 |
| CN | 111303280 A | 6/2020 |
| CN | 111333722 A | 6/2020 |
| CN | 111423508 A | 7/2020 |
| CN | 111592504 A | 8/2020 |
| EP | 0404097 A2 | 12/1990 |
| JP | 2007043942 A | 2/2007 |
| KR | 20090128837 A | 12/2009 |
| KR | 20120139512 A | 12/2012 |
| WO | 87/00195 A1 | 1/1987 |
| WO | 90/03430 A1 | 4/1990 |
| WO | 93/11161 A1 | 6/1993 |
| WO | 93/16185 A2 | 8/1993 |
| WO | 94/04678 A1 | 3/1994 |
| WO | 94/04690 A1 | 3/1994 |
| WO | 94/25591 A1 | 11/1994 |
| WO | 94/29351 A2 | 12/1994 |
| WO | 97/34631 A1 | 9/1997 |
| WO | 99/51642 A1 | 10/1999 |
| WO | 00/42072 A2 | 7/2000 |
| WO | 02/060919 A2 | 8/2002 |
| WO | 2005/023083 A2 | 3/2005 |
| WO | 2006/019447 A1 | 2/2006 |
| WO | 2006/034488 A2 | 3/2006 |
| WO | 2009/086320 A1 | 7/2009 |
| WO | 2014/110601 A1 | 7/2014 |

(Continued)

OTHER PUBLICATIONS

Henry et al. (Frontiers in Immunology 8:1-15 (Dec. 12, 2017).*
Kim et al. (Biochimica et Biophysica Acta 1844 (2014) 1983-2001).*
Ju et al (Nature Aug. 2020;584(7819):115-119. doi: 10.1038/s41586-020-2380-z. Epub May 26, 2020).*
Yan et al. (Cell Res. Mar. 17, 2021:1-9).*
Ge et al. (Nature Communications | (2021)12:250 | https://doi.org/10.1038/s41467-020-20501-9).*
Pinto, D. et al. "Structural and functional analysis of a potent sarbecovirus neutralizing antibody", BioRxiv (Apr. 2020). DOI: 10.1101/2020.04.07.023903.

(Continued)

*Primary Examiner* — Lynn A Bristol
(74) *Attorney, Agent, or Firm* — Jun He Law Offices P.C.; Zhaohui Wang

(57) ABSTRACT

Provided herein are modified anti-SARS-COV-2 antibodies or antigen binding fragments thereof having extended half life and optimized immune activities. Disclosed herein is also directed to pharmaceutical compositions comprising the same and a method for treating or preventing a disease in human patients that is caused by or related to the infection of SARS-COV-2.

15 Claims, 49 Drawing Sheets

Specification includes a Sequence Listing.

(56) References Cited

FOREIGN PATENT DOCUMENTS

| WO | 2014/145806 A2 | 9/2014 |
|---|---|---|
| WO | 2015179535 A1 | 11/2015 |
| WO | 2016/049000 A2 | 3/2016 |
| WO | 2016/086186 A2 | 6/2016 |
| WO | 2016/086189 A2 | 6/2016 |
| WO | 2016/086196 A2 | 6/2016 |
| WO | 2016/182751 A1 | 11/2016 |
| WO | 2016/196228 A1 | 12/2016 |
| WO | 2019/057122 A1 | 3/2019 |
| WO | 2020/052692 A2 | 3/2020 |

OTHER PUBLICATIONS

Al-Lazikani, B. et al., "Standard conformations for the canonical structures of immunoglobulins", J.Mol.Biol. (1997), vol. 273(4), pp. 927-948.
Chothia, C. et al., "Domain association in immunoglobulin molecules", J.Mol.Biol. (1985), vol. 186(3), pp. 651-663.
Chothia, C. et al., "Canonical structures for the hypervariable regions of immunoglobulins", J.Mol.Biol. (1987), vol. 196, pp. 901-917.
Chothia, C. et al., "Conformations of immunoglobulin hypervariable regions", Nature (1989), vol. 342(6252), pp. 877-883.
Huston et al., "Protein engineering of antibody binding sites: recovery of specific activity in an anti-digoxin single-chain Fv analogue produced in *Escherichia coli*". Proc. Natl. Acad. Sci. USA (1988), vol. 85, pp. 5879-5883.
Riechmann et al., "Single domain antibodies: comparison of camel VH and camelised human VH domains", Journal of Immunological Methods(1999), vol. 231(1-2), pp. 25-38.
Muyldermans, "Single domain camel antibodies: current status", Reviews in Molecular Biotechnology(2001), vol. 74(4), pp. 277-302.
Holliger et al., ""Diabodies": small bivalent and bispecific antibody fragments", Proc. Natl. Acad. Sci. USA (Jul. 1993), vol. 90(14), pp. 6444-6448.
Altschul et al., "Basic local alignment search tool" J. Mol. Biol. (1990), vol. 215, pp. 403-410.
Stephen F. Altschul et al., "Gapped BLAST and PSI-BLAST: a new generation of protein database search programs", Nucleic Acids Research(1997), vol. 25, No. 17, pp. 3389-3402.
Higgins, D.G. et al., "Using CLUSTAL for Multiple Sequence Alignments", Methods in Enzymology(1996), vol. 266, pp. 383-402.
Larkin, M.A. et al., "Clustal W and Clustal X version 2.0", Bioinformatics (Oxford, England, 2007), vol. 23, No. 21, pp. 2947-2948.
Shields et al., "High resolution mapping of the binding site on human IgG1 for Fc gamma RI, Fc gamma RII, Fc gamma RIII, and FcRn and design of IgG1 variants with improved binding to the Fc gamma R", The Journal of Biological Chemistry (2001), vol. 276, No. 9, pp. 6591-6604.
Carter et al., "High level *Escherichia coli* expression and production of a bivalent humanized antibody fragment", Bio/Technology (1992), vol. 10, pp. 163-167.
Graham et al., "Characteristics of a human cell line transformed by DNA from human adenovirus type 5", J. Gen. Virol. (1977), vol. 36, pp. 59-72.
Urlaub et al., "Isolation of Chinese hamster cell mutants deficient in dihydrofolate reductase activity", Proc. Natl. Acad. Sci. USA (1980), vol. 77(7), pp. 4216-4220.
Mather, "Establishment and characterization of two distinct mouse testicular epithelial cell lines", Biology of Reproduction (1980), vol. 23, pp. 243-252.
Mather et al., "Culture of testicular cells in hormone-supplemented serum-free medium", Annals N.Y. Acad. Sci. (1982), vol. 383, pp. 44-68.
Ham et al., "Media and growth requirements", Meth. Enz. (1979), vol. 58, pp. 44-93.
Barnes et al., "Methods for growth of cultured cells in serum-free medium", Anal. Biochem. (1980), vol. 102, pp. 255-270.
Lindmark et al., "Binding of immunoglobulins to protein A and immunoglobulin levels in mammalian sera", J. Immunol. Meth. (1983), vol. 62, pp. 1-13.
Guss et al., "Structure of the IgG-binding regions of streptococcal protein G", EMBO J. (1986), vol. 5(7), pp. 1567-1575.
Lefranc, M.-P. et al., "IMGT unique numbering for immunoglobulin and T cell receptor variable domains and Ig superfamily V-like domains", Developmental and Comparative Immunology (2003), vol. 27, pp. 55-77.
Lefranc, M.-P. et al., "IMGT, the international ImMunoGeneTics information system®: a standardized approach for immunogenetics and immunoinformatics", Immunome Research(2005), vol. 1(3), pp. 1-11.
Lefranc, M.-P. et al., "IMGT® Immunoglobulin Repertoire Analysis and Antibody Humanization", Molecular Biology of B Cells(2015), chapter 26, pp. 481-514.
Hamers-Casterman, C. et al., "Naturally occurring antibodies devoid of light chains", Nature (Jun. 1993), vol. 363 (428), pp. 446-448.
Nguyen, V. K. et al., "Heavy-chain antibodies in Camelidae; a case of evolutionary innovation", Immunogenetics (2002), vol. 54(1), pp. 39-47.
Nguyen, V. K. et al., "Heavy-chain only antibodies derived from dromedary are secreted and displayed by mouse B cells", Immunology (2003), vol. 109(1), pp. 93-101.
Koch-Nolte, F. et al., "Single domain antibodies from llama effectively and specifically block T cell ecto-ADP-ribosyltransferase ART2.2 in vivo", The FASEB Journal (Nov. 2007), vol. 21(13), pp. 3490-3498.
Brinkmann, U. et al., "The making of bispecific antibodies", mAbs (2017), vol. 9(2), pp. 182-212.
Ravetch, J. V. et al., "Fc Receptors", Annu. Rev. Immunol. (1991), vol. 9, pp. 457-492.
Batzer, M. A. et al., "Enhanced evolutionary PCR using oligonucleotides with inosine at the 3'-terminus", Nucleic Acids Research (1991), vol. 19(18), pp. 5081.
Ohtsuka, E. et al., "An alternative approach to deoxyoligonucleotides as hybridization probes by insertion of deoxyinosine at ambiguous codon positions", The Journal of Biological Chemistry (1985), vol. 260(5), pp. 2605-2608.
Rossolini, G. M. et al., "Use of deoxyinosine-containing primers vs degenerate primers for polymerase chain reaction based on ambiguous sequence information", Molecular and Cellular Probes (1994), vol. 8, pp. 91-98.
Idusogie, E. E. et al., "Mapping of the C1q Binding Site on Rituxan, a Chimeric Antibody with a Human IgG1 Fc", The Journal of Immunology (2000), vol. 164, pp. 4178-4184.
Steurer, W. et al., "Ex vivo coating of islet cell allografts with murine CTLA4/Fc promotes graft tolerance", The Journal of Immunology (1995), vol. 155, pp. 1165-1174.
Idusogie, E. E. et al., "Engineered Antibodies with Increased Activity to Recruit Complement", The Journal of Immunology (2001), vol. 166, pp. 2571-2575.
Lazar, G. A. et al., "Engineered antibody Fc variants with enhanced effector function", PNAS (Mar. 2006), vol. 103 (11), pp. 4005-4010.
Ryan, M. C. et al., "Antibody targeting of B-cell maturation antigen on malignant plasma cells", Molecular Cancer Therapeutics (Nov. 2007), vol. 6, pp. 3009-3018.
Richards, J. O. et al., "Optimization of antibody binding to FcγRIIa enhances macrophage phagocytosis of tumor cells", Mol. Cancer Ther. (Aug. 2008), vol. 7(8), pp. 2517-2527.
Shields, R. L. et al.,"Lack of Fucose on Human IgG1 N-Linked Oligosaccharide Improves Binding to Human FcγRIII and Antibody-dependent Cellular Toxicity", The Journal of Biological Chemistry (Jul. 2002), vol. 277(30), pp. 26733-26740.
Shinkawa, T. et al.,"The absence of fucose but not the presence of galactose or bisecting N-acetylglucosamine of human IgG1 complex-type oligosaccharides shows the critical role of enhancing antibody-dependent cellular cytotoxicity". The Journal of Biological Chemistry (2003), vol. 278(5), pp. 3466-3473.

(56) References Cited

OTHER PUBLICATIONS

Duncan, A. R. et al.,"The binding site for C1q on IgG", Nature (Apr. 1988), vol. 332, pp. 738-740.
Kellner, C. et al.,"Modulating Cytotoxic Effector Functions by Fc Engineering to Improve Cancer Therapy", Transfusion Medicine and Hemotherapy (2017), vol. 44, p. 327-336.
Chung, A. W. et al.,"Identification of antibody glycosylation structures that predict monoclonal antibody Fc-effector function", AIDS (Nov. 2014), vol. 28(17), pp. 2523-2530.
Wang, X. et al.,"IgG Fc engineering to modulate antibody effector functions", Protein Cell (2018), vol. 9(1), pp. 63-73.
Kang, T. H. et al.,"Boosting therapeutic potency of antibodies by taming Fc domain functions", Experimental & Molecular Medicine (2019), vol. 51, pp. 138.
Moore, G. L. et al.,"Engineered Fc variant antibodies with enhanced ability to recruit complement and mediate effector functions", mAbs (2010), vol. 2(2), pp. 181-189.
Strohl, W. R. et al.,"Optimization of Fc-mediated effector functions of monoclonal antibodies", Current Opinion in Biotechnology (2009), vol. 20, pp. 685-691.
Awan, F. T. et al.,"CD19 targeting of chronic lymphocytic leukemia with a novel Fc-domain-engineered monoclonal antibody". Blood (Feb. 2010), vol. 115(6), pp. 1204-1213.
Desjarlais, J. R et al."Modulation of antibody effector function", Experimental Cell Research (2011), vol. 317, pp. 1278-1285.
Stavenhagen, J. B. et al.,"Fc Optimization of Therapeutic Antibodies Enhances Their Ability to Kill Tumor Cells In vitro and Controls Tumor Expansion In vivo via Low-Affinity Activating Fcγ Receptors", Cancer Research (Sep. 2007), vol. 67(18), pp. 8882-8890. .
Rother, R. P. et al.,"Discovery and development of the complement inhibitor eculizumab for the treatment of oaroxysmal nocturnal hemoglobinuria", Nature Biotechnology (Nov. 2007), vol. 25(11), pp. 1256-1264.
Vaughn, D. E. et al., "Structural basis of pH-dependent antibody binding by the neonatal Fc receptor", Structure (1998), vol. 6(1), pp. 63-73.
Yeung, Y. A. et al., "A Therapeutic Anti-VEGF Antibody with Increased Potency Independent of Pharmacokinetic Half-life", Cancer Research (2010), vol. 70(8), pp. 3269-3277.
Hinton, P. R. et al., "An Engineered Human IgG1 Antibody with Longer Serum Half-Life", The Journal of Immunology (2006), vol. 176, pp. 346-356.
Petkova, S. B. et al., "Enhanced half-life of genetically engineered human IgG1 antibodies in a humanized FcRn mouse model: potential application in humorally mediated autoimmune disease", International Immunology (2006), vol. 18(12), pp. 1759-1769.
Dall' Acqua, W. F. et al., "Increasing the Affinity of a Human IgG1 for the Neonatal Fc Receptor: Biological Consequences", The Journal of Immunology (2002), vol. 169, pp. 5171-5180.
Zalevsky, J. et al., "Enhanced antibody half-life improves in vivo activity", Nature Biotechnology (Feb. 2010), vol. 28(2), pp. 157-159.
Morimoto, K. et al., "Single-step purification of F(ab')2 fragments of mouse monoclonal antibodies (immunoglobulins G1) by hydrophobic interaction high performance liquid chromatography using TSKgel Phenyl-5PW", Journal of Biochemical and Biophysical Methods (1992), vol. 24, pp. 107-117.
Brennan, M. et al., "Preparation of bispecific antibodies by chemical recombination of monoclonal immunoglobulin G1 fragments", Science (1985), vol. 229, pp. 81-83.
Spiess, C. et al., "Alternative molecular formats and therapeutic applications for bispecific antibodies", Molecular Immunology (2015), vol. 67, pp. 95-106.
Milstein, C. et al., "Hybrid hybridomas and their use in immunohistochemistry", Nature (Oct. 1983), vol. 305, pp. 537-540.
Suresh, M. R. et al., "Bispecific monoclonal antibodies from hybrid hybridomas", Methods in Enzymology (1986), vol. 121, pp. 210-228.

Gunasekaran, K. et al., "Enhancing Antibody Fc Heterodimer Formation through Electrostatic Steering Effects", The Journal of Biological Chemistry (Jun. 2010), vol. 285(25), pp. 19637-19646.
Dufès, C. et al., "Dendrimers in gene delivery", Advanced Drug Delivery Reviews (2005), vol. 57, pp. 2177-2202.
Liu, C. et al., "Research and Development on Therapeutic Agents and Vaccines for COVID-19 and Related Human Coronavirus Diseases", ACS Central Science (Mar. 2020), vol. 6, pp. 315-331.
Tian, X. et al., "Potent binding of 2019 novel coronavirus spike protein by a SARS coronavirus-specific human monoclonal antibody", Emerging Microbes Infections, Feb. 17, 2020(Feb. 17, 2020), vol. 9, the abstract, figure 1.
Wang, X. et al., "Crystal structure of SARS-CoV-2 spike receptor-binding domain bound with ACE2", ChainE, 2019-nCoV receptor-binding domain PDB: 6MOJ_E, Mar. 20, 2020(Mar. 20, 2020), "Origin".
Zheng, M.et al., "Novel antibody epitopes dominate the antigenicity of spike glycoprotein in SARS-CoV-2 compared to SARS-CoV", Cellular & Molecular Immunology, Mar. 4, 2020(Mar. 4, 2020), vol. 17, pp. 536-538.
Tai, W.et al., "Characterization of the receptor-binding domain (RBD) of 2019 novel coronavirus: implication for development of RBD protein as a viral attachment inhibitor and vaccine", Cellular & Molecular Immunology, Mar. 19, 2020(Mar .19, 2020), vol. 17, pp. 613-620.
Ahmed, S.et al., "Preliminary Identification of Potential Vaccine Targets for the COVID-19 Coronavirus (SARS-CoV-2) Based on SARS-Co V Immunological Studies", Viruses 25, Feb. 2020(Feb. 25, 2020), vol. 12, No. 254, pp. 1-15.
Walls, A. et al., "Structure, Function, and Antigenicity of the SARS-CoV-2 Spike Glycoprotein", Cell, Mar. 9, 2020 (Mar. 9, 2020), vol. 180, pp. 1-12.
Du, L.et al., "The spike protein of SARS-Co V—a target for vaccine and therapeutic development", Nature Reviews, Feb. 9, 2009(Feb. 9, 2009),vol. 7, pp. 226-236.
International Search Report of PCT Application No. PCT/CN2020/ 080532, dated Dec. 21, 2020.
Ju, B. et al., "Human neutralizing antibodies elicited by SARS-CoV-2 infection", Nature (Aug. 2020), vol. 584, pp. 115-119.
Li, Q. et al.,"Early Transmission Dynamics in Wuhan, China, of Novel Coronavirus-Infected Pneumonia", The New England Journal of Medicine (Mar. 2020), vol. 382, No. 13, pp. 1199-1207. DOI:10.1056/NEJMoa2001316.
Zhou, P. et al.,"A pneumonia outbreak associated with a new coronavirus of probable bat origin", Nature (Mar. 2020), vol. 579, pp. 270-273. DOI:10.1038/s41586-020-2012-7.
Zhu, N. et al., "A Novel Coronavirus from Patients with Pneumonia in China, 2019", The New England Journal of Medicine (Feb. 2020), vol. 382(8), pp. 727-733. DOI: 10.1056/NEJMoa2001017.
Wu, F. et al., "A new coronavirus associated with human respiratory disease in China", Nature (Mar. 2020), vol. 579, pp. 265-269. DOI: 10.1038/s41586-020-2008-3.
Chan, J. F.-W. et al., "A familial cluster of pneumonia associated with the 2019 novel coronavirus indicating person-to-person transmission: a study of a family cluster", The Lancet(Feb. 2020), vol. 395, pp. 514-523. DOI: 10.1016/S0140-6736(20)30154-9.
Guan, W. et al., "Clinical Characteristics of Coronavirus Disease 2019 in China", The New England Journal of Medicine (Apr. 2020), vol. 382(18), pp. 1708-1720. DOI: 10.1056/NEJMoa2002032.
Huang, C. et al., "Clinical features of patients infected with 2019 novel coronavirus in Wuhan, China", The Lancet (Feb. 2020), vol. 395, pp. 497-506. DOI: 10.1016/80140-6736(20)30183-5.
Wang, D. et al., "Clinical Characteristics of 138 Hospitalized Patients with 2019 Novel Coronavirus-Infected Pneumonia in Wuhan, China", JAMA—Journal of the American Medical Association (Feb. 2020), vol. 323(11), pp. 1061-1069. DOI: 10.1001/jama.2020. 1585.
Chinazzi, M. et al., "The effect of travel restrictions on the spread of the 2019 novel coronavirus (COVID-19) outbreak", Science (Mar. 2020), vol. 368, pp. 395-400. DOI: 10.1126/science.aba9757.
Lu, R. et al., "Genomic characterisation and epidemiology of 2019 novel coronavirus: implications for virus origins and receptor

(56) References Cited

OTHER PUBLICATIONS binding", The Lancet(Feb. 2020), vol. 395, pp. 565-574. DOI: 10.1016/80140-6736(20)30251-8.
Wu, A. et al., "Genome Composition and Divergence of the Novel Coronavirus (2019-nCoV) Originating in China", Cell Host & Microbe (Mar. 2020), vol. 27, pp. 325-328. DOI: 10.1016/j.chom.2020.02.001.
Ge, X.-Y. et al., "Isolation and characterization of a bat SARS-like coronavirus that uses the ACE2 receptor", Nature (Nov. 2013), vol. 503, pp. 535-538. DOI: 10.1038/nature12711.
Hoffmann, M. et al., "SARS-CoV-2 Cell Entry Depends on ACE2 and TMPRSS2 and is Blocked by a Clinically Proven Protease Inhibitor", Cell (Apr. 2020), vol. 181, pp. 271-280. DOI: 10.1016/j.cell.2020.02.052.
Walls, A. C. et al., "Structure, Function, and Antigenicity of the SARS-CoV-2 Spike Glycoprotein", Cell (Apr. 2020), vol. 180, pp. 281-292. DOI: 10.1016/j.cell.2020.02.058.
Du, L. et al., "The spike protein of SARS-CoV—a target for vaccine and therapeutic development", Nature Review, Microbiology 7(Mar. 2009), vol. 7, pp. 226-236. DOI: 10.1038/nrmicro2090.
Li, F., "Structure, Function, and Evolution of Coronavirus Spike Proteins", Annu. Rev. Virol. (2016), vol. 3, pp. 237-261. DOI: 10.1146/annurev-virology-110615-042301.
Wrapp, D. et al., "Cryo-EM structure of the 2019-nCoV spike in the prefusion conformation", Science(Mar. 2020), vol. 367, pp. 1260-1263. DOI: 10.1126/science.abb2507.
Gui, M. et al., "Cryo-electron microscopy structures of the SARS-CoV spike glycoprotein reveal a prerequisite conformational state for receptor binding", Cell Research (2017), vol. 27, pp. 119-129. DOI: 10.1038/cr.2016.152.
Song, W. et al., "Cryo-EM structure of the SARS coronavirus spike glycoprotein in complex with its host cell receptor ACE2", PLoS Pathogens (Aug. 2018), vol. 14(8), pp. e1007236-e1007236. DOI: 10.1371/journal.ppat.1007236.
Kirchdoerfer, R. N. et al., "Stabilized coronavirus spikes are resistant to conformational changes induced by receptor-recognition or proteolysis", Scientific Reports(2018), vol. 8, pp. 15701-15701. DOI: 10.1038/s41598-018-34171-7.
Yuan, Y. et al., "Cryo-EM structures of MERS-CoV and SARS-CoV spike glycoproteins reveal the dynamic receptor binding domains", Nature Communications (2017), vol. 8, pp. 15092-15092. DOI: 10.1038/ncomms15092.
Wan, Y. et al., "Receptor Recognition by the Novel Coronavirus from Wuhan: an Analysis Based on Decade-Long Structural Studies of SARS Coronavirus", Journal of Virology (Apr. 2020), vol. 94(7), e00127-20. DOI: 10.1128/JVI.00127-20.
Kruse, R. L. et al., "Therapeutic strategies in an outbreak scenario to treat the novel coronavirus originating in Wuhan, China", F1000Research (Feb. 2020), vol. 9, pp. 72-72. DOI:10.12688/f1000research.22211.2.
Li, W. et al., "Angiotensin-converting enzyme 2 is a functional receptor for the SARS coronavirus", Nature(2003), vol. 426, pp. 450-454. DOI:10.1038/nature02145.
Hamming, I. et al., "The emerging role of ACE2 in physiology and disease", Journal of Pathology(2007), vol. 212, pp. 1-11. DOI:10.1002/path.2162.
Xu, J. et al., "Antibodies and vaccines against Middle East respiratory syndrome coronavirus". Emerging Microbes & Infections(2019), vol. 8, pp. 841-856. DOI:10.1080/22221751.2019.1624482.
Sanders, R. W. et al., "Stabilization of the soluble, cleaved, trimeric form of the envelope glycoprotein complex of human immunodeficiency virus type 1", Journal of Virology(Sep. 2002), vol. 76, No. 17, p. 8875-8889. DOI:10.1128/JVI.76.17.8875-8889.2002.
Kong, L. et al., "Key gp120 Glycans Pose Roadblocks to the Rapid Development of VRC01-Class Antibodies in an HIV-1-Infected Chinese Donor", Immunity (2016), vol. 44(4), p. 939-950. DOI:10.1016/j.immuni.2016.03.006.

Liao, H.-X. et al., "High-throughput isolation of immunoglobulin genes from single human B cells and expression as monoclonal antibodies", J Virol Methods(2009),vol. 158(1-2), p. 171-179. DOI:10.1016/j.jviromet.2009.02.014.
Yu, L. et al., "Delineating antibody recognition against Zika virus during natural infection", JCI Insight(2017), vol. 2(12), e93042. DOI: 10.1172/jci.insight.93042.
Corti, D. et al., "Broadly neutralizing antiviral antibodies", Annu. Rev. Immunol. (2013), vol. 31, p. 705-742. DOI:10.1146/annurev-immunol-032712-095916.
Stettler, K. et al., "Specificity, cross-reactivity, and function of antibodies elicited by Zika virus infection", Science (Aug. 2016), vol. 353, Issue 6301, p. 823-826. DOI:10.1126/science.aaf8505.
Scheid, J. F. et al., "Broad diversity of neutralizing antibodies isolated from memory B cells in HIV-infected individuals", Nature (2009), vol. 458, p. 636-640. DOI:10.1038/nature07930.
Wu, X. et al., "Focused evolution of HIV-1 neutralizing antibodies revealed by structures and deep sequencing", Science (2011), vol. 333, p. 1593-1602. DOI:10.1126/science.1207532.
Liao, H.-K. et al., "Co-evolution of a broadly neutralizing HIV-1 antibody and founder virus", Nature(2013), vol. 496, p. 469-476. DOI:10.1038/nature12053.
Yuan M. et al., "A highly conserved cryptic epitope in the receptor-binding domains of SARS-CoV-2 and SARS-CoV", Science (May 2020), vol. 368, p. 630-633. DOI:10.1126/science.abb7269.
Pinto, D. et al., "Cross-neutralization of SARS-CoV-2 by a human monoclonal SARS-CoV antibody", Nature (Jul. 2020), vol. 583, pp. 290-295. DOI:10.1038/s41586-020-2349-y.
Tian, X. et al., "Potent binding of 2019 novel coronavirus spike protein by a SARS coronavirus-specific human monoclonal antibody", Emerging Microbes & Infections(Feb. 2020), vol. 9, pp. 382-385. DOI:10.1080/22221751.2020.1729069.
Wang, N. et al., "Structure of MERS-CoV spike receptor-binding domain complexed with human receptor DPP4", Cell Research(2013), vol. 23, pp. 986-993. DOI:10.1038/cr.2013.92 .
Jiang, L. et al., "Potent neutralization of MERS-CoV by human neutralizing monoclonal antibodies to the viral spike glycoprotein". Science Translation Medicine (2014), vol. 6, Issue 234, 234ra59. DOI:10.1126/scitranslmed.3008140.
Zhang, S. et al., "Structural Definition of a Unique Neutralization 774 Epitope on the Receptor-Binding Domain of MERS-CoV Spike Glycoprotein", Cell Reports (2018), vol. 24, pp. 441-452. DOI:10.1016/j.celrep.2018.06.041.
Wu, X. et al., "Rational design of envelope identifies broadly neutralizing human monoclonal antibodies to HIV-1", Science (2010), vol. 329, pp. 856-861. DOI:10.1126/science.1187659.
Tiller, T. et al., "Efficient generation of monoclonal antibodies from single human B cells by single cell RT-PCR and expression vector cloning", J Immunol Methods(2008), vol. 329(1-2), pp. 112-124. DOI:10.1016//j.jim.2007.09.017 .
Zhu, Z.et al., "Potent cross-reactive neutralization of SARS coronavirus isolates by human monoclonal antibodies", PNAS (2007), vol. 104, No. 29, pp. 12123-12128. DOI:10.1073/pnas.0701000104.
Niu, P.et al., "Ultrapotent Human Neutralizing Antibody Repertoires Against Middle East Respiratory Syndrome Coronavirus From a Recovered Patient", The Journal of Infectious Diseases Dis(2018), vol. 218, pp. 1249-1260. DOI:10.1093/infdis/jiy311.
Jia, W.et al., "Single intranasal immunization with chimpanzee adenovirus-based vaccine induces sustained and protective immunity against MERS-CoV infection", Emerging Microbes & Infections(2019), vol. 8, pp. 760-772. DOI:10.1080/22221751.2019.1620083.
Zhang, L.et al., "Antibody responses against SARS coronavirus are correlated with disease outcome of infected individuals", Journal of Medical Virology(2006), vol. 78, pp. 1-8. DOI:10.1002/jmv.20499.
Zhang, Q. et al., "Potent neutralizing monoclonal antibodies against Ebola virus infection", Scientific Reports(2016), vol. 6, pp. 25856-25856. DOI:10.1038/srep25856.
McCoy, A. J. et al., "Phaser crystallographic software", Journal of applied crystallography (2007), vol. 40, pp. 658-674. DOI:10.1107/s0021889807021206.

(56) References Cited

OTHER PUBLICATIONS

Cohen, S. X. et al., "ARP/wARP and molecular replacement: the next generation", Acta crystallographica. Section D, Biological crystallography(2008), vol. D64, pp. 49-60. DOI:10.1107/s0907444907047580.
Emsley, P. et al., "Coot: model-building tools for molecular graphics", Acta crystallographica. Section D, Biological crystalography(2004), vol. D60, pp. 2126-2132. DOI:10.1107/s0907444904019158.
Adams, P. D. et al., "PHENIX: building new software for automated crystallographic structure determination", Acta crytallographica. Section D, Biological crystallography(2002), vol. D58, pp. 1948-1954.
Janson, G. et al., "PyMod 2.0: improvements in protein sequence-structure analysis and homology modeling within PyMOL", Bioinformatics(2017), vol. 33(3), pp. 444-446. DOI:10.1093/bioinformatics/btw638.
Arentz, G. et al., "Secreted human Ro52 autoantibody proteomes express a restricted set of public clonotypes", Journal of autoimmunity(2012), vol. 39, pp. 466-470.
Barnes, C.O. et al., "Structures of human antibodies bound to SARS-CoV-2 spike reveal common epitopes and recurrent features of antibodies", Cell (Aug. 2020), vol. 182, pp. 828-842.
Baum, A. et al., "Antibody cocktail to SARS-CoV-2 spike protein prevents rapid mutational escape seen with individual antibodies", Science(Jun. 2020). DOI: 10.1126/science.abd0831.
Brouwer, P.J.M.et al., "Potent neutralizing antibodies from COVID-19 patients define multiple targets of vulnerability", Science (Aug. 2020), vol. 369, pp. 643-650. DOI: 10.1126/science.abc5902.
Cao, Y. et al., "Potent neutralizing antibodies against SARS-CoV-2 identified by high-throughput single-cell sequencing of convalescent patients' B cells", Cell (Jul. 2020), vol. 182, pp. 73-84. DOI: 10.1016/j.cell.2020.05.025.
Chi, X.et al., "A neutralizing human antibody binds to the N-terminal domain of the Spike protein of SARS-CoV-2", Science(Aug. 2020), vol. 369, pp. 650-655.10. DOI: 1126/science.abc6952.
Hansen, J. et al., "Studies in humanized mice and convalescent humans yield a SARS-CoV-2 antibody cocktail", Science(Aug. 2020), vol. 369, pp. 1010-1014. DOI: 10.1126/science.abd0827.
Dunand, C.J.H. et al., "Restricted, canonical, stereotyped and convergent immunoglobulin responses", Phil. Trans. R. Soc. B. (2015), vol. 370: 20140238. DOI: 10.1098/rstb.2014.0238.
Jackson, K.J.L. et al., "Human responses to influenza vaccination show seroconversion signatures and convergent antibody rearrangements", Cell host & microbe (2014), vol. 16, pp. 105-114. DOI: 10.1016/j.chom.2014.05.013.
Ju, B et al., "Human neutralizing antibodies elicited by SARS-CoV-2 infection", Nature(Aug. 2020), vol. 584, pp. 115-119. DOI: 10.1038/s41586-020-2380-z.
Lan, J. et al., "Structure of the SARS-CoV-2 spike receptor-binding domain bound to the ACE2 receptor", Nature(May 2020), vol. 581, pp. 215-220. DOI: 10.1038/s41586-020-2180-5.
Liu, L. et al., "Potent Neutralizing Monoclonal Antibodies Directed to Multiple Epitopes on the SARS-CoV-2 Spike", BioRxiv.(Jul. 2020). DOI: 10.1101/2020.06.17.153486.
Lv, H. et al., "Cross-reactive antibody response between SARS-CoV-2 and SARS-CoV infections", Cell Reports (Jun. 2020), vol. 31, pp. 107725. DOI: 10.1016/j.celrep.2020.107725.

Parameswaran, P. et al., "Convergent antibody signatures in human dengue", Cell host & microbe (2013), vol. 13, pp. 1691-1700. DOI: 10.1016/j.chom.2013.05.008.
Pieper, K. et al., "Public antibodies to malaria antigens generated by two LAIR1 insertion modalities", Nature (2017), vol. 548, pp. 597-601.
Ravichandran, S. et al., "Antibody signature induced by SARS-CoV-2 spike protein immunogens in rabbits", Science Translational Medicine(Jul. 2020), vol. 12, eabc3539. DOI: 10.1126/scitranslmed.abc3539.
Robbiani, D.F. et al., "Convergent antibody responses to SARS-CoV-2 in convalescent individuals", BioRxiv.(May 2020). DOI: 10.1101/2020.05.13.092619.
Rogers, T.F. et al., "Isolation of potent SARS-CoV-2 neutralizing antibodies and protection from disease in a small animal model", Science (Aug. 2020), vol. 369, pp. 956-963.
Setliff, I. et al., "Multi-Donor Longitudinal Antibody Repertoire Sequencing Reveals the Existence of Public Antibody Clonotypes in HIV-1 Infection", Cell host & microbe (2018), vol. 23, pp. 845-854, e1-e6. DOI: 10.1016/j.chom.2018.05.001.
Seydoux, E. et al., "Analysis of a SARS-CoV-2-Infected Individual Reveals Development of Potent Neutralizing Antibodies with Limited Somatic Mutation", Immunity(Jul. 2020), vol. 53, pp. 98-105. DOI: 10.1016/j.immuni.2020.06.001.
Shang, J. et al., "Structural basis of receptor recognition by SARS-CoV-2", Nature (May 2020), vol. 581, pp. 221-224. DOI: 10.1038/s41586-020-2179-y.
Trück, J. et al., "Identification of antigen-specific B cell receptor sequences using public repertoire analysis", The Journal of immunology (2015), vol. 194, pp. 252-261. DOI: 10.4049/jimmunol.1401405.
Wang, C. et al., "A human monoclonal antibody blocking SARS-CoV-2 infection", Nature Communications(2020), vol. 11, pp. 2251. DOI: 10.1038/s41467-020-16256-y.
Wec, A.Z. et al., "Broad neutralization of SARS-related viruses by human monoclonal antibodies", Science (Aug. 2020), vol. 369, pp. 731-736. DOI: 10.1126/science.abc7424.
Wu, Y. et al., "A noncompeting pair of human neutralizing antibodies block COVID-19 virus binding to its receptor ACE2", Science (Jun. 2020), vol. 368, pp. 1274-1278. DOI: 10.1126/science.abc2241.
Yan, R. et al., "Structural basis for the recognition of SARS-CoV-2 by full-length human ACE2", Science (Mar. 2020), vol. 367(6485), pp. 1444-1448. DOI: 10.1126/science.abb2762.
Yuan, M.et al., "Structural basis of a public antibody response to SARS-CoV-2", bioRxiv. (Jun. 2020). DOI: 10.1101/2020.06.08.141267.
Zost, S.J. et al., "Potently neutralizing human antibodies that block SARS-CoV-2 receptor binding and protect animals" bioRxv. (May 2020). DOI: 10.1101/2020.05.22.111005.
Dall'Acqua, W. F. et al., "Properties of human IgG1s engineered for enhanced binding to the neonatal Fc receptor (FcRn)", Journal of Biological Chemistry(2006), vol. 281, No. 33, pp. 23514-23524.
Shi ZL. et al. A pneumonia outbreak associated with a new coronavirus of probable bat origin. Nature Feb. 3, 2020 (Feb. 3, 2020).
Jiang SB. et al. SARS Vaccine Development. Emerg Infect Dis. Jul. 31, 2005 (Jul. 31, 2005) No. 7 vol. 11.
The International Search Report dated Jul. 1, 2021 (Jul. 1, 2021) for International Application No. PCT/CN2021/081739.

\* cited by examiner

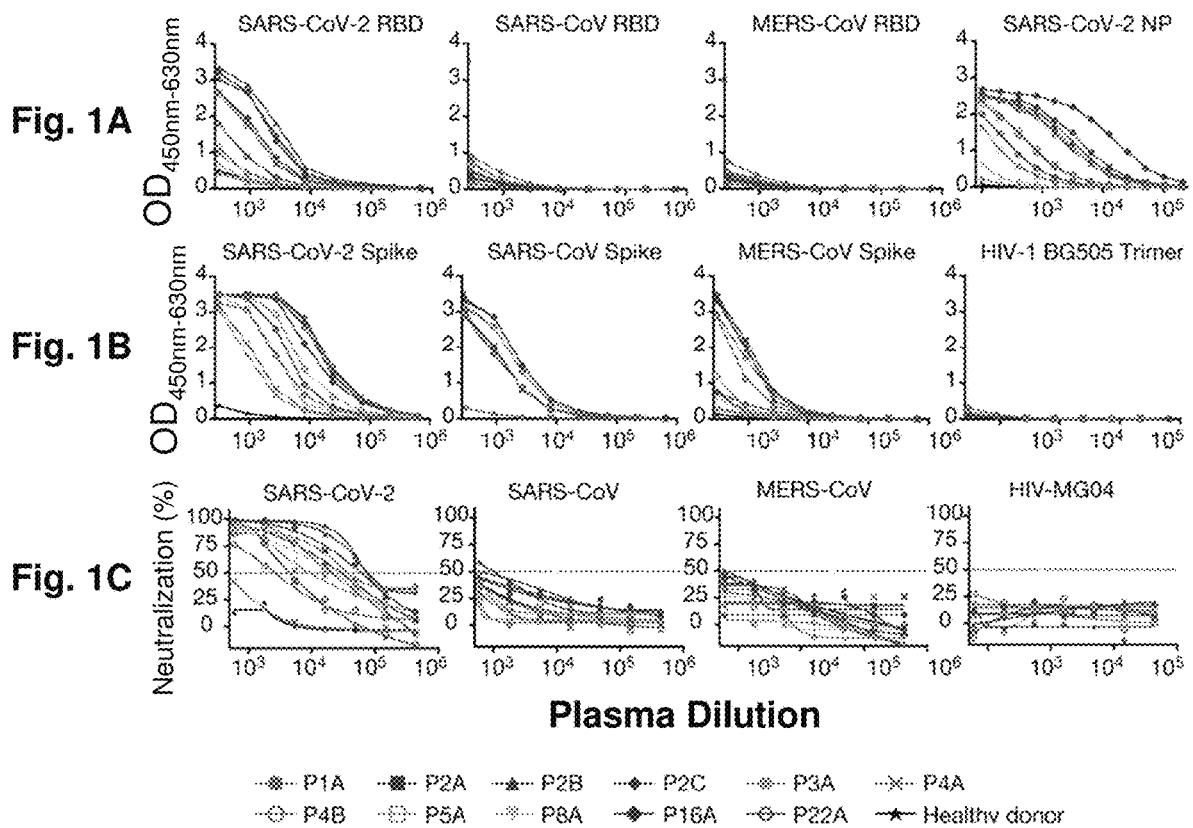
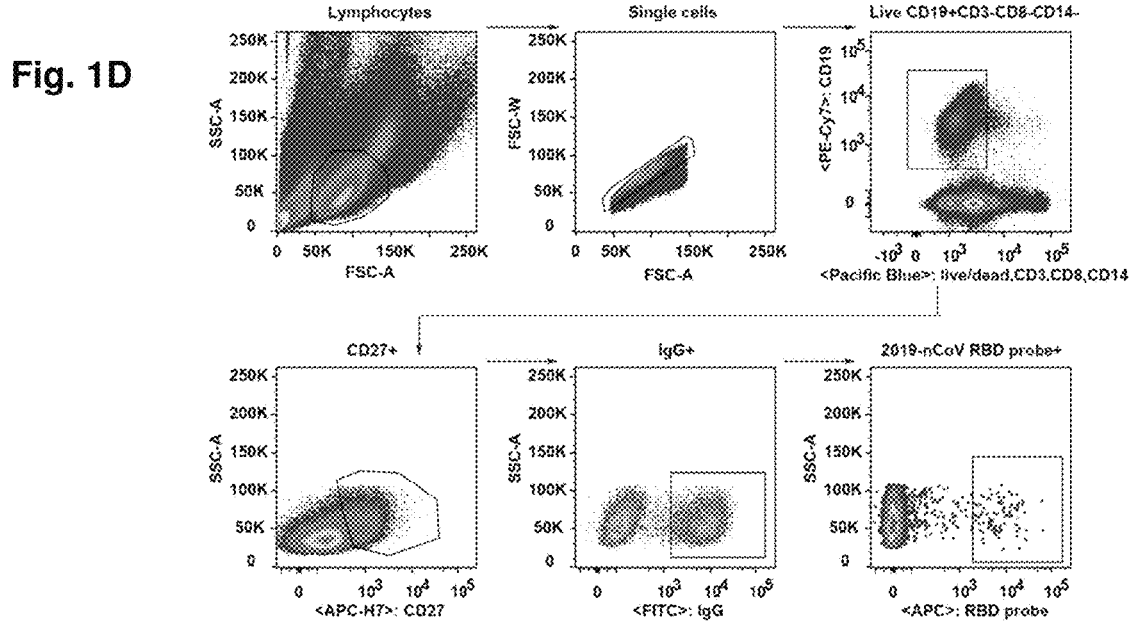

| Patient | mAbs | Binding to RBD | | Pseudovirus neutralization | | Live virus neutralization | | Gene family analysis | | | | |
|---|---|---|---|---|---|---|---|---|---|---|---|---|
| | | Kd (nM) | competing w/ ACE2 | IC50 (μg/ml) | IC80 (μg/ml) | IC50 (μg/ml) | IC80 (μg/ml) | IGHV | IGHJ | IGHD | CDR3 length | SHM (%) |
| P#2 | P2C-1F11 | 2.12 | +++ | 0.03 | 0.12 | 0.03 | 0.18 | 3-46*01,3-46*04 | 6*02 | 2-15*01 | 11 | 1.75 |
| | P2B-2F6 | 5.14 | +++ | 0.05 | 0.61 | 0.41 | 2.43 | 4-38-2*02 | 3*02 | 2-2*01 | 20 | 0.89 |
| | P2C-1A3 | 2.47 | +++ | 0.62 | 5.94 | 0.28 | 1.46 | 3-11*04 | 5*01,5*02 | 6-13*01 | 12 | 0.00 |
| | P2C-1C10 | 15.23 | ++ | 2.62 | 4.84 | 11.12 | >50 | 1.69*01,1.69*01 | 4*02 | 4-23*01 | 11 | 0.35 |
| | P2B-2G4 | 21.29 | + | 5.11 | >50 | 2.90 | 47.70 | 3-33*01,3-33*06 | 4*02 | 5-18*01 | 11 | 0.00 |
| | P2A-1A8 | 8.91 | ++ | 7.68 | 26.41 | 35.87 | >50 | 3-9*01 | 6*02 | 5-12*01 | 23 | 3.82 |
| | P2A-1A10 | 4.65 | +++ | 8.57 | 39.44 | 1.94 | 22.15 | 1-2*06 | 2*01 | 2-2*01 | 19 | 0.00 |
| | P2C-1D5 | 1.38 | - | 10.65 | 25.36 | n.d. | n.d. | 3-23*04 | 4*02 | 3-10*01 | 14 | 0.89 |
| | P2C-1B3 | 6.00 | ++ | 18.77 | >50 | n.d. | n.d. | 3-48*02 | 5*02 | 3-10*01 | 16 | 10.07 |
| | P2A-1A9 | 15.18 | ++ | 26.27 | >50 | n.d. | n.d. | 3-9*01 | 6*02 | 3-22*01 | 17 | 2.66 |
| | P2C-1C8 | 8.76 | ++ | 24.38 | >50 | n.d. | n.d. | 3-33*01,3-33*06 | 4*02 | 3-22*01 | 13 | 0.89 |
| | P2B-2G11 | 17.57 | ++ | 34.84 | >50 | n.d. | n.d. | 3-9*01 | 6*02 | 1-26*01 | 17 | 2.08 |
| | P2C-1E1 | 14.99 | ++ | >50 | >50 | n.d. | n.d. | 3-66*01,3-66*04 | 4*02 | 5-12*01 | 9 | 0.00 |
| P#1 | P1A-1C7 | 51.08 | - | >50 | >50 | n.d. | n.d. | 1-46*01,1-46*03 | 4*02 | 2-2*01 | 15 | 0.00 |
| | P1A-1C10 | 8.48 | + | >50 | >50 | n.d. | n.d. | 1-68*09 | 4*02 | 2-3*01 | 16 | 10.42 |
| | P1A-1D1 | 260.50 | - | >50 | >50 | n.d. | n.d. | 3-53*01 | 4*02 | 6-13*01 | 12 | 4.21 |
| | P1A-1B2 | n.d. | n.d. | n.d. | n.d. | n.d. | n.d. | 3-38*03,3-30*18,3-30.5*01 | 4*02 | 5-24*01 | 12 | 11.46 |
| | P1A-1C1 | n.d. | n.d. | n.d. | n.d. | n.d. | n.d. | 3-33*01,3-33*05,3-33*06 | 4*02 | 3-10*01 | 17 | 6.25 |

Fig. 4U

| Patients | mAbs | Pseudovirus neutralization | | Gene family analysis | | | |
|---|---|---|---|---|---|---|---|
| | | IC₅₀ (μg/ml) | IC₉₀ (μg/ml) | IGHV | IGHJ | IGHD | CDR3 length |
| P#1 | P1A-1C10 | 21.4977 | | 1-69*09 F | 4*02 F | 3-3*01 F | 16 |
| P#4 | P4A-1H6 | 0.1370 | 0.7670 | 2.2136 | 3-30*03 F, 3-30*18 F or 3-30-5*01 F | 4*02 F | 2-2*01 F | 21 |
| | P4B-1F4 | 3.4486 | 9.0132 | 14.5293 | 3-30*03 F, 3-30*18 F or 3-30-5*01 F | 6*02 F | 6-13*01 F | 22 |
| P#5 | P5A-1B6 | 0.2528 | 1.3719 | 4.2043 | 3-30*04 F, or 3-30-3*03 F | 4*02 F | 3-10*01 F | 20 |
| | P5A-1B8 | 0.0115 | 0.0509 | 0.1365 | 3-53*01 F | 4*02 F | 2-15*01 F | 9 |
| | P5A-1B9 | 0.0014 | 0.0052 | 0.0109 | 4-59*01 F | 2*01 F | 3-9*01 F | 22 |
| | P5A-1D1 | 0.0096 | 0.0691 | 0.2318 | 3-53*01 F | 6*02 F | 3-16*01 F | 11 |
| | P5A-1D10 | 5.7212 | 28.8679 | 43.7611 | 3-11*01 F | 4*02 F | 3-16*02 F | 21 |
| | P5A-2D11 | 0.3889 | 1.4758 | 2.0624 | 5-51*01 F | 4*02 F | 4-23*01 ORF | 13 |
| | P5A-2G9 | 0.0158 | 0.1466 | 0.4976 | 3-53*01 F, or 3-53*06 F | 4*02 F | 3-10*01 F | 12 |
| | P5A-2H3 | 0.5042 | 2.0522 | 3.3394 | 5-51*01 F | 4*02 F | 4-23*01 ORF | 13 |
| | P5A-3A1 | 0.9231 | 4.2357 | 7.2009 | 3-53*01 F | 4*02 F | 4-17*01 F | 11 |
| | P5A-3A6 | 0.2343 | 1.2672 | 2.7716 | 3-9*01 F | 6*02 F | 3-10*01 F | 27 |
| | P5A-3B4 | 0.0993 | 1.0657 | 3.0529 | 5-51*01 F | 4*02 F | 4-23*01 ORF | 13 |
| | P5A-3C12 | 0.0996 | 0.4679 | 0.9552 | 2-5*02 F | 4*02 F | 6-13*01 F | 19 |
| P#22 | P22A-1D1 | 0.0038 | 0.0625 | 0.3992 | 3-53*01 F | 6*02 F | | 11 |

Fig. 4V

Contacting residues (a distance cutoff 4 Å) at the SARS-CoV-2 RBD/2F6 interface

| name | residue | region | name | residue | region |
|---|---|---|---|---|---|
| SARS-CoV-2 RBD | K444 | RBM | 2F6-H | Y27 | CDR1 |
| | G446* | | | S28 | |
| | G447 | | | S30 | |
| | N448 | | | S31 | |
| | Y449* | | | Y33 | |
| | N450 | | | H54 | CDR2 |
| | L452 | | | G102 | CDR3 |
| | V483 | | | I103 | |
| | E484 | | | V105 | |
| | G485 | | | V106 | |
| | F490 | | | P107 | |
| | S494 | | 2F6-L | G31 | CDR1 |
| Buried surface (Å²) | 534 | | | Y32 | |
| | | | | N33 | |
| | | | Buried surface (Å²) | 542 For H | |

*Residues that are used by ACE2 to bind SARS-CoV-2.

Contacting residues (a distance cutoff 4Å at the SARS-Cov-2 RBD/1F11 interface

| Name | residue | region | Name | residue | region |
|---|---|---|---|---|---|
| SARS-Cov-2 RBD | R403 | Core | 1F11-K | I2 | FR1 |
| | T415 | | | S28 | CDR1 |
| | G416 | | | S30 | |
| | K417* | | | Y33 | |
| | D420 | | 1F11-H | V2 | FR1 |
| | Y421 | | | G26 | CDR1 |
| | Y453* | RBM | | I27 | |
| | L455* | | | T28 | |
| | F456* | | | S31 | |
| | R457 | | | N32 | |
| | K458 | | | Y33 | |
| | S459 | | | Y52 | CDR2 |
| | N460 | | | S53 | |
| | Y473 | | | G54 | |
| | A475* | | | S56 | |
| | G476 | | | Y58 | FR3 |
| | S477 | | | R97 | CDR3 |
| | F486* | | | L99 | |
| | N487* | | | V100 | |
| | Y489* | | | V101 | |
| | Q493* | | | Y102 | |
| | G502* | | | D105 | |
| | Y505* | | Buried surface (Å²) | 754 for H, 205 for K | |
| Buried surface (Å²) | 722 | | | | |

*Residues that are used by ACE2 to bind SARS-Cov-2.

```
                                      HCDR1                          HCDR2
P5A-1D2   EVQLVESGGGLIQPGGSLRLSCAAS GFTVSSNY MSWVRQAPGKGLEWVS IIYSGGST YYADS
P22A-1D1  EVQLVESGGGLIQPGGSLRLSCAAS GFTVSSNY MSWVRQAPGKGLEWVS IYSGGST  YYADS
P5A-3C8   EVQLVESGGGLIQPGGSLRLSCAAS GFTVSSNY MSWVRQAPGKGLEWVS FIYSGGST YYADS
IGHV3-53  EVQLVESGGGLIQPGGSLRLSCAAS GFTVSSNY MSWVRQAPGKGLEWVS IYSGGST  YYADS
P2C-1F11  EVQLVESGGGLVQPGGSLRLSCAAS FITVSSNY INWVRQAPGKGLEWVS LIYSGGST YYADS
IGHV3-66  EVQLVESGGGLVQPGGSLRLSCAAS GFTVSSNY MSWVRQAPGKGLEWVS IYSGGST  YYADS

HCDR3
P5A-1D2   VKGRFTISRDNSNNTLYLQMNSLRAEDTAVYY ARALQVGATSDYFDI WGQGTLVTVSS
P22A-1D1  VKGRFTISRDNSKNTLYLQMNSLRAEDTAVYY ARDRIYYG----MDV WGQGTTVTVSS
P5A-3C8   VKGRFTISRDNSKNTLYLQMNSLRAEDTAVYY ARDLQEHG----MDV WGQGTTVTVSS
IGHV3-53  VKGRFTISRDNSKNTLYLQMNSLRAEDTAVYY AR-------------------------
P2C-1F11  VKGRFTISRDNSKNTLYLQMNSLRAEDTAVYH ARDLVYYG----MDV WGQGTTVTVSS
IGHV3-66  VKGRFTISRDNSKNTLYLQMNSLRAEDTAVYH AR-------------------------
```

ANTI-SARS-COV-2 ANTIBODIES AND USES THEREOF

CROSS REFERENCE

This application claims the priorities of Foreign Applications No. CN202010203065.1, filed on Mar. 20, 2020; PCT/CN2020/080532, filed Mar. 21, 2020; PCT/CN2020/084097, filed on Apr. 10, 2020; PCT/CN2020/084805, filed on Apr. 14, 2020; and PCT/CN2020/108718, filed on Aug. 12, 2020; which are hereby incorporated by reference.

FIELD OF THE DISCLOSURE

The present disclosure generally relates to novel anti-SARS-COV-2 antibodies, pharmaceutical composition containing the same and the use thereof.

BACKGROUND

The recent outbreak of the new coronavirus, SARS-CoV-2 poses a serious global health emergency. SARS-CoV-2 is a positive-sense single-stranded RNA (+ssRNA) virus which belongs to the betacoronavirus family and shares substantial genetic and functional similarity with other pathogenic human betacoronaviruses, including Severe Acute Respiratory Syndrome Coronavirus (SARS-CoV, also called SARS-CoV-1) and Middle East Respiratory Syndrome Coronavirus (MERS-CoV). Like other coronaviruses, SARS-CoV-2 has four structural proteins, known as the S (spike), E (envelope), M (membrane), and N (nucleocapsid) proteins; the S, E, and M proteins together create the viral envelope; inside the envelope is the N protein bounding to the RNA genome (~30 kb) in a continuous beads-on-a-string type conformation.

The spike protein is the protein responsible for allowing the SARS-CoV-2 virus to attach to the membrane of a host cell, the receptor binding domain (RBD) of the spike protein of SARS-CoV-2 recognizes and attaches to the angiotensin-converting enzyme 2 (ACE2) receptor of host cells to use them as a mechanism of cell entry. The overall ACE2-binding mechanism is virtually the same between SARS-CoV-2 RBD and SARS-CoV RBD, indicating convergent ACE2-binding evolution between these two viruses. This suggests that disruption of the RBD and ACE2 interaction would block the entry of SARS-CoV-2 into the target cell. Indeed, a few such disruptive agents targeted to ACE2 have been shown to inhibit SARS-CoV infection. However, given the important physiological roles of ACE2 in vivo, these agents may have undesired side effects. Anti-RBD antibodies, on the other hand, are therefore more favorable. Furthermore, SARS-CoV-RBD or MERS-CoV RBD-based vaccine studies in experimental animals have also shown strong polyclonal antibody responses that inhibit viral entry. Such critical proof-of-concept findings indicate that anti-RBD antibodies might effectively block SARS-CoV-2 entry.

No SARS-CoV-2-specific treatments or vaccine are currently available, and the currently existing detective measures for SARS-CoV-2 infection are time-consuming and insensitive. Hence, there is an urgent need for novel anti-SARS-CoV-2 antibodies.

BRIEF SUMMARY OF THE INVENTION

In one aspect, the present disclosure is directed to a modified antibody or an antigen-binding fragment thereof comprising at least an antigen-binding domain having an antigen-binding affinity and a covalently linked modified human IgG constant domain, wherein the antigen-binding affinity comprises SARS-CoV-2 binding affinity, the antigen-binding affinity comprises at least 50% less or non-detectable binding affinity to SARS-CoV or MERS-CoV compared to the SARS-CoV-2 binding affinity, and wherein the modified human IgG constant domain comprises a substitution with tyrosine at amino acid residue 252, a substitution with threonine at amino acid residue 254, and a substitution with glutamic acid at amino acid residue 256, numbered according to the EU index as in Kabat, the modified antibody has an increased affinity for FcRn compared to the affinity to FcRn of an antibody having a wild type human IgG constant domain.

In another aspect, the present disclosure is directed to a pharmaceutical composition comprising at least one the modified antibody or an antigen-binding fragment thereof of disclosed herein, at least one nucleic acid encoding the modified antibody or the antigen-binding fragment thereof, or a combination thereof, and one or more pharmaceutically acceptable carriers.

In another aspect, the present disclosure is directed to a method for treating or preventing a disease in a subject in need thereof, the method comprising administering an effective dosage of any of the pharmaceutical composition of disclosed herein to the subject;

wherein the pharmaceutical composition is configured to be administered to the subject to maintain a plasma concentration of the modified antibody or an antigen-binding fragment thereof in a therapeutic effective range of from 10 µg/mL to 3500 µg/mL for a time period in a range of from 1 day to 12 months after administering the pharmaceutical composition; and wherein the subject is infected with, exhibiting one or more symptoms of being infected with, or at risk of being infected with the SARS-CoV-2.

In another aspect, the present disclosure provides an isolated or recombinant antibody or an antigen-binding fragment thereof, which is capable of specifically binding to SARS-CoV-2, and exhibiting at least 50% less binding or non-detectable binding to SARS-CoV or MERS-CoV.

In another aspect, the present disclosure provides an isolated or recombinant antibody or an antigen-binding fragment thereof, having one or more features selected from the group consisting of: a) capable of specifically binding to spike protein of SARS-CoV-2 and exhibiting at least 50% less binding to spike protein of SARS-CoV or spike protein of MERS-CoV; b) capable of specifically binding to receptor-binding domain (RBD) of the spike protein of SARS-CoV-2 comprising the amino acid sequence of SEQ ID NO: 128; c) exhibiting binding to RBD of spike protein of SARS-CoV comprising the amino acid sequence of SEQ ID NO: 124 at a level that is non-detectable or that is no more than 50% of the binding to the RBD of spike protein of SARS-CoV-2; d) exhibiting binding to RBD of spike protein of MERS-CoV comprising the amino acid sequence of SEQ ID NO: 126 at a level that is non-detectable or that is no more than 50% of the binding to RBD of the spike protein of SARS-CoV-2; e) capable of binding to the RBD of spike protein of SARS-CoV-2 at a $K_d$ value of no more than $1 \times 10^{-7}$ M as measured by Surface Plasmon resonance (SPR); f) exhibiting binding to the RBD of spike protein of SARS-CoV or the RBD of spike protein of MERS-CoV at a $K_d$ value of at least $1 \times 10^{-6}$ M as measured by SPR; g) capable of exhibiting at least 30% competition at 1 µM, with 2 µM angiotensin converting enzyme 2 (ACE2) receptor, for binding to the RBD of spike protein of SARS-CoV-2 immobilized at a resonance units (RU) of 250, as measured by SPR; h) capable of binding to the RBD of spike protein of SARS-CoV-2 at an neutralizing activity at an $IC_{50}$ value of no more than 100 μg/ml (for example, no more than 50 μg/ml, no more than 40 μg/ml, no more than 30 μg/ml, no more than 25 μg/ml, no more than 20 μg/ml, no more than 15 μg/ml, no more than 10 μg/ml, no more than 8 μg/ml, no more than 6 μg/ml, no more than 4 μg/ml, no more than 2 μg/ml, or no more than 1 μg/ml), as measured by pseudovirus neutralization assay, and i) capable of binding to the RBD of spike protein of SARS-CoV-2 at an neutralizing activity at an $IC_{50}$ value of no more than 1 μg/ml (for example, no more than 50 ng/ml, no more than 40 ng/ml, no more than 30 ng/ml, no more than 25 ng/ml, no more than 20 ng/ml, no more than 15 ng/ml, no more than 10 ng/ml, no more than 8 ng/ml, no more than 6 ng/ml, no more than 4 ng/ml, no more than 2 ng/ml, or no more than 1 ng/ml), as measured by live virus neutralization assay using focus reduction neutralization test (FRNT) method.

In yet another aspect, the present disclosure provides an isolated or recombinant antibody or an antigen-binding fragment thereof capable of specifically binding to RBD of spike protein of SARS-CoV-2.

In some embodiments, the antibody or antigen binding fragment of the present disclosure comprises 1, 2, or 3 heavy chain CDR sequences selected from SEQ ID NO: 1, SEQ ID NO: 2, and SEQ ID NO: 3.

In some embodiments, the antibody or antigen binding fragment of the present disclosure comprises 1, 2, or 3 heavy chain CDR sequences selected from SEQ ID NO: 11, SEQ ID NO: 12, and SEQ ID NO: 13.

In some embodiments, the antibody or antigen binding fragment of the present disclosure comprises 1, 2, or 3 heavy chain CDR sequences selected from SEQ ID NO: 21, SEQ ID NO: 22, and SEQ ID NO: 23.

In some embodiments, the antibody or antigen binding fragment of the present disclosure comprises 1, 2, or 3 heavy chain CDR sequences selected from SEQ ID NO: 31, SEQ ID NO: 32, and SEQ ID NO: 33.

In some embodiments, the antibody or antigen binding fragment of the present disclosure comprises 1, 2, or 3 heavy chain CDR sequences selected from SEQ ID NO: 41, SEQ ID NO: 42, and SEQ ID NO: 43.

In some embodiments, the antibody or antigen binding fragment of the present disclosure comprises 1, 2, or 3 heavy chain CDR sequences selected from SEQ ID NO: 51, SEQ ID NO: 52, and SEQ ID NO: 53.

In some embodiments, the antibody or antigen binding fragment of the present disclosure comprises 1, 2, or 3 heavy chain CDR sequences selected from SEQ ID NO: 65, SEQ ID NO: 66, and SEQ ID NO: 67.

In some embodiments, the antibody or antigen binding fragment of the present disclosure comprises 1, 2, or 3 heavy chain CDR sequences selected from SEQ ID NO: 75, SEQ ID NO: 76, and SEQ ID NO: 77.

In some embodiments, the antibody or antigen binding fragment of the present disclosure comprises 1, 2, or 3 heavy chain CDR sequences selected from SEQ ID NO: 85, SEQ ID NO: 86, and SEQ ID NO: 87.

In some embodiments, the antibody or antigen binding fragment of the present disclosure comprises 1, 2, or 3 heavy chain CDR sequences selected from SEQ ID NO: 95, SEQ ID NO: 96, and SEQ ID NO: 97.

In some embodiments, the antibody or antigen binding fragment of the present disclosure comprises 1, 2, or 3 heavy chain CDR sequences selected from SEQ ID NO: 105, SEQ ID NO: 106, and SEQ ID NO: 107.

In some embodiments, the antibody or antigen binding fragment of the present disclosure comprises 1, 2, or 3 heavy chain CDR sequences selected from SEQ ID NO: 136, SEQ ID NO: 137, and SEQ ID NO: 138.

In some embodiments, the antibody or antigen binding fragment of the present disclosure comprises 1, 2, or 3 heavy chain CDR sequences selected from SEQ ID NO: 146, SEQ ID NO: 147, and SEQ ID NO: 148.

In some embodiments, the antibody or antigen binding fragment of the present disclosure comprises 1, 2, or 3 heavy chain CDR sequences selected from SEQ ID NO: 156, SEQ ID NO: 157, and SEQ ID NO: 158.

In some embodiments, the antibody or antigen binding fragment of the present disclosure comprises 1, 2, or 3 heavy chain CDR sequences selected from SEQ ID NO: 166, SEQ ID NO: 167, and SEQ ID NO: 168.

In some embodiments, the antibody or antigen binding fragment of the present disclosure comprises 1, 2, or 3 heavy chain CDR sequences selected from SEQ ID NO: 176, SEQ ID NO: 177, and SEQ ID NO: 178.

In some embodiments, the antibody or antigen binding fragment of the present disclosure comprises 1, 2, or 3 heavy chain CDR sequences selected from SEQ ID NO: 186, SEQ ID NO: 187, and SEQ ID NO: 188.

In some embodiments, the antibody or antigen binding fragment of the present disclosure comprises 1, 2, or 3 heavy chain CDR sequences selected from SEQ ID NO: 196, SEQ ID NO: 197, and SEQ ID NO: 198.

In some embodiments, the antibody or antigen binding fragment of the present disclosure comprises 1, 2, or 3 heavy chain CDR sequences selected from SEQ ID NO: 206, SEQ ID NO: 207, and SEQ ID NO: 208.

In some embodiments, the antibody or antigen binding fragment of the present disclosure comprises 1, 2, or 3 heavy chain CDR sequences selected from SEQ ID NO: 216, SEQ ID NO: 217, and SEQ ID NO: 218.

In some embodiments, the antibody or antigen binding fragment of the present disclosure comprises 1, 2, or 3 heavy chain CDR sequences selected from SEQ ID NO: 226, SEQ ID NO: 227, and SEQ ID NO: 228.

In some embodiments, the antibody or antigen binding fragment of the present disclosure comprises 1, 2, or 3 heavy chain CDR sequences selected from SEQ ID NO: 236, SEQ ID NO: 237, and SEQ ID NO: 238.

In some embodiments, the antibody or antigen binding fragment of the present disclosure comprises 1, 2, or 3 heavy chain CDR sequences selected from SEQ ID NO: 246, SEQ ID NO: 247, and SEQ ID NO: 248.

In some embodiments, the antibody or antigen binding fragment of the present disclosure comprises 1, 2, or 3 heavy chain CDR sequences selected from SEQ ID NO: 256, SEQ ID NO: 257, and SEQ ID NO: 258.

In some embodiments, the antibody or antigen binding fragment of the present disclosure comprises 1, 2, or 3 heavy chain CDR sequences selected from SEQ ID NO: 266, SEQ ID NO: 267, and SEQ ID NO: 268.

In some embodiments, the antibody or antigen binding fragment of the present disclosure comprises 1, 2, or 3 heavy chain CDR sequences selected from SEQ ID NO: 276, SEQ ID NO: 277, and SEQ ID NO: 278.

In some embodiments, the antibody or antigen binding fragment of the present disclosure comprises 1, 2, or 3 heavy chain CDR sequences selected from SEQ ID NO: 286, SEQ ID NO: 287, and SEQ ID NO: 288.

In some embodiments, the antibody or antigen binding fragment of the present disclosure comprises 1, 2, or 3 heavy chain CDR sequences selected from SEQ ID NO: 296, SEQ ID NO: 297, and SEQ ID NO: 298.

In some embodiments, the antibody or antigen binding fragment of the present disclosure comprises 1, 2, or 3 heavy chain CDR sequences selected from SEQ ID NO: 306, SEQ ID NO: 307, and SEQ ID NO: 308.

In some embodiments, the antibody or antigen binding fragment of the present disclosure comprises 1, 2, or 3 heavy chain CDR sequences selected from SEQ ID NO: 316, SEQ ID NO: 317, and SEQ ID NO: 318.

In some embodiments, the antibody or antigen binding fragment of the present disclosure comprises 1, 2, or 3 heavy chain CDR sequences selected from SEQ ID NO: 326, SEQ ID NO: 327, and SEQ ID NO: 328.

In some embodiments, the antibody or antigen binding fragment of the present disclosure comprises 1, 2, or 3 heavy chain CDR sequences selected from SEQ ID NO: 336, SEQ ID NO: 337, and SEQ ID NO: 338.

In some embodiments, the antibody or antigen binding fragment of the present disclosure comprises 1, 2, or 3 heavy chain CDR sequences selected from SEQ ID NO: 346, SEQ ID NO: 347, and SEQ ID NO: 348.

In some embodiments, the antibody or antigen binding fragment of the present disclosure comprises 1, 2, or 3 heavy chain CDR sequences selected from SEQ ID NO: 266, SEQ ID NO: 267, and SEQ ID NO: 268.

In some embodiments, the antibody or antigen binding fragment of the present disclosure comprises 1, 2, or 3 heavy chain CDR sequences selected from SEQ ID NO: 356, SEQ ID NO: 357, and SEQ ID NO: 358.

In some embodiments, the antibody or antigen binding fragment of the present disclosure comprises 1, 2, or 3 heavy chain CDR sequences selected from SEQ ID NO: 366, SEQ ID NO: 367, and SEQ ID NO: 368.

In some embodiments, the antibody or antigen binding fragment of the present disclosure comprises 1, 2, or 3 heavy chain CDR sequences selected from SEQ ID NO: 376, SEQ ID NO: 377, and SEQ ID NO: 378.

In some embodiments, the antibody or antigen binding fragment of the present disclosure comprises 1, 2, or 3 heavy chain CDR sequences selected from SEQ ID NO: 386, SEQ ID NO: 387, and SEQ ID NO: 388.

In some embodiments, the antibody or antigen binding fragment of the present disclosure comprises 1, 2, or 3 heavy chain CDR sequences selected from SEQ ID NO: 396, SEQ ID NO: 397, and SEQ ID NO: 398.

In some embodiments, the antibody or antigen binding fragment of the present disclosure comprises 1, 2, or 3 heavy chain CDR sequences selected from SEQ ID NO: 406, SEQ ID NO: 407, and SEQ ID NO: 408.

In some embodiments, the antibody or antigen binding fragment of the present disclosure comprises 1, 2, or 3 heavy chain CDR sequences selected from SEQ ID NO: 416, SEQ ID NO: 417, and SEQ ID NO: 418.

In some embodiments, the antibody or antigen binding fragment of the present disclosure comprises 1, 2, or 3 heavy chain CDR sequences selected from SEQ ID NO: 426, SEQ ID NO: 427, and SEQ ID NO: 428.

In some embodiments, the antibody or antigen binding fragment of the present disclosure comprises 1, 2, or 3 light chain CDR sequences selected from SEQ ID NO: 4, SEQ ID NO: 5, and SEQ ID NO: 6.

In some embodiments, the antibody or antigen binding fragment of the present disclosure comprises 1, 2, or 3 light chain CDR sequences selected from SEQ ID NO: 14, SEQ ID NO: 15, and SEQ ID NO: 16.

In some embodiments, the antibody or antigen binding fragment of the present disclosure comprises 1, 2, or 3 light chain CDR sequences selected from SEQ ID NO: 24, SEQ ID NO: 25 and SEQ ID NO: 26.

In some embodiments, the antibody or antigen binding fragment of the present disclosure comprises 1, 2, or 3 light chain CDR sequences selected from SEQ ID NO: 34, SEQ ID NO: 35 and SEQ ID NO: 36.

In some embodiments, the antibody or antigen binding fragment of the present disclosure comprises 1, 2, or 3 light chain CDR sequences selected from SEQ ID NO: 44, SEQ ID NO: 45 and SEQ ID NO: 46.

In some embodiments, the antibody or antigen binding fragment of the present disclosure comprises 1, 2, or 3 light chain CDR sequences selected from SEQ ID NO: 54, SEQ ID NO: 55 and SEQ ID NO: 56.

In some embodiments, the antibody or antigen binding fragment of the present disclosure comprises 1, 2, or 3 light chain CDR sequences selected from SEQ ID NO: 68, SEQ ID NO: 69, and SEQ ID NO: 70.

In some embodiments, the antibody or antigen binding fragment of the present disclosure comprises 1, 2, or 3 light chain CDR sequences selected from SEQ ID NO: 78, SEQ ID NO: 79, and SEQ ID NO: 80.

In some embodiments, the antibody or antigen binding fragment of the present disclosure comprises 1, 2, or 3 light chain CDR sequences selected from SEQ ID NO: 88, SEQ ID NO: 89, and SEQ ID NO: 90.

In some embodiments, the antibody or antigen binding fragment of the present disclosure comprises 1, 2, or 3 light chain CDR sequences selected from SEQ ID NO: 98, SEQ ID NO: 99, and SEQ ID NO: 100.

In some embodiments, the antibody or antigen binding fragment of the present disclosure comprises 1, 2, or 3 light chain CDR sequences selected from SEQ ID NO: 108, SEQ ID NO: 109, and SEQ ID NO: 110.

In some embodiments, the antibody or antigen binding fragment of the present disclosure comprises 1, 2, or 3 light chain CDR sequences selected from SEQ ID NO: 139, SEQ ID NO: 140, and SEQ ID NO: 141.

In some embodiments, the antibody or antigen binding fragment of the present disclosure comprises 1, 2, or 3 light chain CDR sequences selected from SEQ ID NO: 149, SEQ ID NO: 150, and SEQ ID NO: 151.

In some embodiments, the antibody or antigen binding fragment of the present disclosure comprises 1, 2, or 3 light chain CDR sequences selected from SEQ ID NO: 159, SEQ ID NO: 160, and SEQ ID NO: 161.

In some embodiments, the antibody or antigen binding fragment of the present disclosure comprises 1, 2, or 3 light chain CDR sequences selected from SEQ ID NO: 169, SEQ ID NO: 170, and SEQ ID NO: 171.

In some embodiments, the antibody or antigen binding fragment of the present disclosure comprises 1, 2, or 3 light chain CDR sequences selected from SEQ ID NO: 179, SEQ ID NO: 180, and SEQ ID NO: 181.

In some embodiments, the antibody or antigen binding fragment of the present disclosure comprises 1, 2, or 3 light chain CDR sequences selected from SEQ ID NO: 189, SEQ ID NO: 190, and SEQ ID NO: 191.

In some embodiments, the antibody or antigen binding fragment of the present disclosure comprises 1, 2, or 3 light chain CDR sequences selected from SEQ ID NO: 199, SEQ ID NO: 200, and SEQ ID NO: 201.

In some embodiments, the antibody or antigen binding fragment of the present disclosure comprises 1, 2, or 3 light chain CDR sequences selected from SEQ ID NO: 209, SEQ ID NO: 210, and SEQ ID NO: 211.

In some embodiments, the antibody or antigen binding fragment of the present disclosure comprises 1, 2, or 3 light chain CDR sequences selected from SEQ ID NO: 219, SEQ ID NO: 220, and SEQ ID NO: 221.

In some embodiments, the antibody or antigen binding fragment of the present disclosure comprises 1, 2, or 3 light chain CDR sequences selected from SEQ ID NO: 229, SEQ ID NO: 230, and SEQ ID NO: 231.

In some embodiments, the antibody or antigen binding fragment of the present disclosure comprises 1, 2, or 3 light chain CDR sequences selected from SEQ ID NO: 239, SEQ ID NO: 240, and SEQ ID NO: 241.

In some embodiments, the antibody or antigen binding fragment of the present disclosure comprises 1, 2, or 3 light chain CDR sequences selected from SEQ ID NO: 249, SEQ ID NO: 250, and SEQ ID NO: 251.

In some embodiments, the antibody or antigen binding fragment of the present disclosure comprises 1, 2, or 3 light chain CDR sequences selected from SEQ ID NO: 259, SEQ ID NO: 260, and SEQ ID NO: 261.

In some embodiments, the antibody or antigen binding fragment of the present disclosure comprises 1, 2, or 3 light chain CDR sequences selected from SEQ ID NO: 269, SEQ ID NO: 270, and SEQ ID NO: 271.

In some embodiments, the antibody or antigen binding fragment of the present disclosure comprises 1, 2, or 3 light chain CDR sequences selected from SEQ ID NO: 279, SEQ ID NO: 280, and SEQ ID NO: 281.

In some embodiments, the antibody or antigen binding fragment of the present disclosure comprises 1, 2, or 3 light chain CDR sequences selected from SEQ ID NO: 289, SEQ ID NO: 290, and SEQ ID NO: 291.

In some embodiments, the antibody or antigen binding fragment of the present disclosure comprises 1, 2, or 3 light chain CDR sequences selected from SEQ ID NO: 299, SEQ ID NO: 300, and SEQ ID NO: 301.

In some embodiments, the antibody or antigen binding fragment of the present disclosure comprises 1, 2, or 3 light chain CDR sequences selected from SEQ ID NO: 309, SEQ ID NO: 310, and SEQ ID NO: 311.

In some embodiments, the antibody or antigen binding fragment of the present disclosure comprises 1, 2, or 3 light chain CDR sequences selected from SEQ ID NO: 319, SEQ ID NO: 320, and SEQ ID NO: 321.

In some embodiments, the antibody or antigen binding fragment of the present disclosure comprises 1, 2, or 3 light chain CDR sequences selected from SEQ ID NO: 329, SEQ ID NO: 330, and SEQ ID NO: 331.

In some embodiments, the antibody or antigen binding fragment of the present disclosure comprises 1, 2, or 3 light chain CDR sequences selected from SEQ ID NO: 339, SEQ ID NO: 340, and SEQ ID NO: 341.

In some embodiments, the antibody or antigen binding fragment of the present disclosure comprises 1, 2, or 3 light chain CDR sequences selected from SEQ ID NO: 349, SEQ ID NO: 350, and SEQ ID NO: 351.

In some embodiments, the antibody or antigen binding fragment of the present disclosure comprises 1, 2, or 3 light chain CDR sequences selected from SEQ ID NO: 359, SEQ ID NO: 360, and SEQ ID NO: 361.

In some embodiments, the antibody or antigen binding fragment of the present disclosure comprises 1, 2, or 3 light chain CDR sequences selected from SEQ ID NO: 369, SEQ ID NO: 370, and SEQ ID NO: 371.

In some embodiments, the antibody or antigen binding fragment of the present disclosure comprises 1, 2, or 3 light chain CDR sequences selected from SEQ ID NO: 379, SEQ ID NO: 380, and SEQ ID NO: 381.

In some embodiments, the antibody or antigen binding fragment of the present disclosure comprises 1, 2, or 3 light chain CDR sequences selected from SEQ ID NO: 389, SEQ ID NO: 390, and SEQ ID NO: 391.

In some embodiments, the antibody or antigen binding fragment of the present disclosure comprises 1, 2, or 3 light chain CDR sequences selected from SEQ ID NO: 399, SEQ ID NO: 400, and SEQ ID NO: 401.

In some embodiments, the antibody or antigen binding fragment of the present disclosure comprises 1, 2, or 3 light chain CDR sequences selected from SEQ ID NO: 409, SEQ ID NO: 410, and SEQ ID NO: 411.

In some embodiments, the antibody or antigen binding fragment of the present disclosure comprises 1, 2, or 3 light chain CDR sequences selected from SEQ ID NO: 419, SEQ ID NO: 420, and SEQ ID NO: 421.

In some embodiments, the antibody or antigen binding fragment of the present disclosure comprises 1, 2, or 3 light chain CDR sequences selected from SEQ ID NO: 429, SEQ ID NO: 430, and SEQ ID NO: 431.

In some embodiments, the antibody or antigen binding fragment of the present disclosure comprises a heavy chain CDR1 (HCDR1) comprising the sequence of SEQ ID NO: 1, a heavy chain CDR2 (HCDR2) comprising the sequence of SEQ ID NO: 2, a heavy chain CDR3 (HCDR3) comprising the sequence of SEQ ID NO: 3; a light chain CDR1 (LCDR1) comprising the sequence of SEQ ID NO: 4, a light chain CDR2 (LCDR2) comprising the sequence of SEQ ID NO: 5, and a light chain CDR3 (LCDR3) comprising the sequence of SEQ ID NO: 6.

In some embodiments, the antibody or antigen binding fragment of the present disclosure comprises a HCDR1 comprising the sequence of SEQ ID NO: 11, a HCDR2 comprising the sequence of SEQ ID NO: 12, a HCDR3 comprising the sequence of SEQ ID NO: 13, a LCDR1 comprising the sequence of SEQ ID NO: 14, a LCDR2 comprising the sequence of SEQ ID NO: 15, and a LCDR3 comprising the sequence of SEQ ID NO: 16.

In some embodiments, the antibody or antigen binding fragment of the present disclosure comprises a HCDR1 comprising the sequence of SEQ ID NO: 21, a HCDR2 comprising the sequence of SEQ ID NO: 22, a HCDR3 comprising the sequence of SEQ ID NO: 23, a LCDR1 comprising the sequence of SEQ ID NO: 24, a LCDR2 comprising the sequence of SEQ ID NO: 25, and a LCDR3 comprising the sequence of SEQ ID NO: 26.

In some embodiments, the antibody or antigen binding fragment of the present disclosure comprises a HCDR1 comprising the sequence of SEQ ID NO: 31, a HCDR2 comprising the sequence of SEQ ID NO: 32, a HCDR3 comprising the sequence of SEQ ID NO: 33, a LCDR1 comprising the sequence of SEQ ID NO: 34, a LCDR2 comprising the sequence of SEQ ID NO: 35, and a LCDR3 comprising the sequence of SEQ ID NO: 36.

In some embodiments, the antibody or antigen binding fragment of the present disclosure comprises a HCDR1 comprising the sequence of SEQ ID NO: 41, a HCDR2 comprising the sequence of SEQ ID NO: 42, a HCDR3 comprising the sequence of SEQ ID NO: 43, a LCDR1 comprising the sequence of SEQ ID NO: 44, a LCDR2 comprising the sequence of SEQ ID NO: 45, and a LCDR3 comprising the sequence of SEQ ID NO: 46.

In some embodiments, the antibody or antigen binding fragment of the present disclosure comprises a HCDR1 comprising the sequence of SEQ ID NO: 51, a HCDR2 comprising the sequence of SEQ ID NO: 52, a HCDR3 comprising the sequence of SEQ ID NO: 53, a LCDR1 comprising the sequence of SEQ ID NO: 54, a LCDR2 comprising the sequence of SEQ ID NO: 55, and a LCDR3 comprising the sequence of SEQ ID NO: 56.

In some embodiments, the antibody or antigen binding fragment of the present disclosure comprises a HCDR1 comprising the sequence of SEQ ID NO: 65, a HCDR2 comprising the sequence of SEQ ID NO: 66, a HCDR3 comprising the sequence of SEQ ID NO: 67, a LCDR1 comprising the sequence of SEQ ID NO: 68, a LCDR2 comprising the sequence of SEQ ID NO: 69, and a LCDR3 comprising the sequence of SEQ ID NO: 70.

In some embodiments, the antibody or antigen binding fragment of the present disclosure comprises a HCDR1 comprising the sequence of SEQ ID NO: 75, a HCDR2 comprising the sequence of SEQ ID NO: 76, a HCDR3 comprising the sequence of SEQ ID NO: 77, a LCDR1 comprising the sequence of SEQ ID NO: 78, a LCDR2 comprising the sequence of SEQ ID NO: 79, and a LCDR3 comprising the sequence of SEQ ID NO: 80.

In some embodiments, the antibody or antigen binding fragment of the present disclosure comprises a HCDR1 comprising the sequence of SEQ ID NO: 85, a HCDR2 comprising the sequence of SEQ ID NO: 86, a HCDR3 comprising the sequence of SEQ ID NO: 87, a LCDR1 comprising the sequence of SEQ ID NO: 88, a LCDR2 comprising the sequence of SEQ ID NO: 89, and a LCDR3 comprising the sequence of SEQ ID NO: 90.

In some embodiments, the antibody or antigen binding fragment of the present disclosure comprises a HCDR1 comprising the sequence of SEQ ID NO: 95, a HCDR2 comprising the sequence of SEQ ID NO: 96, a HCDR3 comprising the sequence of SEQ ID NO: 97, a LCDR1 comprising the sequence of SEQ ID NO: 98, a LCDR2 comprising the sequence of SEQ ID NO: 99, and a LCDR3 comprising the sequence of SEQ ID NO: 100.

In some embodiments, the antibody or antigen binding fragment of the present disclosure comprises a HCDR1 comprising the sequence of SEQ ID NO: 105, a HCDR2 comprising the sequence of SEQ ID NO: 106, a HCDR3 comprising the sequence of SEQ ID NO: 107, a LCDR1 comprising the sequence of SEQ ID NO: 108, a LCDR2 comprising the sequence of SEQ ID NO: 109, and a LCDR3 comprising the sequence of SEQ ID NO: 110.

In some embodiments, the antibody or antigen binding fragment of the present disclosure comprises a HCDR1 comprising the sequence of SEQ ID NO: 136, a HCDR2 comprising the sequence of SEQ ID NO: 137, a HCDR3 comprising the sequence of SEQ ID NO: 138, a LCDR1 comprising the sequence of SEQ ID NO: 139, a LCDR2 comprising the sequence of SEQ ID NO: 140, and a LCDR3 comprising the sequence of SEQ ID NO: 141.

In some embodiments, the antibody or antigen binding fragment of the present disclosure comprises a HCDR1 comprising the sequence of SEQ ID NO: 146, a HCDR2 comprising the sequence of SEQ ID NO: 147, a HCDR3 comprising the sequence of SEQ ID NO: 148, a LCDR1 comprising the sequence of SEQ ID NO: 149, a LCDR2 comprising the sequence of SEQ ID NO: 150, and a LCDR3 comprising the sequence of SEQ ID NO: 151.

In some embodiments, the antibody or antigen binding fragment of the present disclosure comprises a HCDR1 comprising the sequence of SEQ ID NO: 156, a HCDR2 comprising the sequence of SEQ ID NO: 157, a HCDR3 comprising the sequence of SEQ ID NO: 158, a LCDR1 comprising the sequence of SEQ ID NO: 159, a LCDR2 comprising the sequence of SEQ ID NO: 160, and a LCDR3 comprising the sequence of SEQ ID NO: 161.

In some embodiments, the antibody or antigen binding fragment of the present disclosure comprises a HCDR1 comprising the sequence of SEQ ID NO: 166, a HCDR2 comprising the sequence of SEQ ID NO: 167, a HCDR3 comprising the sequence of SEQ ID NO: 168, a LCDR1 comprising the sequence of SEQ ID NO: 169, a LCDR2 comprising the sequence of SEQ ID NO: 170, and a LCDR3 comprising the sequence of SEQ ID NO: 171.

In some embodiments, the antibody or antigen binding fragment of the present disclosure comprises a HCDR1 comprising the sequence of SEQ ID NO: 176, a HCDR2 comprising the sequence of SEQ ID NO: 177, a HCDR3 comprising the sequence of SEQ ID NO: 178, a LCDR1 comprising the sequence of SEQ ID NO: 179, a LCDR2 comprising the sequence of SEQ ID NO: 180, and a LCDR3 comprising the sequence of SEQ ID NO: 181.

In some embodiments, the antibody or antigen binding fragment of the present disclosure comprises a HCDR1 comprising the sequence of SEQ ID NO: 186, a HCDR2 comprising the sequence of SEQ ID NO: 187, a HCDR3 comprising the sequence of SEQ ID NO: 188, a LCDR1 comprising the sequence of SEQ ID NO: 189, a LCDR2 comprising the sequence of SEQ ID NO: 190, and a LCDR3 comprising the sequence of SEQ ID NO: 191.

In some embodiments, the antibody or antigen binding fragment of the present disclosure comprises a HCDR1 comprising the sequence of SEQ ID NO: 196, a HCDR2 comprising the sequence of SEQ ID NO: 197, a HCDR3 comprising the sequence of SEQ ID NO: 198, a LCDR1 comprising the sequence of SEQ ID NO: 199, a LCDR2 comprising the sequence of SEQ ID NO: 200, and a LCDR3 comprising the sequence of SEQ ID NO: 201.

In some embodiments, the antibody or antigen binding fragment of the present disclosure comprises a HCDR1 comprising the sequence of SEQ ID NO: 206, a HCDR2 comprising the sequence of SEQ ID NO: 207, a HCDR3 comprising the sequence of SEQ ID NO: 208, a LCDR1 comprising the sequence of SEQ ID NO: 209, a LCDR2 comprising the sequence of SEQ ID NO: 210, and a LCDR3 comprising the sequence of SEQ ID NO: 211.

In some embodiments, the antibody or antigen binding fragment of the present disclosure comprises a HCDR1 comprising the sequence of SEQ ID NO: 216, a HCDR2 comprising the sequence of SEQ ID NO: 217, a HCDR3 comprising the sequence of SEQ ID NO: 218, a LCDR1 comprising the sequence of SEQ ID NO: 219, a LCDR2 comprising the sequence of SEQ ID NO: 220, and a LCDR3 comprising the sequence of SEQ ID NO: 221.

In some embodiments, the antibody or antigen binding fragment of the present disclosure comprises a HCDR1 comprising the sequence of SEQ ID NO: 226, a HCDR2 comprising the sequence of SEQ ID NO: 227, a HCDR3 comprising the sequence of SEQ ID NO: 228, a LCDR1 comprising the sequence of SEQ ID NO: 229, a LCDR2 comprising the sequence of SEQ ID NO: 230, and a LCDR3 comprising the sequence of SEQ ID NO: 231.

In some embodiments, the antibody or antigen binding fragment of the present disclosure comprises a HCDR1 comprising the sequence of SEQ ID NO: 236, a HCDR2 comprising the sequence of SEQ ID NO: 237, a HCDR3 comprising the sequence of SEQ ID NO: 238, a LCDR1 comprising the sequence of SEQ ID NO: 239, a LCDR2 comprising the sequence of SEQ ID NO: 240, and a LCDR3 comprising the sequence of SEQ ID NO: 241.

In some embodiments, the antibody or antigen binding fragment of the present disclosure comprises a HCDR1 comprising the sequence of SEQ ID NO: 246, a HCDR2 comprising the sequence of SEQ ID NO: 247, a HCDR3 comprising the sequence of SEQ ID NO: 248, a LCDR1 comprising the sequence of SEQ ID NO: 249, a LCDR2 comprising the sequence of SEQ ID NO: 250, and a LCDR3 comprising the sequence of SEQ ID NO: 251.

In some embodiments, the antibody or antigen binding fragment of the present disclosure comprises a HCDR1 comprising the sequence of SEQ ID NO: 256, a HCDR2 comprising the sequence of SEQ ID NO: 257, a HCDR3 comprising the sequence of SEQ ID NO: 258, a LCDR1 comprising the sequence of SEQ ID NO: 259, a LCDR2 comprising the sequence of SEQ ID NO: 260, and a LCDR3 comprising the sequence of SEQ ID NO: 261.

In some embodiments, the antibody or antigen binding fragment of the present disclosure comprises a HCDR1 comprising the sequence of SEQ ID NO: 266, a HCDR2 comprising the sequence of SEQ ID NO: 267, a HCDR3 comprising the sequence of SEQ ID NO: 268, a LCDR1 comprising the sequence of SEQ ID NO: 269, a LCDR2 comprising the sequence of SEQ ID NO: 270, and a LCDR3 comprising the sequence of SEQ ID NO: 271.

In some embodiments, the antibody or antigen binding fragment of the present disclosure comprises a HCDR1 comprising the sequence of SEQ ID NO: 276, a HCDR2 comprising the sequence of SEQ ID NO: 277, a HCDR3 comprising the sequence of SEQ ID NO: 278, a LCDR1 comprising the sequence of SEQ ID NO: 279, a LCDR2 comprising the sequence of SEQ ID NO: 280, and a LCDR3 comprising the sequence of SEQ ID NO: 281.

In some embodiments, the antibody or antigen binding fragment of the present disclosure comprises a HCDR1 comprising the sequence of SEQ ID NO: 286, a HCDR2 comprising the sequence of SEQ ID NO: 287, a HCDR3 comprising the sequence of SEQ ID NO: 288, a LCDR1 comprising the sequence of SEQ ID NO: 289, a LCDR2 comprising the sequence of SEQ ID NO: 290, and a LCDR3 comprising the sequence of SEQ ID NO: 291.

In some embodiments, the antibody or antigen binding fragment of the present disclosure comprises a HCDR1 comprising the sequence of SEQ ID NO: 296, a HCDR2 comprising the sequence of SEQ ID NO: 297, a HCDR3 comprising the sequence of SEQ ID NO: 298, a LCDR1 comprising the sequence of SEQ ID NO: 299, a LCDR2 comprising the sequence of SEQ ID NO: 300, and a LCDR3 comprising the sequence of SEQ ID NO: 301.

In some embodiments, the antibody or antigen binding fragment of the present disclosure comprises a HCDR1 comprising the sequence of SEQ ID NO: 306, a HCDR2 comprising the sequence of SEQ ID NO: 307, a HCDR3 comprising the sequence of SEQ ID NO: 308, a LCDR1 comprising the sequence of SEQ ID NO: 309, a LCDR2 comprising the sequence of SEQ ID NO: 310, and a LCDR3 comprising the sequence of SEQ ID NO: 311.

In some embodiments, the antibody or antigen binding fragment of the present disclosure comprises a HCDR1 comprising the sequence of SEQ ID NO: 316, a HCDR2 comprising the sequence of SEQ ID NO: 317, a HCDR3 comprising the sequence of SEQ ID NO: 318, a LCDR1 comprising the sequence of SEQ ID NO: 319, a LCDR2 comprising the sequence of SEQ ID NO: 320, and a LCDR3 comprising the sequence of SEQ ID NO: 321.

In some embodiments, the antibody or antigen binding fragment of the present disclosure comprises a HCDR1 comprising the sequence of SEQ ID NO: 326, a HCDR2 comprising the sequence of SEQ ID NO: 327, a HCDR3 comprising the sequence of SEQ ID NO: 328, a LCDR1 comprising the sequence of SEQ ID NO: 329, a LCDR2 comprising the sequence of SEQ ID NO: 330, and a LCDR3 comprising the sequence of SEQ ID NO: 331.

In some embodiments, the antibody or antigen binding fragment of the present disclosure comprises a HCDR1 comprising the sequence of SEQ ID NO: 336, a HCDR2 comprising the sequence of SEQ ID NO: 337, a HCDR3 comprising the sequence of SEQ ID NO: 338, a LCDR1 comprising the sequence of SEQ ID NO: 339, a LCDR2 comprising the sequence of SEQ ID NO: 340, and a LCDR3 comprising the sequence of SEQ ID NO: 341.

In some embodiments, the antibody or antigen binding fragment of the present disclosure comprises a HCDR1 comprising the sequence of SEQ ID NO: 346, a HCDR2 comprising the sequence of SEQ ID NO: 347, a HCDR3 comprising the sequence of SEQ ID NO: 348, a LCDR1 comprising the sequence of SEQ ID NO: 349, a LCDR2 comprising the sequence of SEQ ID NO: 350, and a LCDR3 comprising the sequence of SEQ ID NO: 351.

In some embodiments, the antibody or antigen binding fragment of the present disclosure comprises a HCDR1 comprising the sequence of SEQ ID NO: 356, a HCDR2 comprising the sequence of SEQ ID NO: 357, a HCDR3 comprising the sequence of SEQ ID NO: 358, a LCDR1 comprising the sequence of SEQ ID NO: 359, a LCDR2 comprising the sequence of SEQ ID NO: 360, and a LCDR3 comprising the sequence of SEQ ID NO: 361.

In some embodiments, the antibody or antigen binding fragment of the present disclosure comprises a HCDR1 comprising the sequence of SEQ ID NO: 366, a HCDR2 comprising the sequence of SEQ ID NO: 367, a HCDR3 comprising the sequence of SEQ ID NO: 368, a LCDR1 comprising the sequence of SEQ ID NO: 369, a LCDR2 comprising the sequence of SEQ ID NO: 370, and a LCDR3 comprising the sequence of SEQ ID NO: 371.

In some embodiments, the antibody or antigen binding fragment of the present disclosure comprises a HCDR1 comprising the sequence of SEQ ID NO: 376, a HCDR2 comprising the sequence of SEQ ID NO: 377, a HCDR3 comprising the sequence of SEQ ID NO: 378, a LCDR1 comprising the sequence of SEQ ID NO: 379, a LCDR2 comprising the sequence of SEQ ID NO: 380, and a LCDR3 comprising the sequence of SEQ ID NO: 381.

In some embodiments, the antibody or antigen binding fragment of the present disclosure comprises a HCDR1 comprising the sequence of SEQ ID NO: 386, a HCDR2 comprising the sequence of SEQ ID NO: 387, a HCDR3 comprising the sequence of SEQ ID NO: 388, a LCDR1 comprising the sequence of SEQ ID NO: 389, a LCDR2 comprising the sequence of SEQ ID NO: 390, and a LCDR3 comprising the sequence of SEQ ID NO: 391.

In some embodiments, the antibody or antigen binding fragment of the present disclosure comprises a HCDR1 comprising the sequence of SEQ ID NO: 396, a HCDR2 comprising the sequence of SEQ ID NO: 397, a HCDR3 comprising the sequence of SEQ ID NO: 398, a LCDR1 comprising the sequence of SEQ ID NO: 399, a LCDR2 comprising the sequence of SEQ ID NO: 400, and a LCDR3 comprising the sequence of SEQ ID NO: 401.

In some embodiments, the antibody or antigen binding fragment of the present disclosure comprises a HCDR1 comprising the sequence of SEQ ID NO: 406, a HCDR2 comprising the sequence of SEQ ID NO: 407, a HCDR3 comprising the sequence of SEQ ID NO: 408, a LCDR1 comprising the sequence of SEQ ID NO: 409, a LCDR2 comprising the sequence of SEQ ID NO: 410, and a LCDR3 comprising the sequence of SEQ ID NO: 411.

In some embodiments, the antibody or antigen binding fragment of the present disclosure comprises a HCDR1 comprising the sequence of SEQ ID NO: 416, a HCDR2 comprising the sequence of SEQ ID NO: 417, a HCDR3 comprising the sequence of SEQ ID NO: 418, a LCDR1 comprising the sequence of SEQ ID NO: 419, a LCDR2 comprising the sequence of SEQ ID NO: 420, and a LCDR3 comprising the sequence of SEQ ID NO: 421.

In some embodiments, the antibody or antigen binding fragment of the present disclosure comprises a HCDR1 comprising the sequence of SEQ ID NO: 426, a HCDR2 comprising the sequence of SEQ ID NO: 427, a HCDR3 comprising the sequence of SEQ ID NO: 428, a LCDR1 comprising the sequence of SEQ ID NO: 429, a LCDR2 comprising the sequence of SEQ ID NO: 430, and a LCDR3 comprising the sequence of SEQ ID NO: 431.

In some embodiments, the antibody or antigen binding fragment of the present disclosure comprises a heavy chain variable region comprises a sequence selected from the group consisting of SEQ ID NO: 7, 17, 27, 37, 47, 57, 61, 71, 81, 91, 101, 111, 142, 152, 162, 172, 182, 192, 202, 212, 222, 232, 242, 252, 262, 272, 282, 292, 302, 312, 322, 332, 342, 352, 362, 372, 382, 392, 402, 412, 422 and 432, or a homologous sequence thereof having at least 80% sequence identity.

In some embodiments, the antibody or antigen binding fragment of the present disclosure comprises a light chain variable region comprises a sequence selected from the group consisting of SEQ ID NO: 8, 18, 28, 38, 48, 58, 62, 72, 82, 92, 102, 112, 143, 153, 163, 173, 183, 193, 203, 213, 223, 233, 243, 253, 263, 273, 283, 293, 303, 313, 323, 333, 343, 353, 363, 373, 383, 393, 403, 413, 423 and 433, or a homologous sequence thereof having at least 80% sequence identity.

In some embodiments, the antibody or antigen binding fragment of the present disclosure comprises a pair of heavy chain variable region and light chain variable region sequences selected from the group consisting of: SEQ ID NOs: 7/8, 17/18, 27/28, 37/38, 47/48, 57/58, 61/62, 71/72, 81/82, 91/92, 101/102, 111/112, and 142/143, 152/153, 162/163, 172/173, 182/183, 192/193, 202/203, 212/213, 222/223, 232/233, 242/243, 252/253, 262/263, 272/273, 282/283, 292/293, 302/303, 312/313, 322/323, 332/333, 342/343, 352/353, 362/363, 372/373, 382/383, 392/393, 402/403, 412/413, 422/423 and 432/433, or a pair of homologous sequences thereof having at least 80% sequence identity yet retaining specific binding affinity to RBD of spike protein of SARS-CoV-2.

In some embodiments, the antibody or antigen binding fragment of the present disclosure further comprises an immunoglobulin constant region. In some embodiments, the immunoglobulin constant region is a constant region of human immunoglobulin. In some embodiments, the immunoglobulin constant region is a constant region of human IgG. In some embodiments, the antibody or antigen binding fragment of the present disclosure comprises a heavy chain constant region of human IgG1, IgG2, IgG3, IgG4, IgA1, IgA2 or IgM. In some embodiments, the antibody or antigen binding fragment of the present disclosure comprises a heavy chain constant region of human IgG1. In some embodiments, the antibody or antigen binding fragment of the present disclosure comprises a constant region of human immunoglobulin kappa 1 light chain. In some embodiments, the antibody or antigen binding fragment of the present disclosure comprises a constant region of human immunoglobulin lambda light chain.

In some embodiments, the antibody or antigen binding fragment of the present disclosure comprises one or more amino acid residue substitutions or modifications yet retains specific binding affinity to RBD of spike protein of SARS-CoV-2.

In some embodiments, the antibody or antigen binding fragment is an affinity variant, a glycosylation variant, a cysteine-engineered variant, or an Fc variant.

In some embodiments, the glycosylation variant comprises a mutation at N297 (e.g. N297A, N297Q, or N297G), for example, to modify the glycosylation site.

In some embodiments, the Fc variant comprises one or more amino acid residue modifications or substitutions resulting in increased effector functions relative to a wild-type Fc. In some embodiments, the Fc variant comprises one or more amino acid substitution(s) at one or more of the positions selected from the group consisting of: 234, 235, 236, 238, 239, 240, 241, 243, 244, 245, 246, 247, 248, 249, 252, 254, 255, 256, 258, 260, 262, 263, 264, 265, 267, 268, 269, 270, 272, 274, 276, 278, 280, 283, 285, 286, 289, 290, 292, 293, 294, 295, 296, 298, 299, 300, 301, 303, 304, 305, 307, 309, 312, 313, 315, 320, 322, 324, 325, 326, 327, 329, 330, 331, 332, 333, 334, 335, 337, 338, 339, 340, 345, 360, 373, 376, 378, 382, 388, 389, 396, 398, 414, 416, 419, 430, 433, 434, 435, 436, 437, 438, 439 and 440 of the Fc region, wherein the numbering of the residues in the Fc region is that of the EU index as in Kabat. In some embodiments, the Fc variant comprises one or more amino acid substitution selected from the group consisting of 234Y, 235Q, 236A, 236W, 239D, 239E, 239M, 243L, 247I, 267E, 268D, 268E, 268F, 270E, 280H, 290S, 292P, 298A, 298D, 298V, 300L, 305I, 324T, 326A, 326D, 326W, 330L, 330M, 333S, 332D, 332E, 333A, 334A, 334E, 339D, 339Q, 345R, 396L, 430G, 440Y, and any combination thereof. In some embodiments, the Fc variant having increased effector function comprises a combination of mutations selected from the group consisting of: a) S239D, I332E, and A330L; b) F243L, R292P, Y300L, V305I and P396L; c) S239D and I332E; d) S239D, I332E and A330L; e) S298A, E333A and K334A; f) L234Y, L235Q, G236W, S239M, H268D, D270E and S298A (in one heavy chain) and D270E, K326D, A330M and K334E (in the opposing heavy chain); G236A, S239D and I332E; g) K326W and E333S; h) S267E, H268F and S324T; i) E345R, E430G and S440Y.

In some embodiments, the Fc variant comprises one or more amino acid residue modifications or substitutions resulting in reduced effector functions relative to a wildtype Fc. In some embodiments, the Fc variant comprises one or more amino acid substitution(s) at a position selected from the group consisting of: 220, 226, 229, 233, 234, 235, 236, 237, 238, 267, 268, 269, 270, 297, 309, 318, 320, 322, 325, 328, 329, 330, and 331 of the Fc region, wherein the numbering of the residues in the Fc region is that of the EU index as in Kabat. In some embodiments, the Fc variant comprises one or more amino acid substitution(s) selected from the group consisting of 220S, 226S, 228P, 229S, 233P, 234V, 234G, 234A, 234F, 234A, 235A, 235G, 235E, 236E, 236R, 237A, 237K, 238S, 267R, 268A, 268Q, 269R, 297A, 297Q, 297G, 309L, 318A, 322A, 325L, 328R, 330S, 331S and any combination thereof. In some embodiments, the Fc variant having reduced effector function comprises a combination of mutations selected from the group consisting of: a) K322A, L234A, and L235A; b) P331S, L234F, and L235E; c) L234A and L235A; c) N297A; d) N297Q; e) N297G; f) L235E; g) L234A and L235A (IgG1); h) F234A and L235A (IgG4); i) H268Q, V309L, A330S and P331S (IgG2); j) V234A, G237A, P238S, H268A, V309L, A330S and P331S (IgG2).

In some embodiments, the Fc variant comprises one or more amino acid residue modifications or substitutions resulting in improved binding affinity to neonatal Fc receptor (FcRn) at pH 6.0 while retaining minimal binding at pH 7.4, or increased serum half life of the antibody. In some embodiments, the Fc variant comprises one or more amino acid substitution(s) at a position selected from the group consisting of: 234 (e.g., with F), 235 (e.g., with Q), 238 (e.g., with D), 250 (e.g., with E or Q), 252 (e.g., with L/Y/F/W or T), 254 (e.g., with S or T), 256 (e.g., with S/R/Q/E/D or T); 259 (e.g., with I); 272 (e.g., with A), 305 (e.g., with A), 307 (e.g., with A or P), 308 (e.g., with F, C or P), 311 (e.g., with A or R), 312 (e.g., with A), 322 (e.g., Q), 328 (e.g. E), 331 (e.g., with A), 378 (e.g., with A), 380 (e.g., with A), 382 (e.g., with A), 428 (e.g., with L or F), 432 (e.g., with C), 433 (e.g., with H/L/R/S/P/Q or K), 434 (e.g., with H/F or Y or S or A or W), 435 (e.g. with H), 436 (e.g., with L) and 437 (e.g., with C)) (all positions by EU numbering). In some embodiments, the Fc variant comprises one or more amino acid substitution(s) selected from the group consisting of 234F, 235Q, 238D, 250Q, 252T, 252Y, 254T, 256E, 259I, 272A, 305A, 307A, 308F, 311A, 322Q, 328E, 331S, 380A, 428L, 432C, 433K, 433S, 434S, 434Y, 434F, 434W, 434A, 435H, 436L, 437C and any combination thereof. In some embodiments, the Fc variant having increased serum half-life or improved pH-dependent binding to FcRn comprises a combination of mutations selected from the group consisting of: a) M428L and N434S; b) P238D and L328E; c) M252Y, S254T and T256E; d) L234F, L235Q, K322Q, M252T, S254T and T256E; e) M428L, V259I and V308F; f) H433K and N434Y; g) H433K and N434F; h) T250Q and M428L; i) T307A, E380A and N434A; and j) 432C, 433S, 434W, 435H, 436L, 437C.

In some embodiments, at least one of the substitutions or modifications is in one or more of the CDR sequences. In some embodiments, at least one of the substitutions or modifications is in one or more of the non-CDR sequences of the heavy chain variable region or light chain variable region. In some embodiments, at least one of the substitutions is a conservative substitution.

In some embodiments, the antibody or antigen binding fragment of the present disclosure is a monoclonal antibody, a bispecific antibody, a multi-specific antibody, a recombinant antibody, a labeled antibody, a bivalent antibody, an anti-idiotypic antibody, a fusion protein, or a dimerized or polymerized antibody, or a modified antibody (e.g. glycosylated antibody). In some embodiments, the antibody or antigen binding fragment of the present disclosure is a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a bispecific scFv dimer, a multi-specific antibody, a heavy chain antibody, a camelized single domain antibody, a nanobody, a domain antibody, or a bivalent domain antibody. In some embodiments, the antibody or antigen binding fragment of the present disclosure is a full human antibody.

In some embodiments, the antibody or antigen binding fragment of the present disclosure is linked to one or more conjugate moieties. In some embodiments, the conjugate moiety comprises a therapeutic agent, a radioactive isotope, a detectable label, a pharmacokinetic modifying moiety, or a purifying moiety. In some embodiments, the conjugate moiety is covalently attached either directly or via a linker.

In one aspect, the present disclosure provides an isolated or recombinant antibody or an antigen-binding fragment thereof, which competes for binding to RBD of spike protein of SARS-CoV-2 with the antibody or an antigen-binding fragment thereof described herein.

In another aspect, the present disclosure provides bispecific antibody molecules comprising an anti-SARS-CoV-2 antibody or antigen-binding fragment thereof as disclosed herein.

In certain embodiments, the bispecific or bivalent antibodies provided herein comprises a first antigen-binding domain and a second antigen-binding domain, wherein the first antigen-binding domains is derived from a monoclonal antibody selected from the group consisting of P2A-1A8, P2A-1A9, P2B-2G11, P2A-1A10, P2A-1B3, P2B-2F6, P2B-2G4, P2C-1A3, P2C- 1C8, P2C-1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, and P22A-1D1. The second antigen-binding domain can be derived from any suitable antibody.

In certain embodiments, the bispecific antibodies provided herein comprises a first antigen-binding domain and a second antigen-binding domain, wherein the first and the second antigen-binding domains are derived from any two monoclonal antibodies selected from the group consisting of P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A- 3C12, and P22A-1D1. In certain embodiments, the first and the second antigen-binding domains are derived from P2C-1F11 and P2B-2F6, respectively. In certain embodiments, the first and the second antigen-binding domains are derived from P2C-1F11 and P2B-1G5, respectively.

In certain embodiments, the bispecific antibody molecules have at least two distinct antigen-binding sites with different specificities.

In certain embodiments, the bispecific antibody molecules provided herein are capable of binding to different epitopes on the spike protein of SARS-CoV-2 virus. In some embodiments, the two or more antibodies bind to different epitopes in RBD of spike protein of SARS-CoV-2.

In certain embodiments, the bispecific antibody molecules provided herein has a first antigen-binding domains specificity directed to the RBD of the spike protein of SARS-CoV-2 virus and a second antigen-binding domains specificity directed to a second antigen.

In another aspect, the present disclosure provides an isolated polynucleotide encoding the antibody or antigen binding fragment thereof as described herein.

In some embodiments, the isolated polynucleotide of the present disclosure comprises a nucleotide sequence selected from a group consisting of: SEQ ID NOs: 9-10, 19-20, 29-30, 39-40, 49-50, 59-60, 63-64, 73-74, 83-84, 93-94, 103-104, 113-114, 144-145, 154-155, 164-165, 174-175, 184-185, 194-195, 204-205, 214-215, 224-225, 234-235, 244-245, 254-255, 264-265, 274-275, 284-285, 294-295, 304-305, 314-315, 324-325, 334-335, 344-345, 354-355, 364-365, 374-375, 384-385, 394-395, 404-405, 414-415, 424-425, and 434-435, or a homologous sequence thereof having at least 80% sequence identity.

In some embodiments, the homologue sequence encodes the same protein as encoded by any nucleotide sequence selected from the group consisting of SEQ ID NOs: 9-10, 19-20, 29-30, 39-40, 49-50, 59-60, 63-64, 73-74, 83-84, 93-94, 103-104, 113-114, 144-145, 154-155, 164-165, 174-175, 184-185, 194-195, 204-205, 214-215, 224-225, 234-235, 244-245, 254-255, 264-265, 274-275, 284-285, 294-295, 304-305, 314-315, 324-325, 334-335, 344-345, 354-355, 364-365, 374-375, 384-385, 394-395, 404-405, 414-415, 424-425, and 434-435.

In one aspect, the present disclosure provides a vector comprising the isolated polynucleotide of the present disclosure. In some embodiments, said vector is an expression vector.

In one aspect, the present disclosure provides a host cell comprising the vector of the present disclosure.

In one aspect, the present disclosure provides a method of producing the antibody or antigen binding fragment of the present disclosure. In some embodiments, the method comprises culturing the host cell of the present disclosure under the condition at which the expression vector of the present disclosure is expressed. In some embodiments, the method of the present disclosure further comprises purifying the antibody produced by the host cell.

In some embodiments, the pharmaceutical composition disclosed herein can comprise a combination of two or more antibodies or antigen binding fragments of the present disclosure. In some embodiments, the pharmaceutical composition comprises a combination of two or more monoclonal antibodies, each of which comprises heavy chain CDR sequences and light chain CDR sequences derived from an antibody selected from the group consisting of P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C-1F11, P2B-1G5, P2B-1A1, P2C-1D7, P2B-1A10, P2B-1D9, P2B- 1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A- 2D11, P5A-2G9, P5A-2H3, P5A-3A1, P5A-3A6, P5A-3B4, P5A-3C12, and P22A-1D1.

In certain embodiments, the pharmaceutical composition comprises a first antibody comprising heavy chain CDR sequences and light chain CDR sequences derived from P2C-1F11, and a second antibody comprising heavy chain CDR sequences and light chain CDR sequences derived from antibody P2B-2F6. In certain embodiments, the pharmaceutical composition comprises a first antibody comprising heavy chain CDR sequences and light chain CDR sequences derived from P2C-1F11, and a second antibody comprising heavy chain CDR sequences and light chain CDR sequences derived from antibody P2B-1G5.

In some embodiments, the two or more antibodies or antigen binding fragments bind to different epitopes in RBD of spike protein of SARS-CoV-2. In some embodiments, the two or more antibodies comprise a first antibody which comprises P2C-1F11 or an antigen binding fragment thereof, and a second antibody which is selected from the group consisting of P2C-1A3, P2C-1C10, P2B-2F6, P2B-1G5, and P2A-1B3, or an antigen binding fragment thereof. In some embodiments, the two or more antibodies comprise a first antibody which comprises P2C-1A3 or an antigen binding fragment thereof, and a second antibody which is selected from the group consisting of P5A-3C8, P5A-1D2, P22A-1D1, P2C-1F11, and P2A-1B3, or an antigen binding fragment thereof. In some embodiments, the two or more antibodies comprise a first antibody which comprises P2B-2F6 or an antigen binding fragment thereof, and a second antibody selected from the group consisting of P5A-3C8, P5A-1D2, P22A-1D1, P2C-1C10, P2C-1F11, P2B-1G5, and P2A-1B3, or an antigen binding fragment thereof. In some embodiments, the two or more antibodies comprise a first antibody which comprises P2A-1B3 or an antigen binding fragment thereof, and a second antibody selected from the group consisting of P5A-3C8, P5A-1D2, P22A-1D1, P2C-1A3, P2C-1C10, P2C-1F11, P2B-2F6, and P2A-1A10, or an antigen binding fragment thereof. In some embodiments, the two or more antibodies comprise a first antibody which comprises P2C-1C10 or an antigen binding fragment thereof, and a second antibody selected from the group consisting of P5A-3C8, P5A-1D2, P22A-1D1, P2C-1A3, P2C-1F11, and P2A-1B3, or an antigen binding fragment thereof.

In some embodiments, the pharmaceutical compositions comprise the polynucleotides encoding the anti-SARS-CoV-2 antibodies or the antigen-binding fragments thereof, and one or more pharmaceutically acceptable carriers. The present disclosure further provides pharmaceutical compositions comprising the polynucleotides encoding the combination of the two or more anti-SARS-CoV-2 antibodies or the antigen-binding fragments thereof, and one or more pharmaceutically acceptable carriers. In certain embodiments, the polynucleotides comprise an expression vector. In certain embodiments, the expression vector comprises a viral vector or a non-viral vector. In certain embodiments, the expression vector is suitable for gene therapy in human. In certain embodiments, the expression vector comprises a DNA vector or a RNA vector.

In some embodiments, the pharmaceutical composition further comprises a second bioactive agent, such as a second therapeutic agent or a second prophylactic agent.

In one aspect, the present disclosure provides a kit for detecting a SARS-CoV-2 antigen, comprising the antibody or antigen binding fragment of the present disclosure. In some embodiments, the kit of further comprises a control reagent comprising RBD of spike protein of the SARS-CoV-2. In some embodiments, the kit further comprises a set of reagents for detecting complex of the antibody or the antigen-binding fragment bound to the SARS-CoV-2 antigen.

In one aspect, the present disclosure provides a method of treating SARS-CoV-2 infection in a subject. The present disclosure also provides methods of treating a disease, disorder or condition associated with SARs-CoV-2 infection in a subject. In some embodiments, the method comprises administering a therapeutically effective amount of one or more of the antibody, the antigen binding fragment, or one or more polynucleotides encoding one or more of the antibody or antigen-binding fragment thereof provided herein, or the pharmaceutical composition of the present disclosure to the subject.

In one aspect, the present disclosure provides a method of preventing SARS-CoV-2 infection in a subject. The present disclosure also provides methods of preventing a disease, disorder or condition associated with SARs-CoV-2 infection in a subject. In some embodiments, the method comprises administering a prophylactically effective amount of one or more of the antibody or antigen binding fragment, or the pharmaceutical composition of the present disclosure to the subject.

In some embodiments, the administration is via oral, nasal, intravenous, subcutaneous, or intramuscular administration. In some embodiments, the subject is human. In some embodiments, the polynucleotide provided herein can be administered to a subject by, for example, transfection techniques such as electroporation, or hydrodynamic injection. In some embodiments, the polynucleotides comprise viral vectors such as AAV, and can be administered via local injection (e.g. intramuscular, intranasal, intradermal, subcutaneous, etc.) or systematic administration (e.g. intravenous administration).

In some embodiments, the method further comprises administering a therapeutically effective amount of a second bioactive agent which can be a therapeutic agent or a prophylactic agent. In some embodiments, the second therapeutic agent is an anti-viral agent. In some embodiments, an anti-viral agent comprises an antiviral peptide, an anti-viral antibody, an anti-viral compound, an anti-viral cytokine, or an anti-viral oligonucleotide. In some embodiments, the second therapeutic agent is an RNA dependent RNA polymerase inhibitor, a non-nucleoside reverse transcriptase inhibitor (NNRTI), nucleoside reverse transcriptase inhibitor (NRTI), purine nucleoside, antiviral interferon, adamantine antiviral compound, or any other suitable antiviral agent. In some embodiments, the second therapeutic agent is remdesivir, chloroquine, hydroxychloroquine, lopinavir, ritonavir, APN01, favilavir, mesalazine, toremifene, eplerenone, paroxetine, sirolimus, dactinomycin, irbesartan, emodin, mercaptopurine, melatonin, quinacrine, carvedilol, colchicine, camphor, equilin, oxymetholone, nafamosta, camostat, baricitinib, darunavir, ribavirin, galidesivir, BCX-4430, Arbidol, nitazoxanide, derivatives thereof, or any combination thereof.

In one aspect, the present disclosure provides a method of detecting presence or amount of SARS-CoV-2 virus antigen in a sample. In some embodiments, the method comprises contacting the sample with one or more of the antibody or antigen binding fragment of the present disclosure, and determining the presence or the amount of the SARS-CoV-2 virus antigen in the sample.

In one aspect, the present disclosure provides use of one or more of the antibody or antigen binding fragment of the present disclosure in the manufacture of a medicament for treating or preventing SARS-CoV-2 infection or a disease, disorder or condition associated with SARs-CoV-2 infection. In one aspect, the present disclosure provides use of one or more of the antibody or antigen binding fragment of the present disclosure in the manufacture of a medicament for preventing, managing, treating and/or ameliorating in a subject a disease or a disorder caused by or associated with coronavirus (e.g. SARs-COV-2) infection and/or a symptom or respiratory condition relating thereto.

In one aspect, the present disclosure provides use of one or more of the antibody or antigen binding fragment of the present disclosure in the manufacture of a diagnostic reagent for detecting SARS-CoV-2 infection.

In one aspect, the present disclosure provides a kit for detecting an antibody capable of specifically binding to receptor-binding domain (RBD) of the spike protein of SARS-CoV-2, comprising a polypeptide comprising an amino acid sequence comprising SEQ ID NO: 128. In some embodiments, the polypeptide is immobilized on a substrate. In some embodiments, the kit further comprises a set of reagents for detecting complex of the antibody bound to the polypeptide.

In one aspect, the present disclosure provides a method of detecting presence or amount of an antibody capable of specifically binding to RBD of the spike protein of SARS-CoV-2 in a sample, comprising contacting the sample with a polypeptide comprising an amino acid sequence comprising SEQ ID NO: 128, and determining the presence or the level of the antibody in the sample. In some embodiments, the absence of the antibody in the sample or the level of the antibody in the sample being below a threshold indicates that the subject is more likely to suffer from disease progression.

In another aspect, the present disclosure provides a method of determining the likelihood of disease progression in a subject infected with SARS-CoV-2, the method comprising: contacting a sample obtained from the subject with a polypeptide comprising an amino acid sequence comprising SEQ ID NO: 128, and detecting the presence or the level of an antibody in the sample wherein the antibody is capable of specifically binding to RBD of the spike protein of the SARS-CoV-2, wherein the subject is likely to experience disease progression when the antibody in the sample is absent or is below a threshold.

In yet another aspect, the present disclosure provides a method of monitoring treatment response in a subject infected with SARS-CoV-2 and received a treatment, the method comprising: (i) contacting a sample from the subject with a peptide comprising an amino acid sequence of SEQ ID NO: 128; (ii) detecting a first level of an antibody in the sample wherein the antibody is capable of specifically binding to RBD of the spike protein of the SARS-CoV-2; and (iii) comparing the first level of the antibody with a second level of the antibody detected in the subject prior to the treatment; wherein the first level being higher than the second level indicates that the subject is responsive to the treatment.

In yet another aspect, the present disclosure provides a method of neutralizing SARS-CoV-2 in a subject or in a sample in vitro, comprising administering a therapeutically effective amount of one or more of the antibody or antigen binding fragment thereof provided herein, or the pharmaceutical composition provided herein to the subject or to the sample.

In yet another aspect, the present disclosure provides a crystal of RBD of the spike protein of SARS-CoV-2 in complex with an antibody. In some embodiments, the antibody in complex with the RBD comprises a heavy chain variable region of SEQ ID NO: 47 and a light chain variable region of SEQ ID NO: 48. In some embodiments, the antibody in complex with the RBD comprises a heavy chain variable region of SEQ ID NO: 111 and a light chain variable region of SEQ ID NO: 112.

In some embodiment, the crystal has or consists of a $P2_12_12_1$ space group with unit cell dimensions of a=70.23 Å, b=90.15 Å, and c=112.35 Å.

In some embodiment, the crystal has or consists of a C121 space group with unit cell dimensions of a=194.88 Å, b=85.39 Å, and c=58.51 Å.

In some embodiment, the crystal has or consists of a C2 space group with unit cell dimensions of a=193.34 Å, b=86.60 Å, and c=57.16 Å.

In some embodiment, the crystal has or consists of a C2 space group with unit cell dimensions of a=158.75 Å, b=67.51 Å, and c=154.37 Å.

In some embodiment, the crystal has or consists of a $P2_12_12_1$ space group with unit cell dimensions of a=112.54 Å, b=171.57 Å, and c=54.87 Å.

BRIEF DESCRIPTION OF FIGURES

The following drawings form part of the present specification and are included to further demonstrate certain aspects of the present disclosure. The disclosure may be better understood by reference to one or more of these drawings in combination with the detailed description of specific embodiments presented herein.

FIG. 1A-FIG. 1F. Analyses of plasma and B cell responses specific to SARS-CoV-2. Serial dilutions of plasma samples were analyzed for binding to the (A) RBDs or (B) trimeric Spikes of SARS-CoV-2, SARS-CoV and MERS-CoV by ELISA and (C) for neutralizing activity against pseudoviruses bearing envelope glycoprotein of SARS-CoV-2, SARS-CoV and MERS-CoV. Binding to SARS-CoV-2 NP protein was also evaluated (A). All results were derived from at least two independent experiments. (D) Gating strategy for analysis and isolation of RBD-specific memory B cells and (E and F) their representation among the total and memory subpopulation of B cells in the eight study subjects. Samples were named as either A, B, or C depending on collection sequence. FSC-W, forward scatter width; FSC-A, forward scatter area; and SSC-A side scatter area.

FIG. 6A-FIG. 6C. Analysis of plasma binding to cell surface expressed trimeric Spike protein. (A) and (B) HEK 293T cells transfected with expression plasmid encoding the full length spike of SARS-CoV-2, SARS-CoV or MERS-CoV were incubated with 1:100 dilutions of convalescent plasma from the study subjects. The cells were then stained with PE labeled anti-human IgG Fc secondary antibody and analyzed by FACS. Positive control antibodies include S230 and m396 targeting the RBD of SARS-CoV Spike, and Mab-GD33 targeting the RBD of MERS-CoV Spike.

Figure 1E:
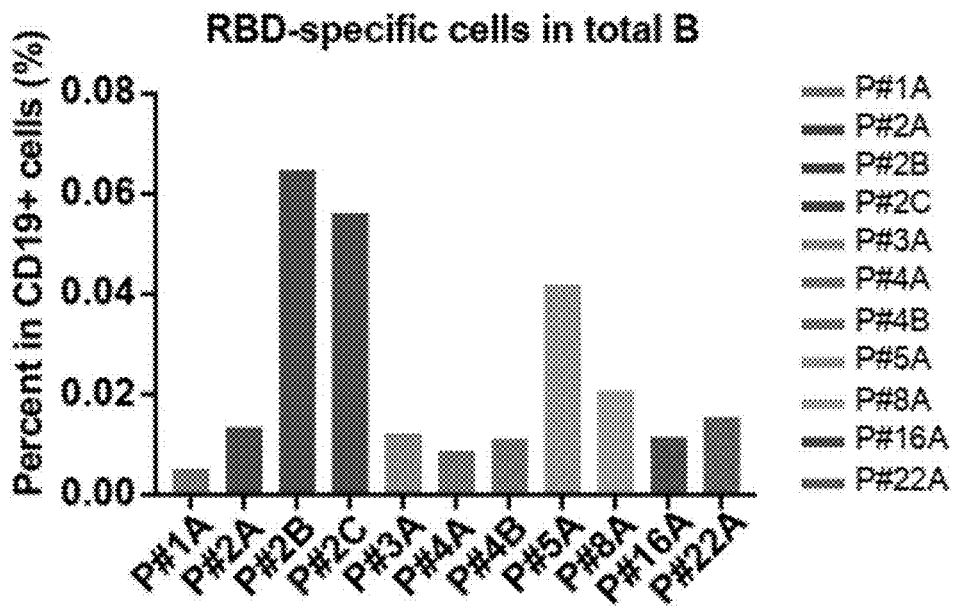

VRC01 is negative control antibody targeting HIV-1 envelope glycoprotein. (C) Impact of epitope mutations on binding of antibodies P22A-1D1, P5A-1D2, P5A-3C8, P2C-1F11 and P2B-2F6. Cell surface expressed wild type or mutant spike glycoprotein of SARS-Cov-2 were incubated with the ACE2, the tested antibodies, and control antibodies S2 mAb, followed by staining with anti-human IgG Fc PE (for identified human antibodies), anti-mouse IgG FITC (for S2 mAb) or anti-his PE (for ACE2) secondary antibody and analyzed by FACS. P2B-2F6 recognizes a distinct epitope on SARS-CoV-2 RBD from those public antibodies and used here as positive control for the S1 protein of the spike. S2 is a mouse monoclonal specific for S2 protein of the spike. The cell percentage in the gate are shown. Mutants that resulted in more than 80% reduction in binding are highlighted in either grey boxes for public antibodies or in orange boxes for ACE2. The percent reduction was determined by the MFI weighted by multiplying the number of positive cells in the selected gates and normalized in relative to that of wild type and S2 control. Data shown were from at least two independent experiments.

FIG. 7A-FIG. 7K. RBD-specific memory B cells analyzed and isolated through FACS (A)-(K). The recombinant RBD was labeled with either a Strep or His tag and used alone or in combination to identify and isolate RBD-specific single B cells through staining with the Streptavidin-APC and/or Streptavidin-PE, or anti-His-APC and anti-His-PE antibodies. B cells to be isolated are highlighted in boxes or ovals. Samples were named as either A, B, or C depending on collection sequence. FSC-W, forward scatter width; FSC-A, forward scatter area; and SSC-A side scatter area.

FIG. 8. ELISA screening of SARS-CoV-2 RBD-specific antibodies in the supernatant of transfected cells. The study subjects and the date of sampling are indicated on the top. Samples were named as either A, B, or C depending on collection sequence. Antibodies tested for each sample are aligned in one vertical column whenever possible. For each evaluated antibody, at least two independent measurements were performed and are presented adjacently on the same row. Binding activities were assessed by OD 450 and indicated by the color scheme on the right. Negatives (no binding activity) are shown in gray for OD 450 values less than 0.1.

FIG. 9A-FIG. 9G. Binding kinetics of isolated mAbs with SARS-CoV-2 RBD measured by SPR and ELISA respectively. (A, B) For SPR, the purified soluble SARS-CoV-2 RBD, SARS-CoV RBD and MERS-CoV2 RBD were covalently immobilized onto a CM5 sensor chip followed by injection of individual antibody at five different concentrations. The black lines indicate the experimentally derived curves while the grey lines represent fitted curves based on the SPR experimental data. For ELISA analysis, recombinant SARS-CoV RBD and MERS-CoV2 RBD were coated on the ELISA plate, and a serial dilution of each antibody was evaluated against SARS-CoV RBD and MERS-CoV2 RBD coated plates respectively and their binding activity was recorded at an optical density (OD) of 450 nm and 630 nm. (C-F) For ELISA analysis, 5230 was used as a positive control antibody against SARS-COV, MAB-GD33 was used as a positive control antibody against MERS-COV, and VRC01 was used as negative control antibody. (G) Binding kinetics of isolated mAbs with SARS-CoV-2 RBD were measured by SPR.

FIG. 10A-FIG. 10C. Antibody and ACE2 competition for binding to SARS-CoV-2 RBD measured by SPR for patient #2 (A), patient #1 (B), and patient #5, #22 and #2 (C). The sensorgrams show distinct binding patterns of ACE2 to SARS-CoV-2 RBD with (corresponding to curves for "antibody+ACE2") or without (corresponding to curves for "ACE2") prior incubation with each testing antibody. The competition capacity of each antibody is indicated by the level of reduction in response unit of ACE2 comparing with or without prior antibody incubation.

FIG. 11A-FIG. 11B. Analysis of antibody binding to cell surface expressed trimeric Spike protein. HEK 293T cells transfected with expression plasmid encoding the full length spike of SARS-CoV-2, SARS-CoV or MERS-CoV were incubated with 20 ug/ml testing antibodies (A) and (B). The cells were then stained with PE labeled anti-human IgG Fc secondary antibody and analyzed by FACS. Positive control antibodies include 5230 and m396 targeting the RBD of SARS-CoV Spike, and Mab-GD33 targeting the RBD of MERS-CoV Spike. VRC01 is the negative control antibody targeting HIV-1 envelope glycoprotein.

FIG. 12A-FIG. 12D. Neutralization activity of mAbs against live SARS-CoV-2 analyzed by focus reduction neutralization test (FRNT). Serial dilution of each antibody was tested against live SARS-CoV-2 infection. Their neutralizing activities are represented by the reduction in the number of SARS-CoV-2 foci calculated by an EliSpot reader (Cellular Technology Ltd) (A)-(D).

FIG. 13. Epitope mapping through competitive binding measured by SPR. The sensorgrams show distinct binding patterns when pairs of testing antibodies were sequentially applied to the purified SARS-CoV-2 RBD covalently immobilized onto a CM5 sensor chip. The level of reduction in response unit comparing with or without prior antibody incubation is the key criteria for determining the two mAbs recognize the separate or closely situated epitopes.

FIG. 14. Multiple sequence alignment of the CDR1-CDR3 regions of the heavy chain sequences from the public clonetypes. Included are antibodies P22A-1D1 (SEQ ID NO: 432), P5A-1D2 (SEQ ID NO: 242), P5A-3C8 (SEQ ID NO: 232) and P2C-1F11 (SEQ ID NO: 111) along with IGVH3-53 (SEQ ID NO: 436) and/IGVH3-66 (SEQ ID NO: 437), a top germline allele assignment for public antibodies shown. Grey letters show mutations from germline.

FIG. 15A-FIG. 15B. Antibody individual PK profiles of single administration fit the population PK prediction model and the measurement data for mAb1 (A) and mAb2 (B). Solid lines: predicted medians. Dashed lines and the dots: measured concentrations in the subjects. The shaded areas represent the 5th-95th percentiles.

Figure 16:
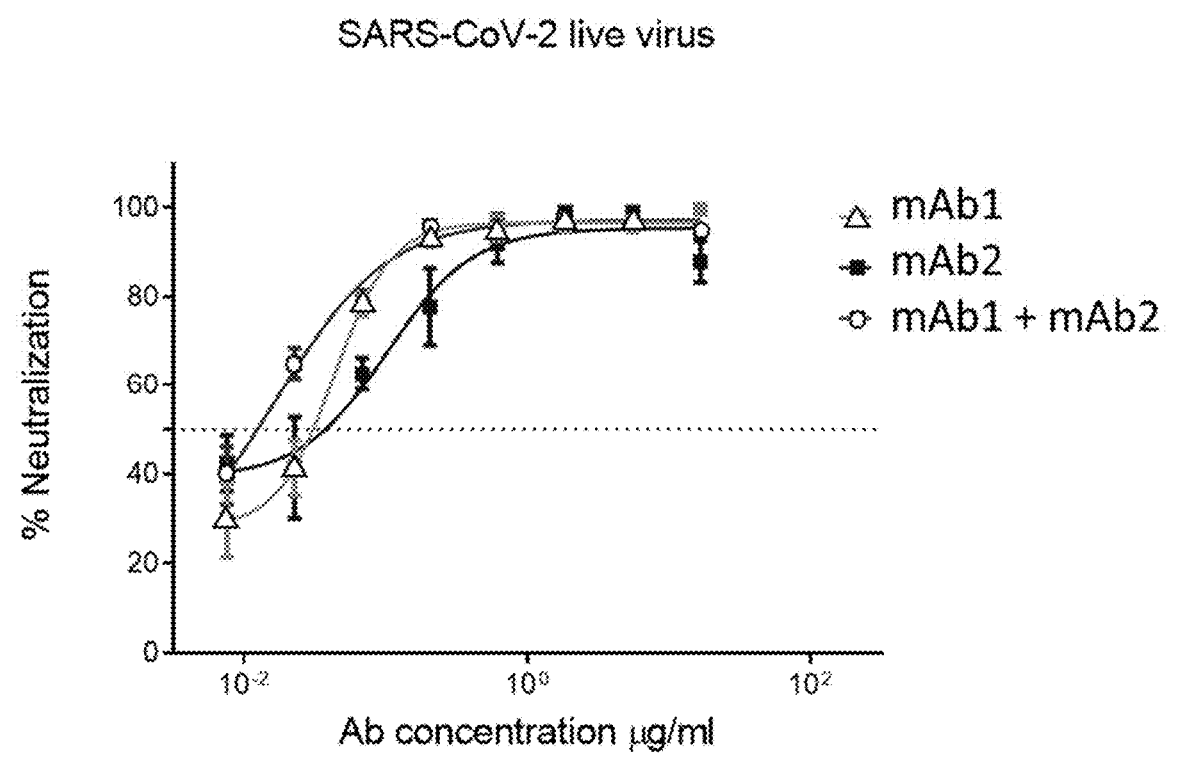

FIG. 16. In vitro Neutralization Activity of mAb1 and mAb2 Combination in SARS-CoV-2 Live Virus Micro-Neutralization Assay.

FIG. 17A-FIG. 17B. Mean serum concentration profiles of in cynomolgus monkeys following single IV infusion administration of at 10 mg/kg for mAb1 (A) and mAb2 (B).

DETAILED DESCRIPTION

Throughout the present disclosure, the articles "a", "an" and "the" are used herein to refer to one or to more than one (i.e., to at least one) of the grammatical object of the article. By way of example, "an antibody" means one antibody or more than one antibody.

The features and advantages of the disclosed compositions and methods will be more readily understood, by those of ordinary skill in the art, from reading the following detailed description. It is to be appreciated that certain features of the disclosed compositions and methods, which are, for clarity, described above and below in the context of separate embodiments, may also be provided in combination in a single embodiment. Conversely, various features of the disclosed compositions and methods that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

Definitions

Antibody Related Terms

The term "antibody" as used herein includes any immunoglobulin, monoclonal antibody, polyclonal antibody, monovalent antibody, bivalent antibody, multivalent antibody, bispecific antibody, multi-specific antibody that binds to a specific antigen. A native intact antibody comprises two heavy (H) chains and two light (L) chains. Mammalian heavy chains are classified as alpha, delta, epsilon, gamma, and mu, each heavy chain consists of a variable region (VH) and a first, second, third, and optionally fourth constant region (CH1, CH2, CH3, CH4 respectively); mammalian light chains are classified as λ or κ, while each light chain consists of a variable region (VL) and a constant region. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., *J. Mol. Biol.*, 273(4), 927 (1997); Chothia, C. et al., *J. Mol Biol.* December 5; 186(3):651-63 (1985); Chothia, C. and Lesk, A. M., *J. Mol. Biol.*, 196, 901 (1987); Chothia, C. et al., *Nature*. December 21-28; 342(6252):877-83 (1989); Kabat E. A. et al., Sequences of Proteins of immunological Interest, 5th Ed. Public Health Service, National Institutes of Health, Bethesda, Md. (1991); Marie-Paule Lefranc et al., *Developmental and Comparative Immunology,* 27: 55-77 (2003); Marie-Paule Lefranc et al., *Immunome Research,* 1(3), (2005); Marie-Paule Lefranc, Molecular Biology of B cells (second edition), chapter 26, 481-514, (2015)). The three CDRs are interposed between flanking stretches known as framework regions (FRs) (light chain FRs including LFR1, LFR2, LFR3, and LFR4, heavy chain FRs including HFR1, HFR2, HFR3, and HFR4), which are more highly conserved than the CDRs and form a scaffold to support the highly variable loops. The constant regions of the heavy and light chains are not involved in antigen-binding, but exhibit various effector functions. Antibodies are assigned to classes based on the amino acid sequences of the constant regions of their heavy chains. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain).

The term "antigen-binding fragment" as used herein refers to an antibody fragment formed from a portion of an antibody comprising one or more CDRs, or any other antibody fragment that binds to an antigen but does not comprise an intact native antibody structure. Examples of antigen-binding fragment include, without limitation, a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a bispecific scFv dimer, a single-chain Fv-Fc antibody (scFv-Fc), a camelized single domain antibody, a nanobody, a domain antibody, and a bivalent domain antibody. An antigen-binding fragment is capable of binding to the same antigen to which the parent antibody binds.

As used herein, a "bispecific" antibody refers to an artificial antibody which has fragments derived from two different monoclonal antibodies. A bispecific antibody may bind to overlapping epitopes or to two different epitopes. The two epitopes may present on the same antigen, or they may present on two different antigens. As such, the terms "multi-specific" antibody refers to an artificial antibody which has fragments derived from multiple different monoclonal antibodies, and may be capable of binding to more than one epitope.

The term "chimeric" as used herein, means an antibody or antigen-binding fragment, having a portion of heavy and/or light chain derived from one species, and the rest of the heavy and/or light chain derived from a different species.

The term "epitope" as used herein refers to the specific group of atoms or amino acids on an antigen to which an antibody binds. Two antibodies may bind the same or a closely related epitope within an antigen if they exhibit competitive binding for the antigen. An epitope can be linear or conformational (i.e. including amino acid residues spaced apart). For example, if an antibody or antigen-binding fragment blocks binding of a reference antibody to the antigen by at least 50%, at least 55%, at least 60%, at least 65%, at least 70%, at least 75%, at least 80%, at least 85%, or at least 90%, or at least 95%, then the antibody or antigen-binding fragment may be considered to bind the same/closely related epitope as the reference antibody. The capacity to block, or compete with, the binding of the antibody or the antigen-binding fragment of the present disclosure to SARS-CoV-2 typically indicates that an antibody or the antigen-binding fragment to be screened binds to an epitope or binding site on SARS-CoV-2 that structurally overlaps with the binding site on SARS-CoV-2 that is immunospecifically recognized by the antibody or the antigen-binding fragment of the present disclosure. Alternatively, this can indicate that an antibody or an antigen-binding fragment of the present disclosure to be screened binds to an epitope or binding site that is sufficiently proximal to the binding site immunospecifically recognized by the antibody or the antigen-binding fragment of the present disclosure to sterically or otherwise inhibit binding of the antibodies or the antigen-binding fragment of the present disclosure to SARS-CoV-2.

"Fab" with regard to an antibody refers to that portion of the antibody consisting of a single light chain (both variable and constant regions) bound to the variable region and first constant region of a single heavy chain by a disulfide bond. The heavy chain fragment of the Fab is known as "Fd".

"Fab'" refers to a Fab fragment that includes a portion of the hinge region.

"$F(ab')_2$" refers to a dimer of Fab'.

"Fc" with regard to an antibody (e.g. of IgG, IgA, or IgD isotype) refers to that portion of the antibody consisting of the second and third constant domains of a first heavy chain bound to the second and third constant domains of a second heavy chain via disulfide bonding. Fc with regard to antibody of IgM and IgE isotype further comprises a fourth constant domain. The Fc portion of the antibody is responsible for various effector functions such as antibody-dependent cell-mediated cytotoxicity (ADCC), Antibody-dependent cellular phagocytosis (ADCP) and complement dependent cytotoxicity (CDC), but does not function in antigen binding.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Huston J S et al. *Proc Natl Acad Sci USA,* 85:5879(1988)).

"ScFab" refers to a fusion polypeptide with a Fd linked to a light chain via a polypeptide linker, resulting in the formation of a single chain Fab fragment (scFab).

"Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann L. and Muyldermans S., *J. Immunol Methods. December* 10; 231(1-2): 25-38 (1999); Muyldermans S., *J Biotechnol. June;* 74(4): 277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., *Nature*. June 3; 363(6428):446-8 (1993); Nguyen V K. et al. *Immunogenetics*. April; 54(1):39-47 (2002); Nguyen V K. et al. *Immunology*. May; 109(1):93-101 (2003)). The variable domain of a heavy chain antibody (VHH domain) represents the smallest known antigen-binding unit generated by adaptive immune responses (Koch-Nolte F. et al., *FASEB J. November;* 21(13):3490-8. Epub 2007 Jun. 15 (2007)).

A "nanobody" refers to an antibody fragment that consists of a VHH domain from a heavy chain antibody and two constant domains, CH2 and CH3.

A "domain antibody" refers to an antibody fragment containing only the variable region of a heavy chain or the variable region of a light chain. In certain instances, two or more VH domains are covalently joined with a peptide linker to create a bivalent or multivalent domain antibody. The two VH domains of a bivalent domain antibody may target the same or different antigens.

The term "valent" as used herein refers to the presence of a specified number of antigen binding sites in a given molecule. The term "monovalent" refers to an antibody or an antigen-binding fragment having only one single antigen-binding site; and the term "multivalent" refers to an antibody or an antigen-binding fragment having multiple antigen-binding sites. As such, the terms "bivalent", "tetravalent", and "hexavalent" denote the presence of two binding sites, four binding sites, and six binding sites, respectively, in an antigen-binding molecule. In some embodiments, the antibody or antigen-binding fragment thereof is bivalent.

"TriFabs" refers to a trivalent, bispecific fusion protein composed of three units with Fab-functionalities. TriFabs harbor two regular Fabs fused to an asymmetric Fab-like moiety.

"Fab-Fab" refers to a fusion protein formed by fusing the Fd chain of a first Fab arm to the N-terminus of the Fd chain of a second Fab arm.

"Fab-Fv" refers to a fusion protein formed by fusing a heavy chain variable domain to the C-terminus of an Fd chain and a light chain variable domain to the C-terminus of a light chain. A "Fab-dsFv" molecule can be formed by introducing an interdomain disulphide bond between the heavy chain variable domain and the heavy chain variable domain.

An "scFv dimer" is a bivalent diabody or bispecific scFv (BsFv) comprising $V_H$-$V_L$ (linked by a peptide linker) dimerized with another VH-VL moiety such that $V_H$'s of one moiety coordinate with the $V_L$'s of the other moiety and form two binding sites which can target the same antigens (or epitopes) or different antigens (or epitopes).

A bispecific "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

A "dsFv" refers to a disulfide-stabilized Fv fragment that the linkage between the variable region of a single light chain and the variable region of a single heavy chain is a disulfide bond. In some embodiments, a "$(dsFv)_2$" or "(dsFv-dsFv')" comprises three peptide chains: two VH moieties linked by a peptide linker (e.g. a long flexible linker) and bound to two VL moieties, respectively, via disulfide bridges. In some embodiments, dsFv-dsFv' is bispecific in which each disulfide paired heavy and light chain has a different antigen specificity.

"Bibody" refers to a fusion protein formed by fusing a scFv to the C-terminus of either the light chain (Fab-L-scFv) or Fd (Fab-H-scFv).

"Tribody" refers to a fusion protein formed by fusing a scFv to both light chain and heavy chain (Fab-$(scFv)_2$).

"MAb-Fv" or "IgG-Fv" refers to a fusion protein formed by fusion of heavy chain variable domain (VH domain) to the C-terminus of one Fc chain and the VL domain either expressed separately or fused to the C-terminus of the other resulted in a bispecific, trivalent IgG-Fv (mAb-Fv) fusion protein, with the Fv stabilized by an interdomain disulphide bond.

"ScFab-Fc-scFv$_2$" and "ScFab-Fc-scFv" refer to a fusion protein formed by fusion of a single-chain Fab with Fc and disulphide-stabilized Fv domains.

"Appended IgG" refers to a fusion protein with a Fab arm fused to an IgG to form the format of bispecific (Fab)$_2$-Fc. It can form an "IgG-Fab" or a "Fab-IgG", with a Fab fused to the C-terminus or N-terminus of an IgG molecule with or without a connector. In certain embodiments, the appended IgG can be further modified to a format of IgG-Fab$_4$ (see, Brinkman et al., mAbs, 9(2), pp. 182-212 (2017)).

"DVD-Ig" refers to a dual-variable-domain antibody that is formed by fusion of an additional VH domain and VL domain of a second specificity to an IgG heavy chain and light chain. "CODV-Ig" refers to a related format where the two VH domain and two VL domains are linked in a way that allows crossover pairing of the variable VH domain-VL domain, which are arranged either (from N- to C-terminus) in the order VH domain A-VH domain B and VL domain B-VL domain A, or in the order VH domain B-VH domain A and VL domain A-VL domain B.

A "CrossMab" refers to a technology of pairing of unmodified light chain with the corresponding unmodified heavy chain and pairing of the modified light chain with the corresponding modified heavy chain, thus resulting an antibody with reduced mispairing in the light chain.

A "WuxiBody" refers to is a bispecific antibody comprising a chimeric protein with variable domains of an antibody and the constant domains of TCR, wherein the subunits (such as alpha and beta domains) of TCR constant domains are associated by engineered disulfide bond (see, more details in WO2019057122A1).

A "BITE" is a bispecific T-cell engager molecule, comprising a first scFv with a first antigen specificity in the VL domain-VH domain orientation linked to a second scFv with a second specificity in the VH domain-VL domain orientation.

A "diabody" or "dAb" includes small antibody fragments with two antigen-binding sites, wherein the fragments comprise a VH domain connected to a VL domain in the same polypeptide chain ($V_H$-$V_L$ or $V_L$-$V_H$) (see, e.g. Holliger P. et al., Proc Natl Acad Sci USA. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same or different antigens (or epitopes).

A "DART" is a diabody-like entity that has the VH of a first variable region linked to the VL of a second variable region, and the VH of the second variable region linked to the VL of the first variable region.

A "TandAb" is a bispecific fusion protein with four binding sites, two of which bind to a first antigen and the other two bind to a second antigen.

A "bispecific ds diabody" is a diabody target two different antigens (or epitopes).

The term "fully human" when used with reference to an antibody, refers to an antibody that are either directly derived from a human or based upon a human sequence. When an antibody is derived from or based on a human sequence and subsequently modified, it is still to be considered fully human as used throughout the specification. In other words, the term "fully human" when used with reference to an antibody, is intended to include binding molecules having variable and constant regions derived from human germline immunoglobulin sequences or based on variable or constant regions occurring in a human or human lymphocyte and modified in some form. Thus, the fully human antibody may include amino acid residues not encoded by human germline immunoglobulin sequences, comprise substitutions and/or deletions (e.g., mutations introduced by, for instance, random or site-specific mutagenesis in vitro or by somatic mutation in vivo). "Based on" as used herein refers to the situation that a nucleic acid sequence may be exactly copied from a template, or with minor mutations, such as by error-prone PCR methods, or synthetically made matching the template exactly or with minor modifications. Semi-synthetic molecules based on human sequences are also considered to be human as used herein.

Other Terms

The term "affinity" as used herein refers to the strength of non-covalent interaction between an immunoglobulin molecule (i.e. antibody) or fragment thereof and an antigen.

The term "amino acid" as used herein refers to an organic compound containing amine (—NH$_2$) and carboxyl (—COOH) functional groups, along with a side chain specific to each amino acid. The names of amino acids are also represented as standard single letter or three-letter codes in the present disclosure, which are summarized as follows.

| Name of Amino Acid | Three-letter Code | Single-letter Code |
| --- | --- | --- |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "diagnosis", "diagnose" or "diagnosing" refers to the identification of a pathological state, disease or condition, such as identification of SARS-CoV-2 infection, or refer to identification of a subject with SARS-CoV-2 infection who may benefit from a particular treatment regimen. In some embodiments, diagnosis contains the identification of presence or amount of SARS-CoV-2. In some embodiments, diagnosis refers to the identification of SARS-CoV-2 infection in a subject.

"Effector functions" as used herein refer to biological activities attributable to the binding of Fc region of an antibody to its effectors such as C1 complex and Fc receptor. Exemplary effector functions include: complement dependent cytotoxicity (CDC) mediated by interaction of antibodies and C1q on the C1 complex; antibody-dependent cell-mediated cytotoxicity (ADCC) mediated by binding of Fc region of an antibody to Fc receptor on an effector cell; and phagocytosis. Effector functions can be evaluated using various assays such as Fc receptor binding assay, C1q binding assay, and cell lysis assay.

The term "Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target ceil and subsequently cause lysis of the target cell. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol 9:457-92 (1991).

The term "specific binding" or "specifically binds" in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. Antibodies or fragments thereof that immunospecifically bind to an antigen may be cross-reactive with related antigens, carrying the same epitope. Specific binding can be characterized in binding affinity, for example, represented by $K_d$ value, i.e., the dissociation constant between the antigen and antigen-binding molecule. $K_d$ may be determined by using any conventional method known in the art, including but are not limited to radioimmunoassays (RIA), enzyme-linked immunosorbent assays (ELISA), surface plasmon resonance method, microscale thermophoresis method, HPLC-MS method and flow cytometry (such as FACS) method. A $K_d$ value of $\leq 10^{-6}$ M (e.g. $\leq 5 \times 10^{-7}$ M, $\leq 2 \times 10^{-7}$ M, $\leq 10^{-7}$ M, $\leq 5 \times 10^{-8}$ M, $\leq 2 \times 10^{-8}$ M, $\leq 10^{-8}$ M, $\leq 5 \times 10^{-9}$ M, $\leq 4 \times 10^{-9}$ M, $\leq 3 \times 10^{-9}$ M, $\leq 2 \times 10^{-9}$ M, or $\leq 10^{-9}$ M) can indicate specific binding between an antibody or antigen binding fragments thereof and SARS-CoV-2 (e.g. spike protein of SARS-CoV-2, or receptor binding domain of the spike protein of SARS-CoV-2).

The ability to "compete for binding to RBD" as used herein refers to the ability of a SARS-CoV-2 antibody or antigen-binding fragment thereof to inhibit the binding interaction between RBD of spike protein of SARS-CoV-2 and its binding partner (e.g. a second SARS-CoV-2 antibody, or ACE2 receptor) to any detectable degree. In certain embodiments, an antibody or antigen-binding fragment that compete for binding to SARS-CoV-2 inhibits the binding interaction between RBD of spike protein of SARS-CoV-2 and its binding partner by at least 85%, or at least 90%. In certain embodiments, this inhibition may be greater than 95%, or greater than 99%. In general, competitive inhibition is measured by means of an assay, wherein an antigen composition, i.e., a composition comprising SARS-CoV-2 or fragments thereof, is admixed with reference binding molecules, for example, the antibodies or antigen binding fragments of the present disclosure, or the ACE receptor (e.g. a recombinant binding moiety thereof), and the antibodies or antigen binding fragments to be screened. Usually, the antibodies or antigen binding fragments to be screened are present in excess. Protocols based upon ELISAs and Western blotting are suitable for use in such simple competition studies.

In certain embodiments, an antibody or antigen-binding fragment exhibits at least 30% competition at 1 μM, with 2 μM angiotensin converting enzyme 2 (ACE2) receptor for binding to the RBD of spike protein of SARS-CoV-2 immobilized at a resonance units (RU) of 250, as measured by SPR.

The term "homologous" as used herein refers to nucleic acid sequences (or its complementary strand) or amino acid sequences that have sequence identity of at least 60% (e.g. at least 65%, 70%, 75%, 80%, 85%, 88%, 90%, 91%, 92%, 93%, 94%, 95%, 96%, 97%, 98%, 99%) to another sequences when optimally aligned.

The phrase "host cell" as used herein refers to a cell into which an exogenous polynucleotide and/or a vector can be or has been introduced.

The term "isolated" means one substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated nucleic acid sequence" refers to the sequence of an isolated nucleic acid molecule. In certain embodiments, an "isolated antibody or an antigen-binding fragment thereof" refers to the antibody or antigen-binding fragments thereof having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC). In some embodiment, an isolated antibody or antigen binding fragment is a recombinant protein or antigen binding fragment.

The term "modified antibody", "modified antibodies", or a grammatic variation as used herein refers to an antibody that has been modified, bioengineered, or combined with one or more modification elements so it is not a naturally occurring antibody.

The term "kit" as used herein refers to a packaged combination of reagents in predetermined amounts with instructions for performing a therapeutics, or a diagnostic or detection assay.

The term "neutralizing" as used herein in relation to the antibody or the antigen binding fragment of the present disclosure refers to antibody or the antigen binding fragment that inhibit SARS-CoV-2 virus from infecting a target cell for replication, regardless of the mechanism by which neutralization is achieved. Thus, neutralization can, for example, be achieved by inhibiting the attachment or adhesion of SARS-CoV-2 virus or a pseudo SARS-CoV-2 virus bearing the spike protein to the cell surface, or by inhibition of the fusion of viral and cellular membranes following attachment of the virus to the target cell, and the like. Exemplary assays for determining neutralizing activity are described in the Examples provided herein.

In some embodiments, the neutralizing activity of an antibody can be represented as half-maximal inhibitory concentrations ($IC_{50}$) of the antibody against the binding to ACE2.

The term "nucleic acid" or "polynucleotide" as used herein refers to deoxyribonucleic acids (DNA) or ribonucleic acids (RNA) and polymers thereof in either single- or double-stranded form. Unless otherwise indicated, a particular polynucleotide sequence also implicitly encompasses conservatively modified variants thereof (e.g. degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al., *J. Mol. Biol.*, 215:403-410 (1990); Stephen F. et al., *Nucleic Acids Res.*, 25:3389-3402 (1997)), ClustalW2 (available on the website of European Bioinformatics Institute, see also, Higgins D. G. et al., *Methods in Enzymology*, 266:383-402 (1996); Larkin M. A. et al., Bioinformatics (Oxford, England), 23(21): 2947-8 (2007)), and ALIGN or Megalign (DNASTAR) software. A person skilled in the art may use the default parameters provided by the tool, or may customize the parameters as appropriate for the alignment, such as for example, by selecting a suitable algorithm.

The term "polypeptide" or "protein" means a string of at least two amino acids linked to one another by peptide bonds. Polypeptides and proteins may include moieties in addition to amino acids (e.g., may be glycosylated) and/or may be otherwise processed or modified. Those of ordinary skill in the art will appreciate that a "polypeptide" or "protein" can be a complete polypeptide chain as produced by a cell (with or without a signal sequence), or can be a functional portion thereof. Those of ordinary skill will further appreciate that a polypeptide or protein can sometimes include more than one polypeptide chain, for example linked by one or more disulfide bonds or associated by other means. The term also includes amino acid polymers in which one or more amino acids are chemical analogs of a corresponding naturally-occurring amino acid and polymers.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "recombinant" when used with reference to a polypeptide (e.g., antibody, antigen) or a polynucleotide, refers to a polypeptide or polynucleotide that is produced by a recombinant method. A "recombinant polypeptide" includes any polypeptide expressed from a recombinant polynucleotide. A "recombinant polynucleotide" includes any polynucleotide which has been modified by the introduction of at least one exogenous (i.e., foreign, and typically heterologous) nucleotide or the alteration of at least one native nucleotide component of the polynucleotide, and need not include all of the coding sequence or the regulatory elements naturally associated with the coding sequence. A "recombinant vector" refers to a non-naturally occurring vector, including, e.g., a vector comprising a recombinant polynucleotide sequence.

As used herein, the term "sample" refers to a biological specimen that is obtained or derived from a subject of interest. The sample contains a cellular and/or other molecular entity that is to be characterized and/or identified, for example based on physical, biochemical, chemical and/or physiological characteristics.

The term "subject" includes human and non-human animals. Non-human animals include all vertebrates, e.g., mammals and non-mammals, such as non-human primates, mice, rats, cats, rabbits, sheep, dogs, cows, chickens, amphibians, and reptiles. Except when noted, the terms "patient" or "subject" are used herein interchangeably.

The term "treating" or "treatment" of a disease, disorder or condition as used herein includes alleviating a disease, disorder or condition, slowing the rate of development of a disease, disorder or condition, reducing or ending symptoms associated with a disease, disorder or condition, generating a complete or partial regression of a disease, disorder or condition, curing a disease, disorder or condition, or some combination thereof.

The term "prevent" or "preventing" of a disease, disorder or condition as used herein includes slowing the onset of a disease, disorder or condition, reducing the risk of developing a disease, disorder or condition, preventing or delaying the development of symptoms associated with a disease, disorder or condition, reducing the severity of a subsequent contraction or development of a disease, disorder or condition, ameliorating a related symptom, and inducing immunity to protect against a disease, disorder or condition.

The term "SARS-CoV-2 virus antigen" as used herein refers to a SARS-CoV-2 virus particle or an antigen found in a SARS-CoV-2 virus particle (e.g. a protein or protein fragments of envelop protein or spike protein (includes, extracellular domain of the spike protein, or RBD of the spike protein) and the like). Spike protein is composed of S1 protein (which contains RBD) and S2 protein, which are initially in one protein molecule until cleaved by protease into S1 and S2.

The term "vector" as used herein refers to a vehicle into which a genetic element may be operably inserted so as to bring about the expression of that genetic element, such as to produce the protein, RNA or DNA encoded by the genetic element, or to replicate the genetic element. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g. expression vectors) containing the nucleic acid sequence provided herein encoding the antibody or an antigen-binding fragment thereof, at least one promoter (e.g. SV40, CMV, EF-1α) operably linked to the nucleic acid sequence, and at least one selection marker.

Anti-SARS-CoV-2 Antibodies

The present disclosure in one aspect provides anti-SARS-CoV-2 antibodies and antigen-binding fragments thereof.

In some embodiments, the disclosure is directed to a modified antibody or an antigen-binding fragment thereof comprising at least an antigen-binding domain having an antigen-binding affinity and a covalently linked modified human IgG constant domain, wherein the antigen-binding affinity comprises SARS-CoV-2 binding affinity, the antigen-binding affinity comprises at least 50% less or non-detectable binding affinity to SARS-CoV or MERS-CoV compared to the SARS-CoV-2 binding affinity, and wherein the modified human IgG constant domain comprises a substitution with tyrosine at amino acid residue 252, a substitution with threonine at amino acid residue 254, and a substitution with glutamic acid at amino acid residue 256, numbered according to the EU index as in Kabat, the modified antibody has an increased affinity for FcRn compared to the affinity to FcRn of an antibody having a wild type human IgG constant domain.

The modified human IgG constant domain comprises a substitution with tyrosine at amino acid residue 252, a substitution with threonine at amino acid residue 254, and a substitution with glutamic acid at amino acid residue 256, numbered according to the EU index as in Kabat, can be referred to YTE domain or YTE domain Fc.

In some cases, the antigen-binding affinity can comprise:
a) binding affinity to spike protein of SARS-CoV-2 with at least 50% less binding to spike protein of SARS-CoV or spike protein of MERS-CoV;
b) binding affinity to receptor-binding domain (RBD) of the spike protein of SARS-CoV-2 comprising the amino acid sequence of SEQ ID NO: 128;
c) binding affinity to RBD of said spike protein of SARS-CoV comprising the amino acid sequence of SEQ ID NO: 124 at a level that is non-detectable or that is no more than 50% of said binding affinity to said RBD of said spike protein of SARS-CoV-2;
d) binding affinity to RBD of said spike protein of MERS-CoV comprising the amino acid sequence of SEQ ID NO: 126 at a level that is non-detectable or that is no more than 50% of said binding affinity to said RBD of the spike protein of SARS-CoV-2;
e) binding affinity to said RBD of said spike protein of SARS-CoV-2 at a Kd value of no more than $1\times10^{-7}$ M as measured by Surface Plasmon Resonance (SPR);
f) binding affinity to said RBD of said spike protein of SARS-CoV or the RBD of spike protein of MERS-CoV at a $K_d$ value of at least $1\times10^{-6}$M as measured by SPR;
g) exhibiting at least 30% competition at 104, with 2 μM angiotensin converting enzyme 2 (ACE2) receptor, for binding to said RBD of said spike protein of SARS-CoV-2 immobilized at a resonance unit (RU) of 250, as measured by SPR;
h) binding affinity to said RBD of said spike protein of SARS-CoV-2 at a neutralizing activity at an $IC_{50}$ value of no more than 100 μg/ml (for example, no more than 50 μg/ml, no more than 40 μg/ml, no more than 30 μg/ml, no more than 25 μg/ml, no more than 20 μg/ml, no more than 15 μg/ml, no more than 10 μg/ml, no more than 8 μg/ml, no more than 6 μg/ml, no more than 4 μg/ml, no more than 2 μg/ml, or no more than 1 μg/ml), as measured by pseudovirus, live virus microneutralization, inactivated virus neutralization assay, or a combination thereof;
i) capable of binding to the RBD of spike protein of SARS-CoV-2 at an neutralizing activity at an $IC_{50}$ value of no more than 1 μg/ml (for example, no more than 50 ng/ml, no more than 40 ng/ml, no more than 30 ng/ml, no more than 25 ng/ml, no more than 20 ng/ml, no more than 15 ng/ml, no more than 10 ng/ml, no more than 8 ng/ml, no more than 6 ng/ml, no more than 4 ng/ml, no more than 2 ng/ml, or no more than 1 ng/ml), as measured by live virus neutralization assay using focus reduction neutralization test (FRNT) method or
a combination thereof.

In some cases, the antigen-binding affinity can be selected from the group consisting of:
a) binding affinity to spike protein of SARS-CoV-2 with at least 50% less binding to spike protein of SARS-CoV or spike protein of MERS-CoV;
b) binding affinity to receptor-binding domain (RBD) of the spike protein of SARS-CoV-2 comprising the amino acid sequence of SEQ ID NO: 128;
c) binding affinity to RBD of said spike protein of SARS-CoV comprising the amino acid sequence of SEQ ID NO: 124 at a level that is non-detectable or that is no more than 50% of said binding affinity to said RBD of said spike protein of SARS-CoV-2;
d) binding affinity to RBD of said spike protein of MERS-CoV comprising the amino acid sequence of SEQ ID NO: 126 at a level that is non-detectable or that is no more than 50% of said binding affinity to said RBD of the spike protein of SARS-CoV-2;
e) binding affinity to said RBD of said spike protein of SARS-CoV-2 at a $K_d$ value of no more than 1×10-7M as measured by Surface Plasmon Resonance (SPR);
f) binding affinity to said RBD of said spike protein of SARS-CoV or the RBD of spike protein of MERS-CoV at a $K_d$ value of at least 1×10-6M as measured by SPR;
g) exhibiting at least 30% competition at 1 μM, with 2 μM angiotensin converting enzyme 2 (ACE2) receptor, for binding to said RBD of said spike protein of SARS-CoV-2 immobilized at a resonance unit (RU) of 250, as measured by SPR;
h) binding affinity to said RBD of said spike protein of SARS-CoV-2 at a neutralizing activity at an $IC_{50}$ value of no more than 100 μg/ml, as measured by pseudovirus, live virus microneutralization, inactivated virus neutralization assay, or a combination thereof;
i) capable of binding to the RBD of spike protein of SARS-CoV-2 at an neutralizing activity at an $IC_{50}$ value of no more than 1 μg/ml (for example, no more than 50 ng/ml, no more than 40 ng/ml, no more than 30 ng/ml, no more than 25 ng/ml, no more than 20 ng/ml, no more than 15 ng/ml, no more than 10 ng/ml, no more than 8 ng/ml, no more than 6 ng/ml, no more than 4 ng/ml, no more than 2 ng/ml, or no more than 1 ng/ml), as measured by live virus neutralization assay using focus reduction neutralization test (FRNT) method;
and a combination thereof.

In some embodiments, the anti-SARS-CoV-2 antibodies and antigen-binding fragments provided herein are capable of specifically binding to SARS-CoV-2. In certain embodiments, the antibodies and the antigen-binding fragments thereof provided herein specifically bind to SARS-CoV-2 at an Kd value of no more than $10^{-7}$M as measured by SPR.

In certain embodiments, the antibodies and the antigen-binding fragments thereof provided herein are capable of binding to the RBD of spike protein of SARS-CoV-2 at a $K_d$ value of no more than $1\times10^{-7}$M (e.g. no more than $5\times10^{-7}$ M, no more than $2\times10^{-7}$ M, no more than $10^{-7}$ M, no more than $5\times10^{-8}$ M, no more than $2\times10^{-8}$ M, no more than $10^{-8}$ M, no more than $5\times10^{-9}$ M, no more than $4\times10^{-9}$M, no more than $3\times10^{-9}$M, no more than $2\times10^{-9}$ M, or no more than $10^{-9}$ M) as measured by SPR.

In certain embodiments, the antibodies and the antigen-binding fragments thereof provided herein bind to the RBD of spike protein of SARS-CoV or the RBD of spike protein of MERS-CoV at a significantly lower affinity or degree. In certain embodiments, the antibodies and the antigen-binding fragments thereof provided herein exhibit binding to the RBD of spike protein of SARS-CoV or the RBD of spike protein of MERS-CoV at a Kd value of at least $1\times10^{-6}$M (e.g. at least $2\times10^{-6}$ M, at least $5\times10^{-6}$ M, at least $10^{-5}$ M) as measured by SPR.

In certain embodiments, the antibodies and the antigen-binding fragments thereof provided herein do not detectably bind to SARS-CoV or MERS-CoV. In certain embodiments, the antibodies and the antigen-binding fragments thereof provided herein exhibits at least 50% (e.g., at least 55%, at least 60%, at least 65%, at least 70%, at least 75%, at least 80%, at least 85%, at least 90%, at least 95%, at least 96%, at least 97%, at least 98%, at least 99%) less binding or non-detectable binding to SARS-CoV or MERS-CoV, than the binding to SARS-CoV-2 under equivalent assay conditions. In certain embodiments, the antibodies and the antigen-binding fragments thereof provided herein are capable of specifically binding to spike protein of SARS-CoV-2 and exhibiting at least 50% (e.g., at least 55%, at least 60%, at least 65%, at least 70%, at least 75%, at least 80%, at least 85%, at least 90%, at least 95%, at least 96%, at least 97%, at least 98%, at least 99%) less binding to spike protein of SARS-CoV or spike protein of MERS-CoV, than the binding to spike protein of SARS-CoV-2 under equivalent assay conditions. In certain embodiments, the full length of spike protein of SARS-CoV-2 can comprise an amino acid sequence of SEQ ID NO: 134, optionally encoded by a polynucleotide sequence of SEQ ID NO: 135. In certain embodiments, the antibodies and the antigen-binding fragments thereof provided herein are capable of specifically binding to receptor-binding domain (RBD) of the spike protein of SARS-CoV-2 comprising the amino acid sequence of SEQ ID NO: 128. In certain embodiments, the antibodies and the antigen-binding fragments thereof provided herein exhibit binding to RBD of spike protein of SARS-CoV comprising the amino acid sequence of SEQ ID NO: 124 at a level that is non-detectable or that is no more than 50% (e.g., no more than 45%, 40%, 35%, 30%, 25%, 20%, 15%, 10%, 5%, 2%, 1%) of the binding to the RBD of spike protein of SARS-CoV-2 under equivalent assay conditions. In certain embodiments, the antibodies and the antigen-binding fragments thereof provided herein exhibit binding to RBD of spike protein of MERS-CoV comprising the amino acid sequence of SEQ ID NO: 126 at a level that is non-detectable or that is no more than 50% (e.g., no more than 45%, 40%, 35%, 30%, 25%, 20%, 15%, 10%, 5%, 2%, 1%) of the binding to RBD of the spike protein of SARS-CoV-2 under equivalent assay conditions.

In certain embodiments, the antibodies and the antigen-binding fragments thereof provided herein are capable of exhibiting at least 30% competition at 1 µM, with 2 µM ACE2 receptor for binding to the RBD of spike protein of SARS-CoV-2 immobilized at a (RU of 250, as measured by SPR. For example, SARS-CoV-2 RBD can be immobilized to a CM5 sensor chip via amine group for a final RU around 250. 1 µM of the antibodies or the antigen-binding fragments thereof provided herein can be injected onto the chip until binding steady-state is reached. 2 µM of human ACE2 or human ACE2 peptidase domain can be injected for 60 seconds. Blocking efficacy can be determined by comparison of response units with and without the antibody incubation. Instruments and kits for SPR are commercially available as, for example, Biacore T200, GE Healthcare.

In certain embodiments, the antibodies and the antigen-binding fragments thereof provided herein are capable of binding to the RBD of spike protein of SARS-CoV-2 at an neutralizing activity at an $IC_{50}$ value of no more than 100 µg/ml (e.g., no more than 90 µg/ml, 80 µg/ml, 70 µg/ml, 60 µg/ml, 50 µg/ml, 40 µg/ml, 30 µg/ml, 20 µg/ml, 10 µg/ml, 5 µg/ml, 2 µg/ml, 1 µg/ml, 0.5 µg/ml, 0.2 µg/ml, 0.1 µg/ml, 0.05 µg/ml, 0.03m/ml), as measured by pseudovirus neutralization assay. Pseudovirus neutralization assay are known in the art, and in general involves generating a pseudovirus expressing a reporter gene and a viral protein of interest (such as the full length spike protein of SARS-CoV-2 of SEQ ID NO: 134). The antibodies and the antigen-binding fragments thereof provided herein can be incubated with the pseudovirus, and the titer of the pseudovirus can be determined via the report gene. $IC_{50}$ is the concentration of the antibodies or the antigen-binding fragment thereof can inhibit 50% of the pseudovirus titer in the assay.

Illustrative Anti-SARS-CoV-2 Antibodies

In certain embodiments, the present disclosure provides SARS-CoV-2 antibodies and antigen-binding fragments thereof comprising one or more (e.g. 1, 2, 3, 4, 5, or 6) CDRs comprising the sequences selected from the group consisting of SEQ ID NO: 1-6, 11-16, 21-26, 31-36, 41-46, 51-56, 65-70, 75-80, 85-90, 95-100, 105-110, 136-141, 146-151, 156-161, 166-171, 176-181, 186-191, 196-201, 206-211, 216-221, 226-231, 236-241, 246-251, 256-261, 266-271, 276-281, 286-291, 296-301, 306-311, 316-321, 326-331, 336-341, 346-351, 356-361, 366-371, 376-381, 386-391, 396-401, 406-411, 416-421, and 426-431.

Antibody "P2A-1A8" as used herein refers to a monoclonal fully human antibody having a heavy chain variable region having the sequence of SEQ ID NO: 7, and a light chain variable region having the sequence of SEQ ID NO: 8.

Antibody "P2A-1A9" as used herein refers to a monoclonal fully human antibody having a heavy chain variable region having the sequence of SEQ ID NO: 17, and a light chain variable region having the sequence of SEQ ID NO: 18.

Antibody "P2A-1A10" as used herein refers to a monoclonal fully human antibody having a heavy chain variable region having the sequence of SEQ ID NO: 27, and a light chain variable region having the sequence of SEQ ID NO: 28.

Antibody "P2A-1B3" as used herein refers to a monoclonal fully human antibody having a heavy chain variable region having the sequence of SEQ ID NO: 37, and a light chain variable region having the sequence of SEQ ID NO: 38.

Antibody "P2B-2F6" as used herein refers to a monoclonal fully human antibody having a heavy chain variable region having the sequence of SEQ ID NO: 47, and a light chain variable region having the sequence of SEQ ID NO: 48.

Antibody "P2B-2G4" as used herein refers to a monoclonal fully human antibody having a heavy chain variable region having the sequence of SEQ ID NO: 57, and a light chain variable region having the sequence of SEQ ID NO: 58.

Antibody "P2B-2G11" as used herein refers to a monoclonal fully human antibody having a heavy chain variable region having the sequence of SEQ ID NO: 61, and a light chain variable region having the sequence of SEQ ID NO: 62.

Antibody "P2C-1A3" as used herein refers to a monoclonal fully human antibody having a heavy chain variable region having the sequence of SEQ ID NO: 71, and a light chain variable region having the sequence of SEQ ID NO: 72.

Antibody "P2C-1C8" as used herein refers to a monoclonal fully human antibody having a heavy chain variable region having the sequence of SEQ ID NO: 81, and a light chain variable region having the sequence of SEQ ID NO: 82.

Antibody "P2C-1C10" as used herein refers to a monoclonal fully human antibody having a heavy chain variable region having the sequence of SEQ ID NO: 91, and a light chain variable region having the sequence of SEQ ID NO: 92.

Antibody "P2C-1D5" as used herein refers to a monoclonal fully human antibody having a heavy chain variable region having the sequence of SEQ ID NO: 101, and a light chain variable region having the sequence of SEQ ID NO: 102.

Antibody "P2C-1F11" as used herein refers to a monoclonal fully human antibody having a heavy chain variable region having the sequence of SEQ ID NO: 111, and a light chain variable region having the sequence of SEQ ID NO: 112.

Antibody "P2B-1G5" as used herein refers to a monoclonal fully human antibody having a heavy chain variable region having the sequence of SEQ ID NO: 142, and a light chain variable region having the sequence of SEQ ID NO: 143.

Antibody "P2B-1A1" as used herein refers to a monoclonal fully human antibody having a heavy chain variable region having the sequence of SEQ ID NO: 152, and a light chain variable region having the sequence of SEQ ID NO: 153.

Antibody "2C-1D7" as used herein refers to a monoclonal fully human antibody having a heavy chain variable region having the sequence of SEQ ID NO: 162, and a light chain variable region having the sequence of SEQ ID NO: 163.

Antibody "2B-1A10" as used herein refers to a monoclonal fully human antibody having a heavy chain variable region having the sequence of SEQ ID NO: 172, and a light chain variable region having the sequence of SEQ ID NO: 173.

Antibody "P2B-1D9" as used herein refers to a monoclonal fully human antibody having a heavy chain variable region having the sequence of SEQ ID NO: 182, and a light chain variable region having the sequence of SEQ ID NO: 183.

Antibody "P2B-1E4" as used herein refers to a monoclonal fully human antibody having a heavy chain variable region having the sequence of SEQ ID NO: 192, and a light chain variable region having the sequence of SEQ ID NO: 193.

Antibody "P2B-1G1" as used herein refers to a monoclonal fully human antibody having a heavy chain variable region having the sequence of SEQ ID NO: 202, and a light chain variable region having the sequence of SEQ ID NO: 203.

Antibody "P4A-2D9" as used herein refers to a monoclonal fully human antibody having a heavy chain variable region having the sequence of SEQ ID NO: 212, and a light chain variable region having the sequence of SEQ ID NO: 213.

Antibody "P5A-2G7" as used herein refers to a monoclonal fully human antibody having a heavy chain variable region having the sequence of SEQ ID NO: 222, and a light chain variable region having the sequence of SEQ ID NO: 223.

Antibody "P5A-3C8" as used herein refers to a monoclonal fully human antibody having a heavy chain variable region having the sequence of SEQ ID NO: 232, and a light chain variable region having the sequence of SEQ ID NO: 233.

Antibody "P5A-1D2" as used herein refers to a monoclonal fully human antibody having a heavy chain variable region having the sequence of SEQ ID NO: 242, and a light chain variable region having the sequence of SEQ ID NO: 243.

Antibody "P5A-2F11" as used herein refers to a monoclonal fully human antibody having a heavy chain variable region having the sequence of SEQ ID NO: 252, and a light chain variable region having the sequence of SEQ ID NO: 253.

Antibody "P5A-2E1" as used herein refers to a monoclonal fully human antibody having a heavy chain variable region having the sequence of SEQ ID NO: 262, and a light chain variable region having the sequence of SEQ ID NO: 263.

Antibody "P5A-1C8" as used herein refers to a monoclonal fully human antibody having a heavy chain variable region having the sequence of SEQ ID NO: 272, and a light chain variable region having the sequence of SEQ ID NO: 273.

Antibody "P1A-1C10" as used herein refers to a monoclonal fully human antibody having a heavy chain variable region having the sequence of SEQ ID NO: 282, and a light chain variable region having the sequence of SEQ ID NO: 283.

Antibody "P4A-1H6" as used herein refers to a monoclonal fully human antibody having a heavy chain variable region having the sequence of SEQ ID NO: 292, and a light chain variable region having the sequence of SEQ ID NO: 293.

Antibody "P4B-1F4" as used herein refers to a monoclonal fully human antibody having a heavy chain variable region having the sequence of SEQ ID NO: 302, and a light chain variable region having the sequence of SEQ ID NO: 303.

Antibody "P5A-1B6" as used herein refers to a monoclonal fully human antibody having a heavy chain variable region having the sequence of SEQ ID NO: 312, and a light chain variable region having the sequence of SEQ ID NO: 313.

Antibody "P5A-1B8" as used herein refers to a monoclonal fully human antibody having a heavy chain variable region having the sequence of SEQ ID NO: 322, and a light chain variable region having the sequence of SEQ ID NO: 323.

Antibody "P5A-1B9" as used herein refers to a monoclonal fully human antibody having a heavy chain variable region having the sequence of SEQ ID NO: 332, and a light chain variable region having the sequence of SEQ ID NO: 333.

Antibody "P5A-1D1" as used herein refers to a monoclonal fully human antibody having a heavy chain variable region having the sequence of SEQ ID NO: 342, and a light chain variable region having the sequence of SEQ ID NO: 343.

Antibody "P5A-1D10" as used herein refers to a monoclonal fully human antibody having a heavy chain variable region having the sequence of SEQ ID NO: 352, and a light chain variable region having the sequence of SEQ ID NO: 353.

Antibody "P5A-2D11" as used herein refers to a monoclonal fully human antibody having a heavy chain variable region having the sequence of SEQ ID NO: 362, and a light chain variable region having the sequence of SEQ ID NO: 363.

Antibody "P5A-2G9" as used herein refers to a monoclonal fully human antibody having a heavy chain variable region having the sequence of SEQ ID NO: 372, and a light chain variable region having the sequence of SEQ ID NO: 373.

Antibody "P5A-2H3" as used herein refers to a monoclonal fully human antibody having a heavy chain variable region having the sequence of SEQ ID NO: 382, and a light chain variable region having the sequence of SEQ ID NO: 383.

Antibody "P5A-3A1" as used herein refers to a monoclonal fully human antibody having a heavy chain variable region having the sequence of SEQ ID NO: 392, and a light chain variable region having the sequence of SEQ ID NO: 393.

Antibody "P5A-3A6" as used herein refers to a monoclonal fully human antibody having a heavy chain variable region having the sequence of SEQ ID NO: 402, and a light chain variable region having the sequence of SEQ ID NO: 403.

Antibody "P5A-3B4" as used herein refers to a monoclonal fully human antibody having a heavy chain variable region having the sequence of SEQ ID NO: 412, and a light chain variable region having the sequence of SEQ ID NO: 413.

Antibody "P5A-3C12" as used herein refers to a monoclonal fully human antibody having a heavy chain variable region having the sequence of SEQ ID NO: 422, and a light chain variable region having the sequence of SEQ ID NO: 423.

Antibody "P22A-1D1" as used herein refers to a monoclonal fully human antibody having a heavy chain variable region having the sequence of SEQ ID NO: 432, and a light chain variable region having the sequence of SEQ ID NO: 433.

Table 1 below shows the CDR amino acid sequences of antibodies P2A-1A8, P2A-1A9, P2B-2G11, P2A-1A10, P2A-1B3, P2B-2F6, P2B-2G4, P2C-1A3, P2C-1C8, P2C-1C10, P2C- 1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A- 1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, and P22A-1D1.

TABLE 1

CDR amino acid sequences of 42 antibodies

| | | CDR1 | CDR2 | CDR3 |
|---|---|---|---|---|
| P2A-1A8 | HCDR | SEQ ID NO: 1<br>GFAFDDYA | SEQ ID NO: 2<br>STWNSGTI | SEQ ID NO: 3<br>AKLGGYSDYDYPR<br>PGDHYYGLDV |
| | LCDR | SEQ ID NO: 4<br>SSDVGSYNL | SEQ ID NO: 5<br>DVN | SEQ ID NO: 6<br>RSYTDSNTYV |
| P2A-1A9 | HCDR | SEQ ID NO: 11<br>GFTFDDYA | SEQ ID NO: 12<br>ISWNGGII | SEQ ID NO: 13<br>AKVAGRGDYDYY<br>YGMDV |
| | LCDR | SEQ ID NO: 14<br>SSNIGAGYD | SEQ ID NO: 15<br>GNN | SEQ ID NO: 16<br>QSYDSSLSGSV |
| P2A-1A10 | HCDR | SEQ ID NO: 21<br>GYTFTGYY | SEQ ID NO: 22<br>INPNSGGT | SEQ ID NO: 23<br>ARVPYCSSTSCHRD<br>WYFDL |
| | LCDR | SEQ ID NO: 24<br>QSLLDSDDGNTY | SEQ ID NO: 25<br>TLS | SEQ ID NO: 26<br>MQRIEFPLT |
| P2A-1B3 | HCDR | SEQ ID NO: 31<br>GFSFNRYS | SEQ ID NO: 32<br>ISASGNTI | SEQ ID NO: 33<br>ARPAMVREGTYN<br>WFDP |
| | LCDR | SEQ ID NO: 34<br>QSVSNDY | SEQ ID NO: 35<br>YAS | SEQ ID NO: 36<br>QQYGDSPPIT |
| P2B-2F6 | HCDR | SEQ ID NO: 41<br>GYSISSGYY | SEQ ID NO: 42<br>IYHSGST | SEQ ID NO: 43<br>ARAVVGIVVVPAA<br>GRRAFDI |
| | LCDR | SEQ ID NO: 44<br>SSDVGGYNY | SEQ ID NO: 45<br>EVS | SEQ ID NO: 46<br>SSYAGSNNLV |
| P2B-2G4 | HCDR | SEQ ID NO: 51<br>GFTFSSYG | SEQ ID NO: 52<br>IWYDGSNK | SEQ ID NO: 53<br>ARGAAMWLDY |
| | LCDR | SEQ ID NO: 54<br>SSDVGGYNY | SEQ ID NO: 55<br>DVS | SEQ ID NO: 56<br>CSYAGSYTFVV |

TABLE 1-continued

CDR amino acid sequences of 42 antibodies

| | | CDR1 | CDR2 | CDR3 |
|---|---|---|---|---|
| P2B-2G11 | HCDR | SEQ ID NO: 11<br>GFTFDDYA | SEQ ID NO: 12<br>ISWNGGII | SEQ ID NO: 13<br>AKVAGRGDYYYGMDV |
| | LCDR | SEQ ID NO: 14<br>SSNIGAGYD | SEQ ID NO: 15<br>GNN | SEQ ID NO: 16<br>QSYDSSLSGSV |
| P2C-1A3 | HCDR | SEQ ID NO: 65<br>GFTFSDYY | SEQ ID NO: 66<br>ISSSGSTI | SEQ ID NO: 67<br>ARDFSHQQLVPS |
| | LCDR | SEQ ID NO: 68<br>QGISSY | SEQ ID NO: 69<br>AAS | SEQ ID NO: 70<br>QQLNSYPLT |
| P2C-1C8 | HCDR | SEQ ID NO: 75<br>GFTFRSYG | SEQ ID NO: 76<br>IWYDGSNK | SEQ ID NO: 77<br>ARDIEIVVVNIDY |
| | LCDR | SEQ ID NO: 78<br>QSLVYSDGNTY | SEQ ID NO: 79<br>KVS | SEQ ID NO: 80<br>MQGTHWPYT |
| P2C-1C10 | HCDR | SEQ ID NO: 85<br>GGTFSSYA | SEQ ID NO: 86<br>IIPIFGTA | SEQ ID NO: 87<br>ARVVTGYYFDY |
| | LCDR | SEQ ID NO: 88<br>QSVSSY | SEQ ID NO: 89<br>DAS | SEQ ID NO: 90<br>QQRSNWPS |
| P2C-1D5 | HCDR | SEQ ID NO: 95<br>GFTFSSFA | SEQ ID NO: 96<br>ISGSGGST | SEQ ID NO: 97<br>AKDPDGSGSWYFDY |
| | LCDR | SEQ ID NO: 98<br>NIGSKS | SEQ ID NO: 99<br>YDS | SEQ ID NO: 100<br>QVWDSSSDHHV |
| P2C-1F11 | HCDR | SEQ ID NO: 105<br>GITVSSNY | SEQ ID NO: 106<br>IYSGGST | SEQ ID NO: 107<br>ARDLVVYGMDV |
| | LCDR | SEQ ID NO: 108<br>QSVSSSY | SEQ ID NO: 109<br>GAS | SEQ ID NO: 110<br>QQYGSSPT |
| P2B-1G5 | HCDR | SEQ ID NO: 136<br>GYTFTTYV | SEQ ID NO: 137<br>INTNTGNP | SEQ ID NO: 138<br>SCEITTLGGMDV |
| | LCDR | SEQ ID NO: 139<br>NIGSKS | SEQ ID NO: 140<br>YDS | SEQ ID NO: 141<br>QVWDSISDHRV |
| P2B-1A1 | HCDR | SEQ ID NO: 146<br>GGSISSYY | SEQ ID NO: 147<br>IYYSGST | SEQ ID NO: 148<br>ARLERDWPLDAFDI |
| | LCDR | SEQ ID NO: 149<br>SSDVGGYNY | SEQ ID NO: 150<br>DVS | SEQ ID NO: 151<br>SSYTSNNTFA |
| P2C-1D7 | HCDR | SEQ ID NO: 156<br>GFTVSSNY | SEQ ID NO: 157<br>IYSGGST | SEQ ID NO: 158<br>ARELYEVGATDY |
| | LCDR | SEQ ID NO: 159<br>QSLVYSDGNTY | SEQ ID NO: 160<br>KVS | SEQ ID NO: 161<br>MQRYTLAGV |
| P2B-1A10 | HCDR | SEQ ID NO: 166<br>GFTVSSNY | SEQ ID NO: 167<br>IYSGGST | SEQ ID NO: 168<br>AREGPKSITGTAFDI |
| | LCDR | SEQ ID NO: 169<br>QDISNY | SEQ ID NO: 170<br>DAS | SEQ ID NO: 171<br>QQYDNLPMYT |
| P2B-1D9 | HCDR | SEQ ID NO: 176<br>GFSLSTSGVG | SEQ ID NO: 177<br>IYWDDDK | SEQ ID NO: 178<br>AHTRILYYGSGSYYDY |
| | LCDR | SEQ ID NO: 179<br>SSNIGSNY | SEQ ID NO: 180<br>SNN | SEQ ID NO: 181<br>AAWDDSLSGVV |
| P2B-1E4 | HCDR | SEQ ID NO: 186<br>GFSLSTSGVG | SEQ ID NO: 187<br>IYWDDDK | SEQ ID NO: 188<br>AHQIVATIIDY |
| | LCDR | SEQ ID NO: 189<br>SSDVGGYNY | SEQ ID NO: 190<br>DVS | SEQ ID NO: 191<br>SSYTSSSVV |
| P2B-1G1 | HCDR | SEQ ID NO: 196<br>GFTVSSNY | SEQ ID NO: 197<br>IYSGGST | SEQ ID NO: 198<br>ARDYGDYWFDP |
| | LCDR | SEQ ID NO: 199<br>QSVSSSY | SEQ ID NO: 200<br>GAS | SEQ ID NO: 201<br>QQYGSSPRT |
| P4A-2D9 | HCDR | SEQ ID NO: 206<br>GFTFSSYG | SEQ ID NO: 207<br>ISDDGSNQ | SEQ ID NO: 208<br>AKRGGYCSTTSCLVRWVYFDY |
| | LCDR | SEQ ID NO: 209<br>QFISSY | SEQ ID NO: 210<br>ATS | SEQ ID NO: 211<br>QQSYNTLT |

TABLE 1-continued

CDR amino acid sequences of 42 antibodies

| | | CDR1 | CDR2 | CDR3 |
|---|---|---|---|---|
| P5A-2G7 | HCDR | SEQ ID NO: 216<br>GDSVSSGSYY | SEQ ID NO: 217<br>IYYSGST | SEQ ID NO: 218<br>ARERCYYGSGRAP<br>RCVWFDP |
| | LCDR | SEQ ID NO: 219<br>SSDVGGYNY | SEQ ID NO: 220<br>DVS | SEQ ID NO: 221<br>SSYTSSSTLVV |
| P5A-3C8 | HCDR | SEQ ID NO: 226<br>GFTVSSNY | SEQ ID NO: 227<br>IYSGGST | SEQ ID NO: 228<br>ARDLQEHGMDV |
| | LCDR | SEQ ID NO: 229<br>QGISSY | SEQ ID NO: 230<br>AAS | SEQ ID NO: 231<br>QHLNSYPPGYT |
| P5A-1D2 | HCDR | SEQ ID NO: 236<br>GFIVSSNY | SEQ ID NO: 237<br>IYSGGST | SEQ ID NO: 238<br>ARALQVGATSDYF<br>DY |
| | LCDR | SEQ ID NO: 239<br>SSNIGAGYD | SEQ ID NO: 240<br>GNS | SEQ ID NO: 241<br>QSCDSSLSVVV |
| P5A-2F11 | HCDR | SEQ ID NO: 246<br>GYTFTSYD | SEQ ID NO: 247<br>MNPNSGNT | SEQ ID NO: 248<br>ARYIVVPAAKGF<br>DP |
| | LCDR | SEQ ID NO: 249<br>QSVLYSSNNKY | SEQ ID NO: 250<br>WAS | SEQ ID NO: 251<br>QQYYSTPLT |
| P5A-2E1 | HCDR | SEQ ID NO: 256<br>GYSFTSYW | SEQ ID NO: 257<br>IYPGDSDT | SEQ ID NO: 258<br>AQTSVTRNWFDP |
| | LCDR | SEQ ID NO: 259<br>NIGSKS | SEQ ID NO: 260<br>YDS | SEQ ID NO: 261<br>QVWDSSSDHVV |
| P5A-1C8 | HCDR | SEQ ID NO: 266<br>GYTFTSYY | SEQ ID NO: 267<br>INPSGGST | SEQ ID NO: 268<br>ARSARDYYDSSGY<br>YYRAEYFQH |
| | LCDR | SEQ ID NO: 269<br>QDISNY | SEQ ID NO: 270<br>DAS | SEQ ID NO: 271<br>QQYDNLPSIT |
| P1A-1C10 | HCDR | SEQ ID NO: 276<br>GGTSSFYD | SEQ ID NO: 277<br>IIPRLDIA | SEQ ID NO: 278<br>ARGRPGSEWAYGP<br>FDL |
| | LCDR | SEQ ID NO: 279<br>QSSRAW | SEQ ID NO: 280<br>KAS | SEQ ID NO: 281<br>HQYNSSPFT |
| P4A-1H6 | HCDR | SEQ ID NO: 286<br>GFTFSSYG | SEQ ID NO: 287<br>ISDDGSNQ | SEQ ID NO: 288<br>AKRGGYCSTTSCLL<br>RWVYFDF |
| | LCDR | SEQ ID NO: 289<br>QSISSY | SEQ ID NO: 290<br>AAS | SEQ ID NO: 291<br>QQSYNTPT |
| P4B-1F4 | HCDR | SEQ ID NO: 296<br>GFTFSSYG | SEQ ID NO: 297<br>ISYDGSNK | SEQ ID NO: 298<br>AKGPRYSSSWYISL<br>YYYYGMDV |
| | LCDR | SEQ ID NO: 299<br>QSLVYSDGNTY | SEQ ID NO: 300<br>KVS | SEQ ID NO: 301<br>MQATHWPLYT |
| P5A-1B6 | HCDR | SEQ ID NO: 306<br>GFTFSSYA | SEQ ID NO: 307<br>ISYDGSNK | SEQ ID NO: 308<br>ARDGQAITMVQGV<br>IGPPFDY |
| | LCDR | SEQ ID NO: 309<br>QDISNY | SEQ ID NO: 310<br>DAS | SEQ ID NO: 311<br>QQYDNLPYT |
| P5A-1B8 | HCDR | SEQ ID NO: 316<br>GFTVSSNY | SEQ ID NO: 317<br>IYPGGST | SEQ ID NO: 318<br>ARETLAFDY |
| | LCDR | SEQ ID NO: 319<br>QGISSY | SEQ ID NO: 320<br>AAS | SEQ ID NO: 321<br>QQLNSYPPA |
| P5A-1B9 | HCDR | SEQ ID NO: 326<br>GGSISSYY | SEQ ID NO: 327<br>ISYSGST | SEQ ID NO: 328<br>ASNGQYYDILTGQP<br>PDYWYFDL |
| | LCDR | SEQ ID NO: 329<br>QSVLYSSNNKY | SEQ ID NO: 330<br>WAS | SEQ ID NO: 331<br>QQYYSTPLT |
| P5A-1D1 | HCDR | SEQ ID NO: 336<br>GLTVSSNY | SEQ ID NO: 337<br>IYSGGST | SEQ ID NO: 338<br>ARDLYYYGMDV |
| | LCDR | SEQ ID NO: 339<br>QGISSY | SEQ ID NO: 340<br>AAS | SEQ ID NO: 341<br>QQLNSYPT |

TABLE 1-continued

CDR amino acid sequences of 42 antibodies

| | | CDR1 | CDR2 | CDR3 |
|---|---|---|---|---|
| P5A-1D10 | HCDR | SEQ ID NO: 346<br>QFTFSDYS | SEQ ID NO: 347<br>ISQSGSTI | SEQ ID NO: 348<br>ARGVSPSYVWGSY<br>RSLYHFDY |
| | LCDR | SEQ ID NO: 349<br>SSDVGGYNY | SEQ ID NO: 350<br>DVS | SEQ ID NO: 351<br>SSFTSSTTVVV |
| P5A-2D11 | HCDR | SEQ ID NO: 356<br>GYSFTSYW | SEQ ID NO: 357<br>IYPGDSDT | SEQ ID NO: 358<br>ARRDSTYGGNTDY |
| | LCDR | SEQ ID NO: 359<br>SSNIGSNT | SEQ ID NO: 360<br>SNN | SEQ ID NO: 361<br>AAWDDSLNGVV |
| P5A-2G9 | HCDR | SEQ ID NO: 366<br>GFTFSSYG | SEQ ID NO: 367<br>IWYDGSNK | SEQ ID NO: 368<br>ARWFHTGGYFDY |
| | LCDR | SEQ ID NO: 369<br>SDINVSSYN | SEQ ID NO: 370<br>YYSDSDK | SEQ ID NO: 371<br>MIWPSNALYV |
| P5A-2H3 | HCDR | SEQ ID NO: 376<br>GYSFTSYW | SEQ ID NO: 377<br>IYPGDSDT | SEQ ID NO: 378<br>ARRDSTYGGNTDY |
| | LCDR | SEQ ID NO: 379<br>SSNIGSNT | SEQ ID NO: 380<br>SNN | SEQ ID NO: 381<br>AAWDDSLNGVV |
| P5A-3A1 | HCDR | SEQ ID NO: 386<br>GFTVSSNY | SEQ ID NO: 387<br>IYSGGST | SEQ ID NO: 388<br>ARDYGDFYFDY |
| | LCDR | SEQ ID NO: 389<br>QSVSSSY | SEQ ID NO: 390<br>GAS | SEQ ID NO: 391<br>QQYGSSPRT |
| P5A-3A6 | HCDR | SEQ ID NO: 396<br>GFTFDDYA | SEQ ID NO: 397<br>ISWNSGTI | SEQ ID NO: 398<br>AGGGTMVRGVIAG<br>GGTHPVDDYYGM<br>DV |
| | LCDR | SEQ ID NO: 399<br>SSDVGGYNY | SEQ ID NO: 400<br>DVS | SEQ ID NO: 401<br>SSYTSSSTVV |
| P5A-3B4 | HCDR | SEQ ID NO: 406<br>GYSFTSYW | SEQ ID NO: 407<br>IYPGDSDT | SEQ ID NO: 408<br>ARRDSTYGGNTDY |
| | LCDR | SEQ ID NO: 409<br>SSNIGSNT | SEQ ID NO: 410<br>SNN | SEQ ID NO: 411<br>AAWDDSLNGVV |
| P5A-3C12 | HCDR | SEQ ID NO: 416<br>GFSLSTSGVG | SEQ ID NO: 417<br>IYWDDDK | SEQ ID NO: 418<br>AHSLFLTVGYSSSW<br>SPFDY |
| | LCDR | SEQ ID NO: 419<br>QSVLYSSNNKNY | SEQ ID NO: 420<br>WAS | SEQ ID NO: 421<br>QQYYSTPHT |
| P22A-1D1 | HCDR | SEQ ID NO: 426<br>GFTVSSNY | SEQ ID NO: 427<br>IYSGGST | SEQ ID NO: 428<br>ARDRDYYGMDV |
| | LCDR | SEQ ID NO: 429<br>QGISSY | SEQ ID NO: 430<br>AAS | SEQ ID NO: 431<br>LHLNSYRT |

Table 2 below shows the heavy chain and light chain variable region amino acid sequences of antibodies P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, and P22A-1D1, and the corresponding nucleic acid encoding sequence are shown in Table 3.

TABLE 2

Variable region amino acid sequences of 42 antibodies

| | VH | VL |
|---|---|---|
| P2A-1A8 | SEQ ID NO: 7<br>EVQLVESGGDLVQPGRSLRLSCA<br>ASGFAFDDYAMHWVRQAPGKG<br>LEWVSGSTWNSGTIAYADSVKG<br>RFTISRDNAKKSLYLQMNSLRTE<br>DTALYYCAKLGGYSDYDYPRPG<br>DHYYGLDVWGQGTTVTVSS | SEQ ID NO: 8<br>QSALTQPASVSGSPGQSITISCTG<br>TSSDVGSYNLVSWYQQHPGKVP<br>KLLIYDVNKRPSGISNRFSGSKS<br>GNTASLTISGLQAEDEADYYCRS<br>YTDSNTYVFGTGTKVTVL |

TABLE 2-continued

Variable region amino acid sequences of 42 antibodies

| | VH | VL |
|---|---|---|
| P2A-1A9 | SEQ ID NO: 17<br>EVQLVESGGGLVQPGRSLRLSCA<br>ASGFTFDDYAMHWVRQVPGKGL<br>EWVSGISWNGGIIGYADSVKGRF<br>TISRDNAKTSLYLQMNSLRAEDT<br>ALYYCAKVAGRGDYDYYYGMD<br>VWGQGTTVTVSS | SEQ ID NO: 18<br>QSVLTQPPSVSGAPGQRVTISCT<br>GSSSNIGAGYDVHWYQQLPGTA<br>PKLLIYGNNNRPSGVPDRFSGSK<br>SGTSASLAITGLQAEDEADYYCQ<br>SYDSSLSGSVFGGGTKLTVL |
| P2A-1A10 | SEQ ID NO: 27<br>QVQLVQSGAEVKKPGASVKVSC<br>KASGYTFTGYYMHWVRQAPGQ<br>GLEWMGRINPNSGGTNYAQKFQ<br>GRVTMTRDTSISTAYMELSRLRS<br>DDTAVYYCARVPYCSSTSCHRD<br>WYFDLWGRGTLVTVSS | SEQ ID NO: 28<br>DIVMTQTPLSLPVTPGEPASISCR<br>SSQSLLDSDDGNTYLDWYLQKP<br>GQSPQLLIYTLSYRASGVPDRFS<br>GSGSGTDFTLKISRVEAEDVGVY<br>YCMQRIEFPLTFGGGTKVEIK |
| P2A-1B3 | SEQ ID NO: 37<br>EVQLVESGGGLVQPGGSLRLSCV<br>ASGFSFNRYSMNWLRQTPRKGL<br>EWLSYISASGNTIYYADSVRGRF<br>TTSRDNAKNTLYLQMNSLRDDD<br>TAVYFCARPAMVREGTYNWFDP<br>WGQGTLVTVSS | SEQ ID NO: 38<br>EIVLTQSPGTLSLSPGERATLSCR<br>ASQSVSNDYLAWYQQKPGQAP<br>RLLIYYASSRATGIPDRFSGSGSG<br>TDFTLTISRLEPGDSAVYYCQQY<br>GDSPPITFGQGTRLEIK |
| P2B-2F6 | SEQ ID NO: 47<br>QVQLQESGPGLVKPSETLSLTCT<br>VSGYSISSGYYWGWIRQPPGKGL<br>EWIGSIYHSGSTYYNPSLKTRVTI<br>SVDTSKNQFSLKLSSVTAADTAV<br>YYCARAVVGIVVVPAAGRRAFDI<br>WGQGTMVTVSS | SEQ ID NO: 48<br>QSALTQPPASGSPGQSVTISCTG<br>TSSDVGGYNYVSWYQQHPGKA<br>PKLMIYEVSKRPSGVPDRFSGSK<br>SGNTASLTVSGLQAEDEADYYC<br>SSYAGSNNLVFGGGTKLTVL |
| P2B-2G4 | SEQ ID NO: 57<br>QVQLVEGGGVVQPGRSLRLSCA<br>ASGFTFSSYGMHWVRQAPGKGL<br>EWVAVIWYDGSNKYYADSVKG<br>RFTISRDNSKNTLYLQMNSLRAE<br>DTAVYYCARGAAMVWLDYWG<br>QGTLVTVSS | SEQ ID NO: 58<br>QSALTQPRSVSGSPGQSVTISCT<br>GTSSDVGGYNYVSWYQQHPGK<br>APKLMIYDVSKRPSGVPDRFSGS<br>KSGNTASLTISGLQAEDEADYYC<br>CSYAGSYTFVVFGGGTKLTVL |
| P2B-2G11 | SEQ ID NO: 61<br>EVQLVESGGGLVQPGRSLRLSCA<br>ASGFTFDDYAMHWVRQAPGKGL<br>EWVSGISWNGGIIGYADSVKGRF<br>TISRDNAKTSLYLQMNSLKPEDT<br>ALYYCAKVAGRGDYDYYYGMD<br>VWGQGTTVTVSS | SEQ ID NO: 62<br>QSVLTQPPSVSGAPGQRVTISCT<br>GSSSNIGAGYDVHWYQQLPGTA<br>PKLLIYGNNNRPSGVPDRFSGSK<br>SGTSASLAITGLQAEDEADYYCQ<br>SYDSSLSGSVFGGGTKLTVL |
| P2C-1A3 | SEQ ID NO: 71<br>QVQLVESGGGLVKPGGSLRLSCA<br>ASGFTFSDYYMSWIRQAPGKGLE<br>WVSYISSSGSTIYYADSVKGRFTI<br>SRDNAKNSLYLQMNSLRAEDTA<br>VYYCARDFSHQQLVPSWGQGTL<br>VTVSS | SEQ ID NO: 72<br>DIQLTQSPSFLSASVGDRVTITCR<br>ASQGISSYLAWYQQKPGKAPKL<br>LIYAASTLQSGVPSRFSGSGSGTE<br>FTLTISSLQPEDFATYYCQQLNS<br>YPLTFGGGTKVEIK |
| P2C-1C8 | SEQ ID NO: 81<br>QVQLVESGGGVVQPGRSLRLSCA<br>ASGFTFRSYGMHWVRQAPGKGL<br>EWVAVIWYDGSNKYYADSVKG<br>RFTISRDNSKNTLYLQMNSLRAE<br>DTAVYYCARDIEIVVVNIDYWGQ<br>GTLVTVSS | SEQ ID NO: 82<br>DVVMTQSPLSLPVTLGQPASISC<br>RSSQSLVYSDGNTYLNWFQQRP<br>GQSPRRLIYKVSIWDSGVPDRFS<br>GSGSGTDFTLKISRVEAEDVGVY<br>YCMQGTHWPYTFGQGTKLEIK |
| P2C-1C10 | SEQ ID NO: 91<br>QVQLVQSGAEVKKPGSSVKVSC<br>KASGGTFSSYAIIWVRQAPGQGL<br>EWMGGIIPIFGTANYAQKFQGRV<br>TITADESTSTAYMELSSLRSEDTA<br>VYYCARVVTGYYFDYWGQGTL<br>VTVSS | SEQ ID NO: 92<br>EIVLTQSPATLSLSPGERATLSCR<br>ASQSVSSYLAWYQQKPGQAPRL<br>LIYDASNRATGIPARFSGSGSGT<br>DFTLTISSLEPEDFAVYYCQQRS<br>NWPSFGQGTKLEIK |
| P2C-1D5 | SEQ ID NO: 101<br>EVQLVESGGGLVQPGGSLRLSCA<br>ASGFTFSSFAMSWVRQAPGKGLE<br>WVSAISGSGGSTYYADSVKGRFT | SEQ ID NO: 102<br>SYVLTQPPSVSVAPGKTARITCG<br>GNNIGSKSVHWYQQKPGQAPVL<br>VIYYDSDRPSGIPERFSGSNSGNT |

TABLE 2-continued

Variable region amino acid sequences of 42 antibodies

| | VH | VL |
|---|---|---|
| | ISRDNSKNTLYLQMNSLRAEDTA VYYCAKDPDGSGSWYFDYWGQ GTLVTVSS | ATLTISRVEAGDEADYYCQVWD SSSDHHVFGTGTKVTVL |
| P2C-1F11 | SEQ ID NO: 111<br>EVQLVESGGGLVQPGGSLRLSCA ASGITVSSNYMNWVRQAPGKGL EWVSLIYSGGSTYYADSVKGRFT ISRDNSKNTLYLQMNSLRAEDTA VYHCARDLVVYGMDVWGQGTT VTVSS | SEQ ID NO: 112<br>EIVLTQSPGTLSLSPGERATLSCR ASQSVSSSYLAWYQQKPGQAPR LLIYGASSRATGIPDRFSGSGSGT DFTLTISRLEPEDFAVYYCQQYG SSPTFGQGTKLEIK |
| P2B-1G5 | SEQ ID NO: 142<br>QVQLVQSGSELKKPGASVKVSC KASGYTFTTYVMNWVRQAPGQ GLEWMGWINTNTGNPTYAQGFT GRFVFSLDTSVSTASLQISSLKAE DTAVYYCSCEITTLGGMDVWGQ GTTVTVSS | SEQ ID NO: 143<br>SYVLTQPPSVSVAPGKTARITCG GNNIGSKSVHWYQQKPGQAPVL VIYYDSDRPSGIPERFSGSNSGNT ATLTISGVEAGDEADYYCQVWD SISDHRVFGGGTKLTVL |
| P2B-1A1 | SEQ ID NO: 152<br>QVQLQESGPGLVKPSETLSLTCT VSGGSISSYYWSWIRQPPGKGLE WIGYIYYSGSTNYNPSLKSRVTIS VDTSKKQFSLKLSSVTAADTAVY YCARLERDWPLDAFDIWGQGTM VTVSS | SEQ ID NO: 153<br>QSALTQPASVSGSPGQSITISC TGTSSDVGGYNYVSWYQQHP GKAPKFMIYDVSKRPSGVSNR FSGSKSGNTASLTISGLQAEDE ADYYCSSYTSNNTFAFGGGT KLTVL |
| P2C-1D7 | SEQ ID NO: 162<br>EVQLVESGGGLIQPGGSLRLSCA ASGFTVSSNYMSWVRQAPGKGL EWVSVIYSGGSTYYADSVKGRFT ISRDNSKNTLYLQMNSLRAEDTA VYYCARELYEVGATDYWGQGTL VTVSS | SEQ ID NO: 163<br>DVVMTQSPLSLPVTLGQPASISC RSSQSLVYSDGNTYLNWFQQRP GQSPRRLIYKVSNWDSGVPDRFS GSGSGTDFTLKISRVEAEDVGVY YCMQRYTLAGVFGPGTKVDIK |
| P2B-1A10 | SEQ ID NO: 172<br>EVQLVESGGGLIQPGGSLRLSCA ASGFTVSSNYMSWVRQAPGKGL EWVSVIYSGGSTYYADSVKGRFT ISRDNSKNTLYLQMNSLRAEDTA VYYCAREGPKSITGTAFDIWGQG TIVTVSS | SEQ ID NO: 173<br>DIQMTQSPSSLSASVGDRVTITC QASQDISNYFNWYQQKPGKAPK LLIYDASNLETGVPSRFSGSGSG TDFTFTISSLQPEDIATYYCQQYD NLPMYTFGQGTKLEIK |
| P2B-1D9 | SEQ ID NO: 182<br>QITLKESGPTLVKPTQTLTLTCTF SGFSLSTSGVGVGWIRQPPGKAL EWLALIYWDDDKYYSPSLKSRLT ITKDTSKNQVVLTMTNMDPVDT ATYYCAHTRILYYGSGSYYDYW GQGTLVTVSS | SEQ ID NO: 183<br>QSVLTQPPSASGTPGQRVTISCS GSSSNIGSNYVYWYQQLPGTAP KLLIYSNNQRPSGVPDRFSGSKS GTSASLAISGLRSEDEADYYCAA WDDSLSGVVFGGGTKLTVL |
| P2B-1E4 | SEQ ID NO: 192<br>QITLKESGPTLVKPTQTLTLTCTF SGFSLSTSGVGVGWIRQPPGKAL EWLALIYWDDDKRYSPSLKSRLT ITKDTSKNQVVLTMTNMDPVDT ATYYCAHQIVATIIDYWGQGTLV TVSS | SEQ ID NO: 193<br>QSALTQPASVSGSPGQSITISCTG TSSDVGGYNYVSWYQQHPGKA PKLMIYDVSKRPSGVSNRFSGSK SGNTASLTISGLQAEDEADYYCS SYTSSSVVFGGGTKLTVL |
| P2B-1G1 | SEQ ID NO: 202<br>EVQLVESGGGLVQPGGSLRLSCA ASGFTVSSNYMSWVRQAPGKGL EWVSVIYSGGSTYYADSVKGRFT ISRDNSKNTLYLQMNSLRAEDTA VYYCARDYGDYWFDPWGQGTL VTVSS | SEQ ID NO: 203<br>EIVLTQSPGTLSLSPGERATLSCR ASQSVSSSYLAWYQQKPGQAPR LLIYGASSRATGIPDRFSGSGSGT DFTLTISRLEPEDFAVYYCQQYG SSPRTFGQGTKLEIK |
| P4A-2D9 | SEQ ID NO: 212<br>QVQLVESGGGVVQPGRSLRLSCA ASGFTFSSYGMHWVRQSPGKGL EWVAVISDDGSNQYYADSVKGR FTISRDNSKNTLYLEINSLRVEDT AVYYCAKRGGYCSTTSCLVRWV YFDYWGQGTLVTVSS | SEQ ID NO: 213<br>DIQMTQSPSSLSASVGDRVTITC RASQFISSYLNWYQQKPGKAPK LLIYATSILQTGVPSRFSGSGSGT DFTLTISSLQPEDFATYYCQQSY NTLTFGPGTKVDIK |

TABLE 2-continued

Variable region amino acid sequences of 42 antibodies

| | VH | VL |
|---|---|---|
| P5A-2G7 | SEQ ID NO: 222<br>QVQLQESGPGLVKPSETLSLTCT<br>VSGDSVSSGSYYWSWIRQPPGKG<br>LEWIGYIYYSGSTNYNPSLKSRVT<br>ISVDTSKNQFSLKLSSVTAADTA<br>VYYCARERCYYGSGRAPRCVWF<br>DPWGQGTLVTVSS | SEQ ID NO: 223<br>QSALTQPASVSGSPGQSITISCTG<br>TSSDVGGYNYVSWYQQHPGKA<br>PKLMIYDVSNRPSGVSNRFSGSK<br>SGNTASLTISGLQAEDEADYYCS<br>SYTSSSTLVVFGGGTKLTVL |
| P5A-3C8 | SEQ ID NO: 232<br>EVQLVESGGGLIQPGGSLRLSCA<br>ASGFTVSSNYMSWVRQAPGKGL<br>EWVSFIYSGGSTYYADSVKGRFT<br>ISRDNSKNTLYLQMNSLRAEDTA<br>VYYCARDLQEHGMDVWGQGTT<br>VTVSS | SEQ ID NO: 233<br>DIQLTQSPSSLSASVGDRVTITCR<br>ASQGISSYLAWYQQKPGKAPKL<br>LIYAASTLQSGVPSRFSGSGSGT<br>DFTLTISSLQPEDFATYYCQHLN<br>SYPPGYTFGQGTKLEIK |
| P5A-1D2 | SEQ ID NO: 242<br>EVQLVESGGGLIQPGGSLRLSCA<br>ASGFIVSSNYMSWVRQAPGKGLE<br>WVSIIYSGGSTYYADSVKGRFTIS<br>RDNSNNTLYLQMNSLRAEDTAV<br>YYCARALQVGATSDYFDYWGQ<br>GTLVTVSS | SEQ ID NO: 243<br>QSVLTQPPSVSGAPGQRVTISCT<br>GSSSNIGAGYDVHWYQQLPGTA<br>PKLLIYGNSNRPSGVPDRFSGSK<br>SGTSASLAITGLQAEDETDYYCQ<br>SCDSSLSVVVFGGGTKLTVL |
| P5A-2F11 | SEQ ID NO: 252<br>QVQLVQSGAEVKKPGASVKVSC<br>KASGYTFTSYDINWVRQATGQG<br>LEWMGWMNPNSGNTGYAQKFQ<br>GRVTMTRNTSISTAYMELSSLRS<br>EDTAVYYCARYIVVVPAAKGFD<br>PWGQGTLVTVSS | SEQ ID NO: 253<br>DIVMTQSPDSLAVSLGERATINC<br>KSSQSVLYSSNNKNYLAWYQQ<br>KPGQPPKLLIYWASTRESGVPDR<br>FSGSGSGTDFTLTISSLQAEDVA<br>VYYCQQYYSTPLTFGGGTKVEI<br>K |
| P5A-2E1 | SEQ ID NO: 262<br>EVQLVQSGAEVKKPGESLKISCK<br>GSGYSFTSYWIGWVRQMPGKGL<br>EWMGIIYPGDSDTRYSPSFQGQV<br>TISADKSISTAYLQWSSLKASDTA<br>MYYCAQTSVTRNWFDPWGQGT<br>LVTVSS | SEQ ID NO: 263<br>SYVLTQPPSVSVAPGKTARITCG<br>GNNIGSKSVHWYQQKPGQAPVL<br>VIYYDSDRPSGIPERFSGSNSGNT<br>ATLTISRVEAGDEADYYCQVWD<br>SSSDHVVFGGGTKLTVL |
| P5A-1C8 | SEQ ID NO: 272<br>QVQLVQSGAEVKKPGASVKVSC<br>KASGYTFTSYYMHWVRQAPGQG<br>LEWMGIINPSGGSTSYAQKFQGR<br>VTMTRDTSTSTVYMELSSLRSED<br>TAVYYCARSARDYYDSSGYYYR<br>AEYFQHWGQGTLVTVSS | SEQ ID NO: 273<br>DIQMTQSPSSLSASVGDRVTITC<br>QASQDISNYLNWYQQKPGKAPK<br>LLIYDASNLETGVPSRFSGSGSG<br>TDFTFTISSLQPEDIATYYCQQYD<br>NLPSITFGQGTRLEIK |
| P1A-1C10 | SEQ ID NO: 282<br>QVQLVQSGAEVKNPGSSVKVSC<br>KAGGGTSSFYDINWVRQAPGQG<br>LEWIGKIIPRLDIADYAQKSQGRV<br>TITADKSTSTVYLELSSLKSDDTA<br>VYFCARGRPGSEWAYGPFDLWG<br>QGTLVTVSS | SEQ ID NO: 283<br>DIQMTQSPSTLSASVGDRVTITC<br>RASQSSRAWLAWYQQKPGKAP<br>KLLISKASSLESGVPSRFSGSGYG<br>TEFTLTISSLQPDDSATYYCHQY<br>NSSPFTFGPGTKVQIK |
| P4A-1H6 | SEQ ID NO: 292<br>QVQLVESGGGVVQPGRSLRLSCA<br>ASGFTFSSYGMHWVRQSPGKGL<br>EWVAVISDDGSNQYYADSVKGR<br>FTISRDNSKNTLYLQMNSLRVED<br>TAVYYCAKRGGYCSTTSCLLRW<br>VYFDFWGQGTLATVSS | SEQ ID NO: 293<br>DIQMTQSPSSLSASVGDRVTITC<br>RASQSISSYLHWYQQKPGKAPN<br>LLIYAASSLQSGVPSRFSGSGSGT<br>DFTLTISSLQPEDFATYYCQQSY<br>NTPTFGPGTKVDIK |
| P4B-1F4 | SEQ ID NO: 302<br>QVQLVESGGGVVQPGRSLRLSCA<br>ASGFTFSSYGMHWVRQAPGKGL<br>EWVAVISYDGSNKYYADSVKGR<br>FTISRDNSKNTLYLQINSLRAEDT<br>AVYYCAKGPRYSSSWYISLYYY<br>YGMDVWGQGTTVTVSS | SEQ ID NO: 303<br>DVVMTQSPLSLPVTLGQPASISC<br>RSSQSLVYSDGNTYLNWFQQRP<br>GQSPRRLIYKVSNRDSGVPDRFS<br>GSGSGTDFTLKISRVEAEDVGVY<br>YCMQATHWPLYTFGQGTKLEIK |
| P5A-1B6 | SEQ ID NO: 312<br>QVQLVESGGGVVQPGRSLRLSCA<br>ASGFTFSSYAMHWVRQAPGKGL<br>EWVAVISYDGSNKYADSVKGR | SEQ ID NO: 313<br>DIQMTQSPSSLSASVGDRVTITC<br>QASQDISNYLNWYQQKPGKAPK<br>LLIYDASNLETGVPSRFSGSGSG |

TABLE 2-continued

Variable region amino acid sequences of 42 antibodies

| | VH | VL |
|---|---|---|
| | FTISRDNSKNTLYLQMNSLRAED<br>TAVYYCARDGQAITMVQGVIGPP<br>FDYWGQGTLVTVSS | TDFTFTISSLQPEDIATYYCQQYD<br>NLPYTFGQGTKLEIK |
| P5A-1B8 | SEQ ID NO: 322<br>EVQLVESGGGLIQPGGSLRLSCA<br>ASGFTVSSNYMSWVRQAPGKGL<br>EWVSVIYPGGSTFYADSVKGRFT<br>ISRDNSKNTLYLQMNSLRAEDTA<br>VYYCARETLAFDYWGQGTLVTV<br>SS | SEQ ID NO: 323<br>DIQLTQSPSFLSASVGDRVTITCR<br>ASQGISSYLAWYQQKPGKAPKL<br>LIYAASTLQSGVPSRFSGSGSTE<br>FTLTISSLQPEDFATYYCQQLNS<br>YPPAFGGGTKVEIK |
| P5A-1B9 | SEQ ID NO: 332<br>QVQLQESGPGLVKPSETLSLTCT<br>VSGGSISSYYWSWIRQPPGKGLE<br>WIGYISYSGSTNYNPSLKSRVTIS<br>LDTSKNQFSLKLSSVTAADTAVY<br>YCASNGQYYDILTGQPPDYWYF<br>DLWGRGTLVTVSS | SEQ ID NO: 333<br>DIVMTQSPDSLAVSLGERATINC<br>KSSQSVLYSSNNKNYLAWYQQ<br>KPGQPPKLLIYWASTRESGVPDR<br>FSGSGSGTDFTLTISSLQAEDVA<br>VYYCQQYYSTPLTFGGGTKVEI<br>K |
| P5A-1D1 | SEQ ID NO: 342<br>EVQLVESGGGLIQPGGSLRLSCA<br>ASGLTVSSNYMSWVRQAPGKGL<br>EWVSVIYSGGSTYYADSVKGRFT<br>ISRDNSKNTLYLQMNSLRAEDTA<br>VYYCARDLYYYGMDVWGQGTT<br>VTVST | SEQ ID NO: 343<br>DIQLTQSPSFLSASVGDRVTITCR<br>ASQGISSYLAWYQQKPGKAPKL<br>LIYAASTLQSGVPSRFSGSGSGT<br>DFTLTISSLQPEDFATYYCQQLN<br>SYPTFGQGTRLEIK |
| P5A-1D10 | SEQ ID NO: 352<br>QVQLVESGGGLVKPGGSLRLSCA<br>ASGFTFSDYSMTWIRQAPGKGLE<br>WVSYISQSGSTIYYADSVKGRFTI<br>SRDNAKNSLYLQMNSLRAEDTA<br>VYYCARGVSPSYVWGSYRSLYH<br>FDYWGQGTLVTVSS | SEQ ID NO: 353<br>QSALTQPASVSGSPGQSITISCTG<br>TSSDVGGYNYVSWYQQHPGKA<br>PKLMIYDVSNRPSGVSNRFSASK<br>SGNTASLTISGLQAEDEADYYCS<br>SFTSSTTVVVFGGGTKLTVL |
| P5A-2D11 | SEQ ID NO: 362<br>EVQLVQSGAEVKKPGESLKISCK<br>GSGYSFTSYWIGWVRQMPGKGL<br>EWMGIIYPGDSDTRYSPSFQGQV<br>TISADKSISTAYLQWSSLKASDTA<br>MYYCARRDSTYGGNTDYWGQG<br>TLVTVSS | SEQ ID NO: 363<br>QSVLTQPPSASGTPGQRVTISCS<br>GSSSNIGSNTVNWYQQLPGTAP<br>KLLIYSNNQRPSGVPDRFSGSKS<br>GTSASLAISGLQSEDEADYYCAA<br>WDDSLNGVVFGGGTKLTVL |
| P5A-2G9 | SEQ ID NO: 372<br>QVQLVESGGGVVQPGRSLRLSCA<br>ASGFTFSSYGMHWVRQAPGKGL<br>EWVAVIWYDGSNKYYADSVKG<br>RFTISRDNSKNTLYLQMNSLRAE<br>DTAVYYCARWFHTGGYFDYWG<br>QGTLVTVSS | SEQ ID NO: 373<br>QPVLTQPPSSASPGESARLTCTL<br>PSDINVSSYNIYWYQQKPGSPPR<br>YLLYYYSDSDKGQGSGVPSRFS<br>GSKDASANTGILLISGLQSEDEA<br>DYYCMIWPSNALYVFGTGTKVT<br>VL |
| P5A-2H3 | SEQ ID NO: 382<br>EVQLVQSGAEVKKPGESLKISCK<br>GSGYSFTSYWIGWVRQMPGKGL<br>EWMGIIYPGDSDTRYSPSFQGQV<br>TISAEKSISTAYLQWSSLKASDTAM<br>YYCARRDSTYGGNTDYWGQGTLVT<br>VSS | SEQ ID NO: 383<br>QSVLTQPPSASGTPGQRVTISCS<br>GSSSNIGSNTVNWYQQLPGTAP<br>KLLIYSNNQRPSGVPDRFSGSKS<br>GTSASLAISGLQSEDEADYYCAAW<br>DDSLNGVVFGGGTKLTVL |
| P5A-3A1 | SEQ ID NO: 392<br>EVQLVESGGGLIQPGGSLRLSCA<br>ASGFTVSSNYMSWVRQAPGKGL<br>EWVSVIYSGGSTYYADSVKGRFT<br>ISRDNSKNTLYLQMNSLRAEDTA<br>VYYCARDYGDFYFDYWGQGTLVTV<br>SS | SEQ ID NO: 393<br>EIVLTQSPGTLSLSPGERATLSCR<br>ASQSVSSSYLAWYQQKPGQAPR<br>LLIYGASSRATGIPDRFSGSGSGT<br>DFTLTISRLEPEDFAVYYCQQYG<br>SSPRTFGQGTKLEIK |
| P5A-3A6 | SEQ ID NO: 402<br>EVQLVESGGGLVQPGRSLRLSCA<br>ASGFTFDDYAMHWVRQAPGKGL<br>EWVSGISWNSGTIGYADSVKGRF<br>IISRDNAKNSLYLQMNSLRAEDT<br>ALYYCAGGGTMVRGVIAGGGTH<br>PVDDYYGMDVWGQGTTVTVSS | SEQ ID NO: 403<br>QSALTQPASVSGSPGQSITISCTG<br>TSSDVGGYNYVSWYQQHPGKA<br>PKLMIYDVSNRPSGVSNRFSGSK<br>SGNTASLTISGLQAEDEADYYCS<br>SYTSSSTVVFGGGTKLTVL |

TABLE 2-continued

Variable region amino acid sequences of 42 antibodies

| | VH | VL |
|---|---|---|
| P5A-3B4 | SEQ ID NO: 412<br>EVQLVQSGAEVKEPGESLKISCK<br>GSGYSFTSYWIGWVRQMPGKGL<br>EWMGIIYPGDSDTRYSPSFQGQV<br>TISADKSISTAYLQWSSLKASDTA<br>MYYCARRDSTYGGNTDYWGQGTLVT<br>VSS | SEQ ID NO: 413<br>QSVLTQPPSASGTPGQRVTISCS<br>GSSSNIGSNTVNWYQQLPGTAP<br>KLLIYSNNQRPSGVPDRFSGSKS<br>GTSASLAISGLQSEDEADYYCAA<br>WDDSLNGVVFGGGTKLTVL |
| P5A-3C12 | SEQ ID NO: 422<br>QITLKESGPTLVKPTQTLTLTCTF<br>SGFSLSTSGVGVGWIRQPPGKAL<br>EWLALIYWDDDKRYSPSLKSRLT<br>ITKDTSKNQVVLTMTNMDPVDT<br>ATYYCAHSLFLTVGYSSSWSPFD<br>YWGQGTLVTVSS | SEQ ID NO: 423<br>DIVMTQSPDSLAVSLGERATINC<br>KSSQSVLYSSNNKNYLAWYQQ<br>KPGQPPKLLIYWASTRESGVPDR<br>FSGSGSGTDFTLTISSLQAEDVA<br>VYYCQQYYSTPHTFGQGTKLEI<br>K |
| P22A-1D1 | SEQ ID NO: 432<br>EVQLVESGGGLIQPGGSLRLSCA<br>ASGFTVSSNYMSWVRQAPGKGL<br>EWVSVIYSGGSTYYADSVKGRFT<br>ISRDNSKNTLYLQMNSLRAEDTA<br>VYYCARDRDYYGMDVWGQGTTVTV<br>SS | SEQ ID NO: 433<br>DIQLTQSPSFLSASVGDRVTITCR<br>ASQGISSYLAWYQQKPGKAPKL<br>LIYAASTLQSGVPSRFSGSGSTE<br>FTLTISSLQPEDFATYYCLHLNSYR<br>TFGLGTKVEIK |

TABLE 3

Variable region nucleotide sequences of 42 antibodies

| | VHnu (nucleic acid) | VLnu (nucleic acid) |
|---|---|---|
| P2A-1A8 | SEQ ID NO: 9<br>GAAGTGCAGCTGGTGGAGTCTG<br>GGGGAGACTTGGTACAGCCTGG<br>CAGGTCCCTGAGACTCTCCTGC<br>GCAGCCTCTGGATTCGCCTTTG<br>ATGATTATGCCATGCACTGGGT<br>CCGGCAAGCTCCAGGGAAGGG<br>CCTGGAGTGGGTCTCAGGTAGT<br>ACTTGGAATAGTGGGACCATAG<br>CCTATGCGGACTCTGTGAAGGG<br>CCGATTCACCATCTCCAGAGAC<br>AACGCCAAGAAGTCCCTGTATC<br>TGCAAATGAACAGTCTGAGAAC<br>TGAGGACACGGCCTTATATTAC<br>TGTGCAAAGTTGGGGGGCTACA<br>GTGACTACGATTACCCGAGGCC<br>GGGAGACCACTATTACGGTTTG<br>GACGTCTGGGGCCAAGGGACCA<br>CGGTCACCGTCTCCTCA | SEQ ID NO: 10<br>CAGTCTGCCCTGACTCAGCCTG<br>CCTCCGTGTCTGGGTCTCCTGG<br>ACAGTCGATCACCATCTCCTGC<br>ACTGGAACCAGCAGTGATGTT<br>GGGAGTTATAACCTTGTCTCCT<br>GGTACCAACAGCACCCAGGCA<br>AAGTCCCCAAACTCTTGATTTA<br>TGATGTCAATAAGCGGCCCTCA<br>GGGATTTCCAATCGCTTCTCTG<br>GCTCCAAGTCTGGCAACACGG<br>CCTCCCTGACCATCTCTGGGCT<br>CCAGGCTGAGGACGAGGCTGA<br>TTATTACTGCAGATCATATACA<br>GACAGCAACACTTATGTCTTCG<br>GAACTGGGACCAAGGTCACCG<br>TCCTA |
| P2A-1A9 | SEQ ID NO: 19<br>GAAGTGCAGCTGGTGGAGTCTG<br>GGGGAGGCTTGGTACAGCCTGG<br>CAGGTCCCTGAGACTCTCCTGT<br>GCAGCCTCTGGATTCACCTTTG<br>ATGATTATGCCATGCACTGGGT<br>CCGGCAAGTTCCAGGGAAGGGC<br>CTGGAGTGGGTCTCAGGTATTA<br>GTTGGAATGGTGGTATCATAGG<br>CTACGCGGACTCTGTGAAGGGC<br>CGATTCACCATCTCCAGAGACA<br>ACGCCAAGACTTCCCTGTATCT<br>GCAAATGAACAGTCTGAGAGCT<br>GAGGACACGGCCTTGTATTACT<br>GTGCAAAGTCGCGGGAAGGG<br>GGGATTACGACTATTACTATGG<br>TATGGACGTCTGGGGCCAAGGG<br>ACCACGGTCACCGTCTCCTCA | SEQ ID NO: 20<br>CAGTCTGTGCTGACGCAGCCGC<br>CCTCAGTGTCTGGGGCCCCAGG<br>GCAGAGGGTCACCATCTCCTGC<br>ACTGGGAGCAGCTCCAACATC<br>GGGGCAGGTTATGATGTACAC<br>TGGTACCAGCAACTTCCAGGA<br>ACAGCCCCCAAACTCCTCATCT<br>ATGGTAACAACAATCGCCCCTC<br>AGGGGTCCCTGACCGATTCTCT<br>GGCTCCAAGTCTGGCACCTCAG<br>CCTCCCTGGCCATCACTGGGCT<br>CCAGGCTGAGGATGAGGCTGA<br>TTATTACTGCCAGTCCTATGAC<br>AGCAGCCTGAGTGGTTCGGTAT<br>TCGCGGAGGGACCAAGCTGA<br>CCGTCCTA |
| P2A-1A10 | SEQ ID NO: 29<br>CAGGTGCAGCTGGTGCAGTCTG<br>GGGCTGAGGTGAAGAAGCCTG<br>GGGCCTCAGTGAAGGTCTCCTG | SEQ ID NO: 30<br>GATATTGTGATGACCCAGACTC<br>CACTCTCCCTGCCCGTCACCCC<br>TGGAGAGCCGGCCTCCATCTCC |

TABLE 3-continued

Variable region nucleotide sequences of 42 antibodies

|  | VHnu (nucleic acid) | VLnu (nucleic acid) |
|---|---|---|
|  | CAAGGCTTCTGGATACACCTTC<br>ACCGGCTACTATATGCACTGGG<br>TGCGACAGGCCCCTGGACAAGG<br>GCTTGAGTGGATGGGACGGATC<br>AACCCTAACAGTGGTGGCACAA<br>ACTATGCACAGAAGTTTCAGGG<br>CAGGGTCACCATGACCAGGGAC<br>ACGTCCATCAGCACAGCCTACA<br>TGGAGCTGAGCAGGCTGAGATC<br>TGACGACACGGCCGTGTATTAC<br>TGTGCGAGAGTCCCCTATTGTA<br>GTAGTACCAGCTGCCATCGGGA<br>CTGGTACTTCGATCTCTGGGGC<br>CGTGGCACCCTGGTCACTGTCT<br>CCTCA | TGCAGGTCTAGTCAGAGCCTCT<br>TGGATAGTGATGATGGAAACA<br>CCTATTTGGACTGGTACCTGCA<br>GAAGCCAGGGCAGTCTCCACA<br>GCTCCTGATCTATACGCTTTCC<br>TATCGGGCCTCTGGAGTCCCAG<br>ACAGGTTCAGTGGCAGTGGGT<br>CAGGCACTGATTTCACACTGAA<br>AATCAGCAGGGTGGAGGCTGA<br>GGATGTTGGAGTTTATTACTGC<br>ATGCAACGTATAGAGTTTCCGC<br>TCACTTTCGGCGGAGGGACCA<br>AGGTGGAGATCAAA |
| P2A-1B3 | SEQ ID NO: 39<br>GAGGTGCAGCTGGTGGAGTCTG<br>GGGGAGGCTTGGTACAGCCTGG<br>GGGGTCCCTCAGACTCTCCTGT<br>GTCGCCTCTGGATTCTCCTTCAA<br>TCGATATAGTATGAATTGGCTC<br>CGCCAGACTCCACGGAAGGGGC<br>TGGAGTGGCTTTCATACATCAG<br>TGCCAGTGGAAACACCATATAC<br>TACGCTGACTCTGTGAGGGGCC<br>GATTCACCACCTCCAGAGACAA<br>TGCCAAGAACACACTGTATCTG<br>CAAATGAACAGCCTGCGAGACG<br>ACGACACGGCTGTCTATTTCTG<br>TGCGCGACCCGCTATGGTTCGG<br>GAGGGGACCTACAACTGGTTCG<br>ACCCCTGGGGCCAGGGAACCCT<br>GGTCACCGTCTCCTCA | SEQ ID NO: 40<br>GAAATTGTGTTGACGCAGTCTC<br>CAGGCACCCTGTCTTTGTCTCC<br>AGGGGAAAGAGCCACCCTCTC<br>CTGCAGGGCCAGTCAGAGTGT<br>TAGCAACGACTACTTAGCCTGG<br>TACCAGCAGAAACCTGGCCAG<br>GCTCCCAGGCTCCTCATCTACT<br>ATGCATCCAGCAGGGCCACTG<br>GCATCCCAGACAGGTTCAGTG<br>GCAGTGGGTCTGGGACAGACT<br>TCACTCTCACCATCAGCAGACT<br>GGAGCCTGGAGATTCTGCAGT<br>GTATTACTGTCAGCAGTATGGT<br>GACTCACCTCCGATCACCTTCG<br>GCCAAGGGACACGACTGGAGA<br>TTAAA |
| P2B-2F6 | SEQ ID NO: 49<br>CAGGTGCAGCTGCAGGAGTCGG<br>GCCCAGGACTGGTGAAGCCTTC<br>GGAGACCCTGTCCCTCACCTGC<br>ACTGTCTCTGGTTACTCCATCAG<br>CAGTGGTTACTACTGGGGCTGG<br>ATCCGGCAGCCCCAGGGAAGG<br>GGCTGGAGTGGATTGGGAGTAT<br>CTATCATAGTGGGAGCACCTAC<br>TACAACCCGTCCCTCAAGACTC<br>GAGTCACCATATCAGTAGACAC<br>GTCCAAGAACCAGTTCTCCCTG<br>AAGCTGAGCTCTGTGACCGCCG<br>CAGACACGGCCGTCTATTACTG<br>TGCGAGAGCGGTGGTAGGGATT<br>GTAGTAGTACCAGCTGCCGGTC<br>GTCGGGCTTTTGATATCTGGGG<br>CCAAGGGACAATGGTCACCGTC<br>TCCTCA | SEQ ID NO: 50<br>CAGTCTGCCCTGACTCAGCCTC<br>CCTCCGCGTCCGGGTCTCCTGG<br>ACAGTCAGTCACCATCTCCTGC<br>ACTGGAACCAGCAGTGACGTT<br>GGTGGTTATAACTATGTCTCCT<br>GGTACCAACAGCACCCAGGCA<br>AAGCCCCCAAACTCATGATTTA<br>TGAGGTCAGTAAGCGGCCCTC<br>AGGGGTCCCTGATCGCTTCTCT<br>GGCTCCAAGTCTGGCAACACG<br>GCCTCCCTGACCGTCTCTGGGC<br>TCCAGGCTGAGGATGAGGCTG<br>ATTATTACTGCAGCTCATATGC<br>AGGCAGCAACAATTTGGTGTTC<br>GGCGGAGGGACCAAGCTGACC<br>GTCCTA |
| P2B-2G4 | SEQ ID NO: 59<br>CAGGTGCAGCTGGTGGAGTCTG<br>GGGGAGGCGTGGTCCAGCCTGG<br>GAGGTCCCTGAGACTCTCCTGT<br>GCAGCGTCTGGATTCACCTTCA<br>GTAGCTATGGCATGCACTGGGT<br>CCGCCAGGCTCCAGGCAAGGGG<br>CTGGAGTGGGTGGCAGTTATAT<br>GGTATGATGGAAGTAATAAATA<br>CTATGCAGACTCCGTGAAGGGC<br>CGATTCACCATCTCCAGAGACA<br>ATTCCAAGAACACGCTGTATCT<br>GCAAATGAACAGCCTGAGAGCC<br>GAGGACACGGCTGTGTATTACT<br>GTGCGAGAGGGGCAGCTATGGT<br>TTGGCTTGACTACTGGGGCCAG<br>GGAACCCTGGTCACCGTCTCCT<br>CA | SEQ ID NO: 60<br>CAGTCTGCCCTGACTCAGCCTC<br>GCTCAGTGTCCGGGTCTCCTGG<br>ACAGTCAGTCACCATCTCCTGC<br>ACTGGAACCAGCAGTGATGTT<br>GGTGGTTATAACTATGTCTCCT<br>GGTACCAACAGCACCCAGGCA<br>AAGCCCCCAAACTCATGATTTA<br>TGATGTCAGTAAGCGGCCCTCA<br>GGGGTCCCTGATCGCTTCTCTG<br>GCTCCAAGTCTGGCAACACGG<br>CCTCCCTGACCATCTCTGGGCT<br>CCAGGCTGAGGATGAGGCTGA<br>TTATTACTGCTGCTCATATGCA<br>GGCAGCTACACTTTCGTGGTAT<br>TCGCGGAGGGACCAAGCTGA<br>CCGTCCTA |

TABLE 3-continued

Variable region nucleotide sequences of 42 antibodies

| | VHnu (nucleic acid) | VLnu (nucleic acid) |
|---|---|---|
| P2B-2G11 | SEQ ID NO: 63<br>GAAGTGCAGCTGGTGGAGTCTG<br>GGGGAGGCTTGGTACAGCCTGG<br>CAGGTCCCTGAGACTCTCCTGT<br>GCAGCCTCTGGATTCACCTTTG<br>ATGATTATGCCATGCACTGGGT<br>CCGGCAAGCTCCAGGGAAGGG<br>CCTGGAGTGGGTCTCAGGTATT<br>AGTTGGAATGGTGGTATCATAG<br>GCTATGCGGACTCTGTGAAGGG<br>CCGATTCACCATCTCCAGAGAC<br>AACGCCAAGACTTCCCTGTATC<br>TGCAAATGAACAGTCTGAAACC<br>TGAGGACACGGCCTTGTATTAC<br>TGTGCAAAAGTCGCGGGAAGG<br>GGGGATTACGACTACTACTACG<br>GTATGGACGTCTGGGGCCAAGG<br>GACCACGGTCACCGTCTCCTCA | SEQ ID NO: 64<br>CAGTCTGTGCTGACGCAGCCGC<br>CCTCAGTGTCTGGGGCCCCAGG<br>GCAGAGGGTCACCATCTCCTGC<br>ACTGGGAGCAGCTCCAACATC<br>GGGGCAGGTTATGATGTACAC<br>TGGTACCAGCAACTTCCAGGA<br>ACAGCCCCCAAACTCCTCATCT<br>ATGGGAACAACAATCGGCCCT<br>CAGGGGTCCCTGACCGATTCTC<br>TGGCTCCAAGTCTGGCACCTCA<br>GCCTCCCTGGCCATCACTGGGC<br>TCCAGGCTGAGGATGAGGCTG<br>ATTATTACTGCCAGTCCTATGA<br>CAGCAGCCTGAGTGGTTCGGT<br>ATTCGGCGGAGGGACCAAGCT<br>GACCGTCCTA |
| P2C-1A3 | SEQ ID NO: 73<br>CAGGTGCAGCTGGTGGAGTCTG<br>GGGGAGGCTTGGTCAAGCCTGG<br>AGGGTCCCTGAGACTCTCCTGT<br>GCAGCCTCTGGATTCACCTTCA<br>GTGACTACTACATGAGCTGGAT<br>CCGCCAGGCTCCAGGGAAGGG<br>GCTGGAGTGGGTTTCATACATT<br>AGTAGTAGTGGTAGTACCATAT<br>ACTACGCAGACTCTGTGAAGGG<br>CCGATTCACCATCTCCAGGGAC<br>AACGCCAAGAACTCACTGTATC<br>TGCAAATGAACAGCCTGAGAGC<br>CGAGGACACGGCTGTGTATTAC<br>TGTGCGAGAGATTTTCTCATC<br>AGCAGCTGGTACCTTCCTGGGG<br>CCAGGGAACCCTGGTCACCGTC<br>TCCTCA | SEQ ID NO: 74<br>GACATCCAGTTGACCCAGTCTC<br>CATCCTTCCTGTCTGCATCTGT<br>AGGAGACAGAGTCACCATCAC<br>TTGCCGGGCCAGTCAGGGCATT<br>AGCAGTTATTTAGCCTGGTATC<br>AGCAAAAACCAGGGAAAGCCC<br>CTAAGCTCCTGATCTATGCTGC<br>ATCCACTTTGCAAAGTGGGGTC<br>CCATCAAGGTTCAGCGGCAGT<br>GGATCTGGGACAGAATTCACT<br>CTCACAATCAGCAGCCTGCAG<br>CCTGAAGATTTTGCAACTTATT<br>ACTGTCAACAGCTTAATAGTTA<br>CCCGCTCACTTTCGGCGGAGGG<br>ACCAAGGTGGAGATCAAA |
| P2C-1C8 | SEQ ID NO: 83<br>CAGGTGCAGCTGGTGGAGTCTG<br>GGGGAGGCGTGGTCCAGCCTGG<br>GAGGTCCCTGAGACTCTCCTGT<br>GCAGCGTCTGGATTCACCTTCA<br>GGAGCTATGGCATGCACTGGGT<br>CCGCCAGGCTCCAGGCAAGGGG<br>CTGGAGTGGGTGGCAGTTATCT<br>GGTATGATGGAAGTAATAAATA<br>CTATGCAGACTCCGTGAAGGGC<br>CGATTCACCATCTCCAGAGACA<br>ATTCCAAGAACACGCTGTATCT<br>GCAAATGAACAGCCTGAGAGCC<br>GAGGACACGGCTGTGTATTACT<br>GTGCGAGAGATATAGAGATAGT<br>AGTGGTAAATATTGACTACTGG<br>GGCCAGGGAACCCTGGTCACCG<br>TCTCCTCA | SEQ ID NO: 84<br>GATGTTGTGATGACTCAGTCTC<br>CACTCTCCCTGCCCGTCACCCT<br>TGGACAGCCGGCCTCCATCTCC<br>TGCAGGTCTAGTCAAAGCCTCG<br>TATACAGTGATGGAAACACCT<br>ACTTGAATTGGTTTCAGCAGAG<br>GCCAGGCCAATCTCCAAGGCG<br>CCTAATTTATAAGGTTTCTATC<br>TGGGACTCTGGGGTCCCAGAC<br>AGATTCAGCGGCAGTGGGTCA<br>GGCACTGATTTCACACTGAAA<br>ATCAGCAGGGTGGAGGCTGAG<br>GATGTTGGGGTTATTACTGCA<br>TGCAAGGTACACACTGGCCGT<br>ACACTTTTGGCCAGGGGACCA<br>AGCTGGAGATCAAA |
| P2C-1C10 | SEQ ID NO: 93<br>CAGGTGCAGCTGGTGCAGTCTG<br>GGGCTGAGGTGAAGAAGCCTG<br>GGTCCTCGGTGAAGGTCTCCTG<br>CAAGGCTTCTGGAGGCACCTTC<br>AGCAGCTATGCTATCATCTGGG<br>TGCGACAGGCCCCTGGACAAGG<br>GCTTGAGTGGATGGGAGGGATC<br>ATCCCTATCTTTGGTACAGCAA<br>ACTACGCACAGAAGTTCCAGGG<br>CAGAGTCACGATTACCGCGGAC<br>GAATCCACGAGCACAGCCTACA<br>TGGAGCTGAGCAGCCTGAGATC<br>TGAGGACACGGCCGTGTATTAC<br>TGTGCGAGAGTGGTAACGGGGT<br>ACTACTTTGACTACTGGGGCCA<br>GGGAACCCTGGTCACCGTCTCC<br>TCA | SEQ ID NO: 94<br>GAAATTGTGTTGACACAGTCTC<br>CAGCCACCCTGTCTTTGTCTCC<br>AGGGGAAAGAGCCACCCTCTC<br>CTGCAGGGCCAGTCAGAGTGT<br>TAGCAGCTACTTAGCCTGGTAC<br>CAACAGAAACCTGGCCAGGCT<br>CCCAGGCTCCTCATCTATGATG<br>CATCCAACAGGGCCACTGGCA<br>TCCCAGCCAGGTTCAGTGGCA<br>GTGGGTCTGGGACAGACTTCA<br>CTCTCACCATCAGCAGCCTAGA<br>GCCTGAAGATTTTGCAGTTTAT<br>TACTGTCAGCAGCGTAGCAACT<br>GGCCTTCTTTTGGCCAGGGGAC<br>CAAGCTGGAGATCAAA |

TABLE 3-continued

Variable region nucleotide sequences of 42 antibodies

| | VHnu (nucleic acid) | VLnu (nucleic acid) |
|---|---|---|
| P2C-1D5 | SEQ ID NO: 103<br>GAGGTGCAGCTGGTGGAGTCTG<br>GGGGAGGCTTGGTACAGCCTGG<br>GGGGTCCCTGAGACTCTCCTGT<br>GCAGCCTCTGGATTCACCTTTA<br>GCAGCTTTGCCATGAGCTGGGT<br>CCGCCAGGCTCCAGGGAAGGG<br>GCTGGAGTGGGTCTCAGCTATT<br>AGTGGTAGTGGTGGTAGCACAT<br>ACTACGCAGACTCCGTGAAGGG<br>CCGGTTCACCATCTCCAGAGAC<br>AATTCCAAGAACACGCTGTATT<br>TGCAAATGAACAGCCTGAGAGC<br>CGAGGACACGGCCGTATATTAC<br>TGTGCGAAAGATCCGGATGGTT<br>CGGGGAGTTGGTACTTTGACTA<br>CTGGGGCCAGGGAACCCTGGTC<br>ACCGTCTCCTCA | SEQ ID NO: 104<br>TCCTATGTGCTGACTCAGCCAC<br>CCTCAGTGTCAGTGGCCCCAGG<br>AAAGACGGCCAGGATTACCTG<br>TGGGGGAAACAACATTGGAAG<br>TAAAAGTGTGCACTGGTACCA<br>GCAGAAGCCAGGCCAGGCCCC<br>TGTGCTGGTCATCTATTATGAT<br>AGCGACCGGCCCTCAGGGATC<br>CCTGAGCGATTCTCTGGCTCCA<br>ACTCTGGGAACACCGCCACCCT<br>GACCATCAGCAGGGTCGAAGC<br>CGGGGATGAGGCCGACTATTA<br>CTGTCAGGTGTGGGATAGTAGT<br>AGTGATCATCATGTCTTCGGAA<br>CTGGGACCAAGGTCACCGTCCTA |
| P2C-1F11 | SEQ ID NO: 113<br>GAGGTGCAGCTGGTGGAGTCTG<br>GGGGAGGCTTGGTCCAGCCTGG<br>GGGGTCCCTGAGACTCTCCTGT<br>GCAGCCTCTGGAATCACCGTCA<br>GTAGCAACTACATGAACTGGGT<br>CCGCCAGGCTCCAGGGAAGGG<br>GCTGGAGTGGGTCTCACTTATT<br>TATAGCGGTGGTAGCACATACT<br>ACGCAGACTCCGTGAAGGGCAG<br>ATTCACCATCTCCAGAGACAAT<br>TCCAAGAACACGTTGTATCTTC<br>AAATGAACAGCCTGAGAGCCG<br>AGGACACGGCTGTGTATCACTG<br>TGCGAGAGATCTGGTGGTATAC<br>GGTATGGACGTCTGGGGCCAAG<br>GGACCACGGTCACCGTCTCCTC<br>A | SEQ ID NO: 114<br>GAAATTGTGTTGACGCAGTCTC<br>CAGGCACCCTGTCTTTGTCTCC<br>AGGGGAAAGAGCCACCCTCTC<br>CTGCAGGGCCAGTCAGAGTGT<br>TAGCAGCAGCTACTTAGCCTGG<br>TACCAGCAGAAACCTGGCCAG<br>GCTCCCAGGCTCCTCATCTATG<br>GTGCATCCAGCAGGGCCACTG<br>GCATCCCAGACAGGTTCAGTG<br>GCAGTGGGTCTGGGACAGACT<br>TCACTCTCACCATCAGCAGACT<br>GGAGCCTGAAGATTTTGCAGT<br>GTATTACTGTCAGCAGTATGGT<br>AGCTCACCCACTTTTGGCCAGG<br>GGACCAAGCTGGAGATCAAA |
| P2B-1G5 | SEQ ID NO: 144<br>CAGGTGCAGCTGGTGCAATCTG<br>GTCTGAGTTGAAGAAGCCTGG<br>GGCCTCAGTGAAGGTTTCCTGC<br>AAGGCTTCTGGATACACCTTCA<br>CTACCTATGTTATGAATTGGGT<br>GCGACAGGCCCCTGGACAAGG<br>GCTTGAGTGGATGGGATGGATC<br>AACACCAACACTGGGAACCCAA<br>CGTATGCCCAGGGCTTCACAGG<br>ACGGTTTGTCTTCTCCTTGGACA<br>CCTCTGTCAGCACGGCATCTCT<br>GCAGATCAGCAGCCTAAAGGCT<br>GAGGACACTGCCGTGTATTACT<br>GTTCGTGTGAAATAACCACCTT<br>GGGCGGTATGGACGTCTGGGGC<br>CAAGGGACCACGGTCACCGTCT<br>CCTCA | SEQ ID NO: 145<br>TCCTATGTGCTGACTCAGCCAC<br>CCTCAGTGTCAGTGGCCCCAGG<br>AAAGACGGCCAGGATTACCTG<br>TGGGGGAAACAACATTGGAAG<br>TAAAAGTGTGCACTGGTACCA<br>GCAGAAGCCAGGCCAGGCCCC<br>TGTGCTGGTCATCTATTATGAT<br>AGCGACCGGCCCTCAGGGATC<br>CCTGAGCGATTCTCTGGCTCCA<br>ACTCTGGGAACACGGCCACCC<br>TGACCATCAGCGGGGTCGAAGC<br>CCGGGGATGAGGCCGACTATT<br>ACTGTCAGGTGTGGGATAGTAT<br>TAGTGATCATCGGGTGTTCGGC<br>GGAGGGACCAAGCTGACCGTCCTA |
| P2B-1A1 | SEQ ID NO: 154<br>CAGGTGCAGCTGCAGGAGTCGG<br>GCCCAGGACTGGTGAAGCCTTC<br>GGAGACCCTGTCCCTCACCTGC<br>ACTGTCTCTGGTGGCTCCATCA<br>GTAGTTACTACTGGAGCTGGAT<br>CCGGCAGCCCCAGGGAAGGG<br>ACTGGAGTGGATTGGGTATATC<br>TATTACAGTGGGAGCACCAACT<br>ACAACCCCTCCCTCAAGAGTCG<br>AGTCACCATATCAGTAGACACG<br>TCCAAGAAGCAGTTCTCCCTGA<br>AGCTGAGCTCTGTGACCGCTGC<br>GGACACGGCCGTGTATTACTGT<br>GCGAGGCTCGAACGAGACTGGC<br>CACTTGATGCTTTTGATATCTGG<br>GGCCAAGGGACAATGGTCACCG<br>TCTCCTCA | SEQ ID NO: 155<br>CAGTCTGCCCTGACTCAGCCTG<br>CCTCCGTGTCTGGGTCTCCTGG<br>ACAGTCGATCACCATCTCCTGC<br>ACTGGAACCAGCAGTGACGTT<br>GGTGGTTATAACTATGTCTCCT<br>GGTACCAACAGCACCCAGGCA<br>AAGCCCCCAAATTCATGATTTA<br>TGATGTCAGTAAGCGGCCCTCA<br>GGGGTTTCTAATCGCTTCTCTG<br>GCTCCAAGTCTGGCAACACGG<br>CCTCCCTGACCATCTCTGGGCT<br>CCAGGCTGAGGACGAGGCTGA<br>TTATTACTGCAGCTCATATACA<br>AGCAACAACACTTTCGCGTTCG<br>GCGGAGGGACCAAGCTGACCG<br>TCCTA |

TABLE 3-continued

Variable region nucleotide sequences of 42 antibodies

| | VHnu (nucleic acid) | VLnu (nucleic acid) |
|---|---|---|
| P2C-1D7 | SEQ ID NO: 164<br>GAGGTGCAGCTGGTGGAGTCTG<br>GAGGAGGCTTGATCCAGCCTGG<br>GGGGTCCCTGAGACTCTCCTGT<br>GCAGCCTCTGGGTTCACCGTCA<br>GTAGCAACTACATGAGCTGGGT<br>CCGCCAGGCTCCAGGGAAGGG<br>GCTGGAGTGGGTCTCAGTTATT<br>TATAGCGGTGGTAGCACATACT<br>ACGCAGACTCCGTGAAGGGCCG<br>ATTCACCATCTCCAGAGACAAT<br>TCCAAGAACACGCTGTATCTTC<br>AAATGAACAGCCTGAGAGCCG<br>AGGACACGGCCGTGTATTACTG<br>TGCGAGAGAATTGTACGAAGTG<br>GGAGCTACGGACTACTGGGGCC<br>AGGGAACCCTGGTCACCGTCTC<br>CTCA | SEQ ID NO: 165<br>GATGTTGTGATGACTCAGTCTC<br>CACTCTCCCTGCCCGTCACCCT<br>TGGACAGCCGGCCTCCATCTCC<br>TGCAGGTCTAGTCAAAGCCTCG<br>TATACAGTGATGGAAACACCT<br>ACTTGAATTGGTTTCAGCAGAG<br>GCCAGGCCAATCTCCAAGGCG<br>CCTAATTTATAAGGTTTCTAAC<br>TGGGACTCTGGGGTCCCAGAC<br>AGATTCAGCGGCAGTGGGTCA<br>GGCACTGATTTCACACTGAAA<br>ATCAGCAGGGTGGAGGCTGAG<br>GATGTTGGGGTTTATTACTGCA<br>TGCAACGGTACACACTGGCCG<br>GCGTTTTCGGCCCTGGGACCAA<br>AGTGGATATCAAA |
| P2B-1A10 | SEQ ID NO: 174<br>GAGGTGCAGCTGGTGGAGTCTG<br>GAGGAGGCTTGATCCAGCCTGG<br>GGGGTCCCTGAGACTCTCCTGT<br>GCAGCCTCTGGGTTCACCGTCA<br>GTAGCAACTACATGAGCTGGGT<br>CCGCCAGGCTCCAGGGAAGGG<br>GCTGGAGTGGGTCTCAGTTATT<br>TATAGCGGTGGTAGCACATACT<br>ACGCAGACTCCGTGAAGGGCCG<br>ATTCACCATCTCCAGAGACAAT<br>TCCAAGAACACGCTGTATCTTC<br>AAATGAACAGCCTGAGAGCCG<br>AGGACACGGCCGTTTATTACTG<br>TGCGAGAGAGGGCCCAAAGTCT<br>ATTACAGGGACGGCTTTTGATA<br>TCTGGGGCCAAGGGACAATTGT<br>CACCGTCTCCTCA | SEQ ID NO: 175<br>GACATCCAGATGACCCAGTCTC<br>CATCCTCCCTGTCTGCATCTGT<br>AGGAGACAGAGTCACCATCAC<br>TTGCCAGGCGAGTCAGGACAT<br>TAGCAACTATTTTAATTGGTAT<br>CAGCAGAAACCAGGGAAAGCC<br>CCTAAGCTCCTGATCTACGATG<br>CATCCAATTTGGAAACAGGGG<br>TCCCATCAAGGTTCAGTGGAA<br>GTGGATCTGGGACAGATTTTAC<br>TTTCACCATCAGCAGCCTGCAG<br>CCTGAAGATATTGCAACATATT<br>ACTGTCAACAGTATGATAATCT<br>CCCCATGTACACTTTTGGCCAG<br>GGGACCAAGCTGGAGATCAAA |
| P2B-1D9 | SEQ ID NO: 184<br>CAGATCACCTTGAAGGAGTCTG<br>GTCCTACGCTGGTGAAACCCAC<br>ACAGACCCTCACGCTGACCTGC<br>ACCTTCTCTGGGTTCTCACTCAG<br>CACTAGTGGAGTGGGTGTGGGC<br>TGGATCCGTCAGCCCCCAGGAA<br>AGGCCCTGGAGTGGCTTGCACT<br>CATTTATTGGGATGATGATAAA<br>TACTACAGCCCATCTCTGAAGA<br>GCAGGCTCACCATCACCAAGGA<br>CACCTCCAAAAACCAGGTGGTC<br>CTTACAATGACCAACATGGACC<br>CTGTGGACACAGCCACATATTA<br>CTGTGCACACACTCGCATCTTA<br>TACTATGGTTCGGGGAGTTATT<br>ATGACTACTGGGGCCAGGGAAC<br>CCTGGTCACCGTCTCCTCA | SEQ ID NO: 185<br>CAGTCTGTGCTGACTCAGCCAC<br>CCTCAGCGTCTGGGACCCCCGG<br>GCAGAGGGTCACCATCTCTTGT<br>TCTGGAAGCAGCTCCAACATC<br>GGAAGTAATTATGTATACTGGT<br>ACCAGCAGCTCCCAGGAACGG<br>CCCCCAAACTCCTCATCTATAG<br>TAATAATCAGCGGCCCTCAGG<br>GGTCCCTGACCGATTCTCTGGC<br>TCCAAGTCTGGCACCTCAGCCT<br>CCCTGGCCATCAGTGGGCTCCG<br>GTCCGAGGATGAGGCTGATTA<br>TTACTGTGCAGCATGGGATGAC<br>AGCCTGAGTGGTGTGGTATTCG<br>GCGGAGGGACCAAGCTGACCG<br>TCCTA |
| P2B-1E4 | SEQ ID NO: 194<br>CAGATCACCTTGAAGGAGTCTG<br>GTCCTACGCTGGTGAAACCCAC<br>ACAGACCCTCACGCTGACCTGC<br>ACCTTCTCTGGGTTCTCACTCAG<br>CACTAGTGGAGTGGGTGTGGGC<br>TGGATCCGTCAGCCCCCAGGAA<br>AGGCCCTGGAGTGGCTTGCACT<br>CATTTATTGGGATGATGATAAG<br>CGCTACAGCCCATCTCTGAAGA<br>GCAGGCTCACCATCACCAAGGA<br>CACCTCCAAAAACCAGGTGGTC<br>CTTACAATGACCAACATGGACC<br>CTGTGGACACAGCCACATATTA<br>CTGTGCACACCAAATAGTGGCT<br>ACGATTATTGACTACTGGGGCC<br>AGGGAACCCTGGTCACCGTCTC<br>CTCA | SEQ ID NO: 195<br>CAGTCTGCCCTGACTCAGCCTG<br>CCTCCGTGTCTGGGTCTCCTGG<br>ACAGTCGATCACCATCTCCTGC<br>ACTGGAACCAGCAGTGACGTT<br>GGTGGTTATAACTATGTCTCCT<br>GGTACCAACAGCACCCAGGCA<br>AAGCCCCCAAACTCATGATTTA<br>TGATGTCAGTAAGCGGCCCTCA<br>GGGGTTTCTAATCGCTTCTCTG<br>GCTCCAAGTCTGGCAACACGG<br>CCTCCCTGACCATCTCTGGGCT<br>CCAGGCTGAGGACGAGGCTGA<br>TTATTACTGCAGCTCATATACA<br>AGCAGCAGCGTGGTATTCGGC<br>GGAGGGACCAAGCTGACCGTCCTA |

TABLE 3-continued

Variable region nucleotide sequences of 42 antibodies

| | VHnu (nucleic acid) | VLnu (nucleic acid) |
|---|---|---|
| P2B-1G1 | SEQ ID NO: 204<br>GAGGTGCAGCTGGTGGAGTCTG<br>GGGGAGGCTTGGTCCAGCCTGG<br>GGGGTCCCTGAGACTCTCCTGT<br>GCAGCCTCTGGATTCACCGTCA<br>GTAGCAACTACATGAGCTGGGT<br>CCGCCAGGCTCCAGGGAAGGG<br>GCTGGAGTGGGTCTCAGTTATT<br>TATAGCGGTGGTAGCACATACT<br>ACGCAGACTCCGTGAAGGGCAG<br>ATTCACCATCTCCAGAGACAAT<br>TCCAAGAACACGCTGTATCTTC<br>AAATGAACAGCCTGAGAGCCG<br>AGGACACGGCTGTGTATTACTG<br>TGCGAGAGACTACGGTGACTAC<br>TGGTTCGACCCCTGGGGCCAGG<br>GAACCCTGGTCACCGTCTCCTCA | SEQ ID NO: 205<br>GAAATTGTGTTGACGCAGTCTC<br>CAGGCACCCTGTCTTTGTCTCC<br>AGGGGAAAGAGCCACCCTCTC<br>CTGCAGGGCCAGTCAGAGTGT<br>TAGCAGCAGCTACTTAGCCTGG<br>TACCAGCAGAAACCTGGCCAG<br>GCTCCCAGGCTCCTCATCTATG<br>GTGCATCCAGCAGGGCCACTG<br>GCATCCCAGACAGGTTCAGTG<br>GCAGTGGGTCTGGGACAGACT<br>TCACTCTCACCATCAGCAGACT<br>GGAGCCTGAAGATTTTGCAGT<br>GTATTACTGTCAGCAGTATGGT<br>AGCTCACCGAGGACTTTTGGCC<br>AGGGGACCAAGCTGGAGATCAAA |
| P4A-2D9 | SEQ ID NO: 214<br>CAGGTGCAGCTGGTGGAGTCTG<br>GGGGAGGCGTGGTCCAGCCTGG<br>GAGGTCCCTGAGACTCTCCTGT<br>GCAGCCTCTGGATTCACCTTCA<br>GTAGCTATGGCATGCACTGGGT<br>CCGCCAGTCTCCAGGCAAGGGG<br>CTGGAGTGGGTGGCAGTTATAT<br>CAGATGATGGAAGTAATCAATA<br>CTATGCAGACTCCGTGAAGGGC<br>CGATTCACCATCTCCAGAGACA<br>ATTCCAAGAACACGCTGTATCT<br>GGAAATCAACAGCCTGAGAGTT<br>GAGGACACGGCTGTGTATTACT<br>GTGCGAAAAGGGGCGGATATTG<br>TAGTACTACCAGCTGCCTCGTT<br>AGGTGGGTCTACTTTGACTACT<br>GGGGCCAGGGAACCCTGGTCAC<br>CGTCTCCTCA | SEQ ID NO: 215<br>GACATCCAGATGACCCAGTCTC<br>CATCCTCCCTGTCTGCATCTGT<br>AGGAGACAGAGTCACCATCAC<br>TTGCCGGGCAAGTCAGTTCATT<br>AGCAGCTACTTAAATTGGTATC<br>AGCAGAAACCAGGGAAAGCCC<br>CTAAGCTCCTGATCTATGCTAC<br>ATCCATTTTGCAAACTGGGGTC<br>CCATCAAGGTTCAGTGGCAGT<br>GGATCTGGGACAGATTTCACTC<br>TCACCATCAGCAGTCTGCAACC<br>TGAAGATTTTGCAACTTACTAC<br>TGTCAACAGAGTTACAATACCC<br>TTACTTTCGGCCCTGGGACCAA<br>AGTCGATATCAAA |
| P5A-2G7 | SEQ ID NO: 224<br>CAGGTGCAGCTGCAGGAGTC<br>GGGCCCAGGACTGGTGAAGC<br>CTTCGGAGACCCTGTCCCTCA<br>CCTGCACTGTCTCTGGTGACT<br>CCGTCAGCAGTGGTAGTTAC<br>TACTGGAGCTGGATCCGGCA<br>GCCCCCAGGGAAGGGACTGG<br>AGTGGATTGGGTATATCTATT<br>ACAGTGGGAGCACCAACTAC<br>AACCCCTCCCTCAAGAGTCG<br>AGTCACCATATCAGTAGACA<br>CGTCCAAGAACCAGTTCTCC<br>CTGAAGCTGAGCTCTGTGAC<br>CGCTGCGGACACGGCCGTGT<br>ATTACTGTGCGAGAGAGCGA<br>TGTTACTATGGTTCAGGGAG<br>AGCCCCCCGTTGTGTCTGGTT<br>CGACCCCTGGGGCCAGGGAA<br>CCCTGGTCACCGTCTCCTCA | SEQ ID NO: 225<br>CAGTCTGCCCTGACTCAGCCTG<br>CCTCCGTGTCTGGGTCTCCTGG<br>ACAGTCGATCACCATCTCCTGC<br>ACTGGAACCAGCAGTGACGTT<br>GGTGGTTATAACTATGTCTCCT<br>GGTACCAACAACACCCAGGCA<br>AAGCCCCCAAACTCATGATTTA<br>TGATGTCAGTAATCGGCCCTCA<br>GGGGTTTCTAATCGCTTCTCTG<br>GCTCCAAGTCTGGCAACACGG<br>CCTCCCTGACCATCTCTGGGCT<br>CCAGGCTGAGGACGAGGCTGA<br>TTATTACTGCAGCTCATATACA<br>AGCAGCAGCACTCTCGTGGTAT<br>TCGGCGGAGGGACCAAGCTGA<br>CCGTCCTA |
| P5A-3C8 | SEQ ID NO: 234<br>GAGGTGCAGCTGGTGGAGTCTG<br>GAGGAGGCTTGATCCAGCCTGG<br>GGGGTCCCTGAGACTCTCCTGT<br>GCAGCCTCTGGGTTCACCGTCA<br>GTAGCAACTACATGAGCTGGGT<br>CCGCCAGGCTCCAGGGAAGGG<br>GCTGGAATGGGTCTCATTTATTT<br>ATAGCGGTGGTAGTACATACTA<br>CGCAGACTCCGTGAAGGGCCGA<br>TTCACCATCTCCAGAGACAATT<br>CCAAGAACACGCTGTATCTTCA<br>AATGAACAGCCTGAGAGCCGA<br>GGACACGGCCGTGTATTACTGT<br>GCGAGAGATCTACAGGAACAC<br>GGTATGGACGTCTGGGGCCAAG<br>GGACCACGGTCACCGTCTCCTCA | SEQ ID NO: 235<br>GACATCCAGTTGACCCAGTCTC<br>CATCCTCCCTGTCTGCATCTGT<br>AGGAGACAGAGTCACCATCAC<br>TTGCCGGGCCAGTCAGGGCATT<br>AGCAGTTATTTAGCCTGGTATC<br>AGCAAAAACCAGGGAAAGCCC<br>CTAAGCTCCTGATCTATGCTGC<br>ATCCACTTTGCAAAGTGGGGTC<br>CCATCAAGGTTCAGCGGCAGT<br>GGATCTGGGACAGATTTCACTC<br>TCACCATCAGCAGCTGCAACC<br>TGAAGATTTTGCAACTTATTAC<br>TGTCAACACCTTAATAGTTACC<br>CTCCGGGGTACACTTTTGGCCA<br>GGGGACCAAGCTGGAGATCAA<br>A |

TABLE 3-continued

Variable region nucleotide sequences of 42 antibodies

| | VHnu (nucleic acid) | VLnu (nucleic acid) |
|---|---|---|
| P5A-1D2 | SEQ ID NO: 244<br>GAGGTGCAGCTGGTGGAGTCTG<br>GAGGAGGCTTGATCCAGCCTGG<br>GGGGTCCCTGAGACTCTCCTGT<br>GCAGCCTCTGGGTTCATCGTCA<br>GTAGCAACTACATGAGCTGGGT<br>CCGCCAGGCTCCAGGGAAGGG<br>GCTGGAGTGGGTCTCAATTATT<br>TATAGCGGTGGTAGCACATACT<br>ACGCAGACTCCGTGAAGGGCCG<br>ATTCACCATCTCCAGAGACAAT<br>TCCAACAACACGCTGTATCTTC<br>AAATGAACAGCCTGAGAGCCG<br>AGGACACGGCCGTATATTACTG<br>TGCGAGAGCCCTCCAGGTGGGA<br>GCTACTTCGGACTACTTTGACT<br>ACTGGGGCCAGGGAACCCTGGT<br>CACCGTCTCCTCA | SEQ ID NO: 245<br>CAGTCTGTGCTGACGCAGCCGC<br>CCTCAGTGTCTGGGGCCCCAGG<br>GCAGAGGGTCACCATCTCCTGC<br>ACTGGGAGCAGCTCCAACATC<br>GGGGCAGGTTATGATGTACAC<br>TGGTACCAGCAACTTCCAGGA<br>ACAGCCCCCAAACTCCTCATCT<br>ATGGTAACAGCAATCGGCCCT<br>CAGGGGTCCCTGACCGATTCTC<br>TGGCTCCAAGTCTGGCACCTCA<br>GCCTCCCTGGCCATCACTGGGC<br>TCCAGGCTGAAGATGAGACTG<br>ATTATTACTGCCAGTCCTGTGA<br>CAGCAGCCTGAGTGTTGTGGTA<br>TTCGGCGGAGGGACCAAGCTG<br>ACCGTCCTA |
| P5A-2F11 | SEQ ID NO: 254<br>CAGGTGCAGCTGGTGCAGTCTG<br>GGGCTGAGGTGAAGAAGCCTG<br>GGGCCTCAGTGAAGGTCTCCTG<br>CAAGGCTTCTGGATACACCTTC<br>ACCAGTTATGATATCAACTGGG<br>TGCGACAGGCCACTGGACAAGG<br>GCTTGAGTGGATGGGATGGATG<br>AACCCTAACAGTGGTAACACAG<br>GCTATGCACAGAAGTTCCAGGG<br>CAGAGTCACCATGACCAGGAAC<br>ACCTCCATAAGCACAGCCTACA<br>TGGAGCTGAGCAGCCTGAGATC<br>TGAGGACACGGCCGTGTATTAC<br>TGTGCGAGATATATTGTAGTAG<br>TACCAGCTGCAAAAGGGTTCGA<br>CCCCTGGGGCCAGGGAACCCTG<br>GTCACCGTCTCCTCA | SEQ ID NO: 255<br>GACATCGTGATGACCCAGTCTC<br>CAGACTCCCTGGCTGTGTCTCT<br>GGGCGAGAGGGCCACCATCAA<br>CTGCAAGTCCAGCCAGAGTGTT<br>TTATACAGCTCCAACAATAAG<br>AACTACTTAGCTTGGTACCAGC<br>AGAAACCAGGACAGCCTCCTA<br>AGCTGCTCATTTACTGGGCATC<br>TACCCGGGAATCCGGGGTCCCT<br>GACCGATTCAGTGGCAGCGGG<br>TCTGGGACAGATTTCACTCTCA<br>CCATCAGCAGCCTGCAGGCTG<br>AAGATGTGGCAGTTTATTACTG<br>TCAGCAATATTATAGTACTCCT<br>CTCACTTTCGGCGGAGGGACC<br>AAGGTGGAGATCAAA |
| P5A-2E1 | SEQ ID NO: 264<br>GAGGTGCAGCTGGTGCAGTCTG<br>GAGCAGAGGTGAAAAAGCCCG<br>GGGAGTCTCTGAAGATCTCCTG<br>TAAGGGTTCTGGATACAGCTTT<br>ACCAGCTACTGGATCGGCTGGG<br>TGCGCCAGATGCCCGGGAAGG<br>CCTGGAGTGGATGGGGATCATC<br>TATCCTGGTGACTCTGATACCA<br>GATACAGCCCGTCCTTCCAAGG<br>CCAGGTCACCATCTCAGCCGAC<br>AAGTCCATCAGCACCGCCTACC<br>TGCAGTGGAGCAGCCTGAAGGC<br>CTCGGACACCGCCATGTATTAC<br>TGTGCCCAGACGTCAGTGACTC<br>GCAACTGGTTCGACCCCTGGGG<br>CCAGGGAACCCTGGTCACCGTC<br>TCCTCA | SEQ ID NO: 265<br>TCCTATGTGCTGACTCAGCCAC<br>CCTCAGTGTCAGTGGCCCCAGG<br>AAAGACGGCCAGGATTACCTG<br>TGGGGGAAACAACATTGGAAG<br>TAAAAGTGTGCACTGGTACCA<br>GCAGAAGCCAGGCCAGGCCCC<br>TGTGCTGGTCATCTATTATGAT<br>AGCGACCGGCCCTCAGGGATC<br>CCTGAGCGATTCTCTGGCTCCA<br>ACTCTGGGAACACGGCCACCC<br>TGACCATCAGCAGGGTCGAAG<br>CCGGGGATGAGGCCGACTATT<br>ACTGTCAGGTGTGGGATAGTA<br>GTAGTGATCATGTGGTATTCGG<br>CGGAGGGACCAAGCTGACCGT<br>CCTA |
| P5A-1C8 | SEQ ID NO: 274<br>CAGGTGCAGCTGGTGCAGTCTG<br>GGGCTGAGGTGAAGAAGCCTG<br>GGGCCTCAGTGAAGGTTTCCTG<br>CAAGGCATCTGGATACACCTTC<br>ACCAGCTACTATATGCACTGGG<br>TGCGACAGGCCCCTGGACAAGG<br>GCTTGAGTGGATGGGAATAATC<br>AACCCTAGTGGTGGTAGCACAA<br>GCTACGCACAGAAGTTCCAGGG<br>CAGAGTCACCATGACCAGGGAC<br>ACGTCCACGAGCACAGTCTACA<br>TGGAGCTGAGCAGCCTGAGATC<br>TGAGGACACGGCCGTGTATTAC<br>TGTGCGAGGTCGGCCCGGGATT<br>ACTATGATAGTAGTGGTTATTA | SEQ ID NO: 275<br>GACATCCAGATGACCCAGTCTC<br>CATCCTCCCTGTCTGCATCTGT<br>AGGAGACAGAGTCACCATCAC<br>TTGCCAGGCGAGTCAGGACAT<br>TAGCAACTATTTAAATTGGTAT<br>CAGCAGAAACCAGGGAAAGCC<br>CCTAAGCTCCTGATCTACGATG<br>CATCCAATTTGGAAACAGGGG<br>TCCCATCAAGGTTCAGTGGAA<br>GTGGATCTGGGACAGATTTTAC<br>TTTCACCATCAGCAGCCTGCAG<br>CCTGAAGATATTGCAACATATT<br>ACTGTCAACAGTATGATAATCT<br>CCCCTCTATCACCTTCGCCAA<br>GGGACACGACTGGAGATTAAA |

TABLE 3-continued

Variable region nucleotide sequences of 42 antibodies

| | VHnu (nucleic acid) | VLnu (nucleic acid) |
|---|---|---|
| | CTACCGCGCTGAATACTTCCAG<br>CACTGGGGCCAGGGCACCCTGG<br>TCACCGTCTCCTCA | |
| P1A-1C10 | SEQ ID NO: 284<br>CAGGTGCAGCTGGTGCAGTCTG<br>GGGCTGAGGTGAAGAACCCGG<br>GGTCCTCGGTGAAGGTCTCCTG<br>TAAGGCTGGTGGAGGCACCTCC<br>AGTTTCTATGATATCAACTGGG<br>TGCGACAGGCCCCTGGACAAGG<br>GCTTGAGTGGATAGGAAAAATC<br>ATCCCTAGGCTTGATATAGCAG<br>ACTACGCACAGAAGTCCCAGGG<br>CAGAGTCACGATTACCGCGGAC<br>AAATCCACGAGTACAGTATACT<br>TGGAATTGAGCAGCCTGAAGTC<br>AGACGACACGGCCGTGTATTTC<br>TGTGCGAGAGGTCGGCCGGGTT<br>CGGAGTGGGCGTATGGCCCATT<br>TGACCTCTGGGGCCAGGGAACC<br>CTGGTCACCGTCTCCTCA | SEQ ID NO: 285<br>GACATCCAGATGACCCAGTCTC<br>CTTCCACCCTGTCTGCATCTGT<br>AGGAGACAGAGTCACCATCAC<br>TTGCCGGGCCAGTCAGAGTTCT<br>AGGGCCTGGTTGGCCTGGTATC<br>AGCAGAAACCAGGGAAAGCCC<br>CTAAACTCCTGATCTCTAAGGC<br>GTCTAGTTTAGAAAGTGGGGTC<br>CCATCAAGGTTCAGCGGCAGT<br>GGATATGGGACAGAATTCACT<br>CTCACCATCAGCAGCCTGCAGC<br>CTGATGATTCTGCAACTTATTA<br>CTGCCACCAGTATAACAGTAG<br>CCCATTCACTTTCGGCCCTGGG<br>ACCAAAGTGCAGATCAAA |
| P4A-1H6 | SEQ ID NO: 294<br>CAGGTGCAGCTGGTGGAGTCTG<br>GGGGAGGCGTGGTCCAGCCTGG<br>GAGGTCCCTGAGACTCTCCTGT<br>GCAGCCTCTGGATTCACCTTCA<br>GTAGCTATGGCATGCACTGGGT<br>CCGCCAGTCTCCAGGCAAGGGG<br>CTGGAGTGGGTGGCAGTTATAT<br>CAGATGATGGAAGTAATCAATA<br>CTATGCAGACTCCGTGAAGGGC<br>CGATTCACCATCTCCAGAGACA<br>ATTCCAAGAACACGCTGTATCT<br>GCAAATGAACAGCCTGAGAGTT<br>GAGGACACGGCTGTGTATTACT<br>GTGCGAAAAGGGGCGGATATTG<br>TAGTACTACCAGCTGCCTCCTT<br>AGGTGGGTCTACTTTGACTTCT<br>GGGGCCAGGGAACCCTGGCCAC<br>CGTCTCCTCA | SEQ ID NO: 295<br>GACATCCAGATGACCCAGTCTC<br>CATCCTCCCTGTCTGCATCTGT<br>AGGAGACAGAGTCACCATCAC<br>TTGCCGGGCAAGTCAGAGCAT<br>TAGCAGCTATTTACATTGGTAT<br>CAGCAAAAACCAGGGAAAGCC<br>CCTAACCTCCTGATCTATGCTG<br>CATCCAGTTTGCAAAGTGGGGT<br>CCCATCAAGGTTCAGTGGCAGT<br>GGATCTGGGACAGATTTCACTC<br>TCACCATCAGCAGTCTGCAACC<br>TGAAGACTTTGCAACTTACTAC<br>TGTCAACAGAGTTACAATACCC<br>CTACTTTCGGCCCTGGGACCAA<br>AGTGGATATCAAA |
| P4B-1F4 | SEQ ID NO: 304<br>CAGGTGCAGCTGGTGGAGTCTG<br>GGGGAGGCGTGGTCCAGCCTGG<br>GAGGTCCCTGAGACTCTCCTGT<br>GCAGCCTCTGGATTCACCTTCA<br>GTAGCTATGGCATGCACTGGGT<br>CCGCCAGGCTCCAGGCAAGGGG<br>CTGGAGTGGGTGGCAGTTATAT<br>CATATGATGGAAGTAATAAATA<br>CTATGCAGACTCCGTGAAGGGC<br>CGATTCACCATCTCCAGAGACA<br>ATTCCAAGAACACGCTGTATCT<br>GCAAATGAACAGCCTGAGAGCT<br>GAGGACACGGCTGTGTATTACT<br>GTGCGAAAGGGCCTCGGTATAG<br>CAGCAGCTGGTACATAAGCCTT<br>TACTACTACTACGCTATGGACG<br>TCTGGGGCCAAGGGACCACGGT<br>CACCGTCTCCTCA | SEQ ID NO: 305<br>GATGTTGTGATGACTCAGTCTC<br>CACTCTCCCTGCCCGTCACCCT<br>TGGACAGCCGGCCTCCATCTCC<br>TGCAGGTCTAGTCAAAGCCTCG<br>TATACAGTGATGGAAACACCT<br>ACTTGAATTGGTTTCAGCAGAG<br>GCCAGGCCAATCTCCAAGGCG<br>CCTAATTTATAAGGTTTCTAAC<br>CGGGACTCTGGGGTCCCAGAC<br>AGATTCAGCGGCAGTGGGTCA<br>GGCACTGATTTCACACTGAAA<br>ATCAGCAGGGTGGAGGCTGAG<br>GATGTTGGGGTTTATTACTGCA<br>TGCAAGCTACACACTGGCCCCT<br>GTACACTTTTGGCCAGGGGACC<br>AAGCTGGAGATCAAA |
| P5A-1B6 | SEQ ID NO: 314<br>CAGGTGCAGCTGGTGGAGTCTG<br>GGGGAGGCGTGGTCCAGCCTGG<br>GAGGTCCCTGAGACTCTCCTGT<br>GCAGCCTCTGGATTCACCTTCA<br>GTAGCTATGCTATGCACTGGGT<br>CCGCCAGGCTCCAGGCAAGGGG<br>CTGGAGTGGGTGGCAGTTATAT<br>CATATGATGGAAGTAATAAATA<br>CTACGCAGACTCCGTGAAGGGC<br>CGATTCACCATCTCCAGAGACA<br>ATTCCAAGAACACGCTGTATCT<br>GCAAATGAACAGCCTGAGAGCT | SEQ ID NO: 315<br>GACATCCAGATGACCCAGTCTC<br>CATCCTCCCTGTCTGCATCTGT<br>AGGAGACAGAGTCACCATCAC<br>TTGCCAGGCGAGTCAGGACAT<br>TAGCAACTATTTAAATTGGTAT<br>CAGCAGAAACCAGGGAAAGCC<br>CCTAAGCTCCTGATCTACGATG<br>CATCCAATTTGGAAACAGGGG<br>TCCCATCAAGGTTCAGTGGAA<br>GTGGATCTGGGACAGATTTTAC<br>TTTCACCATCAGCAGCCTGCAG<br>CCTGAAGATATTGCAACATATT |

TABLE 3-continued

Variable region nucleotide sequences of 42 antibodies

| | VHnu (nucleic acid) | VLnu (nucleic acid) |
|---|---|---|
| | GAGGACACGGCTGTGTATTACT GTGCGAGAGATGGACAGGCTAT TACTATGGTTCAGGGAGTTATC GGCCCACCCTTTGACTACTGGG GCCAGGGAACCCTGGTCACCGT CTCCTCA | ACTGTCAACAGTATGATAATCT CCCGTACACTTTTGGCCAGGGG ACCAAGCTGGAGATCAAA |
| P5A-1B8 | SEQ ID NO: 324<br>GAGGTGCAGCTGGTGGAGTCTG GAGGAGGCTTGATCCAGCCTGG GGGGTCCCTGAGACTCTCCTGT GCAGCCTCTGGGTTCACCGTCA GTAGCAACTACATGAGCTGGGT CCGCCAGGCTCCAGGGAAGGG GCTGGAGTGGGTCTCAGTTATT TATCCCGGTGGTAGCACATTCT ACGCAGACTCCGTGAAGGGCCG ATTCACCATCTCCAGAGACAAT TCCAAGAACACCCTGTATCTTC AAATGAACAGCCTGAGAGCCG AGGACACGGCCGTGTATTACTG TGCGAGAGAGACCCTAGCCTTT GACTACTGGGGCCAGGGAACCC TGGTCACCGTCTCCTCA | SEQ ID NO: 325<br>GACATCCAGTTGACCCAGTCTC CATCCTTCCTGTCTGCATCTGT AGGAGACAGAGTCACCATCAC TTGCCGGGCCAGTCAGGGCATT AGCAGTTATTTAGCCTGGTATC AGCAAAAACCAGGGAAAGCCC CTAAGCTCCTGATCTATGCTGC ATCCACTTTGCAAAGTGGGGTC CCATCAAGGTTCAGCGGCAGT GGATCTGGGACAGAATTCACT CTCACAATCAGCAGCCTGCAG CCTGAAGATTTTGCAACTTATT ACTGTCAACAGCTTAATAGTTA CCCTCCAGCTTTCGGCGGAGGG ACCAAGGTGGAGATCAAA |
| P5A-1B9 | SEQ ID NO: 334<br>CAGGTGCAGCTGCAGGAGTCGG GCCCAGGACTGGTGAAGCCTTC GGAGACCCTGTCCCTCACCTGC ACTGTCTCTGGTGGCTCCATCA GTAGTTACTACTGGAGCTGGAT CCGGCAGCCCCAGGGAAGGG ACTGGAGTGGATTGGGTATATC TCTTACAGTGGGAGCACCAACT ACAACCCCTCCCTCAAGAGTCG AGTCACCATATCACTAGACACG TCCAAGAACCAGTTCTCCCTGA AGCTGAGCTCTGTGACCGCTGC GGACACGGCCGTGTATTACTGT GCGAGCAACGGCCAGTATTACG ATATTTTGACTGGTCAACCTCCTG ACTACTGGTACTTCGATCTCTGGG GCCGTGGCACCCTGGTCACTGTCTC CTCA | SEQ ID NO: 335<br>GACATCGTGATGACCCAGTCTC CAGACTCCCTGGCTGTGTCTCT GGGCGAGAGGGCCACCATCA CTGCAAGTCCAGCCAGAGTGTT TTATACAGCTCCAACAATAAG AACTACTTAGCTTGGTACCAGC AGAAACCAGGACAGCCTCCTA AGCTGCTCATTTACTGGGCATC TACCCGGGAATCCGGGGTCCCT GACCGATTCAGTGGCAGCGGG TCTGGGACAGATTTCACTCTCA CCATCAGCAGCCTGCAGGCTG AAGATGTGGCAGTTTATTACTG TCAGCAATATTATAGTACTCCG CTCACTTTCGGCGGAGGGACCAA GGTGGAGATCAAA |
| P5A-1D1 | SEQ ID NO: 344<br>GAGGTGCAGCTGGTGGAGTCTG GAGGAGGCTTGATCCAGCCTGG GGGGTCCCTGAGACTCTCCTGT GCAGCCTCTGGGCTCACCGTCA GTAGCAACTACATGAGCTGGGT CCGCCAGGCTCCAGGGAAGGG GCTGGAGTGGGTCTCAGTTATT TATAGCGGTGGTAGCACATACT ACGCAGACTCCGTGAAGGGCCG ATTCACCATCTCCAGAGACAAT TCCAAGAACACGCTGTATCTTC AAATGAACAGCCTGAGAGCCG AGGACACGGCCGTGTATTACTG TGCGAGAGATTTGTACTACTAC GGTATGGACGTCTGGGGCCAAG GGACCACGGTCACCGTCTCCAC A | SEQ ID NO: 345<br>GACATCCAGTTGACCCAGTCTC CATCCTTCCTGTCTGCATCTGT AGGAGACAGAGTCACCATCAC TTGCCGGGCCAGTCAGGGCATT AGCAGTTATTTAGCCTGGTATC AGCAAAAACCAGGGAAAGCCC CTAAGCTCCTGATCTATGCTGC ATCCACTTTGCAAAGTGGGGTC CCATCAAGGTTCAGCGGCAGT GGATCTGGGACAGATTTCACTC TCACCATCAGCAGCCTGCAGCC TGAAGATTTTGCAACTTATTAC TGTCAACAGCTTAATAGTTACC CTACCTTCGGCCAAGGGACAC GACTGGAGATTAAA |
| P5A-1D10 | SEQ ID NO: 354<br>CAGGTGCAGCTGGTGGAGTCTG GGGGAGGCTTGGTCAAGCCTGG GGGGTCCCTGAGACTCTCCTGT GCAGCCTCTCAATTCACCTTCA GTGACTACTCCATGACCTGGAT CCGCCAGGCTCCAGGGAAGGG GCTGGAGTGGGTTTCATACATT AGTCAAAGTGGTAGTACCATAT ACTACGCAGACTCTGTGAAGGG CCGATTCACCATCTCCAGGGAC AACGCCAAGAACTCACTGTATC | SEQ ID NO: 355<br>CAGTCTGCCCTGACTCAGCCTG CCTCCGTGTCTGGGTCTCCTGG ACAGTCGATCACCATCTCCTGC ACTGGAACCAGCAGTGACGTT GGTGGTTATAACTATGTCTCCT GGTACCAACAACACCCAGGCA AAGCCCCCAAACTCATGATTTA TGATGTCAGTAATCGGCCCTCA GGGGTTTCTAATCGCTTCTCTG CCTCCAAGTCTGGCAACACGG CCTCCCTGACCATCTCTGGGCT |

TABLE 3-continued

Variable region nucleotide sequences of 42 antibodies

| | VHnu (nucleic acid) | VLnu (nucleic acid) |
|---|---|---|
| | TGCAAATGAACAGCCTGAGAGC<br>CGAGGACACGGCCGTGTATTAC<br>TGTGCGAGAGGTGTCAGCCCAT<br>CCTACGTTTGGGGGAGTTATCG<br>TTCCTTGTACCACTTTGACTACT<br>GGGGCCAGGGAACCCTGGTCACCG<br>TCTCCTCA | CCAGGCTGAGGACGAGGCTGA<br>TTATTACTGCAGCTCATTTACA<br>AGCAGCACCACTGTCGTGGTAT<br>TCGGCGGAGGGACCAAGCTGA<br>CCGTCCTA |
| P5A-2D11 | SEQ ID NO: 364<br>GAGGTGCAGCTGGTGCAGTCTG<br>GAGCAGAGGTGAAAAAGCCCG<br>GGGAGTCTCTGAAGATCTCCTG<br>TAAGGGTTCTGGATACAGCTTT<br>ACCAGCTACTGGATCGGCTGGG<br>TGCGCCAGATGCCCGGGAAAGG<br>CCTGGAGTGGATGGGGATCATC<br>TATCCTGGTGACTCTGATACCA<br>GATACAGCCCGTCCTTCCAAGG<br>CCAGGTCACCATCTCAGCCGAC<br>AAGTCCATCAGCACCGCCTACC<br>TGCAGTGGAGCAGCCTGAAGGC<br>CTCGGACACCGCCATGTATTAC<br>TGTGCGAGACGGGATTCGACCT<br>ACGGTGGTAACACTGACTACTG<br>GGGCCAGGGAACCCTGGTCACC<br>GTCTCCTCA | SEQ ID NO: 365<br>CAGTCTGTGCTGACTCAGCCAC<br>CCTCAGCGTCTGGGACCCCCGG<br>GCAGAGGGTCACCATCTCTTGT<br>TCTGGAAGCAGCTCCAACATC<br>GGAAGTAATACTGTAAACTGG<br>TACCAGCAGCTCCCAGGAACG<br>GCCCCAAAACTCCTCATCTATA<br>GTAATAATCAGCGGCCCTCAG<br>GGGTCCCTGACCGATTCTCTGG<br>CTCCAAGTCTGGCACCTCAGCC<br>TCCCTGGCCATCAGTGGGCTCC<br>AGTCTGAGGATGAGGCTGATT<br>ATTACTGTGCAGCATGGGATG<br>ACAGCCTGAATGGTGTGGTATT<br>CGGCGGAGGGACCAAGCTGAC<br>CGTCCTA |
| P5A-2G9 | SEQ ID NO: 374<br>CAGGTGCAGCTGGTGGAGTCTG<br>GGGGAGGCGTGGTCCAGCCTGG<br>GAGGTCCCTGAGACTCTCCTGT<br>GCAGCGTCTGGATTCACCTTCA<br>GTAGCTATGGCATGCACTGGGT<br>CCGCCAGGCTCCAGGCAAGGGG<br>CTGGAGTGGGTGGCAGTTATAT<br>GGTATGATGGAAGTAATAAATA<br>CTATGCAGACTCCGTGAAGGGC<br>CGATTCACCATCTCCAGAGACA<br>ATTCCAAGAACACGCTGTATCT<br>GCAAATGAACAGCCTGAGAGCC<br>GAGGACACGGCTGTGTATTACT<br>GTGCGAGATGGTTCCACACGGG<br>GGGGTACTTTGACTACTGGGGC<br>CAGGGAACCCTGGTCACCGTCT<br>CCTCA | SEQ ID NO: 375<br>CAGCCTGTGCTGACTCAGCCAC<br>CTTCCTCCTCCGCATCTCCTGG<br>AGAATCCGCCAGACTCACCTG<br>CACCTTGCCCAGTGACATCAAT<br>GTTAGTAGCTACAACATATACT<br>GGTACCAGCAGAAGCCAGGGA<br>GCCCTCCCAGGTATCTCCTGTA<br>CTACTACTCAGACTCAGATAAG<br>GGCCAGGGCTCTGGAGTCCCC<br>AGCCGCTTCTCTGGATCCAAAG<br>ATGCTTCAGCCAATACAGGGA<br>TTTTACTCATCTCCGGGCTCCA<br>GTCTGAGGATGAGGCTGACTA<br>TTACTGTATGATTTGGCCAAGC<br>AATGCTCTTTATGTCTTCGGAA<br>CTGGGACCAAGGTCACCGTCCT<br>A |
| P5A-2H3 | SEQ ID NO: 384<br>GAGGTGCAGCTGGTGCAGTCTG<br>GAGCAGAGGTGAAAAAGCCCG<br>GGGAGTCTCTGAAGATCTCCTG<br>TAAGGGTTCTGGATACAGCTTT<br>ACCAGCTACTGGATCGGCTGGG<br>TGCGCCAGATGCCCGGGAAAGG<br>CCTGGAGTGGATGGGGATCATC<br>TATCCTGGTGACTCTGATACCA<br>GATACAGCCCGTCCTTCCAAGG<br>CCAGGTCACCATCTCAGCCGAG<br>AAGTCCATCAGCACCGCCTACC<br>TGCAGTGGAGCAGCCTGAAGGC<br>CTCGGACACCGCCATGTATTAC<br>TGTGCGAGACGGGATTCGACCT<br>ACGGTGGTAACACTGACTACTG<br>GGGCCAGGGAACCCTGGTCACC<br>GTCTCCTCA | SEQ ID NO: 385<br>CAGTCTGTGCTGACTCAGCCAC<br>CCTCAGCGTCTGGGACCCCCGG<br>GCAGAGGGTCACCATCTCTTGT<br>TCTGGAAGCAGCTCCAACATC<br>GGAAGTAATACTGTAAACTGG<br>TACCAGCAGCTCCCAGGAACG<br>GCCCCAAAACTCCTCATCTATA<br>GTAATAATCAGCGGCCCTCAG<br>GGGTCCCTGACCGATTCTCTGG<br>CTCCAAGTCTGGCACCTCAGCC<br>TCCCTGGCCATCAGTGGGCTCC<br>AGTCTGAGGATGAGGCTGATT<br>ATTACTGTGCAGCATGGGATG<br>ACAGCCTGAATGGTGTGGTATT<br>CGGCGGAGGGACCAAGCTGAC<br>CGTCCTA |
| P5A-3A1 | SEQ ID NO: 394<br>GAGGTGCAGCTGGTGGAGTCTG<br>GAGGAGGCTTGATCCAGCCTGG<br>GGGGTCCCTGAGACTCTCCTGT<br>GCAGCCTCTGGGTTCACCGTCA<br>GTAGCAACTACATGAGCTGGGT<br>CCGCCAGGCTCCAGGGAAGGG<br>GCTGGAGTGGGTCTCAGTTATT<br>TATAGCGGTGGTAGCACATACT<br>ACGCAGACTCCGTGAAGGGCCG<br>ATTCACCATCTCCAGAGACAAT | SEQ ID NO: 395<br>GAAATTGTGTTGACGCAGTCTC<br>CAGGCACCCTGTCTTTGTCTCC<br>AGGGGAAAGAGCCACCCTCTC<br>CTGCAGGGCCAGTCAGAGTGT<br>TAGCAGCAGCTACTTAGCCTGG<br>TACCAGCAGAAACCTGGCCAG<br>GCTCCCAGGCTCCTCATCTATG<br>GTGCATCCAGCAGGGCCACTG<br>GCATCCCAGACAGGTTCAGTG<br>GCAGTGGGTCTGGGACAGACT |

TABLE 3-continued

Variable region nucleotide sequences of 42 antibodies

|  | VHnu (nucleic acid) | VLnu (nucleic acid) |
|---|---|---|
|  | TCCAAGAACACGCTGTATCTTC<br>AAATGAACAGCCTGAGAGCCG<br>AGGACACGGCCGTGTATTACTG<br>TGCGAGAGACTACGGTGACTTT<br>TACTTTGACTACTGGGGCCAGG<br>GAACCCTGGTCACCGTCTCCTCA | TCACTCTCACCATCAGCAGACT<br>GGAGCCTGAAGATTTTGCAGT<br>GTATTACTGTCAGCAGTATGGT<br>AGCTCACCTCGCACTTTTGGCC<br>AGGGGACCAAGCTGGAGATCAAA |
| P5A-3A6 | SEQ ID NO: 404<br>GAAGTGCAGCTGGTGGAGTCTG<br>GGGGAGGCTTGGTACAGCCTGG<br>CAGGTCCCTGAGACTCTCCTGT<br>GCAGCCTCTGGATTCACCTTTG<br>ATGATTATGCCATGCACTGGGT<br>CCGGCAAGCTCCAGGGAAGGG<br>CCTGGAGTGGGTCTCAGGTATT<br>AGTTGGAATAGTGGTACCATAG<br>GCTATGCGGACTCTGTGAAGGG<br>CCGATTCATCATCTCCAGAGAC<br>AACGCCAAGAACTCCCTGTATC<br>TGCAAATGAACAGTCTGAGAGC<br>TGAGGACACGGCCTTGTATTAC<br>TGTGCAGGGGTGGTACTATGG<br>TTCGGGGAGTTATTGCCGGAGG<br>GGGAACTCATCCGGTGGATGAC<br>TACTACGGTATGGACGTCTGGG<br>GCCAAGGGACCACGGTCACCGT<br>CTCCTCA | SEQ ID NO: 405<br>CAGTCTGCCCTGACTCAGCCTG<br>CCTCCGTGTCTGGGTCTCCTGG<br>ACAGTCGATCACCATCTCCTGC<br>ACTGGAACCAGCAGTGACGTT<br>GGTGGTTATAACTATGTCTCCT<br>GGTACCAACAACACCCAGGCA<br>AAGCCCCCAAACTCATGATTTA<br>TGATGTCAGTAATCGGCCCTCA<br>GGGGTTTCTAATCGCTTCTCTG<br>GCTCCAAGTCTGGCAACACGG<br>CCTCCCTGACCATCTCTGGGCT<br>CCAGGCTGAGGACGAGGCTGA<br>TTATTACTGCAGCTCATATACA<br>AGCAGCAGCACTGTGGTATTC<br>GGCGGAGGGACCAAGCTGACC<br>GTCCTA |
| P5A-3B4 | SEQ ID NO: 414<br>GAGGTGCAGCTGGTGCAGTCTG<br>GAGCAGAGGTGAAAGAGCCCG<br>GGGAGTCTCTGAAGATCTCCTG<br>TAAGGGTTCTGGATACAGCTTT<br>ACCAGCTACTGGATCGGCTGGG<br>TGCGCCAGATGCCCGGGAAAGG<br>CCTGGAGTGGATGGGGATCATC<br>TATCCTGGTGACTCTGATACCA<br>GATACAGCCCGTCCTTCCAAGG<br>CCAGGTCACCATCTCAGCCGAC<br>AAGTCCATCAGCACCGCCTACC<br>TGCAGTGGAGCAGCCTGAAGGC<br>CTCGGACACCGCCATGTATTAC<br>TGTGCGAGACGGGATTCGACCT<br>ACGGTGGTAACACTGACTACTG<br>GGGCCAGGGAACCCTGGTCACC<br>GTCTCCTCA | SEQ ID NO: 415<br>CAGTCTGTGCTGACTCAGCCAC<br>CCTCAGCGTCTGGGACCCCCGG<br>GCAGAGGGTCACCATCTCTTGT<br>TCTGGAAGCAGCTCCAACATC<br>GGAAGTAATACTGTAAACTGG<br>TACCAGCAGCTCCCAGGAACG<br>GCCCCCAAACTCCTCATCTATA<br>GTAATAATCAGCGGCCCTCAG<br>GGGTCCCTGACCGATTCTCTGG<br>CTCCAAGTCTGGCACCTCAGCC<br>TCCCTGGCCATCAGTGGGCTCC<br>AGTCTGAGGATGAGGCTGATT<br>ATTACTGTGCAGCATGGGATG<br>ACAGCCTGAATGGTGTGGTATT<br>CGGCGGAGGGACCAAGCTGAC<br>CGTCCTA |
| P5A-3C12 | SEQ ID NO: 424<br>CAGATCACCTTGAAGGAGTCTG<br>GTCCTACGCTGGTGAAACCCAC<br>ACAGACCCTCACGCTGACCTGC<br>ACCTTCTCTGGGTTCTCACTCAG<br>CACTAGTGGAGTGGGTGTGGGC<br>TGGATCCGTCAGCCCCCAGGAA<br>AGGCCCTGGAGTGGCTTGCACT<br>CATTTATTGGGATGATGATAAG<br>CGCTACAGCCCATCTCTGAAGA<br>GCAGGCTCACCATCACCAAGGA<br>CACCTCCAAAAACCAGGTGGTC<br>CTTACAATGACCAACATGGACC<br>CTGTGGACACAGCCACATATTA<br>CTGTGCACACAGTTTGTTTCTA<br>CGGTAGGGTATAGCAGCAGCTG<br>GTCCCCTTTTGACTACTGGGGC<br>CAGGGAACCCTGGTCACCGTCTCC<br>TCA | SEQ ID NO: 425<br>GACATCGTGATGACCCAGTCTC<br>CAGACTCCCTGGCTGTGTCTCT<br>GGGCGAGAGGGCCACCATCAA<br>CTGCAAGTCCAGCCAGAGTGTT<br>TTATACAGCTCCAACAATAAG<br>AACTACTTAGCTTGGTACCAGC<br>AGAAACCAGGACAGCCTCCTA<br>AGCTGCTCATTTACTGGGCATC<br>TACCCGGGAATCCGGGGTCCCT<br>GACCGATTCAGTGGCAGCGGG<br>TCTGGGACAGATTTCACTCTCA<br>CCATCAGCAGCCTGCAGGCTG<br>AAGATGTGGCAGTTTATTACTG<br>TCAGCAATATTATAGTACTCCT<br>CACACTTTTGGCCAGGGGACC<br>AAGCTGGAGATCAAA |
| P22A-1D1 | SEQ ID NO: 434<br>GAGGTGCAGCTGGTGGAGTCTG<br>GAGGAGGCTTGATCCAGCCTGG<br>GGGGTCCCTGAGACTCTCCTGT<br>GCAGCCTCTGGGTTCACCGTCA<br>GTAGCAACTACATGAGCTGGGT<br>CCGCCAGGCTCCAGGGAAGGG<br>GCTGGAGTGGGTCTCAGTTATT<br>TATAGCGGTGGTAGCACATACT | SEQ ID NO: 435<br>GACATCCAGTTGACCCAGTCTC<br>CATCCTTCCTGTCTGCATCTGT<br>AGGAGACAGAGTCACCATCAC<br>TTGCCGGGCCAGTCAGGGCATT<br>AGCAGTTATTTAGCCTGGTATC<br>AGCAAAAACCAGGGAAAGCCC<br>CTAAGCTCCTGATCTATGCTGC<br>ATCCACTTTGCAAAGTGGGGTC |

TABLE 3-continued

Variable region nucleotide sequences of 42 antibodies

| VHnu (nucleic acid) | VLnu (nucleic acid) |
| --- | --- |
| ACGCAGACTCCGTGAAGGGCCG ATTCACCATCTCCAGAGACAAT TCCAAGAACACGCTGTATCTTC AAATGAACAGCCTGAGAGCCG AGGACACGGCCGTGTATTACTG TGCGAGAGATCGAGACTACTAC GGTATGGACGTCTGGGGCCAAG GGACCACGGTCACCGTCTCCTCA | CCATCAAGGTTTAGCGGCAGT GGATCTGGGACAGAATTCACT CTCACAATCAGCAGCCTGCAG CCTGAAGATTTTGCAACTTATT ACTGTCTACACCTTAATAGTTA CAGGACGTTCGGCCTAGGGAC CAAGGTGGAAATCAAA |

In certain embodiments, the antibodies or the antigen-binding fragments thereof provided herein further comprise an immunoglobulin (Ig) constant region, which optionally further comprises a heavy chain and/or a light chain constant region. In certain embodiments, the heavy chain constant region comprises CH1, hinge, and/or CH2-CH3 regions (or optionally CH2-CH3-CH4 regions). In certain embodiments, the antibodies or the antigen-binding fragments thereof provided herein comprises heavy chain constant regions of human IgG1, IgG2, IgG3, IgG4, IgA1, IgA2 or IgM. In certain embodiments, the light chain constant region comprises Cκ or Cλ. The constant region of the antibodies or the antigen-binding fragments thereof provided herein may be identical to the wild-type constant region sequence or be different in one or more mutations.

In certain embodiments, the heavy chain constant region comprises an Fc region. Fc region is known to mediate effector functions such as antibody-dependent cellular cytotoxicity (ADCC), Antibody-dependent cellular phagocytosis (ADCP) and complement-dependent cytotoxicity (CDC) of the antibody. Fc regions of different Ig isotypes have different abilities to induce effector functions. For example, Fc regions of IgG1 and IgG3 have been recognized to induce both ADCC and CDC more effectively than those of IgG2 and IgG4. In certain embodiments, the antibodies and antigen-binding fragments thereof provided herein comprises an Fc region of IgG1, or IgG3 isotype, which could induce ADCC or CDC. Alternatively, the antibodies and antigen-binding fragments thereof provided herein comprise a constant region of IgG4 or IgG2 isotype, which has reduced or depleted effector function. In certain embodiments, the anti-SARS-COV-2 antibodies or antigen-binding fragments thereof comprises a wild type human IgG1 Fc region comprising the sequence of SEQ ID NO: 115 or other wild type human IgG1 alleles.

Table 4 shows the amino acid sequences for the heavy chain and light chain constant regions of the monoclonal antibodies: P2A-1A8, P2A-1A9, P2A-1A10, P2A-1B3, P2B-2F6, P2B-2G4, P2B-2G11, P2C-1A3, P2C-1C8, P2C-1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, and P22A-1D1 wherein the antibodies P2A-1A8, P2A-1A9, P2B-2F6, P2B-2G4, P2B-2G11, P2C-1D5, P2B-1G5, P2B-1A1, P2B-1D9, P2B-1E4, P5A-2G7, P5A-1D2, P5A-2E1, P5A-1D10, P5A-2D11, P5A-2G9, P5A-2H3, P5A-3A6, and P5A-3B4 have lambda light chains (with a lambda light chain constant region sequence of SEQ ID NO: 116), the antibodies P2A-1A10, P2A-1B3, P2C-1A3, P2C-1C8, P2C-1C10, P2C-1F11, P2C-1D7, P2B-1A10, P2B-1G1, P4A-2D9, P5A-3C8, P5A-2F11, P5A-1C8, P1A-1C10, P4A-1H6, P4B-1F4, P5A-1B6, P5A-1B8, P5A-1B9, P5A-1D1, P5A-3A1, P5A-3C12, and P22A-1D1 have kappa light chains (with a kappa light chain constant region sequence of SEQ ID NO: 117), and all 42 antibodies have the same heavy chain constant region (SEQ ID NO: 115).

TABLE 4

Amino acid and nucleic acid sequences of constant regions

| | | |
| --- | --- | --- |
| HC (Heavy Chain constant region) | Amino acid | SEQ ID NO. 115<br>ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSRDELTKNQV SLTCLVKGFYPSDIAVEWESNGQPENNYKTTPPVLDSDGSFF LYSKLTVDKSRWQQGNVFSCSVMHEALHNHYTQKSLSLSP GK |
| | Nucleic Acid | SEQ ID NO: 118<br>GCGTCGACCAAGGGCCCATCGGTCTTCCCCCTGGCACCCT CCTCCAAGAGCACCTCTGGGGGCACAGCGGCCCTGGGCT GCCTGGTCAAGGACTACTTCCCCGAACCCGTGACGGTGTC GTGGAACTCAGGCGCCCTGACCAGCGGCGTGCACACCTT CCCGGCTGTCCTACAGTCCTCAGGACTCTACTCCCTCAGC AGCGTGGTGACCGTGCCCTCCAGCAGCTTGGGCACCCAG ACCTACATCTGCAACGTGAATCACAAGCCCAGCAACACC AAGGTGGACAAGAAAGTTGAGCCCAAATCTTGTGACAAA ACTCACACATGCCCACCGTGCCCAGCACCTGAACTCCTGG GGGGACCGTCAGTCTTCCTCTTCCCCCCAAAACCCAAGGA CACCCTCATGATCTCCCGGACCCCTGAGGTCACATGCGTG GTGGTGGACGTGAGCCACGAAGACCCTGAGGTCAAGTTC |

TABLE 4-continued

Amino acid and nucleic acid sequences of constant regions

|  |  |  |
|---|---|---|
|  |  | AACTGGTACGTGGACGGCGTGGAGGTGCATAATGCCAAG<br>ACAAAGCCGCGGGAGGAGCAGTACAACAGCACGTACCGT<br>GTGGTCAGCGTCCTCACCGTCCTGCACCAGGACTGGCTGA<br>ATGGCAAGGAGTACAAGTGCAAGGTCTCCAACAAAGCCC<br>TCCCAGCCCCCATCGAGAAAACCATCTCCAAAGCCAAAG<br>GGCAGCCCCGAGAACCACAGGTGTACACCCTGCCCCCAT<br>CCCGGGATGAGCTGACCAAGAACCAGGTCAGCCTGACCT<br>GCCTGGTCAAAGGCTTCTATCCCAGCGACATCGCCGTGG<br>AGTGGGAGAGCAATGGGCAGCCGGAGAACAACTACAAG<br>ACCACGCCTCCCGTGCTGGACTCCGACGGCTCCTTCTTCC<br>TCTACAGCAAGCTCACCGTGGACAAGAGCAGGTGGCAGC<br>AGGGGAACGTCTTCTCATGCTCCGTGATGCATGAGGCTCT<br>GCACAACCACTACACGCAGAAGAGCCTCTCCCTGTCTCC<br>GGGTAAA |
| LC<br>(lambda<br>Chain<br>constant<br>region) | Amino<br>acid | SEQ ID NO: 116<br>GQPKAAPSVTLFPPSSEELQANKATLVCLISDFYPGAVTVA<br>WKADSSPVKAGVETTTPSKQSNNKYAASSYLSLTPEQWKS<br>HRSYSCQVTHEGSTVEKTVAPTECS |
|  | Nucleic<br>Acid | SEQ ID NO: 119<br>GGTCAGCCCAAGGCTGCCCCCTCGGTCACTCTGTTCCCAC<br>CCTCGAGTGAGGAGCTTCAAGCCAACAAGGCCACACTGG<br>TGTGTCTCATAAGTGACTTCTACCCGGGAGCCGTGACAGT<br>GGCCTGGAAGGCAGATAGCAGCCCCGTCAAGGCGGGAGT<br>GGAGACCACCACACCCTCCAAACAAAGCAACAACAAGTA<br>CGCGGCCAGCAGCTACCTGAGCCTGACGCCTGAGCAGTG<br>GAAGTCCCACAGAAGCTACAGCTGCCAGGTCACGCATGA<br>AGGGAGCACCGTGGAGAAGACAGTGGCCCCTACAGAATG<br>TTCA |
| KC<br>(kappa<br>Chain<br>constant<br>region) | Amino<br>acid | SEQ ID NO: 117<br>RTVAAPSVFIFPPSDEQLKSGTASVVCLLNNFYPREAKVQW<br>KVDNALQSGNSQESVTEQDSKDSTYSLSSTLTLSKADYEKH<br>KVYACEVTHQGLSSPVTKSFNRGEC |
|  | Nucleic<br>Acid | SEQ ID NO: 120<br>CGTACGGTGGCTGCACCATCTGTCTTCATCTTCCCGCCAT<br>CTGATGAGCAGTTGAAATCTGGAACTGCCTCTGTTGTGTG<br>CCTGCTGAATAACTTCTACCCCAGAGAAGCCAAAGTGCA<br>GTGGAAGGTGGACAACGCCCTGCAGAGCGGAAACAGCC<br>AGGAAAGCGTGACAGAGCAGGATTCCAAGGATTCCACAT<br>ACAGCCTGAGCAGCACACTGACACTGTCCAAGGCCGACT<br>ACGAGAAGCACAAGGTGTACGCCTGCGAAGTGACACACC<br>AGGGACTGTCCTCCCCTGTGACAAAGAGCTTCAACAGAG<br>GAGAATGC |

In some embodiments, signal peptide may be added when expressing the antibodies of the present disclosure, these signal peptides may be partially or full removed by host cells during the secretion of the antibody. In certain embodiments, for expressing the 26 exemplary antibodies of the present disclosure, signal peptide (SEQ ID NO: 130: MGWSCIIL-FLVATATGVHS) is included when expressing the heavy chain, signal peptide (SEQ ID NO: 131: MGWSCIILFL-VATATGSWA) is included when expressing the light chain.

Table 11 which is appended at the end of the specification shows sequences and SEQ ID NOs mentioned or used in the present application.

Antibody Variants

In certain embodiments, the antibody or antigen binding fragments thereof provided herein comprise one or more mutations in one or more of the CDR sequences provided in Table 1 above, one or more of the non-CDR sequences of the heavy chain variable region or light chain variable region provided in Table 2, and/or the constant region (e.g. Fc region) in Table 4, yet retaining specific binding affinity to RBD of spike protein of SARS-CoV-2. These are also referred to as variants of antibodies P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A- 3A1, P5A-3A6, P5A-3B4, P5A-3C12, P22A-1D1, or the antigen binding fragments thereof. "Mutations" or "mutated" as used herein include substitutions, insertions, and/or deletions in an amino acid sequence or polynucleotide sequence. In certain embodiments, at least one (or all) of the mutation(s) comprises a conservative substitution.

In certain embodiments, the variants comprise 1, 2, or 3 CDR sequences having at least 80% (e.g. at least 85%, 88%, 90%, 91%, 92%, 93%, 94%, 95%, 96%, 97%, 98%, 99%) sequence identity to that (or those) listed in Table 1 above, and in the meantime retain the binding specificity to SARS-COV-2, optionally having binding affinity at a level similar to or even higher than its parent antibody.

In certain embodiments, the variants comprise one or more variable region sequences having at least 80% (e.g. at least 85%, 88%, 90%, 91%, 92%, 93%, 94%, 95%, 96%, 97%, 98%, 99%) sequence identity to that (or those) listed in Table 2 above, and in the meantime retain the binding specificity to SARS-COV-2, optionally having binding affinity to SARS-COV-2 at a level similar to or even higher than its parent antibody. In some embodiments, a total of 1 to 10 amino acids have been mutated in a variable region sequence listed in Table 2 above. In some embodiments, the mutations occur in the non-CDR sequences (e.g. in the FRs). In some embodiments, the mutations are conservative substitutions.

In certain embodiments, the present disclosure provides a variant of antibody P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, or P22A-1D1, wherein the variant comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to a HCDR1 sequence of the parent antibody listed in Table 1, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to a HCDR2 sequence of the parent antibody listed in Table 1, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to a HCDR3 sequence of the parent antibody listed in Table 1, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to a LCDR1 sequence of the parent antibody listed in Table 1, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to a LCDR2 sequence of the parent antibody listed in Table 1, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to a LCDR3 sequence of the parent antibody listed in Table 1, and in the meantime retain the binding specificity to SARS-COV-2, optionally having binding affinity to SARS-COV-2 at a level similar to or even higher than its parent antibody.

In certain embodiments, the antibody variants provided herein comprises an HCDR1 having no more than 3, 2, or 1 amino acid mutations in a HCDR1 sequence of the parent antibody listed in Table 1, an HCDR2 having no more than 6, 5, 4, 3, 2, or 1 amino acid mutations in a HCDR2 sequence of the parent antibody listed in Table 1, HCDR3 having no more than 6, 5, 4, 3, 2, or 1 amino acid mutations in a HCDR3 sequence of the parent antibody listed in Table 1, LCDR1 having no more than 2 or 1 amino acid mutations in a LCDR1 sequence of the parent antibody listed in Table 1, LCDR2 having no more than 3, 2, or 1 amino acid mutations in a LCDR2 sequence of the parent antibody listed in Table 1, and/or LCDR3 having no more than 3, 2, or 1 amino acid mutations in a LCDR3 sequence of the parent antibody listed in Table 1, and in the meantime retain the binding specificity to SARS-COV-2, optionally having binding affinity to SARS-COV-2 at a level similar to or even higher than its parent antibody.

In certain embodiments, the antibody variants provided herein comprises:

a) at least one heavy chain CDR sequence having no more than 3, 2, or 1 amino acid substitutions in a heavy chain CDR sequence of the parent antibody listed in Table 1, or b) at least two heavy chain CDR sequences each having no more than 3, 2, or 1 amino acid substitutions in a heavy chain CDR sequence of the parent antibody listed in Table 1, or c) three heavy chain CDR sequences each having no more than 3, 2, or 1 amino acid substitutions in a heavy chain CDR sequence of the parent antibody listed in Table 1, or d) at least one light chain sequence having no more than 3, 2, or 1 amino acid substitutions in a heavy chain CDR sequence of the parent antibody listed in Table 1, or e) at least two light chain CDR sequences each having no more than 3, 2, or 1 amino acid substitutions in a heavy chain CDR sequence of the parent antibody listed in Table 1, or f) three light chain CDR sequences each having no more than 3, 2, or 1 amino acid substitutions in a heavy chain CDR sequence of the parent antibody listed in Table 1, and in the meantime retains the binding specificity to SARS-COV-2, optionally having binding affinity at a level similar to or even higher than its parent antibody.

In certain embodiments, the antibody variants provided herein retains at least part of (or the entirety of) the paratope of their parent antibodies. As used herein, the term "paratope" with respect to an antibody refers to a group of amino acid residues on the variable regions of the antibody that makes direct contact with the antigen and form the antigen binding site of the variable regions. A paratope normally comprises or consists of amino acid residues in one or more CDR sequences.

In certain embodiments, the present disclosure provides variants of antibody P2B-2F6, wherein the variant comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 41, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 42, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 43, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 44, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 45, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 46, and in the meantime retain the binding specificity to SARS-COV-2, optionally having binding affinity to SARS-COV-2 at a level similar to or even higher than antibody P2B-2F6.

In certain embodiments, the antibody variants of antibody P2B-2F6 comprises an HCDR1 having no more than 4, 3, 2, or 1 amino acid mutations in SEQ ID NO: 41, an HCDR2 having no more than 3, 2, or 1 amino acid mutations in SEQ ID NO: 42, HCDR3 having no more than 6, 5, 4, 3, 2, or 1 amino acid substitutions in SEQ ID NO: 43, LCDR1 having no more than 4, 3, 2, or 1 amino acid mutations in SEQ ID NO: 44, LCDR2 having no more than 3, 2, or 1 amino acid mutations in SEQ ID NO: 45, and/or LCDR3 having no more than 4, 3, 2, or 1 amino acid mutations in SEQ ID NO: 46, and in the meantime retain the binding specificity to SARS-COV-2, optionally having binding affinity to SARS-COV-2 at a level similar to or even higher than antibody P2B-2F6.

In certain embodiments, the variants of antibody P2B-2F6 retain the entirety of the paratope of antibody P2B-2F6 while one or more of the amino acid residues outside the paratope of the antibody may be mutated. In certain embodiments, the paratope of antibody P2B-2F6 comprises or consists of: Y27, S28, S30, S31, and Y33 of HCDR1; H54 of HCDR2; G102, I103, V105, V106 and P107 of HCDR3; and/or G31, Y32 and N33 of LCDR1; wherein the numbering of residues in the heavy chain CDRs is according to SEQ ID NO: 47, and the numbering of residues in the light chain CDR is according to SEQ ID NO: 48.

In certain embodiments, the variants of antibody P2B-2F6 retain at least part of the paratope of antibody P2B-2F6. For example, the variants of antibody P2B-2F6 retain at least 60%, at least 70%, at least 80%, or at least 90% of the residues of the paratope of antibody P2B-2F6. In certain embodiments, the variants of antibody P2B-2F6 comprises one or more mutations (e.g. conservative substitutions) in the paratope of antibody P2B-2F6. In certain embodiments, the variants of antibody P2B-2F6 comprises no more than 5, 4, 3, 2 or 1 mutations (e.g. substitutions) in the paratope of antibody P2B-2F6. In certain embodiments, the variants of antibody P2B-2F6 comprises no more than 5, 4, 3, 2 or 1 conservative substitutions in the paratope of antibody P2B-2F6.

In certain embodiments, the present disclosure provides variants of antibody P2C-1F11, wherein the variant comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 105, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 106, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 107, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 108, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 109, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 110, and in the meantime retain the binding specificity to SARS-COV-2, optionally having binding affinity to SARS-COV-2 at a level similar to or even higher than antibody P2C-1F11.

In certain embodiments, the antibody variants of antibody P2C-1F11 comprises an HCDR1 having no more than 4, 3, 2, or 1 amino acid mutations in SEQ ID NO: 105, an HCDR2 having no more than 3, 2, or 1 amino acid mutations in SEQ ID NO: 106, HCDR3 having no more than 6, 5, 4, 3, 2, or 1 amino acid mutations in SEQ ID NO: 107, LCDR1 having no more than 4, 3, 2, or 1 amino acid mutations in SEQ ID NO: 108, LCDR2 having no more than 3, 2, or 1 amino acid mutations in SEQ ID NO: 109, and/or LCDR3 having no more than 4, 3, 2, or 1 amino acid mutations in SEQ ID NO: 110, and in the meantime retain the binding specificity to SARS-COV-2, optionally having binding affinity to SARS-COV-2 at a level similar to or even higher than antibody P2C-1F11.

In certain embodiments, the variants of antibody P2C-1F11 retain the entirety of the paratope of antibody P2C-1F11 while one or more of the amino acid residues outside the paratope of the antibody may be mutated. In certain embodiments, the paratope of antibody P2C-1F11 comprises or consists of: G26, I27, T28, S31, N32 and Y33 of HCDR1; Y52, S53, G54, and S56 of HCDR2; R97, L99, V100, V101, Y102 and D105 of HCDR3; and/or S28, S30 and Y33 of LCDR1; wherein the numbering of residues in heavy chain is according to SEQ ID NO: 111, and the numbering of residues in light chain CDR is according to SEQ ID NO: 112.

In certain embodiments, the variants of antibody P2C-1F11 retain at least part of the paratope of antibody P2C-1F11. For example, the variants of antibody P2C-1F11 retain at least 60%, at least 70%, at least 80%, or at least 90% of the residues of the paratope of antibody P2C-1F11. In certain embodiments, the variants of antibody P2C-1F11 comprises one or more mutations or substitutions (e.g. conservative substitutions) in the paratope of antibody P2C-1F11. In certain embodiments, the variants of antibody P2C-1F11 comprises no more than 6, 5, 4, 3, 2 or 1 mutations (e.g. substitutions) in the paratope of antibody P2C-1F11. In certain embodiments, the variants of antibody P2C-1F11 comprises no more than 6, 5, 4, 3, 2 or 1 conservative substitutions in the paratope of antibody P2C-1F11.

In certain embodiments, the present disclosure provides variants of antibody P22A-1D1, wherein the variant comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 426, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 427, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 428, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 429, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 430, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 431, and in the meantime retain the binding specificity to SARS-COV-2, optionally having binding affinity to SARS-COV-2 at a level similar to or even higher than antibody P22A-1D1.

In certain embodiments, the antibody variants of antibody P22A-1D1 comprises an HCDR1 having no more than 6, 5, 4, 3, 2, or 1 amino acid mutations in SEQ ID NO: 426, an HCDR2 having no more than 5, 4, 3, 2, or 1 amino acid mutations in SEQ ID NO: 427, HCDR3 having no more than 6, 5, 4, 3, 2, or 1 amino acid substitutions in SEQ ID NO: 428, LCDR1 having no more than 5, 4, 3, 2, or 1 amino acid mutations in SEQ ID NO: 429, LCDR2 having no more than 3, 2, or 1 amino acid mutations in SEQ ID NO: 430, and/or LCDR3 having no more than 4, 3, 2, or 1 amino acid mutations in SEQ ID NO: 431, and in the meantime retain the binding specificity to SARS-COV-2, optionally having binding affinity to SARS-COV-2 at a level similar to or even higher than antibody P22A-1D1.

In certain embodiments, the variants of antibody P22A-1D1 retain the entirety of the paratope of antibody P22A-1D1 while one or more of the amino acid residues outside the paratope of the antibody may be mutated. In certain embodiments, the paratope of antibody P22A-1D1 comprises or consists of: G26, F27, T28, S31, N32 and Y33 of HCDR1; Y52, S53, G54, and S56 of HCDR2; Y58 of heavy chain framework region 3, R97, R99, D100, Y101, Y102 and D105 of HCDR3; Q27, G28, I29, S30 and Y32 of LCDR1; S67 of LCDR2; and/or H90, L91, N92 and Y94 of LCDR3; wherein the numbering of residues in the heavy chain CDRs is according to SEQ ID NO: 432, and the numbering of residues in the light chain CDR is according to SEQ ID NO: 433.

In certain embodiments, the variants of antibody P22A-1D1 retain at least part of the paratope of antibody P22A-1D1. For example, the variants of antibody P22A-1D1 retain at least 60%, at least 70%, at least 80%, or at least 90% of the residues of the paratope of antibody P22A-1D1. In certain embodiments, the variants of antibody P22A-1D1 comprises one or more mutations (e.g. conservative substitutions) in the paratope of antibody P22A-1D1. In certain embodiments, the variants of antibody P22A-1D1 comprises no more than 5, 4, 3, 2 or 1 mutations (e.g. substitutions) in the paratope of antibody P22A-1D1. In certain embodiments, the variants of antibody P22A-1D1 comprises no more than 5, 4, 3, 2 or 1 conservative substitutions in the paratope of antibody P22A-1D1.

In certain embodiments, the present disclosure provides variants of antibody P5A-1D2, wherein the variant comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 236, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 237, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 238, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 239, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 240, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 241, and in the meantime retain the binding specificity to SARS-COV-2, optionally having binding affinity to SARS-COV-2 at a level similar to or even higher than antibody P5A-1D2.

In certain embodiments, the antibody variants of antibody P5A-1D2 comprises an HCDR1 having no more than 6, 5, 4, 3, 2, or 1 amino acid mutations in SEQ ID NO: 236, an HCDR2 having no more than 9, 8, 7, 6, 5, 4, 3, 2, or 1 amino acid mutations in SEQ ID NO: 237, HCDR3 having no more than 6, 5, 4, 3, 2, or 1 amino acid substitutions in SEQ ID NO: 238, LCDR1 having no more than 4, 3, 2, or 1 amino acid mutations in SEQ ID NO: 239, LCDR2 having no more than 4, 3, 2, or 1 amino acid mutations in SEQ ID NO: 240, and/or LCDR3 having no more than 4, 3, 2, or 1 amino acid mutations in SEQ ID NO: 241, and in the meantime retain the binding specificity to SARS-COV-2, optionally having binding affinity to SARS-COV-2 at a level similar to or even higher than antibody P5A-1D2.

In certain embodiments, the variants of antibody P5A-1D2 retain the entirety of the paratope of antibody P5A-1D2 while one or more of the amino acid residues outside the paratope of the antibody may be mutated. In certain embodiments, the paratope of antibody P5A-1D2 comprises or consists of: G26, F27, I28, S31, N32 and Y33 of HCDR1; Y52, S53, G54, and S56 of HCDR2; Y58 and R87 of heavy chain framework region 3, R97, L99, Q100, V101, G102, A103, T104 and D106 of HCDR3; A31 and Y33 of LCDR1; and/or S95 of LCDR3; wherein the numbering of residues in the heavy chain CDRs is according to SEQ ID NO: 242, and the numbering of residues in the light chain CDR is according to SEQ ID NO: 243.

In certain embodiments, the variants of antibody P5A-1D2 retain at least part of the paratope of antibody P5A-1D2. For example, the variants of antibody P5A-1D2 retain at least 60%, at least 70%, at least 80%, or at least 90% of the residues of the paratope of antibody P5A-1D2. In certain embodiments, the variants of antibody P5A-1D2 comprises one or more mutations (e.g. conservative substitutions) in the paratope of antibody P5A-1D2. In certain embodiments, the variants of antibody P5A-1D2 comprises no more than 5, 4, 3, 2 or 1 mutations (e.g. substitutions) in the paratope of antibody P5A-1D2. In certain embodiments, the variants of antibody P5A-1D2 comprises no more than 5, 4, 3, 2 or 1 conservative substitutions in the paratope of antibody P5A-1D2.

In certain embodiments, the present disclosure provides variants of antibody P5A-3C8, wherein the variant comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 226, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 227, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 228, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 229, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 230, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 231, and in the meantime retain the binding specificity to SARS-COV-2, optionally having binding affinity to SARS-COV-2 at a level similar to or even higher than antibody P5A-3C8.

In certain embodiments, the antibody variants of antibody P5A-3C8 comprises an HCDR1 having no more than 6, 5, 4, 3, 2, or 1 amino acid mutations in SEQ ID NO: 226, an HCDR2 having no more than 5, 4, 3, 2, or 1 amino acid mutations in SEQ ID NO: 227, HCDR3 having no more than 6, 5, 4, 3, 2, or 1 amino acid substitutions in SEQ ID NO: 228, LCDR1 having no more than 5, 4, 3, 2, or 1 amino acid mutations in SEQ ID NO: 229, LCDR2 having no more than 3, 2, or 1 amino acid mutations in SEQ ID NO: 230, and/or LCDR3 having no more than 5, 4, 3, 2, or 1 amino acid mutations in SEQ ID NO: 231, and in the meantime retain the binding specificity to SARS-COV-2, optionally having binding affinity to SARS-COV-2 at a level similar to or even higher than antibody P5A-3C8.

In certain embodiments, the variants of antibody P5A-3C8 retain the entirety of the paratope of antibody P5A-3C8 while one or more of the amino acid residues outside the paratope of the antibody may be mutated. In certain embodiments, the paratope of antibody P5A-3C8 comprises or consists of: G26, F27, T28, S31, N32 and Y33 of HCDR1; Y52, S53, G54, and S56 of HCDR2; Y58 of heavy chain framework region 3, R97, L99, Q100, E101 and H102 of HCDR3; and G28, I29, S30, S31 and Y32 of LCDR1; S67 of LCDR2; G68 of light chain framework region 3, H90, L91, N92, S93 and Y94 of LCDR3; wherein the numbering of residues in the heavy chain CDRs is according to SEQ ID NO: 232, and the numbering of residues in the light chain CDR is according to SEQ ID NO: 233.

In certain embodiments, the variants of antibody P5A-3C8 retain at least part of the paratope of antibody P5A-3C8. For example, the variants of antibody P5A-3C8 retain at least 60%, at least 70%, at least 80%, or at least 90% of the residues of the paratope of antibody P5A-3C8. In certain embodiments, the variants of antibody P5A-3C8 comprises one or more mutations (e.g. conservative substitutions) in the paratope of antibody P5A-3C8. In certain embodiments, the variants of antibody P5A-3C8 comprises no more than 5, 4, 3, 2 or 1 mutations (e.g. substitutions) in the paratope of antibody P5A-3C8. In certain embodiments, the variants of antibody P5A-3C8 comprises no more than 5, 4, 3, 2 or 1 conservative substitutions in the paratope of antibody P5A-3C8.

The variants of the antibodies or the antigen binding fragments thereof can retain their parent antibodies' binding specificity to RBD of the spike protein of SARS-CoV-2, or may further have one or more desirable properties conferred by the mutation(s). For example, the variants may have improved antigen-binding affinity, improved glycosylation pattern, reduced risk of glycosylation, reduced deamination, reduced or depleted effector function(s), improved FcRn receptor binding in a pH dependent manner, increased pharmacokinetic half-life, pH sensitivity, and/or compatibility to conjugation (e.g. one or more introduced cysteine residues). Such variants are also known as affinity variants, glycosylation variants, cysteine variants, Fc variants, and so on, which are described in more details as follows.

a) Affinity Variant

Affinity variant may contain modifications or substitutions in one or more CDR sequences as provided in Table 1 above, one or more framework (FR) sequences provided herein, or the heavy or light chain variable region sequences provided in Table 2 above. FR sequences can be readily identified by a skilled person in the art based on the CDR sequences in Table 1 above and variable region sequences in Table 2 above, as it is well-known in the art that a CDR region is flanked by two FR regions in the variable region.

The affinity variants retain specific binding affinity to RBD of the spike protein of SARS-COV-2 of the parent antibody, or even have improved specific binding affinity to the RBD of the spike protein of SARS-CoV-2 over the parent antibody. Various methods known in the art can be used to achieve this purpose. For example, a library of antibody variants (such as Fab or scFv variants) can be generated and expressed with phage display technology, and then screened for the binding affinity to the RBD of the spike protein of SARS-COV-2. For another example, computer software can be used to virtually simulate the binding of the antibodies to the RBD of the spike protein of SARS-COV-2, and identify the amino acid residues on the antibodies which form the binding interface. Such residues may be either avoided in the substitution so as to prevent reduction in binding affinity, or targeted for substitution to provide for a stronger binding.

In certain embodiments, the affinity variant provided herein comprises one or more amino acid residue substitutions in one or more CDR sequences, and/or one or more FR sequences. In certain embodiments, an affinity variant comprises no more than 20, 15, 10, 9, 8, 7, 6, 5, 4, 3, 2, or 1 substitutions in the CDR sequences and/or FR sequences in total.

b) Glycosylation Variant

The anti-SARS-COV-2 antibodies and antigen-binding fragments provided herein also encompass a glycosylation variant, which can be obtained to either increase or decrease the extent of glycosylation of the antibody or antigen binding fragment thereof.

The antibody or antigen binding fragment thereof may comprise one or more modifications that introduces or removes a glycosylation site. A glycosylation site is an amino acid residue with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence in the is substituted. A new glycosylation site can be created in a similar way by introducing such a tripeptide sequence or serine or threonine residue.

In certain embodiments, the anti-SARS-COV-2 antibodies and antigen-binding fragments provided herein comprise a mutation at N297 (e.g. N297A, N297Q, or N297G) to remove the glycosylation site.

c) Cysteine-Engineered Variant

The anti-SARS-COV-2 antibodies and antigen-binding fragments provided herein also encompass a cysteine-engineered variant, which comprises one or more introduced free cysteine amino acid residues.

A free cysteine residue is one which is not part of a disulfide bridge. A cysteine-engineered variant is useful for conjugation with for example, a cytotoxic and/or imaging compound, a label, or a radioisotype among others, at the site of the engineered cysteine, through for example a maleimide or haloacetyl. Methods for engineering antibodies or antigen-binding fragments thereof to introduce free cysteine residues are known in the art, see, for example, WO2006/034488.

d) Fc Variant

The anti-SARS-COV-2 antibodies and antigen-binding fragments provided herein also encompass an Fc variant, which comprises one or more amino acid residue modifications or substitutions at its Fc region and/or hinge region, for example, to provide for altered effector functions such as ADCC, ADCP and CDC. Methods of altering ADCC activity by antibody engineering have been described in the art, see for example, Shields R L. et al., J Biol Chem. 2001. 276(9): 6591-604; Idusogie E E. et al., J Immunol. 2000.164 (8):4178-84; Steurer W. et al., J Immunol. 1995, 155(3): 1165-74; Idusogie E E. et al., J Immunol. 2001, 166(4): 2571-5; Lazar G A. et al., PNAS, 2006, 103(11): 4005-4010; Ryan M C. et al., Mol. Cancer Ther., 2007, 6: 3009-3018; Richards J O., et al., Mol Cancer Ther. 2008, 7(8): 2517-27; Shields R. L. et al, J. Biol. Chem, 2002, 277: 26733-26740; Shinkawa T. et al, J. Biol. Chem, 2003, 278: 3466-3473.

CDC activity of the antibodies provided herein can also be altered, for example, by improving or diminishing C1q binding and/or CDC (see, for example, WO99/51642; Duncan & Winter Nature 322:738-40 (1988); U.S. Pat. Nos. 5,648,260; 5,624,821); and WO94/29351 concerning other examples of Fe region variants. One or more amino acids selected from amino acid residues 329, 331 and 322 of the Fc region can be replaced with a different amino acid residue to alter C1q binding and/or reduced or abolished complement dependent cytotoxicity (CDC) (see, U.S. Pat. No. 6,194,551 by Idusogie et al). One or more amino acid substitution(s) can also be introduced to alter the ability of the antibody to fix complement (see PCT Publication WO 94/29351 by Bodmer et al.).

The term "Antibody-dependent cellular phagocytosis" and "ADCP" refer to a process by which antibody-coated cells or particles are internalized, either in whole or in part, by phagocytic immune cells (e.g., macrophages, neutrophils and dendritic cells) that bind to an immunoglobulin Fc region. Methods for altering the ADCP activity of antibodies by antibody engineering are known in the art, see for example, Kellner C et al., Transfus Med Hemother, (2017) 44:327-336 and Chung A W et al., AIDS, (2014) 28:2523-2530.

Examples of Fc variants are known in the art, see, for example, Wang et al., Protein Cell 2018, 9(1): 63-73 and Kang et al., Exp & Mol., Med. (2019) 51:138, which are incorporated herein to their entirety.

i) Fc Variant with Enhanced Effector Functions

In certain embodiments, the Fc variants provided herein has increased ADCC and/or increased affinity to an Fcγ receptor (e.g. FcγRI (CD64), FcγRII (CD32) and/or FcγRIII (CD16)) relative to a wildtype Fc (e.g. Fc of IgG1). In certain embodiments, an Fc variant comprises one or more amino acid substitution(s) at one or more of the following positions: 234, 235, 236, 238, 239, 240, 241, 243, 244, 245, 246, 247, 248, 249, 252, 254, 255, 256, 258, 260, 262, 263, 264, 265, 267, 268, 269, 270, 272, 274, 276, 278, 280, 283, 285, 286, 289, 290, 292, 293, 294, 295, 296, 298, 299, 300, 301, 303, 304, 305, 307, 309, 312, 313, 315, 320, 322, 324, 325, 326, 327, 329, 330, 331, 332, 333, 334, 335, 337, 338, 339, 340, 345, 360, 373, 376, 378, 382, 388, 389, 396, 398, 414, 416, 419, 430, 433, 434, 435, 436, 437, 438, 439 and 440 of the Fc region (see WO 00/42072 by Presta, WO2006/019447 by Lazar, and WO2016/196228, incorporated herein to its entirety), wherein the numbering of the residues in the Fc region is that of the EU index as in Kabat (see, Kabat E. A. et al., Sequences of Proteins of immunological Interest, 5th Ed. Public Health Service, National Institutes of Health, Bethesda, Md. (1991)). Exemplary substitutions for increased effector functions include, without limitation, 234Y, 235Q, 236A, 236W, 239D, 239E, 239M, 243L, 247I, 268D, 267E, 268D, 268E, 268F, 270E, 280H, 290S, 292P, 298A, 298D, 298V, 300L, 305I, 324T, 326A, 326D, 326W, 330L, 330M, 333S, 332D, 332E, 298A, 333A, 334A, 334E, 326A, 247I, 339D, 339Q, 345R, 280H, 290S, 298D, 298V, 243L, 292P, 300L, 396L, 305I, 396L, 430G, 440Y, or any combination thereof (such as 239D/332E, 239D/332E/330L, 236A/332E, 236A/239D/332E, 268F/324T, 267E/268F, 267E/324T, and 267E/268F/324T) (see, WO2016/196228; Richards et al. (2008) *Mol. Cancer Therap.* 7:2517; Moore et al. (2010) mAbs 2:181; and Strohl (2009) *Current Opinion in Biotechnology* 20:685-691).

Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A, F243L/R292P/Y300L/V305I/P396L, S298A/E333A/K334A and L234Y/L235Q/G236W/S239M/H268D/D270E/S298A in one heavy chain and D270E/K326D/A330M/K334E in the opposing heavy chain (having enhanced FcγRIII binding and ADCC activity). Other Fc variants with strongly enhanced binding to FcγRIIIa include variant with S239D/I332E and S239D/I332E/A330L mutations, which showed the greatest increase in affinity for FcγRIIIa, a decrease in FcγRIIb binding, and strong cytotoxic activity, and variants with L235V, F243L, R292P, Y300L, V305I and P396L mutations, which exhibited enhancing FcγRIIIa and concomitantly enhanced ADCC activity. (see Lazar et a. (2006) Proc. Nat'l Acad Sci. (USA) 103:4005; Awan et al. (2010) Blood 115: 1204; Desjarlais & Lazar (2011) Exp. Cell Res, Stavenhagen et al. (2007) *Cancer Res* 67:8882). Modifications that increase binding to C1q can be introduced in order to enhance CDC activity. Exemplary modifications include, a K326 (e.g., K326W) and/or E333 modification in an IgG2, or a S267E/H268F/S324T modification, alone or in any combination, in an IgG1 (see Idusogie et al. (2001) J. Immunol. 166:2571, Moore et al. (2010) mAbs 2: 181). Other exemplary modifications include, K326W/E333S, S267E/H268F/S324T, and E345R/E430G/S440Y.

ii) Fc with Reduced Effector Functions

In certain embodiments, the Fc variants provided herein has reduced effector functions relative to a wildtype Fc (e.g. Fc of IgG1), and comprise one or more amino acid substitution(s) at a position selected from the group consisting of: 220, 226, 229, 233, 234, 235, 236, 237, 238, 267, 268, 269, 270, 297, 309, 318, 320, 322, 325, 328, 329, 330, and 331 of the Fc region (see, WO2016/196228; Richards et al. (2008) *Mol. Cancer Therap.* 7:2517; Moore et al. (2010) *mAbs* 2:181; and Strohl (2009) *Current Opinion in Biotechnology* 20:685-691), wherein the numbering of the residues in the Fc region is that of the EU index as in Kabat. Exemplary substitutions for reduced effector functions include, without limitation, 220S, 226S, 228P, 229S, 233P, 234V, 234G, 234A, 234F, 234A, 235A, 235G, 235E, 236E, 236R, 237A, 237K, 238S, 267R, 268A, 268Q, 269R, 297A, 297Q, 297G, 309L, 318A, 322A, 325L, 328R, 330S, 331S, or any combination thereof (see, WO2016/196228; and Strohl (2009) *Current Opinion in Biotechnology* 20:685-691).

In certain embodiments, the Fc variant provided herein is of IgG1 isotype and comprises one or more amino acid substitution(s) selected from the group consisting of: L234A, L234F, L234V, F234A, V234A, L235A, L235E, G237A, P238S, H268Q, H268A, N297A, N297Q, N297G, V309L, A330S, and P331S, or any combination thereof (such as L234A/L235A). In certain embodiments, the Fc variant provided herein is of IgG2 isotype, and comprises one or more amino acid substitution(s) selected from the group consisting of: H268Q, V309L, A330S, P331S, V234A, G237A, P238S, H268A, and any combination thereof. In certain embodiments, the Fc variant provided herein is of IgG4 isotype, and comprises one or more amino acid substitution(s) selected from the group consisting of: S228P, F234A, L235E, L235A, G237A, E318A, N297A, N297Q, N297G, and any combination thereof. In certain embodiments, the anti-SARS-COV-2 antibodies and antigen-binding fragments provided herein is of IgG2/IgG4 cross isotype. Examples of IgG2/IgG4 cross isotype is described in Rother R P et al, Nat Biotechnol 25:1256-1264 (2007).

iii) Fc with Altered Binding to FcRn

In certain embodiments, the Fc variant comprises one or more amino acid substitution(s) that improves binding affinity to neonatal Fc receptor (FcRn) at pH 6.0 while retaining minimal binding at pH 7.4. Such a variant can have an extended pharmacokinetic half-life, as it binds to FcRn at acidic pH which allows it to escape from degradation in the lysosome and then be translocated and released out of the cell. Methods of engineering an antibody and antigen-binding fragment thereof to improve binding affinity with FcRn are well-known in the art, see, for example, Vaughn, D. et al, Structure, 6(1): 63-73, 1998; Kontermann, R. et al, Antibody Engineering, Volume 1, Chapter 27: Engineering of the Fc region for improved PK, published by Springer, 2010; Yeung, Y. et al, Cancer Research, 70: 3269-3277 (2010); Hinton, P. et al, J. Immunology, 176:346-356 (2006); Petkova et al. (2006) Int. Immunol. 18:1759, Ball Acqua et al. Journal of Immunology 2002, 169:5171-5180, Dall'Acqua W F. et al., J Biol Chem. 281:23514-23524 (2006); Zalevsky J, et al, Nat Biotechnol.; 28:157-159 (2010); WO 2009/086320; U.S. Pat. Nos. 6,277,375; 6,821,505; WO 97/34631; and WO 2002/060919.

Non-limiting examples of Fc modifications that may result in an increase in serum half-life of the antibody when administered include, e.g., substitution(s) at one or more positions selected from: 234 (e.g., with F), 235 (e.g., with Q), 238 (e.g., with D), 250 (e.g., with E or Q), 252 (e.g., with L/Y/F/W or T), 254 (e.g., with S or T), 256 (e.g., with S/R/Q/E/D or T); 259 (e.g., with I); 272 (e.g., with A), 305 (e.g., with A), 307 (e.g., with A or P), 308 (e.g., with F, C or P), 311 (e.g., with A or R), 312 (e.g., with A), 322 (e.g., Q), 328 (e.g. E), 331 (e.g., with A), 378 (e.g., with A), 380 (e.g., with A), 382 (e.g., with A), 428 (e.g., with L or F), 432 (e.g., with C), 433 (e.g., with H/L/R/S/P/Q or K), 434 (e.g., with H/F or Y or S or A or W), 435 (e.g. with H), 436 (e.g., with L) and 437 (e.g., with C) (all positions by EU numbering) (see, WO2016049000A2; WO2020052692; WO2016196228). In some embodiments, the Fc variant comprises one or more amino acid substitution(s) selected from the group consisting of 234F, 235Q, 238D, 250Q, 252T, 252Y, 254T, 256E, 259I, 272A, 305A, 307A, 308F, 311A, 322Q, 328E, 331S, 380A, 428L, 432C, 433K, 433S, 434S, 434Y, 434F, 434W, 434A, 435H, 436L, 437C and any combination thereof. In some embodiments, the Fc modifications comprises one or pairs or groups of modifications selected from: a) a 428L (e.g., M428L) and 434S (e.g., N434S) substitution; a 428L, 259I (e.g., V259I), and 308F (e.g., V308F) substitution; b) a 433K (e.g., H433K) and 434 (e.g., N434Y or N434F) substitution; c) a 252Y, 254T, and 256E (e.g., M252Y, S254T, and T256E) substitution; d) a 250Q and 428L substitution (e.g., T250Q and M428L); e) a 307A, 380A and 434A substitution (e.g., T307A, E380A and N434A); f) a P238D and L328E substitution; g) a L234F, L235Q, K322Q, M252T, S254T and T256E substitution; and h) and a L432C, H433S, N434W, Y436L and T437C substitution.

In some embodiments, hybrid IgG isotypes may be used to increase FcRn binding and half-life of antibodies. A hybrid Ig can be generated from two or more isotypes. For example, an IgG1/IgG3 hybrid variant may be constructed by substituting IgG1 positions in the CH2 and/or CH3 region with the amino acids from IgG3 at positions where the two isotypes differ. In some embodiments, a hybrid Ig can comprises one or more modifications (e.g. substitutions) disclosed here.

Antigen-Binding Fragments

Provided herein are also anti-SARS-CoV-2 antigen-binding fragments. In some embodiments, the antibodies and antigen-binding fragments provided herein comprise all or a portion of the heavy chain variable domain and/or all or a portion of the light chain variable domain.

Various types of antigen-binding fragments are known in the art and can be developed based on the anti-SARS-CoV-2 antibodies provided herein, including for example, the exemplary antibodies whose CDR are shown in Tables 1 above, and variable sequences are shown in Tables 2 and 3, and their different variants (such as affinity variants, glycosylation variants, Fc variants, cysteine-engineered variants and so on).

In certain embodiments, an anti-SARS-CoV-2 antigen-binding fragment provided herein is a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a bispecific scFv dimer, a multispecific antibody, a heavy chain antibody, a camelized single domain antibody, a nanobody, a domain antibody, and a bivalent domain antibody.

Various techniques can be used for the production of such antigen-binding fragments. Illustrative methods include, enzymatic digestion of intact antibodies (see, e.g. Morimoto et al., *Journal of Biochemical and Biophysical Methods* 24:107-117 (1992); and Brennan et al., *Science*, 229:81 (1985)), recombinant expression by host cells such as *E. coli* (e.g. for Fab, Fv and ScFv antibody fragments), screening from a phage display library as discussed above (e.g. for ScFv), and chemical coupling of two Fab'-SH fragments to form F(ab')$_2$ fragments (Carter et al., Bio/Technology 10:163-167 (1992)). Other techniques for the production of antibody fragments will be apparent to a person skilled in the art.

In certain embodiments, the antigen-binding fragment is a scFv. Generation of scFv is described in, for example, WO 93/16185; U.S. Pat. Nos. 5,571,894; and 5,587,458. ScFv may be fused to an effector protein at either the amino or the carboxyl terminus to provide for a fusion protein (see, for example, Antibody Engineering, ed. Borrebaeck).

In certain embodiments, the anti-SARS-CoV-2 antibodies or antigen-binding fragments thereof provided herein are bivalent, tetravalent, hexavalent, or multivalent. Any molecule being more than bivalent is considered multivalent, encompassing for example, trivalent, tetravalent, hexavalent, and so on.

A bivalent molecule can be monospecific if the two binding sites are both specific for binding to the same antigen or the same epitope. This, in certain embodiments, provides for stronger binding to the antigen or the epitope than a monovalent counterpart. Similar, a multivalent molecule may also be monospecific. In certain embodiments, in a bivalent or multivalent antigen-binding moiety, the first valent of binding site and the second valent of binding site are structurally identical (i.e. having the same sequences), or structurally different (i.e. having different sequences albeit with the same specificity).

A bivalent can also be bispecific, if the two binding sites are specific for different or overlapping antigens or epitopes. This also applies to a multivalent molecule. For example, a trivalent molecule can be bispecific when two binding sites are monospecific for a first antigen (or epitope) and the third binding site is specific for a second antigen (or epitope).

Bispecific (or Bivalent) Antibody or Antigen-Binding Fragments

In another aspect, the present disclosure provides bispecific (or bivalent) antibody molecules comprising an anti-SARS-CoV-2 antibody or antigen-binding fragment thereof as disclosed herein. In certain embodiments, the bispecific (or bivalent) antibodies provided herein comprises a first antigen-binding domain and a second antigen-binding domain, wherein the first antigen-binding domains is derived from a monoclonal antibody selected from the group consisting of P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, PIA-1C10, P4A-1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A- 3C12, and P22A-1D1. The second antigen-binding domain can be derived from any suitable antibody.

In certain embodiments, the bispecific (or bivalent) antibodies provided herein comprises a first antigen-binding domain and a second antigen-binding domain, wherein the first and the second antigen-binding domains are derived from any two monoclonal antibodies selected from the group consisting of P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C-1F11, P2B-1G5, P2B- 1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, and P22A-1D1. Any two monoclonal antibodies from the above 42 antibodies can be combined, as if each and every possible combination of two antibodies have been set forth herein individually. In certain embodiments, the bispecific (or bivalent) antibodies provided herein comprises a first antigen-binding domain and a second antigen-binding domain, wherein the first and the second antigen-binding domains are derived from any two monoclonal antibodies selected from the group consisting of P2B-2F6, P2C-1F11, P2B-1G5, P2B-TAT, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A- 3A1, P5A-3A6, P5A-3B4, P5A-3C12, and P22A-1D1. Any two monoclonal antibodies from the above 32 antibodies can be combined, as if each and every possible combination of two antibodies have been set forth herein individually.

In certain embodiments, the first and the second antigen-binding domains are derived from P2C-1F11 and P2B-2F6, respectively. In certain embodiments, the first and the second antigen-binding domains are derived from P2C-1F11 and P2A-1A8, respectively. In certain embodiments, the first and the second antigen-binding domains are derived from P2C-1F11 and P2A-1A9, respectively. In certain embodiments, the first and the second antigen-binding domains are derived from P2C-1F11 and P2B-2G11, respectively. In certain embodiments, the first and the second antigen-binding domains are derived from P2C-1F11 and P2A-1A10, respectively. In certain embodiments, the first and the second antigen-binding domains are derived from P2C-1F11 and P2A-1B3, respectively. In certain embodiments, the first and the second antigen-binding domains are derived from P2C-1F11 and P2B-2G4, respectively. In certain embodiments, the first and the second antigen-binding domains are derived from P2C-1F11 and P2C-1A3, respectively. In certain embodiments, the first and the second antigen-binding domains are derived from P2C-1F11 and P2C-1C8, respectively. In certain embodiments, the first and the second antigen-binding domains are derived from P2C-1F11 and P2C-1C10, respectively. In certain embodiments, the first and the second antigen-binding domains are derived from P2C-1F11 and P2C-1D5, respectively. In certain embodiments, the first and the second antigen-binding domains are derived from P2C-1F11 and P2C-1F11, respectively.

In certain embodiments, the first and the second antigen-binding domains are derived from P2A-1A8 and P2A-1A9, respectively. In certain embodiments, the first and the second antigen-binding domains are derived from P2A-1A8 and P2B-2G11, respectively. In certain embodiments, the first and the second antigen-binding domains are derived from P2A-1A8 and P2A-1A10, respectively. In certain embodiments, the first and the second antigen-binding domains are derived from P2A-1A8 and P2A-1B3, respectively. In certain embodiments, the first and the second antigen-binding domains are derived from P2A-1A8 and P2B-2F6, respectively. In certain embodiments, the first and the second antigen-binding domains are derived from P2A-1A8 and P2B-2G4, respectively. In certain embodiments, the first and the second antigen-binding domains are derived from P2A-1A8 and P2C-1A3, respectively. In certain embodiments, the first and the second antigen-binding domains are derived from P2A-1A8 and P2C-1C8, respectively. In certain embodiments, the first and the second antigen-binding domains are derived from P2A-1A8 and P2C-1C10, respectively. In certain embodiments, the first and the second antigen-binding domains are derived from P2A-1A8 and P2C-1D5, respectively.

In certain embodiments, the first and the second antigen-binding domains are derived from P2A-1A9 and 2B-2G11, respectively. In certain embodiments, the first and the second antigen-binding domains are derived from P2A-1A9 and P2A-1A10, respectively. In certain embodiments, the first and the second antigen-binding domains are derived from P2A-1A9 and P2A-1B3, respectively. In certain embodiments, the first and the second antigen-binding domains are derived from P2A-1A9 and P2B-2F6, respectively. In certain embodiments, the first and the second antigen-binding domains are derived from P2A-1A9 and P2B-2G4, respectively. In certain embodiments, the first and the second antigen-binding domains are derived from P2A-1A9 and P2C-1A3, respectively. In certain embodiments, the first and the second antigen-binding domains are derived from P2A-1A9 and P2C-1C8, respectively. In certain embodiments, the first and the second antigen-binding domains are derived from P2A-1A9 and P2C-1C10, respectively. In certain embodiments, the first and the second antigen-binding domains are derived from P2A-1A9 and P2C-1D5, respectively.

In certain embodiments, the first and the second antigen-binding domains are derived from P2B-2G11 and P2A-1A10, respectively. In certain embodiments, the first and the second antigen-binding domains are derived from P2B-2G11 and P2A-1B3, respectively. In certain embodiments, the first and the second antigen-binding domains are derived from P2B-2G11 and P2B-2F6, respectively. In certain embodiments, the first and the second antigen-binding domains are derived from P2B-2G11 and P2B-2G4, respectively. In certain embodiments, the first and the second antigen-binding domains are derived from P2B-2G11 and P2C-1A3, respectively. In certain embodiments, the first and the second antigen-binding domains are derived from P2B-2G11 and P2C-1C8, respectively. In certain embodiments, the first and the second antigen-binding domains are derived from P2B-2G11 and P2C-1C10, respectively. In certain embodiments, the first and the second antigen-binding domains are derived from P2B-2G11 and P2C-1D5, respectively.

In certain embodiments, the first and the second antigen-binding domains are derived from P2A-1A10 and P2A-1B3, respectively. In certain embodiments, the first and the second antigen-binding domains are derived from P2A-1A10 and P2B-2F6, respectively. In certain embodiments, the first and the second antigen-binding domains are derived from P2A-1A10 and P2B-2G4, respectively. In certain embodiments, the first and the second antigen-binding domains are derived from P2A-1A10 and P2C-1A3, respectively. In certain embodiments, the first and the second antigen-binding domains are derived from P2A-1A10 and P2C-1C8, respectively. In certain embodiments, the first and the second antigen-binding domains are derived from P2A-1A10 and P2C-1C10, respectively. In certain embodiments, the first and the second antigen-binding domains are derived from P2A-1A10 and P2C-1D5, respectively.

In certain embodiments, the first and the second antigen-binding domains are derived from P2A-1B3 and P2B-2F6, respectively. In certain embodiments, the first and the second antigen-binding domains are derived from P2A-1B3 and P2B-2G4, respectively. In certain embodiments, the first and the second antigen-binding domains are derived from P2A-1B3 and P2C-1A3, respectively. In certain embodiments, the first and the second antigen-binding domains are derived from P2A-1B3 and P2C-1C8, respectively. In certain embodiments, the first and the second antigen-binding domains are derived from P2A-1B3 and P2C-1C10, respectively. In certain embodiments, the first and the second antigen-binding domains are derived from P2A-1B3 and P2C-1D5, respectively.

In certain embodiments, the first and the second antigen-binding domains are derived from P2B-2F6 and P2B-2G4, respectively. In certain embodiments, the first and the second antigen-binding domains are derived from P2B-2F6 and P2C-1A3, respectively. In certain embodiments, the first and the second antigen-binding domains are derived from P2B-2F6 and P2C-1C8, respectively. In certain embodiments, the first and the second antigen-binding domains are derived from P2B-2F6 and P2C-1C10, respectively. In certain embodiments, the first and the second antigen-binding domains are derived from P2B-2F6 and P2C-1D5, respectively.

In certain embodiments, the first and the second antigen-binding domains are derived from P2B-2G4 and P2C-1A3, respectively. In certain embodiments, the first and the second antigen-binding domains are derived from P2B-2G4 and P2C-1C8, respectively. In certain embodiments, the first and the second antigen-binding domains are derived from P2B-2G4 and P2C-1C10, respectively. In certain embodiments, the first and the second antigen-binding domains are derived from P2B-2G4 and P2C-1D5, respectively.

In certain embodiments, the first and the second antigen-binding domains are derived from P2C-1A3 and P2C-1C8, respectively. In certain embodiments, the first and the second antigen-binding domains are derived from P2C-1A3 and P2C-1C10, respectively. In certain embodiments, the first and the second antigen-binding domains are derived from P2C-1A3 and P2C-1D5, respectively.

In certain embodiments, the first and the second antigen-binding domains are derived from P2C-1C8 and P2C-1C10, respectively. In certain embodiments, the first and the second antigen-binding domains are derived from P2C-1C8 and P2C-1D5, respectively.

In certain embodiments, the first and the second antigen-binding domains are derived or from P2C-1C10 and P2C-1D5, respectively.

In certain embodiments, the first and the second antigen-binding domains are derived or from P2C-1F11 and P2B-1G5, respectively. In certain embodiments, the first and the second antigen-binding domains are derived or from P2C-1F11 and P2B-TAT respectively. In certain embodiments, the first and the second antigen-binding domains are derived or from P2C-1F11 and P2C-1D7, respectively. In certain embodiments, the first and the second antigen-binding domains are derived or from P2C-1F11 and P2B-1A10, respectively. In certain embodiments, the first and the second antigen-binding domains are derived or from P2C-1F11 and P2B-1D9, respectively. In certain embodiments, the first and the second antigen-binding domains are derived or from P2C-1F11 and P2B-1E4, respectively. In certain embodiments, the first and the second antigen-binding domains are derived or from P2C-1F11 and P2B-1G1, respectively. In certain embodiments, the first and the second antigen-binding domains are derived or from P2C-1F11 and P4A-2D9, respectively. In certain embodiments, the first and the second antigen-binding domains are derived or from P2C-1F11 and P5A-2G7, respectively. In certain embodiments, the first and the second antigen-binding domains are derived or from P2C-1F11 and P5A-3C8, respectively. In certain embodiments, the first and the second antigen-binding domains are derived or from P2C-1F11 and P5A-1D2, respectively. In certain embodiments, the first and the second antigen-binding domains are derived or from P2C-1F11 and P5A-2F11, respectively. In certain embodiments, the first and the second antigen-binding domains are derived or from P2C-1F11 and P5A-2E1, respectively. In certain embodiments, the first and the second antigen-binding domains are derived or from P2C-1F11 and P5A-1C8, respectively.

In certain embodiments, the first and the second antigen-binding domains are derived or from P2B-2F6 and P2B-1G5, respectively. In certain embodiments, the first and the second antigen-binding domains are derived or from P2B-2F6 and P2B-1A1 respectively. In certain embodiments, the first and the second antigen-binding domains are derived or from P2B-2F6 and P2C-1D7, respectively. In certain embodiments, the first and the second antigen-binding domains are derived or from P2B-2F6 and P2B-1A10, respectively. In certain embodiments, the first and the second antigen-binding domains are derived or from P2B-2F6 and P2B-1D9, respectively. In certain embodiments, the first and the second antigen-binding domains are derived or from P2B-2F6 and P2B-1E4, respectively. In certain embodiments, the first and the second antigen-binding domains are derived or from P2B-2F6 and P2B-1G1, respectively. In certain embodiments, the first and the second antigen-binding domains are derived or from P2B-2F6 and P4A-2D9, respectively. In certain embodiments, the first and the second antigen-binding domains are derived or from P2B-2F6 and P5A-2G7, respectively. In certain embodiments, the first and the second antigen-binding domains are derived or from P2B-2F6 and P5A-3C8, respectively. In certain embodiments, the first and the second antigen-binding domains are derived or from P2B-2F6 and P5A-1D2, respectively. In certain embodiments, the first and the second antigen-binding domains are derived or from P2B-2F6 and P5A-2F11, respectively. In certain embodiments, the first and the second antigen-binding domains are derived or from P2B-2F6 and P5A-2E1, respectively. In certain embodiments, the first and the second antigen-binding domains are derived or from P2B-2F6 and P5A-1C8, respectively.

In certain embodiments, the first and the second antigen-binding domains are derived or from P2B-1G5 and P2B-1A1 respectively. In certain embodiments, the first and the second antigen-binding domains are derived or from P2B-1G5 and P2C-1D7, respectively. In certain embodiments, the first and the second antigen-binding domains are derived or from P2B-1G5 and P2B-1A10, respectively. In certain embodiments, the first and the second antigen-binding domains are derived or from P2B-1G5 and P2B-1D9, respectively. In certain embodiments, the first and the second antigen-binding domains are derived or from P2B-1G5 and P2B-1E4, respectively. In certain embodiments, the first and the second antigen-binding domains are derived or from P2B-1G5 and P2B-1G1, respectively. In certain embodiments, the first and the second antigen-binding domains are derived or from P2B-1G5 and P4A-2D9, respectively. In certain embodiments, the first and the second antigen-binding domains are derived or from P2B-1G5 and P5A-2G7, respectively. In certain embodiments, the first and the second antigen-binding domains are derived or from P2B-1G5 and P5A-3C8, respectively. In certain embodiments, the first and the second antigen-binding domains are derived or from P2B-1G5 and P5A-1D2, respectively. In certain embodiments, the first and the second antigen-binding domains are derived or from P2B-1G5 and P5A-2F11, respectively. In certain embodiments, the first and the second antigen-binding domains are derived or from P2B-1G5 and P5A-2E1, respectively. In certain embodiments, the first and the second antigen-binding domains are derived or from P2B-1G5 and P5A-1C8, respectively.

In certain embodiments, the first and the second antigen-binding domains are derived or from P2B-1 A1 and P2C-1D7, respectively. In certain embodiments, the first and the second antigen-binding domains are derived or from P2B-1A1 and P2B-1A10, respectively. In certain embodiments, the first and the second antigen-binding domains are derived or from P2B-1A1 and P2B-1D9, respectively. In certain embodiments, the first and the second antigen-binding domains are derived or from P2B-1A1 and P2B-1E4, respectively. In certain embodiments, the first and the second antigen-binding domains are derived or from P2B-1A1 and P2B-1G1, respectively. In certain embodiments, the first and the second antigen-binding domains are derived or from P2B-1A1 and P4A-2D9, respectively. In certain embodiments, the first and the second antigen-binding domains are derived or from P2B-1A1 and P5A-2G7, respectively. In certain embodiments, the first and the second antigen-binding domains are derived or from P2B-1A1 and P5A-3C8, respectively. In certain embodiments, the first and the second antigen-binding domains are derived or from P2B-1A1 and P5A-1D2, respectively. In certain embodiments, the first and the second antigen-binding domains are derived or from P2B-1A1 and P5A-2F11, respectively. In certain embodiments, the first and the second antigen-binding domains are derived or from P2B-1A1 and P5A-2E1, respectively. In certain embodiments, the first and the second antigen-binding domains are derived or from P2B-1A1 and P5A-1C8, respectively.

In certain embodiments, the first and the second antigen-binding domains are derived or from P2C-1D7 and P2B-1A10, respectively. In certain embodiments, the first and the second antigen-binding domains are derived or from P2C-1D7 and P2B-1D9, respectively. In certain embodiments, the first and the second antigen-binding domains are derived or from P2C-1D7 and P2B-1E4, respectively. In certain embodiments, the first and the second antigen-binding domains are derived or from P2C-1D7 and P2B-1G1, respectively. In certain embodiments, the first and the second antigen-binding domains are derived or from P2C-1D7 and P4A-2D9, respectively. In certain embodiments, the first and the second antigen-binding domains are derived or from P2C-1D7 and P5A-2G7, respectively. In certain embodiments, the first and the second antigen-binding domains are derived or from P2C-1D7 and P5A-3C8, respectively. In certain embodiments, the first and the second antigen-binding domains are derived or from P2C-1D7 and P5A-1D2, respectively. In certain embodiments, the first and the second antigen-binding domains are derived or from P2C-1D7 and P5A-2F11, respectively. In certain embodiments, the first and the second antigen-binding domains are derived or from P2C-1D7 and P5A-2E1, respectively. In certain embodiments, the first and the second antigen-binding domains are derived or from P2C-1D7 and P5A-1C8, respectively.

In certain embodiments, the first and the second antigen-binding domains are derived or from P2B-1A10 and P2B-1D9, respectively. In certain embodiments, the first and the second antigen-binding domains are derived or from P2B-1A10 and P2B-1E4, respectively. In certain embodiments, the first and the second antigen-binding domains are derived or from P2B-1A10 and P2B-1G1, respectively. In certain embodiments, the first and the second antigen-binding domains are derived or from P2B-1A10 and P4A-2D9, respectively. In certain embodiments, the first and the second antigen-binding domains are derived or from P2B-1A10 and P5A-2G7, respectively. In certain embodiments, the first and the second antigen-binding domains are derived or from P2B-1A10 and P5A-3C8, respectively. In certain embodiments, the first and the second antigen-binding domains are derived or from P2B-1A10 and P5A-1D2, respectively. In certain embodiments, the first and the second antigen-binding domains are derived or from P2B-1A10 and P5A-2F11, respectively. In certain embodiments, the first and the second antigen-binding domains are derived or from P2B-1A10 and P5A-2E1, respectively. In certain embodiments, the first and the second antigen-binding domains are derived or from P2B-1A10 and P5A-1C8, respectively.

In certain embodiments, the first and the second antigen-binding domains are derived or from P2B-1D9 and P2B-1E4, respectively. In certain embodiments, the first and the second antigen-binding domains are derived or from P2B-1D9 and P2B-1G1, respectively. In certain embodiments, the first and the second antigen-binding domains are derived or from P2B-1D9 and P4A-2D9, respectively. In certain embodiments, the first and the second antigen-binding domains are derived or from P2B-1D9 and P5A-2G7, respectively. In certain embodiments, the first and the second antigen-binding domains are derived or from P2B-1D9 and P5A-3C8, respectively. In certain embodiments, the first and the second antigen-binding domains are derived or from P2B-1D9 and P5A-1D2, respectively. In certain embodiments, the first and the second antigen-binding domains are derived or from P2B-1D9 and P5A-2F11, respectively. In certain embodiments, the first and the second antigen-binding domains are derived or from P2B-1D9 and P5A-2E1, respectively. In certain embodiments, the first and the second antigen-binding domains are derived or from P2B-1D9 and P5A-1C8, respectively.

In certain embodiments, the first and the second antigen-binding domains are derived or from P2B-1E4 and P2B-1G1, respectively. In certain embodiments, the first and the second antigen-binding domains are derived or from P2B-1E4 and P4A-2D9, respectively. In certain embodiments, the first and the second antigen-binding domains are derived or from P2B-1E4 and P5A-2G7, respectively. In certain embodiments, the first and the second antigen-binding domains are derived or from P2B-1E4 and P5A-3C8, respectively. In certain embodiments, the first and the second antigen-binding domains are derived or from P2B-1E4 and P5A-1D2, respectively. In certain embodiments, the first and the second antigen-binding domains are derived or from P2B-1E4 and P5A-2F11, respectively. In certain embodiments, the first and the second antigen-binding domains are derived or from P2B-1E4 and P5A-2E1, respectively. In certain embodiments, the first and the second antigen-binding domains are derived or from P2B-1E4 and P5A-1C8, respectively.

In certain embodiments, the first and the second antigen-binding domains are derived or from P2B-1G1 and P4A-2D9, respectively. In certain embodiments, the first and the second antigen-binding domains are derived or from P2B-1G1 and P5A-2G7, respectively. In certain embodiments, the first and the second antigen-binding domains are derived or from P2B-1G1 and P5A-3C8, respectively. In certain embodiments, the first and the second antigen-binding domains are derived or from P2B-1G1 and P5A-1D2, respectively. In certain embodiments, the first and the second antigen-binding domains are derived or from P2B-1 G1 and P5A-2F11, respectively. In certain embodiments, the first and the second antigen-binding domains are derived or from P2B-1G1 and P5A-2E1, respectively. In certain embodiments, the first and the second antigen-binding domains are derived or from P2B-1G1 and P5A-1C8, respectively.

In certain embodiments, the first and the second antigen-binding domains are derived or from P4A-2D9 and P5A-2G7, respectively. In certain embodiments, the first and the second antigen-binding domains are derived or from P4A-2D9 and P5A-3C8, respectively. In certain embodiments, the first and the second antigen-binding domains are derived or from P4A-2D9 and P5A-1D2, respectively. In certain embodiments, the first and the second antigen-binding domains are derived or from P4A-2D9 and P5A-2F11, respectively. In certain embodiments, the first and the second antigen-binding domains are derived or from P4A-2D9 and P5A-2E1, respectively. In certain embodiments, the first and the second antigen-binding domains are derived or from P4A-2D9 and P5A-1C8, respectively.

In certain embodiments, the first and the second antigen-binding domains are derived or from P5A-2G7 and P5A-3C8, respectively. In certain embodiments, the first and the second antigen-binding domains are derived or from P5A-2G7 and P5A-1D2, respectively. In certain embodiments, the first and the second antigen-binding domains are derived or from P5A-2G7 and P5A-2F11, respectively. In certain embodiments, the first and the second antigen-binding domains are derived or from P5A-2G7 and P5A-2E1, respectively. In certain embodiments, the first and the second antigen-binding domains are derived or from P5A-2G7 and P5A-1C8, respectively.

In certain embodiments, the first and the second antigen-binding domains are derived or from P5A-3C8 and P5A-1D2, respectively. In certain embodiments, the first and the second antigen-binding domains are derived or from P5A-3C8 and P5A-2F11, respectively. In certain embodiments, the first and the second antigen-binding domains are derived or from P5A-3C8 and P5A-2E1, respectively. In certain embodiments, the first and the second antigen-binding domains are derived or from P5A-3C8 and P5A-1C8, respectively.

In certain embodiments, the first and the second antigen-binding domains are derived or from P5A-1D2 and P5A-2F11, respectively. In certain embodiments, the first and the second antigen-binding domains are derived or from P5A-1D2 and P5A-2E1, respectively. In certain embodiments, the first and the second antigen-binding domains are derived or from P5A-1D2 and P5A-1C8, respectively.

In certain embodiments, the first and the second antigen-binding domains are derived or from P5A-2F11 and P5A-2E1, respectively. In certain embodiments, the first and the second antigen-binding domains are derived or from P5A-2F11 and P5A-1C8, respectively.

In certain embodiments, the first and the second antigen-binding domains are derived or from P5A-2E1 and P5A-1C8, respectively.

In certain embodiments, the bispecific antibody molecules can have at least two distinct antigen-binding sites with different specificities. In certain embodiments, the bispecific antibody molecules provided herein are capable of binding to different epitopes on the spike protein of SARS-CoV-2 virus. In some embodiments, the bispecific antibody molecules provided herein comprises antigen-binding fragments derived from two or more antibodies provided herein. In some embodiments, the two or more antibodies bind to different epitopes in RBD of spike protein of SARS-CoV-2. In some embodiments, the two or more antibodies are no more than 70% (or no more than 60%, or no more than 50%) competitive against each other in binding to RBD of spike protein of SARS-CoV-2 virus. In certain embodiments, the bispecific antibody comprises a first antigen-binding domain derived from P2C-1F11 and a second antigen-binding domain derived from an antibody selected from the group consisting of P2C-1A3, P2C-1C10, P2B-2F6, P2B-1G5, and P2A-1B3. In certain embodiments, the bispecific antibody comprises a first antigen-binding domain derived from P2C-1A3 and a second antigen-binding domain derived from an antibody selected from the group consisting of P2C-1F11, and P2A-1B3. In certain embodiments, the bispecific antibody comprises a first antigen-binding domain derived from P2B-2F6 and a second antigen-binding domain derived from an antibody selected from the group consisting of P2C-

1C10, P2C-1F11, P2B-1G5, and P2A-1B3. In certain embodiments, the bispecific antibody comprises a first antigen-binding domain derived from P2A-1B3 and a second antigen-binding domain derived from an antibody selected from the group consisting of P2C-1A3, P2C-1C10, P2C-1F11, P2B-2F6, and P2A-1A10. In some embodiments, the two or more antibodies comprise a first antibody which comprises P2C-1C10 or an antigen binding fragment thereof, and a second antibody selected from the group consisting of P2C-1A3, P2C-1F11, and P2A-1B3, or an antigen binding fragment thereof.

The term "derived from" as used herein with respect to antigen-binding domain, means that the antigen-binding domain comprise at least one heavy chain CDR sequence (e.g. comprising heavy chain CDR3, or three heavy chain CDRs) or at least one light chain CDR sequence (e.g. comprising light chain CDR3, or three heavy chain CDRs) of the specified monoclonal antibody. In certain embodiments, the first and the second antigen-binding domains comprises the heavy chain CDR sequences of the specified monoclonal antibodies, and/or the light chain CDR sequences of the specified monoclonal antibodies. In certain embodiments, the first and the second antigen-binding domains comprises the heavy chain variable region sequences of the specified monoclonal antibodies, and/or the light chain variable region sequences of the specified monoclonal antibodies. All the CDR sequences and variable region sequences of the specific monoclonal antibodies are provided in Tables 1 and 2 of the present disclosure.

In certain embodiments, the bispecific antibody molecules provided herein has a first antigen-binding domains specificity directed to the RBD of the spike protein of SARS-CoV-2 virus and a second antigen-binding domains specificity directed to a second antigen. In certain embodiments, the second antigen can be for example, an epitope outside of RBD on the spike protein of SARS-CoV-2, S2 protein (i.e. which is cleaved from the spike protein), nucleocapsid protein of SARS-CoV-2, or alternatively the second antigen can be an antigen on human immune cells such as T cell, macrophage cell, natural killer cells, or antigen-presenting cells.

In certain embodiments, the bispecific antibody molecules as provided herein are based on the format of a "whole" antibody, such as whole IgG or IgG-like molecules. Examples of such bispecific antibody include but are not limited to, those produced by a quadroma cell line. In another embodiment, a bispecific IgG-like molecule can be an appended IgG, which is engineered by appending either the amino or carboxyl termini of either light or heavy chains of an IgG of a first specificity with additional antigen-binding units of a second specificity. The appended antigen-binding units can be, for example, single domain antibodies (e.g. unpaired VL or VH, or VHH (i.e. heavy chain variable domain of a heavy chain antibody)), paired antibody variable domains (e.g. Fv or scFv) or engineered protein scaffolds. Examples of appended IgG include, without limitation, Double-variable domain (DVD)-Ig, which has a second heavy chain variable domain (VH) fused to the VH of a first heavy chain and a second variable light chain domain (VL) fused to a first light chain of the IgG. A DVD-Ig can be bispecific when the first VH/VL and the second VH/VL are selected to bind to two different antigens. In certain embodiments, a bispecific IgG or IgG-like molecules can be monovalent for each antigen and can be produced by co-expression of the two light and two heavy chains in a single host cell.

In certain embodiments, the bispecific antibody molecules as provided herein can be small recombinant bispecific formats based on variable domains, such as single domain antibody, Fv, and Fab, which may lack some or all of the antibody constant domains. Examples of small recombinant bispecific formats include, without limitation, tandem single chain variable fragment molecules (taFvs), diabodies (Dbs), single chain diabodies (scDbs) and various other derivatives of these (see, bispecific antibody formats as described by Byrne H. et al. (2013) Trends Biotech, 31 (11): 621-632, BiTE (bispecific T cell engager), DARTs, and TandAb. In certain embodiments, the two antigen-binding moieties can be linked by a peptide linker.

In certain embodiments, the bispecific antibody molecules as provided herein are in a bispecific format selected from bispecific IgG-like antibodies (BsIgG) comprising CrossMab; DAF (two-in-one); DAF (four-in-one); DutaMab; DT-IgG; Knobs-in-holes common LC; Knobs-in-holes assembly; Charge pair; Fab-arm exchange; SEEDbody; Triomab; LUZ-Y; Fcab; kappa-lamda-body; and Orthogonal Fab. For detailed description of the bispecific antibody formats please see Spiess C., Zhai Q. and Carter P. J. (2015) Molecular Immunology 67: 95-106, which is incorporated herein by reference to its entirety.

In certain embodiments, the bispecific antibody molecules as provided herein are in a bispecific format selected from IgG-appended antibodies with an additional antigen-binding moiety consisting of DVD-IgG; IgG(H)-scFv; scFv-(H)IgG; IgG(L)-scFv; scFV-(L)IgG; IgG(L,H)-Fv; IgG(H)-V; V(H)-IgG; IgG(L)-V; V(L)-IgG; IgG-scFab; 2scFv-IgG; IgG-2scFv; scFv4-Ig; scFv4-Ig; and Zybody (see Id.).

In certain embodiments, the bispecific antibody molecules as provided herein are in a bispecific format selected from WuxiBody (WuXi Biologics, see, WO2019057122A1, incorporated herein to its entirety); Triomabs; hybrid hybridoma (quadroma); Multispecific anticalin platform (Pieris); Diabodies; Single chain diabodies; Tandem single chain Fv fragments; TandAbs, Trispecific Abs (Affimed); Darts (dual affinity retargeting; Macrogenics); Bispecific Xmabs (Xencor); Bispecific T cell engagers (Bites; Amgen; 55 kDa); Triplebodies; Tribody (Fab-scFv); Fusion Protein (CreativeBiolabs); multifunctional recombinant antibody derivates; Duobody platform (Genmab); Dock and lock platform; Knob into hole (KIH) platform; Humanized bispecific IgG antibody (REGN1979) (Regeneron); Mab$_2$ bispecific antibodies (F-Star); DVD-Ig (dual variable domain immunoglobulin) (Abbvie); kappa-lambda bodies; TBTI (tetravalent bispecific tandem Ig); and CrossMab.

In certain embodiments, the bispecific antibody molecules as provided herein are in a format selected from bispecific antibody fragments comprising Nanobody; Nanobody-HAS; BiTE; Diabody; DART; TandAb; scDiabody; sc-Diabody-CH3; Diabody-CH3; Triple Body; Miniantibody; Minibody; TriBi minibody; scFv-CH3 KIH; Fab-scFv; scFv-CH-CL-scFv; F(ab')2; F(ab')2-scFv2; scFv-KIH; Fab-scFv-Fc; Tetravalent HCAb; scDiabody-Fc; Diabody-Fc; Tandem scFv-Fc; and Intrabody (see Id.).

In certain embodiments, the bispecific antibody molecules as provided herein are in a bispecific format such as Dock and Lock; ImmTAC; HSAbody; scDiabody-HAS; and Tandem scFv-Toxin (see Id.).

In certain embodiments, the bispecific antibody molecules as provided herein are based on a format selected from bispecific antibody conjugates comprising IgG-IgG; Cov-X-Body; and scFv1-PEG-scFv2 (see Id.).

The bispecific antibody molecules provided herein can be made with any suitable methods known in the art. In a conventional approach, two immunoglobulin heavy chain-light chain pairs having different antigen-binding specificities can be co-expressed in a host cell to produce bispecific antibodies in a recombinant way (see, for example, Milstein and Cuello, Nature, 305: 537 (1983)), followed by purification by affinity chromatography.

Recombinant approach may also be used, where sequences encoding the antibody heavy chain variable domains for the two specificities are respectively fused to immunoglobulin constant domain sequences, followed by insertion to an expression vector which is co-transfected with an expression vector for the light chain sequences to a suitable host cell for recombinant expression of the bispecific antibody (see, for example, WO 94/04690; Suresh et al., Methods in Enzymology, 121:210 (1986)). Similarly, scFv dimers can also be recombinantly constructed and expressed from a host cell (see, e.g. Gruber et al., J. Immunol., 152:5368 (1994).)

Bispecific antibody molecule may be generated from a bispecific antibody, for example, by proteolytic cleavage, or by chemical linking. For example, an antigen-binding fragment (e.g. Fab') of an antibody may be prepared and converted to Fab'-thiol derivative and then mixed and reacted with another converted Fab' derivative having a different antigenic specificity to form a bispecific antibody molecule (see, for example, Brennan et al., Science, 229: 81 (1985)).

In certain embodiments, the bispecific antibody molecules may be engineered to promote heavy chain heterodimerization of the two different antigen-binding sites. In certain embodiments, the Fc region is modified at the interface so that a knob-into-hole association can be formed to promote heterodimerization. "Knob-into-hole" as used herein, refers to an interaction between two polypeptides (such as CH3 domain), where one polypeptide has a protuberance (i.e. "knob") due to presence of an amino acid residue having a bulky side chain (e.g. tyrosine or tryptophan), and the other polypeptide has a cavity (i.e. "hole") where a small side chain amino acid residue resides (e.g. alanine or threonine), and the protuberance is positionable in the cavity so as to promote interaction of the two polypeptides to form a heterodimer or a complex. Methods of generating polypeptides with knobs-into-holes are known in the art, e.g., as described in U.S. Pat. No. 5,731,168.

In some embodiments, "charged pairs" can be introduced to the Fc polypeptides to electrostatically steer the formation towards heterodimerization. Exemplary pairs include, D221E/P228E/L368E paired with D221R/P228R/K409R and C220E/P228E/368E paired with C220R/E224R/P228R/K409R (see Gunasekaran et al., 2010, J. Biol. Chem. 285 (25):19637.).

In some embodiments, the binding interface of the two Fc polypeptide chains can be engineered such that in the heterodimer configuration, residues interact with residues of similar physical property (e.g., polar residues interacting with polar residues, or hydrophobic residues interact with hydrophobic residues), while in the homodimer configuration residues interact with residues of different physical property. Exemplary modifications include substitution at positions 364, 368, 399, 405, 409, 411, or any combination thereof (see, e.g., WO2014/145806, WO2014/110601, WO2016/086186, WO2016/086189, WO2016/086196, and WO2016/182751).

In some embodiments, the bispecific antibody molecules may be engineered to reduce random pairing of two different light chain variable regions with the two different heavy chain variable regions. In some embodiments, the bispecific antibody molecule comprise a common light chain capable of pairing with the two heavy chain variable regions. In some other embodiments, CH1 domain of one heavy chain is exchanged with the constant region (CL) of the corresponding light chain (such as that applied in CrossMab technology). In some other embodiments, mutations are introduced into the CH1-CL interface and/or the VH-VL interface of the Fab fragments, so as to enforce correct pairing of the light chains with the corresponding heavy chains. In some other embodiments, the CH1 domain and CL domain in one antigen-binding domain are replaced by TCR constant domains, so as to minimize mispairing between heavy chain of the first antigen-binding domain and light chain of the second antigen-binding domain (such as that applied in WuxiBody technology).

In some embodiments, the modified antibody or an antigen-binding fragment thereof of this disclosure, wherein the antigen-binding domain can comprise:

a. 1, 2, or 3 heavy chain CDR sequences selected from SEQ ID NO: 1, SEQ ID NO: 2, and SEQ ID NO: 3;
b. 1, 2, or 3 heavy chain CDR sequences selected from SEQ ID NO: 11, SEQ ID NO: 12, and SEQ ID NO: 13;
c. 1, 2, or 3 heavy chain CDR sequences selected from SEQ ID NO: 21, SEQ ID NO: 22, and SEQ ID NO: 23;
d. 1, 2, or 3 heavy chain CDR sequences selected from SEQ ID NO: 31, SEQ ID NO: 32, and SEQ ID NO: 33;
e. 1, 2, or 3 heavy chain CDR sequences selected from SEQ ID NO: 41, SEQ ID NO: 42, and SEQ ID NO: 43;
f. 1, 2, or 3 heavy chain CDR sequences selected from SEQ ID NO: 51, SEQ ID NO: 52, and SEQ ID NO: 53;
g. 1, 2, or 3 heavy chain CDR sequences selected from SEQ ID NO: 65, SEQ ID NO: 66, and SEQ ID NO: 67;
h. 1, 2, or 3 heavy chain CDR sequences selected from SEQ ID NO: 75, SEQ ID NO: 76, and SEQ ID NO: 77;
i. 1, 2, or 3 heavy chain CDR sequences selected from SEQ ID NO: 85, SEQ ID NO: 86, and SEQ ID NO: 87;
j. 1, 2, or 3 heavy chain CDR sequences selected from SEQ ID NO: 95, SEQ ID NO: 96, and SEQ ID NO: 97;
k. 1, 2, or 3 heavy chain CDR sequences selected from SEQ ID NO: 105, SEQ ID NO: 106, and SEQ ID NO: 107;
l. 1, 2, or 3 heavy chain CDR sequences selected from SEQ ID NO: 136, SEQ ID NO: 137, and SEQ ID NO: 138;
m. 1, 2, or 3 heavy chain CDR sequences selected from SEQ ID NO: 146, SEQ ID NO: 147, and SEQ ID NO: 148;
n. 1, 2, or 3 heavy chain CDR sequences selected from SEQ ID NO: 156, SEQ ID NO: 157, and SEQ ID NO: 158;
o. 1, 2, or 3 heavy chain CDR sequences selected from SEQ ID NO: 166, SEQ ID NO: 167, and SEQ ID NO: 168;
p. 1, 2, or 3 heavy chain CDR sequences selected from SEQ ID NO: 176, SEQ ID NO: 177, and SEQ ID NO: 178;
q. 1, 2, or 3 heavy chain CDR sequences selected from SEQ ID NO: 186, SEQ ID NO: 187, and SEQ ID NO: 188;
r. 1, 2, or 3 heavy chain CDR sequences selected from SEQ ID NO: 196, SEQ ID NO: 197, and SEQ ID NO: 198;
s. 1, 2, or 3 heavy chain CDR sequences selected from SEQ ID NO: 206, SEQ ID NO: 207, and SEQ ID NO: 208;

t. 1, 2, or 3 heavy chain CDR sequences selected from SEQ ID NO: 216, SEQ ID NO: 217, and SEQ ID NO: 218;
u. 1, 2, or 3 heavy chain CDR sequences selected from SEQ ID NO: 226, SEQ ID NO: 227, and SEQ ID NO: 228;
v. 1, 2, or 3 heavy chain CDR sequences selected from SEQ ID NO: 236, SEQ ID NO: 237, and SEQ ID NO: 238;
w. 1, 2, or 3 heavy chain CDR sequences selected from SEQ ID NO: 246, SEQ ID NO: 247, and SEQ ID NO: 248;
x. 1, 2, or 3 heavy chain CDR sequences selected from SEQ ID NO: 256, SEQ ID NO: 257, and SEQ ID NO: 258;
y. 1, 2, or 3 heavy chain CDR sequences selected from SEQ ID NO: 266, SEQ ID NO: 267, and SEQ ID NO: 268;
z. 1, 2, or 3 heavy chain CDR sequences selected from SEQ ID NO: 276, SEQ ID NO: 277, and SEQ ID NO: 278;
aa. 1, 2, or 3 heavy chain CDR sequences selected from SEQ ID NO: 286, SEQ ID NO: 287, and SEQ ID NO: 288;
bb. 1, 2, or 3 heavy chain CDR sequences selected from SEQ ID NO: 296, SEQ ID NO: 297, and SEQ ID NO: 298;
cc. 1, 2, or 3 heavy chain CDR sequences selected from SEQ ID NO: 306, SEQ ID NO: 307, and SEQ ID NO: 308;
dd. 1, 2, or 3 heavy chain CDR sequences selected from SEQ ID NO: 316, SEQ ID NO: 317, and SEQ ID NO: 318;
ee. 1, 2, or 3 heavy chain CDR sequences selected from SEQ ID NO: 326, SEQ ID NO: 327, and SEQ ID NO: 328;
ff. 1, 2, or 3 heavy chain CDR sequences selected from SEQ ID NO: 336, SEQ ID NO: 337, and SEQ ID NO: 338;
gg. 1, 2, or 3 heavy chain CDR sequences selected from SEQ ID NO: 346, SEQ ID NO: 347, and SEQ ID NO: 348;
hh. 1, 2, or 3 heavy chain CDR sequences selected from SEQ ID NO: 356, SEQ ID NO: 357, and SEQ ID NO: 358;
ii. 1, 2, or 3 heavy chain CDR sequences selected from SEQ ID NO: 366, SEQ ID NO: 367, and SEQ ID NO: 368;
jj. 1, 2, or 3 heavy chain CDR sequences selected from SEQ ID NO: 376, SEQ ID NO: 377, and SEQ ID NO: 378;
kk. 1, 2, or 3 heavy chain CDR sequences selected from SEQ ID NO: 386, SEQ ID NO: 387, and SEQ ID NO: 388;
ll. 1, 2, or 3 heavy chain CDR sequences selected from SEQ ID NO: 396, SEQ ID NO: 397, and SEQ ID NO: 398;
mm. 1, 2, or 3 heavy chain CDR sequences selected from SEQ ID NO: 406, SEQ ID NO: 407, and SEQ ID NO: 408;
nn. 1, 2, or 3 heavy chain CDR sequences selected from SEQ ID NO: 416, SEQ ID NO: 417, and SEQ ID NO: 418;
oo. 1, 2, or 3 heavy chain CDR sequences selected from SEQ ID NO: 426, SEQ ID NO: 427, and SEQ ID NO: 428; or
a combination thereof.

In some embodiments, the modified antibody or antigen binding fragment disclosed above, wherein the antigen-binding domain comprises:
a. 1, 2, or 3 light chain CDR sequences selected from SEQ ID NO: 4, SEQ ID NO: 5, and SEQ ID NO: 6;
b. 1, 2, or 3 light chain CDR sequences selected from SEQ ID NO: 14, SEQ ID NO: 15, and SEQ ID NO: 16;
c. 1, 2, or 3 light chain CDR sequences selected from SEQ ID NO: 24, SEQ ID NO: 25 and SEQ ID NO: 26;
d. 1, 2, or 3 light chain CDR sequences selected from SEQ ID NO: 34, SEQ ID NO: 35 and SEQ ID NO: 36;
e. 1, 2, or 3 light chain CDR sequences selected from SEQ ID NO: 44, SEQ ID NO: 45 and SEQ ID NO: 46;
f. 1, 2, or 3 light chain CDR sequences selected from SEQ ID NO: 54, SEQ ID NO: 55 and SEQ ID NO: 56;
g. 1, 2, or 3 light chain CDR sequences selected from SEQ ID NO: 68, SEQ ID NO: 69, and SEQ ID NO: 70;
h. 1, 2, or 3 light chain CDR sequences selected from SEQ ID NO: 78, SEQ ID NO: 79, and SEQ ID NO: 80;
i. 1, 2, or 3 light chain CDR sequences selected from SEQ ID NO: 88, SEQ ID NO: 89, and SEQ ID NO: 90.
j. 1, 2, or 3 light chain CDR sequences selected from SEQ ID NO: 98, SEQ ID NO: 99, and SEQ ID NO: 100;
k. 1, 2, or 3 light chain CDR sequences selected from SEQ ID NO: 108, SEQ ID NO: 109, and SEQ ID NO: 110;
l. 1, 2, or 3 light chain CDR sequences selected from SEQ ID NO: 139, SEQ ID NO: 140, and SEQ ID NO: 141;
m. 1, 2, or 3 light chain CDR sequences selected from SEQ ID NO: 149, SEQ ID NO: 150, and SEQ ID NO: 151;
n. 1, 2, or 3 light chain CDR sequences selected from SEQ ID NO: 159, SEQ ID NO: 160, and SEQ ID NO: 161;
o. 1, 2, or 3 light chain CDR sequences selected from SEQ ID NO: 169, SEQ ID NO: 170, and SEQ ID NO: 171;
p. 1, 2, or 3 light chain CDR sequences selected from SEQ ID NO: 179, SEQ ID NO: 180, and SEQ ID NO: 181;
q. 1, 2, or 3 light chain CDR sequences selected from SEQ ID NO: 189, SEQ ID NO: 190, and SEQ ID NO: 191;
r. 1, 2, or 3 light chain CDR sequences selected from SEQ ID NO: 199, SEQ ID NO: 200, and SEQ ID NO: 201;
s. 1, 2, or 3 light chain CDR sequences selected from SEQ ID NO: 209, SEQ ID NO: 210, and SEQ ID NO: 211;
t. 1, 2, or 3 light chain CDR sequences selected from SEQ ID NO: 219, SEQ ID NO: 220, and SEQ ID NO: 221;
u. 1, 2, or 3 light chain CDR sequences selected from SEQ ID NO: 229, SEQ ID NO: 230, and SEQ ID NO: 231;
v. 1, 2, or 3 light chain CDR sequences selected from SEQ ID NO: 239, SEQ ID NO: 240, and SEQ ID NO: 241;
w. 1, 2, or 3 light chain CDR sequences selected from SEQ ID NO: 249, SEQ ID NO: 250, and SEQ ID NO: 251;
x. 1, 2, or 3 light chain CDR sequences selected from SEQ ID NO: 259, SEQ ID NO: 260, and SEQ ID NO: 261;
y. 1, 2, or 3 light chain CDR sequences selected from SEQ ID NO: 269, SEQ ID NO: 270, and SEQ ID NO: 271;
z. 1, 2, or 3 light chain CDR sequences selected from SEQ ID NO: 279, SEQ ID NO: 280, and SEQ ID NO: 281;
aa. 1, 2, or 3 light chain CDR sequences selected from SEQ ID NO: 289, SEQ ID NO: 290, and SEQ ID NO: 291;
bb. 1, 2, or 3 light chain CDR sequences selected from SEQ ID NO: 299, SEQ ID NO: 300, and SEQ ID NO: 301;
cc. 1, 2, or 3 light chain CDR sequences selected from SEQ ID NO: 309, SEQ ID NO: 310, and SEQ ID NO: 311;

dd. 1, 2, or 3 light chain CDR sequences selected from SEQ ID NO: 319, SEQ ID NO: 320, and SEQ ID NO: 321;
ee. 1, 2, or 3 light chain CDR sequences selected from SEQ ID NO: 329, SEQ ID NO: 330, and SEQ ID NO: 331;
ff. 1, 2, or 3 light chain CDR sequences selected from SEQ ID NO: 339, SEQ ID NO: 340, and SEQ ID NO: 341;
gg. 1, 2, or 3 light chain CDR sequences selected from SEQ ID NO: 349, SEQ ID NO: 350, and SEQ ID NO: 351;
hh. 1, 2, or 3 light chain CDR sequences selected from SEQ ID NO: 359, SEQ ID NO: 360, and SEQ ID NO: 361;
ii. 1, 2, or 3 light chain CDR sequences selected from SEQ ID NO: 369, SEQ ID NO: 370, and SEQ ID NO: 371;
jj. 1, 2, or 3 light chain CDR sequences selected from SEQ ID NO: 379, SEQ ID NO: 380, and SEQ ID NO: 381;
kk. 1, 2, or 3 light chain CDR sequences selected from SEQ ID NO: 389, SEQ ID NO: 390, and SEQ ID NO: 391;
ll. 1, 2, or 3 light chain CDR sequences selected from SEQ ID NO: 399, SEQ ID NO: 400, and SEQ ID NO: 401;
mm. 1, 2, or 3 light chain CDR sequences selected from SEQ ID NO: 409, SEQ ID NO: 410, and SEQ ID NO: 411;
nn. 1, 2, or 3 light chain CDR sequences selected from SEQ ID NO: 419, SEQ ID NO: 420, and SEQ ID NO: 421;
oo. 1, 2, or 3 light chain CDR sequences selected from SEQ ID NO: 429, SEQ ID NO: 430, and SEQ ID NO: 431; or
a combination thereof.

In some embodiments, the modified antibody or an antigen-binding fragment thereof disclosed herein, wherein the antigen-binding domain can comprise:
a. a heavy chain CDR1 (HCDR1) comprising the sequence of SEQ ID NO: 1, a heavy chain CDR2 (HCDR2) comprising the sequence of SEQ ID NO: 2, a heavy chain CDR3 (HCDR3) comprising the sequence of SEQ ID NO: 3; a light chain CDR1 (LCDR1) comprising the sequence of SEQ ID NO: 4, a light chain CDR2 (LCDR2) comprising the sequence of SEQ ID NO: 5, and a light chain CDR3 (LCDR3) comprising the sequence of SEQ ID NO: 6;
b. a HCDR1 comprising the sequence of SEQ ID NO: 11, a HCDR2 comprising the sequence of SEQ ID NO: 12, a HCDR3 comprising the sequence of SEQ ID NO: 13, a LCDR1 comprising the sequence of SEQ ID NO: 14, a LCDR2 comprising the sequence of SEQ ID NO: 15, and a LCDR3 comprising the sequence of SEQ ID NO: 16;
c. a HCDR1 comprising the sequence of SEQ ID NO: 21, a HCDR2 comprising the sequence of SEQ ID NO: 22, a HCDR3 comprising the sequence of SEQ ID NO: 23, a LCDR1 comprising the sequence of SEQ ID NO: 24, a LCDR2 comprising the sequence of SEQ ID NO: 25, and a LCDR3 comprising the sequence of SEQ ID NO: 26;
d. a HCDR1 comprising the sequence of SEQ ID NO: 31, a HCDR2 comprising the sequence of SEQ ID NO: 32, a HCDR3 comprising the sequence of SEQ ID NO: 33, a LCDR1 comprising the sequence of SEQ ID NO: 34, a LCDR2 comprising the sequence of SEQ ID NO: 35, and a LCDR3 comprising the sequence of SEQ ID NO: 36;
e. a HCDR1 comprising the sequence of SEQ ID NO: 41, a HCDR2 comprising the sequence of SEQ ID NO: 42, a HCDR3 comprising the sequence of SEQ ID NO: 43, a LCDR1 comprising the sequence of SEQ ID NO: 44, a LCDR2 comprising the sequence of SEQ ID NO: 45, and a LCDR3 comprising the sequence of SEQ ID NO: 46;
f. a HCDR1 comprising the sequence of SEQ ID NO: 51, a HCDR2 comprising the sequence of SEQ ID NO: 52, a HCDR3 comprising the sequence of SEQ ID NO: 53, a LCDR1 comprising the sequence of SEQ ID NO: 54, a LCDR2 comprising the sequence of SEQ ID NO: 55, and a LCDR3 comprising the sequence of SEQ ID NO: 56;
g. a HCDR1 comprising the sequence of SEQ ID NO: 65, a HCDR2 comprising the sequence of SEQ ID NO: 66, a HCDR3 comprising the sequence of SEQ ID NO: 67, a LCDR1 comprising the sequence of SEQ ID NO: 68, a LCDR2 comprising the sequence of SEQ ID NO: 69, and a LCDR3 comprising the sequence of SEQ ID NO: 70;
h. a HCDR1 comprising the sequence of SEQ ID NO: 75, a HCDR2 comprising the sequence of SEQ ID NO: 76, a HCDR3 comprising the sequence of SEQ ID NO: 77, a LCDR1 comprising the sequence of SEQ ID NO: 78, a LCDR2 comprising the sequence of SEQ ID NO: 79, and a LCDR3 comprising the sequence of SEQ ID NO: 80;
i. a HCDR1 comprising the sequence of SEQ ID NO: 85, a HCDR2 comprising the sequence of SEQ ID NO: 86, a HCDR3 comprising the sequence of SEQ ID NO: 87, a LCDR1 comprising the sequence of SEQ ID NO: 88, a LCDR2 comprising the sequence of SEQ ID NO: 89, and a LCDR3 comprising the sequence of SEQ ID NO: 90;
j. a HCDR1 comprising the sequence of SEQ ID NO: 95, a HCDR2 comprising the sequence of SEQ ID NO: 96, a HCDR3 comprising the sequence of SEQ ID NO: 97, a LCDR1 comprising the sequence of SEQ ID NO: 98, a LCDR2 comprising the sequence of SEQ ID NO: 99, and a LCDR3 comprising the sequence of SEQ ID NO: 100;
k. a HCDR1 comprising the sequence of SEQ ID NO: 105, a HCDR2 comprising the sequence of SEQ ID NO: 106, a HCDR3 comprising the sequence of SEQ ID NO: 107, a LCDR1 comprising the sequence of SEQ ID NO: 108, a LCDR2 comprising the sequence of SEQ ID NO: 109, and a LCDR3 comprising the sequence of SEQ ID NO: 110;
l. a HCDR1 comprising the sequence of SEQ ID NO: 136, a HCDR2 comprising the sequence of SEQ ID NO: 137, a HCDR3 comprising the sequence of SEQ ID NO: 138, a LCDR1 comprising the sequence of SEQ ID NO: 139, a LCDR2 comprising the sequence of SEQ ID NO: 140, and a LCDR3 comprising the sequence of SEQ ID NO: 141;
m. HCDR1 comprising the sequence of SEQ ID NO: 146, a HCDR2 comprising the sequence of SEQ ID NO: 147, a HCDR3 comprising the sequence of SEQ ID NO: 148, a LCDR1 comprising the sequence of SEQ ID NO: 149, a LCDR2 comprising the sequence of SEQ ID NO: 150, and a LCDR3 comprising the sequence of SEQ ID NO: 151;
n. HCDR1 comprising the sequence of SEQ ID NO: 156, a HCDR2 comprising the sequence of SEQ ID NO: 157, a HCDR3 comprising the sequence of SEQ ID NO: 158, a LCDR1 comprising the sequence of SEQ ID NO: 159, a LCDR2 comprising the sequence of SEQ ID NO: 160, and a LCDR3 comprising the sequence of SEQ ID NO: 161;
o. HCDR1 comprising the sequence of SEQ ID NO: 166, a HCDR2 comprising the sequence of SEQ ID NO: 167, a HCDR3 comprising the sequence of SEQ ID NO: 168, a LCDR1 comprising the sequence of SEQ ID NO: 169, a LCDR2 comprising the sequence of SEQ ID NO: 170, and a LCDR3 comprising the sequence of SEQ ID NO: 171;
p. HCDR1 comprising the sequence of SEQ ID NO: 176, a HCDR2 comprising the sequence of SEQ ID NO: 177, a HCDR3 comprising the sequence of SEQ ID NO: 178, a LCDR1 comprising the sequence of SEQ ID NO: 179, a LCDR2 comprising the sequence of SEQ ID NO: 180, and a LCDR3 comprising the sequence of SEQ ID NO: 181;
q. HCDR1 comprising the sequence of SEQ ID NO: 186, a HCDR2 comprising the sequence of SEQ ID NO: 187, a HCDR3 comprising the sequence of SEQ ID NO: 188, a LCDR1 comprising the sequence of SEQ ID NO: 189, a LCDR2 comprising the sequence of SEQ ID NO: 190, and a LCDR3 comprising the sequence of SEQ ID NO: 191;
r. HCDR1 comprising the sequence of SEQ ID NO: 196, a HCDR2 comprising the sequence of SEQ ID NO: 197, a HCDR3 comprising the sequence of SEQ ID NO: 198, a LCDR1 comprising the sequence of SEQ ID NO: 199, a LCDR2 comprising the sequence of SEQ ID NO: 200, and a LCDR3 comprising the sequence of SEQ ID NO: 201;
s. HCDR1 comprising the sequence of SEQ ID NO: 206, a HCDR2 comprising the sequence of SEQ ID NO: 207, a HCDR3 comprising the sequence of SEQ ID NO: 208, a LCDR1 comprising the sequence of SEQ ID NO: 209, a LCDR2 comprising the sequence of SEQ ID NO: 210, and a LCDR3 comprising the sequence of SEQ ID NO: 211;
t. HCDR1 comprising the sequence of SEQ ID NO: 216, a HCDR2 comprising the sequence of SEQ ID NO: 217, a HCDR3 comprising the sequence of SEQ ID NO: 218, a LCDR1 comprising the sequence of SEQ ID NO: 219, a LCDR2 comprising the sequence of SEQ ID NO: 220, and a LCDR3 comprising the sequence of SEQ ID NO: 221;
u. HCDR1 comprising the sequence of SEQ ID NO: 226, a HCDR2 comprising the sequence of SEQ ID NO: 227, a HCDR3 comprising the sequence of SEQ ID NO: 228, a LCDR1 comprising the sequence of SEQ ID NO: 229, a LCDR2 comprising the sequence of SEQ ID NO: 230, and a LCDR3 comprising the sequence of SEQ ID NO: 231;
v. HCDR1 comprising the sequence of SEQ ID NO: 236, a HCDR2 comprising the sequence of SEQ ID NO: 237, a HCDR3 comprising the sequence of SEQ ID NO: 238, a LCDR1 comprising the sequence of SEQ ID NO: 239, a LCDR2 comprising the sequence of SEQ ID NO: 240, and a LCDR3 comprising the sequence of SEQ ID NO: 241;
w. HCDR1 comprising the sequence of SEQ ID NO: 246, a HCDR2 comprising the sequence of SEQ ID NO: 247, a HCDR3 comprising the sequence of SEQ ID NO: 248, a LCDR1 comprising the sequence of SEQ ID NO: 249, a LCDR2 comprising the sequence of SEQ ID NO: 250, and a LCDR3 comprising the sequence of SEQ ID NO: 251;
x. HCDR1 comprising the sequence of SEQ ID NO: 256, a HCDR2 comprising the sequence of SEQ ID NO: 257, a HCDR3 comprising the sequence of SEQ ID NO: 258, a LCDR1 comprising the sequence of SEQ ID NO: 259, a LCDR2 comprising the sequence of SEQ ID NO: 260, and a LCDR3 comprising the sequence of SEQ ID NO: 261;
y. HCDR1 comprising the sequence of SEQ ID NO: 266, a HCDR2 comprising the sequence of SEQ ID NO: 267, a HCDR3 comprising the sequence of SEQ ID NO: 268, a LCDR1 comprising the sequence of SEQ ID NO: 269, a LCDR2 comprising the sequence of SEQ ID NO: 270, and a LCDR3 comprising the sequence of SEQ ID NO: 271;
z. HCDR1 comprising the sequence of SEQ ID NO: 276, a HCDR2 comprising the sequence of SEQ ID NO: 277, a HCDR3 comprising the sequence of SEQ ID NO: 278, a LCDR1 comprising the sequence of SEQ ID NO: 279, a LCDR2 comprising the sequence of SEQ ID NO: 280, a LCDR3 comprising the sequence of SEQ ID NO: 281;
aa. HCDR1 comprising the sequence of SEQ ID NO: 286, a HCDR2 comprising the sequence of SEQ ID NO: 287, a HCDR3 comprising the sequence of SEQ ID NO: 288, a LCDR1 comprising the sequence of SEQ ID NO: 289, a LCDR2 comprising the sequence of SEQ ID NO: 290, a LCDR3 comprising the sequence of SEQ ID NO: 291;
bb. HCDR1 comprising the sequence of SEQ ID NO: 296, a HCDR2 comprising the sequence of SEQ ID NO: 297, a HCDR3 comprising the sequence of SEQ ID NO: 298, a LCDR1 comprising the sequence of SEQ ID NO: 299, a LCDR2 comprising the sequence of SEQ ID NO: 300, a LCDR3 comprising the sequence of SEQ ID NO: 301;
cc. HCDR1 comprising the sequence of SEQ ID NO: 306, a HCDR2 comprising the sequence of SEQ ID NO: 307, a HCDR3 comprising the sequence of SEQ ID NO: 308, a LCDR1 comprising the sequence of SEQ ID NO: 309, a LCDR2 comprising the sequence of SEQ ID NO: 310, a LCDR3 comprising the sequence of SEQ ID NO: 311;
dd. HCDR1 comprising the sequence of SEQ ID NO: 316, a HCDR2 comprising the sequence of SEQ ID NO: 317, a HCDR3 comprising the sequence of SEQ ID NO: 318, a LCDR1 comprising the sequence of SEQ ID NO: 319, a LCDR2 comprising the sequence of SEQ ID NO: 320, a LCDR3 comprising the sequence of SEQ ID NO: 321;
ee. HCDR1 comprising the sequence of SEQ ID NO: 326, a HCDR2 comprising the sequence of SEQ ID NO: 327, a HCDR3 comprising the sequence of SEQ ID NO: 328, a LCDR1 comprising the sequence of SEQ ID NO: 329, a LCDR2 comprising the sequence of SEQ ID NO: 330, a LCDR3 comprising the sequence of SEQ ID NO: 331;
ff. HCDR1 comprising the sequence of SEQ ID NO: 336, a HCDR2 comprising the sequence of SEQ ID NO: 337, a HCDR3 comprising the sequence of SEQ ID NO: 338, a LCDR1 comprising the sequence of SEQ ID NO: 339, a LCDR2 comprising the sequence of SEQ ID NO: 340, a LCDR3 comprising the sequence of SEQ ID NO: 341;
gg. HCDR1 comprising the sequence of SEQ ID NO: 346, a HCDR2 comprising the sequence of SEQ ID NO: 347, a HCDR3 comprising the sequence of SEQ ID NO: 348, a LCDR1 comprising the sequence of SEQ ID NO: 349, a LCDR2 comprising the sequence of SEQ ID NO: 350, a LCDR3 comprising the sequence of SEQ ID NO: 351;

hh. HCDR1 comprising the sequence of SEQ ID NO: 356, a HCDR2 comprising the sequence of SEQ ID NO: 357, a HCDR3 comprising the sequence of SEQ ID NO: 358, a LCDR1 comprising the sequence of SEQ ID NO: 359, a LCDR2 comprising the sequence of SEQ ID NO: 360, a LCDR3 comprising the sequence of SEQ ID NO: 361;

ii. HCDR1 comprising the sequence of SEQ ID NO: 366, a HCDR2 comprising the sequence of SEQ ID NO: 367, a HCDR3 comprising the sequence of SEQ ID NO: 368, a LCDR1 comprising the sequence of SEQ ID NO: 369, a LCDR2 comprising the sequence of SEQ ID NO: 370, a LCDR3 comprising the sequence of SEQ ID NO: 371;

jj. HCDR1 comprising the sequence of SEQ ID NO: 376, a HCDR2 comprising the sequence of SEQ ID NO: 377, a HCDR3 comprising the sequence of SEQ ID NO: 378, a LCDR1 comprising the sequence of SEQ ID NO: 379, a LCDR2 comprising the sequence of SEQ ID NO: 380, a LCDR3 comprising the sequence of SEQ ID NO: 381;

kk. HCDR1 comprising the sequence of SEQ ID NO: 386, a HCDR2 comprising the sequence of SEQ ID NO: 387, a HCDR3 comprising the sequence of SEQ ID NO: 388, a LCDR1 comprising the sequence of SEQ ID NO: 389, a LCDR2 comprising the sequence of SEQ ID NO: 390, a LCDR3 comprising the sequence of SEQ ID NO: 391;

ll. HCDR1 comprising the sequence of SEQ ID NO: 396, a HCDR2 comprising the sequence of SEQ ID NO: 397, a HCDR3 comprising the sequence of SEQ ID NO: 398, a LCDR1 comprising the sequence of SEQ ID NO: 399, a LCDR2 comprising the sequence of SEQ ID NO: 400, a LCDR3 comprising the sequence of SEQ ID NO: 401;

mm. HCDR1 comprising the sequence of SEQ ID NO: 406, a HCDR2 comprising the sequence of SEQ ID NO: 407, a HCDR3 comprising the sequence of SEQ ID NO: 408, a LCDR1 comprising the sequence of SEQ ID NO: 409, a LCDR2 comprising the sequence of SEQ ID NO: 410, a LCDR3 comprising the sequence of SEQ ID NO: 411;

nn. HCDR1 comprising the sequence of SEQ ID NO: 416, a HCDR2 comprising the sequence of SEQ ID NO: 417, a HCDR3 comprising the sequence of SEQ ID NO: 418, a LCDR1 comprising the sequence of SEQ ID NO: 419, a LCDR2 comprising the sequence of SEQ ID NO: 420, a LCDR3 comprising the sequence of SEQ ID NO: 421;

oo. HCDR1 comprising the sequence of SEQ ID NO: 426, a HCDR2 comprising the sequence of SEQ ID NO: 427, a HCDR3 comprising the sequence of SEQ ID NO: 428, a LCDR1 comprising the sequence of SEQ ID NO: 429, a LCDR2 comprising the sequence of SEQ ID NO: 430, a LCDR3 comprising the sequence of SEQ ID NO: 431; or a combination thereof.

In some embodiments, the modified antibody or an antigen-binding fragment thereof disclosed herein, wherein the antigen-binding domain can comprise:

a HCDR1 comprising the sequence of SEQ ID NO: 105, a HCDR2 comprising the sequence of SEQ ID NO: 106, a HCDR3 comprising the sequence of SEQ ID NO: 107, a LCDR1 comprising the sequence of SEQ ID NO: 108, a LCDR2 comprising the sequence of SEQ ID NO: 109, and a LCDR3 comprising the sequence of SEQ ID NO: 110;

a HCDR1 comprising the sequence of SEQ ID NO: 136, a HCDR2 comprising the sequence of SEQ ID NO: 137, a HCDR3 comprising the sequence of SEQ ID NO: 138, a LCDR1 comprising the sequence of SEQ ID NO: 139, a LCDR2 comprising the sequence of SEQ ID NO: 140, and a LCDR3 comprising the sequence of SEQ ID NO: 141;

or a combination thereof.

In some embodiments, the modified antibody can comprise a first antigen-binding domain comprising a HCDR1 comprising the sequence of SEQ ID NO: 105, a HCDR2 comprising the sequence of SEQ ID NO: 106, a HCDR3 comprising the sequence of SEQ ID NO: 107, a LCDR1 comprising the sequence of SEQ ID NO: 108, a LCDR2 comprising the sequence of SEQ ID NO: 109, and a LCDR3 comprising the sequence of SEQ ID NO: 110; and a second antigen-binding domain comprising a HCDR1 comprising the sequence of SEQ ID NO: 136, a HCDR2 comprising the sequence of SEQ ID NO: 137, a HCDR3 comprising the sequence of SEQ ID NO: 138, a LCDR1 comprising the sequence of SEQ ID NO: 139, a LCDR2 comprising the sequence of SEQ ID NO: 140, and a LCDR3 comprising the sequence of SEQ ID NO: 141; and wherein the antibody comprises the modified human IgG constant domain comprises a substitution with tyrosine at amino acid residue 252, a substitution with threonine at amino acid residue 254, and a substitution with glutamic acid at amino acid residue 256, numbered according to the EU index as in Kabat.

In some embodiments, the modified antibody or an antigen-binding fragment thereof disclosed herein, wherein the modified antibody or the antigen-binding fragment can have a half-life ($T_{1/2}$) in a range of from 50 to 120 days in vivo, such as in a human subject. The modified antibody or the antigen-binding fragment can have a half-life ($T_{1/2}$) in a range of from 50 to 120 days, 60 to 120 days, 70 to 120 days, 80 to 120 days, 90 to 120 days, 100 to 120 day, or 110 to 120 days.

In some embodiments, the modified antibody or an antigen-binding fragment thereof disclosed herein, wherein the modified antibody can comprise at least one amino acid subsequent substitutions in the antigen-binding domain, the human IgG constant domain, a light chain of the modified antibody, a heavy chain of the modified antibody, or a combination thereof. In some cases, the subsequent substitution can comprise substituting a cystine residue to a non-cystine residue. In some cases, the cystine residue can be substituted with a serine residue. In some embodiments, a modified antibody can comprise a C106S substitution, wherein the cystine 106 is substituted with a serine, in the heavy chain variable region HDR3, numbered according to the international ImMunoGeneTics system (IMGT) unique numbering.

In some embodiments, a modified antibody can comprise an antigen-binding domain having an antigen-binding affinity and a covalently linked modified human IgG constant domain, wherein the antigen-binding affinity comprises at least one of the LCDRs and at least one of the HCDRs listed in Table 1, wherein the modified human IgG constant domain comprises a substitution with tyrosine at amino acid residue 252, a substitution with threonine at amino acid residue 254, and a substitution with glutamic acid at amino acid residue 256, numbered according to the EU index as in Kabat, and a C106S substitution, wherein the cystine 106 is substituted with a serine, in the heavy chain variable region HDR3, numbered according to the international ImMunoGeneTics system (IMGT) unique numbering. In some embodiments, a modified antibody can comprise an antigen-binding domain having an antigen-binding affinity and a covalently linked modified human IgG constant domain, wherein the antigen-binding affinity comprises HCDR SEQ ID No.: 136, SEQ ID No.: 137, SEQ ID No.: 138, LCDR SEQ ID No.: 139, SEQ ID. No.: 140 and SEQ ID. No.: 141 (P2B-1G5), wherein the modified human IgG constant domain comprises a substitution with tyrosine at amino acid residue 252, a substitution with threonine at amino acid residue 254, and a substitution with glutamic acid at amino acid residue 256, numbered according to the EU index as in Kabat, and a C106S substitution, wherein the cystine 106 is substituted with a serine, in the heavy chain variable region, numbered according to the international ImMunoGeneTics system (IMGT) unique numbering.

In some embodiments, the modified antibody or an antigen-binding fragment thereof disclosed herein can further comprise one or more subsequent modified antibodies selected from a first subsequent modified antibody comprising two antigen-binding domains each having a same or different affinity to the SARS-CoV-2, a second subsequent modified antibody comprising a first antigen-binding domain having a binding affinity to the SARS-CoV-2 and a second antigen-binding domain having a binding affinity to a second pathogen that is different from the SARS-CoV-2, a third subsequent modified antibody comprising two antigen-binding domains each having a binding affinity to the second pathogen, or a combination thereof. The term "different affinities to the SARS-CoV-2" refers affinity that can bind to a different epitope or binding site of the SARS-CoV-2, a different affinity level that can bind to the same epitope or binding site of the SARS-CoV-2, or a combination thereof.

In some embodiments, the modified antibody or an antigen-binding fragment thereof disclosed herein, wherein the binding affinity to the second pathogen can be selected from a binding affinity to SARS-CoV, MERS-CoV, one or more bacteria, one or more fungus, one or more viruses, one or more parasites, a part thereof, or a combination thereof.

In some embodiments, the modified antibody or an antigen-binding fragment thereof disclosed herein, wherein the modified antibody or the antigen-binding fragment thereof can be a single chain antibody, a diabody, a Fab, a Fab', a F(ab')2, a Fd, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a bispecific scFv dimer, a multispecific antibody, a heavy chain antibody, a camelized single domain antibody, a nanobody, a domain antibody, or a bivalent domain antibody, as disclosed above and hereafter.

Competitive Binding, Crystal Structure and Epitope

In one aspect, the present disclosure provides an isolated or recombinant antibody or an antigen-binding fragment thereof, which competes for binding to RBD of spike protein of SARS-CoV-2 with the antibody or an antigen-binding fragment thereof described herein.

Antibodies or antigen binding fragments that competes with the antibody or antigen-binding fragment provided herein for binding to RBD of spike protein of SARS-CoV-2 include, but are not limited to, antibodies, antibody fragments and other binding agents that bind to an epitope or binding site bound by the antibody or antigen-binding fragment provided herein, or bind to a sufficiently proximal epitope or binding site. Preferably, competitive antibodies or antigen binding fragments of the disclosure will, when present in excess, inhibit specific binding of the antibody or antigen-binding fragment provided herein to RBD of the spike protein of SARS-CoV-2 by at least 10%, preferably by at least 25%, more preferably by at least 50%, and most preferably by at least 75%-90% or even greater. The identification of one or more competitive antibodies or antigen binding fragments that bind to about, substantially, essentially or at the same epitope as the antibodies or antigen binding fragments of the present disclosure is a straightforward technical matter. As the identification of competitive binding molecules is determined in comparison to a reference binding molecule, for example, the antibodies or antigen binding fragments of the present disclosure, it will be understood that actually determining the epitope to which the reference binding molecule and the competitive binding molecule bind is not in any way required in order to identify a competitive binding molecule that binds to the same or substantially the same epitope as the reference binding molecule.

In one aspect, the present disclosure provides a crystal of RBD of the spike protein of SARS-CoV-2 in complex with an antibody. In certain embodiments, the antibody complexed with the RBD in the crystal is any antibody provided herein, or an antigen-binding fragment thereof (e.g. an Fab fragment).

In some embodiment, the crystal provided herein comprises Fab fragment of antibody P2B-2F6 in complex with RBD of the spike protein of SARS-CoV-2. In some embodiment, the crystal consists of a $P2_12_12_1$ space group with unit cell dimensions of a=70.23 Å, b=90.15 Å, and c=112.35 Å.

In some embodiment, the crystal provided herein comprises Fab fragment of antibody P2C-1F11 in complex with RBD of the spike protein of SARS-CoV-2. In some embodiment, the crystal has or consists of a C121 space group with unit cell dimensions of a=194.88 Å, b=85.39 Å, and c=58.51 Å.

In some embodiment, the crystal provided herein comprises Fab fragment of antibody P22A-1D1 in complex with RBD of the spike protein of SARS-CoV-2. In some embodiment, the crystal has or consists of a C2 space group with unit cell dimensions of a=193.34 Å, b=86.60 Å, and c=57.16 Å.

In some embodiment, the crystal provided herein comprises Fab fragment of antibody P5A-1D2 in complex with RBD of the spike protein of SARS-CoV-2. In some embodiment, the crystal has or consists of a C2 space group with unit cell dimensions of a=158.75 Å, b=67.51 Å, and c=154.37 Å.

In some embodiment, the crystal provided herein comprises Fab fragment of antibody P5A-3C8 in complex with RBD of the spike protein of SARS-CoV-2. In some embodiment, the crystal has or consists of a $P2_12_12_1$ space group with unit cell dimensions of a=112.54 Å, b=171.57 Å, and c=54.87 Å.

X-ray crystallography analysis of the antibody bound to RBD of the spike protein of SARS-CoV-2 can be used to determine antibody epitopes. Epitopes may, in particular, be identified in this way by determining residues on RBD of the spike protein of SARS-CoV-2 within 4 Å of an antibody paratope residue. In another aspect, the present disclosure provides an isolated or recombinant antibody or an antigen-binding fragment thereof, which specifically binds to an epitope on RBD of spike protein of SARS-CoV-2, wherein the epitope comprises at least one (at least two, three, four, five, six, seven, eight, nine, ten, eleven, or twelve) residues selected from K444, G446, G447, N448, Y449, N450, L452, V483, E484, G485, F490 and S494, wherein the residue numbering is according to SEQ ID NO: 134. In certain embodiments, the epitope comprises Y449, L452, and F490.

In certain embodiments, the epitope comprises Y449, and G446. In certain embodiments, the antibody or an antigen-binding fragment thereof provided herein has a binding affinity ($K_d$) to the RBD of spike protein of SARS-CoV-2 of no more than 50 nM (e.g. no more than 40 nM, no more than 30 nM, no more than 20 nM, no more than 10 nM, or no more than 5 nM), as measured by Surface Plasmon resonance (SPR).

In another aspect, the present disclosure provides an isolated or recombinant antibody or an antigen-binding fragment thereof, which specifically binds to an epitope on RBD of spike protein of SARS-CoV-2, wherein the epitope comprises at least one (at least two, three, four, five, six, seven, eight, nine, ten, eleven, or twelve) residues selected from Y453, L455, F456, R457, K458, S459, N460, Y473, A475, G476, S477, F486, N487, Y489, Q493, G502, Y505, R403, T415, G416, K417, D420 and Y421, wherein the residue numbering is according to SEQ ID NO: 134. In certain embodiments, the epitope comprises at least one (at least two, three, four, five, six, seven, eight, nine, ten, eleven, or twelve) residues selected from Y453, L455, F456, R457, K458, S459, N460, Y473, A475, G476, S477, F486, N487, Y489, Q493, G502 and Y505, wherein the residue numbering is according to SEQ ID NO: 134. In certain embodiments, the epitope comprises or further comprises at least one (at least two, three, four, five, or six) residues selected from R403, T415, G416, K417, D420 and Y421, wherein the residue numbering is according to SEQ ID NO: 134. In certain embodiments, the epitope comprises at least one (at least two, three, four, five, six, seven, eight, nine, ten, eleven, twelve) residues selected from T415, G416, K417, D420, Y421, L455, F456, R457, K458, N460, Y473, A475, G476, S477, F486, N487, Y489 and Q493, wherein the residue numbering is according to SEQ ID NO: 134. In certain embodiments, the epitope comprises at least one (at least two, three, four, five, six, seven, eight, nine, ten, eleven, or twelve) residues selected from T415, G416, K417, D420, Y421, Y453, L455, F456, R457, K458, N460, Y473, Q474, A475, G476, S477, N487, Y489, Q493 and Y505, wherein the residue numbering is according to SEQ ID NO: 134. In certain embodiments, the epitope comprises at least one (at least two, three, four, five, six, seven, eight, nine, ten, eleven, or twelve) residues selected from T415, G416, K417, D420, Y421, Y453, L455, F456, R457, K458, N460, Y473, A475, G476, S477, F486, N487, Y489 and Q493, wherein the residue numbering is according to SEQ ID NO: 134. In certain embodiments, the epitope comprises at least one (at least two, three, four, five, six, seven, eight, nine, ten, eleven, or twelve) residues selected from T415, G416, K417, D420, Y421, L455, F456, R457, K458, N460, Y473, Q474, A475, G476, S477, F486, N487, Y489 and Q493, wherein the residue numbering is according to SEQ ID NO: 134. In certain embodiments, the epitope comprises at least one (at least two, three, four, five, six or seven) residues selected from L455, K458, Y473, A475, G476, S477 and N487. In certain embodiments, the epitope comprises at least one (at least two, three, four, five, six or seven) residues selected from T415, G416, K417, D420, Y421, K458 and N460. In certain embodiments, the epitope comprises at least one or at least two Y449, and G446. In certain embodiments, the epitope comprises at least one (at least two, three or four) residues selected from K417, Y421, L455 and F456. In certain embodiments, the epitope comprises at least one (at least two, three, or four) residues selected from F456, N487, Y489 and Q493. In certain embodiments, the epitope comprises L455. In certain embodiments, the epitope comprises at least one or at least two residues selected from Y421 and D420. In certain embodiments, the epitope comprises Y421. In certain embodiments, the epitope comprises Y505. In certain embodiments, the epitope comprises Y421A and F456A, wherein the residue numbering is according to SEQ ID NO: 134. In certain embodiments, the epitope comprises T415A, Y473A, and N487A, wherein the residue numbering is according to SEQ ID NO: 134. In certain embodiments, the epitope comprises K417A, D420A, L455A, R457A, N460A, and Y489A, wherein the residue numbering is according to SEQ ID NO: 134. In certain embodiments, the epitope comprises T415A, Y421A, L455A, F456A, R457A, Y473A, N487A, Y489A, and Y505A, wherein the residue numbering is according to SEQ ID NO: 134. In certain embodiments, the antibody or an antigen-binding fragment thereof provided herein has a binding affinity ($K_d$) to the RBD of spike protein of SARS-CoV-2 of no more than 50 nM (e.g. no more than 40 nM, no more than 30 nM, no more than 20 nM, or no more than 10 nM, or no more than 5 nM), as measured by Surface Plasmon resonance (SPR).

In an aspect, the present disclosure provides a computer-implemented method for causing a display of a graphical three-dimensional representation of the structure of a portion of a crystal of RBD of the spike protein of SARS-CoV-2 in complex with an anti-SARS-CoV-2 antibody or an antigen-binding fragment thereof provided herein, wherein the method comprises: causing said display of said graphical three-dimensional representation by a computer system programmed with instructions for transforming structure coordinates into said graphical three-dimensional representation of said structure and for displaying said graphical three-dimensional representation, wherein said graphical three-dimensional representation is generated by transforming said structure coordinates into said graphical three-dimensional representation of said structure, wherein said structure coordinates comprise structure coordinates of the backbone atoms of the portion of the crystal, wherein the portion of the crystal comprises a RBD binding site, and wherein the crystal has the space group symmetry $P2_12_12_1$ or C121.

In another aspect, the present disclosure provides a machine-readable data storage medium comprising a data storage material encoded with machine-readable instructions for: (a) transforming data into a graphical three-dimensional representation for the structure of a portion of a crystal of RBD of the spike protein of SARS-CoV-2 in complex with an anti-SARS-CoV-2 antibody or an antigen-binding fragment thereof provided herein; and (b) causing the display of said graphical three-dimensional representation; wherein said data comprise structure coordinates of the backbone atoms of the amino acids defining a RBD binding site; and wherein the crystal or structural homolog has the space group symmetry $P2_12_12_1$ or C121.

In another aspect, the present disclosure provides a computer system for displaying a three-dimensional graphical representation for the structure of a portion of a crystal of RBD of the spike protein of SARS-CoV-2 in complex with an anti-SARS-CoV-2 antibody or an antigen-binding fragment thereof as provided herein, comprising: (a) a machine-readable data storage medium comprising a data storage material encoded with machine-readable data, wherein said data comprise structure coordinates of the backbone atoms of the amino acids defining a RBD binding site, wherein the crystal has the space group symmetry $P2_12_12_1$ or C121; (b) a working memory; (c) a central processing unit coupled to said working memory and to said machine-readable data storage medium for processing said machine-readable data into sad three-dimensional graphical representation; and (d)

a display coupled to said central processing unit for displaying said three-dimensional graphical representation.

For the above listed aspects, in certain embodiments, the RBD comprises an amino acid sequence as shown in SEQ ID NO: 124. In certain embodiments, the antibody comprises a pair of heavy chain variable region and light chain variable region as listed in Table 2, or the homologous sequence thereof (e.g. having at least 80% sequence identity). In certain embodiments, the antibody comprises: a) a heavy chain variable region of SEQ ID NO: 47 and a light chain variable region of SEQ ID NO: 48; or b) a heavy chain variable region of SEQ ID NO: 111 and a light chain variable region of SEQ ID NO: 112; or c) a heavy chain variable region of SEQ ID NO: 432 and a light chain variable region of SEQ ID NO: 433; or d) a heavy chain variable region of SEQ ID NO: 242 and a light chain variable region of SEQ ID NO: 243; or e) a heavy chain variable region of SEQ ID NO: 232 and a light chain variable region of SEQ ID NO: 233. In certain embodiments, the structure coordinates comprise the structure coordinates of the backbone atoms of the amino acid residues corresponding to K444, G446, G447, N448, Y449, N450, L452, V483, E484, G485, F490 and/or S494 of the RBD, wherein the residue numbering is according to SEQ ID NO: 134. In certain embodiments, the structure coordinates comprise the structure coordinates of the backbone atoms of the amino acid residues corresponding to Y453, L455, F456, R457, K458, S459, N460, Y473, A475, G476, S477, F486, N487, Y489, Q493, G502, Y505, R403, T415, G416, K417, D420 and/or Y421 of the RBD, wherein the residue numbering is according to SEQ ID NO: 134. In certain embodiments, the structure coordinates comprise the structure coordinates of the backbone atoms of the amino acid residues corresponding to T415, G416, K417, D420, Y421, L455, F456, R457, K458, N460, Y473, A475, G476, S477, F486, N487, Y489 and/or Q493 of the RBD, wherein the residue numbering is according to SEQ ID NO: 134. In certain embodiments, the structure coordinates comprise the structure coordinates of the backbone atoms of the amino acid residues corresponding to T415, G416, K417, D420, Y421, Y453, L455, F456, R457, K458, N460, Y473, Q474, A475, G476, S477, N487, Y489, Q493 and/or Y505 of the RBD, wherein the residue numbering is according to SEQ ID NO: 134. In certain embodiments, the structure coordinates comprise the structure coordinates of the backbone atoms of the amino acid residues corresponding to T415, G416, K417, D420, Y421, Y453, L455, F456, R457, K458, N460, Y473, A475, G476, S477, F486, N487, Y489 and/or Q493 of the RBD, wherein the residue numbering is according to SEQ ID NO: 134. In certain embodiments, the structure coordinates comprise the structure coordinates of the backbone atoms of the amino acid residues corresponding to T415, G416, K417, D420, Y421, L455, F456, R457, K458, N460, Y473, Q474, A475, G476, S477, F486, N487, Y489 and/or Q493 of the RBD, wherein the residue numbering is according to SEQ ID NO: 134.

In another aspect, the present disclosure provides a method of screening for molecules that may be a binding molecule of RBD of the spike protein of SARS-CoV-2, comprising: (a) computationally screening agents against a three-dimensional model to identify potential binding molecules of the RBD; wherein the three-dimensional model comprises a three-dimensional model of at least a portion of a crystal of RBD of the spike protein of SARS-CoV-2 in complex with an anti-SARS-CoV-2 antibody or an antigen-binding fragment thereof, wherein the three dimensional model is generated from at least a portion of the structure coordinates of the crystal by a computer algorithm for generating a three-dimensional model of the crystal useful for identifying agents that are potential binding molecules of the RBD.

In certain embodiments, the crystal comprises a polypeptide comprising an amino acid sequence SEQ ID NO: 124, or a homologous sequence thereof, for example derived from a mutant SARS-CoV-2. In certain embodiments, the crystal further comprises an antibody or antigen-binding fragment thereof comprising a pair of heavy chain variable region and light chain variable region as listed in Table 2, or the homologous sequence thereof (e.g. having at least 80% sequence identity). In certain embodiments, the crystal further comprises an antibody or antigen-binding fragment thereof comprising: a) a heavy chain variable region of SEQ ID NO: 47 and a light chain variable region of SEQ ID NO: 48, or b) a heavy chain variable region of SEQ ID NO: 111 and a light chain variable region of SEQ ID NO: 112, wherein the crystal diffracts x-rays for the determination of atomic coordinates to a resolution of 5 Å or better.

A method for obtaining structural information about a molecule or molecular complex comprising applying at least a portion of the structure coordinates of a RBD of the spike protein of SARS-CoV-2 in complex with an anti-SARS-CoV-2 antibody or an antigen-binding fragment thereof provided herein, to an X-ray diffraction pattern of the molecule or molecular complex's crystal structure to cause the generation of a three-dimensional electron density map of at least a portion of the molecule or molecular complex. In certain embodiments, the crystal comprises a polypeptide comprising an amino acid sequence SEQ ID NO: 124, or a homologous sequence thereof, for example derived from a mutant SARS-CoV-2. In certain embodiments, the crystal further comprises an antibody or antigen-binding fragment thereof comprising a pair of heavy chain variable region and light chain variable region as listed in Table 2, or the homologous sequence thereof (e.g. having at least 80% sequence identity). In certain embodiments, the crystal further comprises an antibody or antigen-binding fragment thereof comprising: a) a heavy chain variable region of SEQ ID NO: 47 and a light chain variable region of SEQ ID NO: 48, or b) a heavy chain variable region of SEQ ID NO: 111 and a light chain variable region of SEQ ID NO: 112, wherein the crystal diffracts x-rays for the determination of atomic coordinates to a resolution of 5 Å or better.

Conjugates

In some embodiments, the anti-SARS-CoV-2 antibodies or antigen-binding fragments thereof further comprise one or more conjugate moieties. A conjugate moiety is a moiety that can be attached to the antibodies or antigen-binding fragments thereof either directly or via a linker or through another conjugate moiety. It is contemplated that a variety of conjugate moieties may be linked to the antibodies or antigen-binding fragments thereof provided herein (see, for example, "Conjugate Vaccines", Contributions to Microbiology and Immunology, J. M. Cruse and R. E. Lewis, Jr. (eds.), Carger Press, New York, (1989)). These conjugate moieties may be linked to the antibodies or antigen-binding fragments thereof by covalent binding, affinity binding, intercalation, coordinate binding, complexation, association, blending, or addition, among other methods.

In certain embodiments, the antibodies or antigen-binding fragments thereof provided herein may be engineered to contain specific sites outside the epitope binding portion that may be utilized for binding to one or more conjugate moieties. For example, such a site may include one or more reactive amino acid residues, such as for example cysteine or histidine residues, to facilitate covalent linkage to a conjugate moiety.

Examples of such conjugate moieties include but are not limited to, therapeutic agent, a radioactive isotope, a detectable label, a pharmacokinetic modifying moiety, or a purifying moiety. In some embodiments, the conjugate moiety comprises a clearance-modifying agent (e.g. a polymer such as PEG which extends half-life), a chemotherapeutic agent, a toxin, a radioactive isotope, a lanthanide, a detectable label (e.g. a luminescent label, a fluorescent label, an enzyme-substrate label), a DNA-alkylator, a topoisomerase inhibitor, a tubulin-binder, a purification moiety or other anticancer drugs.

Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P, other lanthanides), luminescent labels, chromophoric moieties, digoxigenin, biotin/avidin, DNA molecules or gold for detection.

In certain embodiments, the conjugate moiety can be a clearance-modifying agent which helps increase half-life of the antibody. Illustrative example include water-soluble polymers, such as PEG, carboxymethylcellulose, dextran, polyvinyl alcohol, polyvinyl pyrrolidone, copolymers of ethylene glycol/propylene glycol, and the like. The polymer may be of any molecular weight, and may be branched or unbranched. The number of polymers attached to the antibody may vary, and if more than one polymer are attached, they can be the same or different molecules. In certain embodiments, the conjugate moiety can be a purification moiety such as a magnetic bead. In certain embodiments, the antibodies or antigen-binding fragments thereof provided herein is used as a base for a conjugate.

Polynucleotides and Recombinant Methods

The present disclosure provides isolated polynucleotides that encode the anti-SARS-CoV-2 antibodies or antigen-binding fragments thereof provided herein. DNA encoding the monoclonal antibody is readily isolated, e.g., from B cells, and sequenced using conventional procedures (e.g. by using oligonucleotide probes that are capable of binding specifically to genes encoding the heavy and light chains of the antibody). The encoding DNA may also be obtained by synthetic methods.

The isolated polynucleotide that encodes the anti-SARS-CoV-2 antibodies or antigen-binding fragments thereof can be inserted into a vector for further cloning (amplification of the DNA) or for expression (i.e., expression vector), using recombinant techniques known in the art. Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

The present disclosure provides vectors comprising the isolated polynucleotide provided herein. In certain embodiments, the polynucleotide provided herein encodes the antibodies or antigen-binding fragments thereof, at least one promoter (e.g. SV40, CMV, EF-1a) operably linked to the nucleic acid sequence, and at least one selection marker. Examples of vectors include, but are not limited to, retrovirus (including lentivirus), adenovirus, adeno-associated virus, herpesvirus (e.g. herpes simplex virus), poxvirus, baculovirus, papillomavirus, papovavirus (e.g. SV40), lambda phage, and M13 phage, plasmid pcDNA3.3, pMD18-T, pOptivec, pCMV, pEGFP, pIRES, pQD-HygGSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

Vectors comprising the polynucleotide sequence encoding the antibody or antigen-binding fragment thereof can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g. *E. coli, Enterobacter, Erwinia, Klebsiella, Proteus, Salmonella*, e.g. *Salmonella typhimurium, Serratia*, e.g. *Serratia marcescans*, and *Shigella*, as well as Bacilli such as *B. subtilis* and *B. licheniformis, Pseudomonas* such as *P. aeruginosa*, and *Streptomyces*.

In addition to prokaryotes, eukaryotic microbes such as filamentous fungi or yeast are suitable cloning or expression hosts for anti-SARS-CoV-2 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g. *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma* reesia (EP 244,234); *Neurospora crassa; Schwanniomyces* such as *Schwanniomyces occidentalis*; and filamentous fungi such as, e.g. *Neurospora, Penicillium, Tolypocladium*, and *Aspergillus* hosts such as *A. nidulans* and *A. niger*.

Suitable host cells for the expression of glycosylated antibodies or antigen-fragment thereof provided herein are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g. the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MIDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). In some embodiments, the host cell is a mammalian cultured cell line, such as CHO, BHK, NS0, 293 and their derivatives.

Host cells are transformed with the above-described expression or cloning vectors for anti-SARS-CoV-2 antibody production and cultured in conventional nutrient media modified as appropriate for inducing promoters, selecting transformants, or amplifying the genes encoding the desired sequences. In another embodiment, the antibody may be produced by homologous recombination known in the art. In certain embodiments, the host cell is capable of producing the antibody or antigen-binding fragment thereof provided herein.

The present disclosure also provides a method of expressing the antibody or an antigen-binding fragment thereof provided herein, comprising culturing the host cell provided herein under the condition at which the vector of the present disclosure is expressed. The host cells used to produce the antibodies or antigen-binding fragments thereof provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to a person skilled in the art. The culture conditions, such as temperature, pH, and the like, are those previously used with the host cell selected for expression, and will be apparent to a person skilled in the art.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-SARS-CoV-2 antibodies or antigen-binding fragments thereof prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody and antigen-binding fragment thereof. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., J. Immunol. Meth. 62:1-13 (1983)). Protein G is recommended for all mouse isotypes and for human gamma3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin crosslinked, beaded-form of agarose SEPHAROSE™ (trademark of GE Healthcare) chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g. from about 0-0.25M salt).

Pharmaceutical Composition

The present disclosure further provides pharmaceutical compositions comprising the anti-SARS-CoV-2 antibodies or antigen-binding fragments thereof and one or more pharmaceutically acceptable carriers.

The present disclosure further provides a pharmaceutical composition comprising at least one or more of the modified antibody or an antigen-binding fragment thereof disclosed herein, at least one nucleic acid encoding the modified antibody or the antigen-binding fragment thereof, or a combination thereof, and one or more pharmaceutically acceptable carriers.

In some embodiments, the pharmaceutical composition comprises a combination of two or more antibodies or the antigen binding fragments of the present disclosure. In some embodiments, the pharmaceutical composition comprises a combination of two or more monoclonal antibodies, each of which comprises heavy chain CDR sequences and light chain CDR sequences derived from an antibody selected from the group consisting of P2A-1A8, P2A-1A9, P2B-2G11, P2A-1A10, P2A-1B3, P2B-2F6, P2B-2G4, P2C-1A3, P2C-1C8, P2C- 1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, and P22A-IDI. In some embodiments, the pharmaceutical composition comprises a first antibody comprising heavy chain CDR sequences and light chain CDR sequences derived from P2C-1F11, and a second antibody comprising heavy chain CDR sequences and light chain CDR sequences derived from antibody P2B-2F6.

In some embodiments, the two or more antibodies or the antigen binding fragments thereof bind to different epitopes in RBD of spike protein of SARS-CoV-2. In certain embodiments, the pharmaceutical composition comprises a first antibody which comprises P2C-1F11 or an antigen binding fragment thereof, and a second antibody which is selected from the group consisting of P2C-1A3, P2C-1C10, P2B-2F6, P2B-1G5, and P2A-1B3, or an antigen binding fragment thereof. In certain embodiments, the pharmaceutical composition comprises a first antibody which comprises P2C-1A3 or an antigen binding fragment thereof, and a second antibody which is selected from the group consisting of P5A-3C8, P5A-1D2, P22A-1D1, P2C-1F11, and P2A-1B3, or an antigen binding fragment thereof. In certain embodiments, the pharmaceutical composition comprises a first antibody which comprises P2B-2F6 or an antigen binding fragment thereof, and a second antibody selected from the group consisting of P2C-1C10, P2C-1F11, P2B-1G5, and P2A-1B3, or an antigen binding fragment thereof. In certain embodiments, the pharmaceutical composition comprises a first antibody which comprises P2A-1B3 or an antigen binding fragment thereof, and a second antibody selected from the group consisting of P5A-3C8, P5A-1D2, P22A-1D1, P2C-1A3, P2C-1C10, P2C-1F1, P2B-2F6, and P2A-TATO, or an antigen binding fragment thereof. In some embodiments, the pharmaceutical composition comprises a first antibody which comprises P2C-1C10 or an antigen binding fragment thereof, and a second antibody selected from the group consisting of P5A-3C8, P5A-1D2, P22A-1D1, P2C-1A3, P2C-1F11, and P2A-1B3, or an antigen binding fragment thereof.

The present disclosure further provides pharmaceutical compositions comprising the polynucleotides encoding the anti-SARS-CoV-2 antibodies or the antigen-binding fragments thereof, and one or more pharmaceutically acceptable carriers. The present disclosure further provides pharmaceutical compositions comprising the polynucleotides encoding the combination of the two or more anti-SARS-CoV-2 antibodies or the antigen-binding fragments thereof, and one or more pharmaceutically acceptable carriers.

The present disclosure further provides pharmaceutical compositions comprising an expression vector comprising the polynucleotides encoding the one or more of anti-SARS-CoV-2 antibodies or the antigen-binding fragments thereof, and one or more pharmaceutically acceptable carriers.

In certain embodiments, the expression vector comprises a viral vector or a non-viral vector. Examples of viral vectors include, without limitation, adeno-associated virus (AAV) vector, lentivirus vector, retrovirus vector, and adenovirus vector. Examples of non-viral vectors include, without limitation, naked DNA, plasmid, exosome, mRNA, and so on. In certain embodiments, the expression vector is suitable for gene therapy in human. Suitable vectors for gene therapy include, for example, adeno-associated virus (AAV), or adenovirus vector. In certain embodiments, the expression vector comprises a DNA vector or a RNA vector. In certain embodiments, the pharmaceutically acceptable carriers are polymeric excipients, such as without limitation, microspheres, microcapsules, polymeric micelles and dendrimers. The polynucleotides, or polynucleotide vectors of the present disclosure may be encapsulated, adhered to, or coated on the polymer-based components by methods known in the art (see for example, W. Heiser, Nonviral gene transfer techniques, published by Humana Press, 2004; U.S. Pat. No. 6,025,337; Advanced Drug Delivery Reviews, 57(15): 2177-2202 (2005)).

In some embodiments, the pharmaceutical composition further comprises a second bioactive agent, such as a second therapeutic agent or a second prophylactic agent.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment thereof and conjugates provided herein decreases oxidation of the antibody or antigen-binding fragment thereof. This reduction in oxidation prevents or reduces loss of binding affinity, thereby improving antibody stability and maximizing shelf-life. Therefore, in certain embodiments, pharmaceutical compositions are provided that comprise one or more antibodies or antigen-binding fragments thereof as disclosed herein and one or more antioxidants such as methionine. Further provided are methods for preventing oxidation of, extending the shelf-life of, and/or improving the efficacy of an antibody or antigen-binding fragment provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as nonionic surfactant Polysorbate 80 (TWEEN®-80, TWEEN is a registered trademark of CRODA AMERICAS LLC), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

The form of pharmaceutical compositions depends on a number of criteria, including, but not limited to, route of administration, extent of disease, or dose to be administered. The pharmaceutical compositions can be formulated for intravenous, oral, nasal, rectal, percutaneous, or intramuscular administration. For example, dosage forms for intravenous administration, may be formulated as lyophilized powder or fluid formulation; dosage forms for nasal administration may conveniently be formulated as aerosols, solutions, drops, gels or dry powders. In accordance to the desired route of administration, the pharmaceutical compositions can be formulated in the form of tablets, capsule, pill, dragee, powder, granule, sachets, cachets, lozenges, suspensions, emulsions, solutions, syrups, aerosols (as a solid or in a liquid medium), spray, inhalant, or suppository.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to a person skilled in the art at, in one embodiment, about neutral pH. Subsequent sterile filtration of the solution followed by lyophilization under standard conditions known to a person skilled in the art provides a desirable formulation. In one embodiment, the resulting solution will be apportioned into vials for lyophilization. Each vial can contain a single dosage or multiple dosages of the anti-SARS-CoV-2 antibody or antigen-binding fragment thereof or composition thereof. Overfilling vials with a small amount above that needed for a dose or set of doses (e.g. about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

The pharmaceutical composition disclosed herein can comprise the modified antibody or an antigen-binding fragment thereof at a concentration in a range of from a concentration in a range of from 10 mg/mL to 150 mg/mL. The concentration of the modified antibody or an antigen-binding fragment thereof can be determined based on total protein concentration, antibody specific protein concentration, or a combination thereof. Typical measurement method for measuring protein concentrations known to those skilled in the art can be suitable.

In some embodiments, the pharmaceutical composition can be configured to be administered to a subject via intravenous injection (IV), intramuscular injection (IM), subcutaneous (SC) injection, or a combination thereof.

In some embodiments, the pharmaceutical composition can be configured for preventing a disease in a person having no symptoms or free from known infections of the SARS-CoV-2, or treatment of a patient being a symptomatic non-hospitalized person of any age or an adult with COVID-19 caused by SARS-CoV-2 infection, aged 60 years and older, any age having at least one of the following conditions selected from smoking, exogenous or endogenous immunosuppression having HIV infection with CD4 count <200 cells/mm$^3$, receiving corticosteroids equivalent to prednisone 20 mg daily for at least 14 consecutive days within 30 days prior to be administered with the pharmaceutical composition, receiving one or more biologics therapeutical agents, one or more immunomodulators, cancer chemotherapy within 90 days prior to be administered with the pharmaceutical composition; having chronic lung disease, chronic asthma; obesity with body mass index [BMI]>35, having symptoms of COVID-19 selected from fever, cough, sore throat, malaise, headache, muscle pain, nausea, vomiting, diarrhea, loss of taste and smell, or a combination thereof, having shortness of breath, dyspnea, or abnormal chest imaging, having evidence of lower respiratory disease during clinical assessment or imaging, having saturation of oxygen (SpO2) ≥94% on room air at sea level, having severe symptoms of the infection of the SARS-CoV-2, having SpO2<94% on room air at sea level, having a ratio of arterial partial pressure of oxygen to fraction of inspired oxygen (PaO2/FiO2)<300 mmHg, respiratory frequency>30 breaths per minute, lung infiltrates >50%, having active symptoms of antibody-dependent enhancement (ADE), having a history of antibody-dependent enhancement (ADE), being allergic to an antibody treatment, being a hospital inpatient requiring supportive management of complications of severe infection of the SARS-CoV-2 selected from pneumonia, hypoxemic respiratory failure/ARDS, sepsis and septic shock, cardiomyopathy and arrhythmia, acute kidney injury, and complications from prolonged hospitalization including secondary bacterial and fungal infections, thromboembolism, gastrointestinal bleeding, critical illness polyneuropathy/myopathy, or a combination thereof.

In some embodiments, the pharmaceutical composition can further comprise one or more bioactive agent that can comprise a therapeutic agent or a prophylactic agent selected from an anti-viral agent, an antiviral peptide, an anti-viral antibody, an anti-viral compound, an anti-viral cytokine, an anti-viral oligonucleotide, an RNA dependent RNA polymerase inhibitor, a non-nucleoside reverse transcriptase inhibitor (NNRTI), nucleoside reverse transcriptase inhibitor (NRTI), purine nucleoside, antiviral interferon, adamantine antiviral compound, remdesivir, chloroquine, hydroxychloroquine, lopinavir, ritonavir, APN01, favilavir, mesalazine, toremifene, eplerenone, paroxetine, sirolimus, dactinomycin, irbesartan, emodin, mercaptopurine, melatonin, quinacrine, carvedilol, colchicine, camphor, equilin, oxymetholone, nafamosta, camostat, baricitinib, darunavir, ribavirin, galidesivir, BCX-4430, Arbidol, nitazoxanide, one or more derivatives thereof, or any combination thereof. In some cases, the pharmaceutical composition can further comprise infliximab, abalizumab, ustekinumab, immunomodulators such as methotrexate, 6MP, azathioprine, or a combination thereof chronic Methods of Treatment or Prevention The present disclosure also provides methods of treating SARs-CoV-2 infection or a disease, disorder or condition associated with SARs-CoV-2 infection in a subject, comprising administering to the subject a therapeutically effective amount of one or more of the antibody or antigen-binding fragment thereof provided herein, or one or more polynucleotides encoding one or more of the antibody or antigen-binding fragment thereof provided herein, or the pharmaceutical composition provided herein.

In certain embodiments, the therapeutically effective amount can be an amount effective to decrease SARs-COV-2 titers, or to alleviate one or more disease symptoms, viremia, or any other measurable manifestation of SARS-CoV-2 infection in the treated subject or population, whether by inducing the regression of or inhibiting the progression of symptom(s) associated with SARs-COV-2 infection by any clinically measurable degree. Decrease in SARs-COV-2 titers can be measured in the lung, for example, by the concentration of SARs-COV-2 in sputum samples or a lavage from the lungs from a mammal. Alleviation of a disease symptom can be assessed by any clinical measurement typically used by physicians or other skilled healthcare providers to assess the severity or progression status of that symptom. Exemplary symptoms associated with SARs-COV-2 infection include, without limitation, fever, dry cough, shortness in breath, pain or pressure in the chest, new confusion or inability to arouse, bluish lips or face, loss of sense of smell and/or loss of sense of taste.

A subject in need of treatment include, for example, those already infected with SARS-CoV-2 (symptomatic or asymptomatic) or inflicted with a condition resulting from infection of SARS-CoV-2. Subjects partially or totally recovered from infection of SARS-CoV-2 might also be in need of treatment. In certain embodiments, the subject is human.

The present disclosure also provides methods of preventing SARs-CoV-2 infection, or a disease, disorder or condition associated with SARs-COV-2 infection in a subject, comprising administering to the subject a prophylactically effective amount of one or more of the antibody or antigen-binding fragment thereof provided herein, or one or more polynucleotides encoding one or more of the antibody or antigen-binding fragment thereof provided herein, or the pharmaceutical composition provided herein. Prevention encompasses inhibiting or reducing the spread of SARS-CoV-2 or inhibiting or reducing the onset, development or progression of one or more of the symptoms associated with infection with SARS-CoV-2.

In certain embodiments, the prophylactically effective amount can be an amount effective to neutralize SARs-COV-2 in the respiratory tract, lungs and/or other affected areas such as eyes, noses and mouth, in order block infection, or effective to ameliorate at least one symptom associated with SARs-COV-2 infection. Whether a symptom has been ameliorated can be assessed by any clinical measurement typically used by physicians or other skilled healthcare providers to assess the severity or progression status of that symptom or in certain instances will ameliorate the need for hospitalization.

A subject in need of prevention include, for example, those in which infection with SARS-CoV-2 is to be prevented, or those who are at risk for SARS-CoV-2 infection. In certain embodiments, the subject is human.

The term "disease, disorder or condition associated with SARS-COV-2 infection" as used herein include those that are caused by or related to SARs-COV-2 infection, such as, upper or lower respiratory tract infections, pharyngitis, pneumonia, tracheobronchitis, bronchiolitis, bronchitis, acute respiratory distress syndrome, diarrhea, and any related infections or inflammatory disorders.

The methods of treatment or prevention provided herein are also suitable for gene therapy by transfer of polynucleotide sequences encoding the antibody product or fragment thereof in a subject, such that the polynucleotide can be expressed in the subject to produce the antibody in vivo. The polynucleotide provided herein can be administered to a subject by, for example, transfection techniques such as electroporation and hydrodynamic injection, which are suitable for administration of naked polynucleotides. For polynucleotides in the form of viral vectors such as AAV, it can be administered via local injection (e.g. intramuscular, intranasal, intradermal, subcutaneous, etc.) or systematic administration (e.g. intravenous administration).

In certain embodiments, the methods can comprise administering to the subject a therapeutically effective amount or a prophylactically effective amount of a combination of two or more of the antibodies (or the antigen-binding fragment thereof) provided herein. In certain embodiments, the two or more antibodies comprises a first antibody comprising heavy chain CDR sequences and light chain CDR sequences derived from P2C-1F11, and a second antibody comprising heavy chain CDR sequences and light chain CDR sequences derived from antibody P2B-2F6. In certain embodiments, the two or more antibodies or the antigen binding fragments thereof bind to different epitopes in RBD of spike protein of SARS-CoV-2. In certain embodiments, the two or more antibodies comprise a first antibody comprising P2C-1F11, and a second antibody which is selected from the group consisting of P2C-1A3, P2C-1C10, P2B-2F6, P2B-1G5, and P2A-1B3. In certain embodiments, the two or more antibodies comprise a first antibody comprising P2C-1A3 and a second antibody which is selected from the group consisting of P5A-3C8, P5A-1D2, P22A-1D1, P2C-1F11, and P2A-1B3, or an antigen binding fragment thereof. In certain embodiments, the two or more antibodies comprise a first antibody comprising P2B-2F6 and a second antibody which is selected from the group consisting of P2C-1C10, P2C-1F11, P2B-1G5, and P2A-1B3, or an antigen binding fragment thereof. In certain embodiments, the two or more antibodies comprises a first antibody comprising P2A-1B3 and a second antibody which selected from the group consisting of P5A-3C8, P5A-1D2, P22A-1D1, P2C-1A3, P2C-1C10, P2C-1F11, P2B-2F6, and P2A-1A10, or an antigen binding fragment thereof. In some embodiments, the two or more antibodies comprise a first antibody which comprises P2C-1C10 or an antigen binding fragment thereof, and a second antibody selected from the group consisting of P5A-3C8, P5A-1D2, P22A-1D1, P2C-1A3, P2C-1F11, and P2A-1B3, or an antigen binding fragment thereof.

The antibodies or antigen-binding fragments thereof provided herein may be administered by any route known in the art, such as for example parenteral (e.g. subcutaneous, intraperitoneal, intravenous, including intravenous infusion, intramuscular, or intradermal injection) or non-parenteral (e.g. oral, intranasal, intraocular, sublingual, rectal, or topical) routes.

In some embodiments, this disclosure is directed to a method for treating or preventing a disease in a subject in need thereof, the method can comprise administering an effective dosage of any one of the pharmaceutical compositions disclosed herein to the subject;

wherein the pharmaceutical composition can be configured to be administered to the subject to maintain a plasma concentration of the modified antibody or an antigen-binding fragment thereof in a therapeutic effective range of from 10 μg/mL to 3500 μg/mL for a time period in a range of from 1 day to 12 months after administering the pharmaceutical composition; and wherein the subject can be infected with, exhibiting one or more symptoms of being infected with, or at risk of being infected with the SARS-CoV-2.

The method disclosed herein can be used for preventing infection of the SARS-CoV-2 in a subject who is at risk of being infected, such as a healthy person who may get in contact with another person who has or had the SARS-CoV-2 infection with or without symptoms, a person who provides case to or handles materials related from another person who has or had the SARS-CoV-2 infection with or without symptoms, such as a healthcare personnel, an emergency responder, a medical diagnosis service personnel, a senior home service provider, or a combination thereof.

In some embodiments, the pharmaceutical composition can be administered to the subject having no symptoms or free from known infections of the SARS-CoV-2, prior to the subject being infected with the SARS-CoV-2, prior to the subject exhibiting any symptoms of the infection of the SARS-CoV-2, or a combination thereof.

In some embodiments, the pharmaceutical composition can be configured to be administered to the subject to maintain the plasma concentration of the modified antibody or an antigen-binding fragment thereof in a therapeutic effective range of from 10 μg/mL to 1500 μg/mL for a time period ranging from 3 to 12 months after the administration and wherein the administration is a single administration. In some embodiments, the pharmaceutical composition can be configured to be administered to the subject to maintain the plasma concentration of the modified antibody or an antigen-binding fragment thereof in a therapeutic effective range of from 10 μg/mL to 1500 μg/mL, 20 μg/mL to 1500 μg/mL, 30 μg/mL to 1500 μg/mL, 40 μg/mL to 1500 μg/mL, 50 μg/mL to 1500 μg/mL, 60 μg/mL to 1500 μg/mL, 70 μg/mL to 1500 μg/mL, 80 μg/mL to 1500 μg/mL, 90 μg/mL to 1500 μg/mL, 100 μg/mL to 1500 μg/mL, 150 μg/mL to 1500 μg/mL, 200 μg/mL to 1500 μg/mL, 300 μg/mL to 1500 μg/mL, 400 μg/mL to 1500 μg/mL, 500 μg/mL to 1500 μg/mL, 600 μg/mL to 1500 μg/mL, 700 μg/mL to 1500 μg/mL, 800 μg/mL to 1500 μg/mL, 900 μg/mL to 1500 μg/mL, 1000 μg/mL to 1500 μg/mL, 1100 μg/mL to 1500 μg/mL, 1200 μg/mL to 1500 μg/mL, 1300 μg/mL to 1500 μg/mL or 1400 μg/mL to 1500 μg/mL, wherein the disclosure of these ranges is intended as a continuous range including every value between the minimum and maximum values. In some embodiments, the time period can range from 3 to 12 months, 4 to 12 months, 5 to 12 months, 6 to 12 months, 7 to 12 months, 8 to 12 months, 9 to 12 months, 10 to 12 months or 11 to 12 months, after administration of the pharmaceutical composition and wherein the administration can be a single administration. The plasma concentration of the modified antibody or an antigen-binding fragment thereof to reach the above mentioned range within a day and can maintain within the above mentioned range for the indicated time periods disclosed above.

In some embodiments, the subject can be a person having no symptoms or free from known infections of the SARS-CoV-2, or treatment of a patient being a symptomatic non-hospitalized adult with COVID-19 caused by SARS-CoV-2 infection, aged 60 years and older, any age having at least one of the following conditions selected from smoking, exogenous or endogenous immunosuppression having HIV infection with CD4 count <200 cells/mm3, receiving corticosteroids equivalent to prednisone ≥20 mg daily for at least 14 consecutive days within 30 days prior to be administered with the pharmaceutical composition, receiving one or more biologics therapeutical agents, one or more immunomodulators, cancer chemotherapy within 90 days prior to be administered with the pharmaceutical composition; having chronic lung disease, chronic asthma; obesity with body mass index [BMI]>35, having symptoms of COVID-19 selected from fever, cough, sore throat, malaise, headache, muscle pain, nausea, vomiting, diarrhea, loss of taste and smell, or a combination thereof, having shortness of breath, dyspnea, or abnormal chest imaging, having evidence of lower respiratory disease during clinical assessment or imaging, having saturation of oxygen (SpO2) ≥94% on room air at sea level, having severe symptoms of the infection of the SARS-CoV-2, having SpO2<94% on room air at sea level, having a ratio of arterial partial pressure of oxygen to fraction of inspired oxygen (PaO2/FiO2)<300 mmHg, respiratory frequency>30 breaths per minute, lung infiltrates >50%, having active symptoms of antibody-dependent enhancement (ADE), having a history of antibody-dependent enhancement (ADE), being allergic to an antibody treatment, being a hospital inpatient requiring supportive management of complications of severe infection of the SARS-CoV-2 selected from pneumonia, hypoxemic respiratory failure/ARDS, sepsis and septic shock, cardiomyopathy and arrhythmia, acute kidney injury, and complications from prolonged hospitalization including secondary bacterial and fungal infections, thromboembolism, gastrointestinal bleeding, critical illness polyneuropathy/myopathy, or a combination thereof.

In some embodiments, the subject can be a person 60 years and older, 65 years and older, 70 years and older, 75 years and older, 80 years and older, 85 years and older or 90 years and older.

In some embodiments of the method disclosed herein, the pharmaceutical composition can be configured to be administered to the subject to maintain the plasma concentration of the modified antibody or an antigen-binding fragment thereof in a therapeutic effective range of from 30 μg/mL to 3500 μg/mL for a time period ranging from 1 to 4 weeks after the administration and wherein the administration is a single administration. In some embodiments, the pharmaceutical composition can be configured to be administered to the subject to maintain the plasma concentration of the modified antibody or an antigen-binding fragment thereof in a therapeutic effective range of from 10 µg/mL to 3500 µg/mL, 20 µg/mL to 3500 µg/mL, 30 µg/mL to 3500 µg/mL, 40 µg/mL to 3500 µg/mL, 50 µg/mL to 3500 µg/mL, 60 µg/mL to 3500 µg/mL, 70 µg/mL to 3500 µg/mL, 80 µg/mL to 3500 µg/mL, 90 µg/mL to 3500 µg/mL, 100 µg/mL to 3500 µg/mL, 150 µg/mL to 3500 µg/mL, 200 µg/mL to 3500 µg/mL, 300 µg/mL to 3500 µg/mL, 400 µg/mL to 3500 µg/mL, 500 µg/mL to 3500 µg/mL, 600 µg/mL to 3500 µg/mL, 700 µg/mL to 3500 µg/mL, 800 µg/mL to 3500 µg/mL, 900 µg/mL to 3500 µg/mL, 1000 µg/mL to 3500 µg/mL, 1100 µg/mL to 3500 µg/mL, 1200 µg/mL to 3500 µg/mL, 1300 µg/mL to 3500 µg/mL, 1400 µg/mL to 3500 µg/mL, 1500 µg/mL to 3500 µg/mL, 1600 µg/mL to 3500 µg/mL, 1700 µg/mL to 3500 µg/mL, 1800 µg/mL to 3500 µg/mL, 1900 µg/mL to 3500 µg/mL, 2000 µg/mL to 3500 µg/mL, 2100 µg/mL to 3500 µg/mL, 2200 µg/mL to 3500 µg/mL, 2300 µg/mL to 3500 µg/mL, 2400 µg/mL to 3500 µg/mL, 2500 µg/mL to 3500 µg/mL, 2600 µg/mL to 3500 µg/mL, 2700 µg/mL to 3500 µg/mL, 2800 µg/mL to 3500 µg/mL, 2900 µg/mL to 3500 µg/mL, 3000 µg/mL to 3500 µg/mL, 3100 µg/mL to 3500 µg/mL, 3200 µg/mL to 3500 µg/mL, 3300 µg/mL to 3500 µg/mL or 3400 µg/mL to 3500 µg/mL, wherein the disclosure of these ranges is intended as a continuous range including every value between the minimum and maximum values. In some embodiments, the time period can range from 1 to 4 weeks, 2 to 4 weeks or 3 to 4 weeks after administration of the pharmaceutical composition and wherein the administration can be a single administration. The plasma concentration of the modified antibody or an antigen-binding fragment thereof to reach the above mentioned range within a day and can maintain within the above mentioned range for the indicated time periods disclosed above.

In some embodiments, the pharmaceutical composition can be administered to maintain a high plasma concentration, such as 30 µg/mL to 3500 µg/mL, of the modified antibody or an antigen-binding fragment thereof immediately after administration, such as 1 day to a few days or 1 to 4 weeks, for treating a patient with the disease or symptoms of the infection of the SARS-CoV-2. In some embodiments, the pharmaceutical composition can be administered to maintain a desired plasma concentration, such as 10 µg/mL to 1500 µg/mL, of the modified antibody or an antigen-binding fragment thereof and maintain within the desired range for 3 to 12 months, for preventing a person from being infected with the SARS-CoV-2. As used herein the "plasma concentration" or "serum concentration" may be used interchangeably for the concentration of the modified antibody or an antigen-binding fragment thereof in the blood of a patient.

In some embodiments, plasma concentration of the modified antibody or an antigen-binding fragment thereof can be at about 100-300 times of in vitro $IC_{90}$ for at least 3 to 6 weeks for treating a patient with the SARS-CoV-2 infection or symptoms of the SARS-CoV-2 infection. In some embodiments, plasma concentration of the modified antibody or an antigen-binding fragment thereof can be at about 10-50 times of in vitro $IC_{90}$ for at least 6-month for preventing the SARS-CoV-2 infection or symptoms of the SARS-CoV-2 infection.

In some embodiments of the method disclosed herein, the modified antibody or the antigen-binding fragment thereof can be configured to have a half-life ($T_{1/2}$) in a range of from 50 to 120 days in the subject. In some embodiments, the half-life ($T_{1/2}$) can be in a range of from 50 to 120 days, 60 to 120 days, 70 to 120 days, 80 to 120 days, 90 to 120 days, 100 to 120 days or 110 to 120 days, in the subject.

In some embodiments of the method disclosed herein, the pharmaceutical composition can be configured to be administered to the subject in a range of from 150 mg/m² to 5000 mg/m². In some cases, the pharmaceutical composition can be administered to the subject in a dosage range of from 150 to 5000 mg/m², 200 to 5000 mg/m², 300 to 5000 mg/m², 400 to 5000 mg/m², 500 to 5000 mg/m², 600 to 5000 mg/m², 700 to 5000 mg/m², 800 to 5000 mg/m², 900 to 5000 mg/m², 1000 to 5000 mg/m², 1200 to 5000 mg/m², 1400 to 5000 mg/m², 1600 to 5000 mg/m², 1800 to 5000 mg/m², 2000 to 5000 mg/m², 2200 to 5000 mg/m², 2400 to 5000 mg/m², 2600 to 5000 mg/m², 2800 to 5000 mg/m², 3000 to 5000 mg/m², 3200 to 5000 mg/m², 3400 to 5000 mg/m², 3600 to 5000 mg/m², 3800 to 5000 mg/m², 4000 to 5000 mg/m², 4200 to 5000 mg/m², 4400 to 5000 mg/m², 4600 to 5000 mg/m² or 4800 to 5000 mg/m², wherein the disclosure of these ranges is intended as a continuous range including every value between the minimum and maximum values.

In some embodiments of the method disclosed herein, the pharmaceutical composition can be configured to be administered to the subject in a range of from 300 mg to 8000 mg. In some cases, the pharmaceutical composition can be administered to the subject in a range of from 300 to 8000 mg, 400 to 8000 mg, 500 to 8000 mg, 600 to 8000 mg, 700 to 8000 mg, 800 to 8000 mg, 900 to 8000 mg, 1000 to 8000 mg, 1200 to 8000 mg, 1400 to 8000 mg, 1600 to 8000 mg, 1800 to 8000 mg, 2000 to 8000 mg, 2500 to 8000 mg, 3000 to 8000 mg, 3500 to 8000 mg, 4000 to 8000 mg, 4500 to 8000 mg, 5000 to 8000 mg, 5500 to 8000 mg, 6000 to 8000 mg, 6500 to 8000 mg, 7000 to 8000 mg or 7500 to 8000 mg. In some cases, the pharmaceutical composition can be administered to the subject in a range of from 5 to 150 mg/kg, 10 to 150 mg/kg, 15 to 150 mg/kg, 20 to 150 mg/kg, 25 to 150 mg/kg, 30 to 150 mg/kg, 35 to 150 mg/kg, 40 to 150 mg/kg, 45 to 150 mg/kg, 50 to 150 mg/kg, 55 to 150 mg/kg, 60 to 150 mg/kg, 65 to 150 mg/kg, 70 to 150 mg/kg, 75 to 150 mg/kg, 80 to 150 mg/kg, 85 to 150 mg/kg, 90 to 150 mg/kg, 95 to 150 mg/kg, 100 to 150 mg/kg, 110 to 150 mg/kg, 120 to 150 mg/kg, 130 to 150 mg/kg or 140 to 150 mg/kg, of the body weight of the subject.

In some embodiments, the pharmaceutical composition can be configured to have the modified antibody at a concentration in a range of from 10 mg/mL to 150 mg/mL. In some cases, the pharmaceutical composition can be configured to have the modified antibody at a concentration at 10 mg/mL to 150 mg/mL, 20 mg/mL to 150 mg/mL, 30 mg/mL to 150 mg/mL, 40 mg/mL to 150 mg/mL, 50 mg/mL to 150 mg/mL, 60 mg/mL to 150 mg/mL, 70 mg/mL to 150 mg/mL, 80 mg/mL to 150 mg/mL, 90 mg/mL to 150 mg/mL, 100 mg/mL to 150 mg/mL, 110 mg/mL to 150 mg/mL, 120 mg/mL to 150 mg/mL, 130 mg/mL to 150 mg/mL or 140 mg/mL to 150 mg/mL. The concentration can be the total protein concentration of the antibody in the pharmaceutical composition.

In some cases of the method disclosed herein, the pharmaceutical composition can be administered to the subject via intravenous injection (IV), intramuscular injection (IM), subcutaneous (SC) injection, or a combination thereof.

In some embodiments of the method disclosed herein, the effective dosage can be determined by a dosing process that can comprise determining concentration progression data based on calculated or measured pharmacokinetics (PK), testing plasma concentrations over a testing period of time, predicted plasma concentrations over a prediction period of time, or a combination thereof, of the modified antibody or the antigen-binding fragment thereof, and producing the effective dosage based on the concentration progression data. In some embodiments, the effective dosage can be determined by predicted plasma concentrations over a prediction period of time, wherein the predicted plasma concentrations can be produced by measuring actual plasma concentrations of the modified antibody in a subject selected form a primate or a human over a measurement period of time to produce measured concentration data and interpolating and extrapolating the measured concentration data to produce the predicted plasma concentrations in a selected prediction period of time.

In some embodiments of the method disclosed herein, the effective dosage can be selected to maintain the plasma concentration in a range of from 10 µg/mL to 1500 µg/mL in 3 to 12 months after the administration. Such effective dosage can be suitable for preventing the disease in a subject for an extended period of time, such as 3 to 12 months.

In some embodiments of the method disclosed herein, the effective dosage can be selected to maintain the plasma concentration in a range of from 1500 µg/mL to 3500 µg/mL in 1 day to 2 months after the administration. Such high effective dosage can be suitable for treating the disease for a shorter period of time, for example, from 1 day to 60 days.

In some embodiments of the method disclosed herein, the pharmaceutical composition further comprises one or more subsequent modified antibodies selected from a first subsequent modified antibody comprising two antigen-binding domains each having same or different affinities to the SARS-CoV-2, a second subsequent modified antibody comprising a first antigen-binding domain having a binding affinity to the SARS-CoV-2 and a second antigen-binding domain having a binding affinity to a second pathogen that is different from the SARS-CoV-2, a third subsequent modified antibody comprising two antigen-binding domains each having a same or different binding affinity to the second pathogen, or a combination thereof. As mentioned above, the term "different affinities to the SARS-CoV-2" refers affinity that can bind to a different epitope or binding site of the SARS-CoV-2, a different affinity level that can bind to the same epitope or binding site of the SARS-CoV-2, or a combination thereof. The binding affinity to the second pathogen can be selected from a binding affinity to SARS-CoV, MERS-CoV, one or more bacteria, one or more fungus, one or more viruses, one or more parasites, a part thereof, or a combination thereof.

In some embodiments of the method disclosed herein can further comprise administering a pharmaceutically effective amount of one or more bioactive agents to the subject simultaneously or sequentially with the pharmaceutical composition, wherein the bioactive agent comprises a therapeutic agent or a prophylactic agent selected from an anti-viral agent, an antiviral peptide, an anti-viral antibody, an anti-viral compound, an anti-viral cytokine, an anti-viral oligonucleotide, an RNA dependent RNA polymerase inhibitor, a non-nucleoside reverse transcriptase inhibitor (NNRTI), nucleoside reverse transcriptase inhibitor (NRTI), purine nucleoside, antiviral interferon, adamantine antiviral compound, remdesivir, chloroquine, hydroxychloroquine, lopinavir, ritonavir, APN01, favilavir, mesalazine, toremifene, eplerenone, paroxetine, sirolimus, dactinomycin, irbesartan, emodin, mercaptopurine, melatonin, quinacrine, carvedilol, colchicine, camphor, equilin, oxymetholone, nafamosta, camostat, baricitinib, darunavir, ribavirin, galidesivir, BCX-4430, Arbidol, nitazoxanide, one or more derivatives thereof, or any combination thereof.

In some embodiments, the antibodies or antigen-binding fragments thereof provided herein may be administered alone or in combination a therapeutically effective amount of a second bioactive agent. The second bioactive agent can be a therapeutic agent or a prophylactic agent.

In some embodiments, the second therapeutic agent is an anti-viral agent. In some embodiments, the anti-viral agent comprises an antiviral peptide, an anti-viral antibody, an anti-viral compound, an anti-viral cytokine, or an anti-viral oligonucleotide. In some embodiments, the anti-viral agent is an RNA dependent RNA polymerase inhibitor, a non-nucleoside reverse transcriptase inhibitor (NNRTI), nucleoside reverse transcriptase inhibitor (NRTI), purine nucleoside, antiviral cytokines such as interferon, adamantine antiviral compound, anti-RBD antibody, anti-S1 antibody, anti-S2 antibody, siRNAs Targeting mRNA of coronavirus proteins M, N, or E (Chinese patent applications CN101173275 and CN1648249), siRNAs targeting replicase and RNA polymerase region (US patent application US20050004063), RNA Aptamers (Korean patent applications KR2009128837 and KR 2012139512), ribozymes (Japanese patent application JP2007043942), antisense oligonucleotides (PCT patent application WO2005023083), or any other suitable antiviral agent. In certain embodiments, the anti-viral compound is selected from the group consisting of remdesivir, chloroquine, hydroxychloroquine, lopinavir, ritonavir, APN01, favilavir, mesalazine, toremifene, eplerenone, paroxetine, sirolimus, dactinomycin, irbesartan, emodin, mercaptopurine, melatonin, quinacrine, carvedilol, colchicine, camphor, equilin, oxymetholone, nafamosta, camostat, baricitinib, darunavir, ribavirin, galidesivir, BCX-4430, Arbidol, nitazoxanide, derivatives thereof, or any combination thereof. More examples of potentially useful anti-viral agents for SARS-CoV-2 reviewed by C. Liu et al, ACS Cent. Sci. 2020, 6, 3, 315-331, which is incorporate herein to its entirety.

In certain embodiments, the second bioactive agent (e.g. prophylactic agent) can be a SARS-CoV-2 vaccine (e.g. mRNA-1273 by Moderna, an AAV-based vaccine capable of expressing an SARS-CoV-2 immunogen), an antibody (e.g. directed to SARS-CoV-2), lymphokines, hematopoietic growth factors (such as IL-2, IL-3, IL-7, and IL-15), which can for example serve to increase the number or activity of effector cells which interact with the antibodies.

In certain embodiments, the second bioactive agent can comprise hormonal therapy, immunotherapy, and anti-inflammatory agents.

In certain of these embodiments, an antibody or antigen-binding fragment thereof provided herein may be administered simultaneously with the one or more additional bioactive agents, and in certain of these embodiments the antibody or antigen-binding fragment thereof and the additional therapeutic agent(s) may be administered as part of the same pharmaceutical composition. However, an antibody or antigen-binding fragment thereof administered "in combination" with another bioactive agent does not have to be administered simultaneously with or in the same composition as the agent. An antibody or antigen-binding fragment thereof administered prior to or after another agent is considered to be administered "in combination" with that agent as the phrase is used herein, even if the antibody or antigen-binding fragment and the second agent are administered via different routes. Where possible, additional bioactive agents administered in combination with the antibodies or antigen-binding fragments thereof disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

One advantage of the modified antibody, the pharmaceutical composition and the method disclosed herein is that the modified antibody or an antigen-binding fragment thereof comprising at least an antigen-binding domain having an antigen-binding affinity and a covalently linked modified human IgG constant domain, wherein the modified human IgG constant domain comprises a substitution with tyrosine at amino acid residue 252, a substitution with threonine at amino acid residue 254, and a substitution with glutamic acid at amino acid residue 256, numbered according to the EU index as in Kabat, said modified antibody has an increased affinity for FcRn compared to the affinity to FcRn of an antibody having a wild type human IgG constant domain. Such antibody can have extended half-life in vivo. Not wishing to be bound by a particular theory or a mechanism, Applicants believe that the increased affinity to FcRn can help the antibody to escape intracellular degradations and increase the antibody recycling, therefore increasing the amount of the antibody remaining in the blood stream of the subject preventing or treating the disease.

Another advantage of the modified antibody, the pharmaceutical composition and the method disclosed herein is that the modified antibody can have a reduced affinity to human Fcγ receptors (FcγR) that belong to the immunoglobulin superfamily. The reduced affinity to human FcγR can help to reduce certain immune response side effects, such as antibody-dependent enhancement (ADE).

Methods of Virus Detection

In another aspect, the present disclosure provides a method of detecting presence or amount of SARS-CoV-2 virus antigen in a sample. In some embodiments, the SARS-CoV-2 virus antigen comprises spike protein, or comprises the SARS-CoV-2 virus particle. In some embodiments, the method comprises contacting the sample with the antibody or antigen binding fragment disclosed herein, and determining the presence or the amount of the SARS-CoV-2 virus antigen in the sample.

In certain embodiments, the anti-SARS-CoV-2 antibody disclosed herein is used in a method of diagnosing a subject suffering from a disorder (e.g., SARS-CoV-2 infection), the method comprising: determining the presence or amount of SARS-CoV-2 virus antigen in a sample obtained from the subject by contacting the sample with an anti-SARS-CoV-2 antibody of the disclosure and detecting the presence of the bound antibody.

Any sample suspected of containing SARS-CoV-2 virus can be used. In some embodiments, a suitable sample can be obtained from respiratory tract of the subject, for example, an upper respiratory nasopharyngeal swab (NP), oropharyngeal swabs (OP), sputum, a lower respiratory tract aspirate, bronchoalveolar lavage sample, nasopharyngeal wash, nasopharyngeal aspirate, nasal aspirate, a nasal swap, a throat swap, a bronchoalveolar lavage fluid (BALF), a cell or tissue sample from respiratory tract or from lung, and the like. In some embodiments, a suitable sample can be a body fluid sample such as a whole blood sample, a serum sample, or a plasma sample. In some embodiments, a suitable sample can be a urine sample or a stool sample.

The presence or level of SARS-CoV-2 virus antigen in a sample can be determined based on the detection of the presence or level of the complex of the virus antigen bound by the antibody or the antigen binding fragment thereof disclosed herein. Any suitable methods can be used for such detection, for example, by immunoassays such as immunohistochemistry (IHC), immunofluorescence (IF), immunoblotting (e.g., Western blotting), flow cytometry (e.g., FACS™), Enzyme-linked Immunosorbant Assay (ELISA), enzyme immunoassay (EIA), and radioimmunoassay (RIA).

For a review of immunological and immunoassay procedures, see Basic and Clinical Immunology (Stites & Terr eds., $7^{th}$ ed. 1991). Moreover, the immunoassays can be performed in any of several configurations, which are reviewed extensively in Enzyme Immunoassay (Maggio, ed., 1980); and Harlow & Lane, supra. For a review of the general immunoassays, see also *Methods in Cell Biology: Antibodies in Cell Biology*, volume 37 (Asai, ed. 1993); Basic and Clinical Immunology (Stites & Terr, eds., $7^{th}$ ed. 1991).

In certain embodiments, the antibodies or the antigen binding fragments thereof disclosed herein are detectably labeled, or are not labeled but can react with a second molecule which is detectably labeled (e.g. a detectably labeled secondary antibody).

In certain embodiments, the antibodies or the antigen binding fragments thereof disclosed herein may be immobilized on a solid substrate. The immobilization can be via covalent linking or non-covalent attachment (e.g. coating). Examples of solid substrate include porous and non-porous materials, latex particles, magnetic particles, microparticles, strips, beads, membranes, microtiter wells and plastic tubes. The choice of solid phase material and method of detectably labeling can be determined based upon desired assay format performance characteristics.

The level of the SARS-CoV-2 antigen can be determined, for example, by normalizing to a control value or to a standard curve. The control value can be predetermined, or determined concurrently.

The assays and methods provided herein for the measurement of the level of the SARS-CoV-2 antigen can be adapted or optimized for use in automated and semi-automated systems, or point of care assay systems.

Methods of Antibody Detection

In another aspect, the present disclosure provides a method of detecting presence or amount of an antibody capable of specifically binding to RBD of the spike protein of SARS-CoV-2 in a sample, comprising contacting the sample with a polypeptide comprising an amino acid sequence comprising SEQ ID NO: 128, and determining the presence or the level of the antibody in the sample. In some embodiments, the absence of the antibody in the sample or the level of the antibody in the sample being below a threshold indicates that the subject is more likely to suffer from disease progression.

In another aspect, the present disclosure provides a method of determining or predicting the likelihood of disease progression in a subject infected with SARS-CoV-2, the method comprising: contacting a sample obtained from the subject with a polypeptide comprising an amino acid sequence comprising SEQ ID NO. 128, and detecting the presence or the level of an antibody in the sample wherein the antibody is capable of specifically binding to RBD of the spike protein of the SARS-CoV-2, wherein the subject is likely to experience disease progression when the antibody in the sample is absent or is below a threshold.

A subject infected with SARS-CoV-2 can produce antibodies against the SARS-CoV-2 antigens. Such antibodies produced by human immune system are polyclonal, and can bind to different antigens or epitopes of SARS-CoV-2. Without wishing to be bound by any theory, it is unexpectedly found by the inventors that the presence or level of the antibodies specific to the RBD of the spike protein of the SARS-CoV-2 can be indicative of likelihood of disease progression in the subject. Antibodies capable of specifically binding to the RBD of the spike protein of the SARS-CoV-2 ("RBD-specific antibodies") are found by the inventors to be capable of effectively competing with ACE2 receptor for binding to the RBD, and also provide for SARS-CoV-2 virus neutralizing activity. The presence of such a RBD-specific antibody can be associated with an effective immune response to the SARS-CoV-2, and the titer of such RBD-specific antibody in the body may correlate to the prognosis of the SARS-CoV-2 infection or a disease, disorder or condition associated with SARs-CoV-2 infection.

A threshold of the level of the RBD-specific antibodies can be predetermined. The threshold refers to a level of the RBD-specific antibodies above which the sample is scored as being positive for RBD-specific antibodies. For example, the threshold can be a level above which the sample is scored as having sufficient neutralizing activity against the SARS-CoV-2. If the level of the RBD-specific antibodies is below the threshold, it could indicate insufficient protective immunity in the subject, and hence likelihood of disease progression. In contrast, if the level of the RBD-specific antibodies in the sample reaches or is above the threshold, it could indicate protective immunity in the subject, and hence less likely to suffer from disease progression.

Any sample suspected of containing antibodies can be used. In some embodiments, a suitable sample can be obtained from blood, for example, a whole blood sample, a serum sample, or a plasma sample. In some embodiments, said sample is obtained from a subject suspected of having, inflicted with, or under treatment for SARS-CoV-2 infection, or a disease, disorder or condition associated with SARs-CoV-2 infection.

Polypeptides comprising the RBD of the spike protein of SARS-CoV-2 can be used in the methods provided to herein to detect presence or level of the RBD-specific antibodies in the subject. In certain embodiments, the RBD of the spike protein of SARS-CoV-2 comprises an amino acid sequence comprising SEQ ID NO: 128. In certain embodiments, the polypeptides can further comprise a tag. Exemplary tag include, without limitation, 6×His tag or its fusion such SEQ ID NO: 132 or SEQ ID NO: 133. The polypeptides comprising RBD may be produced by recombinant methods (e.g., by prokaryotic expression system or eukaryotic expression system), or chemically synthesized (e.g. by solid phase synthesis, or solution synthesis method). Solid phase synthesis method is described by Merrifield in J.A.C.S. 85: 2149-2154 (1963) or the standard solution synthesis method described in "Peptide Synthesis" by Bodanszky, et al, second edition, John Wiley and Sons, 1976. The polypeptides can be purified by methods known in the art. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular polypeptide of the present application produced.

The presence or level of RBD-specific antibodies in a sample can be determined based on the detection of the presence or level of the complex of the RBD bound by the RBD-specific antibodies. Any suitable methods can be used for such detection, for example, by immunoassays such as immunohistochemistry (IHC), immunofluorescence (IF), immunoblotting (e.g., Western blotting), flow cytometry (e.g., FACS™), Enzyme-linked Immunosorbant Assay (ELISA), enzyme immunoassay (EIA), and radioimmunoassay (RIA), as described above.

In certain embodiments, the polypeptide comprising RBD of the spike protein of the SARS-CoV-2 may be immobilized on a solid substrate. The immobilization can be via covalent linking or non-covalent attachment (e.g. coating). The sample suspected of containing the RBD-specific antibodies can be brought into contact with the bound polypeptide. After a suitable period of incubation, for a period of time sufficient to allow capture of the RBD-specific antibodies via formation of antibody-antigen complex. After washing away any unreacted materials, a detection antibody specific to the captured antibody can be added, which can produce a detectable signal to allow detection of the captured antibody. The results may either be qualitative, by simple observation of the visible signal, or may be quantitated by comparing with a control sample containing known amounts of the detectable signal.

In another aspect, the present disclosure provides a method of monitoring treatment response in a subject infected with SARS-CoV-2 and received a treatment, the method comprising: (i) contacting a sample from the subject with a peptide comprising an amino acid sequence comprising SEQ ID NO: 128; (ii) detecting a first level of an antibody in the sample wherein the antibody is capable of specifically binding to RBD of the spike protein of the SARS-CoV-2; and (iii) comparing the first level of the antibody with a second level of the antibody detected in the subject prior to the treatment; wherein the first level being higher than the second level indicates that the subject is responsive to the treatment.

In one embodiment, a sample is obtained from a subject or patient prior to any treatment. In another embodiment, a test sample is obtained during or after treatment such as anti-viral treatment.

In one aspect, the present disclosure provides a kit for detecting an antibody capable of specifically binding to receptor-binding domain (RBD) of the spike protein of SARS-CoV-2, comprising a polypeptide comprising an amino acid sequence comprising SEQ ID NO: 128. In some embodiments, the polypeptide is immobilized on a substrate. In some embodiments, the kit further comprises a set of reagents for detecting complex of the antibody bound to the polypeptide.

Kits

In certain embodiments, the present disclosure provides a kit comprising one or more of the antibody or an antigen-binding fragment thereof provided herein. In certain embodiments, the kit disclosed herein is a therapeutic kit. In certain embodiments, the kit disclosed herein is a diagnostic kit.

Such kits can further include, if desired, one or more of various conventional kit components, such as, for example, containers with one or more pharmaceutically acceptable carriers, additional containers etc., as will be readily apparent to a person skilled in the art. Instructions, either as inserts or a label, indicating quantities of the components to be administered, guidelines for administration, and/or guidelines for mixing the components, can also be included in the kit.

In certain embodiments, where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments, the signal generating means may come pre-associated with an antibody of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemiluminescent or chromogenic product or the reduction of a chemiluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

The detection kits disclosed herein may also be prepared that comprise at least one of the antibodies or antigen-binding fragments disclosed herein and instructions for using the composition as a detection reagent. Containers for use in such kits may typically comprise at least one vial, test tube, flask, bottle, syringe or other suitable container, into which one or more of the detection composition(s) may be placed, and preferably suitably aliquoted. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection composition itself, or may alternatively be placed in a second distinct container means into which this second composition may be placed and suitably aliquoted. Alternatively, the detection reagent may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1

Materials and Methods

Patients and blood samples. A total of eight patients aged 10 to 66 years old infected with SARS-CoV-2 were enrolled (Table 5). A plasma sample from a healthy control was also included. Of these eight patients, six (P #1 through P #4, P #8, and P #16) had exposure history through personal visit and two had direct contact with individuals from exposed area. Four subjects (P #1 through P #4) were part of a family cluster (P #1 through P #5) infected and subsequently transmitted infection to P #5 after returning to Shenzhen. All patients were hospitalized at Shenzhen Third People's Hospital, the designated city hospital for treatment of COVID-19 infected patients, three to nine days after symptom onset. All patients presented with fever, fatigue, and dry cough and three (P #1, P #2 and P #5) developed severe pneumonia. Four patients (P #1, P #2, P #5, and P #22) were 60 years or older, of which three (P #1, P #2, and P #22) had underlying disease such as hypertension. SARS-CoV-2 infection status was verified by RT-PCR of nasopharyngeal swab and throat swab specimens. No patient had detectable influenza A, B, respiratory syncytial virus (RSV), or adenovirus co-infections. Chest computed tomographic scans showed varying degrees of bilateral lung patchy shadows or opacity. All patients received interferon and ribavirin and/or methylprednisolone treatments, recovered and were discharged except for P #1, who succumbed to disease in hospital. Single (P #1, P #3, P #5, P #8, P #16, and P #22) or sequential (P #2 and P #4) blood samples were collected during hospitalization and follow-up visits and separated into plasma and peripheral blood mononuclear cells (PBMCs) by Ficoll-Hypaque gradient (GE Healthcare) centrifugation. All plasma samples were heat-inactivated at 56° C. for 1 h before being stored at −80° C. PBMCs were maintained in freezing media and stored in liquid nitrogen until use.

Recombinant RBDs and trimeric Spike from SARS-CoV-2, SARS-CoV, and MERS-CoV and receptor ACE2. Recombinant RBDs and trimeric Spike for MERS-CoV, SARS-CoV, and SARS-CoV-2 and the N-terminal peptidase domain of human ACE2 (residues Ser19-Asp615) were expressed using the Bac-to-Bac baculovirus system (Invitrogen) as previously described (Gui, M. et al. *Cell Res* 27, 119-129 (2017); Song, W. et al. *PLoS Pathog* 14, e1007236-e1007236 (2018); Wang, N. et al. *Cell Res* 23, 986-993 (2013); Jiang, L. et al. *Sci Transl Med* 6, 234ra259-234ra259

(2014); Zhang, S. et al. *Cell Rep* 24, 441-452 (2018)). Amino acid sequence for RBD of spike protein for MERS-CoV is shown in SEQ ID NO: 126, and the polynucleotide sequence is shown in SEQ ID NO: 127. Amino acid sequence for extracellular domain of the spike protein for MERS-CoV is shown in SEQ ID NO: 123. Amino acid sequence for RBD of spike protein for SARS-CoV is shown in SEQ ID NO: 124, and the polynucleotide sequence is shown in SEQ ID NO: 125. Amino acid sequence for extracellular domain of the spike protein for SARS-CoV is shown in SEQ ID NO: 122. Amino acid sequence for RBD of spike protein for SARS-CoV-2 is shown in SEQ ID NO: 128, and the polynucleotide sequence is shown in SEQ ID NO: 129. Amino acid sequence for extracellular domain of the spike protein for SARS-CoV-2 is shown in SEQ ID NO: 121. Extracellular domains of the spike protein were fused to an artificial sequence to enable formation of a trimeric Spike structure in vitro.

SARS-CoV-2 RBD (residues Arg319-Phe541) containing the gp67 secretion signal peptide (SEQ ID NO: 130) and a C-terminal hexahistidine tag (SEQ ID NO: 132) or strap tag was inserted into pFastBac-Dual vectors (Invitrogen) and transformed into DH10Bac component cells. The bacmid was extracted and further transfected into Sf9 cells using cationic lipid Cellfectin® II Reagents (Invitrogen). The recombinant viruses were harvested from the transfected supernatant and amplified to generate high-titer virus stock. Viruses were then used to infect High Five cells for RBD and trimeric Spike expression. Secreted RBD and trimeric Spike were harvested from the supernatant and purified by gel filtration chromatography as previously reported (Gui, M. et al. Cell Res 27, 119-129 (2017); Song, W. et al. PLoS Pathog 14, e1007236-e1007236 (2018); Wang, N. et al. Cell Res 23, 986-993 (2013); Jiang, L. et al. Sci Transl Med 6, 234ra259-234ra259 (2014); Zhang, S. et al. Cell Rep 24, 441-452 (2018)).

ELISA analysis of plasma and antibody binding to RBD, trimeric Spike, and NP proteins. The recombinant RBDs and trimeric Spike derived from SARS-CoV-2, SARS-CoV and MERS-CoV and the SARS-CoV-2 NP protein (Sino Biological, Beijing) were diluted to final concentrations of 0.5 μg/ml or 2 μg/ml, then coated onto 96-well plates and incubated at 4° C. overnight. Samples were washed with PBS-T (PBS containing 0.05% Tween 20) and blocked with blocking buffer (PBS containing 5% skim milk and 2% BSA) at RT for 1h. Either serially diluted plasma samples or isolated mAbs were added the plates and incubated at 37° C. for 1 h. Wells were then incubated with secondary anti-human IgG labeled with HRP (ZSGB-BIO, Beijing) and TMB substrate (Kinghawk, Beijing) and optical density (OD) was measured by a spectrophotometer at 450 nm and 630 nm. The serially diluted plasma from healthy individuals or mAbs against SARS-CoV, MERS-CoV or HIV-1 were used as controls.

Isolation of RBD-specific single B cells by FACS. RBD-specific single B cells were sorted as previously described (Kong, L. et al. *Immunity* 44, 939-950 (2016); Wu, X. et al. Science 329, 856-861 (2010)). In brief, PBMCs from infected and convalescent individuals were collected and incubated with an antibody and RBD cocktail for identification of RBD-specific B cells. The cocktail consisted of CD19-PE-Cy7, CD3-Pacific Blue, CD8-Pacific Blue, CD14-Pacific Blue, CD27-APC-H7, IgG-FITC (BD Biosciences) and the recombinant RBD-Strep or RBD-His described above. Three consecutive staining steps were conducted. The first was a LIVE/DEAD Fixable Dead Cell Stain Kit (Invitrogen) in 50 μl phosphate-buffered saline (PBS) applied at RT for 20 minutes to exclude dead cells. The second utilized an antibody and RBD cocktail for an additional 30 min at 4° C. The third staining at 4° C. for 30 min involved either: Streptavidin-APC (eBioscience) and/or Streptavidin-PE (BD Biosciences) to target the Strep tag of RBD, or anti-his-APC and anti-his-PE antibodies (Abcam) to target the His tag of RBD. The stained cells were washed and resuspended in PBS before being strained through a 70 m cell mesh (BD Biosciences). RBD-specific single B cells were gated as CD19+CD3-CD8-CD14-IgG+RBD+ and sorted into 96-well PCR plates containing 20 μl of lysis buffer (5 μl of 5×first strand buffer, 0.5 μl of RNase out, 1.25 μl of 0.1 M DTT (Invitrogen) per well and 0.0625 μl of Igepal (Sigma). Plates were then snap-frozen on dry ice and stored at −80° C. until RT reaction.

Single B cell PCR, cloning and expression of monoclonal antibodies (mAbs). The IgG heavy and light chain variable genes were amplified by nested PCR and cloned into linear expression cassettes or expression vectors to produce full IgG1 antibodies as previously described (Liao, H.-X. et al. J Virol Methods, 2009; Tiller, T. et al. J. Immunol Methods, 2008). Specifically, all second round PCR primers containing tag sequences were used to produce the linear Ig expression cassettes by overlapping PCR. Separate primer pairs containing the specific restriction enzyme cutting sites (heavy chain, 5'-AgeI/3'-SalI; kappa chain, 5'-AgeI/3'-BsiWI; and lambda chain, 5'-AgeI/3'-XhoI) were used to amplify the cloned PCR products. The PCR products were purified and cloned into the backbone of antibody expression vectors containing the constant regions of human IgG1. The DNA sequence for the heavy chain constant region of human IgG1 is set forth in SEQ ID NO: 118, and the amino acid sequence for the heavy chain constant region of human IgG1 is shown in SEQ ID NO: 115. Overlapping PCR products of paired heavy and light chain expression cassettes were co-transfected into 293T cells (ATCC) grown in 24-well plates. Antigen-specific ELISA was used to detect the binding capacity of transfected culture supernatants to SARS-CoV-2 RBD. Monoclonal antibodies were produced by transient transfection of 293F cells (Life Technologies) with equal amounts of paired heavy and light chain plasmids.

Specifically, Table 4 shows the amino acid sequences and the encoding DNA sequences for the heavy chain and light chain constant regions of the monoclonal antibodies including P2A-1A8, P2A-1A9, P2A-1A10, P2A-1B3, P2B-2F6, P2B-2G4, P2B-2G11, P2C-1A3, P2C- 1C8, P2C-1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, and P22A-1D1. Antibodies P2A-1A8, P2A-1A9, P2B-2F6, P2B-2G4, P2B-2G11, P2C-1D5, P2B-1G5, P2B-1A1, P2B-1D9, P2B-1E4, P5A-2G7, P5A-1D2, P5A-2E1, P5A-1D10, P5A-2D11, P5A-2G9, P5A-2H3, P5A-3A6, and P5A-3B4 have lambda light chains, and the amino acid sequence and encoding DNA sequence for the lambda constant region are shown in SEQ ID NO: 116 and SEQ ID NO: 119, respectively. Antibodies P2A-1A10, P2A-1B3, P2C-1A3, P2C-1C8, P2C-1C10, P2C-1F11, P2C-1D7, P2B-1A10, P2B-1G1, P4A-2D9, P5A-3C8, P5A-2F11, P5A-1C8, P1A-1C10, P4A-1H6, P4B-1F4, P5A-1B6, P5A-1B8, P5A-1B9, P5A-IDI, P5A-3A1, P5A-3C12, and P22A-1D1 have kappa light chains, and the amino acid sequence and the encoding DNA sequence for the kappa constant region are shown in SEQ ID NO: 117 and SEQ ID NO: 120, respectively.

Antibodies in the culture supernatant was purified by affinity chromatography using Protein A beads columns (National Engineering Research Center for Biotechnology, Beijing) according to the manufacturer's protocol. Concentrations were determined by BCA Protein Assay Kits (Thermo Scientific). SARS-CoV, MERS-CoV, and HIV-1 mAbs were also included as controls. SARS-CoV antibodies (S230 and m396) previously isolated by others (Zhu, Z. et al. Proc Natl Acad Sci USA 104, 12123-12128 (2007)) were synthesized, expressed in 293T cells and purified by protein A chromatography. MERS-CoV antibodies (Mab-GD33) were derived from previously reported (Niu, P. et al. *J Infect Dis* 218, 1249-1260 (2018)). HIV-1 antibody VRC01 was a broadly neutralizing antibody directly isolated from a patient targeting the CD4 binding site of envelope glycoprotein 40.

Antibody binding kinetics, epitope mapping, and competition with receptor ACE2 measured by SPR. The binding kinetics and affinity of mAbs to SARS-CoV-2 RBD were analyzed by SPR (Biacore T200, GE Healthcare). Specifically, purified RBDs were covalently immobilized to a CM5 sensor chip via amine groups in 10 mM sodium acetate buffer (pH 5.0) for a final RU around 250. SPR assays were run at a flow rate of 30 ml/min in HEPE buffer. The sensograms were fit in a 1:1 binding model with BIA Evaluation software (GE Healthcare). For epitope mapping, two different antibodies were sequentially injected and monitored for binding activity to determine whether the two mAbs recognized separate or closely-situated epitopes. To determine competition with the human ACE2 peptidase domain, SARS-CoV-2 RBD was immobilized to a CM5 sensor chip via amine group for a final RU around 250. Antibodies (1 µM) were injected onto the chip until binding steady-state was reached. ACE2 (2 µM), which was produced and purified as above, was then injected for 60 seconds. Blocking efficacy was determined by comparison of response units with and without prior antibody incubation.

Analysis of plasma and antibody binding to cell surface expressed trimeric Spike protein. HEK 293T cells were transfected with expression plasmid encoding the full length spike of SARS-CoV-2, SARS-CoV or MERS-CoV and incubated at 37° C. for 36 h. The cells were removed from the plate using trypsin and distributed into 96 well plates for the individual staining. Cells were washed twice with 200 µl staining buffer (PBS with 2% heated-inactivated FBS) between each of the following. The cells were stained at room temperature for 30 minutes in 100 µl staining buffer with 1:100 dilutions of plasma or 20 µg/ml monoclonal antibodies. The cells were then stained with PE labeled anti-human IgG Fc secondary antibody (Biolegend) at a 1:20 dilution in 50 µl staining buffer at room temperature for 30 minutes. Finally, the cells were re-suspended and analyzed with FACS Calibur instrument (BD Biosciences, USA) and FlowJo 10 software (FlowJo, USA). HEK 293T cells without transfection were also stained as background control. S230 and m396 targeting the RBD of SARS-CoV spike (Zhu, Z. et al. Proc Natl Acad Sci USA 104, 12123-12128 (2007)) and Mab-GD33 targeting the RBD of MERS-CoV spike (Niu, P. et al. *J Infect Dis* 218, 1249-1260 (2018)) were used as positive primary antibody controls, while VRC01 targeting HIV-1 env (Wu, X. et al. *Science* 329, 856-861 (2010)) was used as an irrelevant primary antibody control.

Neutralization activity of mAbs against pseudovirus and live SARS-CoV-2. SARS-CoV-2, SARS-CoV and MERS-CoV pseudovirus were generated by co-transfection of human immunodeficiency virus backbones expressing firefly luciferase (pNL43R-E-luciferase) and pcDNA3.1 (Invitrogen) expression vectors encoding the respective full length S proteins into 293T cells (ATCC) (Wang, N. et al. Cell Res 23, 986-993 (2013); Jiang, L. et al. Sci Transl Med 6, 234ra259-234ra259 (2014); Jia, W. et al. Emerg Microbes Infect 8, 760-772 (2019); Zhang, L. et al. J Med Virol 78, 1-8 (2006)). Viral supernatants were collected 48 h later. Viral titers were measured as luciferase activity in relative light units (Bright-Glo™ Luciferase Assay Vector System, Promega Biosciences). Control envelope glycoproteins derived from human immunodeficiency virus (HIV)-1 and their corresponding pseudoviruses were produced in the same manner. Control mAbs included VRCO1 against HIV-1 40; S230 and m396 against SARS-CoV (Zhu, Z. et al. Proc Natl Acad Sci USA 104, 12123-12128 (2007)); and Merb-GD33 against MERS-CoV 43. Neutralization assays were performed by incubating pseudoviruses with serial dilutions of purified mAbs at 37° C. for 1 h. Huh7 cells (ATCC) (approximately 1.5×104 per well) were added in duplicate to the virus-antibody mixture. Half-maximal inhibitory concentrations (IC50) of the evaluated mAbs were determined by luciferase activity 48h after exposure to virus-antibody mixture using GraphPad Prism 6 (GraphPad Software Inc.), data were shown in Table 6 and Tables 7a, 7b and 7c.

Neutralization activity of mAbs against live SARS CoV 2. SARS-CoV-2 focus reduction neutralization test (FRNT) was performed in a certified Biosafety Level 3 laboratory. Serial dilutions of testing antibodies were conducted, mixed with 75 µl of SARS-CoV-2 (8×103 focus forming unit/ml, FFU/ml) in 96-well microwell plates and incubated for 1 hour at 37° C. Mixtures were then transferred to 96-well plates seeded with Vero E6 cells and allowed absorption for 1 hour at 37° C. Inoculums were then removed before adding the overlay media (100 µl MEM containing 1.6% Carboxymethylcellulose, CMC). The plates were then incubated at 37° C. for 24 hours. Cells were fixed with 4% paraformaldehyde solution for 30 min, and overlays were removed. Cells were permeabilized with 0.2% nonionic surfactant Triton X-100 and incubated with cross-reactive rabbit anti-SARS-CoV-N IgG (Sino Biological, Inc) for 1 hour at room temperature before adding HRP-conjugated goat anti-rabbit IgG(H+L) antibody (Jackson ImmunoResearch). Cells were further incubated at room temperature. The reactions were developed with KPL TrueBlue Peroxidase substrates (Seracare Life Sciences Inc). The numbers of SARS-CoV-2 foci were calculated using an EliSpot reader (Cellular Technology Ltd).

Gene family usage and phylogenetic analysis of mAbs. The program IMGT/V-QUEST (http://www.imgt.org/IMGT_vquest/vquest) was used to analyze germline gene, germline divergence or degree of somatic hypermutation (SHM), the framework region (FR) and the loop length of the complementarity determining region 3 (CDR3) for each antibody clone. The IgG heavy and light chain variable genes were aligned using Clustal W in the BioEdit sequence analysis package (https://bioedit.software.informer.com/7.2/). Phylogenetic analyses were performed by the Maximum Likelihood method using MEGA X (Molecular Evolutionary Genetics Analysis across computing platforms). Several forms of the phylogenetic trees are presented for clarity, data were shown in Table 9a, Table 9b, FIG. 4U and FIG. 4V.

Antibody production. The production of antibodies was conducted as previously described (Jiang, L. et al. Sci Transl Med 6, 234ra259-234ra259 (2014); Zhang, Q. et al. Sci Rep 6, 25856-25856 (2016)). The genes encoding the heavy and light chains of isolated antibodies were separately cloned into expression vectors containing IgG1 constant regions and the vectors were transiently transfected into HEK293T or 293F cells using polyethylenimine (PEI) (Sigma). After 72h, the antibodies secreted into the supernatant were collected and captured by protein A SEPHAROSE™ (GE Healthcare). The bound antibodies were eluted and further purified by gel-filtration chromatography using a Superdex SUPERDEX™ 200 High Performance column (GE Healthcare). The purified antibodies were either used in binding or neutralizing assays.

Crystallization and data collection. The SARS-CoV-2 RBD was mixed with the Fab fragment of P2B-2F6, P5A-1D2, P5A-3C8 or P22A-1D1 respectively at a molar ratio of 1:1.2, incubated for 2 h at 4° C. and further purified by gel-filtration chromatography. The purified complex concentrated to approximately 10 mg/mL in HBS buffer (10 mM HEPES, pH 7.2, 150 mM NaCl) was used for crystallization. The screening trials were performed at 18° C. using the sitting-drop vapor-diffusion method by mixing 0.2 µL of protein with 0.2 µL of reservoir solution. Crystals were successfully obtained in 0.2 M magnesium formate dihydrate, 0.1M sodium acetate trihydrate, pH 4.0, 18% PEG5000mme. The purified complexes of SARS-CoV-2 RBD and the Fab fragment of P2C-1F11, P5A-1D2, P5A-3C8 or P22A-1D1 respectively were obtained using a similar process. Crystals were successfully obtained in 0.2 M magnesium formate dihydrate, 0.1M sodium acetate trihydrate, pH 4.0, 18% PEG5000mme for P2C-1F11; in 0.2M Magnesium chloride hexahydrate, 0.1M tris(hydroxymethyl)aminomethane buffer (Tris™), pH 8.5, 3.4M 1,6-Hexanediol for P5A-1D2; in 0.2M Lithium sulfate monohydrate, 0.1M HEPES, pH 7.5, 25% w/v PEG 3350 for P5A-3C8; and in 0.1M potassium chloride, 0.1M NaHEPES, pH 7.0, 15% PEG 5000MME for P22A-1D1, respectively. Crystals were harvested, soaked briefly in mother liquid with 20% glycerol, and flash-frozen in liquid nitrogen. Diffraction data was collected at 100 K and at a wavelength of 0.97918 Å on the BL17U beam line of the Shanghai Synchrotron Research Facility (SSRF). Diffraction data was auto-processed with aquarium pipeline and the data processing statistics are listed in Table 10a and Table 10b and Table 10c. (McCoy, A. J. et al. *Journal of applied crystallography* 40, 658-674, (2007)).

Structural determination and refinement. The structure was determined by the molecular replacement method with PHASER in CCP4 suite (Cohen, S. X. et al., *Acta crystallographica. Section D, Biological crystallography* 64, 49-60, (2008)). The search models were the SARS-CoV-2 RBD structure (PDB ID: 6M0J) and the structures of the variable domain of the heavy and light chains available in the PDB with the highest sequence identities. Subsequent model building and refinement were performed using COOT and PHENIX, respectively (Emsley, P. & Cowtan, K. *Acta crystallographica. Section D, Biological crystallography* 60, 2126-2132, (2004); Adams, P. D. et al. *Acta crystallographica. Section D, Biological crystallography* 58, 1948-1954, (2002)). Final Ramachandran statistics: 90.02% favoured, 8.24% allowed and 1.74% outliers for the final RBD-P2C-1F11 complex structure. Final Ramachandran statistics: 95% favoured, 3.9% allowed and 0.81% outliers for the final RBD-P22A-1D1 complex structure; Final Ramachandran statistics: 94.23% favoured, 5.44% allowed and 0.32% outliers for the final RBD-P5A-1D2 complex structure; Final Ramachandran statistics: 97% favoured, 3.1% allowed and 0.33% outliers for the final RBD-P5A-3C8 complex structure. The structural refinement statistics are listed in Table 10a and Table 10b. All structural figures were generated using PyMOL (Janson, G., Zhang, C., Prado, M. G. & Paiardini, A. *Bioinformatics (Oxford, England)* 33, 444-446, (2017)).

Analysis of antibody binding to cell surface expressed wild-type and mutant Spike protein. Single Alanine mutations were conducted with QuickChange Site-directed mutagenesis Kit (Agilent 210518) followed the manufacturer's instructions. HEK 293T cells were transfected with expression plasmid encoding either wild-type or mutant full-length SARS-Cov-2 and incubated at 37° C. for 36 h. The cells were removed from the plate using trypsin and distributed into 96 well plates for the individual staining. Cells were kept at 4° C. or on ice in the following incubation or wash steps. Cells were washed twice with 200 µL ice-cold staining buffer (PBS with 2% heated-inactivated FBS) between each of the following. The cells were stained for 1 h in 100 µL staining buffer with 10 ug/mL ACE2 protein or 2 µg/mL monoclonal antibodies. The cells were then stained with one of the following secondary antibodies: anti-his PE (Miltyni 130120787) for ACE2, anti-human IgG Fc PE (Biolegend 410718) for nAbs, or anti-mouse IgG Fc FTIC (ThermoFisher A10673) for S2 mAb (MP 08720401). Finally, the cells were re-suspended and analyzed with FACS Calibur instrument (BD Biosciences, USA) and FlowJo 10 software (FlowJo, USA). HEK 293T cells without mock transfection were stained as background control.

Example 2

This example illustrates the identification of human plasma and B cell that responses specific to SARS-CoV-2 RBD.

Figure 6A:
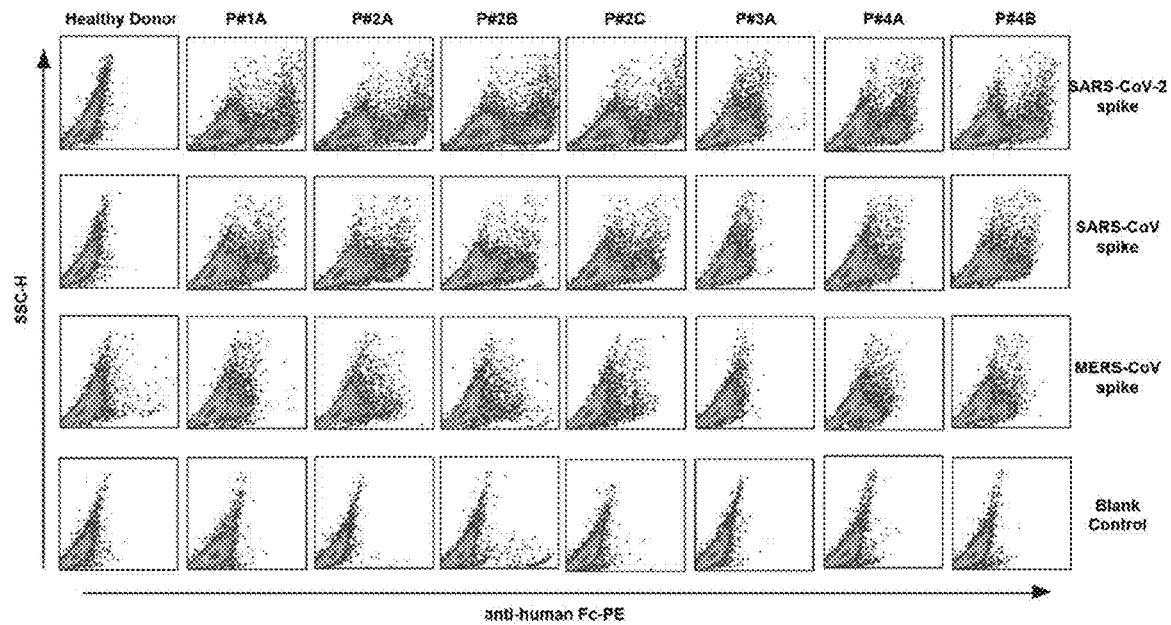
Figure 6B:
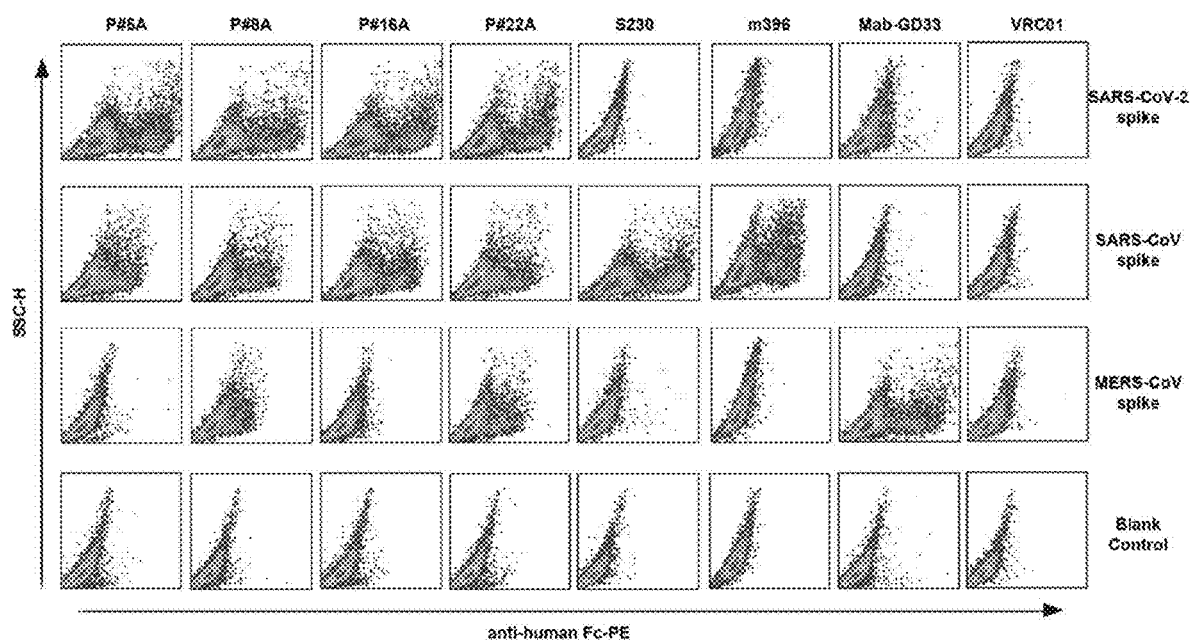
Figures 7A, 7B, 7C, 7D:
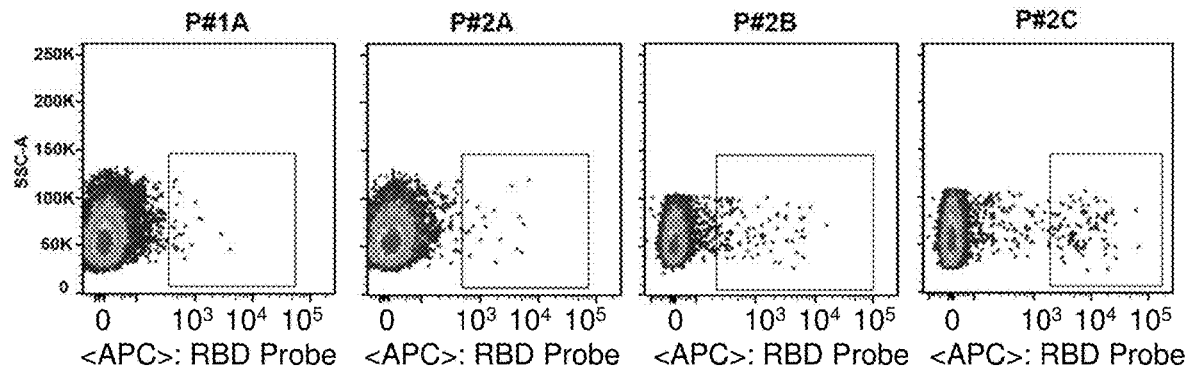
Figures 7E, 7F, 7G, 7H:
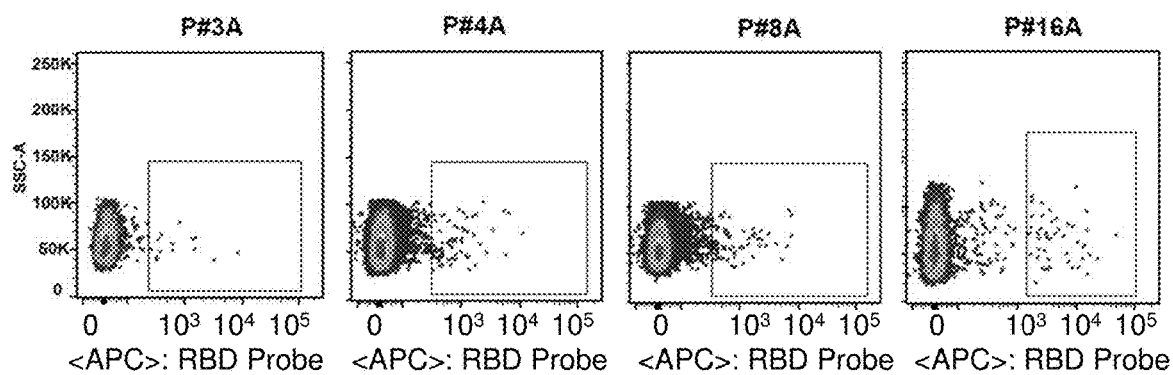
Figures 7I, 7J, 7K:
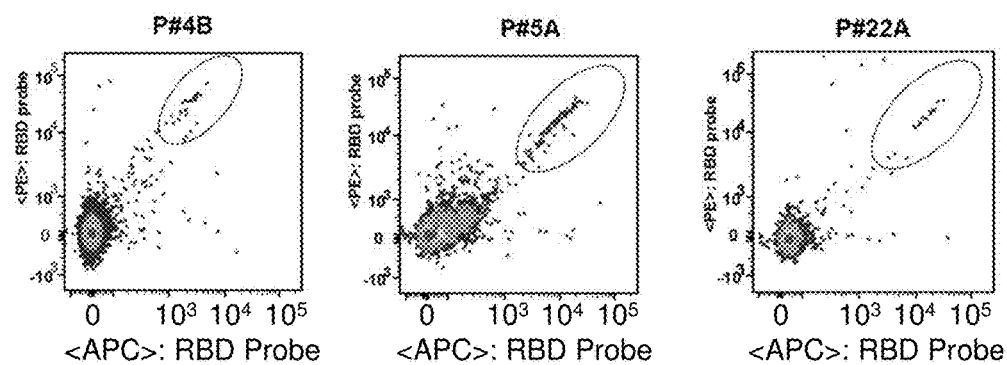

Cross-sectional and longitudinal blood samples from eight SARS-CoV-2-infected and convalescent subjects were collected during the early outbreak in Shenzhen (see Table 5). Samples were named by patient number and either A, B, or C depending on collection sequence. Six patients (P #1 through P #4, P #8, and P #16) had travel history to exposed area and the remaining two (P #5 and P #22) had direct contact with those from exposed area. P #1 through P #5 is a family cluster with the first documented case of human-to-human transmission of SARS-CoV-2 in Shenzhen. All subjects recovered and were discharged from the hospital except for P #1 who succumbed to disease despite intensive intervention. To analyze antibody binding, serial plasma dilutions were applied to enzyme-linked immunosorbent assay (ELISA) plates coated with either recombinant RBD or trimeric Spike derived from SARS-CoV-2, SARS-CoV, and MERS-CoV or recombinant NP from SARS-CoV-2. Binding activity was visualized using anti-human IgG secondary antibodies at an optical density (OD) of 450 nm. Varying degrees of binding were found across individuals and among samples from the same individual. Samples from P #1, P #2, P #5, and P #16 demonstrated higher binding to both SARS-CoV-2 RBD and NP than the rest (FIG. 1A). Three sequential plasma samples collected from P #2 over nine days during early infection showed similar binding to SARS-CoV-2 RBD and NP and remained relative stable over the course of the infection. Surprisingly, virtually no cross-reactivity between SARS-CoV RBD and MERS-CoV RBD was detected (FIG. 1A), despite strong recognition by the positive control antibodies. However, strong cross-reactivity was detected against trimeric Spikes from SARS-CoV and MERS-CoV in both ELISA (FIG. 1B) and cell-surface staining (FIG. 6 A-FIG. 6C). All samples except P #4A demonstrated significant levels of cross-binding to SARS- CoV trimeric Spike while only those from P #1, P #2 and P #4B cross recognized MERS-CoV trimeric Spike (FIG. 1B). None of the plasma samples were reactive to HIV-1 envelope trimer derived from strain BG505 (Sanders, R. W. et al. *J Virol* 76, 8875-8889, (2002)). The same plasma samples were also evaluated for neutralization of pseudoviruses bearing the Spike proteins of either SARS-CoV-2, SARS-CoV, or MERS-CoV. Consistent with the antibody binding results, varying degrees of neutralizing activities against SARS-CoV-2 were found across individuals (FIG. 1C). However, cross-neutralizing against SARS-CoV and MERS-CoV is rather minimal as all plasma samples tested, including healthy control plasma, had negligible levels of neutralization (FIG. 1C). No detectable neutralization was found for any plasma sample against the pseudovirus control bearing the HIV-1 envelope MG04 (FIG. 1C). Taken together, these results suggest that RBDs from SARS-CoV-2, SARS-CoV, and MERS-CoV are likely to be immunologically distinct despite substantial sequence and structural similarities. Thus, regions beyond RBDs likely contribute to the observed cross-reactivity against SARS-CoV and MERS-CoV Spike protein.

Figure 1F:
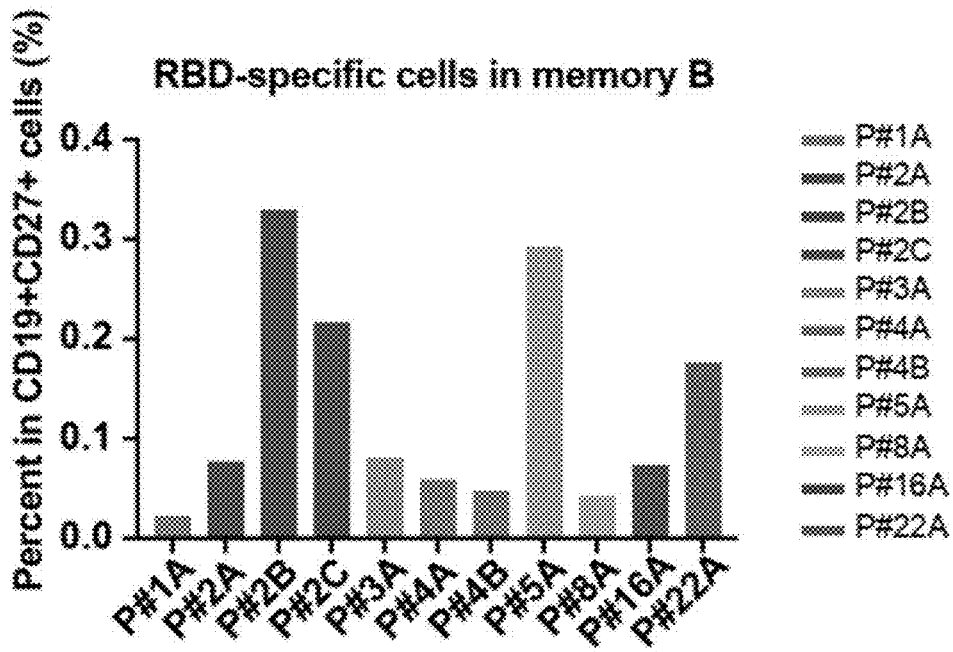

Flow cytometry with a range of gating strategies was used to study SARS-CoV-2-specific B cell responses and identity B cells recognizing fluorescent-labeled RBD probes (FIG. 1D and FIG. 7A-FIG. 7K). As shown in FIG. 1E-FIG. 1F, the RBD-specific B cells constitute about 0.005-0.065% among the total B cell population and 0.023-0.329% among the memory subpopulations. The number of RBD-specific B cells are relatively higher in P #2, P #5, P #16, and P #22 (FIG. 1E-FIG. 1F), which appeared to correlate well with binding activity of corresponding plasma samples to SARS-CoV-2 RBD and trimeric Spike protein (FIG. 1A and FIG. 1B). However, sample P #1A demonstrated the lowest RBD-specific B cell response despite high-level plasma binding. As P #1 was the only patient succumb to disease, it is possible that this dichotomy of high plasma binding activity and low levels of RBD-specific B cells is a surrogate marker of rapid disease progression.

Example 3

This example illustrates the cloning and analysis of single B cell antibody against SARS-CoV-2 RBD.

Figure 2A:
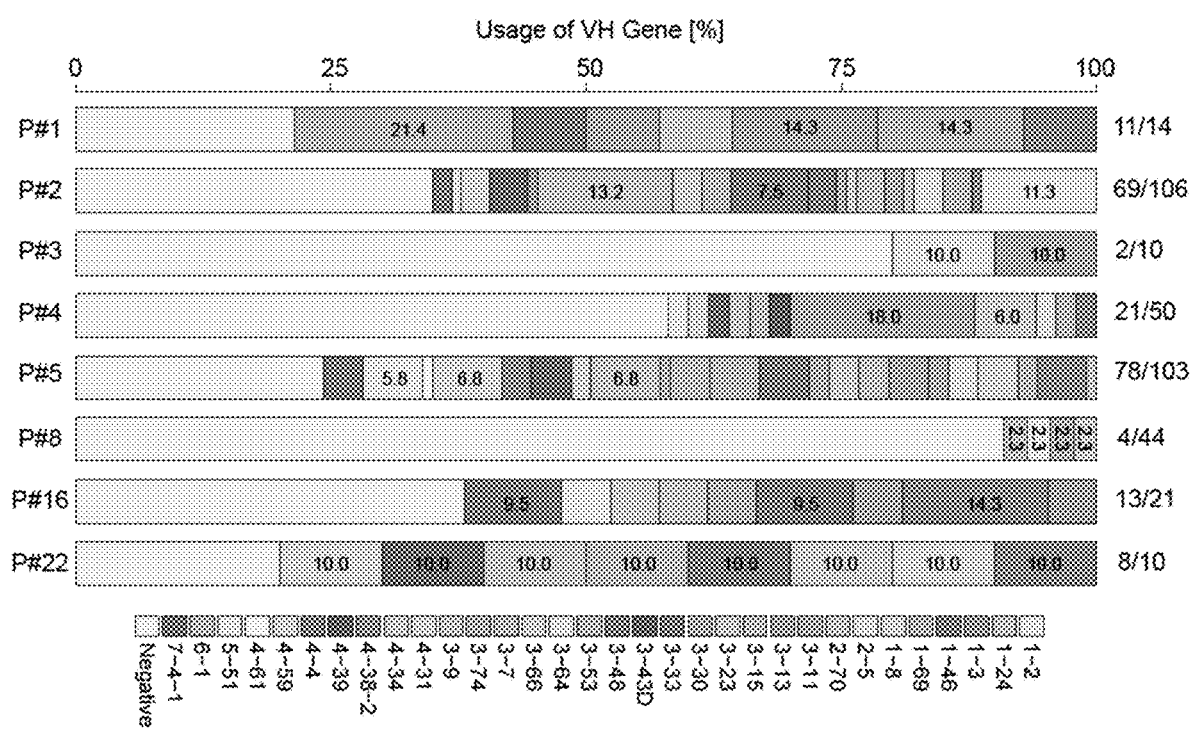
FIG. 2A-FIG. 2B. Heavy chain repertoires of SARS-CoV-2 RBD-specific antibodies analyzed (A) by individual subject or (B) across the eight subjects. (A) Distribution and frequency of heavy chain variable (VH) genes usage in each subject shown along the horizontal bar. The same color scheme is used for each VH family across all study subjects. The VHs that dominate across isolated antibodies are indicated by actual frequencies in their respective color boxes. The number of RBD-binding antibodies versus total antibodies isolated are shown on the right. (B) Clustering of VH genes and their association with ELISA binding activity across the eight subjects analyzed by unrooted phylogenetic tree. Branch lengths are drawn to scale so that sequence relatedness can be readily assessed. Sequences from the same study subject are shown in the same color at the branch tips. Colored circles represent the proportion (light orange, >80%; light yellow, 60%-80%; light green <60%) of VH clusters that bind to SARS-CoV-2 RBD with OD 450 values larger than 3. The VH gene families for the highest binding clusters are shown.
Figure 2B:
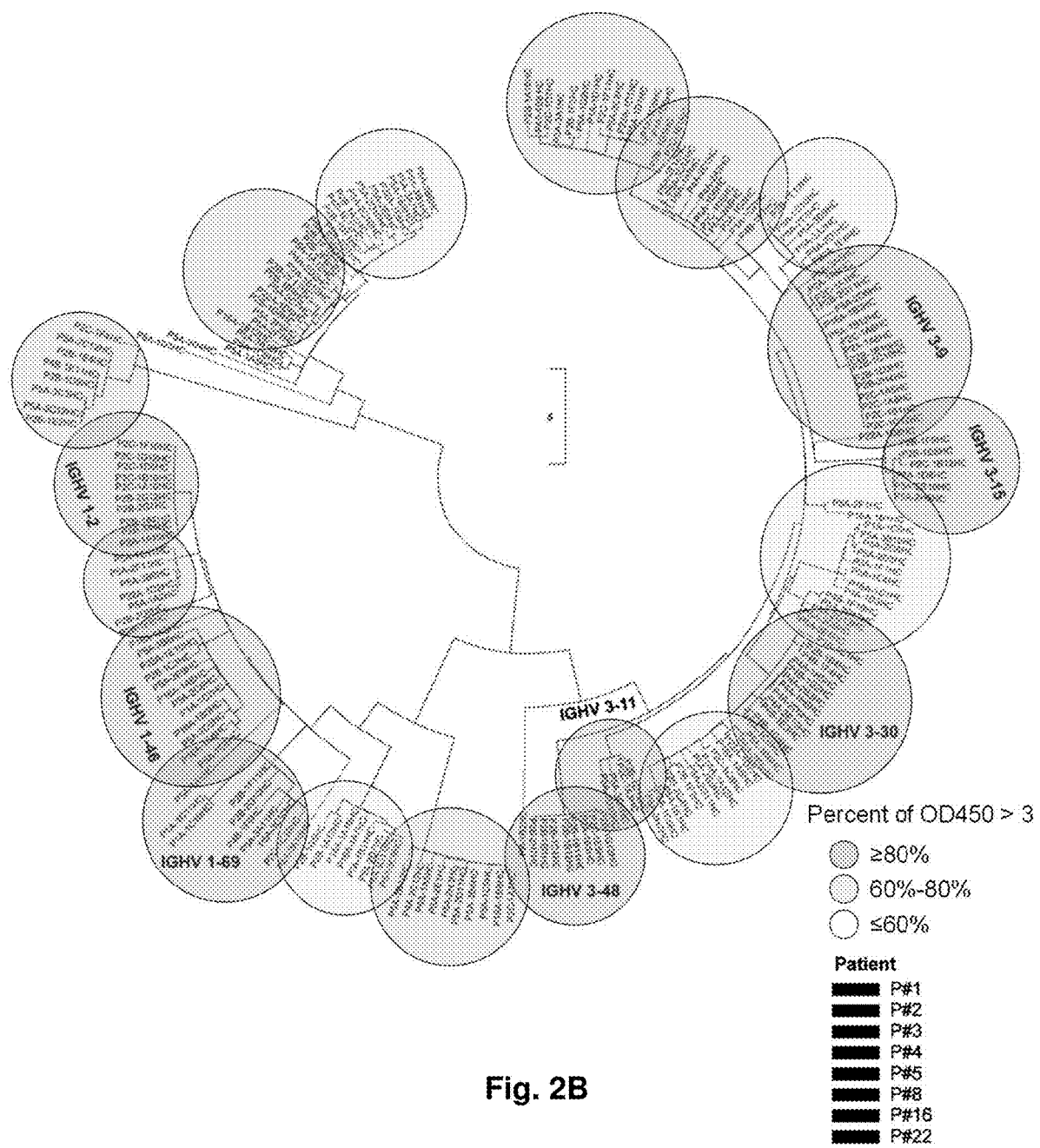
Figure 8:
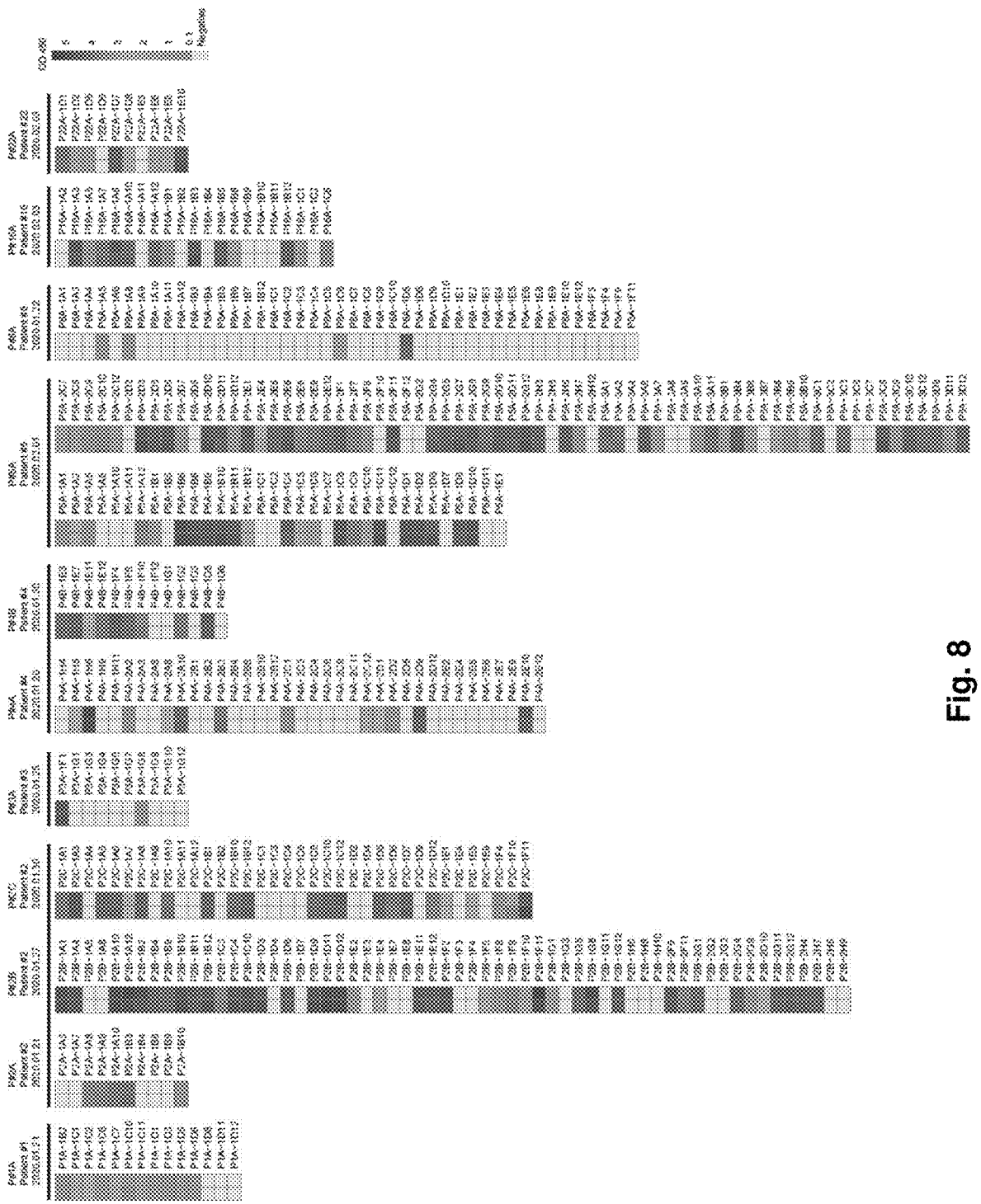

The RBD-binding B cells identified in EXAMPLE 2 were isolated into single cell suspension for cloning and evaluation of the mAb response (FIG. 1D and FIG. 7A-FIG. 7K). Immunoglobulin heavy and light chains were amplified by RT-PCR using nested primers. The amplified products were cloned into linear expression cassettes to produce full IgG1 antibodies as previously described (Kong, L. et al. *Immunity* 44, 939-950 (2016); Liao, H.-X. et al. *J Virol Methods* 158, 171-179). The number of B cell clones varied from 10 to $10^6$ among the subjects (FIG. 8). Individual IgGs were produced by transfection of linear expression cassettes and tested for SARS-CoV-2 RBD reactivity by ELISA. On average, fifty-eight percent of the antibody clones were reactive, although great variability was found among different individuals (FIG. 8). Out of 358 antibodies, 206 antibodies were found to specifically bind to SARS-CoV-2 RBD, and by B cell cloning and sequencing, 165 distinct sequences were obtained (Table 9). These 206 antibodies demonstrated significant differences in binding activity. For example, a large number of antibodies from samples P #2B, P #2C, P #4A, P4 #B, P #5A, P #16A, and P #22A had OD 450 values well over 4.0, while none of those from sample P #1A exceeded 4.0. There were too few antibodies from P #3A and P #8A to make meaningful evaluations (FIG. 8). Furthermore, samples from different study subjects also demonstrated substantial differences in heavy chain variable gene (VH) usage (FIG. 2A). For instance, P #1 samples are dominated by VH3-53, 3-13, and 1-69 which constituted approximately 21.4%, 14.3%, and 14.3% of the entire VH repertoire, respectively. Samples from P #2 and P #5 are more diverse in distribution and frequency of their VH usage. However, no single or group of VH families stood out among study subjects, suggesting patients have immunologically distinct responses to SARS-CoV-2 infection. This hypothesis is supported by the phylogenetic analysis of all 206 VH sequences superimposed with their corresponding binding activities as presented in FIG. 2B. The high-binding clusters (80% of clusters with OD 450>3) were widely distributed across multiple heavy chain families. In fact, majority of the high-binding antibodies were derived by clonal expansion of specific VH families in P #2, P #4, and P #5. Similarly, the middle- (60-80% of clusters with OD 450>3) and low- (<60% cluster with OD 450>3) binding clusters were also widely distributed and each consisted of disproportionally represented VH gene families.

Figure 3A:
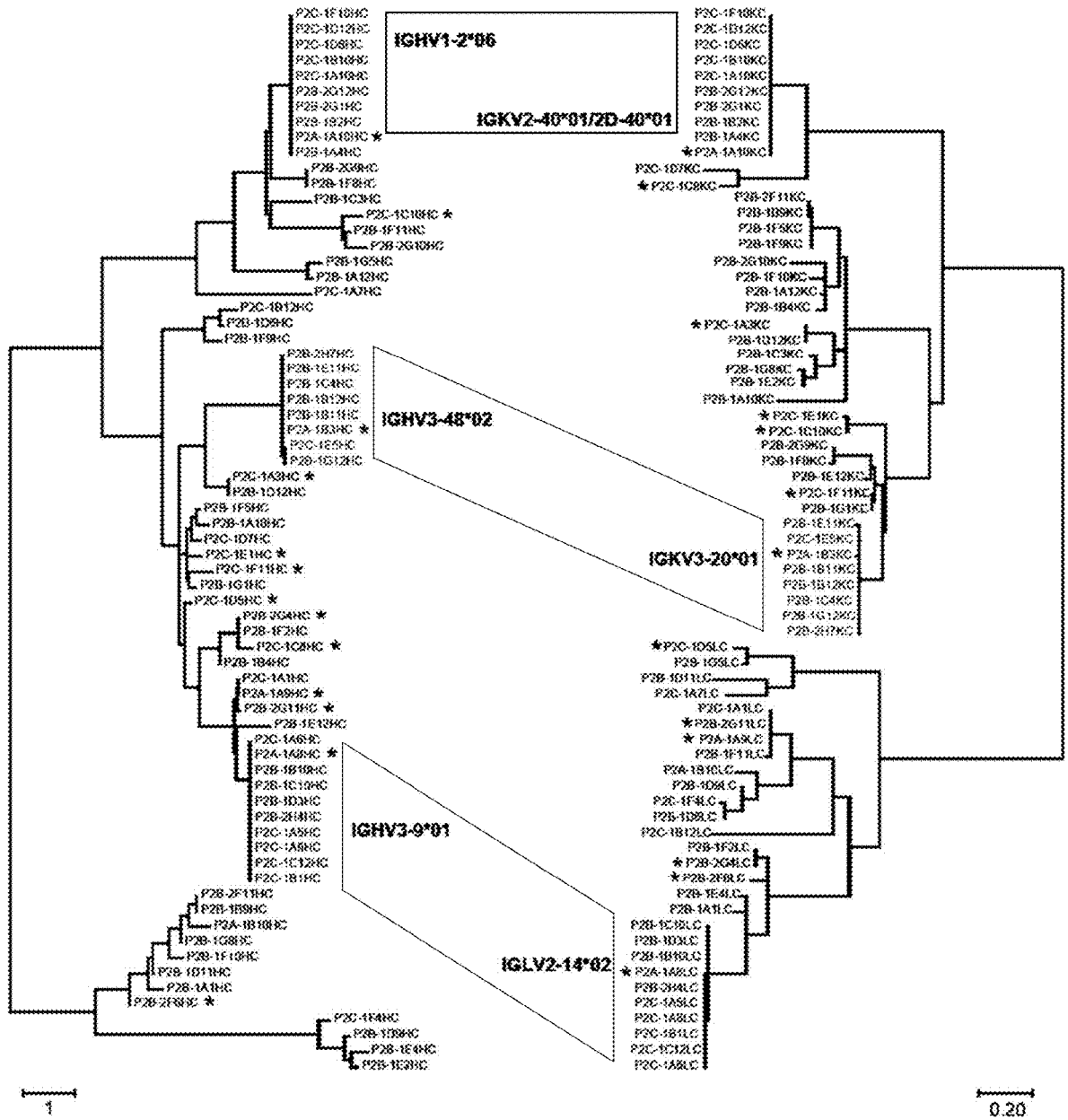
FIG. 3A-FIG. 3F. Clonal expansion of specific heavy and light chain families in the P #2 antibody repertoire. (A) Phylogenetic analysis of VH (left) and VL 20 (right) genes for all RBD-binding antibodies. Clonal expanded VH and VL clusters are paired and highlighted in three different colors. Branch lengths are drawn to scale so that sequence relatedness can be readily assessed. (B)-(C) Clonal expansion in relation to members of other VH and VL families based on somatic hypermutations (SHM) and CDR3 loop lengths. For the pie charts of VH (left) and VL (right) genes, the radii represent the CDR3 loop length and the color scale indicates the degree of SHIM. Heavy and light chain repertoires for each antibody are shown along the pie circles. (D)-(E) Lineage analysis for heavy and light chains in pie charts. The numbers in the center represent the number of RBD-specific antibodies. Each slice represents a unique clone and proportional to its own size. (F) Counts of various HCDR3 length from IGHV3-53 and IGHV3-66 as well as RBD binders.
Figure 3C:
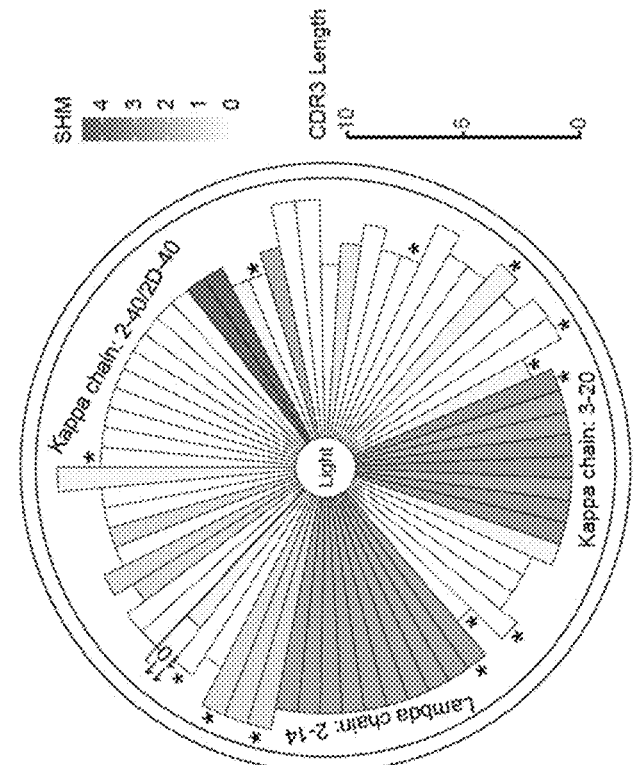
Figure 3B:
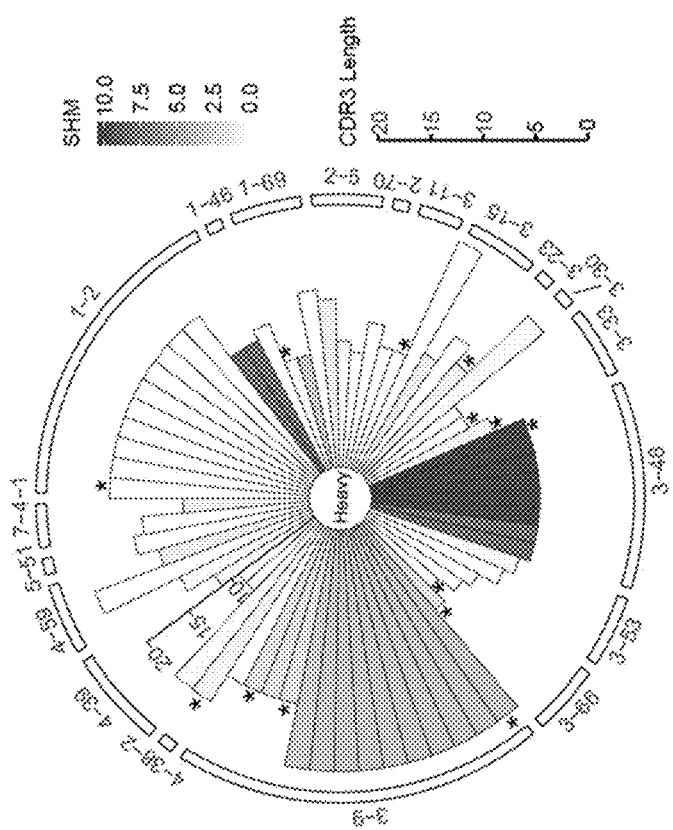

As P #2 showed a large number of RBD-binding antibodies and was the only patient with three sequential blood samples, more detailed characterization of P #2 antibodies were conducted. Among a total of 69 antibodies from P #2, the majority (59%) were scattered across various branches and the remaining (41%) were clonally expanded into three major clusters (FIG. 3A). Antibodies from the three time points (A, B, C) do not appear to group together but rather interdigitate among themselves, suggesting they are highly related during early infection. Three clones were significantly enriched and each constituted between 12-14% of the entire tested repertoire (FIG. 3A). Their heavy-chain variable regions belong to the VH1-2*06, VH3-48*02, and VH3-9*01 families. The corresponding light-chain kappa (Igk) belongs to 2-40*01/2D-40*01, 3-20*01, and light-chain lambda (Igl) to 2-14*02 with the respective joining segment kappa 4 (Jk4), Jk5 and joining segment lambda 1 (Jl1) (Table 9). More importantly, these clonally expanded antibodies were identified in all three samples indicating that they are strongly selected for during infection. When comparing their representation within each cluster, VH1-2*06 and VH3-9*01 appeared to increase from approximately 33 to 45%, whereas VH3-48*02 decreased from 33 to 9% over the three time points, although the number of clones was too small for statistical significance. Interestingly, the somatic hypermutation (SUNM) or germline divergence for VH1-2*06 was 0% and this cluster persisted during the study period. However, the SHM for VH3-48*02 reached as high as 9.6% and for VH3-9*01 reached 3.8% compared to the overall average of 2.2%±3.3% among the 69 VH sequences. Furthermore, the CDR3 length for VH1-2*06, VH3-48*02, and VH3-9*01 was 19aa, 16aa, and 23aa, respectively, compared with the overall average of 16±4aa among the 69 VH sequences. Close examination of the longest CDR3 from the VH3-9*01 cluster revealed richness in tyrosine, indicating potential hydrogen bonding and hydrophobic interactions with the surrounding residues. These results shed light on the clonal expansion and broad diversity of RBD-specific antibodies during early infection and their potential role in controlling SARS-CoV-2 infection.

Figure 3D:
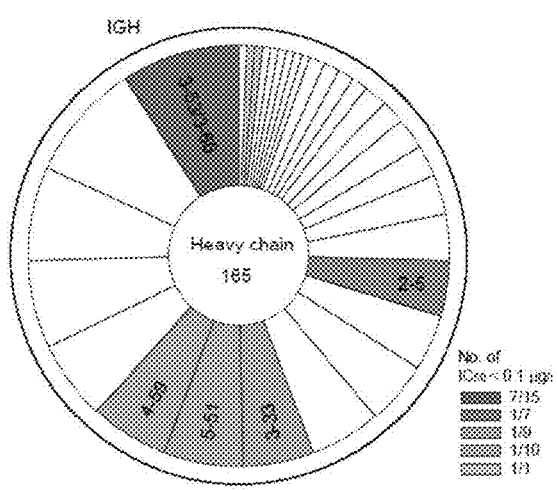
Figure 3E:
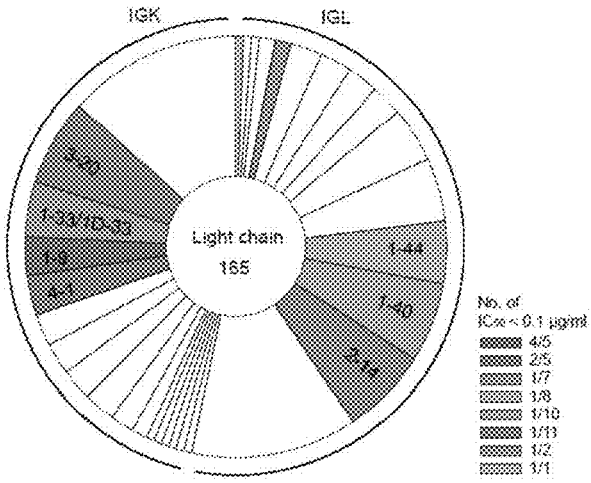
Figure 3F:
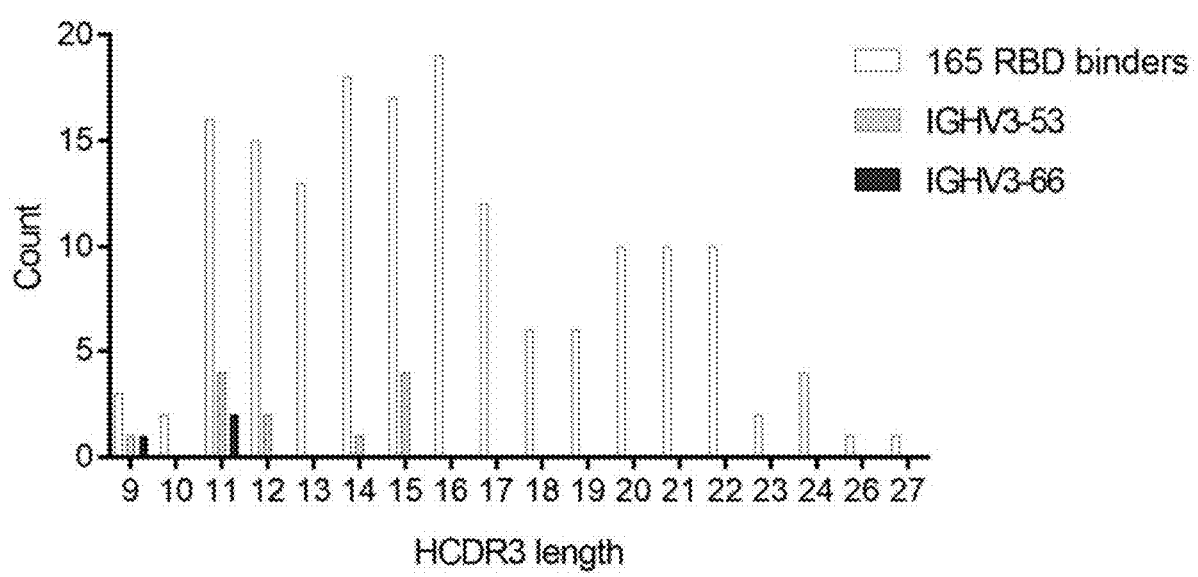

Furthermore, we also conducted a genomic analysis and compared the heavy chain variable gene (VH) and kappa or lambda light chain variable (VK/VL) genes usage in the 13 mAbs (P22A-1D1, P5A-1B9, P5A-2G7, P5A-2G9, P5A-1D1, P5A-1B8, P5A-1D2, P5A-3B4, P5A-3C8, P5A-3C12, P2C-1F11, P2B-2F6 and P2B-1A10) with lowest $IC_{50}$ identified in the pesudovirus neutralizing analysis in Example 6. Of these 13 mAbs, 7 were found to use IGHV3-53/3-66 and paired predominantly with IGK1-9*01 (Table 9b). Four of the seven were derived from P #5 (P5A-1D1, P5A-1B8, P5A-1D2, and P5A-3C8) whereas two from P #2 (P2C-1F11 and P2B-1A10) and one from P #22 (P22A-1D1). Such high prevalence (53.8%) and from diverse individuals among the top neutralizers indicated that IGHV3-53/3-66 represented one major and public antibody responses against SARS-CoV-2 (FIG. 3B-FIG. 3E). This finding is consistent with recent reports have also recognized disproportionally high prevalence of IGHV3-53/3-66 among SARS-CoV-2 patients (Barnes et al., 2020; Yuan et al., 2020). Furthermore, the CDR3 length of the antibodies varied from 9 to 15, located in the shorter range among the total 165 RBD-specific antibodies identified (FIG. 3F). Their somatic hypermutation (SHM) were generally low and some reached 0% for heavy chain (P22A-1D1) or light chain (P5A-1B8 and P2C-1F11).

Example 4

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

This example illustrates the binding properties of the antibodies against SARS-CoV-2 RBD.

Figure 4A:
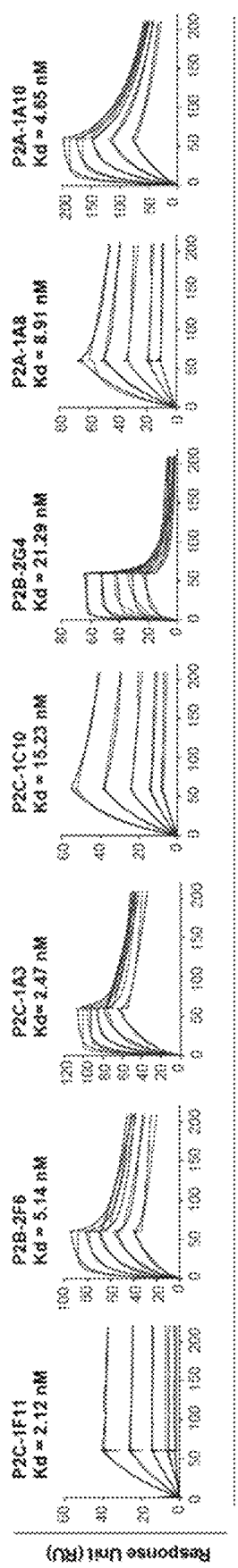
FIG. 4A-FIG. 4V. Antibody binding, competition with ACE2, and neutralization analyzed by pseudovirus and live SARS-CoV-2. (A) Binding kinetics of representative mAbs to SARS-CoV-2 RBD measured by SPR. The black lines indicate the experimentally derived curves while the grey lines represent fitted curves based on the experimental data. (B) Antibody and ACE2 competition for binding to SARS-CoV-2 RBD measured by SPR. The sensorgrams show distinct binding patterns of ACE2 to SARS-CoV-2 RBD with or without prior incubation with each representative antibody. (C and D) Antibody neutralization analyzed by SARS-CoV-2 RBD binding assay. (E through R) Antibody neutralization analyzed by pseudovirus assay. (S)-(T) Antibody neutralization analyzed by live SARS-CoV-2 neutralization assay, in which dashed lines indicated 50% reduction in viral infectivity. VRC01 is an HIV-1 specific antibody and used here as a negative control. (U)-(V) Summary of actual values from studies in FIG. 4A through FIG. 4T. Antibody binding to RBD was presented either by Kd or by competing with ACE2 where "+++" indicates >80% competition; "++" indicates 50-80%; "+" indicates 20-50%; and "−" indicates <20%. $IC_{50}$ represents the half-maximal whereas $IC_{80}$ the 80% inhibitory concentrations and $IC_{90}$ the 90% inhibitory concentrations tested in the pseudovirus and live SARS-CoV-2 neutralization assay. Only the antibody heavy chains are indicated at the upper left corner for their family designation, CDR3 length, and SHM in relative to corresponding germline ancestor sequence. n.d. not done.
Figure 4B:
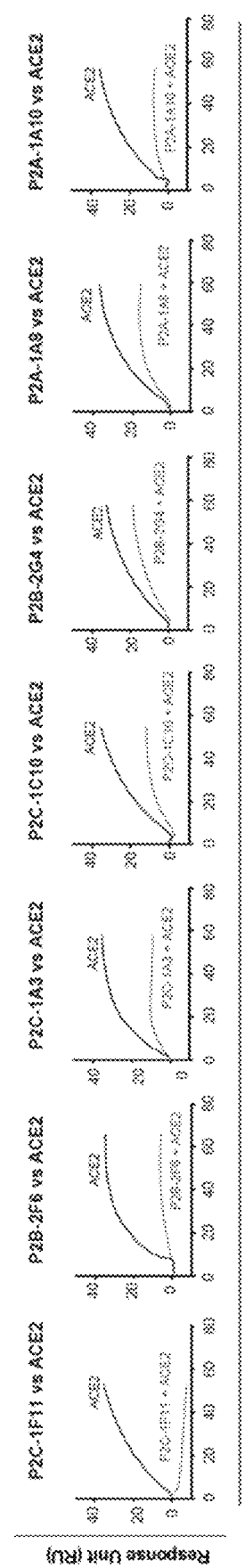
Figure 4C:
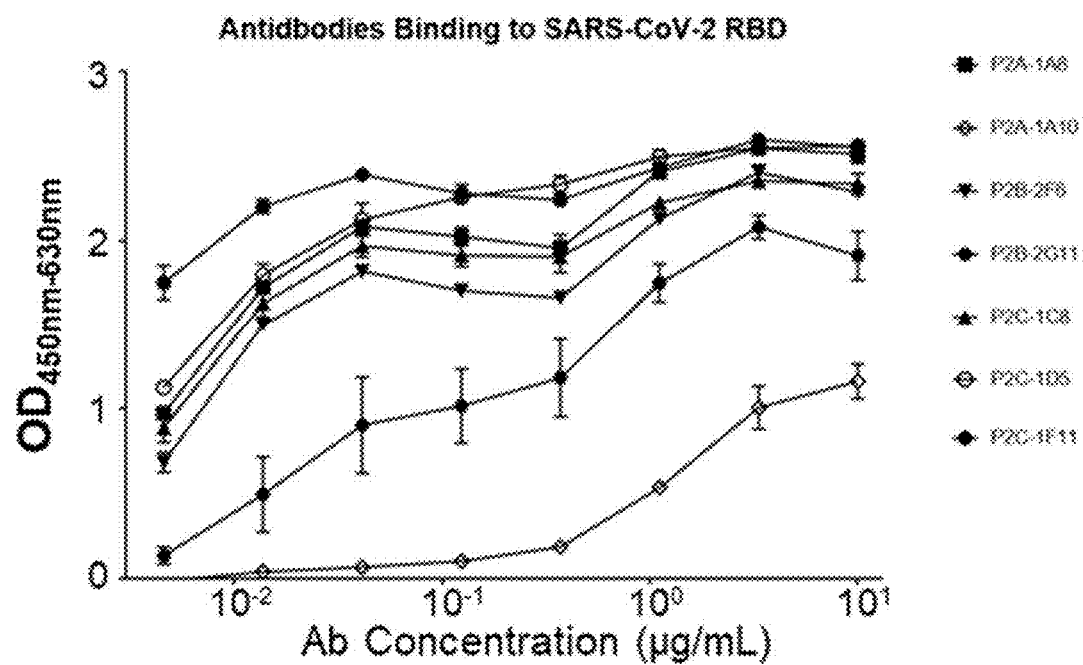
Figure 4D:
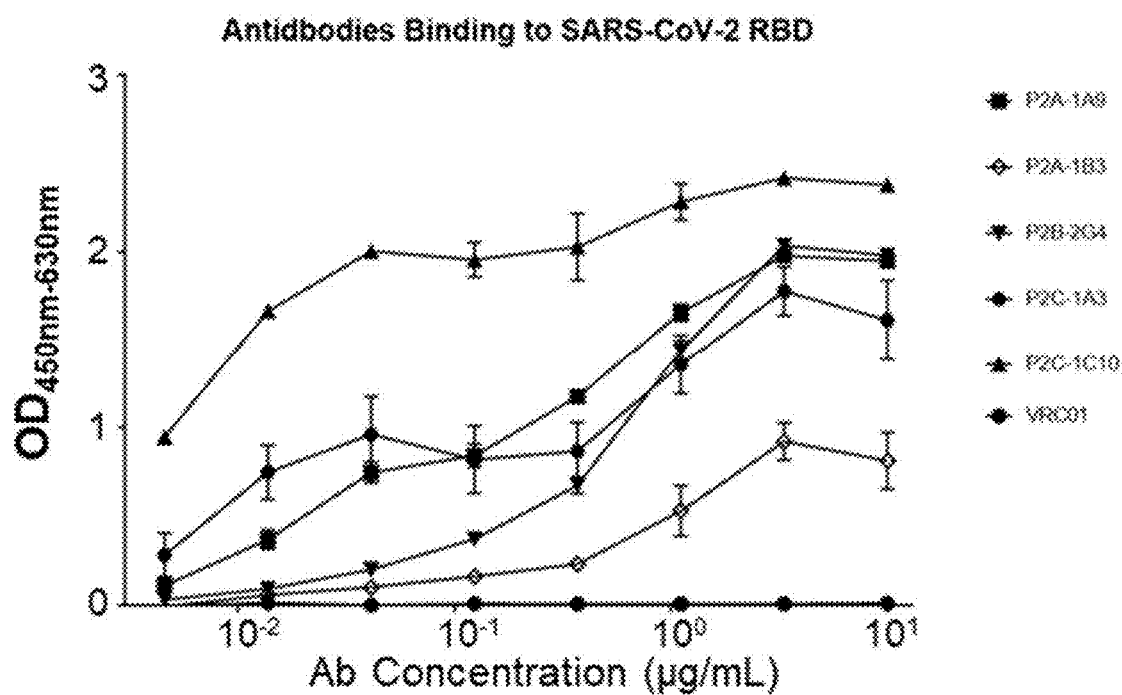
Figure 4E:
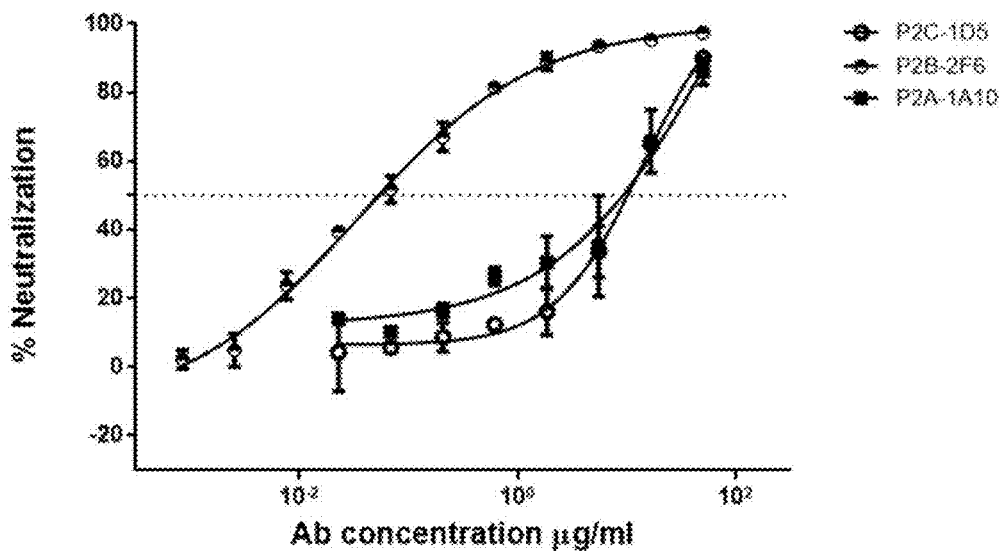
Figure 4F:
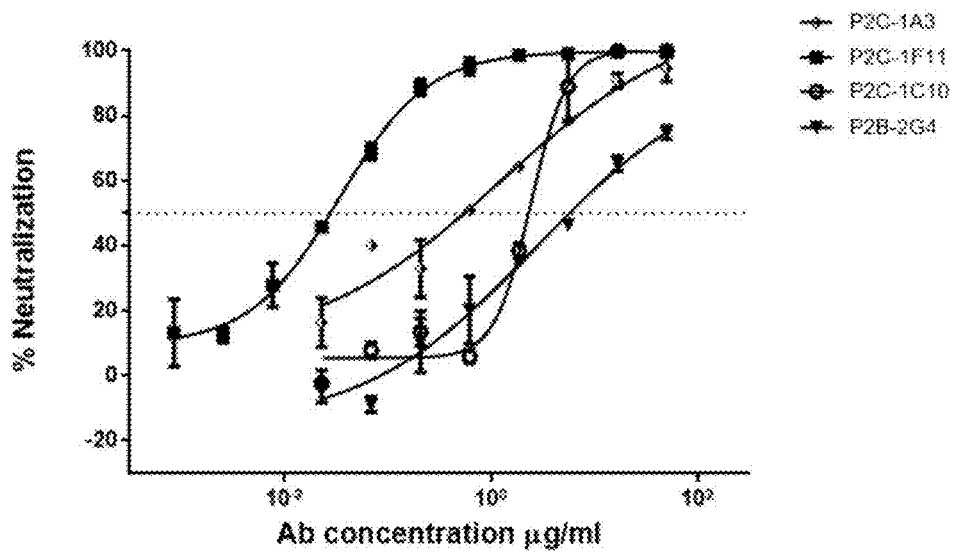
Figure 4G:
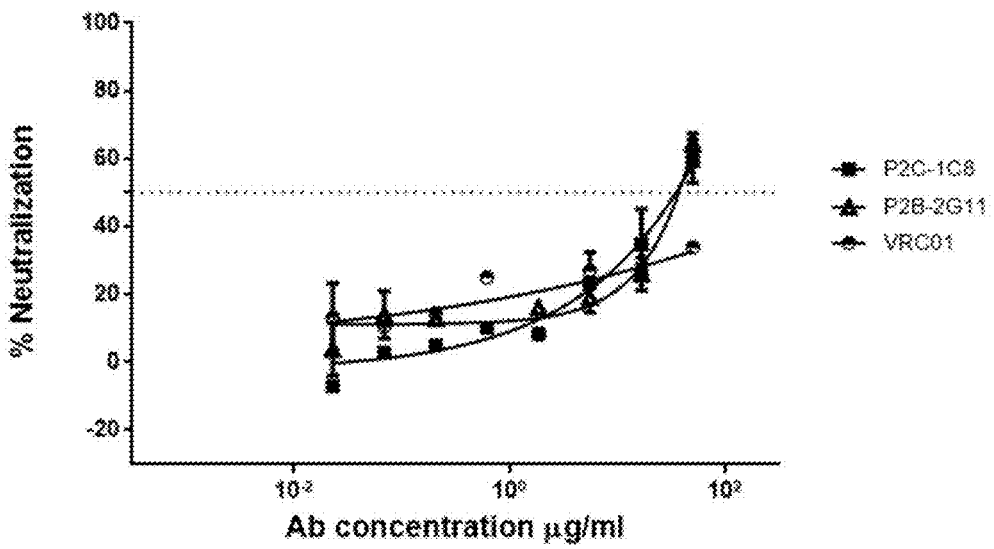
Figure 4H:
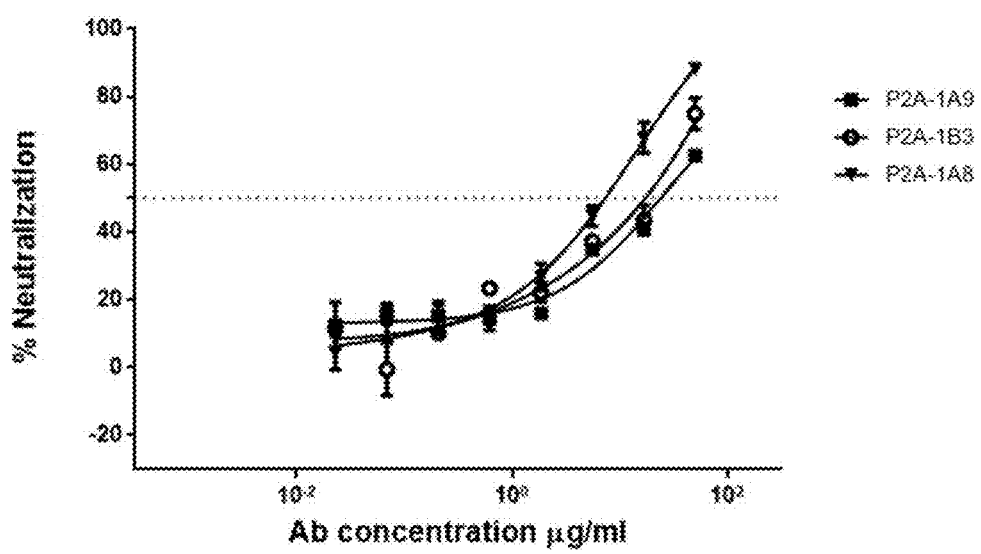
Figure 4I:
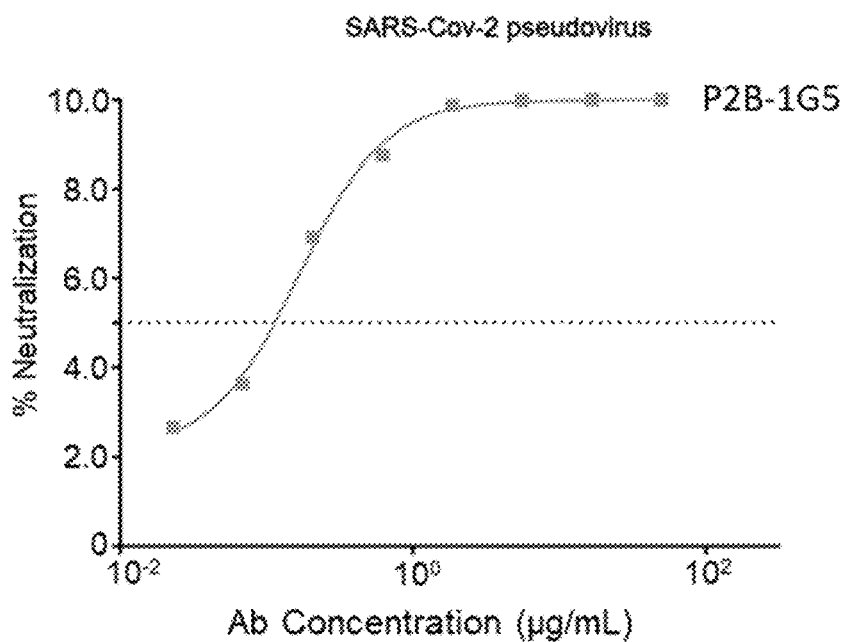
Figure 4J:
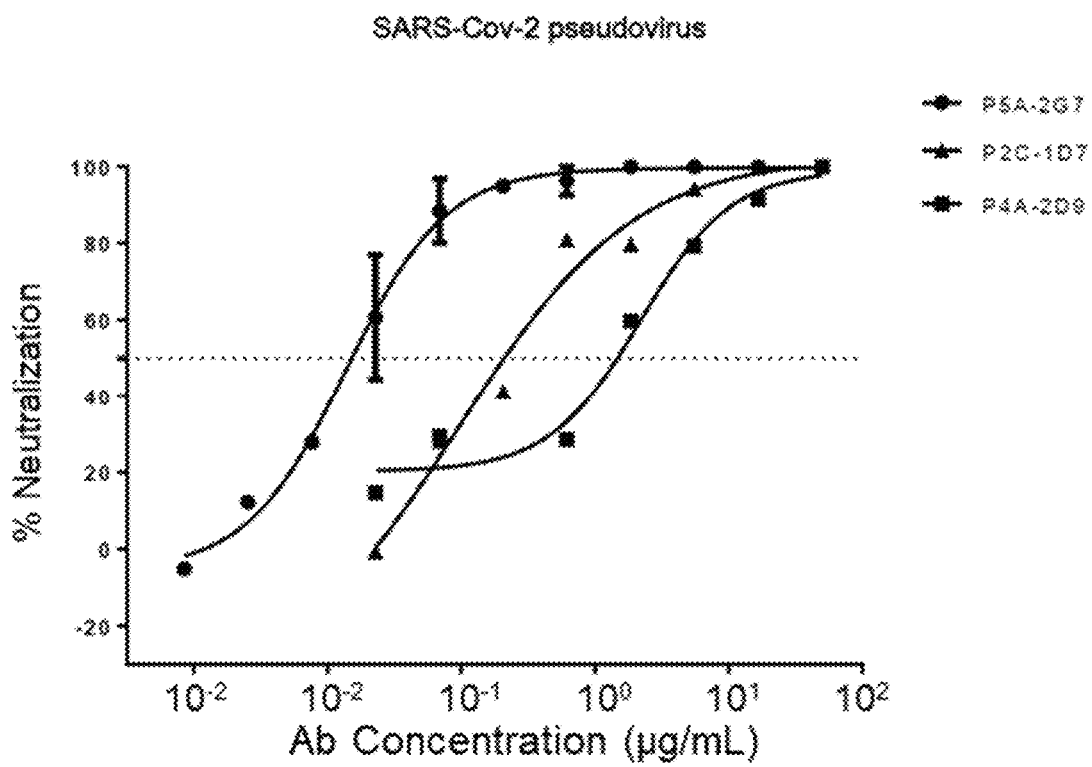
Figures 4K, 4L:
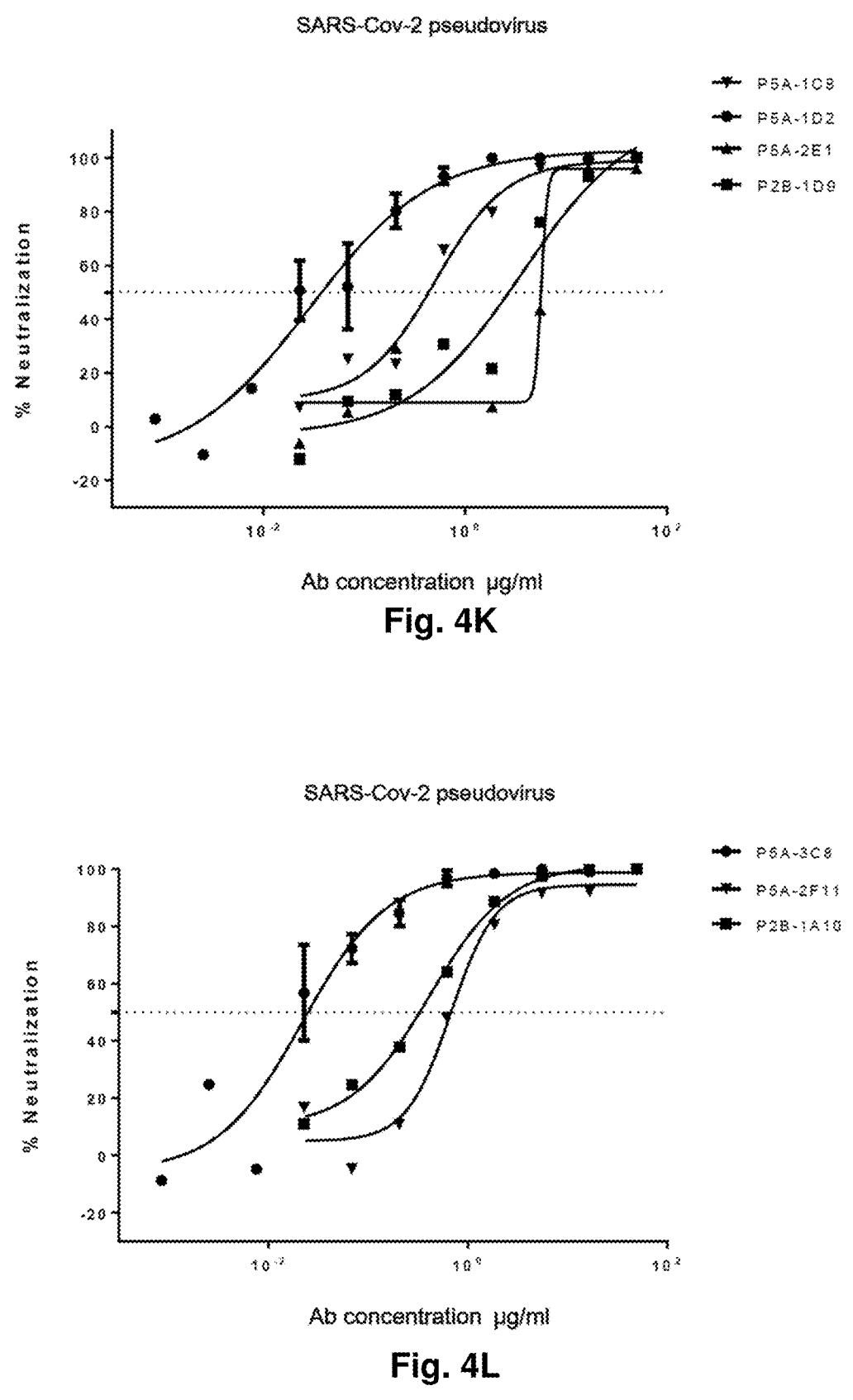
Figure 4M:
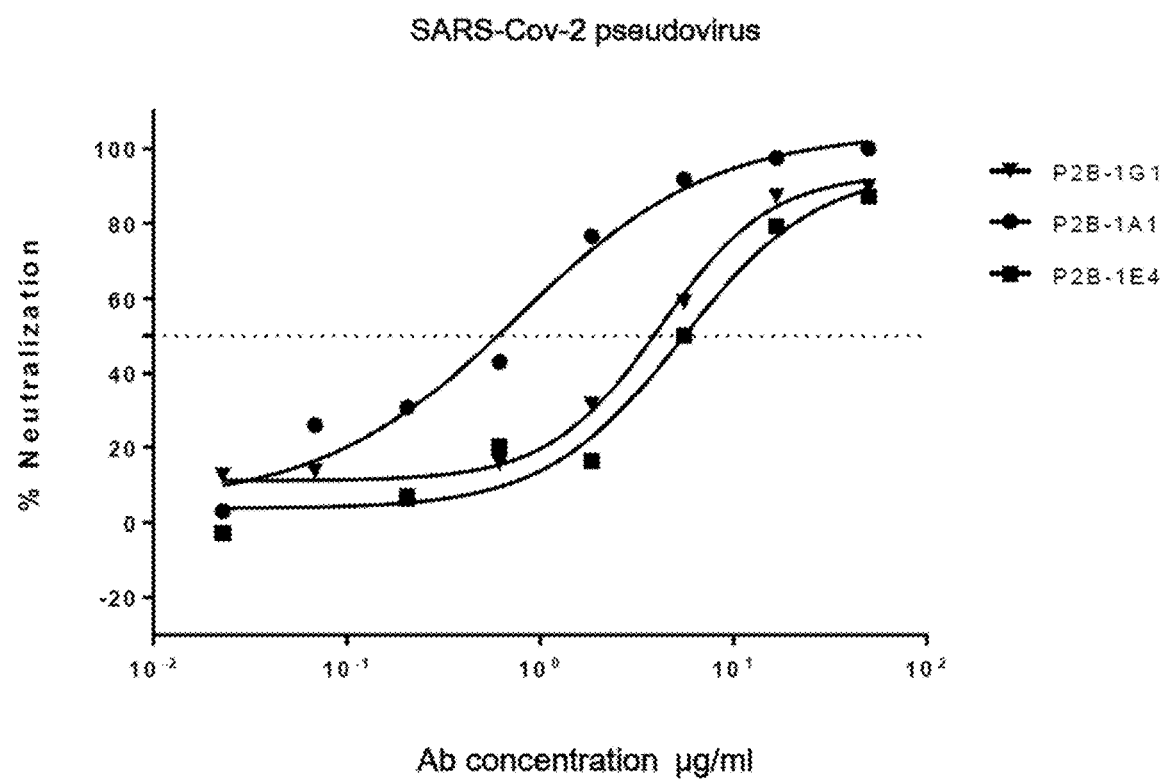
Figure 4N:
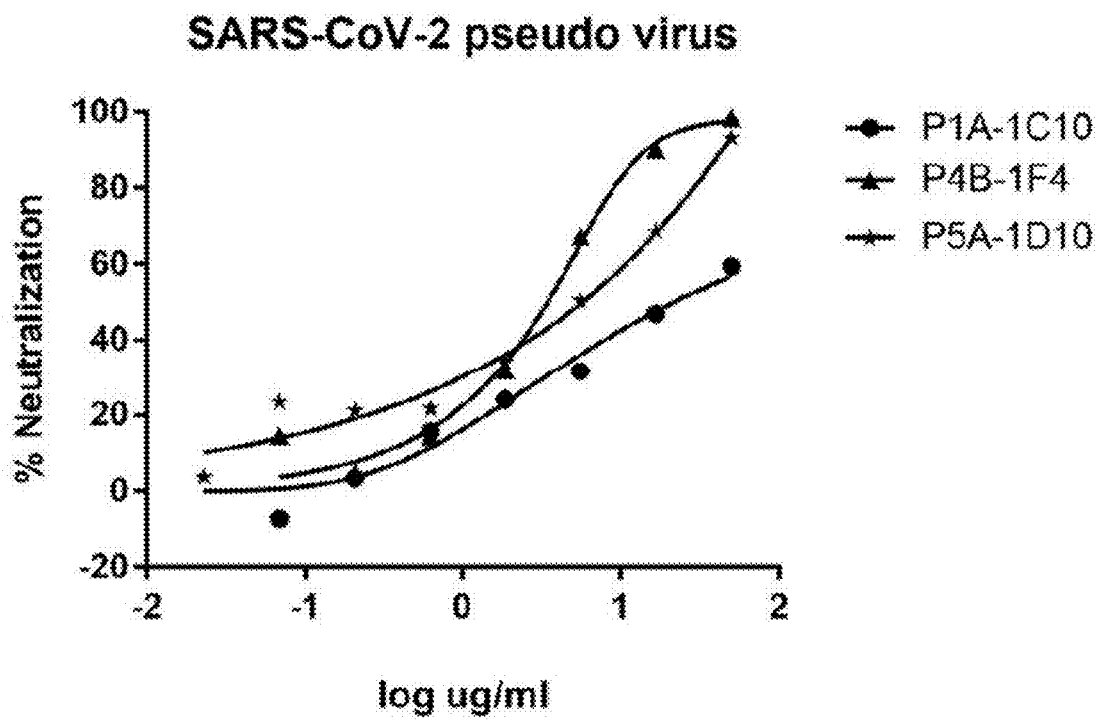
Figure 4O:
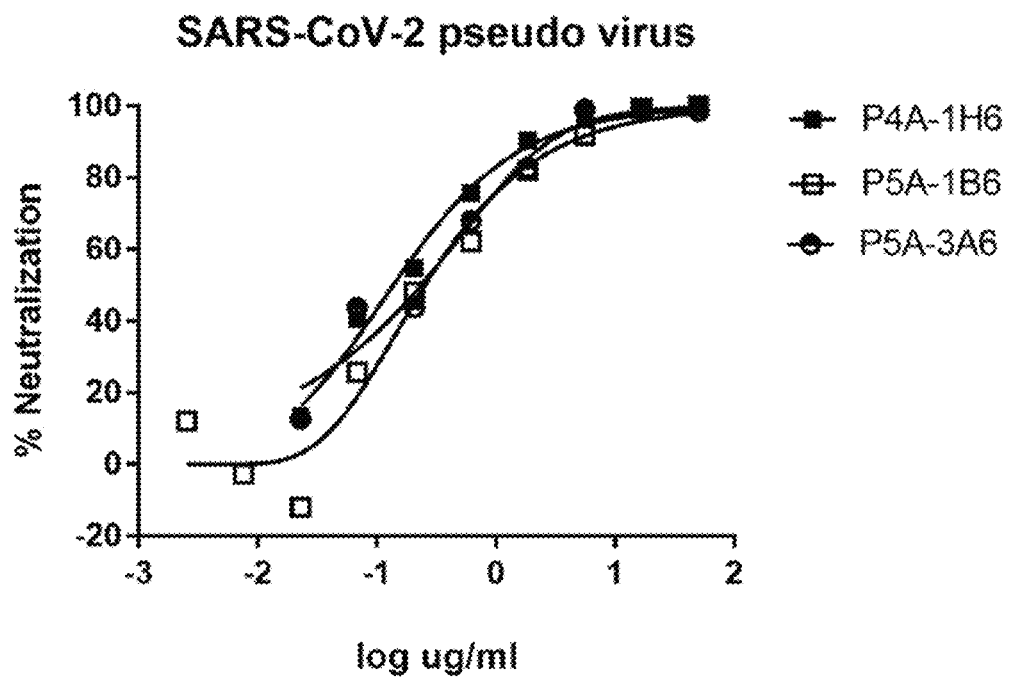
Figure 4P:
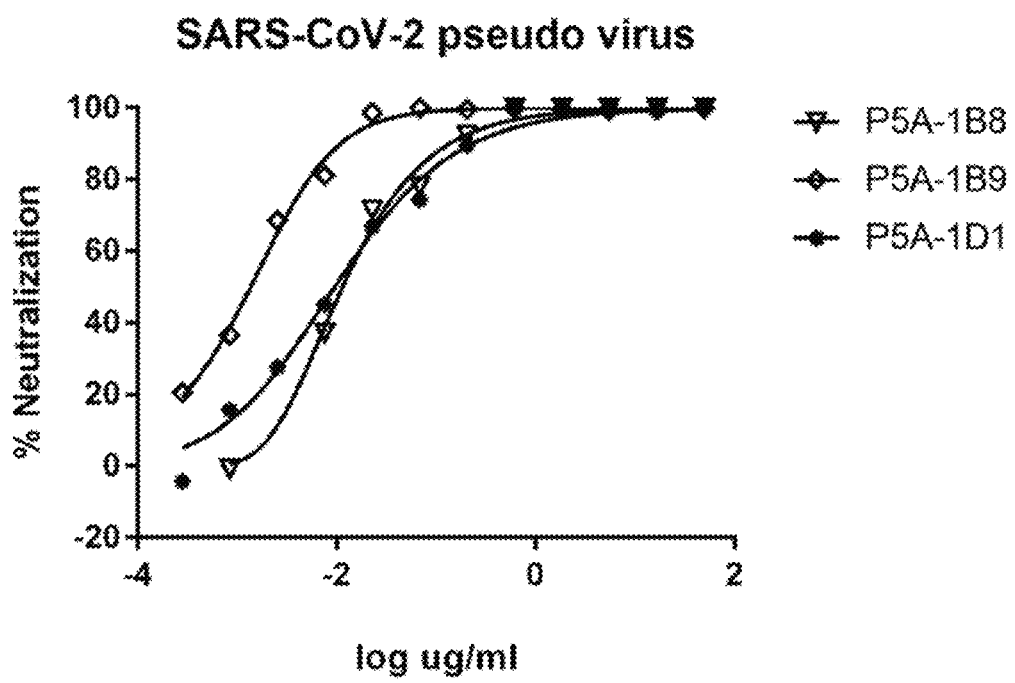
Figure 4Q:
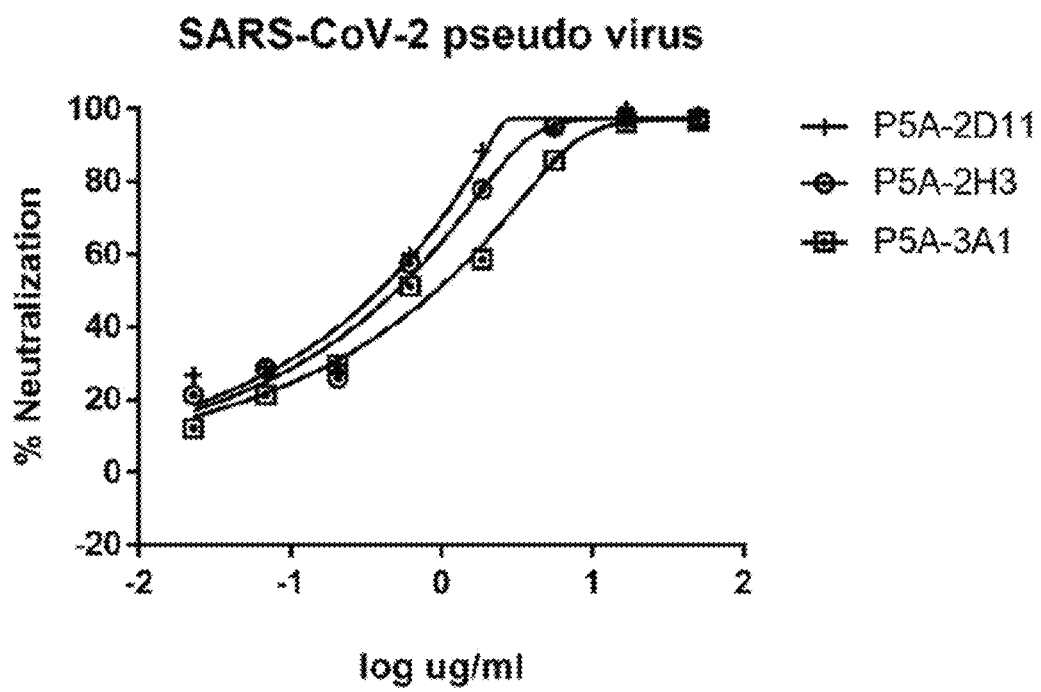
Figure 4R:
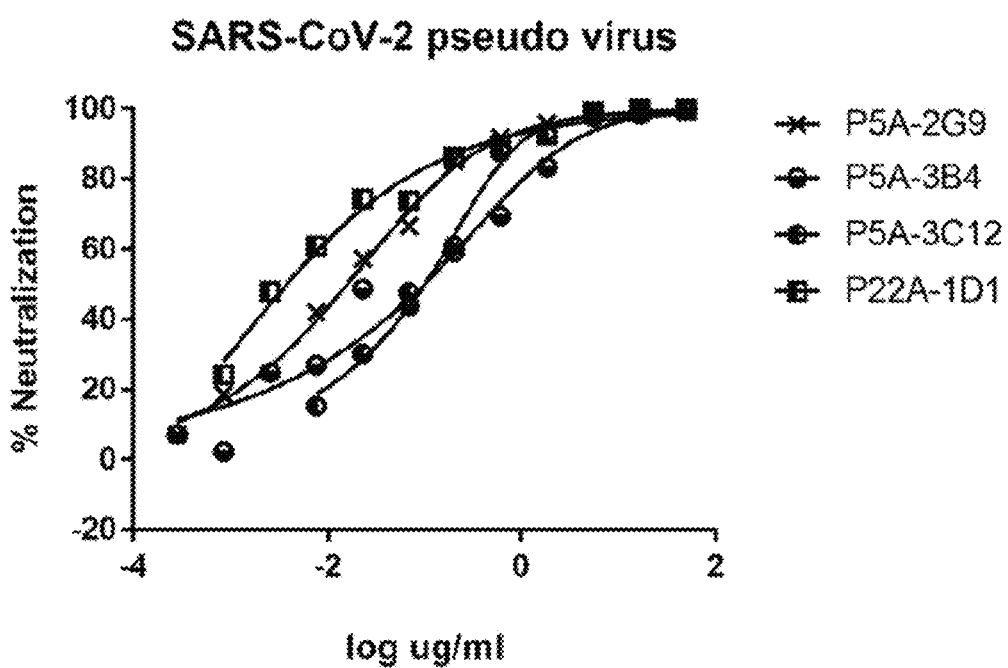
Figure 9A:
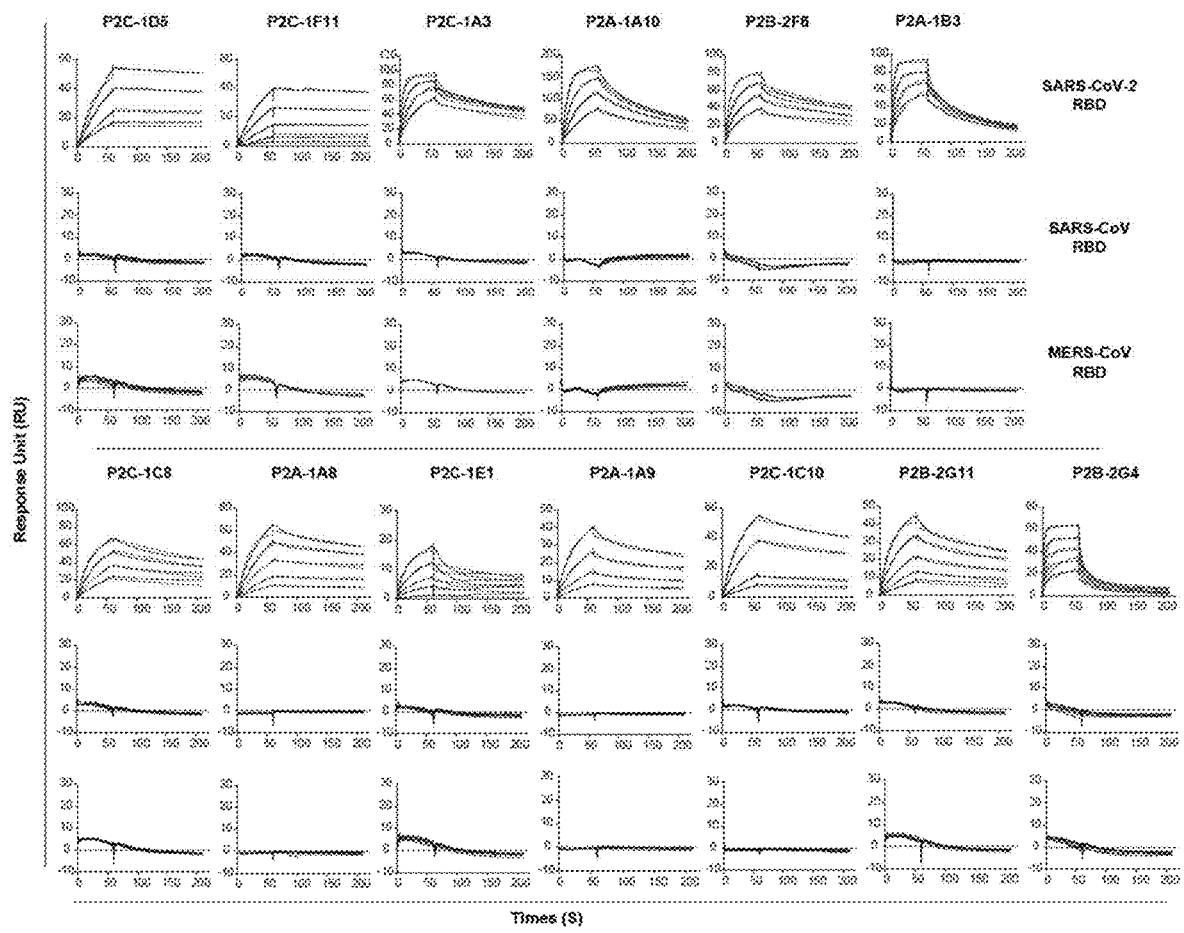
Figure 9B:
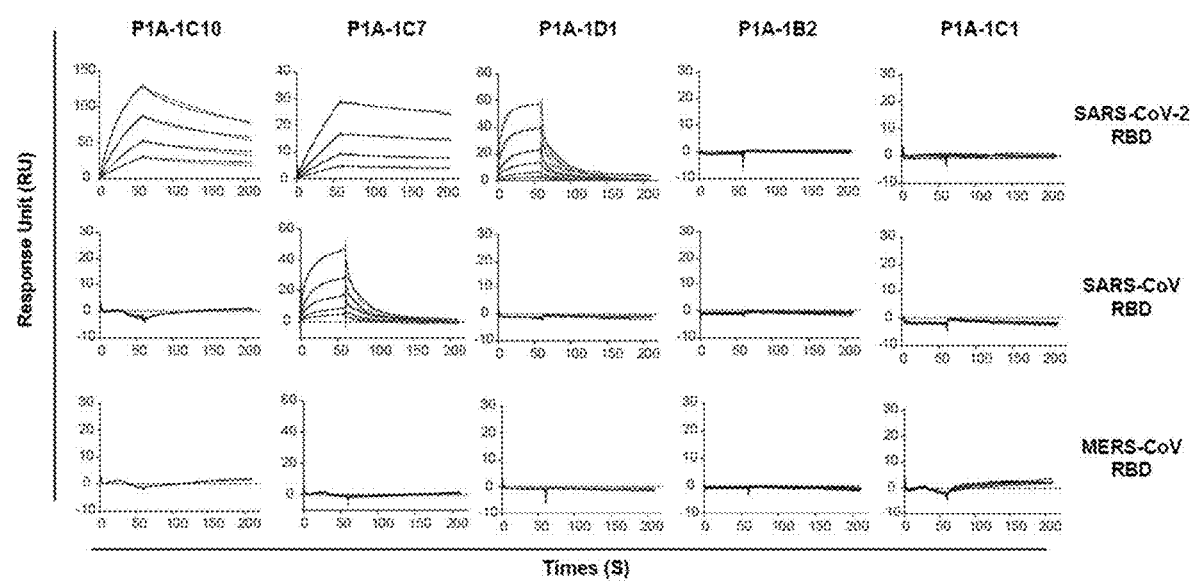
Figure 9C:
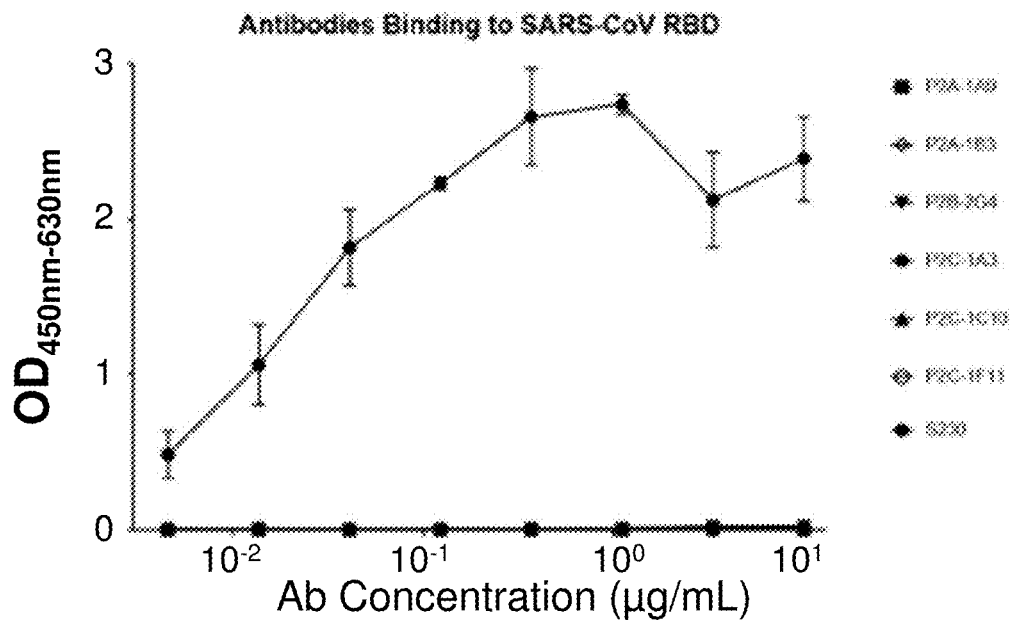
Figure 9D:
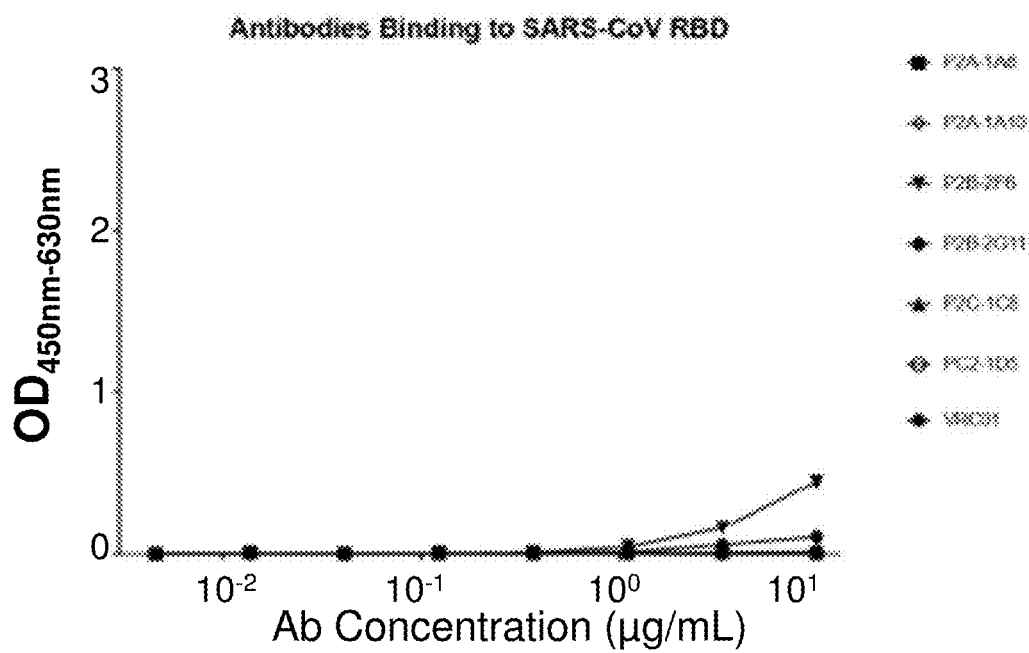
Figure 9E:
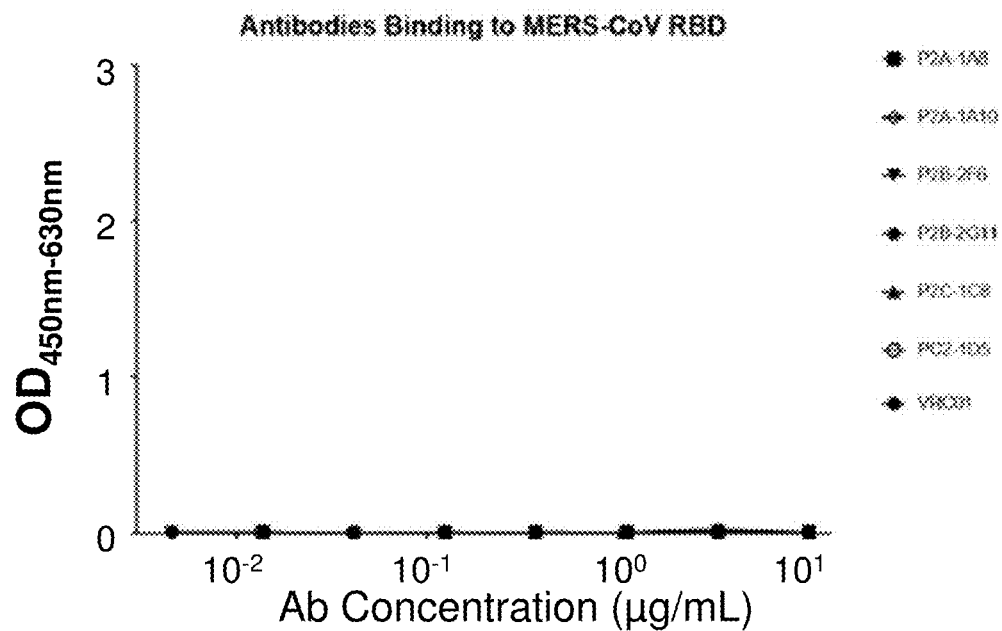
Figure 9F:
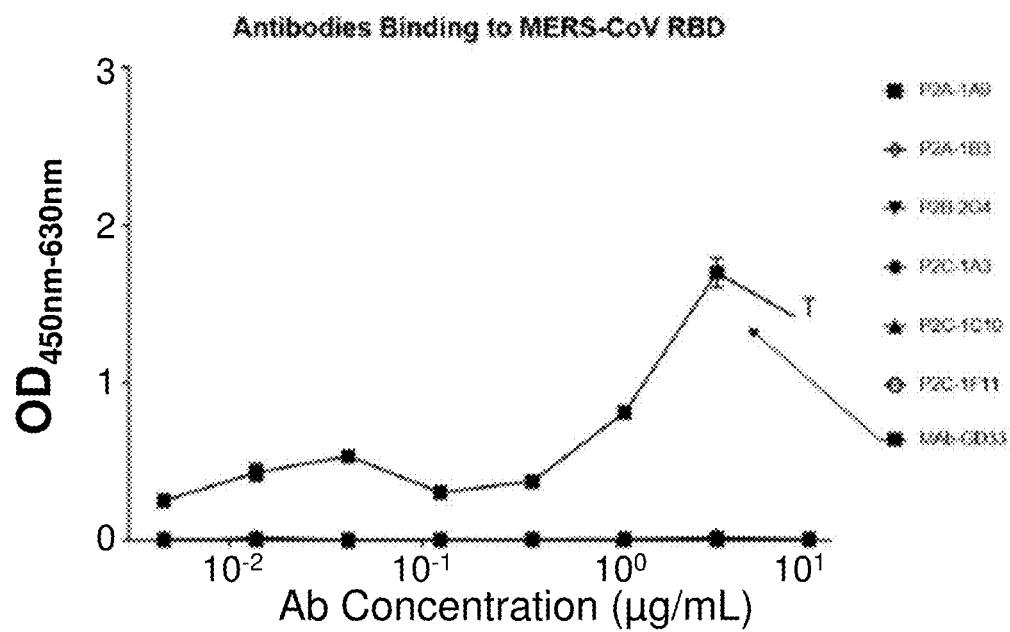
Figure 10A:
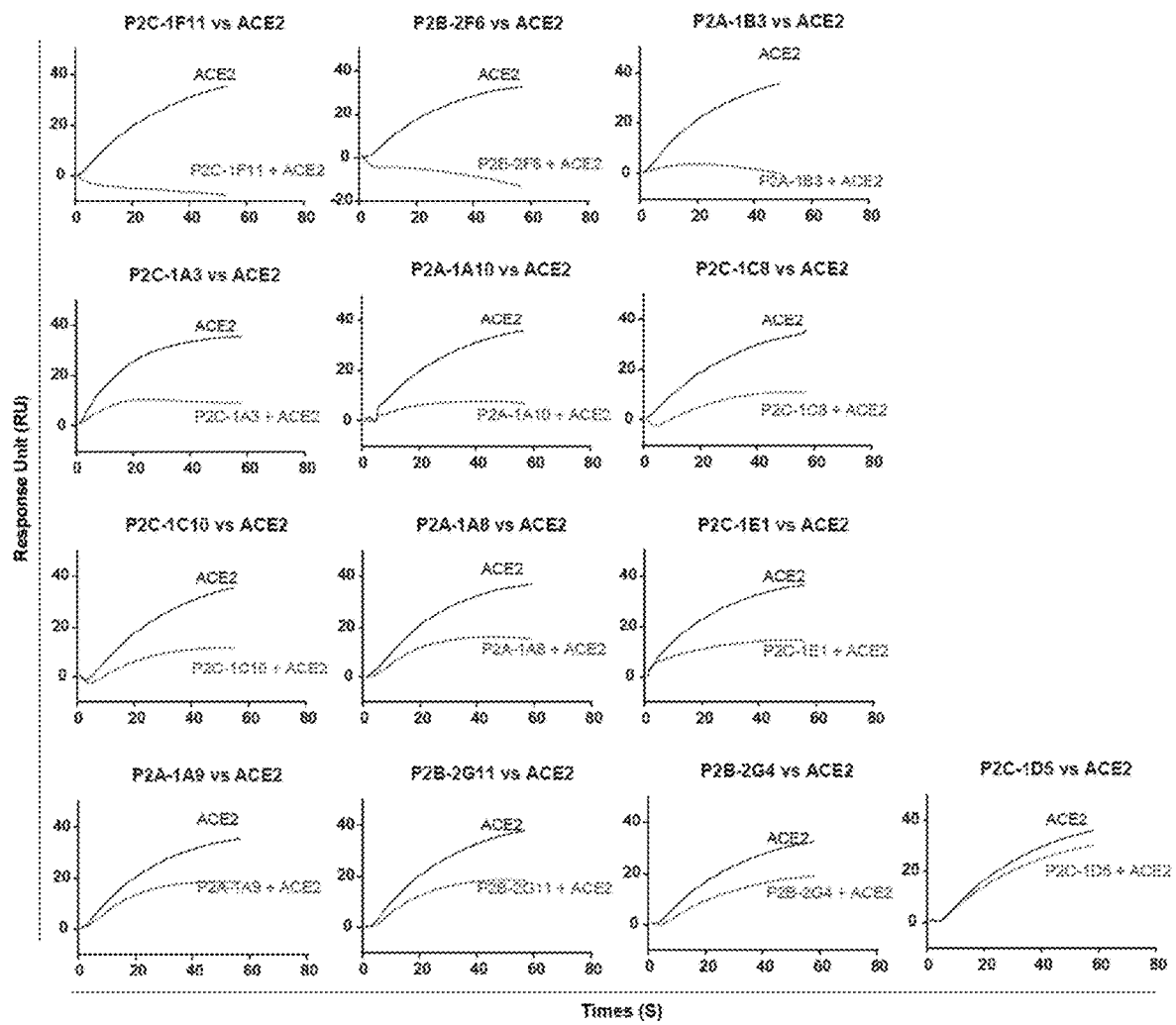
Figure 10B:
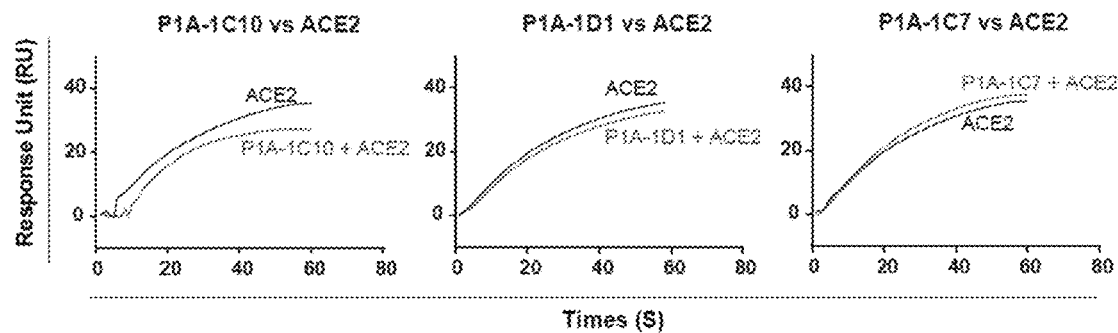

Based on their representation and distribution on the phylogenetic tree, 13 of the 69 P #2 antibodies sequences were selected for further analysis (FIG. 3A, starred). Five P #1A antibody clones were used as controls. Surface plasmon resonance (SPR) with SARS-CoV-2 RBD showed that P #2 antibodies had dissociation constants (Kd) ranging from 1.38 to 21.29 nM while those from P #1 ranged from 8.48 to 260.50 nM or not detectable at all (FIG. 4U and FIG. 9A-FIG. 9B). SHM did not appear to correlate with Kd; some germline clones with 0% divergence in both VH and VL genes (P2A-1A10, P2B-2G4, P2C-1A3, and P2C-1E1) had Kd values ranging from 2.47 to 21.19 nM, which comparable to that (1.38 to 17.57 nM) of clones with higher levels of SHM (FIG. 4U). The Kd of representative clones (P2A-1A8, P2A-1A10, and P2A-1B3) from the three clonally expanded clusters span from 4.65 to 8.91 nM, suggesting that their expansion may not be driven by affinity maturation. Antibody P2B-1G5 was also tested for RBD binding, and the Kd value was 0.1 nM (Table 7a). Next, each antibody for competition with ACE2 for binding to the SARS-CoV-2 RBD were measured (FIG. 4B, FIG. 4U, FIG. 4V and FIG. 10A-FIG. 10B). Specifically, the RBD was covalently immobilized on a CM5 sensor chip and first saturated by antibody and then flowed through with soluble ACE2. Competing capacity of each antibody was measured as percent reduction in ACE2 binding with the RBD. As shown in (FIG. 4U, FIG. 10A, FIG. 10B), the evaluated antibodies demonstrated various competing capacity with ACE2. The most powerful was P2C-1F11. Two of the three representative antibodies from the clonal expanded clusters (P2A-1A10 and P2A-1B3) had also strong reduction. The third representative (P2A-1A8) only showed mild reduction. Many antibodies had only limited competing power with ACE2 despite impressive Kd values, suggesting binding affinity is not predictive of ACE2 competing capacity. Antibody P2B-1 G5 was also tested for ACE2 competition, and showed 17.54% competition with ACE2 (Table 7a). Control antibodies from P #1 demonstrated even lower competing power with ACE2. Surprisingly, none of the antibodies tested demonstrated cross-binding with SARS-CoV and MERS-CoV RBD except P1A-1C7 (Kd=4.85 M), for which only limited cross reactivity with SARS-CoV RBD was detected (FIG. 9A-FIG. 9F).

Figure 9G:
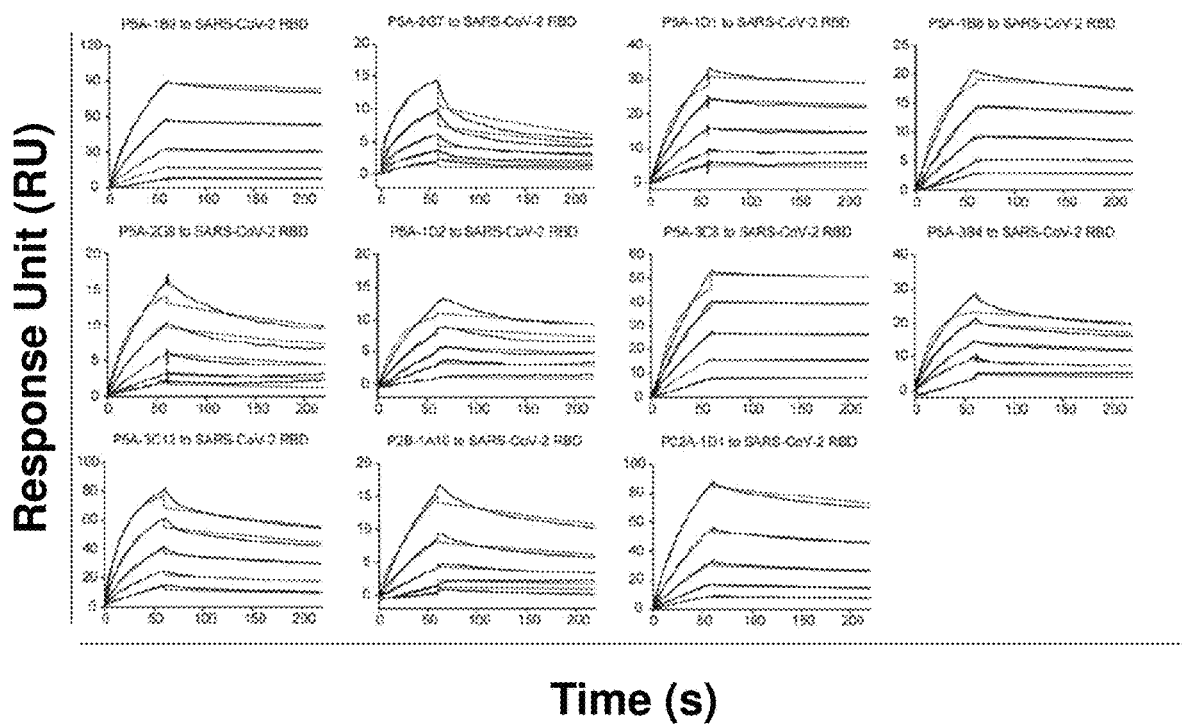

An additional set of 13 neutralizing antibodies were also identified (see Example 5) These neutralizing antibodies demonstrated high yet varying binding affinity to the SARS-CoV-2 RBD measured by surface plasmon resonance (SPR) (FIG. 9G and Table 9b). Most interestingly, of the top 13 neutralizing antibodies, 7 were found to use IGHV3-53/3-66 and paired predominantly with IGK1-9*01 (Table 9b). Four of the seven were derived from P #5 (P5A-1D1, P5A-1B8, P5A-1D2, and P5A-3C8) whereas two from P #2 (P2C-1F11 and P2B-1A10) and one from P #22 (P22A-1D1) (FIG. 3D-3E). Such high prevalence (53.8%) and from diverse individuals among the top neutralizers indicated that IGHV3-53/3-66 represented one major and public antibody responses against SARS-CoV-2. Furthermore, their CDR3 length varied from 9 to 15, located in the shorter range among the total 165 RBD-specific antibodies identified (FIG. 3F). Their somatic hypermutation (SHM) were generally low and some reached 0% for heavy chain (P22A-1D1) or light chain (P5A-1B8 and P2C-1F11). Recent reports have also recognized disproportionally high prevalence of IGHV3-53/3-66 among SARS-CoV-2 patients (Barnes et al., 2020; Yuan et al., 2020).

Figure 10C:
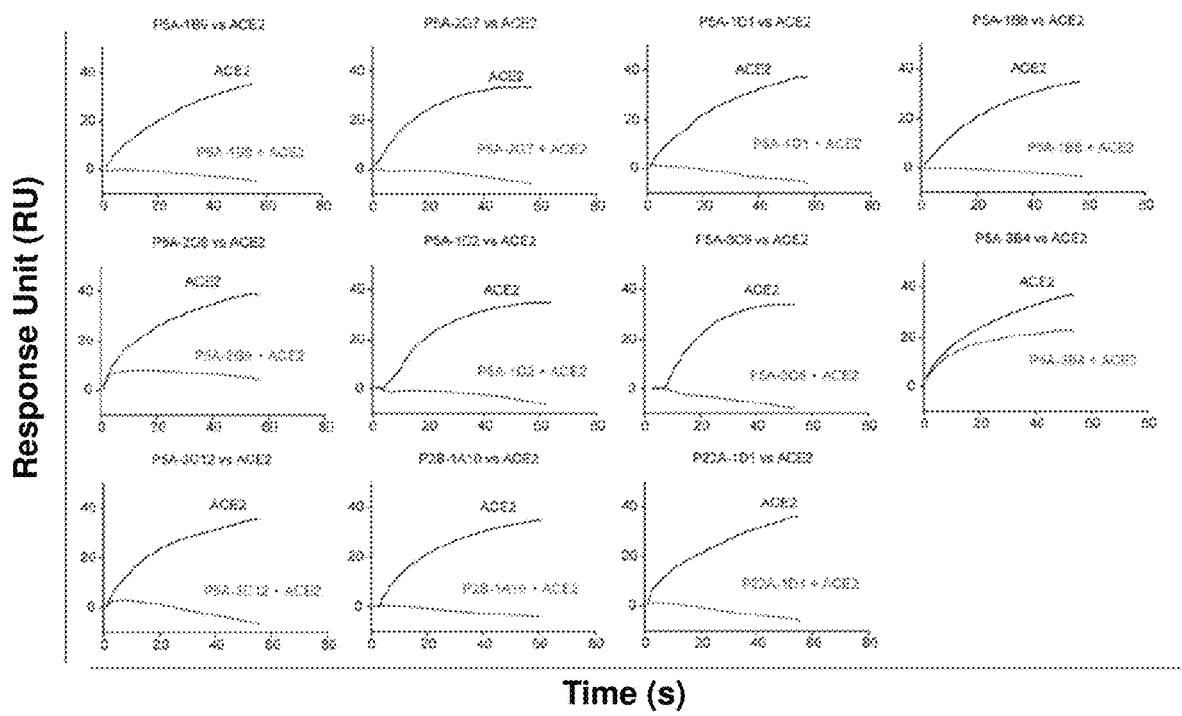

These 13 mAbs demonstrated high yet varying binding affinity to the SARS-CoV-2 RBD measured by surface plasmon resonance (SPR) (FIG. 10C and Table 9b). All except P2B-1A10 displayed single digit or less nanomolar binding affinity. Apart from P5A-3B4, these mAbs shared strong competitive capacity with ACE2 in binding to SARS-CoV-2 RBD, suggesting their potential mechanism of neutralization (FIG. 10C and Table 9b).

Example 5

This example illustrates the neutralizing properties of the antibodies against pseudoviruses bearing the Spike protein of SARS-CoV-2.

Figure 11A:
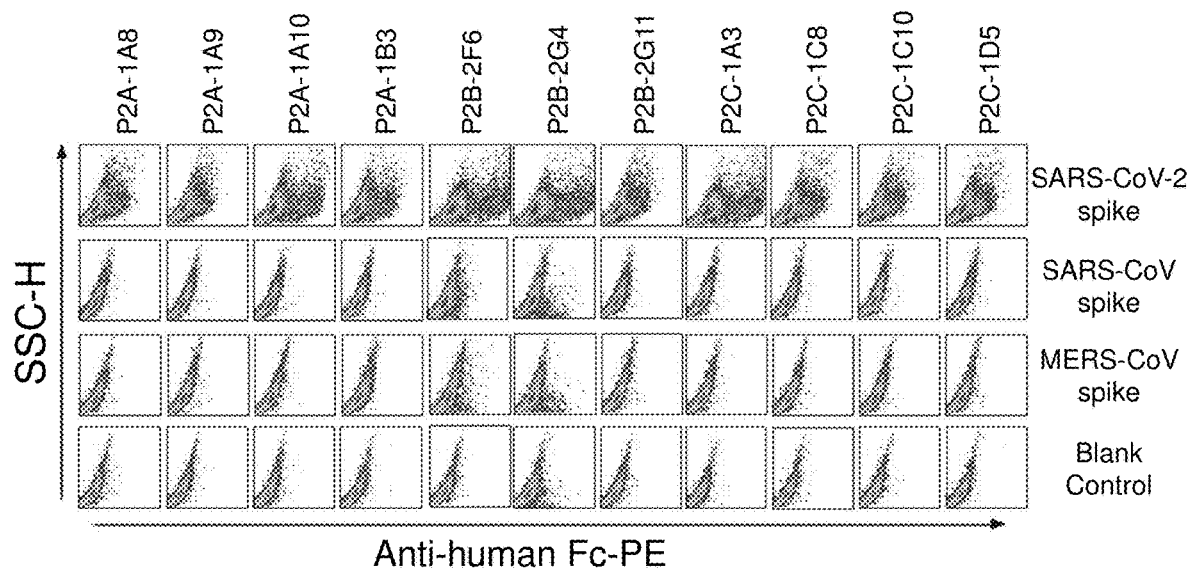
Figure 11B:
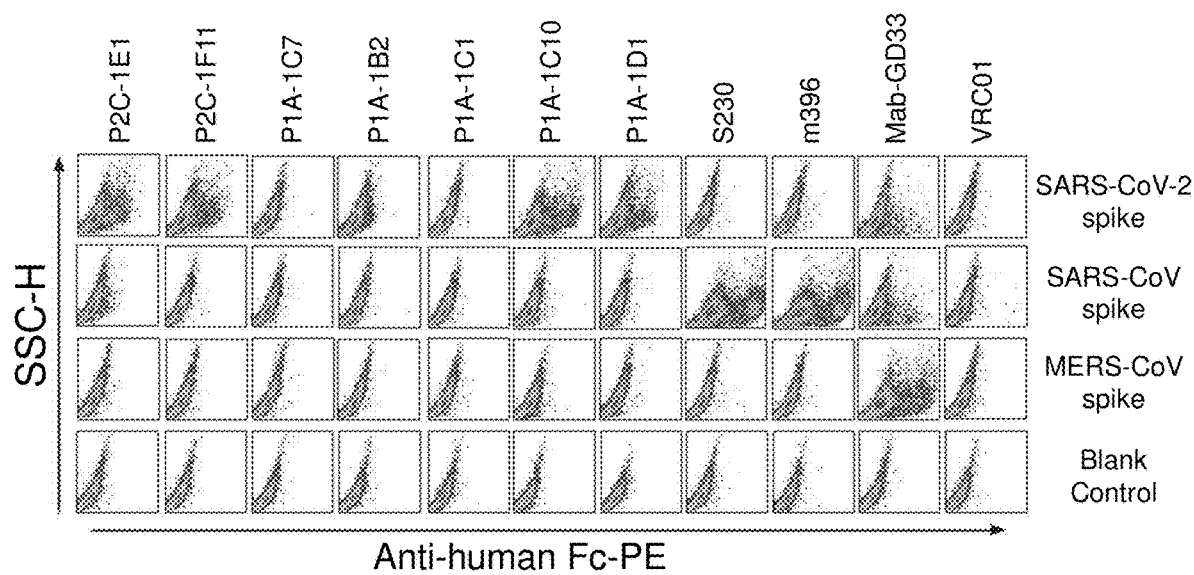
Figure 12A:
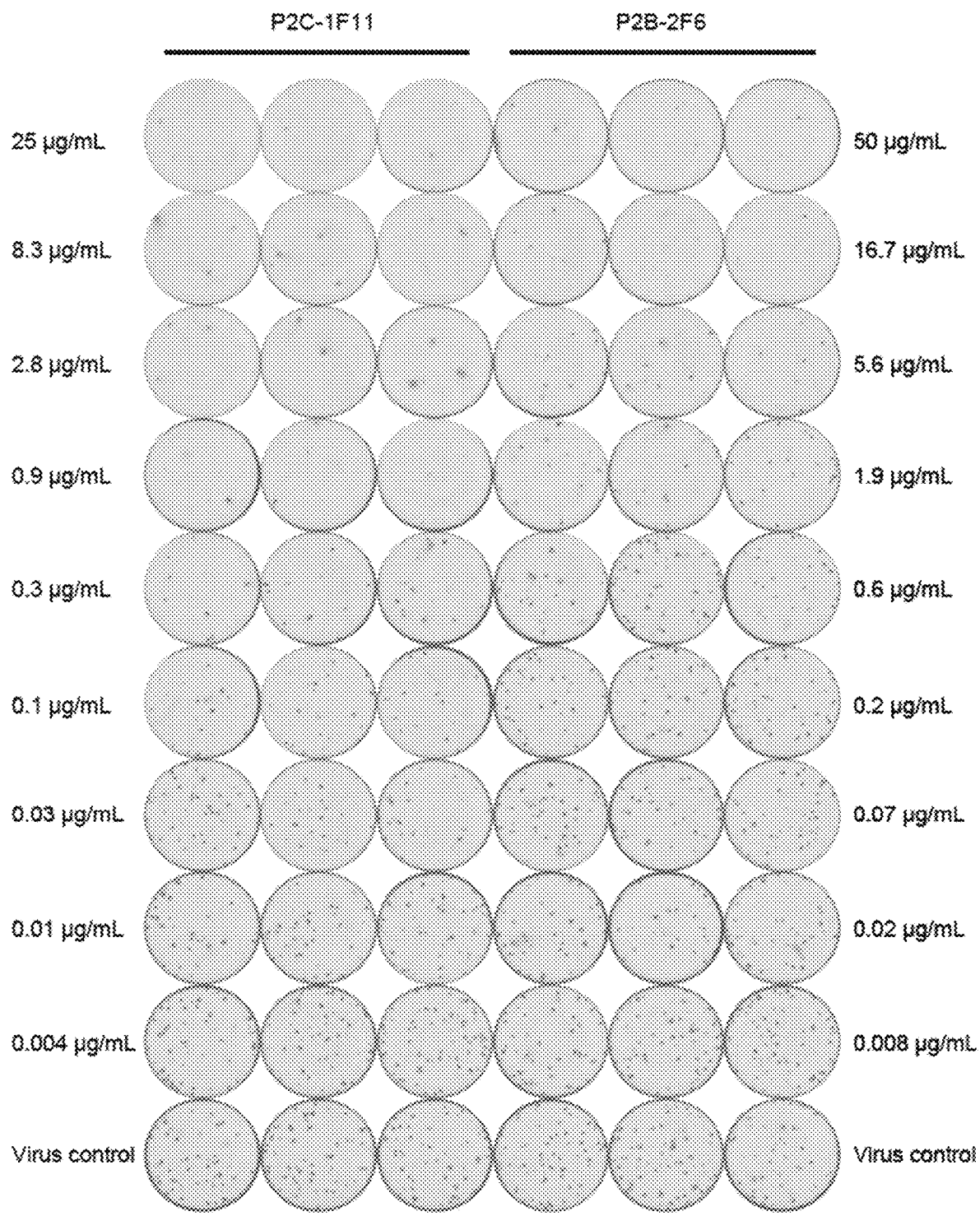
Figure 12B:
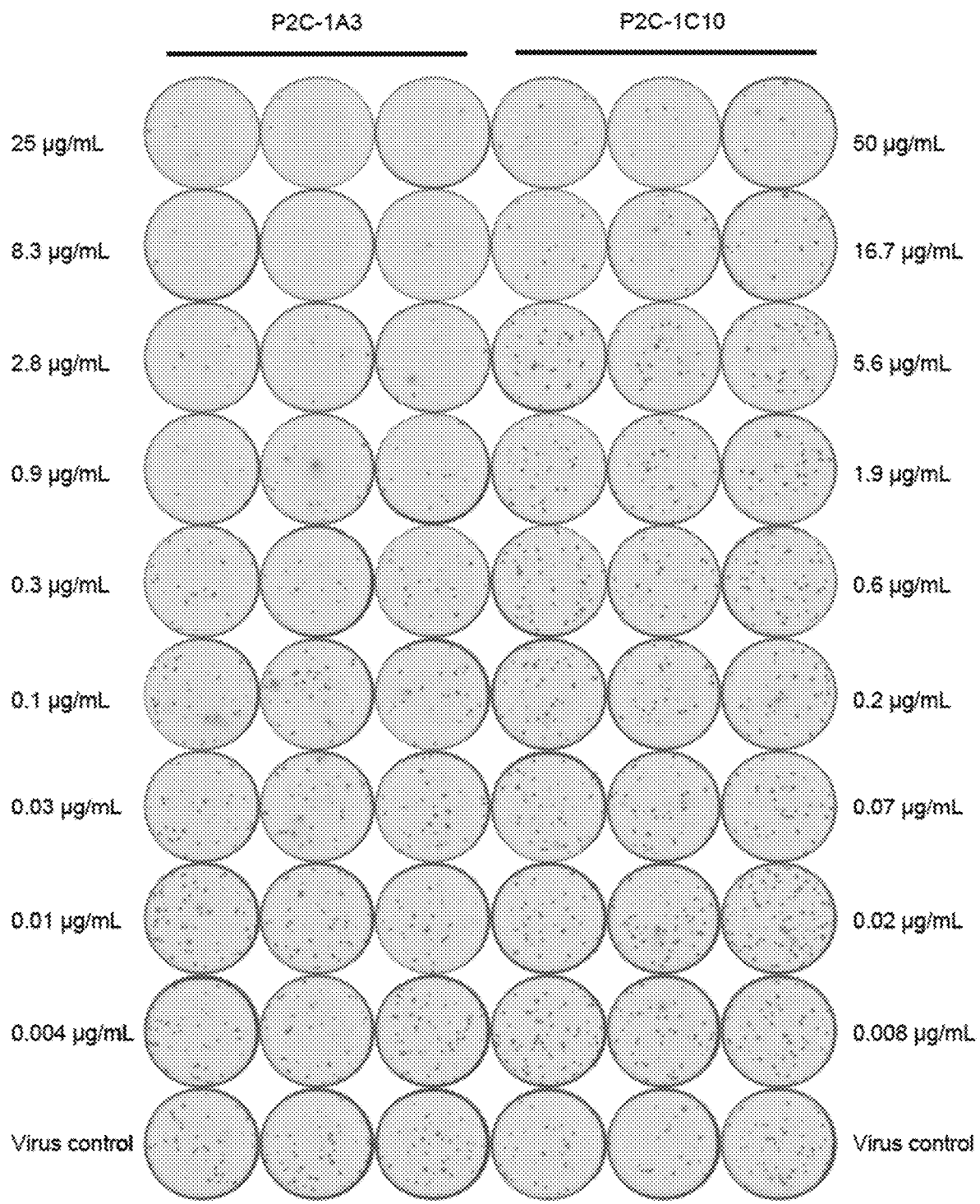
Figure 12C:
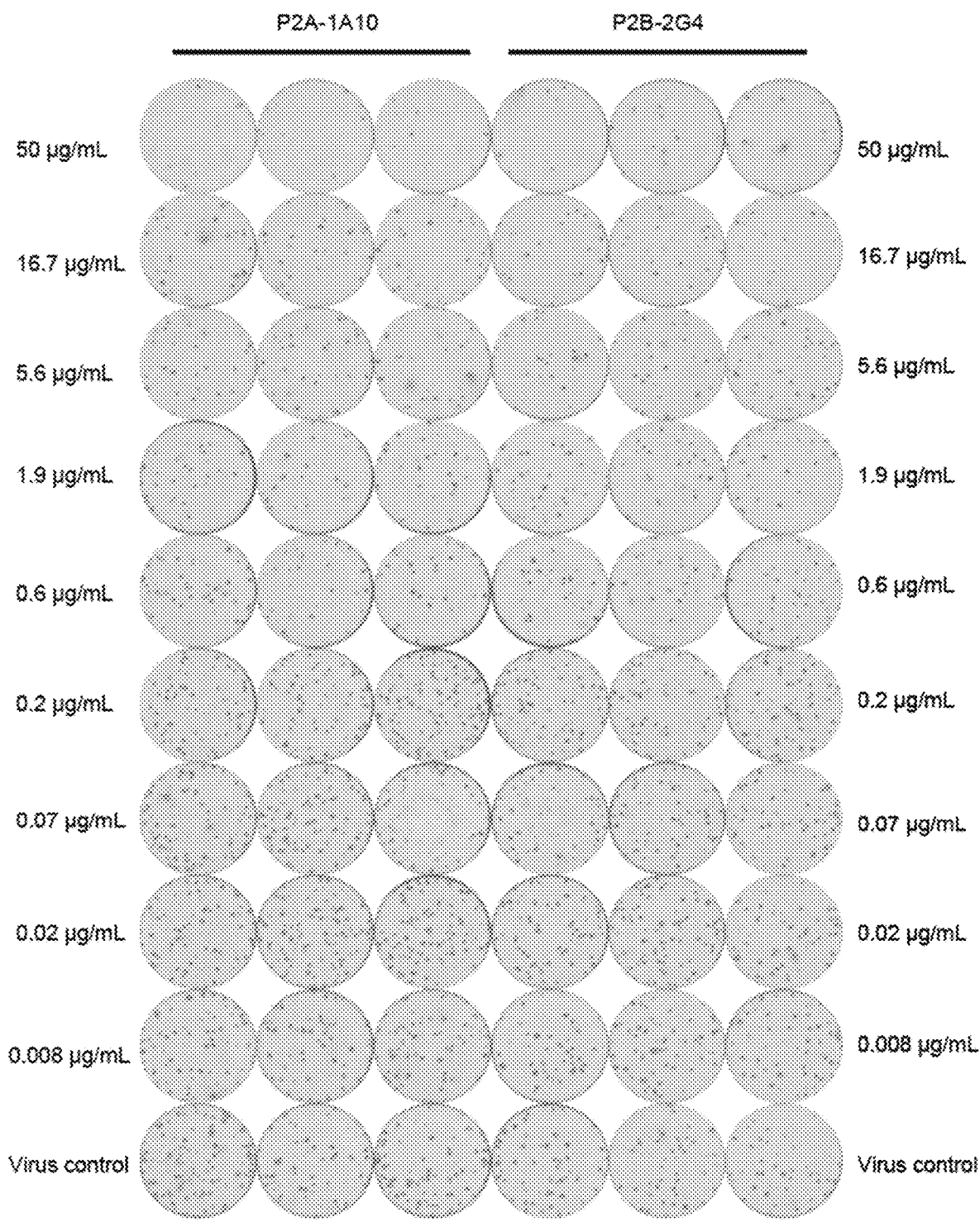
Figure 12D:
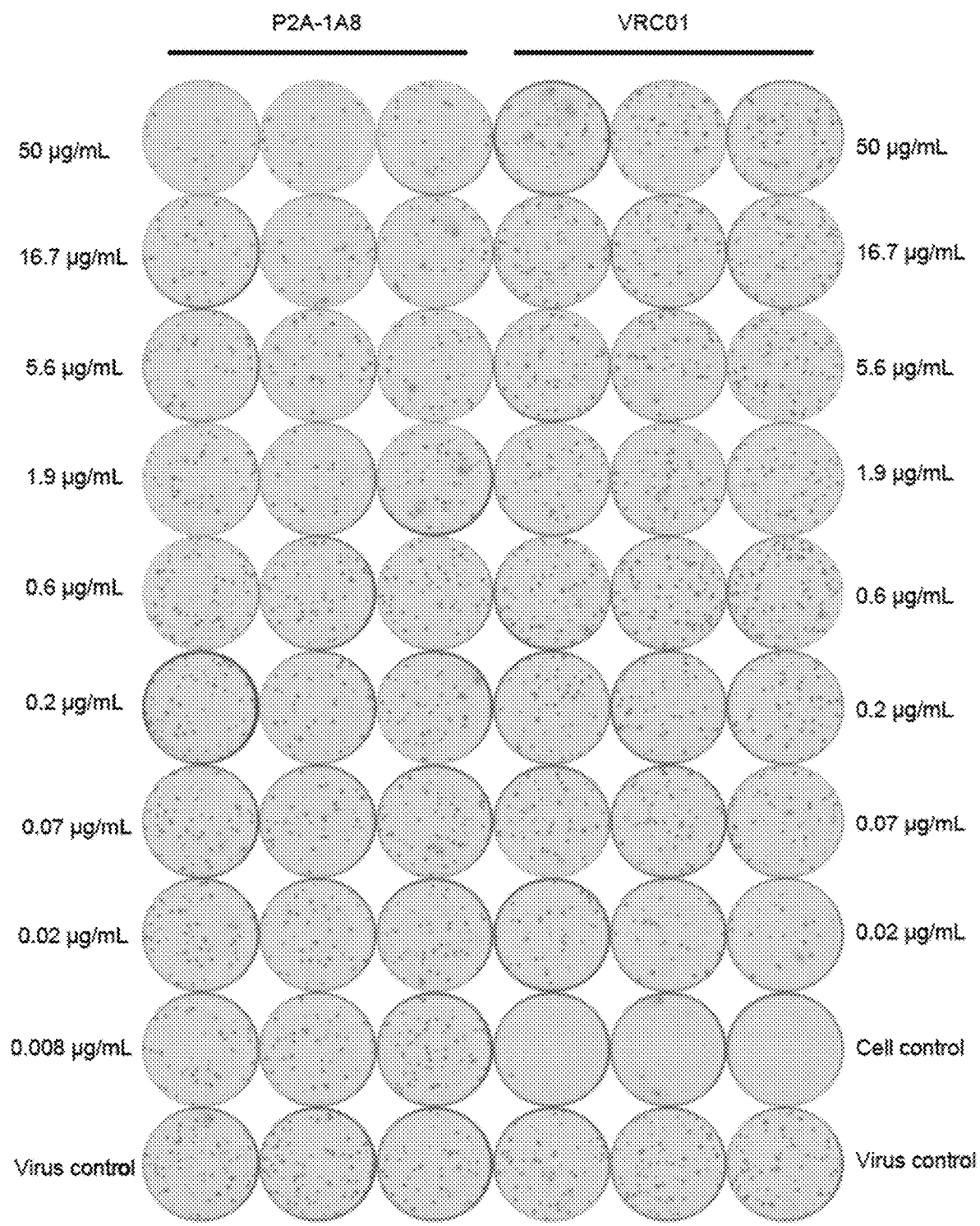

For a first set of antibodies P2A-1A8, P2A-1A9, P2A-1A10, P2A-1B3, P2B-2F6, P2B-2G4, P2B-2G11, P2C-1A3, P2C-1C8, P2C-1C10, P2C-1D5, and P2C-1F11, RBD binding and pseudoviruses neutralizing activities were tested. Consistent with the competing capacity findings, neutralizing activity varied considerably with $IC_{50}$ values ranging from 0.03 to >50 µg/ml (FIG. 4C-FIG. 4M). Within this first set of antibodies, P2C-1F11, P2B-2F6 and P2C-1A3 were the most potent with $IC_{50}$ 0.03, 0.05, and 0.63 µg/ml, respectively. Overall, ACE2 competing capacity correlated well with the neutralizing activities, although this correlation was not exact in some instances. Notably, no cross-neutralization was found either against pseudoviruses bearing the full length Spike of SARS-CoV or MERS-CoV or with cell-surface staining of trimeric SARS-CoV and MERS-CoV Spike (FIG. 11A-FIG. 11B).

Antibody P2B-1G5 was also tested for pseudoviruses neutralizing activities, with an $IC_{50}$ value of 0.11 µg/ml. The results are shown in Table 7a.

Pseudoviruses neutralizing activities were further tested using a second set of antibodies P5A-2G7, P5A-3C8, P5A-

1D2, P2B-1G1, P5A-1C8, P5A-2F11, P5A-2E1, P2B-1A1, P2C-1D7, P2B-1A10, P2B-1D9, P2B-1E4, and P4A-2D9. Results showed that most of these antibodies were potent, and $IC_{50}$ was found below 1 μg/ml for antibodies P2B-1G5, P5A-2G7, P5A-3C8, P5A-1D2, P5A-1C8, P5A-2F11, P2B-1A1, P2C-1D7, and P2B-1A10 (Table 7b).

Pseudoviruses neutralizing activities were also tested using a third set of antibodies P1A-1C10, P4A-1H6, P4B-1F4, P5A-1B6, P5A-1B8, P5A-1B9, P5A-1D1, P5A-1D10, P5A- 2D11, P5A-2G9, P5A-2H3, P5A-3A1, P5A-3A6, P5A-3B4, P5A-3C12, and P22A-IDI. Results showed that most of these antibodies were potent, and $IC_{50}$ was found below 1 μg/ml for antibodies P4A-1H6, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, and P22A-1D1 (Table 7c and FIG. 4V). Among them, P5A-1B9, P22A-1D1, P5A-1D1, P5A-1B8, P5A-2G9, P5A-3B4 and P5A-3C12 were the most potent with $IC_{50}$ lower than 0.1 μg/ml (0.0014, 0.0038, 0.0096, 0.0115, 0.0158, 0.0993 and 0.0996 μg/ml, respectively).

By summarizing the initial screening result by using pseudovirus, we identified 13 mAbs (P22A-1D1, P5A-1B9, P5A-2G7, P5A-2G9, P5A-1D1, P5A-1B8, P5A-1D2, P5A-3B4, P5A-3C8, P5A-3C12, P2C-1F11, P2B-2F6 and P2B-1A10) with $IC_{50}$ ranging from 0.0014 g/mL to 0.0996 μg/mL (FIG. 4N through FIG. 4R). The $IC_{50}$ of remaining antibodies, however, spans between 0.1 μg/mL and 50 μg/mL or higher (Table 7d).

Figure 4S:
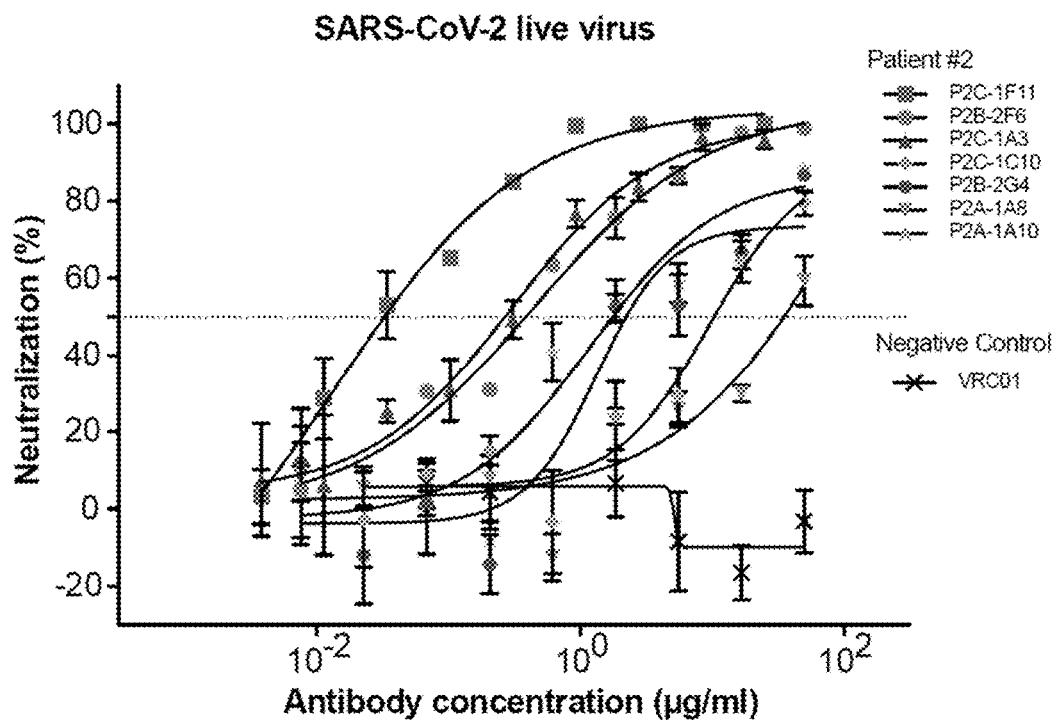
Figure 4T:
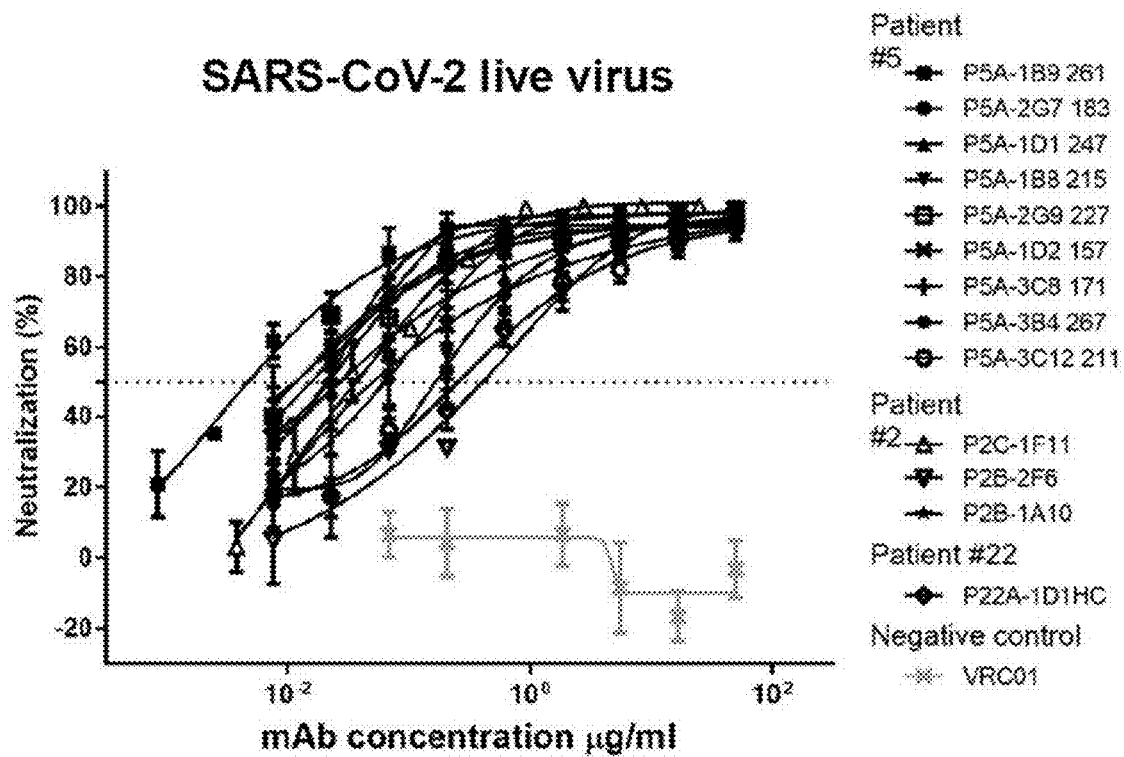

We selected the top seven potent neutralizing antibodies against pseudovirus in the first set of antibodies to analyze their inhibitory activities against live SARS-CoV-2 using focus reduction neutralization test (FRNT) (FIG. 4S) and FIG. 12A-FIG. 12D). Consistent with their respective pseudovirus assay findings, P2C-1F11, P2B-2F6 and P2C-1A3 demonstrated the most potent neutralization activity with $IC_{50}$ 0.03 0.41, and 0.28 μg/ml, respectively (FIG. 4U). The remaining antibodies demonstrated moderate neutralizing activities with IC50 ranging from 1.64 to 35.87 μg/ml (FIG. 4U). The further identified top 13 neutralizing antibodies also demonstrated strong inhibitory activity against live SARS-CoV-2 based on focus reduction neutralization tests (FRNT) (FIG. 4T). For instance, the $IC_{50}$ for the best antibody P5A-1B9 reached as low as 0.0043 μg/mL and the $IC_{50}$ 0.0441 μg/mL, at least 10-fold more potent than those tested in the first set (FIG. 4V).

Figure 13:
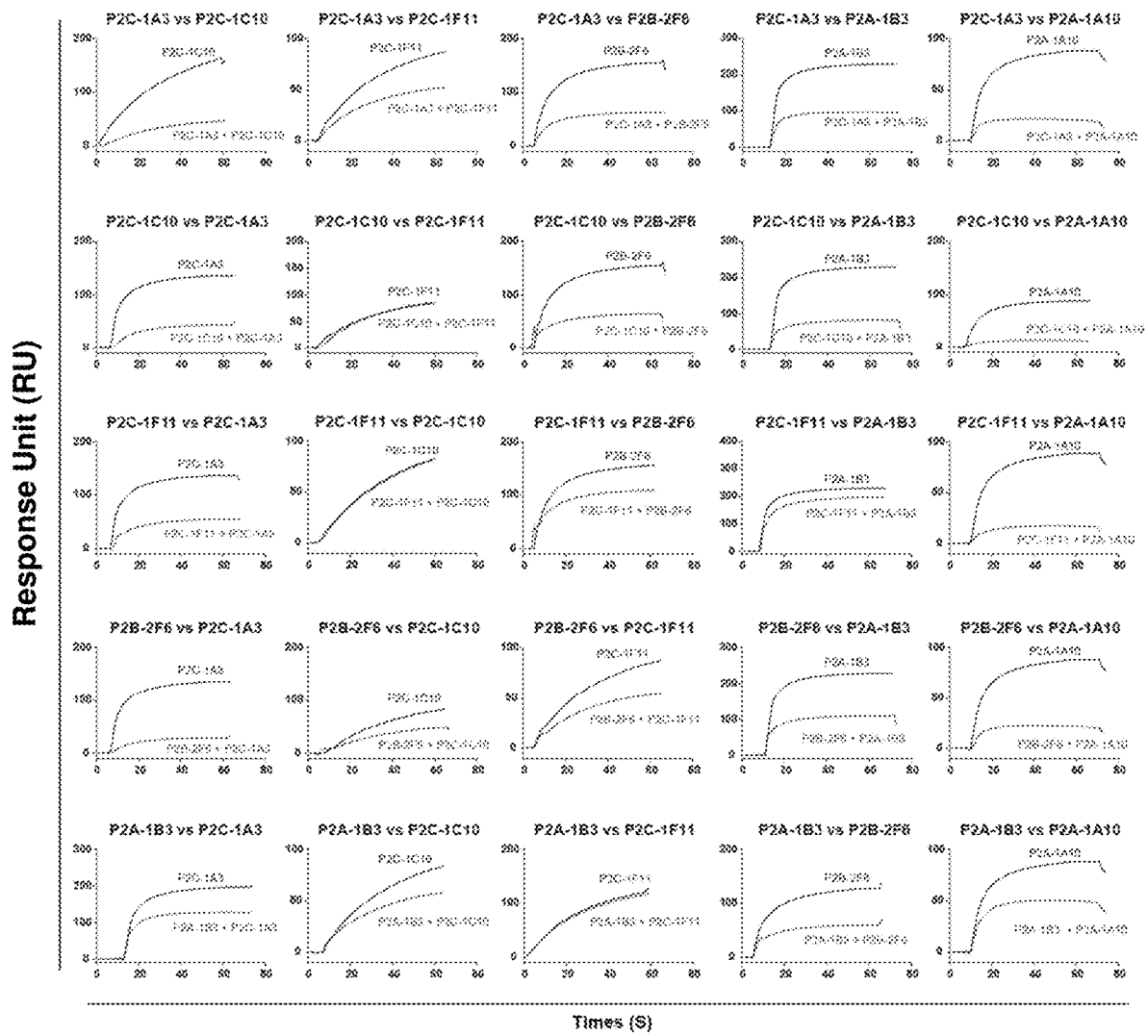
Figure 15A:
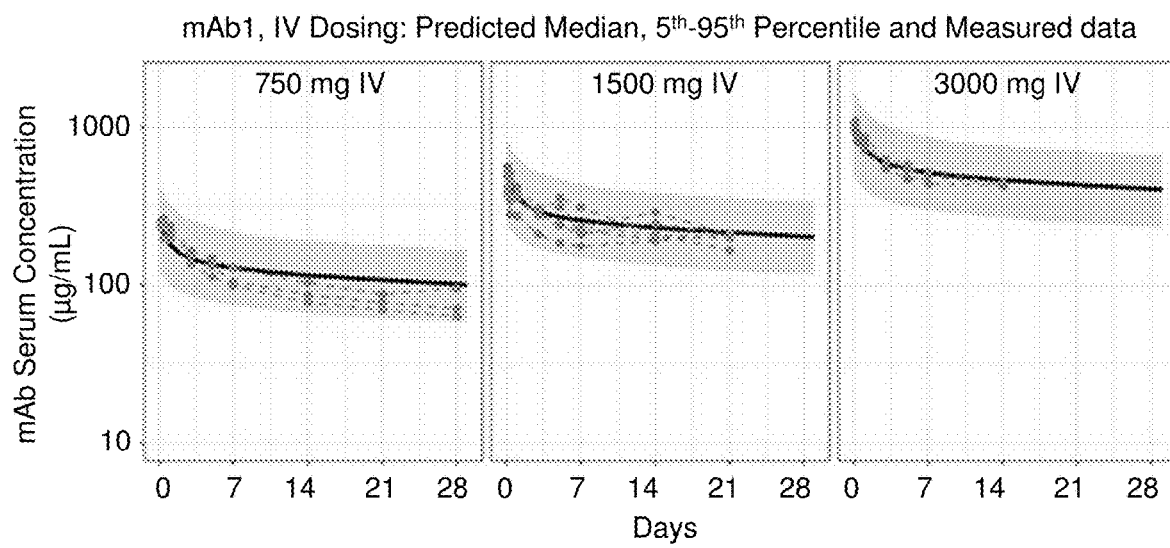
Figure 15B:
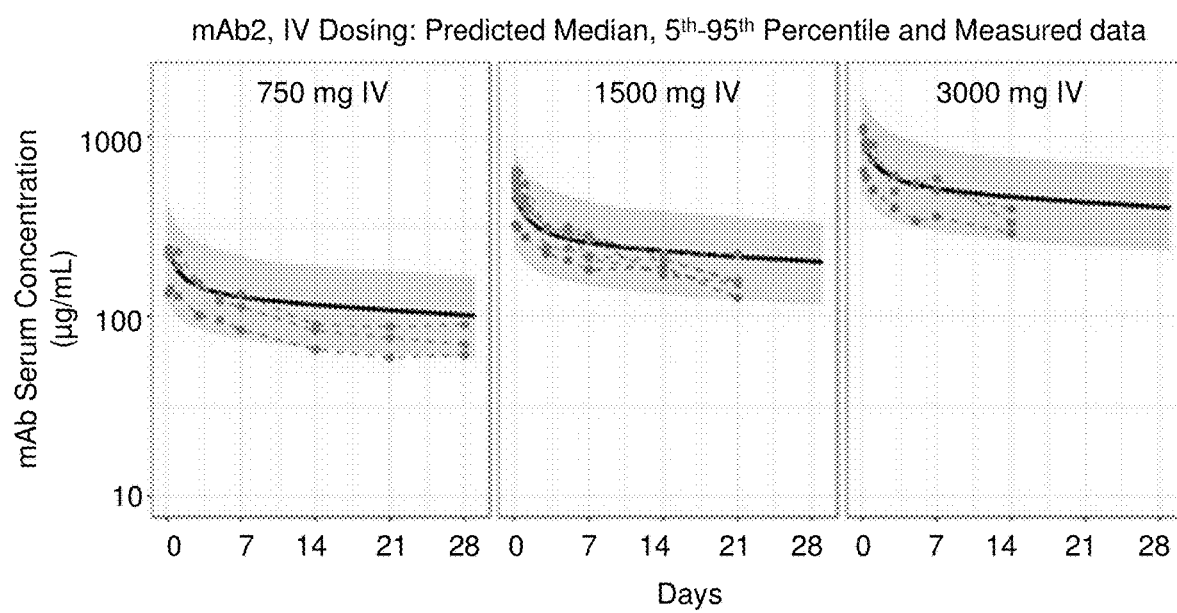
Figure 17A:
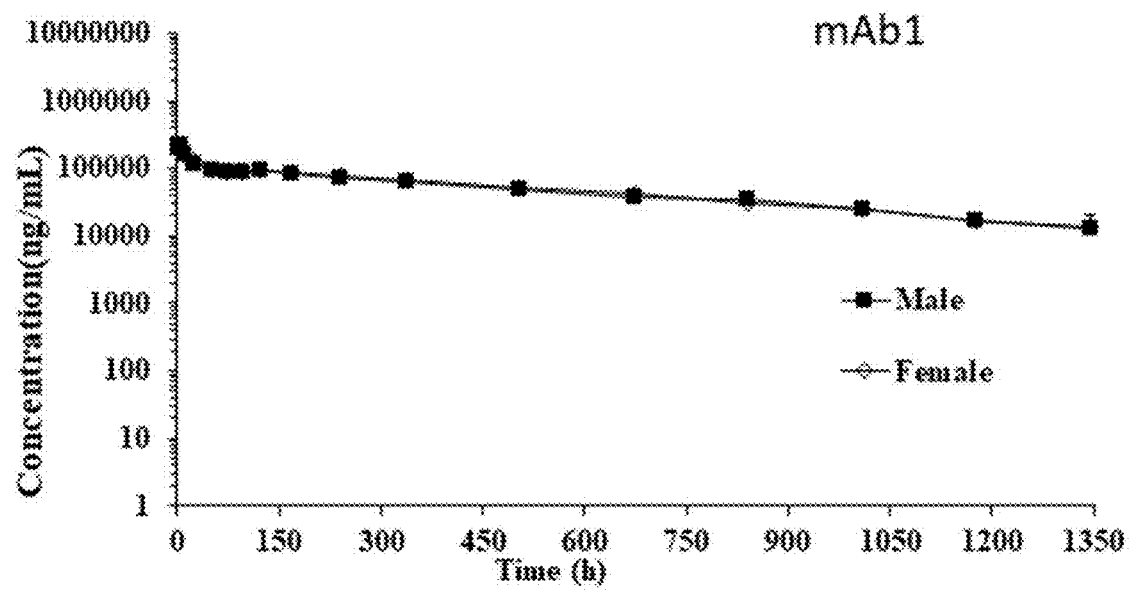
Figure 17B:
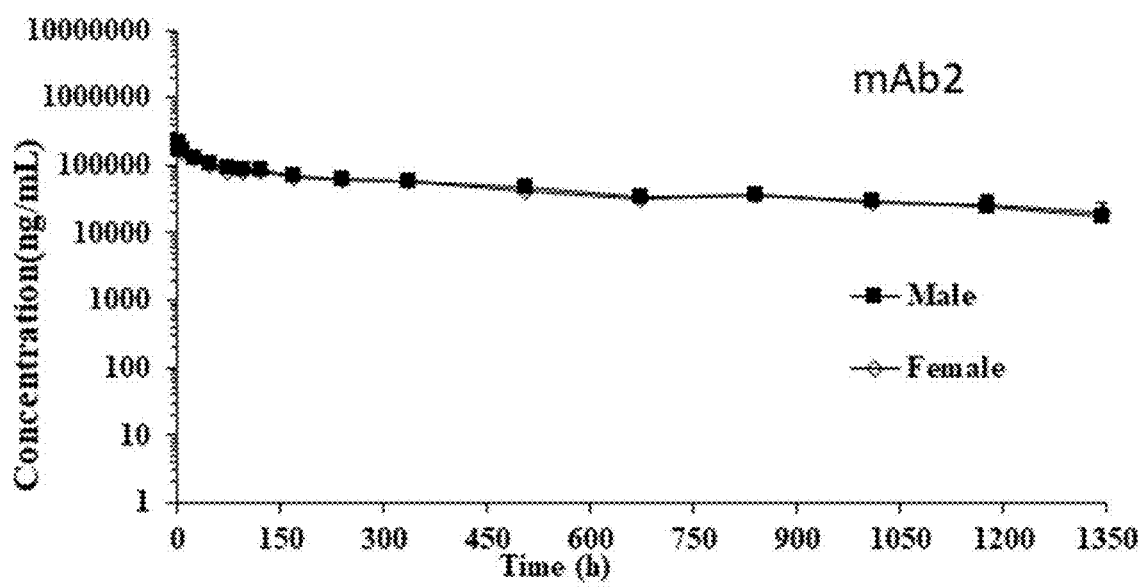

To determine whether these antibodies compete for similar epitopes on the SARS-CoV-2 RBD, a total of six antibodies with relative strong ACE2 competitive capacities and neutralization potency and analyzed in a pairwise competition fashion using SPR. As shown in Table 8 and FIG. 13, variable degrees of competition were found among the pairs of antibodies. P2C-1A3, for instance, was competitive against all antibodies tested with strong reduction capacity (FIG. 13). P2C-1F11, on the other hand, was less competitive with other antibodies and in particular, only minimally competitive with P2C-1C10. P2B-2F6, another potent neutralizing antibody, was broadly competitive with all antibodies tested. These results indicate that the antibodies analyzed recognized both overlapping and distinct epitopes. Different mAbs may therefore exert their neutralizing activity through different mechanisms.

Antibody P2B-1G5 was also analyzed in a pairwise competition fashion with P2C-1F11 using SPR. Results was shown in Table 7a, which suggested that P2B-1G5 is only minimally competitive with P2C-1F11.

Example 6

This example illustrates the structural basis for antibody neutralization.

Figure 5A:
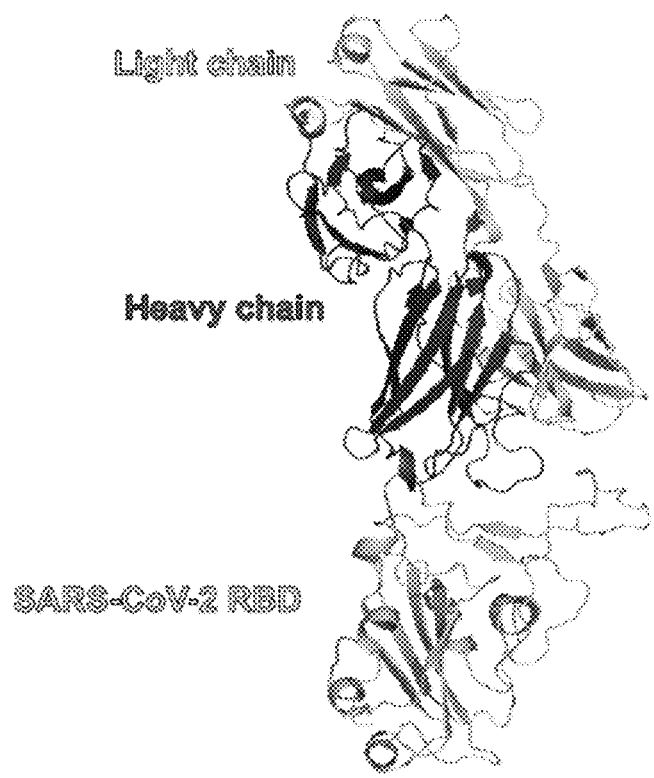
FIG. 5-FIG. 5T. Crystal structures of 2F6 and P2C-1F11 in complex with SARS-CoV-2 RBD respectively, and the lists of determined contacting residues at the antibody/SARS-CoV-2 interfaces. (A) Overall structure of 2F6 Fab in complex with SARS-CoV-2 RBD. (B) The critical interactions between 2F6 and SARS-CoV-2 RBD. (C) 2F6/RBD complex was aligned to ACE2/RBD complex (PDB ID: 6M0J). Circle indicated the clash between ACE2 and 2F6. (D) The SARS-CoV-2 spike (PDB ID: 6VSB) is shown as a molecular surface, with each protomer colored either light orange, blue and green. 2F6/RBD complex could be aligned to both the "up" RBD (light orange) and the "down" RBD (light blue) in spike. 2F6 heavy chain is colored in magenta, 2F6 light chain in yellow, SARS-CoV-2 RBD in cyan, and ACE2 in green. (E) Contacting residues at the SARS-CoV-2/2F6 interface. (F) Overall structure of P2C-1F11 Fab in complex with SARS-CoV-2 RBD. (G) Contacting residues at the SARS-CoV-2/1F11 interface. (H)-(K) Overall structures, crystal structures of the RBD and Fab complexes and RBD binding residues shared with ACE2 were shown for antibodies P22A-1D1, P5A-1D2, P5A-3C8 and P2C-1F11 respectively. (I) The footprint of Fabs and ACE2 on SARS-CoV-2 RBD. The color of the epitope was depicted as in panel (H). The epitope of ACE2 was colored by green. (J) (M) Conserved HCDR1, HCDR2 and different HCDR3. RBD was shown as surface. CDR loops of the heavy chain were shown as ribbons. (N) The interactions between three conserved tyrosine at HCDR1 and HCDR2. (O) The interactions between HCDR2-SGGS- segment and RBD. Hydrogen bonds were shown as black dashed line and P5A-3C8/RBD complex was used as an example in panel L and M. Y505 residue on RBD protruded into the wedge hole of the light chain For P22A-1D1 (Q), P5A-3C8 (R) and P2C-1F11 (S), whereas for P5A-1D2 (P) Y505 displayed a different conformation because of the binding of the long HCDR3. (T) Summary of contacts between SARS-CoV-2 RBD and P22A-1D1, P5A-3C8, P5A-1D2, P2C-1F11 (distance cutoff 4 Å).

The crystal structure of the top three most potent neutralizing antibodies in the first set of antibodies (P2C-1F11, P2B-2F6 and P2C-1A3) was determined. Of which, P2B-2F6 Fab and P2C-1F11 Fab bound to the SARS-CoV-2 RBD were able to form crystals and the structures of which were resolved at a resolution of 2.85 angstrom (FIG. 5A and FIG. 5F).

Figure 5B:
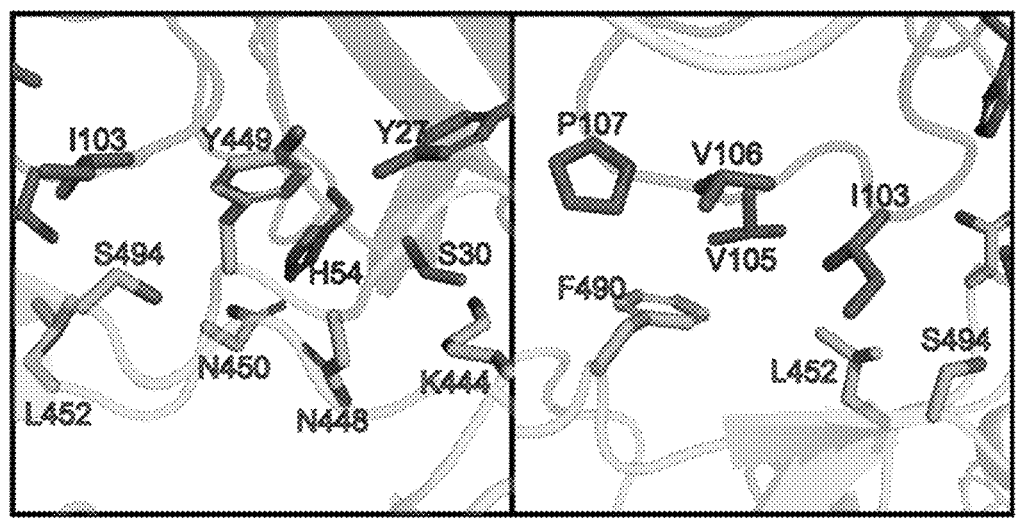
Figure 5C:
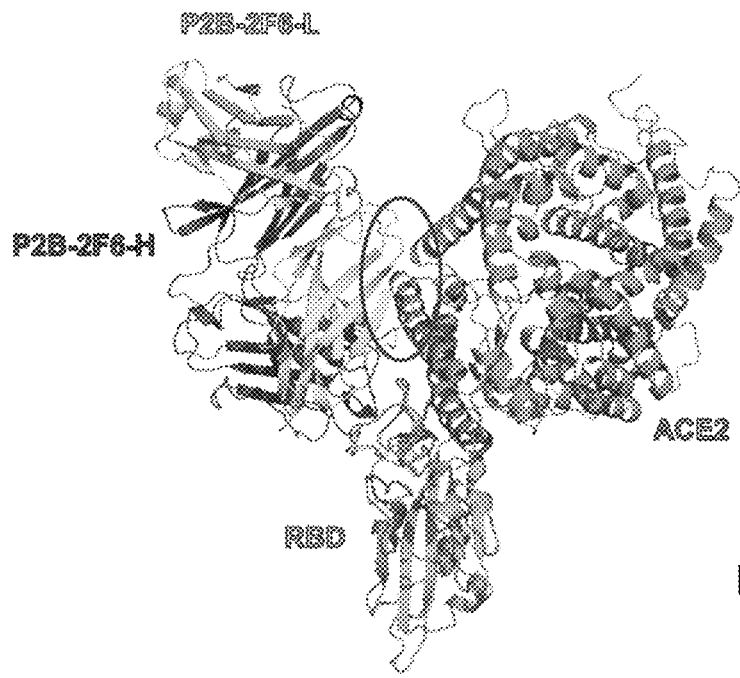
Figure 5D:
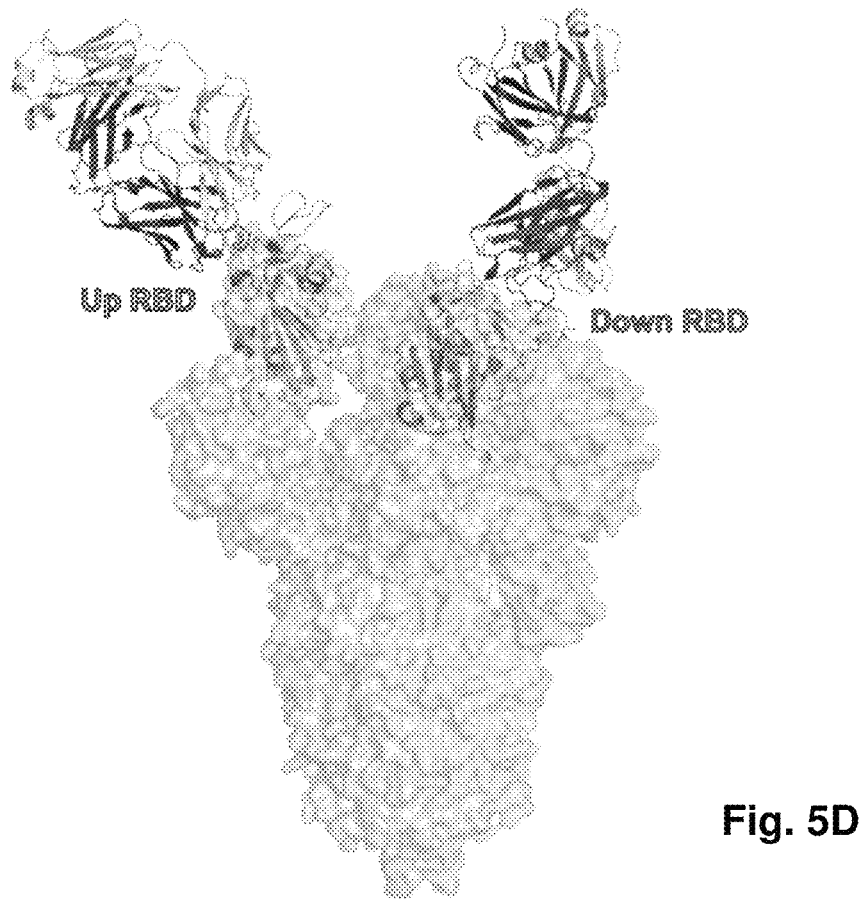
Figure 5H:
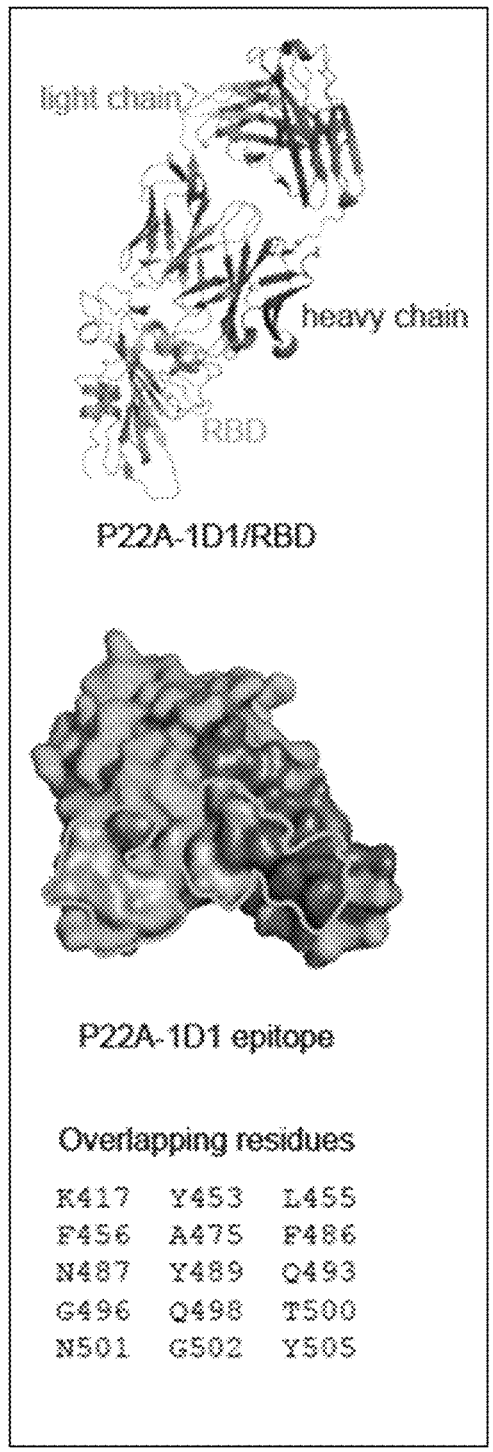

Antibody 2F6 mainly uses the heavy chain for interactions with the RBD, and the paratope region consists of 14 residues from the heavy chain (Y27, S28, S30, S31 and Y33 of HCDR1; H54 of HCDR2; G102, I103, V105, V106 and P107 of HCDR3) and 3 residues from the light chain (G31, Y32 and N33 of LCDR1) (FIG. 5E). The buried surface area on the RBD is 534 $A^2$ and the recognized epitope residues are all from the receptor-binding motif (RBM) of the RBD, including residues K444, G446, G447, N448, Y449, N450, L452, V483, E484, G485, F490 and S494 (FIG. 5E). SARS-CoV-2 recognition by 2F6 is largely driven by hydrophobic interactions around RBD residues Y449, L452 and F490 (FIG. 5B). Structural superimposition of the RBD-2F6 and RBD-ACE2 crystal structures indicated that the binding of 2F6 would clash with ACE2 (FIG. 5C). The clash would happen between the P2B-2F6 light chain (residues R56, S58, G59, R63, S78, G79) and the ACE2 (residues D67, K68, A71, K74, E110, K114). The overlapping residues recognized by 2F6 and ACE2 only include G446 and Y449, largely due to their difference in angles when they approach RBD. However, the high affinity binding of 2F6 to the RBD (5.14 nM), which is comparable to the binding affinity between RBD and ACE2 (4.70 nM), is expected to preclude the receptor ACE2 engagement, further supported by the high ACE2 competition efficiency of 2F6 in the SPR analysis (98.80% in FIG. 4O), second column). We also superimposed the RBD-2F6 crystal structure onto the cryo-EM structure of the SARS-COV-2 spike trimer, in which the RBD has two different "up" and "down" conformations. Unlike the ACE2 that only binds the "up" RBD, the 2F6 Fab is able bind to the RBD in both "up" and "down" conformations without clashing with two other monomers in the spike trimer (FIG. 5D). Therefore, we suggest that structural basis for 2F6 neutralization relies on directly competition with receptor ACE2 on spike binding.

Antibody 1F11 mainly uses the heavy chain for interactions with the RBD, and the paratope region consists of 17 residues from the heavy chain (G26, I27, T28, S31, N32 and Y33 of HCDR1; Y52, S53, G54, and S56 of HCDR2; Y58 of HFR3; R97, L99, V100, V101, Y102 and D105 of HCDR3) and 4 residues from the light chain (12 from the LFR1; S28, S30 and Y33 of LCDR1) (FIG. 5G). The buried surface area on the RBD is shown in FIG. 5G and the recognized 23 epitope residues are located in the RBM (Y453, L455, F456, R457, K458, S459, N460, Y473, A475, G476, S477, F486, N487, Y489, Q493, G502 and Y505) and the core (R403, T415, G416, K417, D420 and Y421) of the SARS-CoV-2 RBD (FIG. 5G). A network of hydrogen-bonding interactions (18 between heavy chain and RBD and 2 between light chain and RBD) dominates in the recognition of SARS-CoV-2 by 1F11.

Figure 5I:
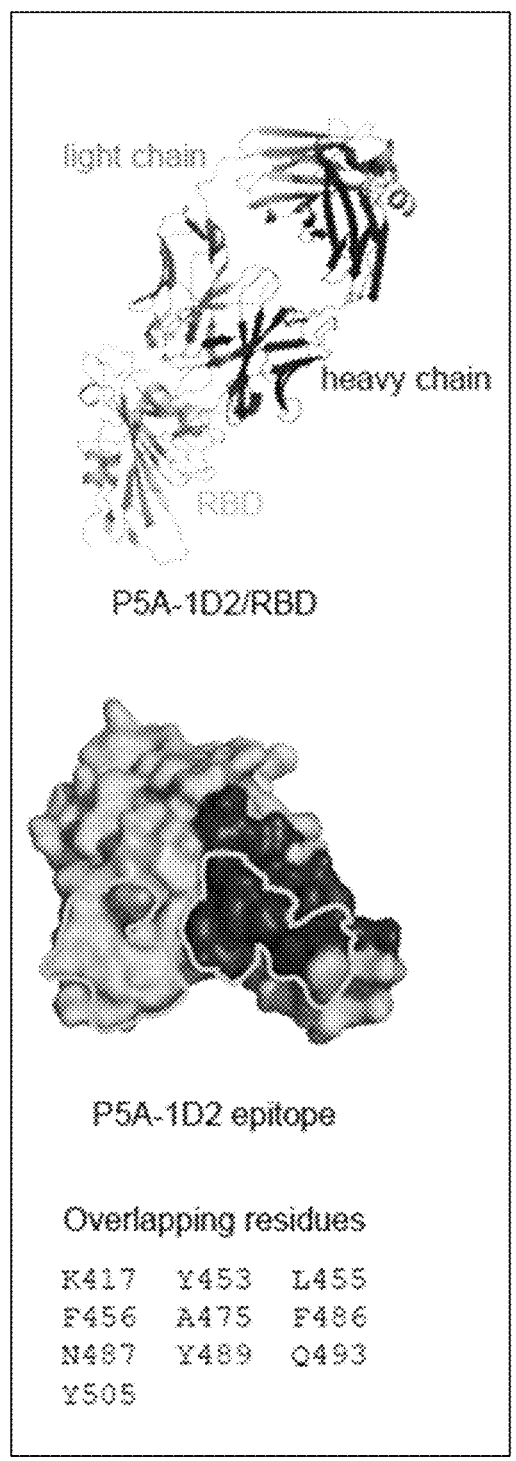
Figure 5J:
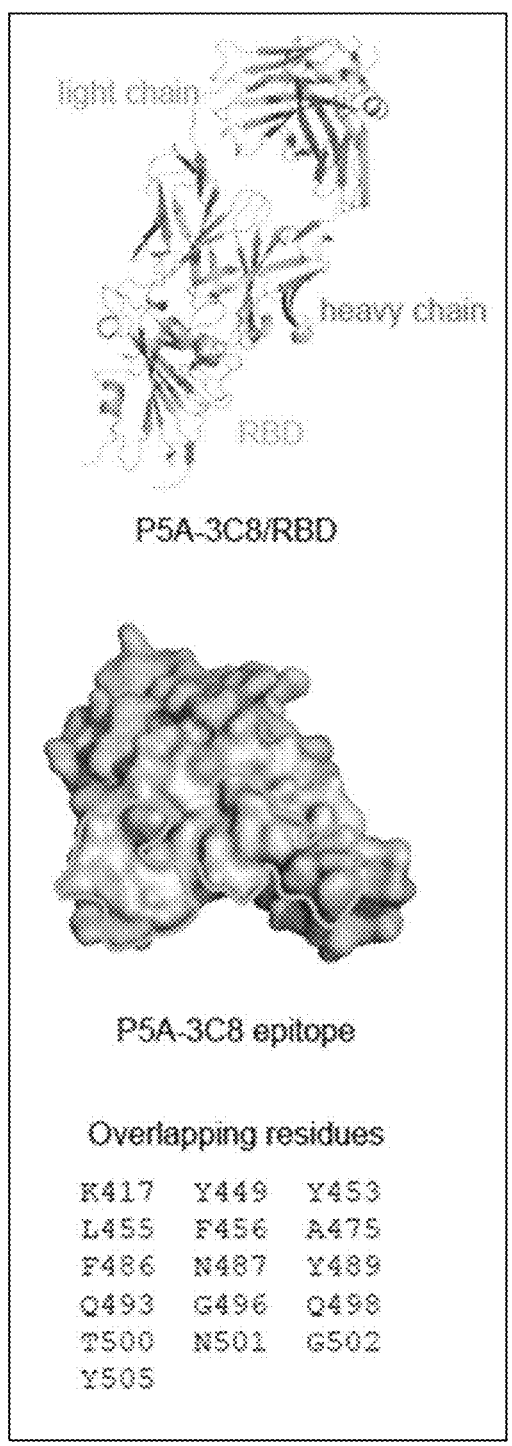
Figure 5K:
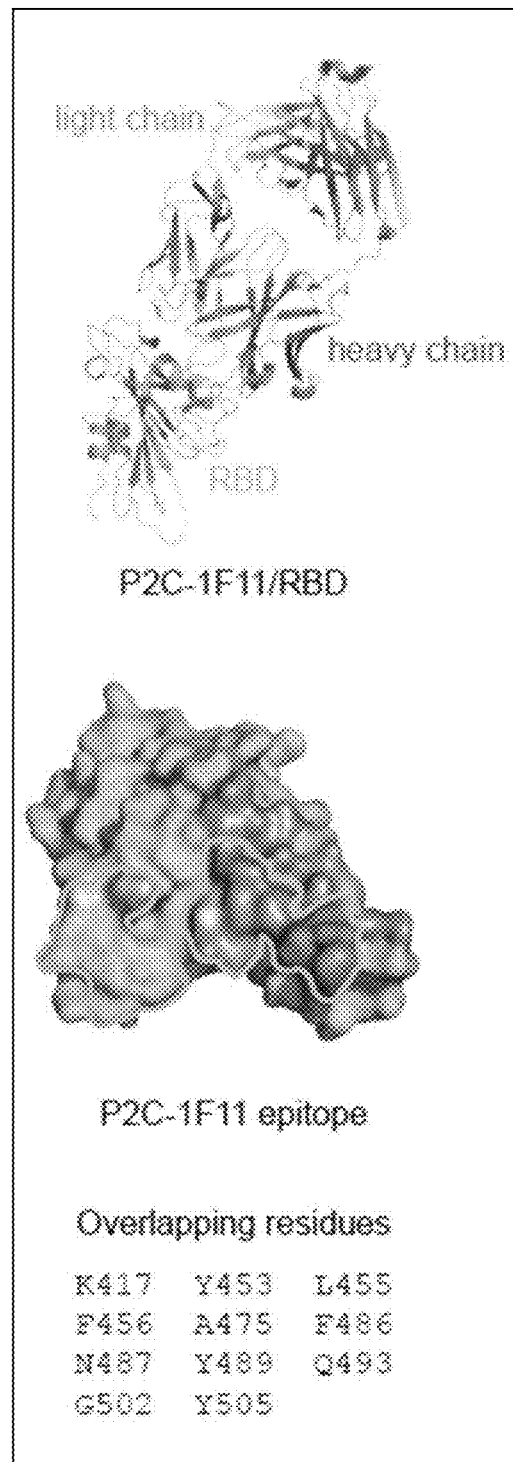
Figure 5L:
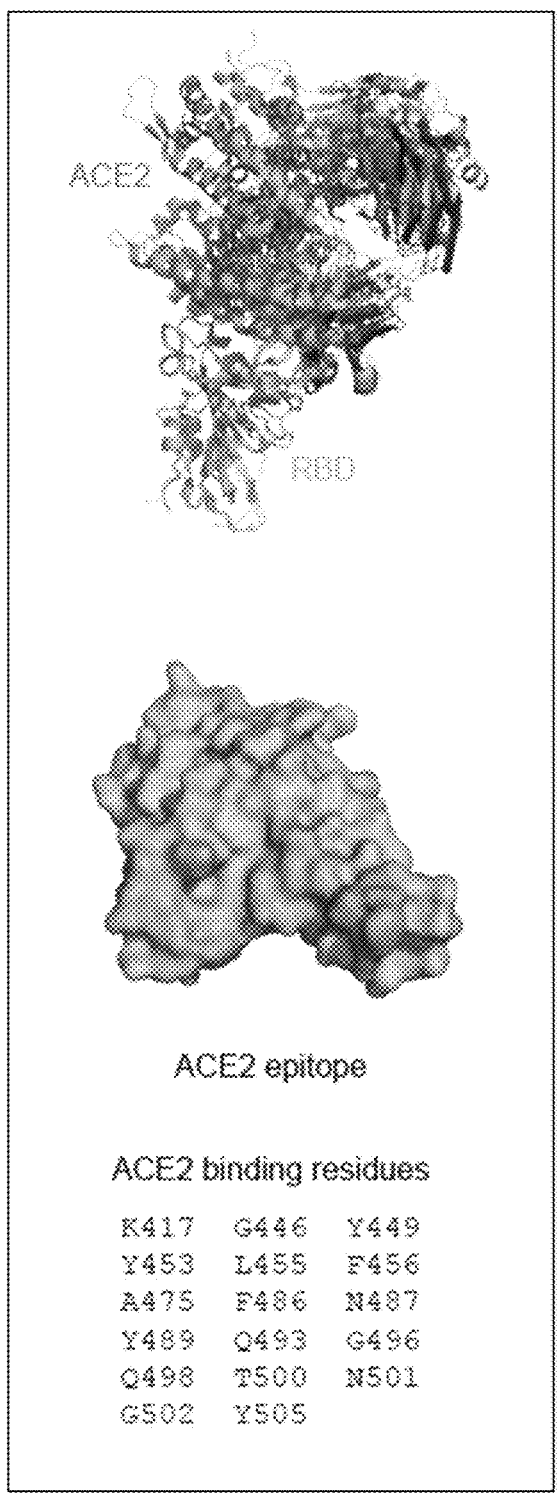
Figure 5M:
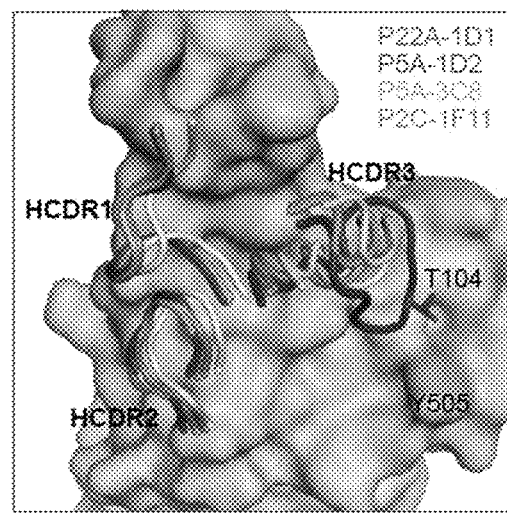
Figure 5N:
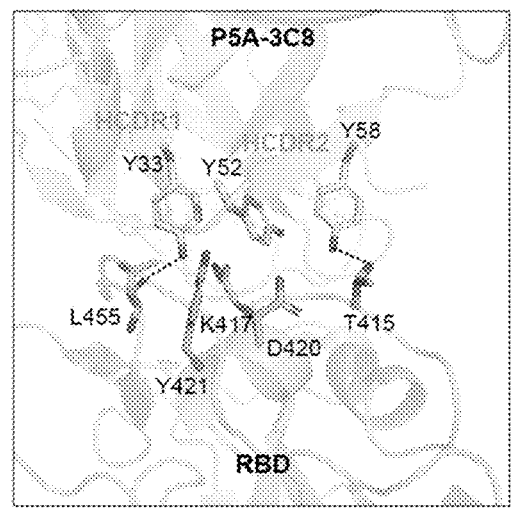
Figure 5O:
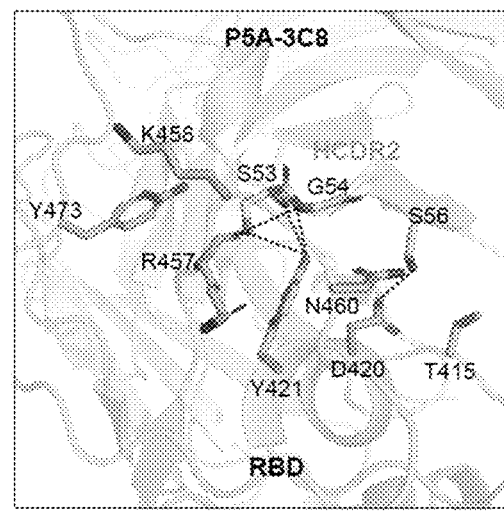
Figure 5P:
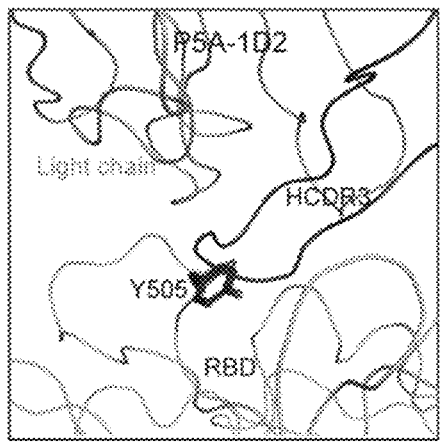
Figure 5Q:
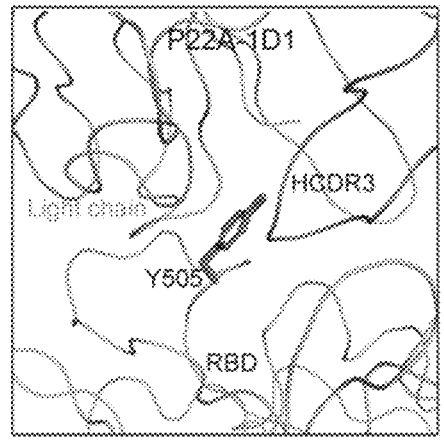
Figure 5R:
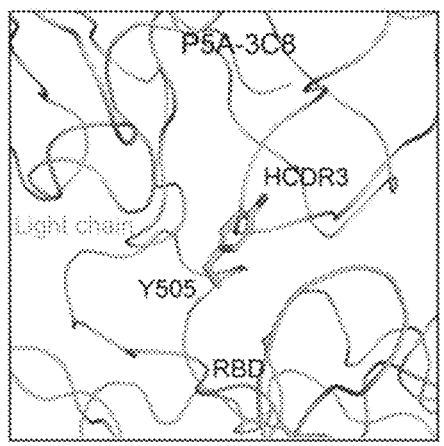
Figure 5S:
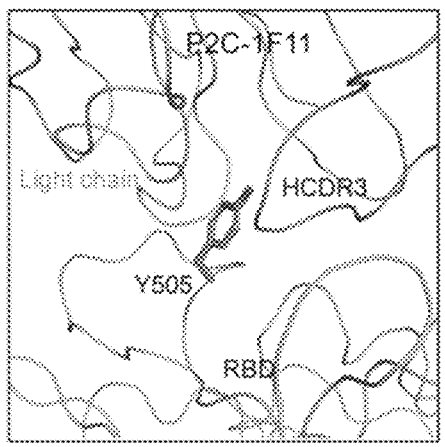

The crystal structures of P22A-1D1, P5A-3C8, and P5A-1D2 complexed with SARS-CoV-2 RBD (FIG. 5H and Table 10c) were also determined at a resolution of 2.40 Å, 2.36 Å, and 2.60 Å respectively. Antibody P2C-1F11 (2.96 Å) was used it for head to head comparison. As shown in FIGS. 5H, 5I, 5J, and 5K, these four antibodies (P22A-1D1, P5A-3C8, P5A-1D2 and P2C-1F11) bound to the RBD with a nearly identical angle of approach. The estimated clash volume with ACE2 was about ~20,000 $Å^3$ (FIG. 5H), consistent with biochemical data showing strong capacities to compete with ACE2 in binding to SARS-CoV-2 RBD (Table 9b). The heavy chains of antibodies P22A-1D1, P5A-3C8, P5A-1D2 and P2C-1F11 share similar buried surfaces on the RBD. The estimated areas are 726 Å$^2$ for P22A-1D1, 668 Å$^2$ for P5A-3C8, 823 Å$^2$ for P5A-1D2 and 725 Å$^2$ for P2C-1F11 (FIG. 5I). In contrast, the buried surface areas of the light chain are rather different. P22A-1D1 (413 Å$^2$) and P5A-3C8 (480 Å$^2$) are significantly larger than P5A-1D2 (152 Å$^2$) and P2C-1F11 (230 Å$^2$) (FIG. 5I). The larger buried areas are translated into more epitope residues. For instance, P22A-1D1 and P5A-3C8 have 28 and 31 epitope residues on the RBD whereas P5A-1D2 and P2C-1F11 have 22 and 23, respectively (FIG. 5S). Furthermore, the epitopes of these antibodies significantly overlap with the ACE2 binding residues on RBD. Out of 17 ACE2-binding residues on RBD, P22A-1D1 shared by 15, P5A-3C8 by 16, P5A-1D2 by 10, and P2C-1F11 by 11 (FIG. 5L). The similar angles of approach to and the large overlap in binding residues on the RBD suggest that these four public antibodies resemble ACE2 in binding to SARS-CoV-2. The coordinates and structure factor files for the P5A-1D2, P5A-3C8 and P22A-1D1/SARS-CoV-2 RBD complexes have been deposited in the Protein Data Bank (PDB) under accession numbers 7CHO, 7CHP, 7CHS, respectively.

As described in Example 3, the four antibodies P22A-1D1, P5A-3C8, P5A-1D2 and P2C-1F11 were all found to use IGHV3-53 or IGHV3-66 (Table 9b). The IGHV3-53 and IGHV3-66 share the identical germline amino acid sequence except one residue. It is therefore expected that the four antibodies shared their binding features to RBD primarily through residues in the heavy chain. As shown in FIG. 5M, all three HCDRs are involved in the binding of these four antibodies to the RBD. Heavy chain sequence alignments showed that the HCDR1 and HCDR2 are highly conserved, whereas the HCDR3 are rather different (FIG. 5P-FIG. 5S). Of note, P5A-1D2 has a longer HCDR3 (15 residues) than the rest three antibodies (11 residues).

Figure 5T:
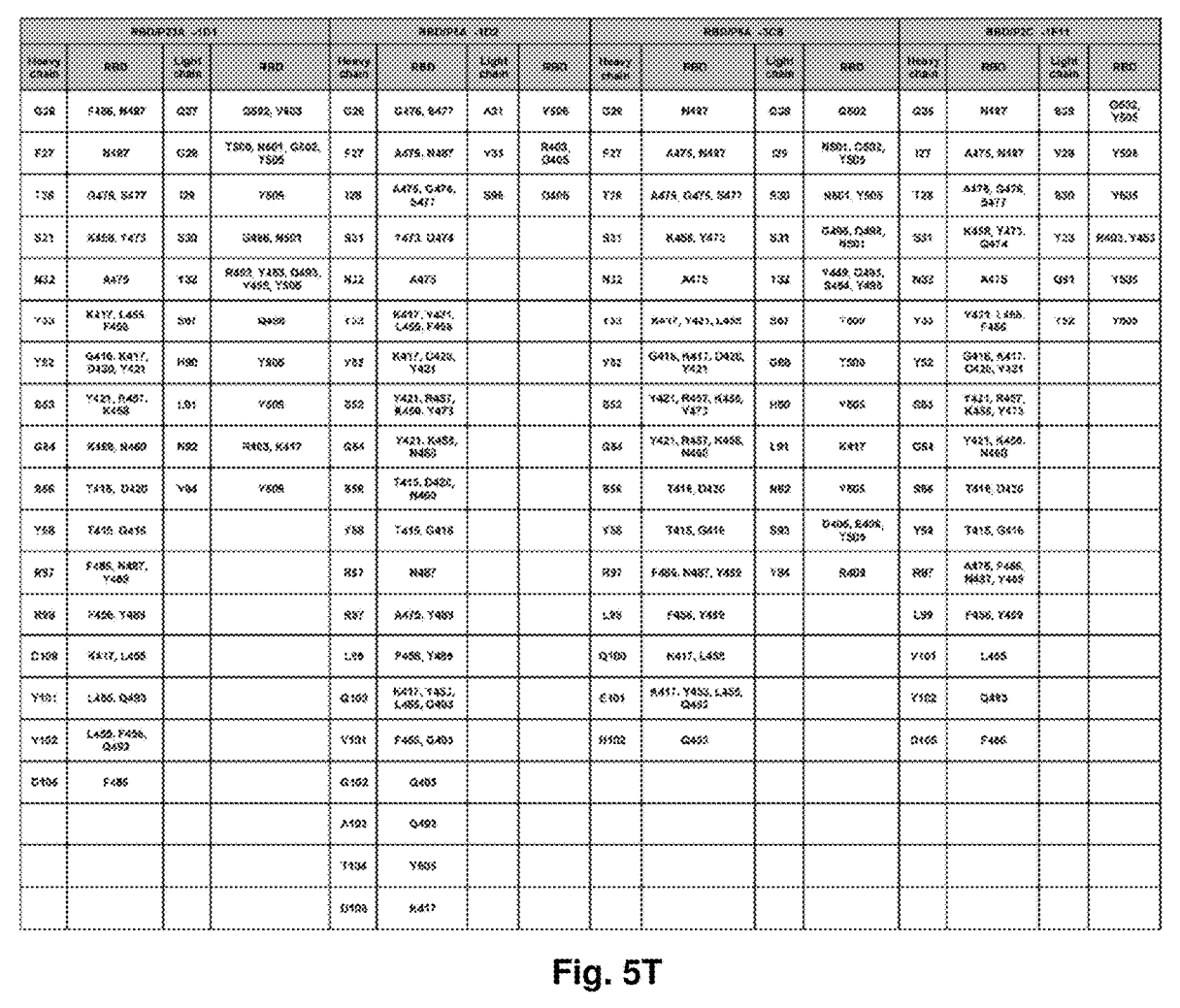

Antibody P22A-1D1 mainly uses the heavy chain for interactions with the RBD, and the paratope region consists of 17 residues from the heavy chain (G26, F27, T28, S31, N32, Y33, H52, S53, G54, S56, Y58, R97, R99, D100, Y101, Y102 and D105) and 10 residues from the light chain (Q27, G28, I29, S30, Y32, S67, H90, L91, N92 and Y94) (FIG. 5T). The buried surface area on the RBD is shown in FIG. 5T and the recognized 18 epitope residues are located in the SARS-CoV-2 RBD (T415, G416, K417, D420, Y421, L455, F456, R457, K458, N460, Y473, A475, G476, S477, F486, N487, Y489 and Q493) (FIG. 5T).

Antibody P5A-1D2 mainly uses the heavy chain for interactions with the RBD, and the paratope region consists of 20 residues from the heavy chain (G26, F27, I28, S31, N32, Y33, Y52, S53, G54, S56, Y58, R87, R97, L99, Q100, V101, G102, A103, T104 and D106) and 3 residues from the light chain (A31, Y33, S95) (FIG. 5T). The buried surface area on the RBD is shown in FIG. 5T and the recognized 20 epitope residues are located in the SARS-CoV-2 RBD (T415, G416, K417, D420, Y421, Y453, L455, F456, R457, K458, N460, Y473, Q474, A475, G476, S477, N487, Y489, Q493 and Y505) (FIG. 5T).

Antibody P5A-3C8 mainly uses the heavy chain for interactions with the RBD, and the paratope region consists of 16 residues from the heavy chain (G26, F27, T28, S31, N32, Y33, Y52, S53, G54, S56, Y58, R97, L99, Q100, E101 and H102) and 12 residues from the light chain (G28, I29, S30, S31, S67, G68, H90, L91, N92, S93 and Y94) (FIG. 5T). The buried surface area on the RBD is shown in FIG. 5T and the recognized 19 epitope residues are located in the SARS-CoV-2 RBD (T415, G416, K417, D420, Y421, Y453, L455, F456, R457, K458, N460, Y473, A475, G476, S477, F486, N487, Y489 and Q493) (FIG. 5T).

Antibody P2C-1F11 mainly uses the heavy chain for interactions with the RBD, and the paratope region consists of 16 residues from the heavy chain (G26, I27, T28, S31, N32, Y33, Y52, S53, G54, S56, R97, L99, V100, V101, Y102 and D105) and 3 residues from the light chain (S28, S30 and Y33) (FIG. 5T). The buried surface area on the RBD is shown in FIG. 5T and the recognized 19 epitope residues are located in the SARS-CoV-2 RBD (T415, G416, K417, D420, Y421, L455, F456, R457, K458, N460, Y473, Q474, A475, G476, S477, F486, N487, Y489 and Q493) (FIG. 5T).

In the shared HCDR1-RBD interface, the conserved HCDR1 residues G26, F27, T28/I28, S31, N32 and Y33 interact with RBD residues L455, K458, Y473, A475, G476, S477 and N487. In the shared HCDR2-RBD interface, interactions are largely mediated through HCDR2 residues Y52, S53, G54, S56 and Y58 and RBD residues T415, G416, K417, D420, Y421, K458 and N460. In particular, one unique feature shared by the four antibodies is the participation of three conserved tyrosines (Y33, Y52 and Y58) in forming a network of hydrophobic and hydrophilic interactions with the RBD (FIG. 5N). For example, the Y33 forms extensive hydrophobic interactions with RBD K417, Y421, L455 and F456 (FIG. 5N). Its side chain —OH also forms a conserved hydrogen bond with the main chain oxygen atom of RBD L455 (FIG. 5N). Another unique and shared feature is the interactions mediated by the -SGGS- segment in the HCDR2. Apart from the close contacts through Van der Waals forces, specific hydrogen-bonding interactions also occur between the beginning S53 and ending S56 with RBD Y421 and D420, respectively (FIG. 5O). In addition, RBD Y421 also forms a conserved hydrogen bond with main chain N atom of the G44 (FIG. 5O).

Despite of common and shared features, the four antibodies also demonstrated some minor differences due to their sequence and structure variations. P22A-1D1, P5A-3C8, and P2C-1F11 have the same 11-residue long HCDR3, but actual sequence varies. For example, the -RDYYG- in P22A-1D1 is replaced by -LQEHG- in P5A-3C8 and by -LVVYG- in P2C-1F11 (Table 9b). Therefore, although interacting with the same RBD residues such as F456, N487, Y489 and Q493, the specific residues in the HCDR3 in mediating such interactions are different. Compared to the other three, P5A-1D2 has a relatively longer HCDR3 with 15 residues (FIG. 5K and Table 9b), providing more residues to interact with RBD. For instance, the T104 at the tip of the P5A-1D2 HCDR3 has interactions with RBD Y505, which is absent in other three HCDR3-RBD interfaces (FIG. 5K). RBD Y505 is instead recognized by the light chain of P22A-1D1, P5A-3C8 and P2C-1F11, and appears to serves as an anchor residue for light chain binding (FIG. 5P-FIG. 5S). However, recognition by the long HCDR3 of P5A-1D2 resulted in significant change in the side chain conformation of Y505, precluding Y505 serving as an anchor for P5A-1D2 light chain binding (FIG. 5P-FIG. 5S).

To further dissect the impact of epitope residues on the binding of public antibodies, we conducted single-site alanine scanning mutagenesis for the 15 epitope residues shared among the public antibodies. All mutant spikes were successfully expressed on the surface of HEK 293T cells, as measured by the median fluorescence intensity (MFI) of the control S2 antibody through flow cytometry. However, of the 15 mutant residues, 12 resulted in more than 80% reduction in the binding of the four public antibodies although some antibodies are more sensitive than others (FIG. 6C, highlighted in grey boxes). For example, Y421A and F456A have broad impact on all four public antibodies, whereas T415A, Y473A, and N487A on three of the four. On the other hand, K417A, D420A, L455A, R457A, N460A, and Y489A only reduced binding for two of the four antibodies. In particular, Y505A appears to have more profound impact on P5A-1D2 than the rest three antibodies. This is perhaps due to the importance of Y505 in the heavy chain recognition through T104 at the tip of the HCDR3 as illustrated above. Taken together, these results indicate that some minor differences do exist among the four public antibodies despite of their overall similarity, which may account for their minor differences in binding and neutralizing activities. Lastly, 9 out of the 15 mutant residues also resulted in significant reduction of ACE2 binding to the surface expressed spike glycoprotein. These residues are highlighted in orange boxes including T415A, Y421A, L455A, F456A, R457A, Y473A, N487A, Y489A, and Y505A. The shared impact of these residues on ACE2 and the public antibodies support the abovementioned structural analysis (FIG. 5H-FIG. 5L).

Example 7

Half-Life and Human PK Results in Healthy Adult Subjects.

The half-life of the monoclonal antibody (mAb) in a typical 70 kg subject was determined:

mAb $T_{1/2}$=23.2 days (mAb with wild type human constant domain Fe)

mAb-YTE $T_{1/2}$=89.5 days (mAb with the YTE constant domain Fc)

The mAb1 and mAb2 antibodies were constructed and produced to contain the antigen-binding domain P2C-1F11 and P2B-1G5, respectively. Both antibodies contain the modified human IgG constant domain comprising a substitution with tyrosine at amino acid residue 252, a substitution with threonine at amino acid residue 254, and a substitution with glutamic acid at amino acid residue 256, numbered according to the EU index as in Kabat.

Healthy human adult subjects were administered with the antibody at specific dosages after obtaining consent according to protocols approved by the institutional review board (IRB) (IRB approval number (025)-02 and (026)-02, Ethical Committee of the Beijing Ditan Hospital, Capital Medical University). Blood samples were taken at indicated time points. Quantitation of mAb1 and mAb2 serum concentrations was conducted using a validated sandwich ELISA method using a commercially available His-tag SARS-CoV-2 Spike protein receptor binding domain as a capture reagent, and a commercially available mouse Anti-Human IgG Fc antibody labelled with horseradish peroxidase as detection reagent.

Three dose levels were performed: cohort 1 (750 mg), cohort 2 (1500 mg) and cohort 3 (3000 mg).

Using the established human population PK model, mAb1 and mAb2 PK profiles at different dose levels were measured and predicted using Monte Carlo simulation. The predicted medians are shown in FIG. 15A-FIG. 15B as solid lines for each cohort. Dashed lines and the dots represent measured concentrations in the subjects. The shaded areas represent the 5th-95th percentiles.

Example 8

Neutralization Effect.

The neutralizing activity of the mAb1 and mAb2 alone or in combination against live virus SARS-CoV-2 were measured using focus reduction neutralization test (FRNT) method. The two antibodies exhibited potent antiviral activity and the combination of two antibodies demonstrated a moderate additive effect in neutralizing live SARS-CoV-2 virus (FIG. 16).

Example 9

In Vivo Pharmacokinetics Assay.

The mAb1 and mAb2 single-dose PK was characterized after a 60-minutes IV infusion administration of the mAb1 and mAb2, respectively, to male and female naïve cynomolgus monkeys at 10 mg/kg (n=3 animals per sex group). The animal study was conducted under the approved protocols.

Blood samples were collected at pre-dose, 5 min, 30 minutes, 1 hour, 2 hours, 4 hours, 8 hours, 24 hours, 48 hours, 72 hours, 96 hours, 120 hours, 168 hours, 240 hours, 336 hours, 504 hours, 672 hours, 840 hours, 1008 hours, 1176 hours and 1344 hours post-end of infusion. Anti-drug antibody (ADA) samples were collected at pre-dose, 336 hours, 504 hours, 672 hours, 840 hours, 1008 hours, 1176 hours, and 1344 hours post-end of infusion. Concentrations of mAb1 or mAb2 in serum samples were determined by an ELISA method. The level of ADA responses in collected samples were determined using a validated ECL method. Pharmacokinetic non-compartmental analyses (NCA) were based on the time of IV infusion initiation time, Pharmacokinetics (PK) data for the mAb1 and mAb2 in Cynomolgus Monkey are shown in FIG. 17A (mAb1) and FIG. 17B (mAb2). mAb1 showed no marked sex differences at the dose level. Serum mAb1 and mAb2 concentrations declined in a biphasic manner after a single 10 mg/kg IV dose, with a concentration-time profile that indicated linear elimination.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Numbered Embodiments of the Disclosure

Other subject matter contemplated by the present disclosure is set out in the following numbered embodiments:

1. An isolated or recombinant antibody or an antigen-binding fragment thereof, which is capable of specifically binding to SARS-CoV-2, and exhibiting at least 50% less binding or non-detectable binding to SARS-CoV or MERS-CoV.

2. An isolated or recombinant antibody or an antigen-binding fragment thereof, having one or more features selected from the group consisting of:

a) capable of specifically binding to spike protein of SARS-CoV-2 and exhibiting at least 50% less binding to spike protein of SARS-CoV or spike protein of MERS-CoV;
b) capable of specifically binding to receptor-binding domain (RBD) of the spike protein of SARS-CoV-2 comprising the amino acid sequence of SEQ ID NO: 128;
c) exhibiting binding to RBD of spike protein of SARS-CoV comprising the amino acid sequence of SEQ ID NO: 124 at a level that is non-detectable or that is no more than 50% of the binding to the RBD of spike protein of SARS-CoV-2;
d) exhibiting binding to RBD of spike protein of MERS-CoV comprising the amino acid sequence of SEQ ID NO: 126 at a level that is non-detectable or that is no more than 50% of the binding to RBD of the spike protein of SARS-CoV-2;
e) capable of binding to the RBD of spike protein of SARS-CoV-2 at a $K_d$ value of no more than $1 \times 10^{-7}$ M as measured by Surface Plasmon Resonance (SPR);
f) exhibiting binding to the RBD of spike protein of SARS-CoV or the RBD of spike protein of MERS-CoV at a $K_d$ value of at least $1 \times 10^{-6}$ M as measured by SPR;
g) capable of exhibiting at least 30% competition at 1 μM, with 2 μM angiotensin converting enzyme 2 (ACE2) receptor, for binding to the RBD of spike protein of SARS-CoV-2 immobilized at a resonance units (RU) of 250, as measured by SPR; and
h) capable of binding to the RBD of spike protein of SARS-CoV-2 at a neutralizing activity at an $IC_{50}$ value of no more than 100 μg/ml, as measured by pseudovirus neutralization assay.

3. An isolated or recombinant antibody or an antigen-binding fragment thereof capable of specifically binding to RBD of spike protein of SARS-CoV-2, comprising:
a) 1, 2, or 3 heavy chain CDR sequences selected from SEQ ID NO: 1, SEQ ID NO: 2, and SEQ ID NO: 3;
b) 1, 2, or 3 heavy chain CDR sequences selected from SEQ ID NO: 11, SEQ ID NO: 12, and SEQ ID NO: 13;
c) 1, 2, or 3 heavy chain CDR sequences selected from SEQ ID NO: 21, SEQ ID NO: 22, and SEQ ID NO: 23;
d) 1, 2, or 3 heavy chain CDR sequences selected from SEQ ID NO: 31, SEQ ID NO: 32, and SEQ ID NO: 33;
e) 1, 2, or 3 heavy chain CDR sequences selected from SEQ ID NO: 41, SEQ ID NO: 42, and SEQ ID NO: 43;
f) 1, 2, or 3 heavy chain CDR sequences selected from SEQ ID NO: 51, SEQ ID NO: 52, and SEQ ID NO: 53;
g) 1, 2, or 3 heavy chain CDR sequences selected from SEQ ID NO: 65, SEQ ID NO: 66, and SEQ ID NO: 67;
h) 1, 2, or 3 heavy chain CDR sequences selected from SEQ ID NO: 75, SEQ ID NO: 76, and SEQ ID NO: 77;
i) 1, 2, or 3 heavy chain CDR sequences selected from SEQ ID NO: 85, SEQ ID NO: 86, and SEQ ID NO: 87;
j) 1, 2, or 3 heavy chain CDR sequences selected from SEQ ID NO: 95, SEQ ID NO: 96, and SEQ ID NO: 97;
k) 1, 2, or 3 heavy chain CDR sequences selected from SEQ ID NO: 105, SEQ ID NO: 106, and SEQ ID NO: 107;
l) 1, 2, or 3 heavy chain CDR sequences selected from SEQ ID NO: 136, SEQ ID NO: 137, and SEQ ID NO: 138;
m) 1, 2, or 3 heavy chain CDR sequences selected from SEQ ID NO: 146, SEQ ID NO: 147, and SEQ ID NO: 148;
n) 1, 2, or 3 heavy chain CDR sequences selected from SEQ ID NO: 156, SEQ ID NO: 157, and SEQ ID NO: 158;
o) 1, 2, or 3 heavy chain CDR sequences selected from SEQ ID NO: 166, SEQ ID NO: 167, and SEQ ID NO: 168;
p) 1, 2, or 3 heavy chain CDR sequences selected from SEQ ID NO: 176, SEQ ID NO: 177, and SEQ ID NO: 178;
q) 1, 2, or 3 heavy chain CDR sequences selected from SEQ ID NO: 186, SEQ ID NO: 187, and SEQ ID NO: 188;
r) 1, 2, or 3 heavy chain CDR sequences selected from SEQ ID NO: 196, SEQ ID NO: 197, and SEQ ID NO: 198;
s) 1, 2, or 3 heavy chain CDR sequences selected from SEQ ID NO: 206, SEQ ID NO: 207, and SEQ ID NO: 208;
t) 1, 2, or 3 heavy chain CDR sequences selected from SEQ ID NO: 216, SEQ ID NO: 217, and SEQ ID NO: 218;
u) 1, 2, or 3 heavy chain CDR sequences selected from SEQ ID NO: 226, SEQ ID NO: 227, and SEQ ID NO: 228;
v) 1, 2, or 3 heavy chain CDR sequences selected from SEQ ID NO: 236, SEQ ID NO: 237, and SEQ ID NO: 238;
w) 1, 2, or 3 heavy chain CDR sequences selected from SEQ ID NO: 246, SEQ ID NO: 247, and SEQ ID NO: 248;
x) 1, 2, or 3 heavy chain CDR sequences selected from SEQ ID NO: 256, SEQ ID NO: 257, and SEQ ID NO: 258;
y) 1, 2, or 3 heavy chain CDR sequences selected from SEQ ID NO: 266, SEQ ID NO: 267, and SEQ ID NO: 268;
z) 1, 2, or 3 heavy chain CDR sequences selected from SEQ ID NO: 276, SEQ ID NO: 277, and SEQ ID NO: 278;
aa) 1, 2, or 3 heavy chain CDR sequences selected from SEQ ID NO: 286, SEQ ID NO: 287, and SEQ ID NO: 288;
bb) 1, 2, or 3 heavy chain CDR sequences selected from SEQ ID NO: 296, SEQ ID NO: 297, and SEQ ID NO: 298;
cc) 1, 2, or 3 heavy chain CDR sequences selected from SEQ ID NO: 306, SEQ ID NO: 307, and SEQ ID NO: 308;
dd) 1, 2, or 3 heavy chain CDR sequences selected from SEQ ID NO: 316, SEQ ID NO: 317, and SEQ ID NO: 318;
ee) 1, 2, or 3 heavy chain CDR sequences selected from SEQ ID NO: 326, SEQ ID NO: 327, and SEQ ID NO: 328;
ff) 1, 2, or 3 heavy chain CDR sequences selected from SEQ ID NO: 336, SEQ ID NO: 337, and SEQ ID NO: 338;
gg) 1, 2, or 3 heavy chain CDR sequences selected from SEQ ID NO: 346, SEQ ID NO: 347, and SEQ ID NO: 348;
hh) 1, 2, or 3 heavy chain CDR sequences selected from SEQ ID NO: 356, SEQ ID NO: 357, and SEQ ID NO: 358;
ii) 1, 2, or 3 heavy chain CDR sequences selected from SEQ ID NO: 366, SEQ ID NO: 367, and SEQ ID NO: 368;

jj) 1, 2, or 3 heavy chain CDR sequences selected from SEQ ID NO: 376, SEQ ID NO: 377, and SEQ ID NO: 378;
kk) 1, 2, or 3 heavy chain CDR sequences selected from SEQ ID NO: 386, SEQ ID NO: 387, and SEQ ID NO: 388;
ll) 1, 2, or 3 heavy chain CDR sequences selected from SEQ ID NO: 396, SEQ ID NO: 397, and SEQ ID NO: 398;
mm) 1, 2, or 3 heavy chain CDR sequences selected from SEQ ID NO: 406, SEQ ID NO: 407, and SEQ ID NO: 408;
nn) 1, 2, or 3 heavy chain CDR sequences selected from SEQ ID NO: 416, SEQ ID NO: 417, and SEQ ID NO: 418; or
oo) 1, 2, or 3 heavy chain CDR sequences selected from SEQ ID NO: 426, SEQ ID NO: 427, and SEQ ID NO: 428.

4. The antibody or antigen binding fragment of any of the preceding embodiments, comprising:
a) 1, 2, or 3 light chain CDR sequences selected from SEQ ID NO: 4, SEQ ID NO: 5, and SEQ ID NO: 6;
b) 1, 2, or 3 light chain CDR sequences selected from SEQ ID NO: 14, SEQ ID NO: 15, and SEQ ID NO: 16;
c) 1, 2, or 3 light chain CDR sequences selected from SEQ ID NO: 24, SEQ ID NO: 25 and SEQ ID NO: 26;
d) 1, 2, or 3 light chain CDR sequences selected from SEQ ID NO: 34, SEQ ID NO: 35 and SEQ ID NO: 36;
e) 1, 2, or 3 light chain CDR sequences selected from SEQ ID NO: 44, SEQ ID NO: 45 and SEQ ID NO: 46;
f) 1, 2, or 3 light chain CDR sequences selected from SEQ ID NO: 54, SEQ ID NO: 55 and SEQ ID NO: 56;
g) 1, 2, or 3 light chain CDR sequences selected from SEQ ID NO: 68, SEQ ID NO: 69, and SEQ ID NO: 70;
h) 1, 2, or 3 light chain CDR sequences selected from SEQ ID NO: 78, SEQ ID NO: 79, and SEQ ID NO: 80; and
i) 1, 2, or 3 light chain CDR sequences selected from SEQ ID NO: 88, SEQ ID NO: 89, and SEQ ID NO: 90.
j) 1, 2, or 3 light chain CDR sequences selected from SEQ ID NO: 98, SEQ ID NO: 99, and SEQ ID NO: 100;
k) 1, 2, or 3 light chain CDR sequences selected from SEQ ID NO: 108, SEQ ID NO: 109, and SEQ ID NO: 110;
l) 1, 2, or 3 light chain CDR sequences selected from SEQ ID NO: 139, SEQ ID NO: 140, and SEQ ID NO: 141;
m) 1, 2, or 3 light chain CDR sequences selected from SEQ ID NO: 149, SEQ ID NO: 150, and SEQ ID NO: 151;
n) 1, 2, or 3 light chain CDR sequences selected from SEQ ID NO: 159, SEQ ID NO: 160, and SEQ ID NO: 161;
o) 1, 2, or 3 light chain CDR sequences selected from SEQ ID NO: 169, SEQ ID NO: 170, and SEQ ID NO: 171;
p) 1, 2, or 3 light chain CDR sequences selected from SEQ ID NO: 179, SEQ ID NO: 180, and SEQ ID NO: 181;
q) 1, 2, or 3 light chain CDR sequences selected from SEQ ID NO: 189, SEQ ID NO: 190, and SEQ ID NO: 191;
r) 1, 2, or 3 light chain CDR sequences selected from SEQ ID NO: 199, SEQ ID NO: 200, and SEQ ID NO: 201;
s) 1, 2, or 3 light chain CDR sequences selected from SEQ ID NO: 209, SEQ ID NO: 210, and SEQ ID NO: 211;
t) 1, 2, or 3 light chain CDR sequences selected from SEQ ID NO: 219, SEQ ID NO: 220, and SEQ ID NO: 221;
u) 1, 2, or 3 light chain CDR sequences selected from SEQ ID NO: 229, SEQ ID NO: 230, and SEQ ID NO: 231;
v) 1, 2, or 3 light chain CDR sequences selected from SEQ ID NO: 239, SEQ ID NO: 240, and SEQ ID NO: 241;
w) 1, 2, or 3 light chain CDR sequences selected from SEQ ID NO: 249, SEQ ID NO: 250, and SEQ ID NO: 251;
x) 1, 2, or 3 light chain CDR sequences selected from SEQ ID NO: 259, SEQ ID NO: 260, and SEQ ID NO: 261;
y) 1, 2, or 3 light chain CDR sequences selected from SEQ ID NO: 269, SEQ ID NO: 270, and SEQ ID NO: 271;
z) 1, 2, or 3 light chain CDR sequences selected from SEQ ID NO: 279, SEQ ID NO: 280, and SEQ ID NO: 281;
aa) 1, 2, or 3 light chain CDR sequences selected from SEQ ID NO: 289, SEQ ID NO: 290, and SEQ ID NO: 291;
bb) 1, 2, or 3 light chain CDR sequences selected from SEQ ID NO: 299, SEQ ID NO: 300, and SEQ ID NO: 301;
cc) 1, 2, or 3 light chain CDR sequences selected from SEQ ID NO: 309, SEQ ID NO: 310, and SEQ ID NO: 311;
dd) 1, 2, or 3 light chain CDR sequences selected from SEQ ID NO: 319, SEQ ID NO: 320, and SEQ ID NO: 321;
ee) 1, 2, or 3 light chain CDR sequences selected from SEQ ID NO: 329, SEQ ID NO: 330, and SEQ ID NO: 331;
ff) 1, 2, or 3 light chain CDR sequences selected from SEQ ID NO: 339, SEQ ID NO: 340, and SEQ ID NO: 341;
gg) 1, 2, or 3 light chain CDR sequences selected from SEQ ID NO: 349, SEQ ID NO: 350, and SEQ ID NO: 351;
hh) 1, 2, or 3 light chain CDR sequences selected from SEQ ID NO: 359, SEQ ID NO: 360, and SEQ ID NO: 361;
ii) 1, 2, or 3 light chain CDR sequences selected from SEQ ID NO: 369, SEQ ID NO: 370, and SEQ ID NO: 371;
jj) 1, 2, or 3 light chain CDR sequences selected from SEQ ID NO: 379, SEQ ID NO: 380, and SEQ ID NO: 381;
kk) 1, 2, or 3 light chain CDR sequences selected from SEQ ID NO: 389, SEQ ID NO: 390, and SEQ ID NO: 391;
ll) 1, 2, or 3 light chain CDR sequences selected from SEQ ID NO: 399, SEQ ID NO: 400, and SEQ ID NO: 401;
mm) 1, 2, or 3 light chain CDR sequences selected from SEQ ID NO: 409, SEQ ID NO: 410, and SEQ ID NO: 411;
nn) 1, 2, or 3 light chain CDR sequences selected from SEQ ID NO: 419, SEQ ID NO: 420, and SEQ ID NO: 421; or
oo) 1, 2, or 3 light chain CDR sequences selected from SEQ ID NO: 429, SEQ ID NO: 430, and SEQ ID NO: 431.

5. The antibody or antigen binding fragment of any of the preceding embodiments, comprising:
a) a heavy chain CDR1 (HCDR1) comprising the sequence of SEQ ID NO: 1, a heavy chain CDR2 (HCDR2) comprising the sequence of SEQ ID NO: 2, a heavy chain CDR3 (HCDR3) comprising the sequence of SEQ ID NO: 3; a light chain CDR1 (LCDR1) comprising the sequence of SEQ ID NO: 4, a light chain CDR2 (LCDR2) comprising the sequence of SEQ ID NO: 5, and a light chain CDR3 (LCDR3) comprising the sequence of SEQ ID NO: 6;

b) a HCDR1 comprising the sequence of SEQ ID NO: 11, a HCDR2 comprising the sequence of SEQ ID NO: 12, a HCDR3 comprising the sequence of SEQ ID NO: 13, a LCDR1 comprising the sequence of SEQ ID NO: 14, a LCDR2 comprising the sequence of SEQ ID NO: 15, and a LCDR3 comprising the sequence of SEQ ID NO: 16;

c) a HCDR1 comprising the sequence of SEQ ID NO: 21, a HCDR2 comprising the sequence of SEQ ID NO: 22, a HCDR3 comprising the sequence of SEQ ID NO: 23, a LCDR1 comprising the sequence of SEQ ID NO: 24, a LCDR2 comprising the sequence of SEQ ID NO: 25, and a LCDR3 comprising the sequence of SEQ ID NO: 26;

d) a HCDR1 comprising the sequence of SEQ ID NO: 31, a HCDR2 comprising the sequence of SEQ ID NO: 32, a HCDR3 comprising the sequence of SEQ ID NO: 33, a LCDR1 comprising the sequence of SEQ ID NO: 34, a LCDR2 comprising the sequence of SEQ ID NO: 35, and a LCDR3 comprising the sequence of SEQ ID NO: 36;

e) a HCDR1 comprising the sequence of SEQ ID NO: 41, a HCDR2 comprising the sequence of SEQ ID NO: 42, a HCDR3 comprising the sequence of SEQ ID NO: 43, a LCDR1 comprising the sequence of SEQ ID NO: 44, a LCDR2 comprising the sequence of SEQ ID NO: 45, and a LCDR3 comprising the sequence of SEQ ID NO: 46;

f) a HCDR1 comprising the sequence of SEQ ID NO: 51, a HCDR2 comprising the sequence of SEQ ID NO: 52, a HCDR3 comprising the sequence of SEQ ID NO: 53, a LCDR1 comprising the sequence of SEQ ID NO: 54, a LCDR2 comprising the sequence of SEQ ID NO: 55, and a LCDR3 comprising the sequence of SEQ ID NO: 56;

g) a HCDR1 comprising the sequence of SEQ ID NO: 65, a HCDR2 comprising the sequence of SEQ ID NO: 66, a HCDR3 comprising the sequence of SEQ ID NO: 67, a LCDR1 comprising the sequence of SEQ ID NO: 68, a LCDR2 comprising the sequence of SEQ ID NO: 69, and a LCDR3 comprising the sequence of SEQ ID NO: 70;

h) a HCDR1 comprising the sequence of SEQ ID NO: 75, a HCDR2 comprising the sequence of SEQ ID NO: 76, a HCDR3 comprising the sequence of SEQ ID NO: 77, a LCDR1 comprising the sequence of SEQ ID NO: 78, a LCDR2 comprising the sequence of SEQ ID NO: 79, and a LCDR3 comprising the sequence of SEQ ID NO: 80;

i) a HCDR1 comprising the sequence of SEQ ID NO: 85, a HCDR2 comprising the sequence of SEQ ID NO: 86, a HCDR3 comprising the sequence of SEQ ID NO: 87, a LCDR1 comprising the sequence of SEQ ID NO: 88, a LCDR2 comprising the sequence of SEQ ID NO: 89, and a LCDR3 comprising the sequence of SEQ ID NO: 90;

j) a HCDR1 comprising the sequence of SEQ ID NO: 95, a HCDR2 comprising the sequence of SEQ ID NO: 96, a HCDR3 comprising the sequence of SEQ ID NO: 97, a LCDR1 comprising the sequence of SEQ ID NO: 98, a LCDR2 comprising the sequence of SEQ ID NO: 99, and a LCDR3 comprising the sequence of SEQ ID NO: 100;

k) a HCDR1 comprising the sequence of SEQ ID NO: 105, a HCDR2 comprising the sequence of SEQ ID NO: 106, a HCDR3 comprising the sequence of SEQ ID NO: 107, a LCDR1 comprising the sequence of SEQ ID NO: 108, a LCDR2 comprising the sequence of SEQ ID NO: 109, and a LCDR3 comprising the sequence of SEQ ID NO: 110;

l) a HCDR1 comprising the sequence of SEQ ID NO: 136, a HCDR2 comprising the sequence of SEQ ID NO: 137, a HCDR3 comprising the sequence of SEQ ID NO: 138, a LCDR1 comprising the sequence of SEQ ID NO: 139, a LCDR2 comprising the sequence of SEQ ID NO: 140, and a LCDR3 comprising the sequence of SEQ ID NO: 141;

m) HCDR1 comprising the sequence of SEQ ID NO: 146, a HCDR2 comprising the sequence of SEQ ID NO: 147, a HCDR3 comprising the sequence of SEQ ID NO: 148, a LCDR1 comprising the sequence of SEQ ID NO: 149, a LCDR2 comprising the sequence of SEQ ID NO: 150, and a LCDR3 comprising the sequence of SEQ ID NO: 151;

n) HCDR1 comprising the sequence of SEQ ID NO: 156, a HCDR2 comprising the sequence of SEQ ID NO: 157, a HCDR3 comprising the sequence of SEQ ID NO: 158, a LCDR1 comprising the sequence of SEQ ID NO: 159, a LCDR2 comprising the sequence of SEQ ID NO: 160, and a LCDR3 comprising the sequence of SEQ ID NO: 161;

o) HCDR1 comprising the sequence of SEQ ID NO: 166, a HCDR2 comprising the sequence of SEQ ID NO: 167, a HCDR3 comprising the sequence of SEQ ID NO: 168, a LCDR1 comprising the sequence of SEQ ID NO: 169, a LCDR2 comprising the sequence of SEQ ID NO: 170, and a LCDR3 comprising the sequence of SEQ ID NO: 171;

p) HCDR1 comprising the sequence of SEQ ID NO: 176, a HCDR2 comprising the sequence of SEQ ID NO: 177, a HCDR3 comprising the sequence of SEQ ID NO: 178, a LCDR1 comprising the sequence of SEQ ID NO: 179, a LCDR2 comprising the sequence of SEQ ID NO: 180, and a LCDR3 comprising the sequence of SEQ ID NO: 181;

q) HCDR1 comprising the sequence of SEQ ID NO: 186, a HCDR2 comprising the sequence of SEQ ID NO: 187, a HCDR3 comprising the sequence of SEQ ID NO: 188, a LCDR1 comprising the sequence of SEQ ID NO: 189, a LCDR2 comprising the sequence of SEQ ID NO: 190, and a LCDR3 comprising the sequence of SEQ ID NO: 191;

r) HCDR1 comprising the sequence of SEQ ID NO: 196, a HCDR2 comprising the sequence of SEQ ID NO: 197, a HCDR3 comprising the sequence of SEQ ID NO: 198, a LCDR1 comprising the sequence of SEQ ID NO: 199, a LCDR2 comprising the sequence of SEQ ID NO: 200, and a LCDR3 comprising the sequence of SEQ ID NO: 201;

s) HCDR1 comprising the sequence of SEQ ID NO: 206, a HCDR2 comprising the sequence of SEQ ID NO: 207, a HCDR3 comprising the sequence of SEQ ID NO: 208, a LCDR1 comprising the sequence of SEQ ID NO: 209, a LCDR2 comprising the sequence of SEQ ID NO: 210, and a LCDR3 comprising the sequence of SEQ ID NO: 211;

t) HCDR1 comprising the sequence of SEQ ID NO: 216, a HCDR2 comprising the sequence of SEQ ID NO: 217, a HCDR3 comprising the sequence of SEQ ID NO: 218, a LCDR1 comprising the sequence of SEQ ID NO: 219, a LCDR2 comprising the sequence of SEQ ID NO: 220, and a LCDR3 comprising the sequence of SEQ ID NO: 221;

u) HCDR1 comprising the sequence of SEQ ID NO: 226, a HCDR2 comprising the sequence of SEQ ID NO: 227, a HCDR3 comprising the sequence of SEQ ID NO: 228, a LCDR1 comprising the sequence of SEQ ID NO: 229, a LCDR2 comprising the sequence of SEQ ID NO: 230, and a LCDR3 comprising the sequence of SEQ ID NO: 231;

v) HCDR1 comprising the sequence of SEQ ID NO: 236, a HCDR2 comprising the sequence of SEQ ID NO: 237, a HCDR3 comprising the sequence of SEQ ID NO: 238, a LCDR1 comprising the sequence of SEQ ID NO: 239, a LCDR2 comprising the sequence of SEQ ID NO: 240, and a LCDR3 comprising the sequence of SEQ ID NO: 241;

w) HCDR1 comprising the sequence of SEQ ID NO: 246, a HCDR2 comprising the sequence of SEQ ID NO: 247, a HCDR3 comprising the sequence of SEQ ID NO: 248, a LCDR1 comprising the sequence of SEQ ID NO: 249, a LCDR2 comprising the sequence of SEQ ID NO: 250, and a LCDR3 comprising the sequence of SEQ ID NO: 251;

x) HCDR1 comprising the sequence of SEQ ID NO: 256, a HCDR2 comprising the sequence of SEQ ID NO: 257, a HCDR3 comprising the sequence of SEQ ID NO: 258, a LCDR1 comprising the sequence of SEQ ID NO: 259, a LCDR2 comprising the sequence of SEQ ID NO: 260, and a LCDR3 comprising the sequence of SEQ ID NO: 261;

y) HCDR1 comprising the sequence of SEQ ID NO: 266, a HCDR2 comprising the sequence of SEQ ID NO: 267, a HCDR3 comprising the sequence of SEQ ID NO: 268, a LCDR1 comprising the sequence of SEQ ID NO: 269, a LCDR2 comprising the sequence of SEQ ID NO: 270, and a LCDR3 comprising the sequence of SEQ ID NO: 271;

z) HCDR1 comprising the sequence of SEQ ID NO: 276, a HCDR2 comprising the sequence of SEQ ID NO: 277, a HCDR3 comprising the sequence of SEQ ID NO: 278, a LCDR1 comprising the sequence of SEQ ID NO: 279, a LCDR2 comprising the sequence of SEQ ID NO: 280, a LCDR3 comprising the sequence of SEQ ID NO: 281;

aa) HCDR1 comprising the sequence of SEQ ID NO: 286, a HCDR2 comprising the sequence of SEQ ID NO: 287, a HCDR3 comprising the sequence of SEQ ID NO: 288, a LCDR1 comprising the sequence of SEQ ID NO: 289, a LCDR2 comprising the sequence of SEQ ID NO: 290, a LCDR3 comprising the sequence of SEQ ID NO: 291;

bb) HCDR1 comprising the sequence of SEQ ID NO: 296, a HCDR2 comprising the sequence of SEQ ID NO: 297, a HCDR3 comprising the sequence of SEQ ID NO: 298, a LCDR1 comprising the sequence of SEQ ID NO: 299, a LCDR2 comprising the sequence of SEQ ID NO: 300, a LCDR3 comprising the sequence of SEQ ID NO: 301;

cc) HCDR1 comprising the sequence of SEQ ID NO: 306, a HCDR2 comprising the sequence of SEQ ID NO: 307, a HCDR3 comprising the sequence of SEQ ID NO: 308, a LCDR1 comprising the sequence of SEQ ID NO: 309, a LCDR2 comprising the sequence of SEQ ID NO: 310, a LCDR3 comprising the sequence of SEQ ID NO: 311;

dd) HCDR1 comprising the sequence of SEQ ID NO: 316, a HCDR2 comprising the sequence of SEQ ID NO: 317, a HCDR3 comprising the sequence of SEQ ID NO: 318, a LCDR1 comprising the sequence of SEQ ID NO: 319, a LCDR2 comprising the sequence of SEQ ID NO: 320, a LCDR3 comprising the sequence of SEQ ID NO: 321;

ee) HCDR1 comprising the sequence of SEQ ID NO: 326, a HCDR2 comprising the sequence of SEQ ID NO: 327, a HCDR3 comprising the sequence of SEQ ID NO: 328, a LCDR1 comprising the sequence of SEQ ID NO: 329, a LCDR2 comprising the sequence of SEQ ID NO: 330, a LCDR3 comprising the sequence of SEQ ID NO: 331;

ff) HCDR1 comprising the sequence of SEQ ID NO: 336, a HCDR2 comprising the sequence of SEQ ID NO: 337, a HCDR3 comprising the sequence of SEQ ID NO: 338, a LCDR1 comprising the sequence of SEQ ID NO: 339, a LCDR2 comprising the sequence of SEQ ID NO: 340, a LCDR3 comprising the sequence of SEQ ID NO: 341;

gg) HCDR1 comprising the sequence of SEQ ID NO: 346, a HCDR2 comprising the sequence of SEQ ID NO: 347, a HCDR3 comprising the sequence of SEQ ID NO: 348, a LCDR1 comprising the sequence of SEQ ID NO: 349, a LCDR2 comprising the sequence of SEQ ID NO: 350, a LCDR3 comprising the sequence of SEQ ID NO: 351;

hh) HCDR1 comprising the sequence of SEQ ID NO: 356, a HCDR2 comprising the sequence of SEQ ID NO: 357, a HCDR3 comprising the sequence of SEQ ID NO: 358, a LCDR1 comprising the sequence of SEQ ID NO: 359, a LCDR2 comprising the sequence of SEQ ID NO: 360, a LCDR3 comprising the sequence of SEQ ID NO: 361;

ii) HCDR1 comprising the sequence of SEQ ID NO: 366, a HCDR2 comprising the sequence of SEQ ID NO: 367, a HCDR3 comprising the sequence of SEQ ID NO: 368, a LCDR1 comprising the sequence of SEQ ID NO: 369, a LCDR2 comprising the sequence of SEQ ID NO: 370, a LCDR3 comprising the sequence of SEQ ID NO: 371;

jj) HCDR1 comprising the sequence of SEQ ID NO: 376, a HCDR2 comprising the sequence of SEQ ID NO: 377, a HCDR3 comprising the sequence of SEQ ID NO: 378, a LCDR1 comprising the sequence of SEQ ID NO: 379, a LCDR2 comprising the sequence of SEQ ID NO: 380, a LCDR3 comprising the sequence of SEQ ID NO: 381;

kk) HCDR1 comprising the sequence of SEQ ID NO: 386, a HCDR2 comprising the sequence of SEQ ID NO: 387, a HCDR3 comprising the sequence of SEQ ID NO: 388, a LCDR1 comprising the sequence of SEQ ID NO: 389, a LCDR2 comprising the sequence of SEQ ID NO: 390, a LCDR3 comprising the sequence of SEQ ID NO: 391;

ll) HCDR1 comprising the sequence of SEQ ID NO: 396, a HCDR2 comprising the sequence of SEQ ID NO: 397, a HCDR3 comprising the sequence of SEQ ID NO: 398, a LCDR1 comprising the sequence of SEQ ID NO: 399, a LCDR2 comprising the sequence of SEQ ID NO: 400, a LCDR3 comprising the sequence of SEQ ID NO: 401;

mm) HCDR1 comprising the sequence of SEQ ID NO: 406, a HCDR2 comprising the sequence of SEQ ID NO: 407, a HCDR3 comprising the sequence of SEQ ID NO: 408, a LCDR1 comprising the sequence of SEQ ID NO: 409, a LCDR2 comprising the sequence of SEQ ID NO: 410, a LCDR3 comprising the sequence of SEQ ID NO: 411;

nn) HCDR1 comprising the sequence of SEQ ID NO: 416, a HCDR2 comprising the sequence of SEQ ID NO: 417, a HCDR3 comprising the sequence of SEQ ID NO: 418, a LCDR1 comprising the sequence of SEQ ID NO: 419, a LCDR2 comprising the sequence of SEQ ID NO: 420, a LCDR3 comprising the sequence of SEQ ID NO: 421; or oo) HCDR1 comprising the sequence of SEQ ID NO: 426, a HCDR2 comprising the sequence of SEQ ID NO: 427, a HCDR3 comprising the sequence of SEQ ID NO: 428, a LCDR1 comprising the sequence of SEQ ID NO: 429, a LCDR2 comprising the sequence of SEQ ID NO: 430, a LCDR3 comprising the sequence of SEQ ID NO: 431.

6. The antibody or antigen binding fragment of any of the preceding embodiments, comprising a pair of heavy chain variable region and light chain variable region sequences selected from the group consisting of: SEQ ID NOs: 7/8, 17/18, 27/28, 37/38, 47/48, 57/58, 61/62, 71/72, 81/82, 91/92, 101/102, 111/112, 142/143, 152/153, 162/163, 172/173, 182/183, 192/193, 202/203, 212/213, 222/223, 232/233, 242/243, 252/253, 262/263, 272/273, 282/283, 292/293, 302/303, 312/313, 322/323, 332/333, 342/343, 352/353, 362/363, 372/373, 382/383, 392/393, 402/403, 412/413, 422/423 and 432/433, or a pair of homologous sequences thereof having at least 80% sequence identity yet retaining binding specificity to RBD of spike protein of SARS-CoV-2.

7. The antibody or antigen binding fragment of embodiments 1 or 2, which is a variant of antibody P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, or P22A-1D1, which comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to a HCDR1 sequence of the parent antibody listed in Table 1, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to a HCDR2 sequence of the parent antibody listed in Table 1, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to a HCDR3 sequence of the parent antibody listed in Table 1, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to a LCDR1 sequence of the parent antibody listed in Table 1, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to a LCDR2 sequence of the parent antibody listed in Table 1, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to a LCDR3 sequence of the parent antibody listed in Table 1, and which retains the binding specificity to SARS-COV-2, optionally having binding affinity to SARS-COV-2 at a level similar to or even higher than its parent antibody.

8. The antibody or antigen binding fragment of embodiment 7, which comprises an HCDR1 having no more than 3, 2, or 1 amino acid mutations in a HCDR1 sequence of the parent antibody listed in Table 1, an HCDR2 having no more than 6, 5, 4, 3, 2, or 1 amino acid mutations in a HCDR2 sequence of the parent antibody listed in Table 1, HCDR3 having no more than 6, 5, 4, 3, 2, or 1 amino acid mutations in a HCDR3 sequence of the parent antibody listed in Table 1, LCDR1 having no more than 2 or 1 amino acid mutations in a LCDR1 sequence of the parent antibody listed in Table 1, LCDR2 having no more than 3, 2, or 1 amino acid mutations in a LCDR2 sequence of the parent antibody listed in Table 1, and/or LCDR3 having no more than 3, 2, or 1 amino acid mutations in a LCDR3 sequence of the parent antibody listed in Table 1.

9. The antibody or antigen binding fragment of any of the preceding embodiments, which comprises:

a) at least one heavy chain CDR sequence having no more than 3, 2, or 1 amino acid substitutions in a heavy chain CDR sequence of the parent antibody listed in Table 1, or b) at least two heavy chain CDR sequences each having no more than 3, 2, or 1 amino acid substitutions in a heavy chain CDR sequence of the parent antibody listed in Table 1, or c) three heavy chain CDR sequences each having no more than 3, 2, or 1 amino acid substitutions in a heavy chain CDR sequence of the parent antibody listed in Table 1, or d) at least one light chain sequence having no more than 3, 2, or 1 amino acid substitutions in a heavy chain CDR sequence of the parent antibody listed in Table 1, or e) at least two light chain CDR sequences each having no more than 3, 2, or 1 amino acid substitutions in a heavy chain CDR sequence of the parent antibody listed in Table 1, or f) three light chain CDR sequences each having no more than 3, 2, or 1 amino acid substitutions in a heavy chain CDR sequence of the parent antibody listed in Table 1.

10. The antibody or antigen binding fragment of embodiments 1 or 2, which is a variant of antibody P2B-2F6 and comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 41, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 42, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 43, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 44, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 45, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 46, and which retains the binding specificity to SARS-COV-2, optionally having binding affinity to SARS-COV-2 at a level similar to or even higher than antibody P2B-2F6.

11. The antibody or antigen binding fragment of embodiment 10, which comprises an HCDR1 having no more than 4, 3, 2, or 1 amino acid mutations in SEQ ID NO: 41, an HCDR2 having no more than 3, 2, or 1 amino acid mutations in SEQ ID NO: 42, HCDR3 having no more than 6, 5, 4, 3, 2, or I amino acid substitutions in SEQ ID NO: 43, LCDR1 having no more than 4, 3, 2, or 1 amino acid mutations in SEQ ID NO: 44, LCDR2 having no more than 3, 2, or 1 amino acid mutations in SEQ ID NO: 45, and/or LCDR3 having no more than 4, 3, 2, or 1 amino acid mutations in SEQ ID NO: 46.

12. The antibody or antigen binding fragment of embodiments 10 or 11, which retains the entirety of or at least part of the paratope of antibody P2B-2F6 while one or more of the amino acid residues outside the paratope of the antibody may be mutated.

13. The antibody or antigen binding fragment of embodiment 12, wherein the paratope of antibody P2B-2F6 comprises or consists of: Y27, S28, S30, S31, and Y33 of HCDR1, H54 of HCDR2, G102, I103, V105, V106 and P107 of HCDR3, and G31, Y32 and N33 of LCDR1, wherein the numbering of residues in the heavy chain CDRs is according to SEQ ID NO: 47, and the numbering of residues in the light chain CDR is according to SEQ ID NO: 48.

14. The antibody or antigen binding fragment of embodiments 1 or 2, which is a variant of antibody P2C-1F11, which comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 105, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 106, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 107, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 108, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 109, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 110, and which retains the binding specificity to SARS-COV-2, optionally having binding affinity to SARS-COV-2 at a level similar to or even higher than antibody P2C-1F11.

15. The antibody or antigen binding fragment of embodiment 14, which comprises an HCDR1 having no more than 4, 3, 2, or 1 amino acid mutations in SEQ ID NO: 105, an HCDR2 having no more than 3, 2, or 1 amino acid mutations in SEQ ID NO: 106, HCDR3 having no more than 6, 5, 4, 3, 2, or 1 amino acid mutations in SEQ ID NO: 107, LCDR1 having no more than 4, 3, 2, or 1 amino acid mutations in SEQ ID NO: 108, LCDR2 having no more than 3, 2, or 1 amino acid mutations in SEQ ID NO: 109, and/or LCDR3 having no more than 4, 3, 2, or 1 amino acid mutations in SEQ ID NO: 110, and in the meantime retain the binding specificity to SARS-COV-2, optionally having binding affinity to SARS-COV-2 at a level similar to or even higher than antibody P2C-1F11.

16. The antibody or antigen binding fragment of embodiment 14, which retains the entirety of or at least part of the paratope of antibody P2C-1F11 while one or more of the amino acid residues outside the paratope of the antibody may be mutated.

17. The antibody or antigen binding fragment of embodiment 16, wherein the paratope of antibody P2C-1F11 comprises or consists of: G26, I27, T28, S31, N32 and Y33 of HCDR1, Y52, S53, G54, and S56 of HCDR2, R97, L99, V100, V101, Y102 and D105 of HCDR3, and S28, S30 and Y33 of LCDR1 of LCDR1, wherein the numbering of residues in heavy chain is according to SEQ ID NO: 111, and the numbering of residues in light chain CDR is according to SEQ ID NO: 112.

18. The antibody or antigen binding fragment of embodiments 1 or 2, which is a variant of antibody P22A-1D1, wherein the variant comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 426, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 427, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 428, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 429, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 430, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 431, and in the meantime retain the binding specificity to SARS-COV-2, optionally having binding affinity to SARS-COV-2 at a level similar to or even higher than antibody P22A-1D1.

19. The antibody or antigen binding fragment of embodiment 18, which comprises an HCDR1 having no more than 6, 5, 4, 3, 2, or I amino acid mutations in SEQ ID NO: 426, an HCDR2 having no more than 5, 4, 3, 2, or 1 amino acid mutations in SEQ ID NO: 427, an HCDR3 having no more than 6, 5, 4, 3, 2, or 1 amino acid substitutions in SEQ ID NO: 428, an LCDR1 having no more than 5, 4, 3, 2, or 1 amino acid mutations in SEQ ID NO: 429, LCDR2 having no more than 1 amino acid mutations in SEQ ID NO: 430, and/or LCDR3 having no more than 4, 3, 2, or 1 amino acid mutations in SEQ ID NO: 431, and in the meantime retain the binding specificity to SARS-COV-2, optionally having binding affinity to SARS-COV-2 at a level similar to or even higher than antibody P22A-1D1.

20. The antibody or antigen binding fragment of embodiment 18, which retain the entirety of the paratope of antibody P22A-1D1 while one or more of the amino acid residues outside the paratope of the antibody may be mutated.

21. The antibody or antigen binding fragment of embodiments 20, wherein the paratope of antibody P22A-1D1 comprises or consists of: G26, F27, T28, S31, N32 and Y33 of HCDR1; Y52, S53, G54, and S56 of HCDR2, Y58 of heavy chain framework region 3; R97, R99, D100, Y101, Y102 and D105 of HCDR3; Q27, G28, I29, S30 and Y32 of LCDR1; S67 of LCDR2; and/or H90, L91, N92 and Y94 of LCDR3; wherein the numbering of residues in the heavy chain CDRs is according to SEQ ID NO: 432, and the numbering of residues in the light chain CDR is according to SEQ ID NO: 433.

22. The antibody or antigen binding fragment of embodiments 1 or 2, which is a variants of antibody P5A-1D2, wherein the variant comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 236, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 237, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 238, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 239, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 240, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 241, and in the meantime retain the binding specificity to SARS-COV-2, optionally having binding affinity to SARS-COV-2 at a level similar to or even higher than antibody P5A-1D2.

23. The antibody or antigen binding fragment of embodiment 22, which comprises an HCDR1 having no more than 4, 3, 2, or 1 amino acid mutations in SEQ ID NO: 236, an HCDR2 having no more than 3, 2, or 1 amino acid mutations in SEQ ID NO: 237, HCDR3 having no more than 6, 5, 4, 3, 2, or 1 amino acid substitutions in SEQ ID NO: 238, LCDR1 having no more than 4, 3, 2, or 1 amino acid mutations in SEQ ID NO: 239, LCDR2 having no more than 3, 2, or 1 amino acid mutations in SEQ ID NO: 240, and/or LCDR3 having no more than 4, 3, 2, or 1 amino acid mutations in SEQ ID NO: 241, and in the meantime retain the binding specificity to SARS-COV-2, optionally having binding affinity to SARS-COV-2 at a level similar to or even higher than antibody P5A-1D2.

24. The antibody or antigen binding fragment of embodiment 22, which retain the entirety of the paratope of antibody P5A-1D2 while one or more of the amino acid residues outside the paratope of the antibody may be mutated.

25. The antibody or antigen binding fragment of embodiment 24, wherein the paratope of antibody P5A-1D2 comprises or consists of: G26, F27, I28, S31, N32 and Y33 of HCDR1; Y52, S53, G54, and S56 of HCDR2; Y58 and R87 of heavy chain framework region 3, R97, L99, Q100, V101, G102, A103, T104 and D106 of HCDR3; A31 and Y33 of LCDR1; and/or S95 of LCDR3; wherein the numbering of residues in the heavy chain CDRs is according to SEQ ID NO: 242, and the numbering of residues in the light chain CDR is according to SEQ ID NO: 243.

26. The antibody or antigen binding fragment of embodiments 1 or 2, which is a variants of antibody P5A-3C8, wherein the variant comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 226, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 227, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 228, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 229, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 230, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 231, and in the meantime retain the binding specificity to SARS-COV-2, optionally having binding affinity to SARS-COV-2 at a level similar to or even higher than antibody P5A-3C8.

27. The antibody or antigen binding fragment of embodiment 26, which comprises an HCDR1 having no more than 4, 3, 2, or 1 amino acid mutations in SEQ ID NO: 226, an HCDR2 having no more than 3, 2, or I amino acid mutations in SEQ ID NO: 227, HCDR3 having no more than 6, 5, 4, 3, 2, or 1 amino acid substitutions in SEQ ID NO: 228, LCDR1 having no more than 4, 3, 2, or 1 amino acid mutations in SEQ ID NO: 229, LCDR2 having no more than 3, 2, or 1 amino acid mutations in SEQ ID NO: 230, and/or LCDR3 having no more than 4, 3, 2, or 1 amino acid mutations in SEQ ID NO: 231, and in the meantime retain the binding specificity to SARS-COV-2, optionally having binding affinity to SARS-COV-2 at a level similar to or even higher than antibody P5A-3C8.

28. The antibody or antigen binding fragment of embodiment 26, which retain the entirety of the paratope of antibody P5A-3C8 while one or more of the amino acid residues outside the paratope of the antibody may be mutated.

29. The antibody or antigen binding fragment of embodiment 28, wherein the paratope of antibody P5A-3C8 comprises or consists of: G26, F27, T28, S31, N32 and Y33 of HCDR1; Y52, S53, G54, and S56 of HCDR2; Y58 of heavy chain framework region 3, R97, L99, Q100, E101 and H102 of HCDR3; and G28, I29, S30, S31 and Y32 of LCDR1; S67 of LCDR2; G68 of light chain framework region 3, H90, L91, N92, S93 and Y94 of LCDR3; wherein the numbering of residues in the heavy chain CDRs is according to SEQ ID NO: 232, and the numbering of residues in the light chain CDR is according to SEQ ID NO: 233.

30. The antibody or antigen binding fragment of any of the preceding embodiments, further comprising an immunoglobulin constant region, optionally a constant region of human immunoglobulin, or optionally a constant region of human IgG.

31. The antibody or antigen binding fragment of any of the preceding embodiments, further comprising one or more amino acid residue mutations yet retains binding specificity to SARS-CoV-2, optionally binding affinity to RBD of spike protein of SARS-CoV-2.

32. The antibody or antigen binding fragment of embodiment 31, which is an affinity variant, a glycosylation variant, a cysteine-engineered variant, or an Fc variant.

33. The antibody or antigen binding fragment of embodiment 32, wherein the Fc variant comprises one or more amino acid residue modifications or substitutions resulting in increased effector functions relative to a wildtype Fc.

34. The antibody or antigen binding fragment of embodiment 33, wherein the Fc variant comprises one or more amino acid substitution(s) at one or more of the following positions: 234, 235, 236, 238, 239, 240, 241, 243, 244, 245, 246, 247, 248, 249, 252, 254, 255, 256, 258, 260, 262, 263, 264, 265, 267, 268, 269, 270, 272, 274, 276, 278, 280, 283, 285, 286, 289, 290, 292, 293, 294, 295, 296, 298, 299, 300, 301, 303, 304, 305, 307, 309, 312, 313, 315, 320, 322, 324, 325, 326, 327, 329, 330, 331, 332, 333, 334, 335, 337, 338, 339, 340, 345, 360, 373, 376, 378, 382, 388, 389, 396, 398, 414, 416, 419, 430, 433, 434, 435, 436, 437, 438, 439 and 440 of the Fc region, wherein the numbering of the residues in the Fc region is that of the EU index as in Kabat.

35. The antibody or antigen binding fragment of embodiment 34, wherein the Fc variant comprises one or more amino acid substitution selected from the group consisting of 234Y, 235Q, 236A, 236W, 239D, 239E, 239M, 243L, 247I, 267E, 268D, 268E, 268F, 270E, 280H, 290S, 292P, 298A, 298D, 298V, 300L, 305I, 324T, 326A, 326D, 326W, 330L, 330M, 333S, 332D, 332E, 298A, 333A, 334A, 334E, 339D, 339Q, 345R, 396L, 430G, 440Y, or any combination thereof.

36. The antibody or antigen binding fragment of embodiment 33, wherein the Fc variant comprises one or more amino acid residue modifications or substitutions resulting in reduced effector functions relative to a wildtype Fc.

37. The antibody or antigen binding fragment of embodiment 36, wherein the Fc variant comprises one or more amino acid substitution(s) at a position selected from the group consisting of: 220, 226, 229, 233, 234, 235, 236, 237, 238, 267, 268, 269, 270, 297, 309, 318, 320, 322, 325, 328, 329, 330, and 331 of the Fc region, wherein the numbering of the residues in the Fc region is that of the EU index as in Kabat.

38. The antibody or antigen binding fragment of embodiment 36, wherein the Fc variant comprises one or more amino acid substitution(s) selected from the group consisting of 220S, 226S, 228P, 229S, 233P, 234V, 234G, 234A, 234F, 234A, 235A, 235G, 235E, 236E, 236R, 237A, 237K, 238S, 267R, 268A, 268Q, 269R, 297A, 297Q, 297G, 309L, 318A, 322A, 325L, 328R, 330S, 331S, and any combination thereof.

39. The antibody or antigen binding fragment of embodiment 33, wherein the Fc variant comprises one or more amino acid residue modifications or substitutions resulting in improved serum half-life or improved binding affinity to neonatal Fc receptor (FcRn) at pH 6.0 while retaining minimal binding at pH 7.4.

40. The antibody or antigen binding fragment of embodiment 39, wherein the Fc variant comprises one or more amino acid substitution(s) at a position selected from the group consisting of: 234, 235, 238, 250, 252, 254, 256; 259; 272, 305, 307, 308, 311, 312, 322, 328, 331, 378, 380, 382, 428, 432, 433, 434, 435, 436 and 437 (all positions by EU numbering).

41. The antibody or antigen binding fragment of embodiment 40, wherein the Fc variant comprises one or more amino acid substitution(s) selected from the group consisting of 234F, 235Q, 238D, 250Q, 252T, 252Y, 254T, 256E, 259I, 272A, 305A, 307A, 308F, 311A, 322Q, 328E, 331S, 380A, 428L, 432C, 433K, 433S, 434S, 434Y, 434F, 434W, 434A, 435H, 436L, 437C and any combination thereof.

42. The antibody or antigen binding fragment of embodiment 31, wherein at least one of the substitutions or modifications is in one or more of the CDR sequences, and/or in one or more of the non-CDR sequences of the heavy chain variable region or light chain variable region.

43. The antibody or an antigen-binding fragment thereof of any one of the preceding embodiments, which is a monoclonal antibody, a bispecific antibody, a multi-specific antibody, a recombinant antibody, a chimeric antibody, a labeled antibody, a bivalent antibody, an anti-idiotypic antibody, a fusion protein, a dimerized or polymerized antibody, or a modified antibody (e.g. glycosylated antibody).

44. The antibody or antigen binding fragment of any of the preceding embodiments, which is a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a bispecific scFv dimer, a multispecific antibody, a heavy chain antibody, a camelized single domain antibody, a nanobody, a domain antibody, or a bivalent domain antibody.

45. The antibody or antigen binding fragment of any of preceding embodiments, which is bispecific and comprises a first antigen-binding domain and a second antigen-binding domain, wherein the first and the second antigen-binding domains are derived from any two monoclonal antibodies selected from the group consisting of P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C-1F11, P2B-1G5, P2B-1A1, P2C-1D7, P2B-1A10, P2B-1D9, P2B-1E4, P2B-1G1, P4A- 2D9, P5A-2G7, P5A-3C8, P5A-1D2, P5A-2F11, P5A-2E1, P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C- 1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B- 1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, and P22A-1D1.

46. The antibody or antigen binding fragment of embodiment 45, wherein the first and the second antigen-binding domains are derived:
   a) from P2C-1F11 and P2B-2F6, respectively;
   b) from P2C-1F11 and P2A-1A8, respectively;
   c) from P2C-1F11 and P2A-1A9, respectively;

d) from P2C-1F11 and P2B-2G11, respectively;
e) from P2C-1F11 and P2A-1A10, respectively;
f) from P2C-1F11 and P2A-1B3, respectively;
g) from P2C-1F11 and P2B-2G4, respectively;
h) from P2C-1F11 and P2C-1A3, respectively;
i) from P2C-1F11 and P2C-1C8, respectively;
j) from P2C-1F11 and P2C-1C10, respectively;
k) from P2C-1F11 and P2C-1D5, respectively;
l) from P2A-1A8 and P2A-1A9, respectively;
m) from P2A-1A8 and P2B-2G11, respectively;
n) from P2A-1A8 and P2A-1A10, respectively;
o) from P2A-1A8 and P2A-1B3, respectively;
p) from P2A-1A8 and P2B-2F6, respectively;
q) from P2A-1A8 and P2B-2G4, respectively;
r) from P2A-1A8 and P2C-1A3, respectively;
s) from P2A-1A8 and P2C-1C8, respectively;
t) from P2A-1A8 and P2C-1C10, respectively;
u) from P2A-1A8 and P2C-1D5, respectively;
v) from P2A-1A9 and 2B-2G11, respectively;
w) from P2A-1A9 and P2A-1A10, respectively;
x) from P2A-1A9 and P2A-1B3, respectively;
y) from P2A-1A9 and P2B-2F6, respectively;
z) from P2A-1A9 and P2B-2G4, respectively;
aa) from P2A-1A9 and P2C-1A3, respectively;
bb) from P2A-1A9 and P2C-1C8, respectively;
cc) from P2A-1A9 and P2C-1C10, respectively;
dd) from P2A-1A9 and P2C-1D5, respectively;
ee) from P2B-2G11 and P2A-1A10, respectively;
ff) from P2B-2G11 and P2A-1B3, respectively;
gg) from P2B-2G11 and P2B-2F6, respectively;
hh) from P2B-2G11 and P2B-2G4, respectively;
ii) from P2B-2G11 and P2C-1A3, respectively;
jj) from P2B-2G11 and P2C-1C8, respectively;
kk) from P2B-2G11 and P2C-1C10, respectively;
ll) from P2B-2G11 and P2C-1D5, respectively;
mm) from P2A-1A10 and P2A-1B3, respectively;
nn) from P2A-1A10 and P2B-2F6, respectively;
oo) from P2A-1A10 and P2B-2G4, respectively;
pp) from P2A-1A10 and P2C-1A3, respectively;
qq) from P2A-1A10 and P2C-1C8, respectively;
rr) from P2A-1A10 and P2C-1C10, respectively;
ss) from P2A-1A10 and P2C-1D5, respectively;
tt) from P2A-1B3 and P2B-2F6, respectively;
uu) from P2A-1B3 and P2B-2G4, respectively;
vv) from P2A-1B3 and P2C-1A3, respectively;
ww) from P2A-1B3 and P2C-1C8, respectively;
xx) from P2A-1B3 and P2C-1C10, respectively;
yy) from P2A-1B3 and P2C-1D5, respectively;
zz) from P2B-2F6 and P2B-2G4, respectively;
aaa) from P2B-2F6 and P2C-1A3, respectively;
bbb) from P2B-2F6 and P2C-1C8, respectively;
ccc) from P2B-2F6 and P2C-1C10, respectively;
ddd) from P2B-2F6 and P2C-1D5, respectively;
eee) from P2B-2G4 and P2C-1A3, respectively;
fff) from P2B-2G4 and P2C-1C8, respectively;
ggg) from P2B-2G4 and P2C-1C10, respectively;
hhh) from P2B-2G4 and P2C-1D5, respectively;
iii) from P2C-1A3 and P2C-1C8, respectively;
jjj) from P2C-1A3 and P2C-1C10, respectively;
kkk) from P2C-1A3 and P2C-1D5, respectively;
lll) from P2C-1C8 and P2C-1C10, respectively;
mmm) from P2C-1C8 and P2C-1D5, respectively; or
nnn) from P2C-1C10 and P2C-1D5, respectively.

47. The antibody or antigen binding fragment of embodiments 1 or 2, which is bispecific and comprises a first antigen-binding domain and a second antigen-binding domain, wherein the first and the second antigen-binding domains are derived from any two monoclonal antibodies selected from the group consisting of P2C-1F11, P2B-2F6, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-1D1, P5A-1D10, P5A-2D11, P5A-2G9, P5A-2H3, P5A-3A1, P5A-3A6, P5A-3B4, P5A-3C12, and P22A-1D1.

48. The antibody or antigen binding fragment of embodiment 47, wherein the first and the second antigen-binding domains are derived:
a) from P2C-1F11 and P2B-1G5, respectively;
b) from P2C-1F11 and P2B-1A1, respectively;
c) from P2C-1F11 and P2C-1D7, respectively;
d) from P2C-1F11 and P2B-1A10, respectively;
e) from P2C-1F11 and P2B-1D9, respectively;
f) from P2C-1F11 and P2B-1E4, respectively;
g) from P2C-1F11 and P2B-1G1, respectively;
h) from P2C-1F11 and P4A-2D9, respectively;
i) from P2C-1F11 and P5A-2G7, respectively;
j) from P2C-1F11 and P5A-3C8, respectively;
k) from P2C-1F11 and P5A-1D2, respectively;
l) from P2C-1F11 and P5A-2F11, respectively;
m) from P2C-1F11 and P5A-2E1, respectively;
n) from P2C-1F11 and P5A-1C8, respectively;
o) from P2B-2F6 and P2B-1G5, respectively;
p) from P2B-2F6 and P2B-1A1, respectively;
q) from P2B-2F6 and P2C-1D7, respectively;
r) from P2B-2F6 and P2B-1A10, respectively;
s) from P2B-2F6 and P2B-1D9, respectively;
t) from P2B-2F6 and P2B-1E4, respectively;
u) from P2B-2F6 and P2B-1G1, respectively;
v) from P2B-2F6 and P4A-2D9, respectively;
w) from P2B-2F6 and P5A-2G7, respectively;
x) from P2B-2F6 and P5A-3C8, respectively;
y) from P2B-2F6 and P5A-1D2, respectively;
z) from P2B-2F6 and P5A-2F11, respectively;
aa) from P2B-2F6 and P5A-2E1, respectively;
bb) from P2B-2F6 and P5A-1C8, respectively;
cc) from P2B-1G5 and P2B-1A1, respectively;
dd) from P2B-1G5 and P2C-1D7, respectively;
ee) from P2B-1G5 and P2B-1A10, respectively;
ff) from P2B-1G5 and P2B-1D9, respectively;
gg) from P2B-1G5 and P2B-1E4, respectively;
hh) from P2B-1G5 and P2B-1G1, respectively;
ii) from P2B-1G5 and P4A-2D9, respectively;
jj) from P2B-1G5 and P5A-2G7, respectively;
kk) from P2B-1G5 and P5A-3C8, respectively;
ll) from P2B-1G5 and P5A-1D2, respectively;
mm) from P2B-1G5 and P5A-2F11, respectively;
nn) from P2B-1G5 and P5A-2E1, respectively;
oo) from P2B-1G5 and P5A-1C8, respectively;
pp) from P2B-1A1 and P2C-1D7, respectively;
qq) from P2B-1A1 and P2B-1A10, respectively;
rr) from P2B-1A1 and P2B-1D9, respectively;
ss) from P2B-1A1 and P2B-1E4, respectively;
tt) from P2B-1A1 and P2B-1G1, respectively;
uu) from P2B-1A1 and P4A-2D9, respectively;
vv) from P2B-1A1 and P5A-2G7, respectively;
ww) from P2B-1A1 and P5A-3C8, respectively;
xx) from P2B-1A1 and P5A-1D2, respectively;
yy) from P2B-1A1 and P5A-2F11, respectively;

zz) from P2B-1A15 and P5A-2E1, respectively;
aaa) from P2B-1A1 and P5A-1C8, respectively;
bbb) from P2C-1D7 and P2B-1A10, respectively;
ccc) from P2C-1D7 and P2B-1D9, respectively;
ddd) from P2C-1D7 and P2B-1E4, respectively;
eee) from P2C-1D7 and P2B-1G1, respectively;
fff) from P2C-1D7 and P4A-2D9, respectively;
ggg) from P2C-1D7 and P5A-2G7, respectively;
hhh) from P2C-1D7 and P5A-3C8, respectively;
iii) from P2C-1D7 and P5A-1D2, respectively;
jjj) from P2C-1D7 and P5A-2F11, respectively;
kkk) from P2B-1A15 and P5A-2E1, respectively;
lll) from P2B-1A1 and P5A-1C8, respectively;
mmm) from P2B-1A10 and P2B-1D9, respectively;
nnn) from P2B-1A10 and P2B-1E4, respectively;
ooo) from P2B-1A10 and P2B-1G1, respectively;
ppp) from P2B-1A10 and P4A-2D9, respectively;
qqq) from P2B-1A10 and P5A-2G7, respectively;
rrr) from P2B-1A10 and P5A-3C8, respectively;
sss) from P2B-1A10 and P5A-1D2, respectively;
ttt) from P2B-1A10 and P5A-2F11, respectively;
uuu) from P2B-1A10 and P5A-2E1, respectively;
vvv) from P2B-1A10 and P5A-1C8, respectively;
www) from P2B-1D9 and P2B-1E4, respectively;
xxx) from P2B-1D9 and P2B-1G1, respectively;
yyy) from P2B-1D9 and P4A-2D9, respectively;
zzz) from P2B-1D9 and P5A-2G7, respectively;
aaaa) from P2B-1D9 and P5A-3C8, respectively;
bbbb) from P2B-1D9 and P5A-1D2, respectively;
cccc) from P2B-1D9 and P5A-2F11, respectively;
dddd) from P2B-1D9 and P5A-2E1, respectively;
eeee) from P2B-1D9 and P5A-1C8, respectively;
ffff) from P2B-1E4 and P2B-1G1, respectively;
gggg) from P2B-1E4 and P4A-2D9, respectively;
hhhh) from P2B-1E4 and P5A-2G7, respectively;
iiii) from P2B-1E4 and P5A-3C8, respectively;
jjjj) from P2B-1E4 and P5A-1D2, respectively;
kkkk) from P2B-1E4 and P5A-2F11, respectively;
llll) from P2B-1E4 and P5A-2E1, respectively;
mmmm) from P2B-1E4 and P5A-1C8, respectively;
nnnn) from P2B-1G1 and P4A-2D9, respectively;
oooo) from P2B-1G1 and P5A-2G7, respectively;
pppp) from P2B-1G1 and P5A-3C8, respectively;
qqqq) from P2B-1G1 and P5A-1D2, respectively;
rrrr) from P2B-1G1 and P5A-2F11, respectively;
ssss) from P2B-1G1 and P5A-2E1, respectively;
tttt) from P2B-1G1 and P5A-1C8, respectively;
uuuu) from P4A-2D9 and P5A-2G7, respectively;
vvvv) from P4A-2D9 and P5A-3C8, respectively;
wwww) from P4A-2D9 and P5A-1D2, respectively;
xxxx) from P4A-2D9 and P5A-2F11, respectively;
yyyy) from P4A-2D9 and P5A-2E1, respectively;
zzzz) from P4A-2D9 and P5A-1C8, respectively;
aaaaa) from P5A-2G7 and P5A-3C8, respectively;
bbbbb) from P5A-2G7 and P5A-1D2, respectively;
ccccc) from P5A-2G7 and P5A-2F11, respectively;
ddddd) from P5A-2G7 and P5A-2E1, respectively;
eeeee) from P5A-2G7 and P5A-1C8, respectively;
fffff) from P5A-3C8 and P5A-1D2, respectively;
ggggg) from P5A-3C8 and P5A-2F11, respectively;
hhhhh) from P5A-3C8 and P5A-2E1, respectively;
iiiii) from P5A-3C8 and P5A-1C8, respectively;
jjjjj) from P5A-1D2 and P5A-2F11, respectively;
kkkkk) from P5A-1D2 and P5A-2E1, respectively;
lllll) from P5A-1D2 and P5A-1C8, respectively;
mmmmm) from P5A-2F11 and P5A-2E1, respectively;
nnnnn) from P5A-2F11 and P5A-1C8, respectively;
ooooo) from P5A-2E1 and P5A-1C8, respectively;

49. The antibody or antigen binding fragment of any of the preceding embodiments, which is a full human antibody.

50. The antibody or antigen binding fragment of any of the preceding embodiments, linked to one or more conjugate moieties.

51. The antibody or antigen binding fragment of embodiment 50, wherein the conjugate moiety comprises a therapeutic agent, a radioactive isotope, a detectable label, a pharmacokinetic modifying moiety, or a purifying moiety, and optionally the conjugate moiety is covalently attached either directly or via a linker.

52. An antibody or an antigen-binding fragment thereof, which competes for binding to RBD of spike protein of SARS-CoV-2 with the antibody or an antigen-binding fragment thereof of any one of embodiments 1-44.

53. An isolated polynucleotide encoding the antibody or antigen binding fragment of any of the embodiments 1-52.

54. The isolated polynucleotide of embodiment 53, comprising a nucleotide sequence selected from a group consisting of: SEQ ID NOs: 9-10, 19-20, 29-30, 39-40, 49-50, 59-60, 63-64, 73-74, 83-84, 93-94, 103-104, 113-114, 144-145, 154-155, 164-165, 174-175, 184-185, 194-195, 204-205, 214-215, 224-225, 234-235, 244-245, 254-255, 264-265, 274-275, 284-285, 294-295, 304-305, 314-315, 324-325, 334-335, 344-345, 354-355, 364-365, 374-375, 384-385, 394-395, 404-405, 414-415, 424-425, and 434-435, or a homologous sequence thereof having at least 80% sequence identity.

55. The isolated polynucleotide of embodiment 54, wherein the homologue sequence encodes the same protein as encoded by any nucleotide sequence selected from the group consisting of SEQ ID NOs: 9-10, 19-20, 29-30, 39-40, 49-50, 59-60, 63-64, 73-74, 83-84, 93-94, 103-104, 113-114, 144-145, 154-155, 164-165, 174-175, 184-185, 194-195, 204-205, 214-215, 224-225, 234-235, 244-245, 254-255, 264-265, 274-275, 284-285, 294-295, 304-305, 314-315, 324-325, 334-335, 344-345, 354-355, 364-365, 374-375, 384-385, 394-395, 404-405, 414-415, 424-425, and 434-435.

56. A vector comprising the isolated polynucleotide of any one of embodiments 53-55, optionally the vector is an expression vector.

57. A host cell comprising the vector of embodiment 56.

58. A pharmaceutical composition comprising the antibody or antigen binding fragment of any one of embodiments 1-52, and a pharmaceutically acceptable carrier, or comprising the polynucleotide of claim 53, and a pharmaceutically acceptable carrier.

59. The pharmaceutical composition of embodiment 58, comprising a combination of two or more antibodies or antigen binding fragments of any one of embodiments 1-52, and a pharmaceutically acceptable carrier.

60. The pharmaceutical composition of embodiment 59, wherein the two or more antibodies or the antigen binding fragments thereof bind to different epitopes in RBD of spike protein of SARS-CoV-2.

61. The pharmaceutical composition of embodiment 60, wherein the two or more antibodies comprise a first antibody and a second antibody selected from the group consisting of P2A-1A8, P2A-1A9, P2B-2G11, P2A-1A10, P2A-1B3, P2B-2F6, P2B-2G4, P2C-1A3, P2C-1C8, P2C-1C10, P2C-1D5, P2C-1F11, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, P5A-1C8, P1A-1C10, P4A-1H6, P4B-1F4, P5A-1B6, P5A-1B8, P5A-1B9, P5A-

1D1, P5A-1D10, P5A-2D11, P5A-2G9, P5A-2H3, P5A-3A1, P5A-3A6, P5A-3B4, P5A-3C12, and P22A-1D1, or an antigen binding fragment thereof.

62. The pharmaceutical composition of embodiment 60, wherein the two or more antibodies comprise a first antibody and a second antibody selected from the group consisting of P2C-1F11, P2B-2F6, P2B-1G5, P2B-1A1, P2C-1D7, P2B-1A10, P2B-1D9, P2B-1E4, P2B-1G1, P4A-2D9, P5A-2G7, P5A-3C8, P5A-1D2, P5A-2F11, P5A-2E1, and P5A-1C8, or an antigen binding fragment thereof.

63. The pharmaceutical composition of embodiment 60, wherein the two or more antibodies comprise a first antibody which comprises P2C-1F11 or an antigen binding fragment thereof, and a second antibody which is selected from the group consisting of P2C-1A3, P2C-1C10, P2B-2F6, P2B-1G5, and P2A-1B3, or an antigen binding fragment thereof, optionally, the pharmaceutical composition comprises a first antibody comprising heavy chain CDR sequences and light chain CDR sequences derived from P2C-1F11, and a second antibody comprising heavy chain CDR sequences and light chain CDR sequences derived from antibody P2B-2F6.

64. The pharmaceutical composition of embodiment 60, wherein the two or more antibodies comprise a first antibody which comprises P2C-1A3 or an antigen binding fragment thereof, and a second antibody which is selected from the group consisting of P2C-1F11, and P2A-1B3, or an antigen binding fragment thereof.

65. The pharmaceutical composition of embodiment 60, wherein the two or more antibodies comprise a first antibody which comprises P2B-2F6 or an antigen binding fragment thereof, and a second antibody selected from the group consisting of P2C-1C10, P2C-1F11, P2B-1G5, and P2A-1B3, or an antigen binding fragment thereof.

66. The pharmaceutical composition of embodiment 60, wherein the two or more antibodies comprise a first antibody which comprises P2A-1B3 or an antigen binding fragment thereof, and a second antibody selected from the group consisting of P2C-1A3, P2C-1C10, P2C-1F11, P2B-2F6, and P2A-1A10, or an antigen binding fragment thereof.

67. A method of producing the antibody or antigen binding fragment of any of embodiments 1-52 comprising culturing the host cell of embodiment 57 under the condition at which the vector of embodiment 56 is expressed.

68. The method of embodiment 67, further comprising purifying the antibody produced by the host cell.

69. A kit for detecting a SARS-CoV-2 antigen, comprising the antibody or antigen binding fragment of any of embodiments 1-52.

70. The kit of embodiment 69, further comprising a control reagent comprising RBD of spike protein of the SARS-CoV-2, optionally, the kit further comprises a set of reagents for detecting complex of the antibody or the antigen-binding fragment bound to the SARS-CoV-2 antigen.

71. A method of treating SARS-CoV-2 infection or a disease, disorder or condition associated with SARs-CoV-2 infection in a subject, comprising administering a therapeutically effective amount of one or more of the antibody or antigen binding fragment of any of embodiments 1-52, or of one or more of the polynucleotides of any embodiments 53-55, or of one or more of the vectors of embodiment 56, or of the pharmaceutical composition of any of embodiments 58-66 to the subject.

72. A method of preventing SARS-CoV-2 infection or a disease, disorder or condition associated with SARs-CoV-2 infection in a subject, comprising administering a therapeutically effective amount of one or more of the antibody or antigen binding fragment of any of embodiments 1-52, or of one or more of the polynucleotides of any embodiments 53-55, or of one or more of the vectors of embodiment 56, or of the pharmaceutical composition of any of embodiments 58-66 to the subject.

73. The method of embodiments 71 or 72, wherein the administration is via oral, nasal, intravenous, subcutaneous, or intramuscular administration.

74. The method of embodiment 73, wherein the subject is human.

75. The method of any of embodiments 71-74, further comprising administering a therapeutically effective amount of a second bioactive agent, optionally the second bioactive agent is a therapeutic agent or a prophylactic agent.

76. The method of embodiment 75, wherein the therapeutic agent is an anti-viral agent, optionally, the anti-viral agent comprises an antiviral peptide, an anti-viral antibody, an anti-viral compound, an anti-viral cytokine, or an anti-viral oligonucleotide.

77. A method of detecting presence or amount of SARS-CoV-2 virus antigen in a sample, comprising contacting the sample with one or more of the antibody or antigen binding fragment of any of embodiments 1-52, and determining the presence or the amount of the SARS-CoV-2 virus antigen in the sample.

78. Use of one or more of the antibody or antigen binding fragment of any of embodiments 1-52 in the manufacture of a medicament for treating SARS-CoV-2 infection or a disease, disorder or condition associated with SARs-CoV-2 infection.

79. Use of one or more of the antibody or antigen binding fragment of any of embodiments 1-52 in the manufacture of a diagnostic reagent for detecting SARS-CoV-2 infection.

80. A kit for detecting an antibody capable of specifically binding to receptor-binding domain (RBD) of the spike protein of SARS-CoV-2, comprising a polypeptide comprising an amino acid sequence comprising SEQ ID NO. 128.

81. The kit of embodiment 80, wherein the polypeptide is immobilized on a substrate.

82. The kit of embodiments 81, further comprising a set of reagents for detecting complex of the antibody bound to the polypeptide.

83. A method of detecting presence or amount of an antibody capable of specifically binding to RBD of the spike protein of SARS-CoV-2 in a sample, comprising contacting the sample with a polypeptide comprising an amino acid sequence comprising SEQ ID NO: 128, and determining the presence or the level of the antibody in the sample.

84. The method of embodiment 83, wherein the absence of the antibody in the sample or the level of the antibody in the sample being below a threshold indicates that the subject is more likely to suffer from disease progression.

85. A method of determining the likelihood of disease progression in a subject infected with SARS-CoV-2, the method comprising: contacting a sample obtained from the subject with a polypeptide comprising an amino acid sequence comprising SEQ ID NO: 128, and detecting the presence or the level of an antibody in the sample wherein the antibody is capable of specifically binding to RBD of the spike protein of the SARS-CoV-2, wherein the subject is likely to experience disease progression when the antibody in the sample is absent or is below a threshold.

86. A method of monitoring treatment response in a subject infected with SARS-CoV-2 and received a treatment, the method comprising:
(i) contacting a sample from the subject with a peptide comprising an amino acid sequence comprising SEQ ID NO: 128;

(ii) detecting a first level of an antibody in the sample wherein the antibody is capable of specifically binding to RBD of the spike protein of the SARS-CoV-2; and (iii) comparing the first level of the antibody with a second level of the antibody detected in the subject prior to the treatment;

wherein the first level being higher than the second level indicates that the subject is responsive to the treatment.

87. A method of neutralizing SARS-CoV-2 in a subject or in a sample in vitro, comprising administering a therapeutically effective amount of one or more of the antibody or antigen binding fragment of any of embodiments 1-52, or the pharmaceutical composition of any of claims 58-66 to the subject or to the sample.

88. A crystal of RBD of the spike protein of SARS-CoV-2 in complex with an antibody.

89. The crystal of embodiment 88, having or consisting of a $P2_12_12_1$ space group with unit cell dimensions of a=70.23 Å, b=90.15 Å, and c=112.35 Å, having or consisting of a C121 space group with unit cell dimensions of a=194.88 Å, b=85.39 Å, and c=58.51 Å, having or consisting of a C2 space group with unit cell dimensions of a=193.34 Å, b=86.60 Å, and c=57.16 Å, having or consisting of a C2 space group with unit cell dimensions of a=158.75 Å, b=67.51 Å, and c=154.37 Å, or having or consisting of a $P2_12_12_1$ space group with unit cell dimensions of a=112.54 Å, b=171.57 Å, and c=54.87 Å.

90. The crystal of embodiment 88, wherein the antibody comprises a heavy chain variable region of SEQ ID NO: 47 and a light chain variable region of SEQ ID NO: 48.

91. The crystal of embodiment 88, wherein the antibody comprises a heavy chain variable region of SEQ ID NO: 111 and a light chain variable region of SEQ ID NO: 112.

92. The crystal of embodiments 88, wherein the antibody comprises a heavy chain variable region of SEQ ID NO: 432 and a light chain variable region of SEQ ID NO: 433.

93. The crystal of embodiments 88, wherein the antibody comprises a heavy chain variable region of SEQ ID NO: 242 and a light chain variable region of SEQ ID NO: 243.

94. The crystal of embodiments 88, wherein the antibody comprises a heavy chain variable region of SEQ ID NO: 232 and a light chain variable region of SEQ ID NO: 233.

95. A computer-implemented method for causing a display of a graphical three-dimensional representation of the structure of a portion of a crystal of RBD of the spike protein of SARS-CoV-2 in complex with an anti-SARS-CoV-2 antibody or an antigen-binding fragment thereof, wherein the method comprises:

causing said display of said graphical three-dimensional representation by a computer system programmed with instructions for transforming structure coordinates into said graphical three-dimensional representation of said structure and for displaying said graphical three-dimensional representation, wherein said graphical three-dimensional representation is generated by transforming said structure coordinates into said graphical three-dimensional representation of said structure, wherein said structure coordinates comprise structure coordinates of the backbone atoms of the portion of the crystal, wherein the portion of the crystal comprises a RBD binding site, and wherein the crystal has the space group symmetry $P2_12_12_1$ or C121.

96. The computer-implemented method of embodiment 95, wherein the RBD comprises an amino acid sequence as shown in SEQ ID NO: 124, and the antibody comprises: a) a heavy chain variable region of SEQ ID NO: 47 and a light chain variable region of SEQ ID NO: 48; or b) a heavy chain variable region of SEQ ID NO: 111 and a light chain variable region of SEQ ID NO: 112; or c) a heavy chain variable region of SEQ ID NO: 432 and a light chain variable region of SEQ ID NO: 433; or d) a heavy chain variable region of SEQ ID NO: 242 and a light chain variable region of SEQ ID NO: 243; or e) a heavy chain variable region of SEQ ID NO: 232 and a light chain variable region of SEQ ID NO: 233.

97. The computer-implemented method of embodiment 95, wherein the structure coordinates comprise the structure coordinates of the backbone atoms of the amino acid residues corresponding to K444, G446, G447, N448, Y449, N450, L452, V483, E484, G485, F490 and/or 5494 of the RBD, wherein the residue numbering is according to SEQ ID NO: 134.

98. The computer-implemented method of embodiment 95, wherein the structure coordinates comprise the structure coordinates of the backbone atoms of the amino acid residues corresponding to Y453, L455, F456, R457, K458, S459, N460, Y473, A475, G476, S477, F486, N487, Y489, Q493, G502, Y505, R403, T415, G416, K417, D420 and/or Y421 of the RBD, wherein the residue numbering is according to SEQ ID NO: 134.

99. The computer-implemented method of embodiment 95, wherein the structure coordinates comprise the structure coordinates of the backbone atoms of the amino acid residues corresponding to T415, G416, K417, D420, Y421, L455, F456, R457, K458, N460, Y473, A475, G476, S477, F486, N487, Y489 and/or Q493 of the RBD, wherein the residue numbering is according to SEQ ID NO: 134.

100. The computer-implemented method of embodiment 95, wherein the structure coordinates comprise the structure coordinates of the backbone atoms of the amino acid residues corresponding to T415, G416, K417, D420, Y421, Y453, L455, F456, R457, K458, N460, Y473, Q474, A475, G476, S477, N487, Y489, Q493 and/or Y505 of the RBD, wherein the residue numbering is according to SEQ ID NO: 134.

101. The computer-implemented method of embodiment 95, wherein the structure coordinates comprise the structure coordinates of the backbone atoms of the amino acid residues corresponding to T415, G416, K417, D420, Y421, Y453, L455, F456, R457, K458, N460, Y473, A475, G476, S477, F486, N487, Y489 and/or Q493 of the RBD, wherein the residue numbering is according to SEQ ID NO: 134.

102. The computer-implemented method of embodiment 95, wherein the structure coordinates comprise the structure coordinates of the backbone atoms of the amino acid residues corresponding to T415, G416, K417, D420, Y421, L455, F456, R457, K458, N460, Y473, Q474, A475, G476, S477, F486, N487, Y489 and/or Q493 of the RBD, wherein the residue numbering is according to SEQ ID NO: 134.

103. A machine-readable data storage medium comprising a data storage material encoded with machine-readable instructions for:

(a) transforming data into a graphical three-dimensional representation for the structure of a portion of a crystal of RBD of the spike protein of SARS-CoV-2 in complex with an anti-SARS-CoV-2 antibody or an antigen-binding fragment thereof, and (b) causing the display of said graphical three-dimensional representation; wherein said data comprise structure coordinates of the backbone atoms of the amino acids defining a RBD binding site; and wherein the crystal or structural homolog has the space group symmetry $P2_12_12_1$ or C121.

104. A method of screening for molecules that may be a binding molecule of RBD of the spike protein of SARS-CoV-2, comprising:

(a) computationally screening agents against a three-dimensional model to identify potential binding molecules of the RBD;

wherein the three-dimensional model comprises a three-dimensional model of at least a portion of a crystal of RBD of the spike protein of SARS-CoV-2 in complex with an anti-SARS-CoV-2 antibody or an antigen-binding fragment thereof;

wherein the three dimensional model is generated from at least a portion of the structure coordinates of the crystal by a computer algorithm for generating a three-dimensional model of the crystal useful for identifying agents that are potential binding molecules of the RBD; wherein the crystal comprises a polypeptide comprising an amino acid sequence SEQ ID NO: 124, and further comprises an antibody comprising: a) a heavy chain variable region of SEQ ID NO: 47 and a light chain variable region of SEQ ID NO: 48, or b) a heavy chain variable region of SEQ ID NO: 111 and a light chain variable region of SEQ ID NO: 112; and wherein the crystal diffracts x-rays for the determination of atomic coordinates to a resolution of 5 Å or better.

105. A method for obtaining structural information about a molecule or molecular complex comprising applying at least a portion of the structure coordinates of a RBD of the spike protein of SARS-CoV-2 in complex with an anti-SARS-CoV-2 antibody or an antigen-binding fragment thereof, to an X-ray diffraction pattern of the molecule or molecular complex's crystal structure to cause the generation of a three-dimensional electron density map of at least a portion of the molecule or molecular complex;

wherein the crystal comprises a polypeptide comprising an amino acid sequence SEQ ID NO: 124, and further comprises an antibody comprising: a) a heavy chain variable region of SEQ ID NO: 47 and a light chain variable region of SEQ ID NO: 48, or b) a heavy chain variable region of SEQ ID NO: 111 and a light chain variable region of SEQ ID NO: 112, wherein the crystal diffracts x-rays for the determination of atomic coordinates to a resolution of 5 Å or better.

106. Use of a composition comprising a modified antibody or an antigen-binding fragment thereof and one or more pharmaceutically acceptable carriers for manufacturing a medicament for treating or preventing a disease, wherein the composition comprises said modified antibody or said antigen-binding fragment thereof that comprises at least an antigen-binding domain having an antigen-binding affinity and a covalently linked modified human IgG constant domain, wherein said antigen-binding affinity comprises SARS-CoV-2 binding affinity, said antigen-binding affinity comprises at least 50% less or non-detectable binding affinity to SARS-CoV or MERS-CoV compared to said SARS-CoV-2 binding affinity, and wherein said modified human IgG constant domain comprises a substitution with tyrosine at amino acid residue 252, a substitution with threonine at amino acid residue 254, and a substitution with glutamic acid at amino acid residue 256, numbered according to the EU index as in Kabat, said modified antibody has an increased affinity for FcRn compared to the affinity to FcRn of an antibody having a wild type human IgG constant domain, and wherein said disease is caused by said SARS-CoV-2 or related to infection of said SARS-CoV-2 in said subject.

107. The use of embodiment 106, wherein said subject is a symptomatic non-hospitalized adult with COVID-19 caused by SARS-CoV-2 infection, is aged 60 years and older, is any age having at least one of the following conditions selected from smoking, has exogenous or endogenous immunosuppression having HIV infection with CD4 count <200 cells/mm3, receives corticosteroids equivalent to prednisone >20 mg daily for at least 14 consecutive days within 30 days prior to the treatment, has a treatment with one or more biologics therapeutical agents, one or more immunomodulators, cancer chemotherapy within 90 days prior to the treatment; has chronic lung disease, chronic asthma; obesity with body mass index [BMI]>35, symptoms of COVID-19 selected from fever, cough, sore throat, malaise, headache, muscle pain, nausea, vomiting, diarrhea, loss of taste and smell, or a combination thereof, has shortness of breath, dyspnea, or abnormal chest imaging, having evidence of lower respiratory disease during clinical assessment or imaging, has saturation of oxygen (SpO2) ≥94% on room air at sea level, has severe symptoms of the infection of said SARS-CoV-2, having SpO2<94% on room air at sea level, having a ratio of arterial partial pressure of oxygen to fraction of inspired oxygen (PaO2/FiO2)<300 mmHg, respiratory frequency>30 breaths per minute, lung infiltrates >50%, active symptoms of antibody-dependent enhancement (ADE), a history of antibody-dependent enhancement (ADE), being allergic to an antibody treatment, being a hospital inpatient requiring supportive management of complications of severe infection of said SARS-CoV-2 selected from pneumonia, has hypoxemic respiratory failure/ARDS, sepsis and septic shock, cardiomyopathy and arrhythmia, acute kidney injury, and complications from prolonged hospitalization, including secondary bacterial and fungal infections, thromboembolism, gastrointestinal bleeding, critical illness polyneuropathy/myopathy, or a combination thereof.

REFERENCES

1 Li, Q. et al. N Engl J Med, 10.1056/NEJMoa2001316, doi:10.1056/NEJMoa2001316 (2020).
2 Zhou, P. et al. A pneumonia outbreak associated with a new coronavirus of probable bat origin. Nature 579, 270-273, doi:10.1038/s41586-020-2012-7 (2020).
3 Zhu, N. et al., 2019. N Engl J Med 382, 727-733, doi:10.1056/NEJMoa2001017 (2020).
4 Wu, F. et al., Nature 579, 265-269, doi:10.1038/s41586-020-2008-3 (2020).
5 Chan, J. F.-W. et al. A familial cluster of pneumonia associated with the 2019 novel coronavirus indicating person-to-person transmission: a study of a family cluster. Lancet 395, 514-523, doi:10.1016/S0140-6736(20)30154-9 (2020).
6 Guan, W.-J. et al., N Engl J Med, 10.1056/NEJMoa2002032, doi:10.1056/NEJMoa2002032 (2020).
7 Huang, C. et al., Lancet 395, 497-506, doi:10.1016/S0140-6736(20)30183-5 (2020).
8 Wang, D. et al., JAMA, e201585, doi:10.1001/jama.2020.1585 (2020).
9 Chinazzi, M. et al. The effect of travel restrictions on the spread of the 2019 novel coronavirus (COVID-19) outbreak. Science, eaba9757, doi:10.1126/science.aba9757 (2020).

10 Lu, R. et al. Genomic characterisation and epidemiology of 2019 novel coronavirus: implications for virus origins and receptor binding. Lancet 395, 565-574, doi:10.1016/S0140-6736(20)30251-8 (2020).
11 Wu, A. et al., Cell Host Microbe, S1931-3128(1920) 30072-X, doi:10.1016/j.chom.2020.02.001 (2020).
12 Ge, X.-Y. et al. Isolation and characterization of a bat SARS-like coronavirus that uses the ACE2 receptor. Nature 503, 535-538, doi: 10.1038/nature12711 (2013).
13 Hoffmann, M. et al. SARS-CoV-2 Cell Entry Depends on ACE2 and TMPRSS2 and Is Blocked by a Clinically Proven Protease Inhibitor. Cell, S0092-8674(0020)30229-30224, doi:10.1016/j.cell.2020.02.052 (2020).
14 Walls, A. C. et al. Structure, Function, and Antigenicity of the SARS-CoV-2 Spike Glycoprotein. Cell, S0092-8674(0020)30262-30262, doi:10.1016/j.cell.2020.02.058 (2020).
15 Du, L. et al. The spike protein of SARS-CoV—a target for vaccine and therapeutic development. Nat Rev Microbiol 7, 226-236, doi:10.1038/nrmicro2090 (2009).
16 Li, F. Structure, Function, and Evolution of Coronavirus Spike Proteins. Annu Rev Virol 3, 237-261, doi:10.1146/annurev-virology-110615-042301 (2016).
17 Wrapp, D. et al. Cryo-EM structure of the 2019-nCoV spike in the prefusion conformation. Science, eabb2507, doi:10.1126/science.abb2507 (2020).
18 Gui, M. et al. Cryo-electron microscopy structures of the SARS-CoV spike glycoprotein reveal a prerequisite conformational state for receptor binding. Cell Res 27, 119-129, doi:10.1038/cr.2016.152 (2017).
19 Song, W., Gui, M., Wang, X. & Xiang, Y. Cryo-EM structure of the SARS coronavirus spike glycoprotein in complex with its host cell receptor ACE2. PLoS Pathog 14, e1007236-e1007236, doi:10.1371/journal.ppat.1007236 (2018).
20 Kirchdoerfer, R. N. et al. Stabilized coronavirus spikes are resistant 725 to conformational changes induced by receptor recognition or proteolysis. Sci Rep 8, 15701-15701, doi:10.1038/s41598-018-34171-7 (2018).
21 Yuan, Y. et al. Cryo-EM structures of MERS-CoV and SARS-CoV spike glycoproteins reveal the dynamic receptor binding domains. Nat Commun 8, 15092-15092, doi:10.1038/ncomms15092 (2017).
22 Wan, Y., Shang, J., Graham, R., Baric, R. S. & Li, F, J Virol, JVI.00127-00120, doi:10.1128/JVI.00127-20 (2020).
23 Kruse, R. L., F1000Res 9, 72-72, doi:10.12688/f1000research.22211.2 (2020).
24 Li, W. et al. Angiotensin-converting enzyme 2 is a functional receptor for the SARS coronavirus. Nature 426, 450-454, doi:10.1038/nature02145 (2003).
25 Hamming, I. et al. The emerging role of ACE2 in physiology and disease. J Pathol 212, 1-11, doi:10.1002/path.2162 (2007).
26 Xu, J. et al. Antibodies and vaccines against Middle East respiratory syndrome coronavirus. Emerg Microbes Infect 8, 841-856, doi:10.1080/22221751.2019.1624482 (2019).
27 Sanders, R. W. et al. Stabilization of the soluble, cleaved, trimeric form of the envelope glycoprotein complex of human immunodeficiency virus type 1. J Virol 76, 8875-8889, doi:10.1128/jvi.76.17.8875-8889.2002 (2002).
28 Kong, L. et al. Key gp120 Glycans Pose Roadblocks to the Rapid Development of VRC01-Class Antibodies in an HIV-1-Infected Chinese Donor. Immunity 44, 939-950, doi:10.1016/j.immuni.2016.03.006 (2016).
29 Liao, H.-X. et al. High-throughput isolation of immunoglobulin genes from single human B cells and expression as monoclonal antibodies. J Virol Methods 158, 171-179, doi:10.1016/j.jviromet.2009.02.014 (2009).
30 Yu, L. et al. Delineating antibody recognition against Zika virus during natural infection. JCI Insight 2, e93042, doi: 10. 1172/jci.insight.93042 (2017).
31 Corti, D. & Lanzavecchia, A. Broadly neutralizing antiviral antibodies. Annu Rev Immunol 31, 705-742, doi: 10.1146/annurev-immunol-032712-095916 (2013).
32 Stettler, K. et al. Specificity, cross-reactivity, and function of antibodies elicited by Zika virus infection. Science 353, 823-826, doi:10.1126/science.aaf8505 (2016).
33 Scheid, J. F. et al. Broad diversity of neutralizing antibodies isolated from memory B cells in HIV-infected individuals. Nature 458, 636-640, doi:10.1038/nature07930 (2009).
34 Wu, X. et al. Focused evolution of HIV-1 neutralizing antibodies revealed by structures and deep sequencing. Science 333, 1593-1602, doi:10.1126/science.1207532 (2011).
35 Liao, H.-X. et al. Co-evolution of a broadly neutralizing HIV-1 antibody and founder virus. Nature 496, 469-476, doi:10.1038/nature12053 (2013).
36. Yuan, M. et al. A highly conserved cryptic epitope in the receptor-binding domains of SARS-CoV-2 and SARS-CoV. Science, doi:10.1126/science.abb7269 (2020).
37. Pinto, D. et al. Structural and functional analysis of a potent sarbecovirus neutralizing 1 antibody. BioRxiv (2020).
38 Tian, X. et al. Potent binding of 2019 novel coronavirus spike protein by a SARS coronavirus-specific human monoclonal antibody. Emerg Microbes Infect 9, 382-385, doi:10.1080/22221751.2020.1729069 (2020).
39 Wang, N. et al. Structure of MERS-CoV spike receptor-binding domain complexed with human receptor DPP4. Cell Res 23, 986-993, doi:10.1038/cr.2013.92 (2013).
40 Jiang, L. et al. Potent neutralization of MERS-CoV by human neutralizing monoclonal antibodies to the viral spike glycoprotein. Sci Transl Med 6, 234ra259-234ra259, doi:10.1126/scitranslmed.3008140 (2014).
41 Zhang, S. et al. Structural Definition of a Unique Neutralization 774 Epitope on the Receptor-Binding Domain of MERS-CoV Spike Glycoprotein. Cell Rep 24, 441-452, doi:10.1016/j.celrep.2018.06.041 (2018).
42 Wu, X. et al. Rational design of envelope identifies broadly neutralizing human monoclonal antibodies to HIV-1. Science 329, 856-861, doi:10.1126/science.1187659 779 (2010).
43 Tiller, T. et al. Efficient generation of monoclonal antibodies from single human B cells by single cell RT-PCR and expression vector cloning. J Immunol Methods 329, 112-124, doi:10.1016//j.jim.2007.09.017 (2008).
44 Zhu, Z. et al. Potent cross-reactive neutralization of SARS coronavirus isolates by human monoclonal antibodies. Proc Natl Acad Sci USA 104, 12123-12128,doi: 10.1073/pnas.0701000104 (2007).
45 Niu, P. et al. Ultrapotent Human Neutralizing Antibody Repertoires Against MiddleEast Respiratory Syndrome Coronavirus From a Recovered Patient. J Infect Dis218, 1249-1260, doi:10.1093/infdis/jiy311 (2018).
46 Jia, W. et al. Single intranasal immunization with chimpanzee adenovirus-based vaccine induces sustained and protective immunity against MERS-CoV infection. Emerg Microbes Infect 8, 760-772, doi:10.1080/22221751.2019.1620083 (2019).

47 Zhang, L. et al. Antibody responses against SARS coronavirus are correlated with disease outcome of infected individuals. J Med Virol 78, 1-8, doi:10.1002/jmv.20499(2006).

48 Zhang, Q. et al. Potent neutralizing monoclonal antibodies against Ebola virus infection. Sci Rep 6, 25856-25856, doi:10.1038/srep25856 (2016).

49. McCoy, A. J. et al. Phaser crystallographic software. Journal of applied crystallography 40, 658-674, doi: 10.1107/s0021889807021206 (2007).

50. Cohen, S. X. et al. ARP/wARP and molecular replacement: the next generation. Acta crystallographica. Section D, Biological crystallography 64, 49-60, doi: 10.1107/s0907444907047580 (2008).

51 Emsley, P. & Cowtan, K. Coot: model-building tools for molecular graphics. Acta crystallographica. Section D, Biological crystallography 60, 2126-2132, doi:10.1107/s0907444904019158 (2004).

52 Adams, P. D. et al. PHENIX: building new software for automated crystallographic structure determination. Acta crystallographica. Section D, Biological crystallography 58, 1948-1954, doi:10.1107/s0907444902016657 (2002).

53 Janson, G., Zhang, C., Prado, M. G. & Paiardini, A. PyMod 2.0: improvements in protein sequence-structure analysis and homology modeling within PyMOL. Bioinformatics (Oxford, England) 33, 444-446, doi:10.1093/bioinformatics/btw638 (2017).

54 Arentz, G., Thurgood, L. A., Lindop, R., Chataway, T. K., and Gordon, T. P. (2012). Secreted human Ro52 autoantibody proteomes express a restricted set of public clonotypes. Journal of autoimmunity 39, 466-470.

55 Barnes, C. O., West, A. P., Jr., Huey-Tubman, K. E., Hoffmann, M. A. G., Sharaf, N. G., Hoffman, P. R., Koranda, N., Gristick, H. B., Gaebler, C., Muecksch, F., et al. (2020). Structures of human antibodies bound to SARS-CoV-2 spike reveal common epitopes and recurrent features of antibodies. bioRxiv.

56 Baum, A., Fulton, B. O., Wloga, E., Copin, R., Pascal, K. E., Russo, V., Giordano, S., Lanza, K., Negron, N., Ni, M., et al. (2020). Antibody cocktail to SARS-CoV-2 spike protein prevents rapid mutational escape seen with individual antibodies. Science.

57 Brouwer, P. J. M., Caniels, T. G., van der Straten, K., Snitselaar, J. L., Aldon, Y., Bangaru, S., Torres, J. L., Okba, N. M. A., Claireaux, M., Kerster, G., et al. (2020). Potent neutralizing antibodies from COVID-19 patients define multiple targets of vulnerability. Science.

58 Cao, Y., Su, B., Guo, X., Sun, W., Deng, Y., Bao, L., Zhu, Q., Zhang, X., Zheng, Y., Geng, C., et al. (2020). Potent neutralizing antibodies against SARS-CoV-2 identified by high-throughput single-cell sequencing of convalescent patients' B cells. Cell.

59 Chi, X., Yan, R., Zhang, J., Zhang, G., Zhang, Y., Hao, M., Zhang, Z., Fan, P., Dong, Y., Yang, Y., et al. (2020). A neutralizing human antibody binds to the N-terminal domain of the Spike protein of SARS-CoV-2. Science.

60 Hansen, J., Baum, A., Pascal, K. E., Russo, V., Giordano, S., Wloga, E., Fulton, B. O., Yan, Y., Koon, K., Patel, K., et al. (2020). Studies in humanized mice and convalescent humans yield a SARS-CoV-2 antibody cocktail. Science.

61 Henry Dunand, C. J., and Wilson, P. C. (2015). Restricted, canonical, stereotyped and convergent immunoglobulin responses. Philos Trans R Soc Lond B Biol Sci 370.

62 Jackson, K. J., Liu, Y., Roskin, K. M., Glanville, J., Hoh, R. A., Seo, K., Marshall, E. L., Gurley, T. C., Moody, M. A., Haynes, B. F., et al. (2014). Human responses to influenza vaccination show seroconversion signatures and convergent antibody rearrangements. Cell host & microbe 16, 105-114.

63 Ju, B., Zhang, Q., Ge, J., Wang, R., Sun, J., Ge, X., Yu, J., Shan, S., Zhou, B., Song, S., et al. (2020). Human neutralizing antibodies elicited by SARS-CoV-2 infection. Nature.

64 Lan, J., Ge, J., Yu, J., Shan, S., Zhou, H., Fan, S., Zhang, Q., Shi, X., Wang, Q., Zhang, L., and Wang, X. (2020). Structure of the SARS-CoV-2 spike receptor-binding domain bound to the ACE2 receptor. Nature 581, 215-220.

65 Liu, L., Wang, P., Nair, M. S., Yu, J., Huang, Y., Rapp, M. A., Wang, Q., Luo, Y., Sahi, V., Figueroa, A., et al. (2020). Potent Neutralizing Monoclonal Antibodies Directed to Multiple Epitopes on the SARS-CoV-2 Spike. bioRxiv.

66 Lv, H., Wu, N. C., Tsang, O T., Yuan, M., Perera, R., Leung, W. S., So, R. T. Y., Chan, J. M. C., Yip, G. K., Chik, T. S. H., et al. (2020). Cross-reactive antibody response between SARS-CoV-2 and SARS-CoV infections. bioRxiv.

67 Parameswaran, P., Liu, Y., Roskin, K. M., Jackson, K. K., Dixit, V. P., Lee, J. Y., Artiles, K. L., Zompi, S., Vargas, M. J., Simen, B. B., et al. (2013). Convergent antibody signatures in human dengue. Cell host & microbe 13, 691-700.

68 Pieper, K., Tan, J., Piccoli, L., Foglierini, M., Barbieri, S., Chen, Y., Silacci-Fregni, C., Wolf, T., Jarrossay, D., Anderle, M., et al. (2017). Public antibodies to malaria antigens generated by two LAIR1 insertion modalities. Nature 548, 597-601.

69 Pinto, D., Park, Y. J., Beltramello, M., Walls, A. C., Tortorici, M. A., Bianchi, S., Jaconi, S., Culap, K., Zatta, F., De Marco, A., et al. (2020). Cross-neutralization of SARS-CoV-2 by a human monoclonal SARS-CoV antibody. Nature.

70 Ravichandran, S., Coyle, E. M., Klenow, L., Tang, J., Grubbs, G., Liu, S., Wang, T., Golding, H., and Khurana, S. (2020). Antibody signature induced by SARS-CoV-2 spike protein immunogens in rabbits. Sci Transl Med 12.

71 Robbiani, D. F., Gaebler, C., Muecksch, F., Lorenzi, J. C. C., Wang, Z., Cho, A., Agudelo, M., Barnes, C. O., Gazumyan, A., Finkin, S., et al. (2020). Convergent antibody responses to SARS-CoV-2 in convalescent individuals. Nature.

72 Rogers, T. F., Zhao, F., Huang, D., Beutler, N., Burns, A., He, W. T., Limbo, O., Smith, C., Song, G., Woehl, J., et al. (2020). Isolation of potent SARS-CoV-2 neutralizing antibodies and protection from disease in a small animal model. Science.

73 Setliff, I., McDonnell, W. J., Raju, N., Bombardi, R. G., Murji, A. A., Scheepers, C., Ziki, R., Mynhardt, C., Shepherd, B. E., Mamchak, A. A., et al. (2018). Multi-Donor Longitudinal Antibody Repertoire Sequencing Reveals the Existence of Public Antibody Clonotypes in HIV-1 Infection. Cell host & microbe 23, 845-854.e846.

74 Seydoux, E., Homad, L. J., MacCamy, A. J., Parks, K. R., Hurlburt, N. K., Jennewein, M. F., Akins, N. R., Stuart, A. B., Wan, Y. H., Feng, J., et al. (2020). Analysis of a SARS-CoV-2-Infected Individual Reveals Development of Potent Neutralizing Antibodies with Limited Somatic Mutation. Immunity.

75 Shang, J., Ye, G., Shi, K., Wan, Y., Luo, C., Aihara, H., Geng, Q., Auerbach, A., and Li, F. (2020). Structural basis of receptor recognition by SARS-CoV-2. Nature 581, 221-224.

76 Truck, J., Ramasamy, M. N., Galson, J. D., Rance, R., Parkhill, J., Lunter, G., Pollard, A. J., and Kelly, D. F. (2015). Identification of antigen-specific B cell receptor sequences using public repertoire analysis. Journal of immunology (Baltimore, Md.: 1950) 194, 252-261.

77 Wang, C., Li, W., Drabek, D., Okba, N. M. A., van Haperen, R., Osterhaus, A., van Kuppeveld, F. J. M., Haagmans, B. L., Grosveld, F., and Bosch, B. J. (2020). A human monoclonal antibody blocking SARS-CoV-2 infection. Nat Commun 11, 2251.

78 Wec, A. Z., Wrapp, D., Herbert, A. S., Maurer, D. P., Haslwanter, D., Sakharkar, M., Jangra, R. K., Dieterle, M. E., Lilov, A., Huang, D., et al. (2020). Broad neutralization of SARS-related viruses by human monoclonal antibodies. Science.

79 Wu, Y., Wang, F., Shen, C., Peng, W., Li, D., Zhao, C., Li, Z., Li, S., Bi, Y., Yang, Y., et al. (2020). A noncompeting pair of human neutralizing antibodies block COVID-19 virus binding to its receptor ACE2. Science 368, 1274-1278.

80 Yan, R., Zhang, Y., Li, Y., Xia, L., Guo, Y., and Zhou, Q. (2020). Structural basis for the recognition of SARS-CoV-2 by full-length human ACE2. Science 367, 1444-1448.

81 Yuan, M., Liu, H., Wu, N. C., Lee, C. D., Zhu, X., Zhao, F., Huang, D., Yu, W., Hua, Y., Tien, H., et al. (2020). Structural basis of a public antibody response to SARS-CoV-2. bioRxiv.

82 Zost, S. J., Gilchuk, P., Case, J. B., Binshtein, E., Chen, R. E., Reidy, J. X., Trivette, A., Nargi, R. S., Sutton, R. E., Suryadevara, N., et al. (2020). Potently neutralizing human antibodies that block SARS-CoV-2 receptor binding and protect animals. bioRxiv.

83 Dall'Acqua, W. F., P. A. Kiener, and H. Wu. 2006. 'Properties of human IgG1s engineered for enhanced binding to the neonatal Fc receptor (FcRn)', J Biol Chem, 281: 23514-24.

TABLE 6

Neutralizing activity of the 12 antibodies from patient #2

| | Antibody conc. in the mixture (µg/ml) | Neutralizing activity (%) Mean | Standard deviation | $IC_{50}$ µg/ml |
|---|---|---|---|---|
| P2A-1A8 | 0.0228624 | 4.34 | 4.98 | 7.68 |
| | 0.0685871 | 13.155 | 5.025 | |
| | 0.2057613 | 14.07 | 4.35 | |
| | 0.6172839 | 16.48 | 0.2600002 | |
| | 1.851852 | 26.705 | 4.004999 | |
| | 5.555555 | 44.755 | 2.985001 | |
| | 16.66667 | 67.8 | 4.530001 | |
| | 50 | 88.235 | 0.5849991 | |
| P2A-1A9 | 0.0228624 | 12.48 | 6.810001 | 26.27 |
| | 0.0685871 | 15.875 | 2.975 | |
| | 0.2057613 | 15.11 | 4.29 | |
| | 0.6172839 | 14.27 | 3.4 | |
| | 1.851852 | 15.89 | 0.79 | |
| | 5.555555 | 34.8 | 1.360001 | |
| | 16.66667 | 41.215 | 0.1349983 | |
| | 50 | 62.645 | 0.2950001 | |
| P2A-1A10 | 0.0228624 | 14.01 | 0 | 8.57 |
| | 0.0685871 | 10.22 | 0 | |
| | 0.2057613 | 16.49 | 2.03 | |
| | 0.6172839 | 26.395 | 2.665 | |
| | 1.851852 | 30.45 | 7.68 | |
| | 5.555555 | 35.195 | 14.675 | |
| | 16.66667 | 65.715 | 9.145 | |
| | 50 | 86.13 | 3.93 | |
| P2A-1B3 | 0.0228624 | 11.465 | 0.4650002 | 16.77 |
| | 0.0685871 | -0.5450001 | 7.745 | |
| | 0.2057613 | 10.195 | 1.045 | |
| | 0.6172839 | 23.32 | 0.7499999 | |
| | 1.851852 | 22.14 | 2.859999 | |
| | 5.555555 | 37.22 | 1.550001 | |
| | 16.66667 | 43.59 | 4.360001 | |
| | 50 | 74.925 | 4.735001 | |
| P2B-2F6 | 0.000847 | 2.21 | 2.72 | 0.05 |
| | 0.00254 | 4.905 | 4.855 | |
| | 0.007621 | 23.61 | 4.05 | |
| | 0.0228624 | 39.415 | 0.7350007 | |
| | 0.0685871 | 51.77 | 3.970001 | |
| | 0.2057613 | 67.06 | 4.16 | |

TABLE 5

Clinical characterization of the study subjects

| | P#1 | P#2 | P#3 | P#4 | P#5 | P#8 | P#16 | P#22 |
|---|---|---|---|---|---|---|---|---|
| Severity | severe | severe | mild | mild | severe | mild | mild | mild |
| Age | 66 | 65 | 36 | 10 | 63 | 35 | 42 | 62 |
| Gender | male | female | male | male | female | male | female | male |
| Exposure history | yes | yes | yes | yes | no | yes | yes | no |
| Symptom onset day | Jan. 3, 2020 | Jan. 2, 2020 | Jan. 9, 2020 | Jan. 11, 2020 | Jan. 8, 2020 | Jan. 8, 2020 | Jan. 18, 2020 | Jan. 20, 2020 |
| First symptom | Fever | Fever | Cough | Cough | Fever/Cough | Fever/Cough | Fever/Cough | Fever/Cough |
| Hospitalization date | Jan. 11, 2020 | Jan. 11, 2020 | Jan. 16, 2020 | Jan. 16, 2020 | Jan. 16, 2020 | Jan. 16, 2020 | Jan. 22, 2020 | Jan. 23, 2020 |
| Chronic basic disease | hypertension | hypertension | none | none | none | none | none | hypertension |
| 2019-nCoV | + | + | + | + | + | + | + | + |
| Influenza A virus | − | − | − | − | − | − | − | − |
| Influenza B virus | − | − | − | − | − | − | − | − |
| RSV | − | − | − | − | − | − | − | − |
| Adenovirus | − | − | − | − | − | − | − | − |
| Interferon atomization | Jan. 14, 2020 | Jan. 26, 2020 | Jan. 16, 2020 | Jan. 17, 2020 | Jan. 16, 2020 | Jan. 16, 2020 | Jan. 21, 2020 | Jan. 23, 2020 |
| Ribavirin | Jan. 14, 2020 | Jan. 14, 2020 | Jan. 16, 2020 | Jan. 17, 2020 | Jan. 16, 2020 | Jan. 16, 2020 | Jan. 21, 2020 | Jan. 23, 2020 |
| | yes | no | no | no | no | no | no | yes |
| CT finding | Bilateral pneumonia | Bilateral pneumonia | Bilateral pneumonia | Bilateral pneumonia | Bilateral pneumonia | Bilateral pneumonia | Bilaetral pneumonia | Bilateral pneumonia |
| Blood Sampling date | Jan 21 | Jan 21, 27, 30, | Jan 25 | Jan 20, 30 | Feb 1 | Jan 22 | Feb 3 | Feb 3 |
| Outcome | dead | cure | cure | cure | cure | cure | cure | cure |

TABLE 6-continued

Neutralizing activity of the 12 antibodies from patient #2

| | Antibody conc. in the mixture (µg/ml) | Neutralizing activity (%) Mean | Standard deviation | IC$_{50}$ µg/ml |
|---|---|---|---|---|
| | 0.6172839 | 81.405 | 1.705002 | |
| | 1.851852 | 88.985 | 2.455002 | |
| | 5.555555 | 93.515 | 0.9550018 | |
| | 16.66667 | 95.36 | 0.6100006 | |
| | 50 | 97.435 | 0.1049995 | |
| P2B-2G4 | 0.0228624 | −3.325 | 5.025 | 5.11 |
| | 0.0685871 | −8.875 | 2.295 | |
| | 0.2057613 | 10.42 | 9.469999 | |
| | 0.6172839 | 20.155 | 10.335 | |
| | 1.851852 | 35.37 | 1.15 | |
| | 5.555555 | 46.395 | 1.314999 | |
| | 16.66667 | 65.23 | 2.27 | |
| | 50 | 74.78 | 1.98 | |
| P2B-2G11 | 0.0228624 | 3.815 | 7.795 | 34.84 |
| | 0.0685871 | 13.93 | 7 | |
| | 0.2057613 | 12.775 | 1.765 | |
| | 1.851852 | 15.96 | 1.47 | |
| | 5.555555 | 18.995 | 4.385 | |
| | 16.66667 | 25.93 | 4.8 | |
| | 50 | 64.36 | 3.159998 | |
| P2C-1A3 | 0.0228624 | 16.36 | 7.55 | 0.62 |
| | 0.0685871 | 40.055 | 0.3850002 | |
| | 0.2057613 | 32.975 | 8.815001 | |
| | 0.6172839 | 50.85 | 0.789999 | |
| | 1.851852 | 64.215 | 1.615002 | |
| | 5.555555 | 78.655 | 0.3050003 | |
| | 16.66667 | 90.72 | 2.25 | |
| | 50 | 94.77 | 4.280003 | |
| P2C-1C8 | 0.0228624 | −7.15 | 0 | 34.38 |
| | 0.0685871 | 2.8 | 0 | |

TABLE 6-continued

Neutralizing activity of the 12 antibodies from patient #2

| | Antibody conc. in the mixture (µg/ml) | Neutralizing activity (%) Mean | Standard deviation | IC$_{50}$ µg/ml |
|---|---|---|---|---|
| | 0.2057613 | 4.92 | 0 | |
| | 0.6172839 | 10.14 | 0 | |
| | 1.851852 | 8.39 | 0 | |
| | 5.555555 | 23.3 | 0 | |
| | 16.66667 | 34.655 | 10.475 | |
| | 50 | 59.235 | 6.415001 | |
| P2C-1C10 | 0.0228624 | −2.34 | 0.25 | 2.62 |
| | 0.0685871 | 7.78 | 2.53 | |
| | 0.2057613 | 13.44 | 4.28 | |
| | 0.6172839 | 5.915 | 2.065 | |
| | 1.851852 | 38.46 | 2.370001 | |
| | 5.555555 | 88.94 | 10.65 | |
| | 16.66667 | 99.915 | 0.0650024 | |
| | 50 | 99.985 | 0.0049973 | |
| P2C-1D5 | 0.0228624 | 4.244075 | 11.36407 | 10.65 |
| | 0.0685871 | 5.653669 | 0 | |
| | 0.2057613 | 8.657233 | 4.172767 | |
| | 0.6172839 | 12.39692 | 1.893085 | |
| | 1.851852 | 16.11835 | 6.848345 | |
| | 5.555555 | 33.64537 | 7.55463 | |
| | 16.66667 | 64.87724 | 0.3027649 | |
| | 50 | 90.16859 | 0.2314072 | |

TABLE 6-continued

Neutralizing activity of the 12 antibodies from patient #2

| | Antibody conc. in the mixture (µg/ml) | Neutralizing activity (%) Mean | Standard deviation | IC$_{50}$ µg/ml |
|---|---|---|---|---|
| P2C-1F11 | 0.000847 | 13.11 | 10.36 | 0.03 |
| | 0.00254 | 12.485 | 2.365 | |
| | 0.007621 | 27.915 | 6.715001 | |
| | 0.0228624 | 45.64 | 0.2099991 | |
| | 0.0685871 | 69.00999 | 2.560001 | |
| | 0.2057613 | 88.665 | 2.514999 | |
| | 0.6172839 | 95.08501 | 2.645 | |
| | 1.851852 | 98.58 | 0.6399994 | |
| | 5.555555 | 98.99 | 0.8199998 | |
| | 16.66667 | 99.66 | 0.3200035 | |
| | 50 | 99.525 | 0.375 | |
| VRC01 | 0.0228624 | 13.185 | 10.075 | |
| | 0.0685871 | 10.435 | 0.7850003 | |
| | 0.2057613 | 14.37 | 0 | |
| | 0.6172839 | 24.945 | 1.014999 | |
| | 1.851852 | 8.1 | 0 | |
| | 5.555555 | 27.065 | 5.345 | |
| | 16.66667 | 26.615 | 2.165 | |
| | 50 | 33.89 | 0 | |

*Antibodies having an IC$_{50}$ < 50 µg/ml are defined as specific neutralizing antibody.

TABLE 7a

| | IC$_{50}$ (µg/ml) | IC$_{80}$ (µg/ml) | IC$_{90}$ (µg/ml) | Compete w/ACE2 | Compete w/1F11 | K$_{on}$ | K$_{off}$ | K$_d$ (nM) |
|---|---|---|---|---|---|---|---|---|
| P2B-1G5 | 0.11 | 0.37 | 0.65 | 17.54% | 42.61/12.70 | 1.375E+6 | 1.312E−4 | 0.10 |

TABLE 7b

| Antibody | IC$_{50}$ (µg/ml) |
|---|---|
| P5A-2G7 | 0.016 |
| P5A-3C8 | 0.024 |
| P5A-1D2 | 0.035 |
| P2B-1G1 | 4.224 |
| P5A-1C8 | 0.434 |
| P5A-2F11 | 0.633 |
| P5A-2E1 | 6.972 |
| P2B-1A1 | 0.687 |
| P2C-1D7 | 0.212 |
| P2B-1A10 | 0.349 |
| P2B-1D9 | 3.121 |
| P2B-1E4 | 5.963 |
| P4A-2D9 | 1.543 |

TABLE 7c

Pesudovirus neutralization

| mAbs | IC$_{50}$ (µg/ml) | IC$_{80}$ (µg/ml) | IC$_{90}$ (µg/ml) |
|---|---|---|---|
| P1A-1C10 | 21.4977 | | |
| P4A-1H6 | 0.1370 | 0.7670 | 2.2136 |
| P4B-1F4 | 3.4486 | 9.0132 | 14.5293 |
| P5A-1B6 | 0.2528 | 1.3719 | 4.2043 |

TABLE 7c-continued

Pesudovirus neutralization

| mAbs | IC$_{50}$ (μg/ml) | IC$_{80}$ (μg/ml) | IC$_{90}$ (μg/ml) |
|---|---|---|---|
| P5A-1B8 | 0.0115 | 0.0509 | 0.1365 |
| P5A-1B9 | 0.0014 | 0.0052 | 0.0109 |
| P5A-1D1 | 0.0096 | 0.0691 | 0.2318 |
| P5A-1D10 | 5.7212 | 28.8679 | 43.7611 |
| P5A-2D11 | 0.3889 | 1.4758 | 2.0624 |
| P5A-2G9 | 0.0158 | 0.1466 | 0.4976 |
| P5A-2H3 | 0.5042 | 2.0522 | 3.3394 |
| P5A-3A1 | 0.9231 | 4.2357 | 7.2009 |
| P5A-3A6 | 0.2343 | 1.2672 | 2.7716 |
| P5A-3B4 | 0.0993 | 1.0657 | 3.0529 |
| P5A-3C12 | 0.0996 | 0.4679 | 0.9552 |
| P22A-1D1 | 0.0038 | 0.0625 | 0.3992 |

TABLE 7d

The IC$_{50}$ of enrolled 165 antibodies with between 0.1 μg/mL and 50 μg/mL or higher.

| mAbs | Pseudovirus IC50 (μg/ml) | Pseudovirus IC80 (μg/ml) | Live virus IC50 (μg/ml) | Live virus IC80 (μg/ml) |
|---|---|---|---|---|
| P5A-1B9 | 0.0014 | 0.0053 | 0.0043 | 0.0441 |
| P22A-1D1 | 0.0038 | 0.0625 | 0.0198 | 0.1321 |
| P5A-2G7 | 0.0044 | 0.0287 | 0.1814 | 0.8355 |
| P5A-1D1 | 0.0096 | 0.0691 | 0.0189 | 0.0743 |
| P5A-1B8 | 0.0115 | 0.0501 | 0.0168 | 0.0857 |
| P5A-2G9 | 0.0158 | 0.1466 | 0.0113 | 0.1187 |
| P5A-1D2 | 0.0186 | 0.1025 | 0.0273 | 0.4325 |
| P5A-3C8 | 0.0206 | 0.1031 | 0.0112 | 0.1499 |
| P2C-1F11* | 0.0286 | 0.1195 | 0.0323 | 0.1779 |
| P2B-2F6* | 0.0500 | 0.6074 | 0.4074 | 2.4309 |
| P2B-1A10 | 0.0974 | 0.7446 | 0.0639 | 0.3053 |
| P5A-3B4 | 0.0993 | 1.0657 | 0.0561 | 1.0080 |
| P5A-3C12 | 0.0996 | 0.4679 | 0.2636 | 2.6783 |
| P2B-1G5 | 0.1100 | 0.3700 | 0.0302 | 0.1725 |
| P5A-1C8 | 0.1162 | 0.4621 | 0.1553 | 1.3370 |
| P4A-1H6 | 0.1370 | 0.7670 | 0.0722 | 2.0307 |
| P2C-1D7 | 0.2100 | 1.0700 | 5.3825 | 26.6333 |
| P5A-3A6 | 0.2340 | 1.2670 | 0.4443 | 18.3749 |
| P5A-1B6 | 0.2528 | 1.3719 | 0.8932 | 5.9133 |
| P5A-2D11 | 0.3889 | 1.4758 | 0.1154 | 4.1504 |
| P5A-2H3 | 0.5042 | 2.0522 | 0.1214 | 0.7471 |
| P2C-1A3* | 0.6200 | 5.9400 | 0.2827 | 1.4587 |
| P5A-2F11 | 0.6300 | 1.9400 | 0.4942 | 6.9416 |
| P2B-1A1 | 0.6900 | 2.4100 | 0.2218 | 2.1498 |
| P5A-3A1 | 0.9231 | 4.2357 | 0.6713 | 26.2193 |
| P22A-1D8 | 0.9889 | 6.1038 | n.d. | n.d. |
| P8A-1D5 | 1.0550 | 5.8355 | n.d. | n.d. |
| P5A-2G5 | 1.1528 | 5.6968 | n.d. | n.d. |
| P4B-1E12 | 1.3813 | 14.9370 | n.d. | n.d. |
| P5A-2D6 | 1.4600 | 15.1300 | n.d. | n.d. |
| P4A-2D9 | 1.5400 | 5.9600 | n.d. | n.d. |
| P2C-1C10* | 2.6200 | 4.6400 | 11.1204 | >50 |
| P5A-2G12 | 2.6540 | 12.1251 | n.d. | n.d. |
| P2B-1D9 | 3.1200 | 6.4200 | n.d. | n.d. |
| P5A-3A7 | 3.2500 | >50 | n.d. | n.d. |
| P4B-1F4 | 3.4486 | 9.0132 | n.d. | n.d. |
| P2B-1G1 | 4.2200 | 11.6200 | n.d. | n.d. |
| P16A-1A3 | 4.5554 | 15.9269 | n.d. | n.d. |
| P1A-1C2 | 5.0337 | 21.4613 | n.d. | n.d. |
| P2B-2G4* | 5.1100 | >50 | 2.9005 | 47.7043 |
| P5A-1D10 | 5.7200 | 28.8700 | n.d. | n.d. |
| P2B-1E4 | 5.9600 | 16.9200 | n.d. | n.d. |
| P5A-2E1 | 6.0300 | 8.7600 | n.d. | n.d. |
| P5A-2C9 | 6.4000 | >50 | n.d. | n.d. |
| P5A-2D10 | 6.5647 | 19.6532 | n.d. | n.d. |
| P2B-1F11 | 6.5900 | 14.4100 | n.d. | n.d. |
| P2B-1A12 | 7.2200 | >50 | n.d. | n.d. |
| P5A-2C12 | 7.3500 | >50 | n.d. | n.d. |
| P2A-1A8* | 7.6800 | 26.4100 | 35.8664 | >50 |
| P5A-3D12 | 7.9600 | >50 | n.d. | n.d. |
| P5A-1B1 | 8.0100 | 40.4900 | n.d. | n.d. |

TABLE 7d-continued

The IC$_{50}$ of enrolled 165 antibodies with between 0.1 μg/mL and 50 μg/mL or higher.

| mAbs | Pseudovirus IC50 (μg/ml) | Pseudovirus IC80 (μg/ml) | Live virus IC50 (μg/ml) | Live virus IC80 (μg/ml) |
|---|---|---|---|---|
| P2A-1A10* | 8.5700 | 39.4400 | 1.6395 | 22.1536 |
| P2B-2G9 | 8.8900 | >50 | n.d. | n.d. |
| P2B-1F10 | 9.7400 | 49.7800 | n.d. | n.d. |
| P2B-1F5 | 10.3000 | >50 | n.d. | n.d. |
| P2C-1D5* | 10.6500 | 25.3600 | n.d. | n.d. |
| P2B-2F11 | 13.1100 | >50 | n.d. | n.d. |
| P16A-1B3 | 13.8943 | >50 | n.d. | n.d. |
| P5A-2E5 | 14.0700 | >50 | n.d. | n.d. |
| P2C-1F4 | 15.9600 | >50 | n.d. | n.d. |
| P2A-1B3* | 16.7700 | >50 | n.d. | n.d. |
| P5A-1D6 | 18.2000 | >50 | n.d. | n.d. |
| P5A-2E12 | 20.4745 | >50 | n.d. | n.d. |
| P5A-1A1 | 23.8500 | >50 | n.d. | n.d. |
| P22A-1D7 | 23.8734 | >50 | n.d. | n.d. |
| P2A-1A9* | 26.2700 | >50 | n.d. | n.d. |
| P16A-1A8 | 33.6854 | >50 | n.d. | n.d. |
| P2C-1C8* | 34.3800 | >50 | n.d. | n.d. |
| P2B-2G11* | 34.8400 | >50 | n.d. | n.d. |
| P2B-1B4 | 35.3200 | >50 | n.d. | n.d. |
| P4A-2E10 | 35.3500 | >50 | n.d. | n.d. |
| P5A-3C3 | 36.1300 | >50 | n.d. | n.d. |
| P1A-1C10* | >50 | >50 | n.d. | n.d. |
| P1A-1C7* | >50 | >50 | n.d. | n.d. |
| P1A-1D1* | >50 | >50 | n.d. | n.d. |
| P2C-1E1* | >50 | >50 | n.d. | n.d. |
| P2C-1B12 | >50 | >50 | n.d. | n.d. |
| P2C-1E5 | >50 | >50 | n.d. | n.d. |
| P2B-1G8 | >50 | >50 | n.d. | n.d. |
| P4A-2A2 | >50 | >50 | n.d. | n.d. |
| P2C-1A7 | >50 | >50 | n.d. | n.d. |
| P5A-1A12 | >50 | >50 | n.d. | n.d. |
| P5A-1B10 | >50 | >50 | n.d. | n.d. |
| P5A-1C9 | >50 | >50 | n.d. | n.d. |
| P5A-1C10 | >50 | >50 | n.d. | n.d. |
| P5A-1C11 | >50 | >50 | n.d. | n.d. |
| P4A-2C1 | >50 | >50 | n.d. | n.d. |
| P2B-1D6 | >50 | >50 | n.d. | n.d. |
| P2B-1E12 | >50 | >50 | n.d. | n.d. |
| P2A-1B10 | >50 | >50 | n.d. | n.d. |
| P2C-2C8 | >50 | >50 | n.d. | n.d. |
| P5A-3B8 | >50 | >50 | n.d. | n.d. |
| P5A-3C10 | >50 | >50 | n.d. | n.d. |
| P5A-3B9 | >50 | >50 | n.d. | n.d. |
| P5A-1C4 | >50 | >50 | n.d. | n.d. |
| P5A-2D3 | >50 | >50 | n.d. | n.d. |
| P5A-1D8 | >50 | >50 | n.d. | n.d. |
| P5A-2G11 | >50 | >50 | n.d. | n.d. |
| P5A-2D12 | >50 | >50 | n.d. | n.d. |
| P5A-2E8 | >50 | >50 | n.d. | n.d. |
| P5A-3A2 | >50 | >50 | n.d. | n.d. |
| P5A-1A5 | >50 | >50 | n.d. | n.d. |
| P5A-3A10 | >50 | >50 | n.d. | n.d. |
| P5A-2D7 | >50 | >50 | n.d. | n.d. |
| P5A-3D9 | >50 | >50 | n.d. | n.d. |
| P5A-3C1 | >50 | >50 | n.d. | n.d. |
| P5A-2G4 | >50 | >50 | n.d. | n.d. |
| P3A-1F1 | >50 | >50 | n.d. | n.d. |
| P4B-1E7 | >50 | >50 | n.d. | n.d. |
| P16A-1B12 | >50 | >50 | n.d. | n.d. |
| P22A-1E10 | >50 | >50 | n.d. | n.d. |
| P5A-3A11 | >50 | >50 | n.d. | n.d. |
| P5A-1B11 | >50 | >50 | n.d. | n.d. |
| P5A-2E9 | >50 | >50 | n.d. | n.d. |
| P5A-1A2 | >50 | >50 | n.d. | n.d. |
| P5A-1B2 | >50 | >50 | n.d. | n.d. |
| P5A-2C7 | >50 | >50 | n.d. | n.d. |
| P5A-2F7 | >50 | >50 | n.d. | n.d. |
| P5A-2F9 | >50 | >50 | n.d. | n.d. |
| P5A-3B10 | >50 | >50 | n.d. | n.d. |
| P5A-1C6 | >50 | >50 | n.d. | n.d. |
| P5A-2C10 | >50 | >50 | n.d. | n.d. |
| P5A-2D5 | >50 | >50 | n.d. | n.d. |
| P5A-2F1 | >50 | >50 | n.d. | n.d. |
| P5A-2G8 | >50 | >50 | n.d. | n.d. |

TABLE 7d-continued

The IC$_{50}$ of enrolled 165 antibodies with between 0.1 μg/mL and 50 μg/mL or higher.

| mAbs | Pseudovirus IC50 (μg/ml) | Pseudovirus IC80 (μg/ml) | Live virus IC50 (μg/ml) | Live virus IC80 (μg/ml) |
|---|---|---|---|---|
| P1A-1C6 | >50 | >50 | n.d. | n.d. |
| P1A-1D3 | >50 | >50 | n.d. | n.d. |
| P1A-1D5 | >50 | >50 | n.d. | n.d. |
| P2C-1A6 | >50 | >50 | n.d. | n.d. |
| P3A-1G8 | >50 | >50 | n.d. | n.d. |
| P4A-2A10 | >50 | >50 | n.d. | n.d. |
| P4B-1F6 | >50 | >50 | n.d. | n.d. |
| P4B-1E11 | >50 | >50 | n.d. | n.d. |
| P4A-2A8 | >50 | >50 | n.d. | n.d. |
| P4A-1H5 | >50 | >50 | n.d. | n.d. |
| P4A-2B3 | >50 | >50 | n.d. | n.d. |
| P4B-1G5 | >50 | >50 | n.d. | n.d. |
| P4B-1F10 | >50 | >50 | n.d. | n.d. |
| P4A-2D1 | >50 | >50 | n.d. | n.d. |
| P4A-2D2 | >50 | >50 | n.d. | n.d. |
| P4A-2C12 | >50 | >50 | n.d. | n.d. |
| P8A-1A8 | >50 | >50 | n.d. | n.d. |
| P8A-1C6 | >50 | >50 | n.d. | n.d. |
| P8A-1A5 | >50 | >50 | n.d. | n.d. |
| P16A-1B5 | >50 | >50 | n.d. | n.d. |
| P16A-1C6 | >50 | >50 | n.d. | n.d. |
| P16A-1C1 | >50 | >50 | n.d. | n.d. |
| P16A-1A5 | >50 | >50 | n.d. | n.d. |
| P16A-1A12 | >50 | >50 | n.d. | n.d. |
| P16A-1B1 | >50 | >50 | n.d. | n.d. |
| P16A-1B8 | >50 | >50 | n.d. | n.d. |
| P16A-1A7 | >50 | >50 | n.d. | n.d. |
| P16A-1A10 | >50 | >50 | n.d. | n.d. |
| P22A-1D2 | >50 | >50 | n.d. | n.d. |
| P22A-1D5 | >50 | >50 | n.d. | n.d. |
| P22A-1E6 | >50 | >50 | n.d. | n.d. |
| P1A-1D6 | >50 | >50 | n.d. | n.d. |
| P2B-2G10 | >50 | >50 | n.d. | n.d. |
| P2B-1C3 | >50 | >50 | n.d. | n.d. |
| P2B-1D11 | >50 | >50 | n.d. | n.d. |
| P2B-1E2 | >50 | >50 | n.d. | n.d. |
| P2B-1F9 | >50 | >50 | n.d. | n.d. |
| P22A-1E8 | >50 | >50 | n.d. | n.d. |
| P1A-1B2* | n.d. | n.d. | n.d. | n.d. |
| P1A-1C1* | n.d. | n.d. | n.d. | n.d. |

*Published in the reference (Bin)

TABLE 8

Epitope mapping of mAbs through competitive binding to SARS-CoV-2 RBD

| mAbs | P2C-1A3 | P2C-1C10 | P2C-1F11 | P2B-2F6 | P2A-1B3 | P2A-1A10 |
|---|---|---|---|---|---|---|
| P2C-1A3 |  | 68.41 | 57.44 | 76.73 | 65.20 | n.a. |
| P2C-1C10 | 75.33 |  | −0.32 | 49.69 | 42.98 | n.a. |
| P2C-1F11 | 52.05 | −2.31 |  | 42.65 | 5.98 | n.a. |
| P2B-2F6 | 74.87 | 70.97 | 30.22 |  | 52.79 | n.a. |
| P2A-1B3 | 57.94 | 63.83 | 14.35 | 51.88 |  | n.a. |
| P2A-1A10 | 76.31 | 84.27 | 79.50 | 73.92 | 42.19 |  | n.a.: not applicable

TABLE 9a

Gene family analysis of monoclonal antibodies.

| Patient | mAbs | IGHV | IGHJ | IGHD | CDR3 length | SHM (%) | IGK(L)V | IGK(L)J | KC or LC | CDR3 length | SHM (%) |
|---|---|---|---|---|---|---|---|---|---|---|---|
| P#1 | P1A-1C7 | 1-46*01, 1-46*03 | 4*02 | 2-2*01 | 15 | 0.00 | 1-39*01, 1D-39*01 | 3*01 | KC | 10 | 0.00 |
| P#1 | P1A-1C10 | 1-69*09 | 4*02 | 3-3*01 | 16 | 10.42 | 1-5*03 | 3*01 | KC | 9 | 3.41 |
| P#1 | P1A-1C11 | 1-69*09 | 4*02 | 3-3*01 | 16 | 10.42 | 1-5*03 | 3*01 | KC | 9 | 3.41 |
| P#1 | P1A-1C6 | 3-13*01 | 2*01 | 4-23*01 | 19 | 0.35 | 1-39*01, 1D-39*01 | 3*01 | KC | 10 | 0.00 |
| P#1 | P1A-1D3 | 3-13*01 | 3*02 | 3-10*01 | 18 | 0.00 | 1-39*01, 1D-39*01 | 1*01 | KC | 10 | 0.00 |
| P#1 | P1A-1C2 | 3-23*03 | 5*02 | 1-26*01 | 10 | 0.00 | 1-36*01 | 3*02 | LC | 11 | 0.00 |
| P#1 | P1A-1B2 | 3-30*03, 3-30*18, 3-30-5*01 | 4*02 | 5-24*01 | 12 | 11.46 | 2-14*01 | 2*01, 3*01 | LC | 10 | 9.26 |
| P#1 | P1A-1C1 | 3-33*01, 3-33*05, 3-33*06 | 4*02 | 3-10*01 | 17 | 6.25 | 1D-13*01 | 5*01 | KC | 9 | 5.68 |
| P#1 | P1A-1D1 | 3-53*01 | 4*02 | 6-13*01 | 12 | 4.21 | 2-8*01 | 1*01 | LC | 10 | 2.22 |
| P#1 | P1A-1D5 | 3-53*01 | 6*02 | 2-15*01 | 15 | 1.05 | 1-33*01, 1D-33*01 | 3*01 | KC | 9 | 0.00 |
| P#1 | P1A-1D6 | 3-53*01 | 6*02 | 2-15*01 | 15 | 4.56 | 1-33*01, 1D-33*01 | 3*01 | KC | 9 | 3.79 |
| P#2 | P2A-1A10 | 1-2*06 | 2*01 | 2-2*01 | 19 | 0.00 | 2-40*01, 2D-40*01 | 4*01 | KC | 9 | 0.00 |
| P#2 | P2B-1A4 | 1-2*06 | 2*01 | 2-2*01 | 19 | 0.00 | 2-40*01, 2D-40*01 | 4*01 | KC | 9 | 0.00 |
| P#2 | P2B-1B2 | 1-2*06 | 2*01 | 2-2*01 | 19 | 0.00 | 2-40*01, 2D-40*01 | 4*01 | KC | 9 | 0.00 |
| P#2 | P2B-2G1 | 1-2*06 | 2*01 | 2-2*01 | 19 | 0.00 | 2-40*01, 2D-40*01 | 4*01 | KC | 9 | 0.00 |
| P#2 | P2B-2G12 | 1-2*06 | 2*01 | 2-2*01 | 19 | 0.00 | 2-40*01, 2D-40*01 | 4*01 | KC | 9 | 0.00 |

TABLE 9a-continued

Gene family analysis of monoclonal antibodies.

| | | Heavy chain | | | | | Kappa chain (KC) or Lambda chain (LC) | | | | |
|---|---|---|---|---|---|---|---|---|---|---|---|
| Patient | mAbs | IGHV | IGHJ | IGHD | CDR3 length | SHM (%) | IGK(L)V | IGK(L)J | KC or LC | CDR3 length | SHM (%) |
| P#2 | P2C-1A10 | 1-2*06 | 2*01 | 2-2*01 | 19 | 0.00 | 2-40*01, 2D-40*01 | 4*01 | KC | 9 | 0.00 |
| P#2 | P2C-1B10 | 1-2*06 | 2*01 | 2-2*01 | 19 | 0.00 | 2-40*01, 2D-40*01 | 4*01 | KC | 9 | 0.00 |
| P#2 | P2C-1D6 | 1-2*06 | 2*01 | 2-2*01 | 19 | 0.00 | 2-40*01, 2D-40*01 | 4*01 | KC | 9 | 0.00 |
| P#2 | P2C-1D12 | 1-2*06 | 2*01 | 2-2*01 | 19 | 0.00 | 2-40*01, 2D-40*01 | 4*01 | KC | 9 | 0.00 |
| P#2 | P2C-1F10 | 1-2*06 | 2*01 | 2-2*01 | 19 | 0.00 | 2-40*01, 2D-40*01 | 4*01 | KC | 9 | 0.00 |
| P#2 | P2B-1F8 | 1-2*06 | 6*02 | 3-9*01 | 14 | 8.33 | 3-20*01 | 1*01 | KC | 9 | 4.49 |
| P#2 | P2B-2G9 | 1-2*06 | 6*02 | 3-9*01 | 14 | 8.33 | 3-20*01 | 1*01 | KC | 9 | 4.49 |
| P#2 | P2B-1C3 | 1-46*01, 1-46*03 | 3*01 | 2-2*01 | 15 | 0.00 | 1-5*03 | 1*01 | KC | 8 | 0.38 |
| P#2 | P2C-1C10 | 1-69*01, 1-69D*01 | 4*02 | 4-23*01 | 11 | 0.35 | 3-11*01 | 2*01, 2*02 | KC | 8 | 0.00 |
| P#2 | P2B-2G10 | 1-69*04 | 4*02 | 1-26*01 | 11 | 3.47 | 1-39*01, 1D-39*01 | 2*01 | KC | 9 | 2.27 |
| P#2 | P2B-1F11 | 1-69*09 | 5*02 | 6-13*01 | 17 | 0.00 | 1-40*01 | 3*02 | LC | 11 | 0.00 |
| P#2 | P2B-1D9 | 2-5*02 | 4*02 | 3-10*01 | 16 | 1.03 | 1-47*02 | 2*01, 3*01 | LC | 11 | 0.00 |
| P#2 | P2B-1E2 | 2-5*02 | 4*02 | 6-13*01 | 12 | 0.34 | 1-5*03 | 3*01 | KC | 8 | 0.00 |
| P#2 | P2B-1E4 | 2-5*02 | 4*02 | 5-12*01 | 11 | 0.00 | 2-14*01 | 2*01, 3*01 | LC | 9 | 0.74 |
| P#2 | P2C-1F4 | 2-70*15 | 4*02 | 1-26*01 | 14 | 0.00 | 1-44*01 | 2*01, 3*01 | LC | 10 | 0.00 |
| P#2 | P2B-1D12 | 3-11*04 | 5*01, 5*02 | 6-13*01 | 12 | 0.00 | 1-9*01 | 4*01 | KC | 9 | 0.00 |
| P#2 | P2C-1A3 | 3-11*04 | 5*01, 5*02 | 6-13*01 | 12 | 0.00 | 1-9*01 | 4*01 | KC | 9 | 0.00 |
| P#2 | P2B-1D6 | 3-15*01 | 6*02 | 3-10*01 | 24 | 0.00 | 1-44*01 | 3*02 | LC | 11 | 0.00 |
| P#2 | P2C-1B12 | 3-15*01 | 6*02 | 3-10*01 | 13 | 1.02 | 6-57*02 | 1*01 | LC | 10 | 0.00 |
| P#2 | P2B-1F9 | 3-15*01 | 4*02 | 3-22*01 | 16 | 0.00 | 1-NL1*01 | 1*01 | KC | 10 | 0.00 |
| P#2 | P2C-1D5 | 3-23*04 | 4*02 | 3-10*01 | 14 | 0.69 | 3-21*01 | 1*01 | LC | 11 | 0.38 |
| P#2 | P2B-1B4 | 3-30*04, 3-30-3*03 | 6*02 | 3-10*01 | 22 | 0.35 | 1-39*01, 1D-39*01 | 3*01 | KC | 10 | 0.00 |
| P#2 | P2B-1F2 | 3-33*01, 3-33*06 | 4*02 | 5-18*01 | 11 | 0.00 | 2-11*01 | 2*01, 3*01 | LC | 11 | 0.00 |
| P#2 | P2B-2G4 | 3-33*01, 3-33*06 | 4*02 | 5-18*01 | 11 | 0.00 | 2-11*01 | 2*01, 3*01 | LC | 11 | 0.00 |
| P#2 | P2C-1C8 | 3-33*01, 3-33*06 | 4*02 | 3-22*01 | 13 | 0.69 | 2D-30*01 | 2*01 | KC | 9 | 0.36 |
| P#2 | P2A-1R.3 | 3-48*02 | 5*02 | 3-10*01 | 16 | 10.07 | 3-20*01 | 5*01 | KC | 10 | 3.00 |
| P#2 | P2B-1B11 | 3-48*02 | 5*02 | 3-10*01 | 16 | 10.07 | 3-20*01 | 5*01 | KC | 10 | 2.62 |
| P#2 | P2B-1B12 | 3-48*02 | 5*02 | 3-10*01 | 16 | 10.07 | 3-20*01 | 5*01 | KC | 10 | 2.62 |
| P#2 | P2B-1C4 | 3-48*02 | 5*02 | 3-10*01 | 16 | 10.07 | 3-20*01 | 5*01 | KC | 10 | 3.00 |
| P#2 | P2B-1E11 | 3-48*02 | 5*02 | 3-10*01 | 16 | 10.07 | 3-20*01 | 5*01 | KC | 10 | 3.00 |
| P#2 | P2B-2H7 | 3-48*02 | 5*02 | 3-10*01 | 16 | 10.07 | 3-20*01 | 5*01 | KC | 10 | 2.62 |
| P#2 | P2B-1G12 | 3-48*02 | 5*02 | 3-10*01 | 16 | 8.33 | 3-20*01 | 5*01 | KC | 10 | 3.00 |
| P#2 | P2C-1E5 | 3-48*02 | 5*02 | 3-10*01 | 16 | 8.33 | 3-20*01 | 5*01 | KC | 10 | 3.00 |
| P#2 | P2B-1A10 | 3-53*01 | 3*02 | 1-20*01 | 15 | 0.35 | 1-33*01, 1D-33*01 | 2*01 | KC | 10 | 0.38 |
| P#2 | P2B-1F5 | 3-53*01 | 4*02 | 2-2*01 | 14 | 0.00 | 1-NL1*01 | 1*01 | KC | 9 | 0.00 |
| P#2 | P2C-1D7 | 3-53*01 | 4*02 | 1-26*01 | 12 | 0.00 | 2D-30*01 | 3*01 | KC | 9 | 0.00 |
| P#2 | P2B-1G1 | 3-66*01, 3-66*04 | 5*02 | 4-17*01 | 11 | 0.00 | 3-20*01 | 2*02 | KC | 9 | 0.00 |
| P#2 | P2C-1E1 | 3-66*01, 3-66*04 | 4*02 | 5-12*01 | 9 | 0.00 | 3-11*01 | 1*01 | KC | 10 | 0.00 |
| P#2 | P2C-1F11 | 3-66*01, 3-66*04 | 6*02 | 2-15*01 | 11 | 1.75 | 3-20*01 | 2*01, 2*02 | KC | 8 | 0.00 |
| P#2 | P2A-1A8 | 3-9*01 | 6*02 | 5-12*01 | 23 | 3.82 | 2-14*02 | 1*01 | LC | 10 | 2.59 |
| P#2 | P2R-1R10 | 3-9*01 | 6*02 | 5-12*01 | 23 | 3.82 | 2-14*02 | 1*01 | LC | 10 | 2.59 |
| P#2 | P2B-1C10 | 3-9*01 | 6*02 | 5-12*01 | 23 | 3.82 | 2-14*02 | 1*01 | LC | 10 | 2.59 |
| P#2 | P2B-1D3 | 3-9*01 | 6*02 | 5-12*01 | 23 | 3.82 | 2-14*02 | 1*01 | LC | 10 | 2.59 |
| P#2 | P2B-2H4 | 3-9*01 | 6*02 | 5-12*01 | 23 | 3.82 | 2-14*02 | 1*01 | LC | 10 | 2.59 |
| P#2 | P2C-1A5 | 3-9*01 | 6*02 | 5-12*01 | 23 | 3.82 | 2-14*02 | 1*01 | LC | 10 | 2.59 |
| P#2 | P2C-1A8 | 3-9*01 | 6*02 | 5-12*01 | 23 | 3.82 | 2-14*02 | 1*01 | LC | 10 | 2.59 |
| P#2 | P2C-1B1 | 3-9*01 | 6*02 | 5-12*01 | 23 | 3.82 | 2-14*02 | 1*01 | LC | 10 | 2.59 |
| P#2 | P2C-1C12 | 3-9*01 | 6*02 | 5-12*01 | 23 | 3.82 | 2-14*02 | 1*01 | LC | 10 | 2.59 |
| P#2 | P2C-1A6 | 3-9*01 | 6*02 | 5-12*01 | 23 | 3.47 | 2-14*02 | 1*01 | LC | 10 | 2.59 |
| P#2 | P2A-1A9 | 3-9*01 | 6*02 | 3-22*01 | 17 | 2.08 | 1-40*01 | 2*01, 3*01 | LC | 11 | 1.11 |

TABLE 9a-continued

Gene family analysis of monoclonal antibodies.

| | | Heavy chain | | | | | Kappa chain (KC) or Lambda chain (LC) | | | | |
|---|---|---|---|---|---|---|---|---|---|---|---|
| Patient | mAbs | IGHV | IGHJ | IGHD | CDR3 length | SHM (%) | IGK(L)V | IGK(L)J | KC or LC | CDR3 length | SHM (%) |
| P#2 | P2C-1A1 | 3-9*01 | 6*02 | 3-22*01 | 17 | 2.08 | 1-40*01 | 2*01, 3*01 | LC | 11 | 1.11 |
| P#2 | P2R-2G11 | 3-9*01 | 6*02 | 1-26*01 | 17 | 2.08 | 1-40*01 | 2*01, 3*01 | LC | 11 | 1.11 |
| P#2 | P2B-1E12 | 3-9*01 | 3*02 | 6-19*01 | 17 | 0.00 | 3-20*01 | 4*01 | KC | 9 | 0.00 |
| P#2 | P2B-2F6 | 4-38-2*02 | 3*02 | 2-2*01 | 20 | 0.69 | 2-8*01 | 3*02 | LC | 10 | 0.00 |
| P#2 | P2A-1B10 | 4-39*01 | 3*02 | 2-15*01 | 20 | 0.34 | 1-47*01 | 3*02 | LC | 8 | 0.37 |
| P#2 | P2B-1B9 | 4-39*07 | 4*02 | 4-17*01 | 9 | 0.00 | 1-NL1*01 | 1*01 | KC | 10 | 0.00 |
| P#2 | P2B-2F11 | 4-39*07 | 4*02 | 4-17*01 | 9 | 0.00 | 1-NL1*01 | 1*01 | KC | 10 | 0.00 |
| P#2 | P2B-1G8 | 4-39*07 | 4*02 | 5-12*01 | 11 | 0.34 | 1-5*03 | 3*01 | KC | 9 | 1.14 |
| P#2 | P2B-1A1 | 4-59*01 | 3*02 | 1-1*01 | 14 | 0.35 | 2-14*01 | 3*02 | LC | 10 | 1.11 |
| P#2 | P2B-1D11 | 4-59*01 | 5*02 | 2-15*01 | 22 | 0.00 | 3-25*03 | 2*01, 3*01 | LC | 9 | 0.00 |
| P#2 | P2B-1F10 | 4-59*01, 4-59*02 | 4*02 | 3-10*01 | 15 | 1.05 | 1-39*01, 1D-39*01 | 2*01 | KC | 9 | 1.14 |
| P#2 | P2C-1A7 | 5-51*01 | 4*02 | 3-10*01 | 17 | 0.00 | 3-1*01 | 2*01, 3*01, 3*02 | LC | 9 | 0.00 |
| P#2 | P2B-1A12 | 7-4-1*02 | 6*02 | 5-12*01 | 16 | 0.00 | 1-39*01, 1D-39*01 | 4*01 | KC | 9 | 0.00 |
| P#2 | P2B-1G5 | 7-4-1*02 | 6*02 | 4-23*01 | 12 | 1.04 | 3-21*01 | 3*02 | LC | 11 | 0.38 |
| P#3 | P3A-1F1 | 3-13*04 | 4*02 | 6-19*01 | 17 | 0.00 | 1-39*01, 1D-39*01 | 1*01 | KC | 10 | 0.00 |
| P#3 | P3A-1G8 | 3-64*05, 3-64D*06 | 6*02 | 3-10*01 | 19 | 0.35 | 1-44*01 | 2*01, 3*01 | LC | 11 | 0.00 |
| P#4 | P4A-2A10 | 1-46*01, 1-46*03 | 6*02 | 2-15*01 | 26 | 7.64 | 1-40*01 | 2*01, 3*01 | LC | 10 | 1.85 |
| P#4 | P4B-1F6 | 1-69*01, 1-69D*01 | 1*01 | 1-26*01 | 15 | 3.47 | 2-23*02 | 1*01 | LC | 10 | 1.85 |
| P#4 | P4B-1E11 | 2-5*02 | 4*02 | 3-10*01 | 18 | 0.00 | 1-36*01 | 3*02 | LC | 11 | 0.37 |
| P#4 | P4A-2A2 | 3-23*04 | 4*02 | 3-10*01 | 14 | 5.90 | 1-51*01 | 3*02 | LC | 11 | 2.25 |
| P#4 | P4A-2A8 | 3-23*04 | 4*02 | 4-11*01 | 11 | 0.00 | 3-21*01 | 2*01, 3*01 | LC | 11 | 0.00 |
| P#4 | P4A-2C1 | 3-23*04 | 6*02 | 6-19*01 | 16 | 2.78 | 2-28*01, 2D-28*01 | 4*01 | KC | 11 | 1.08 |
| P#4 | P4A-1H5 | 3-30*03, 3-30*18, 3-30-5*01 | 4*02 | 2-2*01 | 21 | 1.74 | 1-39*01, 1D-39*01 | 3*01 | KC | 8 | 3.79 |
| P#4 | P4B-1G2 | 3-30*03, 3-30*18, 3-30-5*01 | 4*02 | 2-2*01 | 21 | 1.74 | 1-39*01, 1D-39*01 | 3*01 | KC | 8 | 3.79 |
| P#4 | P4A-2B3 | 3-30*03, 3-30*18, 3-30-5*01 | 4*02 | 2-2*01 | 21 | 1.39 | 1-39*01, 1D-39*01 | 3*01 | KC | 8 | 3.41 |
| P#4 | P4A-1H6 | 3-30*03, 3-30*18, 3-30-5*01 | 4*02 | 2-2*01 | 21 | 1.39 | 1-39*01, 1D-39*01 | 3*01 | KC | 8 | 1.52 |
| P#4 | P4B-1G5 | 3-30*03, 3-30*18, 3-30-5*01 | 4*02 | 2-15*01 | 22 | 1.39 | 3-21*01 | 1*01 | LC | 10 | 0.77 |
| P#4 | P4A-2E10 | 3-30*03, 3-30*18, 3-30-5*01 | 4*02 | 2-2*01 | 21 | 4.86 | 1-39*01, 10-39*01 | 3*01 | KC | 8 | 1.89 |
| P#4 | P4B-1E3 | 3-30*03, 3-30*18, 3-30-5*01 | 4*02 | 2-2*01 | 21 | 4.86 | 1-39*01, 1D-39*01 | 3*01 | KC | 8 | 1.89 |
| P#4 | P4A-2D9 | 3-30*03, 3-30*18, 3-30-5*01 | 4*02 | 2-2*01 | 21 | 2.08 | 1-39*01, 1D-39*01 | 3*01 | KC | 8 | 2.27 |
| P#4 | P4B-1F4 | 3-30*, 3-30*18, 3-30-5*01 | 6*02 | 6-13*01 | 22 | 0.35 | 2-30*01 | 2*01 | KC | 10 | 0.00 |
| P#4 | P4B-1E7 | 3-43D*03 | 6*02 | 4-11*01 | 20 | 0.00 | 3-1*01 | 1*01 | LC | 10 | 0.00 |
| P#4 | P4B-1F10 | 3-7*01 | 6*02 | 3-9*01 | 13 | 0.00 | 3-21*01 | 1*01 | LC | 12 | 0.00 |
| P#4 | P4A-2D1 | 3-9*01 | 4*02 | 4-23*01 | 13 | 0.00 | 1-12*01, 1-12*02, 1D-12*02 | 4*01 | KC | 9 | 0.00 |
| P#4 | P4A-2D2 | 4-39*01 | 6*02 | 3-22*01 | 16 | 0.00 | 3-20*01 | 4*01 | KC | 10 | 0.00 |
| P#4 | P4B-1E12 | 4-59*08 | 4*02 | 2-21*01 | 11 | 1.40 | 1-44*01 | 2*01, 3*01 | LC | 11 | 0.37 |
| P#4 | P4A-2C12 | 5-51*01 | 4*02 | 3-22*01 | 15 | 2.43 | 1-44*01 | 1*01 | LC | 11 | 1.50 |
| P#8 | P8A-1A8 | 3-23*04 | 4*02 | 5-12*01 | 11 | 0.35 | 3-21*01 | 3*02 | LC | 11 | 0.77 |

TABLE 9a-continued

Gene family analysis of monoclonal antibodies.

| | | Heavy chain | | | | | Kappa chain (KC) or Lambda chain (LC) | | | | |
|---|---|---|---|---|---|---|---|---|---|---|---|
| Patient | mAbs | IGHV | IGHJ | IGHD | CDR3 length | SHM (%) | IGK(L)V | IGK(L)J | KC or LC | CDR3 length | SHM (%) |
| P#8 | P8A-1C6 | 3-30*03, 3-30*18, 3-30-5*01 | 4*02 | 2-15*01 | 20 | 0.00 | 1-33*01, 1D-33*01 | 3*01 | KC | 8 | 0.00 |
| P#8 | P8A-1A5 | 5-51*01 | 6*03 | 5-18*01 | 18 | 1.74 | 1-47*02 | 1*01 | LC | 12 | 0.00 |
| P#8 | P8A-1D5 | 6-1*01 | 3*02 | 3-10*01 | 16 | 1.01 | 3-20*01 | 4*01 | KC | 9 | 0.37 |
| P#5 | P5A-1A1 | 1-24*01 | 5*02 | 3-10*01 | 15 | 0.35 | 2-28*01, 2D-28*01 | 4*02 | KC | 9 | 0.00 |
| P#5 | P5A-1C8 | 1-46*01, 1-46*03 | 1*01 | 3-22*01 | 22 | 0.00 | 1-33*01, 1D-33*01 | 5*01 | KC | 10 | 0.00 |
| P#5 | P5A-2D5 | 1-46*01, 1-46*03 | 3*02 | 3-9*01 | 24 | 0.00 | 1-40*01 | 2*01, 3*01 | LC | 11 | 0.00 |
| P#5 | P5A-2C8 | 1-46*01, 1-46*03 | 4*02 | 5-12*01 | 15 | 0.00 | 2-23*02 | 1*01 | LC | 10 | 0.00 |
| P#5 | P5A-2E9 | 1-46*01, 1-46*03 | 4*02 | 4-17*01 | 22 | 0.00 | 2-14*01 | 1*01 | LC | 11 | 0.74 |
| P#5 | P5A-3B8 | 1-46*01, 1-46*03 | 4*02 | 3-10*01 | 16 | 0.69 | 2-23*02 | 7*01 | LC | 11 | 0.37 |
| P#5 | P5A-3A11 | 1-69*01, 1-69D*01 | 6*02 | 2-15*01 | 14 | 0.00 | 1-39*01, 1D-39*01 | 1*01 | KC | 9 | 0.00 |
| P#5 | P5A-3C10 | 1-69*01, 1-69D*01 | 5*02 | 2-15*01 | 22 | 0.00 | 6-57*02 | 2*01, 3*01 | LC | 8 | 0.00 |
| P#5 | P5A-1A2 | 1-8*01 | 5*02 | 3-3*01 | 21 | 0.69 | 1-40*01 | 1*01 | LC | 12 | 0.00 |
| P#5 | P5A-1C11 | 1-8*01 | 5*02 | 3-10*01 | 17 | 0.00 | 3-21*01 | 2*01, 3*01 | LC | 13 | 0.38 |
| P#5 | P5A-2F11 | 1-8*01 | 5*02 | 2-2*01 | 15 | 0.00 | 4-1*01 | 4*01 | KC | 9 | 0.00 |
| P#5 | P5A-3B9 | 1-8*01 | 5*02 | 2-15*01 | 15 | 0.00 | 1-36*01 | 3*02 | LC | 11 | 0.00 |
| P#5 | P5A-2C12 | 2-5*02 | 4*02 | 6-13*01 | 16 | 0.00 | 3-11*01 | 4*01 | KC | 8 | 0.00 |
| P#5 | P5A-3C12 | 2-5*02 | 4*02 | 6-13*01 | 19 | 0.00 | 4-1*01 | 2*01 | KC | 9 | 0.00 |
| P#5 | P5A-3C3 | 2-5*02 | 4*02 | 2-15*01 | 12 | 0.34 | 6-57*02 | 2*01, 3*01 | LC | 9 | 0.00 |
| P#5 | P5A-3C1 | 3-11*01 | 5*02 | 6-13*01 | 13 | 1.39 | 3-21*01 | 2*01 | LC | 13 | 0.00 |
| P#5 | P5A-1C4 | 3-13*01 | 6*02 | 3-10*01 | 20 | 0.00 | 1-39*01, 1D-39*01 | 2*01 | KC | 10 | 0.00 |
| P#5 | P5A-2G8 | 3-13*01 | 4*02 | 1-26*01 | 13 | 0.70 | 1-39*01, 1D-39*01 | 3*01 | KC | 10 | 0.00 |
| P#5 | P5A-2D3 | 3-13*01 | 2*01 | 6-13*01 | 16 | 0.00 | 1-39*01, 1D-39*01 | 5*01 | KC | 10 | 0.00 |
| P#5 | P5A-3B10 | 3-13*01 | 2*01 | 6-13*01 | 16 | 0.00 | 1-39*01, 1D-39*01 | 3*01 | KC | 10 | 0.00 |
| P#5 | P5A-1D8 | 3-15*01 | 3*02 | 3-22*01 | 18 | 0.68 | 3-19*01 | 2*01, 3*01 | LC | 11 | 0.00 |
| P#5 | P5A-2G10 | 3-15*01 | 3*02 | 3-22*01 | 18 | 0.00 | 3-19*01 | 2*01, 3*01 | LC | 11 | 0.00 |
| P#5 | P5A-2H6 | 3-15*01 | 3*02 | 3-22*01 | 18 | 0.00 | 3-19*01 | 2*01, 3*01 | LC | 11 | 0.00 |
| P#5 | P5A-1D6 | 3-23*04 | 4*02 | 1-1*01 | 13 | 0.00 | 3-21*01 | 3*02 | LC | 11 | 0.00 |
| P#5 | P5A-2E12 | 3-23*04 | 4*02 | 6-19*01 | 14 | 0.00 | 3-21*01 | 1*01 | LC | 11 | 0.00 |
| P#5 | P5A-3D12 | 3-23*04 | 3*02 | 3-22*01 | 24 | 0.35 | 1-47*01 | 1*01 | LC | 12 | 0.00 |
| P#5 | P5A-1B6 | 3-30*04, 3-30-3*03 | 4*02 | 3-10*01 | 20 | 0.00 | 1-33*01, 1D-33*01 | 2*01 | KC | 9 | 0.00 |
| P#5 | P5A-2E6 | 3-30*04, 3-30-3*03 | 4*02 | 3-10*01 | 20 | 0.00 | 1-33*01, 1D-33*01 | 2*01 | KC | 9 | 0.00 |
| P#5 | P5A-1B1 | 3-33*01, 3-33*04, 3-33*06 | 4*02 | 4-23*01 | 14 | 3.13 | 3-15*01 | 4*01 | KC | 9 | 1.89 |
| P#5 | P5A-1C5 | 3-33*01, 3-33*04, 3-33*06 | 4*02 | 4-23*01 | 14 | 3.13 | 3-15*01 | 4*01 | KC | 9 | 2.27 |
| P#5 | P5A-2H7 | 3-33*01, 3-33*04, 3-33*06 | 4*02 | 4-23*01 | 14 | 3.13 | 3-15*01 | 4*01 | KC | 9 | 1.89 |
| P#5 | P5A-2G9 | 3-33*01, 3-33*06 | 4*02 | 3-10*01 | 12 | 0.00 | 5-37*01 | 1*01 | LC | 10 | 0.35 |
| P#5 | P5A-2G11 | 3-33*01, 3-33*06 | 6*02 | 3-16*01 | 17 | 0.00 | 2-14*01 | 2*01, 3*01 | LC | 11 | 0.74 |
| P#5 | P5A-1B8 | 3-53*01 | 4*02 | 2-15*01 | 9 | 1.40 | 1-9*01 | 4*01 | KC | 9 | 0.00 |
| P#5 | P5A-1D2 | 3-53*01 | 4*02 | 1-26*01 | 15 | 1.40 | 1-40*01 | 2*01, 3*01 | LC | 11 | 1.11 |
| P#5 | P5A-1D1 | 3-53*01 | 6*02 | 3-16*01 | 11 | 0.35 | 1-9*01 | 5*01 | KC | 8 | 0.76 |
| P#5 | P5A-2C9 | 3-7*01 | 4*02 | 6-19*01 | 14 | 0.00 | 3-20*01 | 5*01 | KC | 10 | 0.00 |
| P#5 | P5A-2E4 | 3-7*01 | 4*02 | 6-19*01 | 14 | 0.35 | 3-20*01 | 5*01 | KC | 10 | 0.00 |
| P#5 | P5A-2G12 | 3-7*01 | 4*02 | 5-18*01 | 12 | 0.00 | 6-57*02 | 2*01, 3*01 | LC | 10 | 0.00 |

TABLE 9a-continued

Gene family analysis of monoclonal antibodies.

| | | Heavy chain | | | | | Kappa chain (KC) or Lambda chain (LC) | | | | |
|---|---|---|---|---|---|---|---|---|---|---|---|
| Patient | mAbs | IGHV | IGHJ | IGHD | CDR3 length | SHM (%) | IGK(L)V | IGK(L)J | KC or LC | CDR3 length | SHM (%) |
| P#5 | P5A-2D12 | 3-7*01 | 6*02 | 4-11*01 | 18 | 0.00 | 2-28*01, 2D-28*01 | 1*01 | KC | 9 | 0.00 |
| P#5 | P5A-2F1 | 3-74*02 | 4*02 | 6-19*01 | 12 | 0.00 | 6-57*02 | 2*01, 3*01 | LC | 9 | 0.00 |
| P#5 | P5A-1C10 | 3-9*01 | 4*02 | 4-17*01 | 14 | 0.00 | 3-21*01 | 1*01 | LC | 12 | 0.00 |
| P#5 | P5A-2E8 | 3-9*01 | 4*02 | 4-17*01 | 13 | 0.00 | 3-21*01 | 1*01 | LC | 11 | 0.00 |
| P#5 | P5A-3A2 | 3-9*01 | 4*02 | 4-17*01 | 14 | 1.74 | 3-21*01 | 1*01 | LC | 11 | 0.00 |
| P#5 | P5A-2D6 | 3-9*01 | 4*02 | 3-10*01 | 14 | 0.35 | 1-40*01 | 2*01, 3*01 | LC | 12 | 0.74 |
| P#5 | P5A-1B12 | 3-9*01 | 6*02 | 4-17*01 | 17 | 0.69 | 1-51*01 | 2*01, 3*01 | LC | 11 | 0.37 |
| P#5 | P5A-3A6 | 3-9*01 | 6*02 | 3-10*01 | 27 | 0.69 | 2-14*01 | 2*01, 3*01 | LC | 10 | 0.74 |
| P#5 | P5A-3D9 | 3-9*01 | 3*02 | 3-3*02 | 16 | 0.00 | 3-15*01 | 4*01 | KC | 11 | 0.38 |
| P#5 | P5A-1D10 | 3-11*01 | 4*02 | 3-16*02 | 21 | 2.43 | 2-14*01 | 2*01, 3*01 | LC | 11 | 1.11 |
| P#5 | P5A-3A1 | 3-53*01 | 4*02 | 4-17*01 | 11 | 0.00 | 3-20*01 | 2*02 | KC | 9 | 0.00 |
| P#5 | P5A-3C8 | 3-53*01 | 6*02 | 4-11*01 | 11 | 1.05 | 1-9*01 | 2*01 | KC | 11 | 1.14 |
| P#5 | P5A-2D10 | 4-31*03 | 5*02 | 5-12*01 | 12 | 0.34 | 6-57*02 | 2*01, 3*01 | LC | 10 | 0.37 |
| P#5 | P5A-2G5 | 4-31*03 | 4*02 | 3-16*02 | 14 | 1.37 | 3-21*01 | 2*01, 3*01 | LC | 11 | 0.00 |
| P#5 | P5A-1A12 | 4-39*01 | 6*02 | 2-21*01 | 17 | 0.69 | 4-1*01 | 1*01 | KC | 9 | 0.00 |
| P#5 | P5A-2C7 | 4-39*01 | 4*02 | 4-17*01 | 16 | 0.00 | 2-23*02 | 3*02 | LC | 10 | 0.00 |
| P#5 | P5A-2F7 | 4-39*01 | 4*02 | 3-22*01 | 18 | 0.00 | 2-23*02 | 1*01 | LC | 11 | 0.00 |
| P#5 | P5A-2F9 | 4-39*01 | 4*02 | 3-9*01 | 14 | 0.00 | 2-23*02 | 2*01, 3*01 | LC | 8 | 0.00 |
| P#5 | P5A-1A5 | 4-4*02 | 4*02 | 4-23*01 | 14 | 0.00 | 2-14*01 | 2*01, 3*01 | LC | 10 | 0.74 |
| P#5 | P5A-1C6 | 4-4*02 | 5*02 | 2-8*02 | 22 | 0.00 | 1-40*01 | 1*01 | LC | 12 | 0.00 |
| P#5 | P5A-3A10 | 4-4*02 | 6*02 | 6-13*01 | 21 | 0.00 | 1-39*01, 1D-39*01 | 2*01 | KC | 9 | 0.00 |
| P#5 | P5A-1B9 | 4-59*01 | 2*01 | 3-9*01 | 22 | 0.70 | 4-1*01 | 4*01 | KC | 9 | 0.00 |
| P#5 | P5A-3A7 | 4-59*01 | 2*01 | 3-9*01 | 22 | 0.00 | 4-1*01 | 4*01 | KC | 9 | 0.00 |
| P#5 | P5A-3B1 | 4-59*01 | 2*01 | 3-9*01 | 22 | 0.00 | 4-1*01 | 4*01 | KC | 9 | 0.00 |
| P#5 | P5A-3B6 | 4-59*01 | 2*01 | 3-9*01 | 22 | 0.00 | 4-1*01 | 4*01 | KC | 9 | 0.00 |
| P#5 | P5A-2C10 | 4-59*01 | 1*01 | 4-17*01 | 17 | 0.00 | 3-21*01 | 2*01, 3*01 | LC | 11 | 0.00 |
| P#5 | P5A-2E5 | 4-59*01 | 4*02 | 5-12*01 | 12 | 0.00 | 6-57*02 | 2*01, 3*01 | LC | 9 | 0.00 |
| P#5 | P5A-2G4 | 4-59*12 | 3*02 | 2-8*02 | 12 | 10.88 | 1D-16*01 | 5*01 | KC | 9 | 2.65 |
| P#5 | P5A-2G7 | 4-61*01 | 5*02 | 3-10*01 | 20 | 0.34 | 2-14*01 | 2*01, 3*01 | LC | 11 | 0.74 |
| P#5 | P5A-1B10 | 5-51*01 | 4*02 | 3-16*01 | 12 | 1.04 | 2-28*01, 2D-28*01 | 2*01 | KC | 11 | 0.72 |
| P#5 | P5A-1C9 | 5-51*01 | 4*02 | 6-19*01 | 11 | 0.00 | 3-19*01 | 1*01 | LC | 12 | 0.00 |
| P#5 | P5A-2D11 | 5-51*01 | 4*02 | 4-23*01 | 13 | 0.00 | 1-44*01 | 2*01, 3*01 | LC | 11 | 0.00 |
| P#5 | P5A-3B4 | 5-51*01 | 4*02 | 4-23*01 | 13 | 0.35 | 1-44*01 | 2*01, 3*01 | LC | 11 | 0.00 |
| P#5 | P5A-2H3 | 5-51*01 | 4*02 | 4-23*01 | 13 | 0.35 | 1-44*01 | 2*01, 3*01 | LC | 11 | 0.00 |
| P#5 | P5A-2E1 | 5-51*01 | 5*02 | 4-11*01 | 12 | 0.00 | 3-21*01 | 2*01, 3*01 | LC | 11 | 0.00 |
| P#5 | P5A-1B11 | 7-4-1*02 | 4*02 | 2-15*01 | 20 | 0.00 | 1-39*01, 1D-39*01 | 4*01 | KC | 10 | 0.00 |
| P#5 | P5A-2D7 | 7-4-1*02 | 6*02 | 6-19*01 | 10 | 0.00 | 6-21*02 | 1*01 | KC | 8 | 0.00 |
| P#5 | P5A-3C9 | 7-4-1*02 | 6*02 | 6-19*01 | 10 | 0.00 | 6-21*02 | 1*01 | KC | 8 | 0.00 |
| P#5 | P5A-3D11 | 7-4-1*02 | 6*02 | 6-19*01 | 10 | 0.00 | 6-21*02 | 1*01 | KC | 8 | 0.00 |
| P#16 | P16A-1A3 | 1-3*01 | 5*02 | 5-18*01 | 11 | 0.00 | 6-57*02 | 2*01, 3*01 | LC | 9 | 0.37 |
| P#16 | P16A-1A8 | 1-46*01, 1-46*03 | 4*02 | 2-2*01 | 20 | 0.00 | 3-21*01 | 1*01 | LC | 13 | 0.00 |
| P#16 | P16A-1B5 | 1-46*01, 1-46*03 | 4*02 | 3-3*01 | 13 | 0.00 | 3-21*02 | 2*01, 3*01 | LC | 12 | 0.00 |
| P#16 | P16A-1C6 | 1-46*01, 1-46*03 | 1*01 | 6-19*01 | 16 | 0.69 | 3-21*02 | 3*02 | LC | 12 | 0.38 |
| P#16 | P16A-1C1 | 3-13*01 | 6*03 | 6-13*01 | 21 | 0.00 | 1-39*01, 1D-39*01 | 1*01 | KC | 10 | 0.00 |
| P#16 | P16A-1A5 | 3-33*01, 3-33*06 | 4*02 | 6-25*01 | 15 | 0.00 | 1-33*01, 1D-33*01 | 4*01 | KC | 9 | 0.38 |
| P#16 | P16A-1A12 | 3-33*01, 3-33*06 | 4*02 | 2-21*02 | 19 | 0.35 | 1-51*01 | 3*02 | LC | 11 | 0.75 |

TABLE 9a-continued

Gene family analysis of monoclonal antibodies.

| Patient | mAbs | Heavy chain | | | | | Kappa chain (KC) or Lambda chain (LC) | | | | |
| | | IGHV | IGHJ | IGHD | CDR3 length | SHM (%) | IGK(L)V | IGK(L)J | KC or LC | CDR3 length | SHM (%) |
|---|---|---|---|---|---|---|---|---|---|---|---|
| P#16 | P16A-1B1 | 3-74*02 | 5*02 | 6-13*01 | 15 | 2.43 | 1-36*01 | 2*01, 3*01 | LC | 11 | 3.37 |
| P#16 | P16A-1B3 | 3-9*01 | 6*02 | 6-13*01 | 24 | 0.35 | 3-1*01 | 1*01 | LC | 10 | 0.00 |
| P#16 | P16A-1B12 | 4-34*01 | 6*03 | 2-2*01 | 16 | 0.00 | 1-51*01 | 2*01, 3*01 | LC | 11 | 0.37 |
| P#16 | P16A-1B8 | 5-51*01 | 4*02 | 3-16*02 | 19 | 0.00 | 3-1*01 | 2*01, 3*01 | LC | 11 | 0.00 |
| P#16 | P16A-1A7 | 7-4-1*02 | 3*02 | 1-26*01 | 14 | 0.69 | 3-21*01 | 2*01, 3*01 | LC | 12 | 0.00 |
| P#16 | P16A-1A10 | 7-4-1*02 | 3*02 | 1-20*01 | 15 | 0.00 | 3-21*02 | 3*02 | LC | 12 | 0.00 |
| P#22 | P22A-1E10 | 1-46*01, 1-46*03 | 6*02 | 2-2*01 | 15 | 0.00 | 3-11*01 | 3*01 | KC | 10 | 0.00 |
| P#22 | P22A-1D2 | 1-8*01 | 5*02 | 3-3*01 | 21 | 0.00 | 1-40*01 | 1*01 | LC | 12 | 0.00 |
| P#22 | P22A-1D8 | 3-23*04 | 4*02 | 3-22*01 | 20 | 10.42 | 3-15*01 | 1*01 | KC | 10 | 3.03 |
| P#22 | P22A-1D7 | 3-33*01, 3-33*06 | 4*02 | 4-17*01 | 13 | 0.35 | 1-39*01, 1D-39*01 | 1*01 | KC | 10 | 0.38 |
| P#22 | P22A-1D1 | 3-53*01 | 6*02 | No results | 11 | 0.00 | 1-9*01 | 1*01 | KC | 8 | 0.38 |
| P#22 | P22A-1E8 | 3-9*01 | 4*02 | 6-19*01 | 16 | 0.00 | 3-15*01 | 4*01 | KC | 11 | 0.00 |
| P#22 | P22A-1D5 | 4-39*01 | 4*02 | 5-24*01 | 14 | 0.00 | 2-23*01, 2-23*03 | 1*01 | LC | 8 | 0.00 |
| P#22 | P22A-1E6 | 4-59*01 | 4*02 | 3-22*01 | 16 | 0.00 | 3-20*01 | 4*01 | KC | 9 | 0.37 |

The program IMGT/V-QUEST was applied to analyze gene germline, complementarity determining region (CDR) 3 length, and somatic hypermutation (SHM). The CDR3 length was calculated from amino acids sequences. The SHM frequency was calculated from the mutated nucleotides.

TABLE 9b

Binding capacity, neutralizing activity, and gene family analysis of 13 monoclonal Abs isolated from Patient #5, Patient #2, and Patient #22.

| Patient | mAbs | Binding to RBD | | Pseudovirus (μg/ml) | | Live virus (μg/ml) | | Heavy chain | |
| | | Kd (nM) | Competing w/ACE2 | $IC_{50}$ | $IC_{80}$ | $IC_{50}$ | $IC_{80}$ | IGHV | HCDR3 |
|---|---|---|---|---|---|---|---|---|---|
| P#5 | P5A-1B9 | 3.41 | +++ | 0.0014 | 0.0053 | 0.0043 | 0.0441 | 4-59*01 | ASNGQYYDILTGQPPDYWYFDL |
| P#22 | P22A-1D1 | 5.79 | +++ | 0.0038 | 0.0625 | 0.0198 | 0.1321 | 3-53*01 | ARDRDYYGMDV |
| P#5 | P5A-2G7 | 3.95 | +++ | 0.0044 | 0.0287 | 0.1814 | 0.8355 | 4-61*01 | ARERCYYGSGRAPRCVWFDP |
| P#5 | P5A-1D1 | 6.83 | +++ | 0.0096 | 0.0691 | 0.0189 | 0.0743 | 3-53*01 | ARDLYYYGMDV |
| P#5 | P5A-1B8 | 4.28 | +++ | 0.0115 | 0.0501 | 0.0168 | 0.0857 | 3-53*01 | ARETLAFDY |
| P#5 | P5A-2G9 | 15.94 | +++ | 0.0158 | 0.1466 | 0.0113 | 0.1187 | 3-33*01, 3-33*06 | ARWFHTGGYFDY |
| P#5 | P5A-1D2 | 14.02 | +++ | 0.0186 | 0.1025 | 0.0273 | 0.4325 | 3-53*01 | ARALQVGATSDYFDY |
| P#5 | P5A-3C8 | 1.30 | +++ | 0.0206 | 0.1031 | 0.0112 | 0.1499 | 3-53*01 | ARDLQEHGMDV |
| P#2 | P2C-1F11* | 3.64 | +++ | 0.0286 | 0.1195 | 0.0323 | 0.1779 | 3-66*01, 3-66*04 | ARDLVVYGMDV |
| P#2 | P2B-2F6* | 5.57 | +++ | 0.0500 | 0.6074 | 0.4074 | 2.4309 | 4-38-2*02 | ARAVVGIVVVPAAGRRAFDI |
| P#2 | P2B-1A10 | 38.41 | +++ | 0.0974 | 0.7446 | 0.0639 | 0.3053 | 3-53*01 | AREGPKSITGTAFDI |
| P#5 | P5A-3B4 | 1.16 | + | 0.0993 | 1.0657 | 0.0561 | 1.0080 | 5-51*01 | ARRDSTYGGNTDY |
| P#5 | P5A-3C12 | 8.47 | +++ | 0.0996 | 0.4679 | 0.2636 | 2.6783 | 2-5*02 | AHSLFLTVGYSSSWSPFDY |

TABLE 9b-continued

Binding capacity, neutralizing activity, and gene family analysis of 13 monoclonal Abs isolated from Patient #5, Patient #2, and Patient #22.

| | Heavy chain | | | Kappa chain (K) or Lambda chain (L) | | |
| | | | | | K(L) | |
| Patient | HCDR3 length | SHM (%) | IGK(L)V | K(L) CDR3 | CDR3 length | SHM (%) |
|---|---|---|---|---|---|---|
| P#5 | 22 | 0.70 | K4-1*01 | QQYYSTPLT | 9 | 0.00 |
| P#22 | 11 | 0.00 | K1-9*01 | LHLNSYRT | 8 | 0.38 |
| P#5 | 20 | 0.34 | L2-14*01 | SSYTSSSTLVV | 11 | 0.74 |
| P#5 | 11 | 0.35 | K1-9*01 | QQLNSYPT | 8 | 0.76 |
| P#5 | 9 | 1.40 | K1-9*01 | QQLNSYPPA | 9 | 0.00 |
| P#5 | 12 | 0.00 | L5-37*01 | MIWPSNALYV | 10 | 0.35 |
| P#5 | 15 | 1.40 | L1-40*01 | QSCDSSLSVVV | 11 | 1.11 |
| P#5 | 11 | 1.05 | K1-9*01 | QHLNSYPPGYT | 11 | 1.14 |
| P#2 | 11 | 1.75 | K3-20*01 | QQYGSSPT | 8 | 0.00 |
| P#2 | 20 | 0.69 | L2-8*01 | SSYAGSNNLV | 10 | 0.00 |
| P#2 | 15 | 0.35 | K1-33*01, K1D-33*01 | QQYDNLPMYT | 10 | 0.38 |
| P#5 | 13 | 0.35 | L1-44*01 | AAWDDSLNGVV | 11 | 0.00 |
| P#5 | 19 | 0.00 | K4-1*01 | QQYYSTPHT | 9 | 0.00 |

*Published in the reference (Bin Ju, et al. Human neutralizing antibodies elicited by SARS-CoV-2 infection. Nature. 2020).

TABLE 10a

Data collection and refinement statistics (molecular replacement)

nCoV RBD-2F6 complex

| Data collection | |
|---|---|
| Space group | $P2_1 2_1 2_1$ |
| Cell dimensions | |
| a, b, c (Å) | 70.23, 90.15, 112.35 |
| α, β, γ (°) | 90, 90, 90 |
| Resolution (Å) | 56.17-2.85 (2.92-2.85) * |
| $R_{sym}$ or $R_{merge}$ | 0.154 (1.452) |
| I/σI | 14.3 (2.2) |
| Completeness (%) | 99.82 (99.94) |
| Redundancy | 12.9 (13.5) |
| Refinement | |
| Resolution (Å) | 56.17-2.85 |
| No. reflections | 17229 |
| $R_{work}/R_{free}$ | 21.9/27.6 |
| No. atoms | |
| Protein | 4813 |
| Ligand/ion | 14 |
| Water | |
| B-factors | |
| Protein | 77.77 |
| Ligand/ion | 82.61 |
| Water | |
| R.m.s. deviations | |
| Bond lengths (Å) | 0.009 |
| Bond angles (°) | 1.35 |

* Number of xtals for each structure should be noted in footnote.
* Values in parentheses are for highest-resolution shell.

TABLE 10b

Data collection and refinement statistics (molecular replacement)

nCoV RBD-1F11 complex

| Data collection | |
|---|---|
| Space group | C121 |
| Cell dimensions | |
| a, b. c (Å) | 194.88, 85.39, 58.51 |
| α, β, γ (°) | 90, 100.29, 90 |
| Resolution (Å) | 29.03-2.96 (3.07-2.96) * |
| $R_{sym}$ or $R_{merge}$ | 0.155 (0.997) |
| I/σI | 10.1 (1.8) |
| Completeness (%) | 99.69 (99.90) |
| Redundancy | 6.8 (6.9) |
| Refinement | |
| Resolution (Å) | 29.03-2.96 |
| No. reflections | 19766 |
| $R_{work}/R_{free}$ | 20.9/25.0 |
| No. atoms | |
| Protein | 4799 |
| Ligand/ion | 14 |
| B-factors | |
| Protein | 56.89 |
| Ligand/ion | 82.81 |
| R.m.s. deviations | |
| Bond lengths (Å) | 0.009 |
| Bond angles (°) | 1.15 |

* Number of xtals for each structure should be noted in footnote.
* Values in parentheses are for highest-resolution shell.

TABLE 10c

Data collection and refinement statistics (molecular replacement).

|  | SARS-CoV-2 RBD-P22A-1D1 complex | SARS-CoV-2 RBD-P5A-1D2 complex | SARS-CoV-2 RBD-P5A-3C8 complex |
|---|---|---|---|
| Data collection |  |  |  |
| Space group | C2 | C2 | P2$_1$2$_1$2 |
| Cell dimensions |  |  |  |
| a, b, c (Å) | 193.34, 86.60, 57.16 | 158.75, 67.51, 154.37 | 112.54, 171.57, 54.87 |
| α, β, γ (°) | 90, 99.25, 90 | 90, 112.18, 90 | 90, 90, 90 |
| Resolution (Å) | 50.00-2.40 (2.46-2.40) * | 50.00-2.60 (2.66-2.60) * | 68.22-2.36 (2.48-2.36) * |
| R$_{sym}$ or R$_{merge}$ | 0.114 (0.983) | 0.117 (0.799) | 0.137 (1.157) |
| I/σI | 13.1 (1.9) | 9.5 (1.0) | 13.0 (2.4) |
| Completeness (%) | 100.00 (100.00) | 95.90 (64.30) | 97.30 (100.00) |
| Redundancy | 6.7 (7.0) | 6.3 (3.7) | 13.2 (13.8) |
| Refinement |  |  |  |
| Resolution (Å) | 47.71-2.40 | 36.52-2.60 | 50.98-2.36 |
| No. reflections | 36392 | 47159 | 43632 |
| R$_{work}$/R$_{free}$ | 17.7/18.4 | 20.3/24.7 | 19.4/21.9 |
| No. atoms |  |  |  |
| Protein | 4797 | 9446 | 4770 |
| Ligand/ion | 14 | 28 | 14 |
| B-factors |  |  |  |
| Protein | 45.63 | 53.90 | 47.25 |
| Ligand/ion | 76.80 | 115.29 | 52.72 |
| R.m.s. deviations |  |  |  |
| Bond lengths (Å) | 0.008 | 0.008 | 0.010 |
| Bond angles (°) | 1.06 | 1.07 | 1.25 |

* One crystal for the data
* Values in parentheses are for highest-resolution shell.

TABLE 11

All sequences mentioned or used in the present application

| Annotation | SEQ ID NO | Sequence |
|---|---|---|
| P2A-1A8 HCDR1 | 1 | GFAFDDYA |
| P2A-1A8 HCDR2 | 2 | STWNSGTI |
| P2A-1A8 HCDR3 | 3 | AKLGGYSDYDYPRPGDHYYGLDV |
| P2A-1A8 LCDR1 | 4 | SSDVGSYNL |
| P2A-1A8 LCDR2 | 5 | DVN |
| P2A-1A8 LCDR3 | 6 | RSYTDSNTYV |
| P2A-1A8 VH | 7 | EVQLVESGGDLVQPGRSLRLSCAASGFAFDDYAMHWVRQAPGKGLEWVSGSTWN SGTIAYADSVKGRFTISRDNAKKSLYLQMNSLRTEDTALYYCAKLGGYSDYDYPRPGDH YYGLDVWGQGTTVTVSS |
| P2A-1A8 VL | 8 | QSALTQPASVSGSPGQSITISCTGTSSDVGSYNLVSWYQQHPGKVPKLLIYDVNKRPS GISNRFSGSKSGNTASLTISGLQAEDEADYYCRSYTDSNTYVFGTGTKVTVL |
| P2A-1A8 VHnu | 9 | GAAGTGCAGCTGGTGGAGTCTGGGGGAGACTTGGTACAGCCTGGCAGGTCCCTG AGACTCTCCTGCGCAGCCTCTGGATTCGCCTTTGATGATTATGCCATGCACTGGGTC CGGCAAGCTCCAGGGAAGGGCCTGGAGTGGGTCTCAGGTAGTACTTGGAATAGT GGGACCATAGCCTATGCGGACTCTGTGAAGGGCCGATTCACCATCTCCAGAGACA ACGCCAAGAAGTCCCTGTATCTGCAAATGAACAGTCTGAGAACTGAGGACACGGC CTTATATTACTGTGCAAAGTTGGGGGGCTACAGTGACTACGATTACCCGAGGCCGG GAGACCACTATTACGGTTTGGACGTCTGGGGCCAAGGGACCACGGTCACCGTCTC CTCA |
| P2A-1A8 VLnu | 10 | CAGTCTGCCCTGACTCAGCCTGCCTCCGTGTCTGGGTCTCCTGGACAGTCGATCAC CATCTCCTGCACTGGAACCAGCAGTGATGTTGGGAGTTATAACCTTGTCTCCTGGT ACCAACAGCACCCAGGCAAAGTCCCCAAACTCTTGATTTATGATGTCAATAAGCGG CCCTCAGGGATTTCCAATCGCTTCTCTGGCTCCAAGTCTGGCAACACGGCCTCCCT |

TABLE 11-continued

All sequences mentioned or used in the present application

| Annotation | SEQ ID NO | Sequence |
|---|---|---|
| | | GACCATCTCTGGGCTCCAGGCTGAGGACGAGGCTGATTATTACTGCAGATCATATA<br>CAGACAGCAACACTTATGTCTTCGGAACTGGGACCAAGGTCACCGTCCTA |
| P2A-1A9/P2B-2G11 HCDR1 | 11 | GFTFDDYA |
| P24-1A9/P2B-2G11 HCDR2 | 12 | ISWNGGII |
| P2A-1A9/P2B-2G11 HCDR3 | 13 | AKVAGRGDYDYYYGMDV |
| P2A-1A9/P2B-2G11 LCDR1 | 14 | SSNIGAGYD |
| P2A-1A9/P2B-2G11 LCDR2 | 15 | GNN |
| P2A-1A9/P2B-2G11 LCDR3 | 16 | QSYDSSLSGSV |
| P2A-1A9 VH | 17 | EVQLVESGGGLVQPGRSLRLSCAASGFTFDDYAMHWVRQVPGKGLEWVSGISWNG<br>GIIGYADSVKGRFTISRDNAKTSLYLQMNSLRAEDTALYYCAKVAGRGDYDYYYGMDV<br>WGQGTTVTVSS |
| P2A-1A9 VL | 18 | QSVLTQPPSVSGAPGQRVTISCTGSSSNIGAGYDVHWYQQLPGTAPKLLIYGNNNRP<br>SGVPDRFSGSKSGTSASLAITGLQAEDEADYYCQSYDSSLSGSVFGGGTKLTVL |
| P2A-1A9 VHnu | 19 | GAAGTGCAGCTGGTGGAGTCTGGGGGAGGCTTGGTACAGCCTGGCAGGTCCCTG<br>AGACTCTCCTGTGCAGCCTCTGGATTCACCTTTGATGATTATGCCATGCACTGGGTC<br>CGGCAAGTTCCAGGGAAGGGCCTGGAGTGGGTCTCAGGTATTAGTTGGAATGG<br>GGTATCATAGGCTACGCGGACTCTGTGAAGGGCCGATTCACCATCTCCAGAGACA<br>ACGCCAAGACTTCCCTGTATCTGCAAATGAACAGTCTGAGAGCTGAGGACACGGC<br>CTTGTATTACTGTGCAAAAGTCGCGGGAAGGGGGGATTACGACTATTACTATGGTA<br>TGGACGTCTGGGGCCAAGGGACCACGGTCACCGTCTCCTCA |
| P2A-1A9 VLnu | 20 | CAGTCTGTGCTGACGCAGCCGCCCTCAGTGTCTGGGGCCCCAGGGCAGAGGGTC<br>ACCATCTCCTGCACTGGGAGCAGCTCCAACATCGGGGCAGGTTATGATGTACACTG<br>GTACCAGCAACTTCCAGGAACAGCCCCCAAACTCCTCATCTATGGTAACAACAATC<br>GCCCCTCAGGGGTCCCTGACCGATTCTCTGGCTCCAAGTCTGGCACCTCAGCCTCC<br>CTGGCCATCACTGGGCTCCAGGCTGAGGATGAGGCTGATTATTACTGCCAGTCCTA<br>TGACAGCAGCCTGAGTGGTTCGGTATTCGGCGGAGGGACCAAGCTGACCGTCCTA |
| P2A-1A10 HCDR1 | 21 | GYTFTGYY |
| P24-1A10 HCDR2 | 22 | INPNSGGT |
| P2A-1A10 HCDR3 | 23 | ARVPYCSSTSCHRDWYFDL |
| P2A-1A10 LCDR1 | 24 | QSLLDSDDGNTY |
| P2A-1A10 LCDR2 | 25 | TLS |
| P2A-1A10 LCDR3 | 26 | MQRIEFPLT |
| P2A-1A10 VH | 27 | QVQLVQSGAEVKKPGASVKVSCKASGYTFTGYYMHWVRQAPGQGLEWMGRINP<br>NSGGTNYAQKFQGRVTMTRDTSISTAYMELSRLRSDDTAVYYCARVPYCSSTSCHRD<br>WYFDLWGRGTLVTVSS |
| P2A-1A10 VL | 28 | DIVMTQTPLSLPVTPGEPASISCRSSQSLLDSDDGNTYLDWYLQKPGQSPQLLIYTLSY<br>RASGVPDRFSGSGSGTDFTLKISRVEAEDVGVYYCMQRIEFPLTFGGGTKVEIK |
| P2A-1A10 VHnu | 29 | CAGGTGCAGCTGGTGCAGTCTGGGGCTGAGGTGAAGAAGCCTGGGGCCTCAGT<br>GAAGGTCTCCTGCAAGGCTTCTGGATACACCTTCACCGGCTACTATATGCACTGGG<br>TGCGACAGGCCCCTGGACAAGGGCTTGAGTGGATGGGACGGATCAACCCTAACA<br>GTGGTGGCACAAACTATGCACAGAAGTTTCAGGGCAGGGTCACCATGACCAGGG<br>ACACGTCCATCAGCACAGCCTACATGGAGCTGAGCAGGCTGAGATCTGACGACAC<br>GGCCGTGTATTACTGTGCGAGAGTCCCCTATTGTAGTAGTACCAGCTGCCATCGGG<br>ACTGGTACTTCGATCTCTGGGGCCGTGGCACCCTGGTCACTGTCTCCTCA |
| P2A-1A10 VLnu | 30 | GATATTGTGATGACCCAGACTCCACTCTCCCTGCCCGTCACCCCTGGAGAGCCGGC<br>CTCCATCTCCTGCAGGTCTAGTCAGAGCCTCTTGGATAGTGATGATGGAAACACCT |

TABLE 11-continued

All sequences mentioned or used in the present application

| Annotation | SEQ ID NO | Sequence |
|---|---|---|
| | | ATTTGGACTGGTACCTGCAGAAGCCAGGGCAGTCTCCACAGCTCCTGATCTATACG CTTTCCTATCGGGCCTCTGGAGTCCCAGACAGGTTCAGTGGCAGTGGGTCAGGCA CTGATTTCACACTGAAAATCAGCAGGGTGGAGGCTGAGGATGTTGGAGTTTATTA CTGCATGCAACGTATAGAGTTTCCGCTCACTTTCGGCGGAGGGACCAAGGTGGAG ATCAAA |
| P2A-1B3 HCDR1 | 31 | GFSFNRYS |
| P2A-1B3 HCDR2 | 32 | ISASGNTI |
| P2A-1B3 HCDR3 | 33 | ARPAMVREGTYNWFDP |
| P2A-1B3 LCDR1 | 34 | QSVSNDY |
| P2A-1B3 LCDR2 | 35 | YAS |
| P2A-1B3 LCDR3 | 36 | QQYGDSPPIT |
| P2A-1B3 VH | 37 | EVQLVESGGGLVQPGGSLRLSCVASGFSFNRYSMNWLRQTPRKGLEWLSYISASGNT IYYADSVRGRFTTSRDNAKNTLYLQMNSLRDDDTAVYFCARPAMVREGTYNWFDP WGQGTLVTVSS |
| P2A-1B3 VL | 38 | EIVLTQSPGTLSLSPGERATLSCRASQSVSNDYLAWYQQKPGQAPRLLIYYASSRATGIP DRFSGSGSGTDFTLTISRLEPGDSAVYYCQQYGDSPPITFGQGTRLEIK |
| P2A-1B3 VHnu | 39 | GAGGTGCAGCTGGTGGAGTCTGGGGGAGGCTTGGTACAGCCTGGGGGGTCCCT CAGACTCTCCTGTGTCGCCTCTGGATTCTCCTTCAATCGATATAGTATGAATTGGCTC CGCCAGACTCCACGGAAGGGGCTGGAGTGGCTTTCATACATCAGTGCCAGTGGA AACACCATATACTACGCTGACTCTGTGAGGGGCCGATTCACCACCTCCAGAGACAA TGCCAAGAACACACTGTATCTGCAAATGAACAGCCTGCGAGACGACGACACGGCT GTCTATTTCTGTGCGCGACCCGCTATGGTTCGGGAGGGGACCTACAACTGGTTCG ACCCCTGGGGCCAGGGAACCCTGGTCACCGTCTCCTCA |
| P2A-1B3 VLnu | 40 | GAAATTGTGTTGACGCAGTCTCCAGGCACCCTGTCTTTGTCTCCAGGGGAAAGAG CCACCCTCTCCTGCAGGGCCAGTCAGAGTGTTAGCAACGACTACTTAGCCTGGTAC CAGCAGAAACCTGGCCAGGCTCCCAGGCTCCTCATCTACTATGCATCCAGCAGGG CCACTGGCATCCCAGACAGGTTCAGTGGCAGTGGGTCTGGGACAGACTTCACTCT CACCATCAGCAGACTGGAGCCTGGAGATTCTGCAGTGTATTACTGTCAGCAGTATG GTGACTCACCTCCGATCACCTTCGGCCAAGGGACACGACTGGAGATTAAA |
| P2B-2F6 HCDR1 | 41 | GYSISSGYY |
| P2B-2F6 HCDR2 | 42 | IYHSGST |
| P2B-2F6 HCDR3 | 43 | ARAVVGIVVVPAAGRRAFDI |
| P2B-2F6 LCDR1 | 44 | SSDVGGYNY |
| P2B-2F6 LCDR2 | 45 | EVS |
| P2B-2F6 LCDR3 | 46 | SSYAGSNNLV |
| P2B-2F6 VH | 47 | QVQLQESGPGLVIKPSETLSLTCTVSGYSISSGYYWGWIRQPPGKGLEWIGSIYHSGST YYNPSLKTRVTISVDTSKNQFSLKLSSVTAADTAVYYCARAVVGIVVVPAAGRRAFDIW GQGTMVTVSS |
| P2B-2F6 VL | 48 | QSALTQPPSASGSPGQSVTISCTGTSSDVGGYNYVSWYQQHPGKAPKLMIYEVSKRP SGVPDRFSGSKSGNTASLTVSGLQAEDEADYYCSSYAGSNNLVFGGGTKLTVL |
| P2B-2F6 VHnu | 49 | CAGGTGCAGCTGCAGGAGTCGGGCCCAGGACTGGTGAAGCCTTCGGAGACCCTG TCCCTCACCTGCACTGTCTCTGGTTACTCCATCAGCAGTGGTTACTACTGGGGCTG GATCCGGCAGCCCCCAGGGAAGGGGCTGGAGTGGATTGGGAGTATCTATCATAGT GGGAGCACCTACTACAACCCGTCCCTCAAGACTCGAGTCACCATATCAGTAGACAC GTCCAAGAACCAGTTCTCCCTGAAGCTGAGCTCTGTGACCGCCGCAGACACGGCC GTCTATTACTGTGCGAGAGCGGTGGTAGGGATTGTAGTAGTACCAGCTGCCGGTC GTCGGGCTTTTGATATCTGGGGCCAAGGGACAATGGTCACCGTCTCCTCA |
| P2B-2F6 VLnu | 50 | CAGTCTGCCCTGACTCAGCCTCCCTCCGCGTCCGGGTCTCCTGGACAGTCAGTCAC CATCTCCTGCACTGGAACCAGCAGTGACGTTGGTGGTTATAACTATGTCTCCTGGTA CCAACAGCACCCAGGCAAAGCCCCCAAACTCATGATTTATGAGGTCAGTAAGCGG CCCTCAGGGGTCCCTGATCGCTTCTCTGGCTCCAAGTCTGGCAACACGGCCTCCCT GACCGTCTCTGGGCTCCAGGCTGAGGATGAGGCTGATTATTACTGCAGCTCATATG CAGGCAGCAACAATTTGGTGTTCGGCGGAGGGACCAAGCTGACCGTCCTA |

TABLE 11-continued

All sequences mentioned or used in the present application

| Annotation | SEQ ID NO | Sequence |
|---|---|---|
| P2B-2G4 HCDR1 | 51 | GFTFSSYG |
| P2B-2G4 HCDR2 | 52 | IWYDGSNK |
| P2B-2G4 HCDR3 | 53 | ARGAAMVWLDY |
| P2B-2G4 LCDR1 | 54 | SSDVGGYNY |
| P2B-2G4 LCDR2 | 55 | DVS |
| P2B-2G4 LCDR3 | 56 | CSYAGSYTFVV |
| P2B-2G4 VH | 57 | QVQLVESGGGVVQPGRSLRLSCAASGFTFSSYGMHWVRQAPGKGLEWVAVIWYD GSNKYYADSVKGRFTISRDNSKNTLYLQMNSLRAEDTAVYYCARGAAMVWLDYWG QGTLVTVSS |
| P2B-2G4 VL | 58 | QSALTQPRSVSGSPGQSVTISCTGTSSDVGGYNYVSWYQQHPGKAPIKLMIYDVSKR PSGVPDRFSGSKSGNTASLTISGLQAEDEADYYCCSYAGSYTFVVFGGGTKLTVL |
| P2B-2G4 VHnu | 59 | CAGGTGCAGCTGGTGGAGTCTGGGGGAGGCGTGGTCCAGCCTGGGAGGTCCCT GAGACTCTCCTGTGCAGCGTCTGGATTCACCTTCAGTAGCTATGGCATGCACTGGG TCCGCCAGGCTCCAGGCAAGGGGCTGGAGTGGGTGGCAGTTATATGGTATGATGG AAGTAATAAATACTATGCAGACTCCGTGAAGGGCCGATTCACCATCTCCAGAGACA ATTCCAAGAACACGCTGTATCTGCAAATGAACAGCCTGAGAGCCGAGGACACGGC TGTGTATTACTGTGCGAGAGGGGCAGCTATGGTTTGGCTTGACTACTGGGGCCAG GGAACCCTGGTCACCGTCTCCTCA |
| P2B-2G4 VLnu | 60 | CAGTCTGCCCTGACTCAGCCTCGCTCAGTGTCCGGGTCTCCTGGACAGTCAGTCAC CATCTCCTGCACTGGAACCAGCAGTGATGTTGGTGGTTATAACTATGTCTCCTGGTA CCAACAGCACCCAGGCAAAGCCCCCAAACTCATGATTTATGATGTCAGTAAGCGG CCCTCAGGGGTCCCTGATCGCTTCTCTGGCTCCAAGTCTGGCAACACGGCCTCCCT GACCATCTCTGGGCTCCAGGCTGAGGATGAGGCTGATTATTACTGCTGCTCATATG CAGGCAGCTACACTTTCGTGGTATTCGGCGGAGGGACCAAGCTGACCGTCCTA |
| P2B-2G11 VH | 61 | EVQLVESGGGLVQPGRSLRLSCAASGFTFDDYAMHWVRQAPGKGLEWVSGISWN GGIIGYADSVKGRFTISRDNAKTSLYLQMNSLKPEDTALYYCAKVAGRGDYDYYYGMD VWGQGTTVTVSS |
| P2B-2G11 VL | 62 | QSVLTQPPSVSGAPGQRVTISCTGSSSNIGAGYDVHWYQQLPGTAPKLLIYGNNNRP SGVPDRFSGSKSGTSASLAITGLQAEDEADYYCQSYDSSLSGSVFGGGTKLTVL |
| P2B-2G11 VHnu | 63 | GAAGTGCAGCTGGTGGAGTCTGGGGGAGGCTTGGTACAGCCTGGCAGGTCCCTG AGACTCTCCTGTGCAGCCTCTGGATTCACCTTTGATGATTATGCCATGCACTGGGTC CGGCAAGCTCCAGGGAAGGGCCTGGAGTGGGTCTCAGGTATTAGTTGGAATGGT GGTATCATAGGCTATGCGGACTCTGTGAAGGGCCGATTCACCATCTCCAGAGACAA CGCCAAGACTTCCCTGTATCTGCAAATGAACAGTCTGAAACCTGAGGACACGGCC TTGTATTACTGTGCAAAGTCGCGGGAAGGGGGGATTACGACTACTACTACGGTAT GGACGTCTGGGGCCAAGGGACCACGGTCACCGTCTCCTCA |
| P2B-2G11 VLnu | 64 | CAGTCTGTGCTGACGCAGCCGCCCTCAGTGTCTGGGGCCCCAGGGCAGAGGGTC ACCATCTCCTGCACTGGGAGCAGCTCCAACATCGGGGCAGGTTATGATGTACACTG GTACCAGCAACTTCCAGGAACAGCCCCCAAACTCCTCATCTATGGGAACAACAATC GGCCCTCAGGGGTCCCTGACCGATTCTCTGGCTCCAAGTCTGGCACCTCAGCCTCC CTGGCCATCACTGGGCTCCAGGCTGAGGATGAGGCTGATTATTACTGCCAGTCCTA TGACAGCAGCCTGAGTGGTTCGGTATTCGGCGGAGGGACCAAGCTGACCGTCCTA |
| P2C-1A3 HCDR1 | 65 | GFTFSDYY |
| P2C-1A3 HCDR2 | 66 | ISSSGSTI |
| P2C-1A3 HCDR3 | 67 | ARDFSHQQLVPS |
| P2C-1A3 LCDR1 | 68 | QGISSY |
| P2C-1A3 LCDR2 | 69 | AAS |
| P2C-1A3 LCDR3 | 70 | QQLNSYPLT |
| P2C-1A3 VH | 71 | QVQLVESGGGLVKPGGSLRLSCAASGFTFSDYYMSWIRQAPGKGLEWVSYISSSGSTI YYADSVKGRFTISRDNAKNSLYLQMNSLRAEDTAVYYCARDFSHQQLVPSWGQGTLV TVSS |
| P2C-1A3 VL | 72 | DIQLTQSPSFLSASVGDRVTITCRASQGISSYLAWYQQKPGKAPKLLIYAASTLQSGVP SRFSGSGSGTEFTLTISSLQPEDFATYYCQQLNSYPLTFGGGTKVEIK |

TABLE 11-continued

All sequences mentioned or used in the present application

| Annotation | SEQ ID NO | Sequence |
|---|---|---|
| P2C-1A3 VHnu | 73 | CAGGTGCAGCTGGTGGAGTCTGGGGGAGGCTTGGTCAAGCCTGGAGGGTCCCT<br>GAGACTCTCCTGTGCAGCCTCTGGATTCACCTTCAGTGACTACTACATGAGCTGGA<br>TCCGCCAGGCTCCAGGGAAGGGGCTGGAGTGGGTTTCATACATTAGTAGTAGTGG<br>TAGTACCATATACTACGCAGACTCTGTGAAGGGCCGATTCACCATCTCCAGGGACA<br>ACGCCAAGAACTCACTGTATCTGCAAATGAACAGCCTGAGAGCCGAGGACACGG<br>CTGTGTATTACTGTGCGAGAGATTTTTCTCATCAGCAGCTGGTACCTTCCTGGGGC<br>CAGGGAACCCTGGTCACCGTCTCCTCA |
| P2C-1A3 VLnu | 74 | GACATCCAGTTGACCCAGTCTCCATCCTTCCTGTCTGCATCTGTAGGAGACAGAGT<br>CACCATCACTTGCCGGGCCAGTCAGGGCATTAGCAGTTATTTAGCCTGGTATCAGC<br>AAAAACCAGGGAAAGCCCCTAAGCTCCTGATCTATGCTGCATCCACTTTGCAAAGT<br>GGGGTCCCATCAAGGTTCAGCGGCAGTGGATCTGGGACAGAATTCACTCTCACAA<br>TCAGCAGCCTGCAGCCTGAAGATTTTGCAACTTATTACTGTCAACAGCTTAATAGTT<br>ACCCGCTCACTTTCGGCGGAGGGACCAAGGTGGAGATCAAA |
| P2C-1C8 HCDR1 | 75 | GFTFRSYG |
| P2C-1C8 HCDR2 | 76 | IWYDGSNK |
| P2C-1C8 HCDR3 | 77 | ARDIEIVVVNIDY |
| P2C-1C8 LCDR1 | 78 | QSLVYSDGNTY |
| P2C-1C8 LCDR2 | 79 | KVS |
| P2C-1C8 LCDR3 | 80 | MQGTHWPYT |
| P2C-1C8 VH | 81 | QVQLVESGGGVVQPGRSLRLSCAASGFTFRSYGMHWVRQAPGKGLEWVAVIWYD<br>GSNKYYADSVKGRFTISRDNSKNTLYLQMNSLRAEDTAVYYCARDIEIVVVNIDYWGQ<br>GTLVTVSS |
| P2C-1C8 VL | 82 | DVVMTQSPLSLPVTLGQPASISCRSSQSLVYSDGNTYLNWFQQRPGQSPRRLIYKVSI<br>WDSGVPDRFSGSGSGTDFTLKISRVEAEDVGVYYCMQGTHWPYTFGQGTKLEIK |
| P2C-1C8 VHnu | 83 | CAGGTGCAGCTGGTGGAGTCTGGGGGAGGCGTGGTCCAGCCTGGGAGGTCCCT<br>GAGACTCTCCTGTGCAGCGTCTGGATTCACCTTCAGGAGCTATGGCATGCACTGG<br>GTCCGCCAGGCTCCAGGCAAGGGGCTGGAGTGGGTGGCAGTTATCTGGTATGAT<br>GGAAGTAATAAATACTATGCAGACTCCGTGAAGGGCCGATTCACCATCTCCAGAGA<br>CAATTCCAAGAACACGCTGTATCTGCAAATGAACAGCCTGAGAGCCGAGGACACG<br>GCTGTGTATTACTGTGCGAGAGATATAGAGATAGTAGTGGTAAATATTGACTACTGG<br>GGCCAGGGAACCCTGGTCACCGTCTCCTCA |
| P2C-1C8 VLnu | 84 | GATGTTGTGATGACTCAGTCTCCACTCTCCCTGCCCGTCACCCTTGGACAGCCGGC<br>CTCCATCTCCTGCAGGTCTAGTCAAAGCCTCGTATACAGTGATGGAAACACCTACTT<br>GAATTGGTTTCAGCAGAGGCCAGGCCAATCTCCAAGGCGCCTAATTTATAAGGTTT<br>CTATCTGGGACTCTGGGGTCCCAGACAGATTCAGCGGCAGTGGGTCAGGCACTGA<br>TTTCACACTGAAAATCAGCAGGGTGGAGGCTGAGGATGTTGGGGTTTATTACTGC<br>ATGCAAGGTACACACTGGCCGTACACTTTTGGCCAGGGGACCAAGCTGGAGATCA<br>AA |
| P2C-1C10 HCDR1 | 85 | GGTFSSYA |
| P2C-1C10 HCDR2 | 86 | IIPIFGTA |
| P2C-1C10 HCDR3 | 87 | ARVVTGYYFDY |
| P2C-1C10 LCDR1 | 88 | QSVSSY |
| P2C-1C10 LCDR2 | 89 | DAS |
| P2C-1C10 LCDR3 | 90 | QQRSNWPS |
| P2C-1C10 VH | 91 | QVQLVQSGAEVKKPGSSVKVSCKASGGTFSSYAIIWVRQAPGQGLEWMGGIIPIFGT<br>ANYAQKFQGRVTITADESTSTAYMELSSLRSEDTAVYYCARVVTGYYFDYWGQGTLVT<br>VSS |
| P2C-1C10 VL | 92 | EIVLTQSPATLSLSPGERATLSCRASQSVSSYLAWYQQKPGQAPRLLIYDASNRATGIPA<br>RFSGSGSGTDFTLTISSLEPEDFAVYYCQQRSNWPSFGQGTKLEIK |
| P2C-1C10 VHnu | 93 | CAGGTGCAGCTGGTGCAGTCTGGGGCTGAGGTGAAGAAGCCTGGGTCCTCGGTG<br>AAGGTCTCCTGCAAGGCTTCTGGAGGCACCTTCAGCAGCTATGCTATCATCTGGGT<br>GCGACAGGCCCCTGGACAAGGGCTTGAGTGGATGGGAGGGATCATCCCTATCTTT<br>GGTACAGCAAACTACGCACAGAAGTTCCAGGGCAGAGTCACGATTACCGCGGAC<br>GAATCCACGAGCACAGCCTACATGGAGCTGAGCAGCCTGAGATCTGAGGACACG |

TABLE 11-continued

All sequences mentioned or used in the present application

| Annotation | SEQ ID NO | Sequence |
|---|---|---|
| | | GCCGTGTATTACTGTGCGAGAGTGGTAACGGGGTACTACTTTGACTACTGGGGCC<br>AGGGAACCCTGGTCACCGTCTCCTCA |
| P2C-1C10 VLnu | 94 | GAAATTGTGTTGACACAGTCTCCAGCCACCCTGTCTTTGTCTCCAGGGGAAAGAG<br>CCACCCTCTCCTGCAGGGCCAGTCAGAGTGTTAGCAGCTACTTAGCCTGGTACCAA<br>CAGAAACCTGGCCAGGCTCCCAGGCTCCTCATCTATGATGCATCCAACAGGGCCAC<br>TGGCATCCCAGCCAGGTTCAGTGGCAGTGGGTCTGGGACAGACTTCACTCTCACC<br>ATCAGCAGCCTAGAGCCTGAAGATTTTGCAGTTTATTACTGTCAGCAGCGTAGCAA<br>CTGGCCTTCTTTTGGCCAGGGGACCAAGCTGGAGATCAAA |
| P2C-1D5 HCDR1 | 95 | GFTFSSFA |
| P2C-1D5 HCDR2 | 96 | ISGSGGST |
| P2C-1D5 HCDR3 | 97 | AKDPDGSGSWYFDY |
| P2C-1D5 LCDR1 | 98 | NIGSKS |
| P2C-1D5 LCDR2 | 99 | YDS |
| P2C-1D5 LCDR3 | 100 | QVWDSSSDHHV |
| P2C-1D5 VH | 101 | EVQLVESGGGLVQPGGSLRLSCAASGFTFSSFAMSWVRQAPGKGLEWVSAISGSGG<br>STYYADSVKGRFTISRDNSKNTLYLQMNSLRAEDTAVYYCAKDPDGSGSWYFDYWG<br>QGTLVTVSS |
| P2C-1D5 VL | 102 | SYVLTQPPSVSVAPGKTARITCGGNNIGSKSVHWYQQKPGQAPVLVIYYDSDRPSGIP<br>ERFSGSNSGNTATLTISRVEAGDEADYYCQVWDSSSDHHVFGTGTKVTVL |
| P2C-1D5 VHnu | 103 | GAGGTGCAGCTGGTGGAGTCTGGGGGAGGCTTGGTACAGCCTGGGGGGTCCCT<br>GAGACTCTCCTGTGCAGCCTCTGGATTCACCTTTAGCAGCTTTGCCATGAGCTGGG<br>TCCGCCAGGCTCCAGGGAAGGGGCTGGAGTGGGTCTCAGCTATTAGTGGTAGTG<br>GTGGTAGCACATACTACGCAGACTCCGTGAAGGGCCGGTTCACCATCTCCAGAGA<br>CAATTCCAAGAACACGCTGTATTTGCAAATGAACAGCCTGAGAGCCGAGGACACG<br>GCCGTATATTACTGTGCGAAAGATCCGGATGGTTCGGGGAGTTGGTACTTTGACTA<br>CTGGGGCCAGGGAACCCTGGTCACCGTCTCCTCA |
| P2C-1D5 VLnu | 104 | TCCTATGTGCTGACTCAGCCACCCTCAGTGTCAGTGGCCCCAGGAAAGACGGCCA<br>GGATTACCTGTGGGGGAAACAACATTGGAAGTAAAAGTGTGCACTGGTACCAGCA<br>GAAGCCAGGCCAGGCCCCTGTGCTGGTCATCTATTATGATAGCGACCGGCCCTCAG<br>GGATCCCTGAGCGATTCTCTGGCTCCAACTCTGGGAACACCGCCACCCTGACCATC<br>AGCAGGGTCGAAGCCGGGGATGAGGCCGACTATTACTGTCAGGTGTGGGATAGT<br>AGTAGTGATCATCATGTCTTCGGAACTGGGACCAAGGTCACCGTCCTA |
| P2C-1F11 HCDR1 | 105 | GITVSSNY |
| P2C-1F11 HCDR2 | 106 | IYSGGST |
| P2C-1F11 HCDR3 | 107 | ARDLVVYGMDV |
| P2C-1F11 LCDR1 | 108 | QSVSSSY |
| P2C-1F11 LCDR2 | 109 | GAS |
| P2C-1F11 LCDR3 | 110 | QQYGSSPT |
| P2C-1F11 VH | 111 | EVQLVESGGGLVQPGGSLRLSCAASGITVSSNYMNWVRQAPGKGLEWVSLIYSGGS<br>TYYADSVKGRFTISRDNSKNTLYLQMNSLRAEDTAVYHCARDLVVYGMDVWGQTT<br>VTVSS |
| P2C-1F11 VL | 112 | EIVLTQSPGTLSLSPGERATLSCRASQSVSSSYLAWYQQKPGQAPRLLIYGASSRATGIP<br>DRFSGSGSGTDFTLTISRLEPEDFAVYYCQQYGSSPTFGQGTKLEIK |
| P2C-1F11 VHnu | 113 | GAGGTGCAGCTGGTGGAGTCTGGGGGAGGCTTGGTCCAGCCTGGGGGGTCCCT<br>GAGACTCTCCTGTGCAGCCTCTGGAATCACCGTCAGTAGCAACTACATGAACTGG<br>GTCCGCCAGGCTCCAGGGAAGGGGCTGGAGTGGGTCTCACTTATTTATAGCGGTG<br>GTAGCACATACTACGCAGACTCCGTGAAGGGCAGATTCACCATCTCCAGAGACAAT<br>TCCAAGAACACGTTGTATCTTCAAATGAACAGCCTGAGAGCCGAGGACACGGCTG<br>TGTATCACTGTGCGAGAGATCTGGTGGTATACGGTATGGACGTCTGGGGCCAAGG<br>GACCACGGTCACCGTCTCCTCA |
| P2C-1F11 VLnu | 114 | GAAATTGTGTTGACGCAGTCTCCAGGCACCCTGTCTTTGTCTCCAGGGGAAAGAG<br>CCACCCTCTCCTGCAGGGCCAGTCAGAGTGTTAGCAGCAGCTACTTAGCCTGGTAC<br>CAGCAGAAACCTGGCCAGGCTCCCAGGCTCCTCATCTATGGTGCATCCAGCAGGG<br>CCACTGGCATCCCAGACAGGTTCAGTGGCAGTGGGTCTGGGACAGACTTCACTCT |

TABLE 11-continued

| All sequences mentioned or used in the present application | | |
|---|---|---|
| Annotation | SEQ ID NO | Sequence |
| | | CACCATCAGCAGACTGGAGCCTGAAGATTTTGCAGTGTATTACTGTCAGCAGTATG GTAGCTCACCCACTTTTGGCCAGGGGACCAAGCTGGAGATCAAA |
| Amino acid sequence of heavy chain constant region | 115 | ASTKGPSVFPLAPSSKSTSGGTAALGCLVKDYFPEPVTVSWNSGALTSGVHTFPAVLQ SSGLYSLSSVVTVPSSSLGTQTYICNVNHKPSNTKVDKKVEPKSCDKTHTCPPCPAPEL LGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVLDSDGSFFLY SKLTVDKSRWQQGNVFSCSVMHEALHNHYTQKSLSLSPGK |
| Amino acid sequence of lambda light chain constant region | 116 | GQPKAAPSVTLFPPSSEELQANKATLVCLISDFYPGAVTVAWKADSSPVKAGVETTTP SKQSNNKYAASSYLSLTPEQWKSHRSYSCQVTHEGSTVEKTVAPTECS |
| Amino acid sequence of kappa light chain constant region | 117 | RTVAAPSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRGEC |
| Nucleic acid sequence of heavy chain constant region | 118 | GCGTCGACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAACCCG TGACGGTGTCGTGGAACTCAGGCGCCCTGACCAGCGGCGTGCACACCTTCCCGG CTGTCCTACAGTCCTCAGGACTCTACTCCCTCAGCAGCGTGGTGACCGTGCCCTCC AGCAGCTTGGGCACCCAGACCTACATCTGCAACGTGAATCACAAGCCCAGCAACA CCAAGGTGGACAAGAAAGTTGAGCCCAAATCTTGTGACAAAACTCACACATGCCC ACCGTGCCCAGCACCTGAACTCCTGGGGGGACCGTCAGTCTTCCTCTTCCCCCCA AAACCCAAGGACACCCTCATGATCTCCCGGACCCCTGAGGTCACATGCGTGGTGG TGGACGTGAGCCACGAAGACCCTGAGGTCAAGTTCAACTGGTACGTGGACGGCG TGGAGGTGCATAATGCCAAGACAAAGCCGCGGGAGGAGCAGTACAACAGCACGT ACCGTGTGGTCAGCGTCCTCACCGTCCTGCACCAGGACTGGCTGAATGGCAAGGA GTACAAGTGCAAGGTCTCCAACAAAGCCCTCCCAGCCCCCATCGAGAAAACCATC TCCAAAGCCAAAGGGCAGCCCCGAGAACCACAGGTGTACACCCTGCCCCCATCCC GGGATGAGCTGACCAAGAACCAGGTCAGCCTGACCTGCCTGGTCAAAGGCTTCTA TCCCAGCGACATCGCCGTGGAGTGGGAGAGCAATGGGCAGCCGGAGAACAACTA CAAGACCACGCCTCCCGTGCTGGACTCCGACGGCTCCTTCTTCCTCTACAGCAAGC TCACCGTGGACAAGAGCAGGTGGCAGCAGGGGAACGTCTTCTCATGCTCCGTGAT GCATGAGGCTCTGCACAACCACTACACGCAGAAGAGCCTCTCCCTGTCTCCGGGT AAA |
| Nucleic acid sequence of lambda light chain constant region | 119 | GGTCAGCCCAAGGCTGCCCCCTCGGTCACTCTGTTCCCACCCTCGAGTGAGGAGC TTCAAGCCAACAAGGCCACACTGGTGTGTCTCATAAGTGACTTCTACCCGGGAGC CGTGACAGTGGCCTGGAAGGCAGATAGCAGCCCCGTCAAGGCGGGAGTGGAGA CCACCACACCCTCCAAACAAAGCAACAACAAGTACGCGGCCAGCAGCTACCTGAG CCTGACGCCTGAGCAGTGGAAGTCCCACAGAAGCTACAGCTGCCAGGTCACGCAT GAAGGGAGCACCGTGGAGAAGACAGTGGCCCCTACAGAATGTTCA |
| Nucleic acid sequence of kappa light chain constant region | 120 | CGTACGGTGGCTGCACCATCTGTCTTCATCTTCCCGCCATCTGATGAGCAGTTGAA ATCTGGAACTGCCTCTGTTGTGTGCCTGCTGAATAACTTCTACCCCAGAGAAGCCA AAGTGCAGTGGAAGGTGGACAACGCCCTGCAGAGCGGAAACAGCCAGGAAAGC GTGACAGAGCAGGATTCCAAGGATTCCACATACAGCCTGAGCAGCACACTGACAC TGTCCAAGGCCGACTACGAGAAGCACAAGGTGTACGCCTGCGAAGTGACACACC AGGGACTGTCCTCCCCTGTGACAAAGAGCTTCAACAGAGGAGAATGC |
| Amino acid sequence of the extracellular domain of S protein of SARS-CoV-2 | 121 | MFVFLVLLPLVSSQCVNLTTRTQLPPAYTNSFTRGVYYPDKVFRSSVLHSTQDLFLPFFS NVTWFHAIHVSGTNGTKRFDNPVLPFNDGVYFASTEKSNIIRGWIFGTTLDSKTQSLL IVNNATNVVIKVCEFQFCNDPFLGVYYHKNNKSWMESEFRVYSSANNCTFEYVSQPF LMDLEGKQGNFKNLREFVFKNIDGYFKIYSKHTPINLVRDLPQGFSALEPLVDLPIGINI TRFQTLLALHRSYLTPGDSSSGWTAGAAAYYVGYLQPRTFLLKYNENGTITDAVDCAL DPLSETKCTLKSFTVEKGIYQTSNFRVQPTESIVRFPNITNLCPFGEVFNATRFASVYAW NRKRISNCVADYSVLYNSASFSTFKCYGVSPTKLNDLCFTNVYADSFVIRGDEVRQIAP GQTGKIADYNYKLPDDFTGCVIAWNSNNLDSKVGGNYNYLYRLFRKSNLKPFERDIST EIYQAGSTPCNGVEGFNCYFPLQSYGFQPTNGVGYQPYRVVVLSFELLHAPATVCGP KKSTNLVKNKCVNFNFNGLTGTGVLTESNKKFLPFQQFGRDIADTTDAVRDPQTLEIL DITPCSFGGVSVITPGTNTSNQVAVLYQDVNCTEVPVAIHADQLTPTWRVYSTGSNV FQTRAGCLIGAEHVNNSYECDIPIGAGICASYQTQTNSPRRARSVASQSIIAYTMSLGA ENSVAYSNNSIAIPTNFTISVTTEILPVSMTKTSVDCTMYICGDSTECSNLLLQYGSFCT QLNRALTGIAVEQDKNTQEVFAQVKQIYKTPPIKDFGGFNFSQILPDPSKPSKRSFIEDL LFNKVTLADAGFIKQYGDCLGDIAARDLICAQKFNGLTVLPPLLTDEMIAQYTSALLAG TITSGWTFGAGAALQIPFAMQMAYRFNGIGVTQNVLYENQKLIANQFNSAIGKIQDS LSSTASALGKLQDVVNQNAQALNTLVKQLSSNFGAISSVLNDILSRLDKVEAEVQIDRL ITGRLQSLQTYVTQQLIRAAEIRASANLAATKMSECVLGOSKRVDFCGKGYHLMSFP |

TABLE 11-continued

All sequences mentioned or used in the present application

| Annotation | SEQ ID NO | Sequence |
|---|---|---|
| | | QSAPHGVVFLHVTYVPAQEKNFTTAPAICHDGKAHFPREGVFVSNGTHWFVTQRNF YEPQIITTDNTFVSGNCDVVIGIVNNTVYDPLQPELDSFKEELDKYFKNHTSPDVDLG DISGINASVVNIQKEIDRLNEVAKNLNESLIDLQELGKYEQYIK |
| Amino acid sequence of the extracellular domain of S protein of SARS-CoV | 122 | MFIFLLFLTLTSGSDLDRCTTFDDVQAPNYTQHTSSMRGVYYPDEIFRSDTLYLTQDLF LPFYSNVTGFHTINHTFGNPVIPFKDGIYFAATEKSNVVRGWVFGSTMNNKSQSVIII NNSTNVVIRACNFELCDNPFFAVSKPMGTQTHTMIFDNAFNCTFEYISDAFSLDVSEK SGNFKHLREFVFKNKDGFLYVYKGYQPIDVVRDLPSGFNTLKPIFKLPLGINITNFRAILT AFSPAQDIWGTSAAAYFVGYLKPTTFMLKYDENGTITDAVDCSQNPLAELKCSVKSFE IDKGIYQTSNFRVVPSGDVVRFPNITNLCPFGEVFNATKFPSVYAWERKKISNCVADYS VLYNSTFFSTFKCYGVSATKLNDLCFSNVYADSFVVKGDDVRQIAPGQTGVIADYNYKL PDDFMGCVLAWNTRNIDATSTGNYNYKYRYLRHGKLRPFERDISNVPFSPDGKPCTP PALNCYWPLNDYGFYTTTGIGYQPYRVVVLSFELLNAPATVCGPKLSTDLIKNQCVNF NFNGLTGTGVLTPSSKRFQPFQQFGRDVSDFTDSVRDPKTSEILDISPCAFGGVSVITP GTNASSEVAVLYQDVNCTDVSTAIHADQLTPAWRIYSTGNNVFQTQAGCLIGAEHVD TSYECDIPIGAGICASYHTVSLLRSTSQKSIVAYTMSLGADSSIAYSNNTIAIPTNFSISITT EVMPVSMAKTSVDCNMYICGDSTECANLLLQYGSFCTQLNRALSGIAAEQDRNTRE VFAQVKQMYKTPTLKYFGGFNFSQILPDPLKPTKRSFIEDLLFNKVTLADAGFMKQYG ECLGDINARDLICAQKFNGLTVLPPLLTDDMIAAYTAALVSGTATAGWTFGAGAALQI PFAMQMAYRFNGIGVTQNVLYENQKQIANQFNKAISQIQESLTTTSTALGKLQDVVN QNAQALNTLVKQLSSNFGAISSVLNDILSRLDKVEAEVQIDRLITGRLQSLQTYVTQQLI RAAEIRASANLAATKMSECVLGQSKRVDFCGKGYHLMSFPQAAPHGVVFLHVTYVP SQERNFTTAPAICHEGKAYFPREGVFVFNGTSWFITQRNFFSPQIITTDNTFVSGNCD VVIGIINNTVYDPLQPELDSFKEELDKYFKNHTSPDVDLGDISGINASVVNIQKEIDRLN EVAKNLNESLIDLQELGKYEQYIKWP |
| Amino acid sequence of the extracellular domain of S protein of MERS-CoV | 123 | MIHSVFLLMFLLTPTESYVDVGPDSVKSACIEVDIQQTFFDIKTWPRPIDVSKADGIIYP QGRTYSNITITYQGLFPYQGDHGDMYVYSAGHATGTTPQKLFVANYSQDVKQFANG FVVRIGAAANSTGTVIISPSTSATIRKIYPAFMLGSSVGNFSDGKMGRFFNHTLVLLPD GCGTLLRAFYCILEPRSGNHCPAGNSYTSFATYHTPATDCSDGNYNRNASLNSFKEYF NLRNCTFMYTYNITEDEILEWFGITQTAQGVHLFSSRYVDLYGGNMFQFATLPVYDTI KYYSIIPHSIRSIQSDRKAWAAFYVYKLQPLTFLLDFSVDGYIRRAIDCGFNDLSQLHCSY ESFDVESGVYSVSSFEAKPSGSVVEQAEGVECDFSPLLSGTPPQVYNFKRLVFTNCNY NLTKLLSLFSVNDFTCSQISPAAIASNCYSSLILDYFSYPLSMKSDLSVSSAGPISQFNYK QSFSNPTCLILATVPHNLTTITKPLKYSYINKCSRLLSDDRTEVPQLVNANQYSPCVSIVP STVWEDGDYYRKQLSPLEGGGWLVASGSTVAMTEQLQMGFGITVQYGTDTNSVCP KLEFANDTKIASQLGNCVEYSLYGVSGRGVFQNCTAVGVRQQRFVYDAYQNLVGYYS DDGNYYCLRACVSVPVSVIYDKETKTHATLFGSVACEHISSTMSQYSRSTRSMLKRRD STYGPLQTPVGCVLGLVNSSLFVEDCKLPLGQSLCALPDTPSTLTPRSVRSVPGEMRLA SIAFNHPIQVDQLNSSYFKLSIPTNFSFGVTQEYIQTTIQKVTVDCKQYVCNGFQKCEQ LLREYGQFCSKINQALHGANLRQDDSVRNLFASVKSSQSSPIIPGFGGDFNLTLLEPVS ISTGSRSARSAIEDLLFDKVTIADPGYMQGYDDCMQQGPASARDLICAQYVAGYKVL PPLMDVNMEAAYTSSLLGSIAGVGWTAGLSSFAAIPFAQSIFYRLNGVGITQQVLSEN QKLIANKFNQALGAMQTGFTTTNEAFQKVQDAVNNNAQALSKLASELSNTFGAISA SIGDIIQRLDVLEQDAQIDRLINGRLTTLNAFVAQQLVRSESAALSAQLAKDKVNECVK AQSKRSGFCGQGTHIVSFVVNAPNGLYFMHVGYYPSNHIEVVSAYGLCDAANPTNCI APVNGYFIKTNNTRIVDEWSYTGSSFYAPEPITSLNTKYVAPQVTYQNISTNLPPPLLG NSTGIDFQDELDEFFKNVSTSIPNFGSLTQINTTLLDLTYEMLSLQQVVKALNESYIDLK ELGNYT |
| Amino acid sequence of the spike protein RBD of SARS-CoV | 124 | RVVPSGDVVRFPNITNLCPFGEVFNATKFPSVYAWERKKISNCVADYSVLYNSTFFSTF KCYGVSATKLNDLCFSNVYADSFVVKGDDVRQIAPGQTGVIADYNYKLPDDFMGCVL AWNTRNIDATSTGNYNYKYRYLRHGKLRPFERDISNVPFSPDGKPCTPPALNCYWPL NDYGFYTTTGIGYQPYRVVVLSFELLNAPATVCGPKLSTDLIKNQCVNF |
| Nucleic acid sequence of the spike protein RBD of SARS-CoV | 125 | CGGGTGGTGCCCAGCGGCGACGTGGTGCGGTTCCCCAACATCACCAACCTGTGCC CCTTCGGCGAGGTGTTCAACGCCACCAAGTTCCCCAGCGTGTACGCCTGGGAGCG GAAGAAGATCAGCAACTGCGTGGCCGACTACAGCGTGCTGTACAACAGCACCTTC TTCAGCACCTTCAAGTGCTACGGCGTGAGCGCCACCAAGCTGAACGACCTGTGCT TCAGCAACGTGTACGCCGACAGCTTCGTGGTGAAGGGCGACGACGTGCGGCAGA TCGCCCCCGGCCAGACCGGCGTGATCGCCGACTACAACTACAAGCTGCCCGACGA CTTCATGGGCTGCGTGCTGGCCTGGAACACCCGGAACATCGACGCCACCAGCACC GGCAACTACAACTACAAGTACCGGTACCTGCGGCACGGCAAGCTGCGGCCCTTCG AGCGGGACATCAGCAACGTGCCCTTCAGCCCCGACGGCAAGCCCTGCACCCCCCC CGCCCTGAACTGCTACTGGCCCCTGAACGACTACGGCTTCTACACCACTACCGGCA TCGGCTACCAGCCCTACCGGGTGGTGGTGCTGAGCTTCGAGCTGCTGAACGCCCC CGCCACCGTGTGCGGCCCCAAGCTGAGCACCGACCTGATCAAGAACCAGTGCGT GAACTTC |
| Amino acid sequence of the spike protein RBD of MERS-CoV | 126 | VECDFSPLLSGTPPQVYNFKRLVFTNCNYNLTKLLSLFSVNDFTCSQISPAAIASNCYSS LILDYFSYPLSMKSDLSVSSAGPISQFNYKQSFSNPTCLILATVPHNLTTITKPLKYSYINK CSRLLSDDRTEVPQLVNANQYSPCVSIVPSTVWEDGDYYRKQLSPLEGGGWLVASGS TVAMTEQLQMGFGITVQYGTDTNSVCPKL |

TABLE 11-continued

All sequences mentioned or used in the present application

| Annotation | SEQ ID NO | Sequence |
|---|---|---|
| Nucleic acid sequence of the spike protein RBD of MERS-CoV | 127 | GTGGAGTGTGACTTCAGCCCACTGCTGTCTGGCACACCTCCACAGGTCTACAACTT<br>CAAGAGACTGGTGTTCACCAACTGTAACTACAACCTGACCAAACTGCTGTCCCTGT<br>TCTCTGTGAATGACTTCACTTGTAGCCAGATTAGCCCTGCTGCCATTGCCAGCAACT<br>GTTACTCCTCCCTGATTCTGGACTACTTCTCCTACCCACTGAGTATGAAGTCTGACC<br>TGTCTGTGTCCTCTGCTGGACCAATCAGCCAGTTCAACTACAAGCAGTCCTTCAGC<br>AACCCAACTTGTCTGATTCTGGCTACAGTGCCACACAACCTGACCACCATCACCAA<br>GCCACTGAAATACTCCTACATCAACAAGTGTAGCAGACTGCTGTCTGATGACAGGA<br>CAGAGGTGCCACAACTAGTGAATGCCAACCAATACAGCCCATGTGTGAGCATTGT<br>GCCAAGCACAGTGTGGGAGGATGGAGACTACTACAGGAAGCAACTTAGCCCATT<br>GGAGGGAGGAGGCTGGCTGGTGGCATCTGGCAGCACAGTGGCTATGACAGAAC<br>AACTCCAAATGGGCTTTGGCATCACAGTCCAATATGGCACAGACACCAACTCTGTG<br>TGTCCAAAATTG |
| Amino acid sequence of the spike protein RBD of SARS-CoV-2 | 128 | RVQPTESIVRFPNITNLCPFGEVFNATRFASVYAWNRKRISNCVADYSVLYNSASFSTF<br>KCYGVSPTKLNDLCFTNVYADSFVIRGDEVRQIAPGQTGKIADYNYKLPDDFTGCVIA<br>WNSNNLDSKVGGNYNYLYRLFRKSNLKPFERDISTEIYQAGSTPCNGVEGFNCYFPL<br>QSYGFQPTNGVGYQPYRVVVLSFELLHAPATVCGPKKSTNLVKNKCVNF |
| Nucleic acid sequence of the spike protein RBD of SARS-CoV-2 | 129 | CGCGTGCAGCCCACCGAGAGCATCGTGCGCTTCCCCAACATCACCAACCTGTGCC<br>CCTTCGGCGAGGTGTTCAACGCCACCCGCTTCGCCAGCGTGTACGCCTGGAACCG<br>CAAGCGCATCAGCAACTGCGTGGCCGACTACAGCGTGCTGTACAACAGCGCCAGC<br>TTCAGCACCTTCAAGTGCTACGGCGTGAGCCCCACCAAGCTGAACGACCTGTGCT<br>TCACCAACGTGTACGCCGACAGCTTCGTGATCCGCGGCGACGAGGTGCGCCAGAT<br>CGCCCCCGGCCAGACCGGCAAGATCGCCGACTACAACTACAAGCTGCCCGACGAC<br>TTCACCGGCTGCGTGATCGCCTGGAACAGCAACAACCTGGACAGCAAGGTGGGC<br>GGCAACTACAACTACCTGTACCGCCTGTTCCGCAAGAGCAACCTGAAGCCCTTCG<br>AGCGCGACATCAGCACCGAGATCTACCAGGCCGGCAGCACCCCCTGCAACGGCG<br>TGGAGGGCTTCAACTGCTACTTCCCCCTGCAGAGCTACGGCTTCCAGCCCACCAA<br>CGGCGTGGGCTACCAGCCCTACCGCGTGGTGGTGCTGAGCTTCGAGCTGCTGCAC<br>GCCCCCGCCACCGTGTGCGGCCCCAAGAAGAGCACCAACCTGGTGAAGAACAAG<br>TGCGTGAACTTC |
| Signal peptide | 130 | MGWSCIILFLVATATGVHS |
| Signal peptide | 131 | MGWSCIILFLVATATGSWA |
| 6XHis Tag | 132 | HHHHHH |
| Tag | 133 | MSYYHHHHHH |
| Amino acid sequence of full length S protein of SARS-CoV-2 | 134 | MFVFLVLLPLVSSQCVNLTTRTQLPPAYTNSFTRGVYYPDKVFRSSVLHSTQDLFLPFFS<br>NVTWFHAIHVSGTNGTKRFDNPVLPFNDGVYFASTEKSNIIRGWIFGTTLDSKTQSLL<br>IVNNATNVVIKVCEFQFCNDPFLGVYYHKNNKSWMESEFRVYSSANNCTFEYVSQPF<br>LMDLEGKQGNFKNLREFVFKNIDGYFKIYSKHTPINLVRDLPQGFSALEPLVDLPIGINI<br>TRFQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFASVYAW<br>NRKRISNCVADYSVLYNSASFSTFKCYGVSPTKLNDLCFTNVYADSFVIRGDEVRQIAP<br>GQTGKIADYNYKLPDDFTGCVIAWNSNNLDSKVGGNYNYLYRLFRKSNLKPFERDIST<br>EIYQAGSTPCNGVEGFNCYFPLQSYGFQPTNGVGYQPYRVVVLSFELLHAPATVCGP<br>KKSTNLVKNKCVNFNFNGLTGTGVLTESNKKFLPFQQFGRDIADTTDAVRDPQTLEIL<br>DITPCSFGGVSVITPGTNTSNQVAVLYQDVNCTEVPVAIHADQLTPTWRVYSTGSNV<br>FQTRAGCLIGAEHVNNSYECDIPIGAGICASYQTQTNSPRRARSVASQSIIAYTMSLGA<br>ENSVAYSNNSIAIPTNFTISVTTEILPVSMTKTSVDCTMYICGDSTECSNLLLQYGSFCT<br>QLNRALTGIAVEQDKNTQEVFAQVKQIYKTPPIKDFGGFNFSQILPDPSKPSKRSFIEDL<br>LFNKVTLADAGFIKQYGDCLGDIAARDLICAQKFNGLTVLPPLLTDEMIAQYTSALLAG<br>TITSGWTFGAGAALQIPFAMQMAYRFNGIGVTQNVLYENQKLIANQFNSAIGKIQDS<br>LSSTASALGKLQDVVNQNAQALNTLVKQLSSNFGAISSVLNDILSRLDKVEAEVQIDRL<br>ITGRLQSLQTYVTQQLIRAAEIRASANLAATKMSECVLGQSKRVDFCGKGYHLMSFP<br>QSAPHGVVFLHVTYVPAQEKNFTTAPAICHDGKAHFPREGVFVSNGTHWFVTQRNF<br>YEPQIITTDNTFVSGNCDVVIGIVNNTVYDPLQPELDSFKEELDKYFKNHTSPDVDLG<br>DISGINASVVNIQKEIDRLNEVAKNLNESLIDLQELGKYEQYIKWPWYIWLGFIAGLIAI<br>VMVTIMLCCMTSCCSCLKGCCSCGSCCKFDEDDSEPVLKGVKLHYTWSHPQFEK |
| Nucleic acid sequence of full length S protein of SARS-CoV-2 | 135 | ATGTTCGTGTTCCTGGTGCTGCTGCCTCTGGTGAGCAGCCAGTGCGTGAATCTGAC<br>CACCAGAACCCAGCTGCCTCCTGCCTACACCAATAGCTTCACCAGAGGAGTTTATT<br>ATCCCGATAAGGTGTTCAGAAGTAGTGTATTACATAGTACCCAGGACCTGTTCCTAC<br>CTTTCTTCAGTAACGTGACCTGGTTCCACGCCATCCACGTGAGCGGCACCAATGGC<br>ACCAAGAGATTCGACAATCCTGTGCTGCCTTTCAATGACGGCGTGTACTTCGCCAG<br>CACCGAGAAGAGCAATATCATCAGAGGCTGGATCTTCGGCACCACCTTGGATTCC<br>AAGACTCAGAGCCTGCTGATTGTAAACAACGCTACAAATGTGGTGATCAAGGTGT<br>GCGAGTTCCAGTTCTGCAATGACCCTTCCTGGGTGTTTATTATCATAAGAACAACA<br>AGAGCTGGATGGAGAGCGAGTTCCGCGTATATTCGTCGGCTAATAATTGCACCTTC<br>GAGTACGTGAGCCAGCCTTTCCTGATGGACCTGGAGGGCAAGCAGGGCAATTTC<br>AAGAATCTGAGAGAGTTCGTGTTCAAGAATATCGACGGCTACTTCAAGATCTACAG |

TABLE 11-continued

All sequences mentioned or used in the present application

| Annotation | SEQ ID NO | Sequence |
|---|---|---|
| | | CAAGCACACACCCATTAATCTGGTGAGAGACCTGCCTCAGGGCTTCAGCGCCCTG<br>GAGCCTCTGGTGGACCTGCCTATCGGCATCAATATCACCAGATTCCAGACCCTGCT<br>GGCCCTGCACAGATCATATCTTACACCAGGCGATTCGTCAAGCGGTTGGACCGCTG<br>GAGCTGCGGCATATTACGTGGGCTACCTGCAGCCTAGAACCTTCCTGCTGAAGTAC<br>AATGAGAATGGTACGATAACCGACGCAGTTGATTGTGCCCTGGACCCTCTGAGCG<br>AGACCAAGTGCACCCTGAAGAGCTTCACCGTGGAGAAGGGCATCTACCAGACCA<br>GCAATTTCAGAGTGCAGCCTACCGAGAGCATCGTGAGATTCCCTAATATCACCAAT<br>CTGTGCCCTTTCGGCGAGGTGTTCAATGCCACCAGATTCGCCAGCGTGTACGCATG<br>GAACCGCAAGCGGATAAGCAATTGCGTGGCCGACTACAGCGTGCTGTACAATAGC<br>GCCAGCTTCAGCACCTTCAAATGTTATGGTGTTTCGCCAACAAAGCTGAATGACCT<br>GTGCTTCACCAATGTGTACGCCGACAGCTTCGTGATCAGAGGCGACGAGGTGAGA<br>CAGATCGCGCCAGGGCAGACCGGCAAGATCGCCGACTACAATTACAAGCTGCCTG<br>ACGACTTCACCGGCTGCGTGATCGCGTGGAACTCTAACAATCTAGATTCGAAAGTT<br>GGAGGCAATTACAATTACCTGTACAGACTGTTCAGAAAGAGCAATCTGAAGCCTTT<br>CGAGAGAGACATCAGCACCGAGATCTACCAGGCCGGCAGCACACCGTGTAATGG<br>CGTGGAGGGCTTCAATTGCTACTTCCCTCTGCAGAGCTACGGCTTCCAGCCTACCA<br>ATGGCGTGGGCTACCAGCCTTACAGAGTGGTGGTGCTGAGCTTCGAGCTGCTGCA<br>CGCTCCCGCTACCGTGTGCGGCCCTAAGAAGAGCACCAATCTGGTGAAGAATAAG<br>TGCGTGAATTTCAATTTCAATGGTCTAACTGGAACGGGCGTGCTGACCGAGAGCA<br>ATAAGAAGTTTCTTCCCTTTCAACAATTCGGCAGAGACATCGCCGACACCACAGAT<br>GCTGTAAGAGACCCTCAGACCCTGGAGATCCTGGACATCACTCCGTGTAGCTTCG<br>GCGGCGTGAGCGTGATCACACCGGGTACCAATACCAGCAATCAGGTGGCCGTGCT<br>GTACCAGGACGTGAATTGCACCGAGGTGCCTGTGGCCATCCACGCCGACCAGCTG<br>ACTCCCACTTGGAGGGTATATTCCACGGGAAGCAATGTGTTCCAGACCAGAGCCG<br>GCTGCCTGATCGGCGCCGAGCACGTGAATAATAGCTACGAGTGCGACATCCCTATC<br>GGCGCCGGCATCTGCGCCAGCTACCAGACCCAGACCAATAGCCCTAGAAGAGCCA<br>GAAGCGTGGCCAGCCAGAGCATCATCGCCTACACCATGAGCCTGGGCGCCGAGA<br>ATAGCGTGGCCTACAGCAATAATAGCATCGCCATCCCTACCAATTTCACCATCAGCG<br>TGACCACCGAAATATTACCAGTCTCCATGACCAAGACCAGCGTGGACTGCACCATG<br>TACATCTGCGGCGACAGCACCGAGTGCAGCAATCTGCTGCTGCAGTACGGCAGCT<br>TCTGCACCCAGCTGAATAGAGCCCTGACCGGCATCGCCGTGGAGCAGGACAAGA<br>ATACCCAGGAGGTGTTCGCCCAGGTGAAGCAGATCTACAAGACTCCGCCGATCAA<br>GGACTTCGGCGGCTTCAATTTCAGCCAAATACTCCCAGATCCAAGCAAGCCTAGCA<br>AGAGGAGCTTCATCGAGGACCTGCTGTTCAATAAGGTGACCCTGGCCGACGCCG<br>GCTTCATCAAGCAGTACGGCGACTGCCTAGGTGATATTGCGGCAAGAGACCTGAT<br>CTGCGCCCAGAAGTTTAACGGTTTGACAGTACTACCTCCTCTGCTGACCGACGAGA<br>TGATAGCACAATATACGTCGGCATTGCTCGCTGGCACGATCACATCGGGCTGGACT<br>TTCGGCGCCGGAGCAGCGTTGCAAATCCCTTTCGCCATGCAGATGGCCTACAGATT<br>CAATGGCATCGGCGTGACCCAGAATGTGCTGTACGAGAATCAGAAGCTGATCGCC<br>AATCAGTTCAATAGCGCCATCGGCAAGATCCAGGACAGCCTGAGCAGCACCGCCA<br>GCGCCCTGGGCAAGCTGCAGGACGTGGTGAATCAGAATGCCCAGGCCCTGAATA<br>CCCTGGTGAAGCAGCTGAGCAGCAATTTCGGCGCCATCAGTAGTGTACTCAACGA<br>TATCCTGAGCAGACTGGACAAGGTGGAGGCCGAGGTGCAAATTGATCGTCTTATT<br>ACTGGCAGACTGCAGAGCCTGCAGACCTACGTGACCCAGCAGCTGATCAGAGCC<br>GCCGAGATCAGAGCCAGCGCCAATCTGGCCGCCACCAAGATGAGCGAGTGCGTG<br>CTGGGCCAGAGCAAGAGAGTGGACTTCTGCGGCAAGGGCTACCACCTGATGAGC<br>TTCCCTCAGAGCGCTCCACATGGCGTGGTGTTCCTGCACGTGACCTACGTGCCTGC<br>CCAGGAGAAGAATTTCACCACCGCACCCGCAATCTGCCACGACGGCAAGGCCCAC<br>TTCCCTAGAGAGGGCGTGTTCGTGAGCAATGGCACCCACTGGTTCGTGACCCAGA<br>GAAATTTCTACGAGCCTCAGATCATCACCACCGACAATACCTTCGTGAGCGGCAAT<br>TGCGACGTGGTGATCGGGATAGTCAATAATACTGTCTACGACCCTCTGCAGCCTGA<br>GCTGGACAGCTTCAAGGAGGAGCTGGACAAGTACTTCAAGAATCACACCAGCCC<br>TGACGTGGACCTCGGTGATATTTCGGGAATCAATGCCAGCGTGGTGAATATCCAGA<br>AGGAAATTGATCGGCTCAACGAAGTGGCCAAGAATCTGAATGAGAGCCTGATCGA<br>CCTGCAGGAGCTGGGCAAGTACGAGCAGTACATCAAGTGGCCTTGGTACATCTGG<br>CTGGGCTTCATCGCCGGCCTGATCGCCATCGTGATGGTGACCATCATGCTGTGCTG<br>CATGACCTCCTGTTGTTCCTGTTTGAAAGGGTGTTGTTCGTGTGGGTCCTGCTGCA<br>AGTTCGACGAGGACGACAGCGAGCCTGTGCTGAAGGGCGTGAAGCTGCACTACA<br>CCTGGAGCCACCCTCAGTTCGAGAAGTGA |
| P2B-1G5 HCDR1 | 136 | GYTFTTYV |
| P2B-1G5 HCDR2 | 137 | INTNTGNP |
| P2B-1G5 HCDR3 | 138 | SCEITTLGGMDV |
| P2B-1G5 LCDR1 | 139 | NIGSKS |
| P2B-1G5 LCDR2 | 140 | YDS |
| P2B-1G5 LCDR3 | 141 | QVWDSISDHRV |
| P2B-1G5 VH | 142 | QVQLVQSGSELKKPGASVKVSCKASGYTFTTYVMNWVRQAPGQGLEWMGWINT<br>NTGNPTYAQGFTGRFVFSLDTSVSTASLQISSLKAEDTAVYYCSCEITTLGGMDVWGQ<br>GTTVTVSS |

TABLE 11-continued

All sequences mentioned or used in the present application

| Annotation | SEQ ID NO | Sequence |
|---|---|---|
| P2B-1G5 VL | 143 | SYVLTQPPSVSVAPGKTARITCGGNNIGSKSVHWYQQKPGQAPVLVIYYDSDRPSGIP<br>ERFSGSNSGNTATLTISGVEAGDEADYYCQVWDSISDHRVFGGGTKLTVL |
| P2B-1G5 VHnu | 144 | CAGGTGCAGCTGGTGCAATCTGGGTCTGAGTTGAAGAAGCCTGGGGCCTCAGTG<br>AAGGTTTCCTGCAAGGCTTCTGGATACACCTTCACTACCTATGTTATGAATTGGGTG<br>CGACAGGCCCCTGGACAAGGGCTTGAGTGGATGGGATGGATCAACACCAACACT<br>GGGAACCCAACGTATGCCCAGGGCTTCACAGGACGGTTTGTCTTCTCCTTGGACA<br>CCTCTGTCAGCACGGCATCTCTGCAGATCAGCAGCCTAAAGGCTGAGGACACTGC<br>CGTGTATTACTGTTCGTGTGAAATAACCACCTTGGGCGGTATGGACGTCTGGGGCC<br>AAGGGACCACGGTCACCGTCTCCTCA |
| P2B-1G5 VLnu | 145 | TCCTATGTGCTGACTCAGCCACCCTCAGTGTCAGTGGCCCCAGGAAAGACGGCCA<br>GGATTACCTGTGGGGGAAACAACATTGGAAGTAAAAGTGTGCACTGGTACCAGCA<br>GAAGCCAGGCCAGGCCCCTGTGCTGGTCATCTATTATGATAGCGACCGGCCCTCAG<br>GGATCCCTGAGCGATTCTCTGGCTCCAACTCTGGGAACACGGCCACCCTGACCATC<br>AGCGGGGTCGAAGCCGGGGATGAGGCCGACTATTACTGTCAGGTGTGGGATAGT<br>ATTAGTGATCATCGGGTGTTCGGCGGAGGGACCAAGCTGACCGTCCTA |
| P2B-1A1 HCDR1 | 146 | GGSISSYY |
| P2B-1A1 HCDR2 | 147 | IYYSGST |
| P2B-1A1 HCDR3 | 148 | ARLERDWPLDAFDI |
| P2B-1A1 LCDR1 | 149 | SSDVGGYNY |
| P2B-1A1 LCDR2 | 150 | DVS |
| P2B-1A1 LCDR3 | 151 | SSYTSNNTFA |
| P2B-1A1 VH | 152 | QVQLQESGPGLVKPSETLSLTCTVSGGSISSYYWSWIRQPPGKGLEWIGYIYYSGSTNY<br>NPSLKSRVTISVDTSKKQFSLKLSSVTAADTAVYYCARLERDWPLDAFDIWGQGTMV<br>TVSS |
| P2B-1A1 VL | 153 | QSALTQPASVSGSPGQSITISCTGTSSDVGGYNYVSWYQQHPGKAPKFMIYDVSKRP<br>SGVSNRFSGSKSGNTASLTISGLQAEDEADYYCSSYTSNNTFAFGGGTKLTVL |
| P2B-1A1 VHnu | 154 | CAGGTGCAGCTGCAGGAGTCGGGCCCAGGACTGGTGAAGCCTTCGGAGACCCTG<br>TCCCTCACCTGCACTGTCTCTGGTGGCTCCATCAGTAGTTACTACTGGAGCTGGATC<br>CGGCAGCCCCCAGGGAAGGGACTGGAGTGGATTGGGTATATCTATTACAGTGGGA<br>GCACCAACTACAACCCCTCCCTCAAGAGTCGAGTCACCATATCAGTAGACACGTCC<br>AAGAAGCAGTTCTCCCTGAAGCTGAGCTCTGTGACCGCTGCGGACACGGCCGTGT<br>ATTACTGTGCGAGGCTCGAACGAGACTGGCCACTTGATGCTTTTGATATCTGGGGC<br>CAAGGGACAATGGTCACCGTCTCCTCA |
| P2B-1A1 VLnu | 155 | CAGTCTGCCCTGACTCAGCCTGCCTCCGTGTCTGGGTCTCCTGGACAGTCGATCAC<br>CATCTCCTGCACTGGAACCAGCAGTGACGTTGGTGGTTATAACTATGTCTCCTGGTA<br>CCAACAGCACCCAGGCAAAGCCCCCAAATTCATGATTTATGATGTCAGTAAGCGGC<br>CCTCAGGGGTTTCTAATCGCTTCTCTGGCTCCAAGTCTGGCAACACGGCCTCCCTG<br>ACCATCTCTGGGCTCCAGGCTGAGGACGAGGCTGATTATTACTGCAGCTCATATAC<br>AAGCAACAACACTTTCGCGTTCGGCGGAGGGACCAAGCTGACCGTCCTA |
| P2C-1D7 HCDR1 | 156 | GFTVSSNY |
| P2C-1D7 HCDR2 | 157 | IYSGGST |
| P2C-1D7 HCDR3 | 158 | ARELYEVGATDY |
| P2C-1D7 LCDR1 | 159 | QSLVYSDGNTY |
| P2C-1D7 LCDR2 | 160 | KVS |
| P2C-1D7 LCDR3 | 161 | MQRYTLAGV |
| P2C-1D7 VH | 162 | EVQLVESGGGLIQPGGSLRLSCAASGFTVSSNYMSWVRQAPGKGLEWVSVIYSGGS<br>TYYADSVKGRFTISRDNSKNTLYLQMNSLRAEDTAVYYCARELYEVGATDYWGQGTL<br>VTVSS |
| P2C-1D7 VL | 163 | DVVMTQSPLSLPVTLGQPASISCRSSQSLVYSDGNTYLNWFQQRPGQSPRRLIYKVS<br>NWDSGVPDRFSGSGSGTDFTLKISRVEAEDVGVYYCMQRYTLAGVFGPGTKVDIK |
| P2C-1D7 VHnu | 164 | GAGGTGCAGCTGGTGGAGTCTGGAGGAGGCTTGATCCAGCCTGGGGGGTCCCTG<br>AGACTCTCCTGTGCAGCCTCTGGGTTCACCGTCAGTAGCAACTACATGAGCTGGGT<br>CCGCCAGGCTCCAGGGAAGGGGCTGGAGTGGGTCTCAGTTATTTATAGCGGTGG |

TABLE 11-continued

All sequences mentioned or used in the present application

| Annotation | SEQ ID NO | Sequence |
|---|---|---|
| | | TAGCACATACTACGCAGACTCCGTGAAGGGCCGATTCACCATCTCCAGAGACAATT<br>CCAAGAACACGCTGTATCTTCAAATGAACAGCCTGAGAGCCGAGGACACGGCCGT<br>GTATTACTGTGCGAGAGAATTGTACGAAGTGGGAGCTACGGACTACTGGGGCCAG<br>GGAACCCTGGTCACCGTCTCCTCA |
| P2C-1D7 VLnu | 165 | GATGTTGTGATGACTCAGTCTCCACTCTCCCTGCCCGTCACCCTTGGACAGCCGGC<br>CTCCATCTCCTGCAGGTCTAGTCAAAGCCTCGTATACAGTGATGGAAACACCTACTT<br>GAATTGGTTTCAGCAGAGGCCAGGCCAATCTCCAAGGCGCCTAATTTATAAGGTTT<br>CTAACTGGGACTCTGGGGTCCCAGACAGATTCAGCGGCAGTGGGTCAGGCACTG<br>ATTTCACACTGAAAATCAGCAGGGTGGAGGCTGAGGATGTTGGGGTTTATTACTG<br>CATGCAACGGTACACACTGGCCGGCGTTTTCGGCCCTGGGACCAAAGTGGATATC<br>AAA |
| P2B-1A10 HCDR1 | 166 | GFTVSSNY |
| P2B-1A10 HCDR2 | 167 | IYSGGST |
| P2B-1A10 HCDR3 | 168 | AREGPKSITGTAFDI |
| P2B-1A10 LCDR1 | 169 | QDISNY |
| P2B-1A10 LCDR2 | 170 | DAS |
| P2B-1A10 LCDR3 | 171 | QQYDNLPMYT |
| P2B-1A10 VH | 172 | EVQLVESGGGLIQPGGSLRLSCAASGFTVSSNYMSWVRQAPGKGLEWVSVIYSGGS<br>TYYADSVKGRFTISRDNSKNTLYLQMNSLRAEDTAVYYCAREGPKSITGTAFDIWGQG<br>TIVTVSS |
| P2B-1A10 VL | 173 | DIQMTQSPSSLSASVGDRVTITCQASQDISNYFNWYQQKPGKAPKLLIYDASNLETG<br>VPSRFSGSGSGTDFTFTISSLQPEDIATYYCQQYDNLPMYTFGQGTKLEIK |
| P2B-1A10 VHnu | 174 | GAGGTGCAGCTGGTGGAGTCTGGAGGAGGCTTGATCCAGCCTGGGGGGTCCCTG<br>AGACTCTCCTGTGCAGCCTCTGGGTTCACCGTCAGTAGCAACTACATGAGCTGGGT<br>CCGCCAGGCTCCAGGGAAGGGGCTGGAGTGGGTCTCAGTTATTTATAGCGGTGG<br>TAGCACATACTACGCAGACTCCGTGAAGGGCCGATTCACCATCTCCAGAGACAATT<br>CCAAGAACACGCTGTATCTTCAAATGAACAGCCTGAGAGCCGAGGACACGGCCGT<br>TTATTACTGTGCGAGAGAGGGCCCAAAGTCTATTACAGGGACGGCTTTTGATATCT<br>GGGGCCAAGGGACAATTGTCACCGTCTCCTCA |
| P2B-1A10 VLnu | 175 | GACATCCAGATGACCCAGTCTCCATCCTCCCTGTCTGCATCTGTAGGAGACAGAGT<br>CACCATCACTTGCCAGGCGAGTCAGGACATTAGCAACTATTTTAATTGGTATCAGC<br>AGAAACCAGGGAAAGCCCCTAAGCTCCTGATCTACGATGCATCCAATTTGGAAAC<br>AGGGGTCCCATCAAGGTTCAGTGGAAGTGGATCTGGGACAGATTTTACTTTCACC<br>ATCAGCAGCCTGCAGCCTGAAGATATTGCAACATATTACTGTCAACAGTATGATAAT<br>CTCCCCATGTACACTTTTGGCCAGGGGACCAAGCTGGAGATCAAA |
| P2B-1D9 HCDR1 | 176 | GFSLSTSGVG |
| P2B-1D9 HCDR2 | 177 | IYWDDDK |
| P2B-1D9 HCDR3 | 178 | AHTRILYYGSGSYYDY |
| P2B-1D9 LCDR1 | 179 | SSNIGSNY |
| P2B-1D9 LCDR2 | 180 | SNN |
| P2B-1D9 LCDR3 | 181 | AAWDDSLSGVV |
| P2B-1D9 VH | 182 | QITLKESGPTLVKPTQTLTLTCTFSGFSLSTSGVGVGWIRQPPGKALEWLALIYWDDD<br>KYYSPSLKSRLTITKDTSKNQVVLTMTNMDPVDTATYYCAHTRILYYGSGSYYDYWGQ<br>GTLVTVSS |
| P2B-1D9 VL | 183 | QSVLTQPPSASGTPGQRVTISCSGSSSNIGSNYVYWYQQLPGTAPKLLIYSNNQRPSG<br>VPDRFSGSKSGTSASLAISGLRSEDEADYYCAAWDDSLSGVVFGGGTKLTVL |
| P2B-1D9 VHnu | 184 | CAGATCACCTTGAAGGAGTCTGGTCCTACGCTGGTGAAACCCACACAGACCCTCA<br>CGCTGACCTGCACCTTCTCTGGGTTCTCACTCAGCACTAGTGGAGTGGGTGTGGG<br>CTGGATCCGTCAGCCCCCAGGAAAGGCCCTGGAGTGGCTTGCACTCATTTATTGG<br>GATGATGATAAATACTACAGCCCATCTCTGAAGAGCAGGCTCACCATCACCAAGGA<br>CACCTCCAAAAACCAGGTGGTCCTTACAATGACCAACATGGACCCTGTGGACACA<br>GCCACATATTACTGTGCACACACTCGCATCTTATACTATGGTTCGGGGAGTTATTATG<br>ACTACTGGGGCCAGGGAACCCTGGTCACCGTCTCCTCA |

TABLE 11-continued

All sequences mentioned or used in the present application

| Annotation | SEQ ID NO | Sequence |
|---|---|---|
| P2B-1D9 VLnu | 185 | CAGTCTGTGCTGACTCAGCCACCCTCAGCGTCTGGGACCCCCGGGCAGAGGGTCA CCATCTCTTGTTCTGGAAGCAGCTCCAACATCGGAAGTAATTATGTATACTGGTACC AGCAGCTCCCAGGAACGGCCCCCAAACTCCTCATCTATAGTAATAATCAGCGGCCC TCAGGGGTCCCTGACCGATTCTCTGGCTCCAAGTCTGGCACCTCAGCCTCCCTGGC CATCAGTGGGCTCCGGTCCGAGGATGAGGCTGATTATTACTGTGCAGCATGGGAT GACAGCCTGAGTGGTGTGGTATTCGGCGGAGGGACCAAGCTGACCGTCCTA |
| P2B-1E4 HCDR1 | 186 | GFSLSTSGVG |
| P2B-1E4 HCDR2 | 187 | IYWDDDK |
| P2B-1E4 HCDR3 | 188 | AHQIVATIIDY |
| P2B-1E4 LCDR1 | 189 | SSDVGGYNY |
| P2B-1E4 LCDR2 | 190 | DVS |
| P2B-1E4 LCDR3 | 191 | SSYTSSSVV |
| P2B-1E4 VH | 192 | QITLKESGPTLVKPTQTLTLTCTFSGFSLSTSGVGVGWIRQPPGKALEWLALIYWDDD KRYSPSLKSRLTITKDTSKNQVVLTMTNMDPVDTATYYCAHQIVATIIDYWGQGTLVT VSS |
| P2B-1E4 VL | 193 | QSALTQPASVSGSPGQSITISCTGTSSDVGGYNYVSWYQQHPGKAPKLMIYDVSKRP SGVSNRFSGSKSGNTASLTISGLQAEDEADYYCSSYTSSSVVFGGGTKLTVL |
| P2B-1E4 VHnu | 194 | CAGATCACCTTGAAGGAGTCTGGTCCTACGCTGGTGAAACCCACACAGACCCTCA CGCTGACCTGCACCTTCTCTGGGTTCTCACTCAGCACTAGTGGAGTGGGTGTGGG CTGGATCCGTCAGCCCCCAGGAAAGGCCCTGGAGTGGCTTGCACTCATTTATTGG GATGATGATAAGCGCTACAGCCCATCTCTGAAGAGCAGGCTCACCATCACCAAGG ACACCTCCAAAAACCAGGTGGTCCTTACAATGACCAACATGGACCCTGTGGACAC AGCCACATATTACTGTGCACACCAAATAGTGGCTACGATTATTGACTACTGGGGCCA GGGAACCCTGGTCACCGTCTCCTCA |
| P2B-1E4 VLnu | 195 | CAGTCTGCCCTGACTCAGCCTGCCTCCGTGTCTGGGTCTCCTGGACAGTCGATCAC CATCTCCTGCACTGGAACCAGCAGTGACGTTGGTGGTTATAACTATGTCTCCTGGTA CCAACAGCACCCAGGCAAAGCCCCCAAACTCATGATTTATGATGTCAGTAAGCGG CCCTCAGGGGTTTCTAATCGCTTCTCTGGCTCCAAGTCTGGCAACACGGCCTCCCT GACCATCTCTGGGCTCCAGGCTGAGGACGAGGCTGATTATTACTGCAGCTCATATA CAAGCAGCAGCGTGGTATTCGGCGGAGGGACCAAGCTGACCGTCCTA |
| P2B-1G1 HCDR1 | 196 | GFTVSSNY |
| P2B-1G1 HCDR2 | 197 | IYSGGST |
| P2B-1G1 HCDR3 | 198 | ARDYGDYWFDP |
| P2B-1G1 LCDR1 | 199 | QSVSSSY |
| P2B-1G1 LCDR2 | 200 | GAS |
| P2B-1G1 LCDR3 | 201 | QQYGSSPRT |
| P2B-1G1 VH | 202 | EVQLVESGGGLVQPGGSLRLSCAASGFTVSSNYMSWVRQAPGKGLEWVSVIYSGGS TYYADSVKGRFTISRDNSKNTLYLQMNSLRAEDTAVYYCARDYGDYWFDPWGQGTL VTVSS |
| P2B-1G1 VL | 203 | EIVLTQSPGTLSLSPGERATLSCRASQSVSSSYLAWYQQKPGQAPRLLIYGASSRATGIP DRFSGSGSGTDFTLTISRLEPEDFAVYYCQQYGSSPRTFGQGTKLEIK |
| P2B-1G1 VHnu | 204 | GAGGTGCAGCTGGTGGAGTCTGGGGGAGGCTTGGTCCAGCCTGGGGGGTCCCT GAGACTCTCCTGTGCAGCCTCTGGATTCACCGTCAGTAGCAACTACATGAGCTGG TCCGCCAGGCTCCAGGGAAGGGGCTGGAGTGGGTCTCAGTTATTTATAGCGGTG GTAGCACATACTACGGAGACTCCGTGAAGGGCAGATTCACCATCTCCAGAGACAAT TCCAAGAACACGCTGTATCTTCAAATGAACAGCCTGAGAGCCGAGGACACGGCTG TGTATTACTGTGCGAGAGACTACGGTGACTACTGGTTCGACCCCTGGGGCCAGGG AACCCTGGTCACCGTCTCCTCA |
| P2B-1G1 VLnu | 205 | GAAATTGTGTTGACGCAGTCTCCAGGCACCCTGTCTTTGTCTCCAGGGGAAAGAG CCACCCTCTCCTGCAGGGCCAGTCAGAGTGTTAGCAGCAGCTACTTAGCCTGGTAC CAGCAGAAACCTGGCCAGGCTCCCAGGCTCCTCATCTATGGTGCATCCAGCAGGG CCACTGGCATCCCAGACAGGTTCAGTGGCAGTGGGTCTGGGACAGACTTCACTCT CACCATCAGCAGACTGGAGCCTGAAGATTTTGCAGTGTATTACTGTCAGCAGTATG GTAGCTCACCGAGGACTTTTGGCCAGGGGACCAAGCTGGAGATCAAA |

TABLE 11-continued

All sequences mentioned or used in the present application

| Annotation | SEQ ID NO | Sequence |
|---|---|---|
| P4A-2D9 HCDR1 | 206 | GFTFSSYG |
| P4A-2D9 HCDR2 | 207 | ISDDGSNQ |
| P4A-2D9 HCDR3 | 208 | AKRGGYCSTTSCLVRWVYFDY |
| P4A-2D9 LCDR1 | 209 | QFISSY |
| P4A-2D9 LCDR2 | 210 | ATS |
| P4A-2D9 LCDR3 | 211 | QQSYNTLT |
| P4A-2D9 VH | 212 | QVQLVESGGGVVQPGRSLRLSCAASGFTFSSYGMHWVRQSPGKGLEWVAVISDDG<br>SNQYYADSVKGRFTISRDNSKNTLYLEINSLRVEDTAVYYCAKRGGYCSTTSCLVRWVY<br>FDYWGQGTLVTVSS |
| P4A-2D9 VL | 213 | DIQMTQSPSSLSASVGDRVTITCRASQFISSYLNWYQQKPGKAPKLLIYATSILQTGVP<br>SRFSGSGSGTDFTLTISSLQPEDFATYYCQQSYNTLTFGPGTKVDIK |
| P4A-2D9 VHnu | 214 | CAGGTGCAGCTGGTGGAGTCTGGGGGAGGCGTGGTCCAGCCTGGGAGGTCCCT<br>GAGACTCTCCTGTGCAGCCTCTGGATTCACCTTCAGTAGCTATGGCATGCACTGGG<br>TCCGCCAGTCTCCAGGCAAGGGGCTGGAGTGGGTGGCAGTTATATCAGATGATGG<br>AAGTAATCAATACTATGCAGACTCCGTGAAGGGCCGATTCACCATCTCCAGAGACA<br>ATTCCAAGAACACGCTGTATCTGGAAATCAACAGCCTGAGAGTTGAGGACACGGC<br>TGTGTATTACTGTGCGAAAAGGGGCGGATATTGTAGTACTACCAGCTGCCTCGTTA<br>GGTGGGTCTACTTTGACTACTGGGGCCAGGGAACCCTGGTCACCGTCTCCTCA |
| P4A-2D9 VLnu | 215 | GACATCCAGATGACCCAGTCTCCATCCTCCCTGTCTGCATCTGTAGGAGACAGAGT<br>CACCATCACTTGCCGGGCAAGTCAGTTCATTAGCAGCTACTTAAATTGGTATCAGC<br>AGAAACCAGGGAAAGCCCCTAAGCTCCTGATCTATGCTACATCCATTTTGCAAACT<br>GGGGTCCCATCAAGGTTCAGTGGCAGTGGATCTGGGACAGATTTCACTCTCACCA<br>TCAGCAGTCTGCAACCTGAAGATTTTGCAACTTACTACTGTCAACAGAGTTACAAT<br>ACCCTTACTTTCGGCCCTGGGACCAAAGTCGATATCAAA |
| P5A-2G7 HCDR1 | 216 | GDSVSSGSYY |
| P5A-2G7 HCDR2 | 217 | IYYSGST |
| P5A-2G7 HCDR3 | 218 | ARERCYYGSGRAPRCVWFDP |
| P5A-2G7 LCDR1 | 219 | SSDVGGYNY |
| P5A-2G7 LCDR2 | 220 | DVS |
| P5A-2G7 LCDR3 | 221 | SSYTSSSTLVV |
| P5A-2G7 VH | 222 | QVQLQESGPGLVKPSETLSLTCTVSGDSVSSGSYYWSWIRQPPGKGLEWIGYIYYSGS<br>TNYNPSLKSRVTISVDTSKNQFSLKLSSVTAADTAVYYCARERCYYGSGRAPRCVWFD<br>PWGQGTLVTVSS |
| P5A-2G7 VL | 223 | QSALTQPASVSGSPGQSITISCTGTSSDVGGYNYVSWYQQHPGKAPKLMIYDVSNRP<br>SGVSNRFSGSKSGNTASLTISGLQAEDEADYYCSSYTSSSTLVVFGGGTKLTVL |
| P5A-2G7 VHnu | 224 | CAGGTGCAGCTGCAGGAGTCGGGCCCAGGACTGGTGAAGCCTTCGGAGACCCTG<br>TCCCTCACCTGCACTGTCTCTGGTGACTCCGTCAGCAGTGGTAGTTACTACTGGAG<br>CTGGATCCGGCAGCCCCCAGGGAAGGGACTGGAGTGGATTGGGTATATCTATTAC<br>AGTGGGAGCACCAACTACAACCCCTCCCTCAAGAGTCGAGTCACCATATCAGTAG<br>ACACGTCCAAGAACCAGTTCTCCCTGAAGCTGAGCTCTGTGACCGCTGCGGACAC<br>GGCCGTGTATTACTGTGCGAGAGAGCGATGTTACTATGGTTCAGGGAGAGCCCCC<br>CGTTGTGTCTGGTTCGACCCCTGGGGCCAGGGAACCCTGGTCACCGTCTCCTCA |
| P5A-2G7 VLnu | 225 | CAGTCTGCCCTGACTCAGCCTGCCTCCGTGTCTGGGTCTCCTGGACAGTCGATCAC<br>CATCTCCTGCACTGGAACCAGCAGTGACGTTGGTGGTTATAACTATGTCTCCTGGTA<br>CCAACAACACCCAGGCAAAGCCCCCAAACTCATGATTTATGATGTCAGTAATCGGC<br>CCTCAGGGGTTTCTAATCGCTTCTCTGGCTCCAAGTCTGGCAACACGGCCTCCCTG<br>ACCATCTCTGGGCTCCAGGCTGAGGACGAGGCTGATTATTACTGCAGCTCATATAC<br>AAGCAGCAGCACTCTCGTGGTATTCGGCGGAGGGACCAAGCTGACCGTCCTA |
| P5A-3C8 HCDR1 | 226 | GFTVSSNY |
| P5A-3C8 HCDR2 | 227 | IYSGGST |
| P5A-3C8 HCDR3 | 228 | ARDLQEHGMDV |
| P5A-3C8 LCDR1 | 229 | QGISSY |

TABLE 11-continued

All sequences mentioned or used in the present application

| Annotation | SEQ ID NO | Sequence |
|---|---|---|
| P5A-3C8 LCDR2 | 230 | AAS |
| P5A-3C8 LCDR3 | 231 | QHLNSYPPGYT |
| P5A-3C8 VH | 232 | EVQLVESGGGLIQPGGSLRLSCAASGFTVSSNYMSWVRQAPGKGLEWVSFIYSGGS<br>TYYADSVKGRFTISRDNSKNTLYLQMNSLRAEDTAVYYCARDLQEHGMDVWGQGTT<br>VTVSS |
| P5A-3C8 VL | 233 | DIQLTQSPSSLSASVGDRVTITCRASQGISSYLAWYQQKPGKAPKLLIYAASTLQSGVP<br>SRFSGSGSGTDFTLTISSLQPEDFATYYCQHLNSYPPGYTFGQGTKLEIK |
| P5A-3C8 VHnu | 234 | GAGGTGCAGCTGGTGGAGTCTGGAGGAGGCTTGATCCAGCCTGGGGGGTCCCTG<br>AGACTCTCCTGTGCAGCCTCTGGGTTCACCGTCAGTAGCAACTACATGAGCTGGGT<br>CCGCCAGGCTCCAGGGAAGGGGCTGGAATGGGTCTCATTTATTTATAGCGGTGGT<br>AGTACATACTACGCAGACTCCGTGAAGGGCCGATTCACCATCTCCAGAGACAATTC<br>CAAGAACACGCTGTATCTTCAAATGAACAGCCTGAGAGCCGAGGACACGGCCGT<br>GTATTACTGTGCGAGAGATCTACAGGAACACGGTATGGACGTCTGGGGCCAAGGG<br>ACCACGGTCACCGTCTCCTCA |
| P5A-3C8 VLnu | 235 | GACATCCAGTTGACCCAGTCTCCATCCTCCCTGTCTGCATCTGTAGGAGACAGAGT<br>CACCATCACTTGCCGGGCCAGTCAGGGCATTAGCAGTTATTTAGCCTGGTATCAGC<br>AAAAACCAGGGAAAGCCCCTAAGCTCCTGATCTATGCTGCATCCACTTTGCAAAGT<br>GGGGTCCCATCAAGGTTCAGCGGCAGTGGATCTGGGACAGATTTCACTCTCACCA<br>TCAGCAGCCTGCAGCCTGAAGATTTTGCAACTTATTACTGTCAACACCTTAATAGTT<br>ACCCTCCGGGGTACACTTTTGGCCAGGGGACCAAGCTGGAGATCAAA |
| P5A-1D2 HCDR1 | 236 | GFIVSSNY |
| P5A-1D2 HCDR2 | 237 | IYSGGST |
| P5A-1D2 HCDR3 | 238 | ARALQVGATSDYFDY |
| P5A-1D2 LCDR1 | 239 | SSNIGAGYD |
| P5A-1D2 LCDR2 | 240 | GNS |
| P5A-1D2 LCDR3 | 241 | QSCDSSLSVVV |
| P5A-1D2 VH | 242 | EVQLVESGGGLIQPGGSLRLSCAASGFIVSSNYMSWVRQAPGKGLEWVSIIYSGGST<br>YYADSVKGRFTISRDNSNNTLYLQMNSLRAEDTAVYYCARALQVGATSDYFDYWGQ<br>GTLVTVSS |
| P5A-1D2 VL | 243 | QSVLTQPPSVSGAPGQRVTISCTGSSSNIGAGYDVHWYQQLPGTAPKLLIYGNSNRP<br>SGVPDRFSGSKSGTSASLAITGLQAEDETDYYCQSCDSSLSVVVFGGGTKLTVL |
| P5A-1D2 VHnu | 244 | GAGGTGCAGCTGGTGGAGTCTGGAGGAGGCTTGATCCAGCCTGGGGGGTCCCTG<br>AGACTCTCCTGTGCAGCCTCTGGGTTCATCGTCAGTAGCAACTACATGAGCTGGGT<br>CCGCCAGGCTCCAGGGAAGGGGCTGGAGTGGGTCTCAATTATTTATAGCGGTGGT<br>AGCACATACTACGCAGACTCCGTGAAGGGCCGATTCACCATCTCCAGAGACAATTC<br>CAACAACACGCTGTATCTTCAAATGAACAGCCTGAGAGCCGAGGACACGGCCGTA<br>TATTACTGTGCGAGAGCCCTCCAGGTGGGAGCTACTTCGGACTACTTTGACTACTG<br>GGGCCAGGGAACCCTGGTCACCGTCTCCTCA |
| P5A-1D2 VLnu | 245 | CAGTCTGTGCTGACGCAGCCGCCCTCAGTGTCTGGGGCCCCAGGGCAGAGGGTC<br>ACCATCTCCTGCACTGGGAGCAGCTCCAACATCGGGGCAGGTTATGATGTACACTG<br>GTACCAGCAACTTCCAGGAACAGCCCCCAAACTCCTCATCTATGGTAACAGCAATC<br>GGCCCTCAGGGGTCCCTGACCGATTCTCTGGCTCCAAGTCTGGCACCTCAGCCTCC<br>CTGGCCATCACTGGGCTCCAGGCTGAAGATGAGACTGATTATTACTGCCAGTCCTG<br>TGACAGCAGCCTGAGTGTTGTGGTATTCGGCGGAGGGACCAAGCTGACCGTCCTA |
| P5A-2F11 HCDR1 | 246 | GYTFTSYD |
| P5A-2F11 HCDR2 | 247 | MNPNSGNT |
| P5A-2F11 HCDR3 | 248 | ARYIVVVPAAKGFDP |
| P5A-2F11 LCDR1 | 249 | QSVLYSSNNKNY |
| P5A-2F11 LCDR2 | 250 | WAS |
| P5A-2F11 LCDR3 | 251 | QQYYSTPLT |

TABLE 11-continued

All sequences mentioned or used in the present application

| Annotation | SEQ ID NO | Sequence |
|---|---|---|
| P5A-2F11 VH | 252 | QVQLVQSGAEVKKPGASVKVSCKASGYTFTSYDINWVRQATGQGLEWMGWMNP NSGNTGYAQKFQGRVTMTRNTSISTAYMELSSLRSEDTAVYYCARYIVVVPAAKGFDP WGQGTLVTVSS |
| P5A-2F11 VL | 253 | DIVMTQSPDSLAVSLGERATINCKSSQSVLYSSNNKNYLAWYQQKPGQPPKLLIYWA STRESGVPDRFSGSGSGTDFTLTISSLQAEDVAVYYCQQYYSTPLTFGGGTKVEIK |
| P5A-2F11 VHnu | 254 | CAGGTGCAGCTGGTGCAGTCTGGGGCTGAGGTGAAGAAGCCTGGGGCCTCAGT GAAGGTCTCCTGCAAGGCTTCTGGATACACCTTCACCAGTTATGATATCAACTGGG TGCGACAGGCCACTGGACAAGGGCTTGAGTGGATGGGATGGATGAACCCTAACA GTGGTAACACAGGCTATGCACAGAAGTTCCAGGGCAGAGTCACCATGACCAGGA ACACCTCCATAAGCACAGCCTACATGGAGCTGAGCAGCCTGAGATCTGAGGACAC GGCCGTGTATTACTGTGCGAGATATATTGTAGTAGTACCAGCTGCAAAAGGGTTCG ACCCCTGGGGCCAGGGAACCCTGGTCACCGTCTCCTCA |
| P5A-2F11 VLnu | 255 | GACATCGTGATGACCCAGTCTCCAGACTCCCTGGCTGTGTCTCTGGGCGAGAGG CCACCATCAACTGCAAGTCCAGCCAGAGTGTTTTATACAGCTCCAACAATAAGAAC TACTTAGCTTGGTACCAGCAGAAACCAGGACAGCCTCCTAAGCTGCTCATTTACTG GGCATCTACCCGGGAATCCGGGGTCCCTGACCGATTCAGTGGCAGCGGGTCTGG GACAGATTTCACTCTCACCATCAGCAGCCTGCAGGCTGAAGATGTGGCAGTTTATT ACTGTCAGCAATATTATAGTACTCCTCTCACTTTCGGCGGAGGGACCAAGGTGGAG ATCAAA |
| P5A-2E1 HCDR1 | 256 | GYSFTSYW |
| P5A-2E1 HCDR2 | 257 | IYPGDSDT |
| P5A-2E1 HCDR3 | 258 | AQTSVTRNWFDP |
| P5A-2E1 LCDR1 | 259 | NIGSKS |
| P5A-2E1 LCDR2 | 260 | YDS |
| P5A-2E1 LCDR3 | 261 | QVWDSSSDHVV |
| P5A-2E1 VH | 262 | EVQLVQSGAEVKKPGESLKISCKGSGYSFTSYWIGWVRQMPGKGLEWMGIIYPGDS DTRYSPSFQGQVTISADKSISTAYLQWSSLKASDTAMYYCAQTSVTRNWFDPWGQG TLVTVSS |
| P5A-2E1 VL | 263 | SYVLTQPPSVSVAPGKTARITCGGNNIGSKSVHWYQQKPGQAPVLVIYYDSDRPSGIP ERFSGSNSGNTATLTISRVEAGDEADYYCQVWDSSSDHVVFGGGTKLTVL |
| P5A-2E1 VHnu | 264 | GAGGTGCAGCTGGTGCAGTCTGGAGCAGAGGTGAAAAAGCCCGGGGAGTCTCT GAAGATCTCCTGTAAGGGTTCTGGATACAGCTTTACCAGCTACTGGATCGGCTGGG TGCGCCAGATGCCCGGGAAAGGCCTGGAGTGGATGGGGATCATCTATCCTGGTGA CTCTGATACCAGATACAGCCCGTCCTTCCAAGGCCAGGTCACCATCTCAGCCGACA AGTCCATCAGCACCGCCTACCTGCAGTGGAGCAGCCTGAAGGCCTCGGACACCGC CATGTATTACTGTGCCCAGACGTCAGTGACTCGCAACTGGTTCGACCCCTGGGGCC AGGGAACCCTGGTCACCGTCTCCTCA |
| P5A-2E1 VLnu | 265 | TCCTATGTGCTGACTCAGCCACCCTCAGTGTCAGTGGCCCCAGGAAAGACGGCCA GGATTACCTGTGGGGGAAACAACATTGGAAGTAAAAGTGTGCACTGGTACCAGCA GAAGCCAGGCCAGGCCCCTGTGCTGGTCATCTATTATGATAGCGACCGGCCCTCAG GGATCCCTGAGCGATTCTCTGGCTCCAACTCTGGGAACACGGCCACCCTGACCATC AGCAGGGTCGAAGCCGGGGATGAGGCCGACTATTACTGTCAGGTGTGGGATAGT AGTAGTGATCATGTGGTATTCGGCGGAGGGACCAAGCTGACCGTCCTA |
| P5A-1C8 HCDR1 | 266 | GYTFTSYY |
| P5A-1C8 HCDR2 | 267 | INPSGGST |
| P5A-1C8 HCDR3 | 268 | ARSARDYYDSSGYYYRAEYFQH |
| P5A-1C8 LCDR1 | 269 | QDISNY |
| P5A-1C8 LCDR2 | 270 | DAS |
| P5A-1C8 LCDR3 | 271 | QQYDNLPSIT |
| P5A-1C8 VH | 272 | QVQLVQSGAEVIKKPGASVIKVSCKASGYTFTSYYMHWVRQAPGQGLEWMGIINPS GGSTSYAQKFQGRVTMTRDTSTSTVYMELSSLRSEDTAVYYCARSARDYYDSSGYYYR AEYFQHWGQGTLVTVSS |
| P5A-1C8 VL | 273 | DIQMTQSPSSLSASVGDRVTITCQASQDISNYLNWYQQKPGKAPKLLIYDASNLETG VPSRFSGSGSGTDFTFTISSLQPEDIATYYCQQYDNLPSITFGQGTRLEIK |

TABLE 11-continued

All sequences mentioned or used in the present application

| Annotation | SEQ ID NO | Sequence |
|---|---|---|
| P5A-1C8 VHnu | 274 | CAGGTGCAGCTGGTGCAGTCTGGGGCTGAGGTGAAGAAGCCTGGGGCCTCAGT<br>GAAGGTTTCCTGCAAGGCATCTGGATACACCTTCACCAGCTACTATATGCACTGGG<br>TGCGACAGGCCCCTGGACAAGGGCTTGAGTGGATGGGAATAATCAACCCTAGTG<br>GTGGTAGCACAAGCTACGCACAGAAGTTCCAGGGCAGAGTCACCATGACCAGGG<br>ACACGTCCACGAGCACAGTCTACATGGAGCTGAGCAGCCTGAGATCTGAGGACAC<br>GGCCGTGTATTACTGTGCGAGGTCGGCCCGGGATTACTATGATAGTAGTGGTTATT<br>ACTACCGCGCTGAATACTTCCAGCACTGGGGCCAGGGCACCCTGGTCACCGTCTC<br>CTCA |
| P5A-1C8 VLnu | 275 | GACATCCAGATGACCCAGTCTCCATCCTCCCTGTCTGCATCTGTAGGAGACAGAGT<br>CACCATCACTTGCCAGGCGAGTCAGGACATTAGCAACTATTTAAATTGGTATCAGC<br>AGAAACCAGGGAAAGCCCCTAAGCTCCTGATCTACGATGCATCCAATTTGGAAAC<br>AGGGGTCCCATCAAGGTTCAGTGGAAGTGGATCTGGGACAGATTTTACTTTCACC<br>ATCAGCAGCCTGCAGCCTGAAGATATTGCAACATATTACTGTCAACAGTATGATAAT<br>CTCCCCTCTATCACCTTCGGCCAAGGGACACGACTGGAGATTAAA |
| P1A-1C10 HCDR1 | 276 | GGTSSFYD |
| P1A-1C10 HCDR2 | 277 | IIPRLDIA |
| P1A-1C10 HCDR3 | 278 | ARGRPGSEWAYGPFDL |
| P1A-1C10 KCDR1 | 279 | QSSRAW |
| P1A-1C10 KCDR2 | 280 | KAS |
| P1A-1C10 KCDR3 | 281 | HQYNSSPFT |
| P1A-1C10 VH | 282 | QVQLVQSGAEVKNPGSSVKVSCKAGGGTSSFYDINWVRQAPGQGLEWIGKIIPRLDI<br>ADYAQKSQGRVTITADKSTSTVYLELSSLKSDDTAVYFCARGRPGSEWAYGPFDLWG<br>QGTLVTVSS |
| P1A-1C10 VL | 283 | DIQMTQSPSTLSASVGDRVTITCRASQSSRAWLAWYQQKPGKAPKLLISKASSLESG<br>VPSRFSGSGYGTEFTLTISSLQPDDSATYYCHQYNSSPFTFGPGTKVQIK |
| P1A-1C10 VHnu | 284 | CAGGTGCAGCTGGTGCAGTCTGGGGCTGAGGTGAAGAACCCGGGGTCCTCGGT<br>GAAGGTCTCCTGTAAGGCTGGTGGAGGCACCTCCAGTTTCTATGATATCAACTGGG<br>TGCGACAGGCCCCTGGACAAGGGCTTGAGTGGATAGGAAAAATCATCCCTAGGCT<br>TGATATAGCAGACTACGCACAGAAGTCCCAGGGCAGAGTCACGATTACCGCGGAC<br>AAATCCACGAGTACAGTATACTTGGAATTGAGCAGCCTGAAGTCAGACGACACGG<br>CCGTGTATTTCTGTGCGAGAGGTCGGCCGGGTTCGGAGTGGGCGTATGGCCCATT<br>TGACCTCTGGGGCCAGGGAACCCTGGTCACCGTCTCCTCA |
| P1A-1C10 VLnu | 285 | GACATCCAGATGACCCAGTCTCCTTCCACCCTGTCTGCATCTGTAGGAGACAGAGT<br>CACCATCACTTGCCGGGCCAGTCAGAGTTCTAGGGCCTGGTTGGCCTGGTATCAG<br>CAGAAACCAGGGAAAGCCCCTAAACTCCTGATCTCTAAGGCGTCTAGTTTAGAAA<br>GTGGGGTCCCATCAAGGTTCAGCGGCAGTGGATATGGGACAGAATTCACTCTCAC<br>CATCAGCAGCCTGCAGCCTGATGATTCTGCAACTTATTACTGCCACCAGTATAACAG<br>TAGCCCATTCACTTTCGGCCCTGGGACCAAAGTGCAGATCAAA |
| P4A-1H6 HCDR1 | 286 | GFTFSSYG |
| P4A-1H6 HCDR2 | 287 | ISDDGSNQ |
| P4A-1H6 HCDR3 | 288 | AKRGGYCSTTSCLLRWVYFDF |
| P4A-1H6 LCDR1 | 289 | QSISSY |
| P4A-1H6 LCDR2 | 290 | AAS |
| P4A-1H6 LCDR3 | 291 | QQSYNTPT |
| P4A-1H6 VH | 292 | QVQLVESGGGVVQPGRSLRLSCAASGFTFSSYGMHWVRQSPGKGLEWVAVISDDG<br>SNQYYADSVKGRFTISRDNSKNTLYLQMNSLRVEDTAVYYCAKRGGYCSTTSCLLRWV<br>YFDFWGQGTLATVSS |
| P4A-1H6 VL | 293 | DIQMTQSPSSLSASVGDRVTITCRASQSISSYLHWYQQKPGKAPNLLIYAASSLQSGV<br>PSRFSGSGSGTDFTLTISSLQPEDFATYYCQQSYNTPTFGPGTKVDIK |
| P4A-1H6 VHnu | 294 | CAGGTGCAGCTGGTGGAGTCTGGGGGAGGCGTGGTCCAGCCTGGGAGGTCCCT<br>GAGACTCTCCTGTGCAGCCTCTGGATTCACCTTCAGTAGCTATGGCATGCACTGGG<br>TCCGCCAGTCTCCAGGCAAGGGGCTGGAGTGGGTGGCAGTTATATCAGATGATGG<br>AAGTAATCAATACTATGCAGACTCCGTGAAGGGCCGATTCACCATCTCCAGAGACA<br>ATTCCAAGAACACGCTGTATCTGCAAATGAACAGCCTGAGAGTTGAGGACACGGC |

TABLE 11-continued

All sequences mentioned or used in the present application

| Annotation | SEQ ID NO | Sequence |
|---|---|---|
| | | TGTGTATTACTGTGCGAAAAGGGGCGGATATTGTAGTACTACCAGCTGCCTCCTTA<br>GGTGGGTCTACTTTGACTTCTGGGGCCAGGGAACCCTGGCCACCGTCTCCTCA |
| P4A-1H6 VInu | 295 | GACATCCAGATGACCCAGTCTCCATCCTCCCTGTCTGCATCTGTAGGAGACAGAGT<br>CACCATCACTTGCCGGGCAAGTCAGAGCATTAGCAGCTATTTACATTGGTATCAGC<br>AAAAACCAGGGAAAGCCCCTAACCTCCTGATCTATGCTGCATCCAGTTTGCAAAGT<br>GGGGTCCCATCAAGGTTCAGTGGCAGTGGATCTGGGACAGATTTCACTCTCACCA<br>TCAGCAGTCTGCAACCTGAAGACTTTGCAACTTACTACTGTCAACAGAGTTACAAT<br>ACCCCTACTTTCGGCCCTGGGACCAAAGTGGATATCAAA |
| P4B-1F4 HCDR1 | 296 | GFTFSSYG |
| P4B-1F4 HCDR2 | 297 | ISYDGSNK |
| P4B-1F4 HCDR3 | 298 | AKGPRYSSSWYISLYYYYGMDV |
| P4B-1F4 LCDR1 | 299 | QSLVYSDGNTY |
| P4B-1F4 LCDR2 | 300 | KVS |
| P4B-1F4 LCDR3 | 301 | MQATHWPLYT |
| P4B-1F4 VH | 302 | QVQLVESGGGVVQPGRSLRLSCAASGFTFSSYGMHWVRQAPGKGLEWVAVISYDG<br>SNKYYADSVKGRFTISRDNSKNTLYLQINSLRAEDTAVYYCAKGPRYSSSWYISLYYYYG<br>MDVWGQGTTVTVSS |
| P4B-1F4 VL | 303 | DVVMTQSPLSLPVTLGQPASISCRSSQSLVYSDGNTYLNWFQQRPGQSPRRLIYKVS<br>NRDSGVPDRFSGSGSGTDFTLKISRVEAEDVGVYYCMQATHWPLYTFGQGTKLEIK |
| P4B-1F4 VHnu | 304 | CAGGTGCAGCTGGTGGAGTCTGGGGGAGGCGTGGTCCAGCCTGGGAGGTCCCT<br>GAGACTCTCCTGTGCAGCCTCTGGATTCACCTTCAGTAGCTATGGCATGCACTGGG<br>TCCGCCAGGCTCCAGGCAAGGGGCTGGAGTGGGTGGCAGTTATATCATATGATGG<br>AAGTAATAAATACTATGCAGACTCCGTGAAGGGCCGATTCACCATCTCCAGAGACA<br>ATTCCAAGAACACGCTGTATCTGCAAATCAACAGCCTGAGAGCTGAGGACACGGC<br>TGTGTATTACTGTGCGAAAGGGCCTCGGTATAGCAGCAGCTGGTACATAAGCCTTT<br>ACTACTACTACGGTATGGACGTCTGGGGCCAAGGGACCACGGTCACCGTCTCCTC<br>A |
| P4B-1F4 VInu | 305 | GATGTTGTGATGACTCAGTCTCCACTCTCCCTGCCCGTCACCCTTGGACAGCCGGC<br>CTCCATCTCCTGCAGGTCTAGTCAAAGCCTCGTATACAGTGATGGAAACACCTACTT<br>GAATTGGTTTCAGCAGAGGCCAGGCCAATCTCCAAGGCGCCTAATTTATAAGGTTT<br>CTAACCGGGACTCTGGGGTCCCAGACAGATTCAGCGGCAGTGGGTCAGGCACTG<br>ATTTCACACTGAAAATCAGCAGGGTGGAGGCTGAGGATGTTGGGGTTTATTACTG<br>CATGCAAGCTACACACTGGCCCCTGTACACTTTTGGCCAGGGGACCAAGCTGGAG<br>ATCAAA |
| P5A-1B6 HCDR1 | 306 | GFTFSSYA |
| P5A-1B6 HCDR2 | 307 | ISYDGSNK |
| P5A-1B6 HCDR3 | 308 | ARDGQAITMVQGVIGPPFDY |
| P5A-1B6 LCDR1 | 309 | QDISNY |
| P5A-1B6 LCDR2 | 310 | DAS |
| P5A-1B6 LCDR3 | 311 | QQYDNLPYT |
| P5A-1B6 VH | 312 | QVQLVESGGGVVQPGRSLRLSCAASGFTFSSYAMHWVRQAPGKGLEWVAVISYDG<br>SNKYYADSVKGRFTISRDNSKNTLYLQMNSLRAEDTAVYYCARDGQAITMVQGVIGP<br>PFDYWGQGTLVTVSS |
| P5A-1B6 VL | 313 | DIQMTQSPSSLSASVGDRVTITCQASQDISNYLNWYQQKPGKAPKLLIYDASNLETG<br>VPSRFSGSGSGTDFTFTISSLQPEDIATYYCQQYDNLPYTFGQGTKLEIK |
| P5A-1B6 VHnu | 314 | CAGGTGCAGCTGGTGGAGTCTGGGGGAGGCGTGGTCCAGCCTGGGAGGTCCCT<br>GAGACTCTCCTGTGCAGCCTCTGGATTCACCTTCAGTAGCTATGCTATGCACTGGGT<br>CCGCCAGGCTCCAGGCAAGGGGCTGGAGTGGGTGGCAGTTATATCATATGATGGA<br>AGTAATAAATACTACGCAGACTCCGTGAAGGGCCGATTCACCATCTCCAGAGACAA<br>TTCCAAGAACACGCTGTATCTGCAAATGAACAGCCTGAGAGCTGAGGACACGGCT<br>GTGTATTACTGTGCGAGAGATGGACAGGCTATTACTATGGTTCAGGGAGTTATCGG<br>CCCACCCTTTGACTACTGGGGCCAGGGAACCCTGGTCACCGTCTCCTCA |
| P5A-1B6 VInu | 315 | GACATCCAGATGACCCAGTCTCCATCCTCCCTGTCTGCATCTGTAGGAGACAGAGT<br>CACCATCACTTGCCAGGCGAGTCAGGACATTAGCAACTATTTAAATTGGTATCAGC |

TABLE 11-continued

All sequences mentioned or used in the present application

| Annotation | SEQ ID NO | Sequence |
|---|---|---|
| | | AGAAACCAGGGAAAGCCCCTAAGCTCCTGATCTACGATGCATCCAATTTGGAAAC<br>AGGGGTCCCATCAAGGTTCAGTGGAAGTGGATCTGGGACAGATTTTACTTTCACC<br>ATCAGCAGCCTGCAGCCTGAAGATATTGCAACATATTACTGTCAACAGTATGATAAT<br>CTCCCGTACACTTTTGGCCAGGGGACCAAGCTGGAGATCAAA |
| P5A-1B8 HCDR1 | 316 | GFTVSSNY |
| P5A-1B8 HCDR2 | 317 | IYPGGST |
| P5A-1B8 HCDR3 | 318 | ARETLAFDY |
| P5A-1B8 LCDR1 | 319 | QGISSY |
| P5A-1B8 LCDR2 | 320 | AAS |
| P5A-1B8 LCDR3 | 321 | QQLNSYPPA |
| P5A-1B8 VH | 322 | EVQLVESGGGLIQPGGSLRLSCAASGFTVSSNYMSWVRQAPGKGLEWVSVIYPGGS<br>TFYADSVKGRFTISRDNSKNTLYLQMNSLRAEDTAVYYCARETLAFDYWGQGTLVTVS<br>S |
| P5A-1B8 VL | 323 | DIQLTQSPSFLSASVGDRVTITCRASQGISSYLAWYQQKPGKAPKLLIYAASTLQSGVP<br>SRFSGSGSGTEFTLTISSLQPEDFATYYCQQLNSYPPAFGGGTKVEIK |
| P5A-1B8 VHnu | 324 | GAGGTGCAGCTGGTGGAGTCTGGAGGAGGCTTGATCCAGCCTGGGGGGTCCCTG<br>AGACTCTCCTGTGCAGCCTCTGGGTTCACCGTCAGTAGCAACTACATGAGCTGGGT<br>CCGCCAGGCTCCAGGGAAGGGGCTGGAGTGGGTCTCAGTTATTTATCCCGGTGGT<br>AGCACATTCTACGCAGACTCCGTGAAGGGCCGATTCACCATCTCCAGAGACAATTC<br>CAAGAACACCCTGTATCTTCAAATGAACAGCCTGAGAGCCGAGGACACGGCCGTG<br>TATTACTGTGCGAGAGAGACCCTAGCCTTTGACTACTGGGGCCAGGGAACCCTGG<br>TCACCGTCTCCTCA |
| P5A-1B8 VLnu | 325 | GACATCCAGTTGACCCAGTCTCCATCCTTCCTGTCTGCATCTGTAGGAGACAGAGT<br>CACCATCACTTGCCGGGCCAGTCAGGGCATTAGCAGTTATTTAGCCTGGTATCAGC<br>AAAAACCAGGGAAAGCCCCTAAGCTCCTGATCTATGCTGCATCCACTTTGCAAAGT<br>GGGGTCCCATCAAGGTTCAGCGGCAGTGGATCTGGGACAGAATTCACTCTCACAA<br>TCAGCAGCCTGCAGCCTGAAGATTTTGCAACTTATTACTGTCAACAGCTTAATAGTT<br>ACCCTCCAGCTTTCGGCGGAGGGACCAAGGTGGAGATCAAA |
| P5A-1B9 HCDR1 | 326 | GGSISSYY |
| P5A-1B9 HCDR2 | 327 | ISYSGST |
| P5A-1B9 HCDR3 | 328 | ASNGQYYDILTGQPPDYWYFDL |
| P5A-1B9 LCDR1 | 329 | QSVLYSSNNKNY |
| P5A-1B9 LCDR2 | 330 | WAS |
| P5A-1B9 LCDR3 | 331 | QQYYSTPLT |
| P5A-1B9 VH | 332 | QVQLQESGPGLVKPSETLSLTCTVSGGSISSYYWSWIRQPPGKGLEWIGYISYSGSTNY<br>NPSLKSRVTISLDTSKNQFSLKLSSVTAADTAVYYCASNGQYYDILTGQPPDYWYFDL<br>WGRGTLVTVSS |
| P5A-1B9 VL | 333 | DIVMTQSPDSLAVSLGERATINCKSSQSVLYSSNNKNYLAWYQQKPGQPPKLLIYWA<br>STRESGVPDRFSGSGSGTDFTLTISSLQAEDVAVYYCQQYYSTPLTFGGGTKVEIK |
| P5A-1B9 VHnu | 334 | CAGGTGCAGCTGCAGGAGTCGGGCCCAGGACTGGTGAAGCCTTCGGAGACCCTG<br>TCCCTCACCTGCACTGTCTCTGGTGGCTCCATCAGTAGTTACTACTGGAGCTGGATC<br>CGGCAGCCCCCAGGGAAGGGACTGGAGTGGATTGGGTATATCTCTTACAGTGGG<br>AGCACCAACTACAACCCCTCCCTCAAGAGTCGAGTCACCATATCACTAGACACGTC<br>CAAGAACCAGTTCTCCCTGAAGCTGAGCTCTGTGACCGCTGCGGACACGGCCGTG<br>TATTACTGTGCGAGCAACGGCCAGTATTACGATATTTTGACTGGTCAACCTCCTGAC<br>TACTGGTACTTCGATCTCTGGGGCCGTGGCACCCTGGTCACTGTCTCCTCA |
| P5A-1B9 VLnu | 335 | GACATCGTGATGACCCAGTCTCCAGACTCCCTGGCTGTGTCTCTGGGCGAGAGGG<br>CCACCATCAACTGCAAGTCCAGCCAGAGTGTTTTATACAGCTCCAACAATAAGAAC<br>TACTTAGCTTGGTACCAGCAGAAACCAGGACAGCCTCCTAAGCTGCTCATTTACTG<br>GGCATCTACCCGGGAATCCGGGGTCCCTGACCGATTCAGTGGCAGCGGGTCTGG<br>GACAGATTTCACTCTCACCATCAGCAGCCTGCAGGCTGAAGATGTGGCAGTTTATT<br>ACTGTCAGCAATATTATAGTACTCCGCTCACTTTCGGCGGAGGGACCAAGGTGGA<br>GATCAAA |

TABLE 11-continued

All sequences mentioned or used in the present application

| Annotation | SEQ ID NO | Sequence |
|---|---|---|
| P5A-1D1 HCDR1 | 336 | GLTVSSNY |
| P5A-1D1 HCDR2 | 337 | IYSGGST |
| P5A-1D1 HCDR3 | 338 | ARDLYYYGMDV |
| P5A-1D1 LCDR1 | 339 | QGISSY |
| P5A-1D1 LCDR2 | 340 | AAS |
| P5A-1D1 LCDR3 | 341 | QQLNSYPT |
| P5A-1D1 VH | 342 | EVQLVESGGGLIQPGGSLRLSCAASGLTVSSNYMSWVRQAPGKGLEWVSVIYSGGS TYYADSVKGRFTISRDNSKNTLYLQMNSLRAEDTAVYYCARDLYYYGMDVWGQGTT VTVST |
| P5A-1D1 VL | 343 | DIQLTQSPSFLSASVGDRVTITCRASQGISSYLAWYQQKPGKAPKLLIYAASTLQSGVP SRFSGSGSGTDFTLTISSLQPEDFATYYCQQLNSYPTFGQGTRLEIK |
| P5A-1D1 VHnu | 344 | GAGGTGCAGCTGGTGGAGTCTGGAGGAGGCTTGATCCAGCCTGGGGGGTCCCTG AGACTCTCCTGTGCAGCCTCTGGGCTCACCGTCAGTAGCAACTACATGAGCTGGGT CCGCCAGGCTCCAGGGAAGGGGCTGGAGTGGGTCTCAGTTATTTATAGCGGTGG TAGCACATACTACGCAGACTCCGTGAAGGGCCGATTCACCATCTCCAGAGACAATT CCAAGAACACGCTGTATCTTCAAATGAACAGCCTGAGAGCCGAGGACACGGCCGT GTATTACTGTGCGAGAGATTTGTACTACTACGGTATGGACGTCTGGGGCCAAGGG ACCACGGTCACCGTCTCCACA |
| P5A-1D1 VLnu | 345 | GACATCCAGTTGACCCAGTCTCCATCCTTCCTGTCTGCATCTGTAGGAGACAGAGT CACCATCACTTGCCGGGCCAGTCAGGGCATTAGCAGTTATTTAGCCTGGTATCAGC AAAAACCAGGGAAAGCCCCTAAGCTCCTGATCTATGCTGCATCCACTTTGCAAAGT GGGGTCCCATCAAGGTTCAGCGGCAGTGGATCTGGGACAGATTTCACTCTCACCA TCAGCAGCCTGCAGCCTGAAGATTTTGCAACTTATTACTGTCAACAGCTTAATAGTT ACCCTACCTTCGGCCAAGGGACACGACTGGAGATTAAA |
| P5A-1D10 HCDR1 | 346 | QFTFSDYS |
| P5A-1D10 HCDR2 | 347 | ISQSGSTI |
| P5A-1D10 HCDR3 | 348 | ARGVSPSYVWGSYRSLYHFDY |
| P5A-1D10 LCDR1 | 349 | SSDVGGYNY |
| P5A-1D10 LCDR2 | 350 | DVS |
| P5A-1D10 LCDR3 | 351 | SSFTSSTTVVV |
| P5A-1D10 VH | 352 | QVQLVESGGGLVKPGGSLRLSCAASQFTFSDYSMTWIRQAPGKGLEWVSYISQSGST IYYADSVKGRFTISRDNAKNSLYLQMNSLRAEDTAVYYCARGVSPSYVWGSYRSLYHF DYWGQGTLVTVSS |
| P5A-1D10 VL | 353 | QSALTQPASVSGSPGQSITISCTGTSSDVGGYNYVSWYQQHPGKAPKLMIYDVSNRP SGVSNRFSASKSGNTASLTISGLQAEDEADYYCSSFTSSTTVVVFGGGTKLTVL |
| P5A-1D10 VHnu | 354 | CAGGTGCAGCTGGTGGAGTCTGGGGGAGGCTTGGTCAAGCCTGGAGGGTCCCT GAGACTCTCCTGTGCAGCCTCTCAATTCACCTTCAGTGACTACTCCATGACCTGGAT CCGCCAGGCTCCAGGGAAGGGGCTGGAGTGGGTTTCATACATTAGTCAAAGTGG TAGTACCATATACTACGCAGACTCTGTGAAGGGCCGATTCACCATCTCCAGGGACA ACGCCAAGAACTCACTGTATCTGCAAATGAACAGCCTGAGAGCCGAGGACACGG CCGTGTATTACTGTGCGAGAGGTGTCAGCCCATCCTACGTTTGGGGGAGTTATCGT TCCTTGTACCACTTTGACTACTGGGGCCAGGGAACCCTGGTCACCGTCTCCTCA |
| P5A-1D10 VLnu | 355 | CAGTCTGCCCTGACTCAGCCTGCCTCCGTGTCTGGGTCTCCTGGACAGTCGATCAC CATCTCCTGCACTGGAACCAGCAGTGACGTTGGTGGTTATAACTATGTCTCCTGGTA CCAACAACACCCAGGCAAAGCCCCCAAACTCATGATTTATGATGTCAGTAATCGGC CCTCAGGGGTTTCTAATCGCTTCTCTGCCTCCAAGTCTGGCAACACGGCCTCCCTG ACCATCTCTGGGCTCCAGGCTGAGGACGAGGCTGATTATTACTGCAGCTCATTTAC AAGCAGCACCACTGTCGTGGTATTCGGCGGAGGGACCAAGCTGACCGTCCTA |
| P5A-2D11 HCDR1 | 356 | GYSFTSYW |
| P5A-2D11 HCDR2 | 357 | IYPGDSDT |
| P5A-2D11 HCDR3 | 358 | ARRDSTYGGNTDY |
| P5A-2D11 LCDR1 | 359 | SSNIGSNT |

TABLE 11-continued

All sequences mentioned or used in the present application

| Annotation | SEQ ID NO | Sequence |
|---|---|---|
| P5A-2D11 LCDR2 | 360 | SNN |
| P5A-2D11 LCDR3 | 361 | AAWDDSLNGVV |
| P5A-2D11 VH | 362 | EVQLVQSGAEVKKPGESLKISCKGSYSFTSYWIGWVRQMPGKGLEWMGIIYPGDSDTRYSPSFQGQVTISADKSISTAYLQWSSLKASDTAMYYCARRDSTYGGNTDYWGQGTLVTVSS |
| P5A-2D11 VL | 363 | QSVLTQPPSASGTPGQRVTISCSGSSSNIGSNTVNWYQQLPGTAPKLLIYSNNQRPSGVPDRFSGSKSGTSASLAISGLQSEDEADYYCAAWDDSLNGVVFGGGTKLTVL |
| P5A-2D11 VHnu | 364 | GAGGTGCAGCTGGTGCAGTCTGGAGCAGAGGTGAAAAAGCCCGGGGAGTCTCTGAAGATCTCCTGTAAGGGTTCTGGATACAGCTTTACCAGCTACTGGATCGGCTGGGTGCGCCAGATGCCCGGGAAAGGCCTGGAGTGGATGGGGATCATCTATCCTGGTGACTCTGATACCAGATACAGCCCGTCCTTCCAAGGCCAGGTCACCATCTCAGCCGACAAGTCCATCAGCACCGCCTACCTGCAGTGGAGCAGCCTGAAGGCCTCGGACACCGCCATGTATTACTGTGCGAGACGGGATTCGACCTACGGTGGTAACACTGACTACTGGGGCCAGGGAACCCTGGTCACCGTCTCCTCA |
| P5A-2D11 VLnu | 365 | CAGTCTGTGCTGACTCAGCCACCCTCAGCGTCTGGGACCCCCGGGCAGAGGGTCACCATCTCTTGTTCTGGAAGCAGCTCCAACATCGGAAGTAATACTGTAAACTGGTACCAGCAGCTCCCAGGAACGGCCCCCAAACTCCTCATCTATAGTAATAATCAGCGGCCCTCAGGGGTCCCTGACCGATTCTCTGGCTCCAAGTCTGGCACCTCAGCCTCCCTGGCCATCAGTGGGCTCCAGTCTGAGGATGAGGCTGATTATTACTGTGCAGCATGGGATGACAGCCTGAATGGTGTGGTATTCGGCGGAGGGACCAAGCTGACCGTCCTA |
| P5A-2G9 HCDR1 | 366 | GFTFSSYG |
| P5A-2G9 HCDR2 | 367 | IWYDGSNK |
| P5A-2G9 HCDR3 | 368 | ARWFHTGGYFDY |
| P5A-2G9 LCDR1 | 369 | SDINVSSYN |
| P5A-2G9 LCDR2 | 370 | YYSDSDK |
| P5A-2G9 LCDR3 | 371 | MIWPSNALYV |
| P5A-2G9 VH | 372 | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARWFHTGGYFDYWGQGTLVTVSS |
| P5A-2G9 VL | 373 | QPVLTQPPSSSASPGESARLTCTLPSDINVSSYNIYWYQQKPGSPPRYLLYYYSDSDKGQGSGVPSRFSGSKDASANTGILLISGLQSEDEADYYCMIWPSNALYVFGTGTKVTVL |
| P5A-2G9 VHnu | 374 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGATGGTTCCACACGGGGGGGTACTTTGACTACTGGGGCCAGGGAACCCTGGTCACCGTCTCCTCA |
| P5A-2G9 VLnu | 375 | CAGCCTGTGCTGACTCAGCCACCTTCCTCCTCCGCATCTCCTGGAGAATCCGCCAGACTCACCTGCACCTTGCCCAGTGACATCAATGTTAGTAGCTACAACATATACTGGTACCAGCAGAAGCCAGGGAGCCCTCCCAGGTATCTCCTGTACTACTACTCAGACTCAGATAAGGGCCAGGGCTCTGGAGTCCCCAGCCGCTTCTCTGGATCCAAAGATGCTTCAGCCAATACAGGGATTTTACTCATCTCCGGGCTCCAGTCTGAGGATGAGGCTGACTATTACTGTATGATTTGGCCAAGCAATGCTCTTTATGTCTTCGGAACTGGGACCAAGGTCACCGTCCTA |
| P5A-2H3 HCDR1 | 376 | GYSFTSYW |
| P5A-2H3 HCDR2 | 377 | IYPGDSDT |
| P5A-2H3 HCDR3 | 378 | ARRDSTYGGNTDY |
| P5A-2H3 LCDR1 | 379 | SSNIGSNT |
| P5A-2H3 LCDR2 | 380 | SNN |
| P5A-2H3 LCDR3 | 381 | AAWDDSLNGVV |

TABLE 11-continued

All sequences mentioned or used in the present application

| Annotation | SEQ ID NO | Sequence |
|---|---|---|
| P5A-2H3 VH | 382 | EVQLVQSGAEVKKPGESLKISCKGSGYSFTSYWIGWVRQMPGKGLEWMGIIYPGDSDTRYSPSFQGQVTISAEKSISTAYLQWSSLKASDTAMYYCARRDSTYGGNTDYWGQGTLVTVSS |
| P5A-2H3 VL | 383 | QSVLTQPPSASGTPGQRVTISCSGSSSNIGSNTVNWYQQLPGTAPKLLIYSNNQRPSGVPDRFSGSKSGTSASLAISGLQSEDEADYYCAAWDDSLNGVVFGGGTKLTVL |
| P5A-2H3 VHnu | 384 | GAGGTGCAGCTGGTGCAGTCTGGAGCAGAGGTGAAAAAGCCCGGGGAGTCTCTGAAGATCTCCTGTAAGGGTTCTGGATACAGCTTTACCAGCTACTGGATCGGCTGGGTGCGCCAGATGCCCGGGAAAGGCCTGGAGTGGATGGGGATCATCTATCCTGGTGACTCTGATACCAGATACAGCCCGTCCTTCCAAGGCCAGGTCACCATCTCAGCCGAGAAGTCCATCAGCACCGCCTACCTGCAGTGGAGCAGCCTGAAGGCCTCGGACACCGCCATGTATTACTGTGCGAGACGGGATTCGACCTACGGTGGTAACACTGACTACTGGGGCCAGGGAACCCTGGTCACCGTCTCCTCA |
| P5A-2H3 VLnu | 385 | CAGTCTGTGCTGACTCAGCCACCCTCAGCGTCTGGGACCCCCGGGCAGAGGGTCACCATCTCTTGTTCTGGAAGCAGCTCCAACATCGGAAGTAATACTGTAAACTGGTACCAGCAGCTCCCAGGAACGGCCCCCAAACTCCTCATCTATAGTAATAATCAGCGGCCCTCAGGGGTCCCTGACCGATTCTCTGGCTCCAAGTCTGGCACCTCAGCCTCCCTGGCCATCAGTGGGCTCCAGTCTGAGGATGAGGCTGATTATTACTGTGCAGCATGGGATGACAGCCTGAATGGTGTGGTATTCGGCGGAGGGACCAAGCTGACCGTCCTA |
| P5A-3A1 HCDR1 | 386 | GFTVSSNY |
| P5A-3A1 HCDR2 | 387 | IYSGGST |
| P5A-3A1 HCDR3 | 388 | ARDYGDFYFDY |
| P5A-3A1 LCDR1 | 389 | QSVSSSY |
| P5A-3A1 LCDR2 | 390 | GAS |
| P5A-3A1 LCDR3 | 391 | QQYGSSPRT |
| P5A-3A1 VH | 392 | EVQLVESGGGLIQPGGSLRLSCAASGFTVSSNYMSWVRQAPGKGLEWVSVIYSGGSTYYADSVKGRFTISRDNSKNTLYLQMNSLRAEDTAVYYCARDYGDFYFDYWGQGTLVTVSS |
| P5A-3A1 VL | 393 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPRTFGQGTKLEIK |
| P5A-3A1 VHnu | 394 | GAGGTGCAGCTGGTGGAGTCTGGAGGAGGCTTGATCCAGCCTGGGGGGTCCCTGAGACTCTCCTGTGCAGCCTCTGGGTTCACCGTCAGTAGCAACTACATGAGCTGGGTCCGCCAGGCTCCAGGGAAGGGGCTGGAGTGGGTCTCAGTTATTTATAGCGGTGGTAGCACATACTACGCAGACTCCGTGAAGGGCCGATTCACCATCTCCAGAGACAATTCCAAGAACACGCTGTATCTTCAAATGAACAGCCTGAGAGCCGAGGACACGGCCGTGTATTACTGTGCGAGAGACTACGGTGACTTTTACTTTGACTACTGGGGCCAGGGAACCCTGGTCACCGTCTCCTCA |
| P5A-3A1 VLnu | 395 | GAAATTGTGTTGACGCAGTCTCCAGGCACCCTGTCTTTGTCTCCAGGGGAAAGAGCCACCCTCTCCTGCAGGGCCAGTCAGAGTGTTAGCAGCAGCTACTTAGCCTGGTACCAGCAGAAACCTGGCCAGGCTCCCAGGCTCCTCATCTATGGTGCATCCAGCAGGGCCACTGGCATCCCAGACAGGTTCAGTGGCAGTGGGTCTGGGACAGACTTCACTCTCACCATCAGCAGACTGGAGCCTGAAGATTTTGCAGTGTATTACTGTCAGCAGTATGGTAGCTCACCTCGCACTTTTGGCCAGGGGACCAAGCTGGAGATCAAA |
| P5A-3A6 HCDR1 | 396 | GFTFDDYA |
| P5A-3A6 HCDR2 | 397 | ISWNSGTI |
| P5A-3A6 HCDR3 | 398 | AGGGTMVRGVIAGGGTHPVDDYYGMDV |
| P5A-3A6 LCDR1 | 399 | SSDVGGYNY |
| P5A-3A6 LCDR2 | 400 | DVS |
| P5A-3A6 LCDR3 | 401 | SSYTSSSTVV |
| P5A-3A6 VH | 402 | EVQLVESGGGLVQPGRSLRLSCAASGFTFDDYAMHWVRQAPGKGLEWVSGISWNSGTIGYADSVKGRFIISRDNAKNSLYLQMNSLRAEDTALYYCAGGGTMVRGVIAGGGTHPVDDYYGMDVWGQGTTVTVSS |
| P5A-3A6 VL | 403 | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTVVFGGGTKLTVL |

TABLE 11-continued

All sequences mentioned or used in the present application

| Annotation | SEQ ID NO | Sequence |
|---|---|---|
| P5A-3A6 VHnu | 404 | GAAGTGCAGCTGGTGGAGTCTGGGGGAGGCTTGGTACAGCCTGGCAGGTCCCTG<br>AGACTCTCCTGTGCAGCCTCTGGATTCACCTTTGATGATTATGCCATGCACTGGGTC<br>CGGCAAGCTCCAGGGAAGGGCCTGGAGTGGGTCTCAGGTATTAGTTGGAATAGT<br>GGTACCATAGGCTATGCGGACTCTGTGAAGGGCCGATTCATCATCTCCAGAGACAA<br>CGCCAAGAACTCCCTGTATCTGCAAATGAACAGTCTGAGAGCTGAGGACACGGCC<br>TTGTATTACTGTGCAGGGGTGGTACTATGGTTCGGGGAGTTATTGCCGGAGGGG<br>GAACTCATCCGGTGGATGACTACTACGGTATGGACGTCTGGGGCCAAGGGACCAC<br>GGTCACCGTCTCCTCA |
| P5A-3A6 VLnu | 405 | CAGTCTGCCCTGACTCAGCCTGCCTCCGTGTCTGGGTCTCCTGGACAGTCGATCAC<br>CATCTCCTGCACTGGAACCAGCAGTGACGTTGGTGGTTATAACTATGTCTCCTGGTA<br>CCAACAACACCCAGGCAAAGCCCCCAAACTCATGATTTATGATGTCAGTAATCGGC<br>CCTCAGGGGTTTCTAATCGCTTCTCTGGCTCCAAGTCTGGCAACACGGCCTCCCTG<br>ACCATCTCTGGGCTCCAGGCTGAGGACGAGGCTGATTATTACTGCAGCTCATATAC<br>AAGCAGCAGCACTGTGGTATTCGGCGGAGGGACCAAGCTGACCGTCCTA |
| P5A-3B4 HCDR1 | 406 | GYSFTSYW |
| P5A-3B4 HCDR2 | 407 | IYPGDSDT |
| P5A-3B4 HCDR3 | 408 | ARRDSTYGGNTDY |
| P5A-3B4 LCDR1 | 409 | SSNIGSNT |
| P5A-3B4 LCDR2 | 410 | SNN |
| P5A-3B4 LCDR3 | 411 | AAWDDSLNGVV |
| P5A-3B4 VH | 412 | EVQLVQSGAEVKEPGESLKISCKGSGYSFTSYWIGWVRQMPGKGLEWMGIIYPGDS<br>DTRYSPSFQGQVTISADKSISTAYLQWSSLKASDTAMYYCARRDSTYGGNTDYWGQ<br>GTLVTVSS |
| P5A-3B4 VL | 413 | QSVLTQPPSASGTPGQRVTISCSGSSSNIGSNTVNWYQQLPGTAPKLLIYSNNQRPSG<br>VPDRFSGSKSGTSASLAISGLQSEDEADYYCAAWDDSLNGVVFGGGTKLTVL |
| P5A-3B4 VHnu | 414 | GAGGTGCAGCTGGTGCAGTCTGGAGCAGAGGTGAAAGAGCCCGGGGAGTCTCT<br>GAAGATCTCCTGTAAGGGTTCTGGATACAGCTTTACCAGCTACTGGATCGGCTGGG<br>TGCGCCAGATGCCCGGGAAAGGCCTGGAGTGGATGGGGATCATCTATCCTGGTGA<br>CTCTGATACCAGATACAGCCCGTCCTTCCAAGGCCAGGTCACCATCTCAGCCGACA<br>AGTCCATCAGCACCGCCTACCTGCAGTGGAGCAGCCTGAAGGCCTCGGACACCGC<br>CATGTATTACTGTGCGAGACGGGATTCGACCTACGGTGGTAACACTGACTACTGGG<br>GCCAGGGAACCCTGGTCACCGTCTCCTCA |
| P5A-3B4 VLnu | 415 | CAGTCTGTGCTGACTCAGCCACCCTCAGCGTCTGGGACCCCCGGGCAGAGGGTCA<br>CCATCTCTTGTTCTGGAAGCAGCTCCAACATCGGAAGTAATACTGTAAACTGGTAC<br>CAGCAGCTCCCAGGAACGGCCCCCAAACTCCTCATCTATAGTAATAATCAGCGGCC<br>CTCAGGGGTCCCTGACCGATTCTCTGGCTCCAAGTCTGGCACCTCAGCCTCCCTGG<br>CCATCAGTGGGCTCCAGTCTGAGGATGAGGCTGATTATTACTGTGCAGCATGGGAT<br>GACAGCCTGAATGGTGTGGTATTCGGCGGAGGGACCAAGCTGACCGTCCTA |
| P5A-3C12 HCDR1 | 416 | GFSLSTSGVG |
| P5A-3C12 HCDR2 | 417 | IYWDDDK |
| P5A-3C12 HCDR3 | 418 | AHSLFLTVGYSSSWSPFDY |
| P5A-3C12 LCDR1 | 419 | QSVLYSSNNKNY |
| P5A-3C12 LCDR2 | 420 | WAS |
| P5A-3C12 LCDR3 | 421 | QQYYSTPHT |
| P5A-3C12 VH | 422 | QITLKESGPTLVKPTQTLTLTCTFSGFSLSTSGVGVGWIRQPPGKALEWLALIYWDDD<br>KRYSPSLKSRLTITKDTSKNQVVLTMTNMDPVDTATYYCAHSLFLTVGYSSSWSPFDY<br>WGQGTLVTVSS |
| P5A-3C12 VL | 423 | DIVMTQSPDSLAVSLGERATINCKSSQSVLYSSNNKNYLAWYQQKPGQPPKLLIYWA<br>STRESGVPDRFSGSGSGTDFTLTISSLQAEDVAVYYCQQYYSTPHTFGQGTKLEIK |
| P5A-3C12 VHnu | 424 | CAGATCACCTTGAAGGAGTCTGGTCCTACGCTGGTGAAACCCACACAGACCCTCA<br>CGCTGACCTGCACCTTCTCTGGGTTCTCACTCAGCACTAGTGGAGTGGGTGTGGG<br>CTGGATCCGTCAGCCCCCAGGAAAGGCCCTGGAGTGGCTTGCACTCATTTATTGG<br>GATGATGATAAGCGCTACAGCCCATCTCTGAAGAGCAGGCTCACCATCACCAAGG<br>ACACCTCCAAAAACCAGGTGGTCCTTACAATGACCAACATGGACCCTGTGGACAC |

TABLE 11-continued

All sequences mentioned or used in the present application

| Annotation | SEQ ID NO | Sequence |
|---|---|---|
| | | AGCCACATATTACTGTGCACACAGTTTGTTTCTCACGGTAGGGTATAGCAGCAGCT GGTCCCCTTTTGACTACTGGGGCCAGGGAACCCTGGTCACCGTCTCCTCA |
| P5A-3C12 VInu | 425 | GACATCGTGATGACCCAGTCTCCAGACTCCCTGGCTGTGTCTCTGGGCGAGAGG CCACCATCAACTGCAAGTCCAGCCAGAGTGTTTTATACAGCTCCAACAATAAGAAC TACTTAGCTTGGTACCAGCAGAAACCAGGACAGCCTCCTAAGCTGCTCATTTACTG GGCATCTACCCGGGAATCCGGGGTCCCTGACCGATTCAGTGGCAGCGGGTCTGG GACAGATTTCACTCTCACCATCAGCAGCCTGCAGGCTGAAGATGTGGCAGTTTATT ACTGTCAGCAATATTATAGTACTCCTCACACTTTTGGCCAGGGGACCAAGCTGGAG ATCAAA |
| P22A-1D1 HCDR1 | 426 | GFTVSSNY |
| P22A-1D1 HCDR2 | 427 | IYSGGST |
| P22A-1D1 HCDR3 | 428 | ARDRDYYGMDV |
| P22A-1D1 LCDR1 | 429 | QGISSY |
| P22A-1D1 LCDR2 | 430 | AAS |
| P22A-1D1 LCDR3 | 431 | LHLNSYRT |
| P22A-1D1 VH | 432 | EVQLVESGGGLIQPGGSLRLSCAASGFTVSSNYMSWVRQAPGKGLEWVSVIYSGGS TYYADSVKGRFTISRDNSKNTLYLQMNSLRAEDTAVYYCARDRDYYGMDVWGQGTT VTVSS |
| P22A-1D1 VL | 433 | DIQLTQSPSFLSASVGDRVTITCRASQGISSYLAWYQQKPGKAPKLLIYAASTLQSGVP SRFSGSGSGTEFTLTISSLQPEDFATYYCLHLNSYRTFGLGTKVEIK |
| P22A-1D1 VHnu | 434 | GAGGTGCAGCTGGTGGAGTCTGGAGGAGGCTTGATCCAGCCTGGGGGGTCCCTG AGACTCTCCTGTGCAGCCTCTGGGTTCACCGTCAGTAGCAACTACATGAGCTGGGT CCGCCAGGCTCCAGGGAAGGGGCTGGAGTGGGTCTCAGTTATTTATAGCGGTGG TAGCACATACTACGCAGACTCCGTGAAGGGCCGATTCACCATCTCCAGAGACAATT CCAAGAACACGCTGTATCTTCAAATGAACAGCCTGAGAGCCGAGGACACGGCCGT GTATTACTGTGCGAGAGATCGAGACTACTACGGTATGGACGTCTGGGGCCAAGGG ACCACGGTCACCGTCTCCTCA |
| P22A-1D1 VInu | 435 | GACATCCAGTTGACCCAGTCTCCATCCTTCCTGTCTGCATCTGTAGGAGACAGAGT CACCATCACTTGCCGGGCCAGTCAGGGCATTAGCAGTTATTTAGCCTGGTATCAGC AAAAACCAGGGAAAGCCCCTAAGCTCCTGATCTATGCTGCATCCACTTTGCAAAGT GGGGTCCCATCAAGGTTTAGCGGCAGTGGATCTGGGACAGAATTCACTCTCACAA TCAGCAGCCTGCAGCCTGAAGATTTTGCAACTTATTACTGTCTACACCTTAATAGTT ACAGGACGTTCGGCCTAGGGACCAAGGTGGAAATCAAA |

What is claimed is:

1. A modified antibody or an antigen-binding fragment thereof comprising at least an antigen-binding domain and a covalently linked modified human IgG constant domain, wherein the antigen-binding domain has a specific binding affinity to receptor binding domain (RBD) comprising the sequence of SEQ ID NO: 128 from the spike protein for SARS-CoV-2, wherein said modified human IgG constant domain comprises a substitution with tyrosine at amino acid residue 252, a substitution with threonine at amino acid residue 254, and a substitution with glutamic acid at amino acid residue 256, numbered according to the EU index as in Kabat, and wherein said antigen-binding domain comprises:

a. a heavy chain CDR1 (HCDR1) comprising the sequence of SEQ ID NO: 1, a heavy chain CDR2 (HCDR2) comprising the sequence of SEQ ID NO: 2, a heavy chain CDR3 (HCDR3) comprising the sequence of SEQ ID NO: 3; a light chain CDR1 (LCDR1) comprising the sequence of SEQ ID NO: 4, a light chain CDR2 (LCDR2) comprising the sequence of SEQ ID NO: 5, and a light chain CDR3 (LCDR3) comprising the sequence of SEQ ID NO: 6;

b. a HCDR1 comprising the sequence of SEQ ID NO: 11, a HCDR2 comprising the sequence of SEQ ID NO: 12, a HCDR3 comprising the sequence of SEQ ID NO: 13, a LCDR1 comprising the sequence of SEQ ID NO: 14, a LCDR2 comprising the sequence of SEQ ID NO: 15, and a LCDR3 comprising the sequence of SEQ ID NO: 16;
c. a HCDR1 comprising the sequence of SEQ ID NO: 21, a HCDR2 comprising the sequence of SEQ ID NO: 22, a HCDR3 comprising the sequence of SEQ ID NO: 23, a LCDR1 comprising the sequence of SEQ ID NO: 24, a LCDR2 comprising the sequence of SEQ ID NO: 25, and a LCDR3 comprising the sequence of SEQ ID NO: 26;
d. a HCDR1 comprising the sequence of SEQ ID NO: 31, a HCDR2 comprising the sequence of SEQ ID NO: 32, a HCDR3 comprising the sequence of SEQ ID NO: 33, a LCDR1 comprising the sequence of SEQ ID NO: 34, a LCDR2 comprising the sequence of SEQ ID NO: 35, and a LCDR3 comprising the sequence of SEQ ID NO: 36;
e. a HCDR1 comprising the sequence of SEQ ID NO: 41, a HCDR2 comprising the sequence of SEQ ID NO: 42, a HCDR3 comprising the sequence of SEQ ID NO: 43, a LCDR1 comprising the sequence of SEQ ID NO: 44, a LCDR2 comprising the sequence of SEQ ID NO: 45, and a LCDR3 comprising the sequence of SEQ ID NO: 46;
f. a HCDR1 comprising the sequence of SEQ ID NO: 51, a HCDR2 comprising the sequence of SEQ ID NO: 52, a HCDR3 comprising the sequence of SEQ ID NO: 53, a LCDR1 comprising the sequence of SEQ ID NO: 54, a LCDR2 comprising the sequence of SEQ ID NO: 55, and a LCDR3 comprising the sequence of SEQ ID NO: 56;
g. a HCDR1 comprising the sequence of SEQ ID NO: 65, a HCDR2 comprising the sequence of SEQ ID NO: 66, a HCDR3 comprising the sequence of SEQ ID NO: 67, a LCDR1 comprising the sequence of SEQ ID NO: 68, a LCDR2 comprising the sequence of SEQ ID NO: 69, and a LCDR3 comprising the sequence of SEQ ID NO: 70;
h. a HCDR1 comprising the sequence of SEQ ID NO: 75, a HCDR2 comprising the sequence of SEQ ID NO: 76, a HCDR3 comprising the sequence of SEQ ID NO: 77, a LCDR1 comprising the sequence of SEQ ID NO: 78, a LCDR2 comprising the sequence of SEQ ID NO: 79, and a LCDR3 comprising the sequence of SEQ ID NO: 80;
i. a HCDR1 comprising the sequence of SEQ ID NO: 85, a HCDR2 comprising the sequence of SEQ ID NO: 86, a HCDR3 comprising the sequence of SEQ ID NO: 87, a LCDR1 comprising the sequence of SEQ ID NO: 88, a LCDR2 comprising the sequence of SEQ ID NO: 89, and a LCDR3 comprising the sequence of SEQ ID NO: 90;
j. a HCDR1 comprising the sequence of SEQ ID NO: 95, a HCDR2 comprising the sequence of SEQ ID NO: 96, a HCDR3 comprising the sequence of SEQ ID NO: 97, a LCDR1 comprising the sequence of SEQ ID NO: 98, a LCDR2 comprising the sequence of SEQ ID NO: 99, and a LCDR3 comprising the sequence of SEQ ID NO: 100;
k. a HCDR1 comprising the sequence of SEQ ID NO: 105, a HCDR2 comprising the sequence of SEQ ID NO: 106, a HCDR3 comprising the sequence of SEQ ID NO: 107, a LCDR1 comprising the sequence of SEQ ID NO: 108, a LCDR2 comprising the sequence of SEQ ID NO: 109, and a LCDR3 comprising the sequence of SEQ ID NO: 110;
l. a HCDR1 comprising the sequence of SEQ ID NO: 136, a HCDR2 comprising the sequence of SEQ ID NO: 137, a HCDR3 comprising the sequence of SEQ ID NO: 138, a LCDR1 comprising the sequence of SEQ ID NO: 139, a LCDR2 comprising the sequence of SEQ ID NO: 140, and a LCDR3 comprising the sequence of SEQ ID NO: 141;
m. HCDR1 comprising the sequence of SEQ ID NO: 146, a HCDR2 comprising the sequence of SEQ ID NO: 147, a HCDR3 comprising the sequence of SEQ ID NO: 148, a LCDR1 comprising the sequence of SEQ ID NO: 149, a LCDR2 comprising the sequence of SEQ ID NO: 150, and a LCDR3 comprising the sequence of SEQ ID NO: 151;
n. HCDR1 comprising the sequence of SEQ ID NO: 156, a HCDR2 comprising the sequence of SEQ ID NO: 157, a HCDR3 comprising the sequence of SEQ ID NO: 158, a LCDR1 comprising the sequence of SEQ ID NO: 159, a LCDR2 comprising the sequence of SEQ ID NO: 160, and a LCDR3 comprising the sequence of SEQ ID NO: 161;
o. HCDR1 comprising the sequence of SEQ ID NO: 166, a HCDR2 comprising the sequence of SEQ ID NO: 167, a HCDR3 comprising the sequence of SEQ ID NO: 168, a LCDR1 comprising the sequence of SEQ ID NO: 169, a LCDR2 comprising the sequence of SEQ ID NO: 170, and a LCDR3 comprising the sequence of SEQ ID NO: 171;
p. HCDR1 comprising the sequence of SEQ ID NO: 176, a HCDR2 comprising the sequence of SEQ ID NO: 177, a HCDR3 comprising the sequence of SEQ ID NO: 178, a LCDR1 comprising the sequence of SEQ ID NO: 179, a LCDR2 comprising the sequence of SEQ ID NO: 180, and a LCDR3 comprising the sequence of SEQ ID NO: 181;
q. HCDR1 comprising the sequence of SEQ ID NO: 186, a HCDR2 comprising the sequence of SEQ ID NO: 187, a HCDR3 comprising the sequence of SEQ ID NO: 188, a LCDR1 comprising the sequence of SEQ ID NO: 189, a LCDR2 comprising the sequence of SEQ ID NO: 190, and a LCDR3 comprising the sequence of SEQ ID NO: 191;
r. HCDR1 comprising the sequence of SEQ ID NO: 196, a HCDR2 comprising the sequence of SEQ ID NO: 197, a HCDR3 comprising the sequence of SEQ ID NO: 198, a LCDR1 comprising the sequence of SEQ ID NO: 199, a LCDR2 comprising the sequence of SEQ ID NO: 200, and a LCDR3 comprising the sequence of SEQ ID NO: 201;
s. HCDR1 comprising the sequence of SEQ ID NO: 206, a HCDR2 comprising the sequence of SEQ ID NO: 207, a HCDR3 comprising the sequence of SEQ ID NO: 208, a LCDR1 comprising the sequence of SEQ ID NO: 209, a LCDR2 comprising the sequence of SEQ ID NO: 210, and a LCDR3 comprising the sequence of SEQ ID NO: 211;
t. HCDR1 comprising the sequence of SEQ ID NO: 216, a HCDR2 comprising the sequence of SEQ ID NO: 217, a HCDR3 comprising the sequence of SEQ ID NO: 218, a LCDR1 comprising the sequence of SEQ ID NO: 219, a LCDR2 comprising the sequence of SEQ ID NO: 220, and a LCDR3 comprising the sequence of SEQ ID NO: 221;
u. HCDR1 comprising the sequence of SEQ ID NO: 226, a HCDR2 comprising the sequence of SEQ ID NO: 227, a HCDR3 comprising the sequence of SEQ ID NO: 228, a LCDR1 comprising the sequence of SEQ ID NO: 229, a LCDR2 comprising the sequence of SEQ ID NO: 230, and a LCDR3 comprising the sequence of SEQ ID NO: 231;
v. HCDR1 comprising the sequence of SEQ ID NO: 236, a HCDR2 comprising the sequence of SEQ ID NO: 237, a HCDR3 comprising the sequence of SEQ ID NO: 238, a LCDR1 comprising the sequence of SEQ ID NO: 239, a LCDR2 comprising the sequence of SEQ ID NO: 240, and a LCDR3 comprising the sequence of SEQ ID NO: 241;
w. HCDR1 comprising the sequence of SEQ ID NO: 246, a HCDR2 comprising the sequence of SEQ ID NO: 247, a HCDR3 comprising the sequence of SEQ ID NO: 248, a LCDR1 comprising the sequence of SEQ ID NO: 249, a LCDR2 comprising the sequence of SEQ ID NO: 250, and a LCDR3 comprising the sequence of SEQ ID NO: 251;
x. HCDR1 comprising the sequence of SEQ ID NO: 256, a HCDR2 comprising the sequence of SEQ ID NO: 257, a HCDR3 comprising the sequence of SEQ ID NO: 258, a LCDR1 comprising the sequence of SEQ ID NO: 259, a LCDR2 comprising the sequence of SEQ ID NO: 260, and a LCDR3 comprising the sequence of SEQ ID NO: 261;
y. HCDR1 comprising the sequence of SEQ ID NO: 266, a HCDR2 comprising the sequence of SEQ ID NO: 267, a HCDR3 comprising the sequence of SEQ ID NO: 268, a LCDR1 comprising the sequence of SEQ ID NO: 269, a LCDR2 comprising the sequence of SEQ ID NO: 270, and a LCDR3 comprising the sequence of SEQ ID NO: 271;
z. HCDR1 comprising the sequence of SEQ ID NO: 276, a HCDR2 comprising the sequence of SEQ ID NO: 277, a HCDR3 comprising the sequence of SEQ ID NO: 278, a LCDR1 comprising the sequence of SEQ ID NO: 279, a LCDR2 comprising the sequence of SEQ ID NO: 280, a LCDR3 comprising the sequence of SEQ ID NO: 281;
aa. HCDR1 comprising the sequence of SEQ ID NO: 286, a HCDR2 comprising the sequence of SEQ ID NO: 287, a HCDR3 comprising the sequence of SEQ ID NO: 288, a LCDR1 comprising the sequence of SEQ ID NO: 289, a LCDR2 comprising the sequence of SEQ ID NO: 290, a LCDR3 comprising the sequence of SEQ ID NO: 291;
bb. HCDR1 comprising the sequence of SEQ ID NO: 296, a HCDR2 comprising the sequence of SEQ ID NO: 297, a HCDR3 comprising the sequence of SEQ ID NO: 298, a LCDR1 comprising the sequence of SEQ ID NO: 299, a LCDR2 comprising the sequence of SEQ ID NO: 300, a LCDR3 comprising the sequence of SEQ ID NO: 301;
cc. HCDR1 comprising the sequence of SEQ ID NO: 306, a HCDR2 comprising the sequence of SEQ ID NO: 307, a HCDR3 comprising the sequence of SEQ ID NO: 308, a LCDR1 comprising the sequence of SEQ ID NO: 309, a LCDR2 comprising the sequence of SEQ ID NO: 310, a LCDR3 comprising the sequence of SEQ ID NO: 311;
dd. HCDR1 comprising the sequence of SEQ ID NO: 316, a HCDR2 comprising the sequence of SEQ ID NO: 317, a HCDR3 comprising the sequence of SEQ ID NO: 318, a LCDR1 comprising the sequence of SEQ ID NO: 319, a LCDR2 comprising the sequence of SEQ ID NO: 320, a LCDR3 comprising the sequence of SEQ ID NO: 321;
ee. HCDR1 comprising the sequence of SEQ ID NO: 326, a HCDR2 comprising the sequence of SEQ ID NO: 327, a HCDR3 comprising the sequence of SEQ ID NO: 328, a LCDR1 comprising the sequence of SEQ ID NO: 329, a LCDR2 comprising the sequence of SEQ ID NO: 330, a LCDR3 comprising the sequence of SEQ ID NO: 331;
ff. HCDR1 comprising the sequence of SEQ ID NO: 336, a HCDR2 comprising the sequence of SEQ ID NO: 337, a HCDR3 comprising the sequence of SEQ ID NO: 338, a LCDR1 comprising the sequence of SEQ ID NO: 339, a LCDR2 comprising the sequence of SEQ ID NO: 340, a LCDR3 comprising the sequence of SEQ ID NO: 341;
gg. HCDR1 comprising the sequence of SEQ ID NO: 346, a HCDR2 comprising the sequence of SEQ ID NO: 347, a HCDR3 comprising the sequence of SEQ ID NO: 348, a LCDR1 comprising the sequence of SEQ ID NO: 349, a LCDR2 comprising the sequence of SEQ ID NO: 350, a LCDR3 comprising the sequence of SEQ ID NO: 351;
hh. HCDR1 comprising the sequence of SEQ ID NO: 356, a HCDR2 comprising the sequence of SEQ ID NO: 357, a HCDR3 comprising the sequence of SEQ ID NO: 358, a LCDR1 comprising the sequence of SEQ ID NO: 359, a LCDR2 comprising the sequence of SEQ ID NO: 360, a LCDR3 comprising the sequence of SEQ ID NO: 361;
ii. HCDR1 comprising the sequence of SEQ ID NO: 366, a HCDR2 comprising the sequence of SEQ ID NO: 367, a HCDR3 comprising the sequence of SEQ ID NO: 368, a LCDR1 comprising the sequence of SEQ ID NO: 369, a LCDR2 comprising the sequence of SEQ ID NO: 370, a LCDR3 comprising the sequence of SEQ ID NO: 371;
jj. HCDR1 comprising the sequence of SEQ ID NO: 376, a HCDR2 comprising the sequence of SEQ ID NO: 377, a HCDR3 comprising the sequence of SEQ ID NO: 378, a LCDR1 comprising the sequence of SEQ ID NO: 379, a LCDR2 comprising the sequence of SEQ ID NO: 380, a LCDR3 comprising the sequence of SEQ ID NO: 381;
kk. HCDR1 comprising the sequence of SEQ ID NO: 386, a HCDR2 comprising the sequence of SEQ ID NO: 387, a HCDR3 comprising the sequence of SEQ ID NO: 388, a LCDR1 comprising the sequence of SEQ ID NO: 389, a LCDR2 comprising the sequence of SEQ ID NO: 390, a LCDR3 comprising the sequence of SEQ ID NO: 391;
ll. HCDR1 comprising the sequence of SEQ ID NO: 396, a HCDR2 comprising the sequence of SEQ ID NO: 397, a HCDR3 comprising the sequence of SEQ ID NO: 398, a LCDR1 comprising the sequence of SEQ ID NO: 399, a LCDR2 comprising the sequence of SEQ ID NO: 400, a LCDR3 comprising the sequence of SEQ ID NO: 401;
mm. HCDR1 comprising the sequence of SEQ ID NO: 406, a HCDR2 comprising the sequence of SEQ ID NO: 407, a HCDR3 comprising the sequence of SEQ ID NO: 408, a LCDR1 comprising the sequence of SEQ ID NO: 409, a LCDR2 comprising the sequence of SEQ ID NO: 410, a LCDR3 comprising the sequence of SEQ ID NO: 411;
nn. HCDR1 comprising the sequence of SEQ ID NO: 416, a HCDR2 comprising the sequence of SEQ ID NO: 417, a HCDR3 comprising the sequence of SEQ ID NO: 418, a LCDR1 comprising the sequence of SEQ ID NO: 419, a LCDR2 comprising the sequence of SEQ ID NO: 420, a LCDR3 comprising the sequence of SEQ ID NO: 421;
oo. HCDR1 comprising the sequence of SEQ ID NO: 426, a HCDR2 comprising the sequence of SEQ ID NO: 427, a HCDR3 comprising the sequence of SEQ ID NO: 428, a LCDR1 comprising the sequence of SEQ ID NO: 429, a LCDR2 comprising the sequence of SEQ ID NO: 430, a LCDR3 comprising the sequence of SEQ ID NO: 431;
or a combination thereof.

2. The modified antibody or an antigen-binding fragment thereof of claim 1, comprising:
a) binding affinity to RBD of said spike protein of SARS-CoV comprising the amino acid sequence of SEQ ID NO: 124 at a level that is non-detectable or that is no more than 50% of said binding affinity to said RBD of said spike protein of SARS-CoV-2;
b) binding affinity to RBD of said spike protein of MERS-CoV comprising the amino acid sequence of SEQ ID NO: 126 at a level that is non-detectable or that is no more than 50% of said binding affinity to said RBD of the spike protein of SARS-CoV-2;
c) binding affinity to said RBD of said spike protein of SARS-CoV-2 at a $K_d$ value of no more than $1\times10^{-7}$M as measured by Surface Plasmon Resonance (SPR);
d) binding affinity to said RBD of said spike protein of SARS-CoV or the RBD of spike protein of MERS-CoV at a $K_d$ value of at least $1\times10^{-6}$M as measured by SPR;
e) exhibiting at least 30% competition at 1 µM, with 2 µM angiotensin converting enzyme 2 (ACE2) receptor, for binding to said RBD of said spike protein of SARS-CoV-2 immobilized at a resonance unit (RU) of 250, as measured by SPR;
f) binding affinity to said RBD of said spike protein of SARS-CoV-2 at a neutralizing activity at an $IC_{50}$ value of no more than 100 µg/ml, as measured by pseudovirus, live virus microneutralization, inactivated virus neutralization assay, or a combination thereof; or
a combination thereof.

3. The modified antibody or an antigen-binding fragment thereof of claim 1, wherein said antigen-binding domain comprises:
a HCDR1 comprising the sequence of SEQ ID NO: 105, a HCDR2 comprising the sequence of SEQ ID NO: 106, a HCDR3 comprising the sequence of SEQ ID NO: 107, a LCDR1 comprising the sequence of SEQ ID NO: 108, a LCDR2 comprising the sequence of SEQ ID NO: 109, and a LCDR3 comprising the sequence of SEQ ID NO: 110;
a HCDR1 comprising the sequence of SEQ ID NO: 136, a HCDR2 comprising the sequence of SEQ ID NO: 137, a HCDR3 comprising the sequence of SEQ ID NO: 138, a LCDR1 comprising the sequence of SEQ ID NO: 139, a LCDR2 comprising the sequence of SEQ ID NO: 140, and a LCDR3 comprising the sequence of SEQ ID NO: 141;
or
a combination thereof.

4. The modified antibody or an antigen-binding fragment thereof of claim 3, wherein said modified antibody or an antigen-binding fragment thereof is bispecific and comprises a first antigen binding domain comprising:
a HCDR1 comprising the sequence of SEQ ID NO: 105, a HCDR2 comprising the sequence of SEQ ID NO: 106, a HCDR3 comprising the sequence of SEQ ID NO: 107, a LCDR1 comprising the sequence of SEQ ID NO: 108, a LCDR2 comprising the sequence of SEQ ID NO: 109, and a LCDR3 comprising the sequence of SEQ ID NO: 110;
and a second antigen binding domain comprising:
a HCDR1 comprising the sequence of SEQ ID NO: 136, a HCDR2 comprising the sequence of SEQ ID NO: 137, a HCDR3 comprising the sequence of SEQ ID NO: 138, a LCDR1 comprising the sequence of SEQ ID NO: 139, a LCDR2 comprising the sequence of SEQ ID NO: 140, and a LCDR3 comprising the sequence of SEQ ID NO: 141.

5. The modified antibody or an antigen-binding fragment thereof of claim 1, wherein said modified antibody or said antigen-binding fragment has a half-life ($T_{1/2}$) in a range of from 50 to 120 days in vivo.

6. The modified antibody or an antigen-binding fragment thereof of claim 1, wherein said modified antibody or said antigen-binding fragment comprises at least one amino acid subsequent substitutions in said human IgG constant domain, at least one amino acid substitution in a light chain of said modified antibody, at least one amino acid substitution in a heavy chain of said modified antibody, or a combination thereof.

7. The modified antibody or an antigen-binding fragment thereof of claim 6, wherein said subsequent substitution comprises substituting a cysteine residue to a non-cysteine residue.

8. The modified antibody or an antigen-binding fragment thereof of claim 1, wherein said modified antibody or said antigen-binding fragment thereof is a diabody, a Fab, a Fab', a F(ab')2, a Fd, an Fv fragment, a disulfide stabilized Fv fragment (dsFv), a (dsFv)2, a bispecific dsFv, a disulfide stabilized diabody, a single-chain antibody molecule (scFv), an scFv dimer, a bispecific scFv dimer, or a multispecific antibody.

9. The modified antibody or an antigen-binding fragment thereof of claim 1, wherein said SARS-CoV-2-binding affinity comprises at least 50% less or non-detectable binding affinity to SARS-CoV or MERS-CoV compared to said SARS-CoV-2 binding affinity, and said modified antibody has an increased affinity for FcRn compared to the affinity to FcRn of an antibody having a wild type human IgG constant domain.

10. A pharmaceutical composition comprising at least one said modified antibody or an antigen-binding fragment thereof of claim 1, at least one nucleic acid encoding said modified antibody or said antigen-binding fragment thereof, or a combination thereof, and one or more pharmaceutically acceptable carriers.

11. The pharmaceutical composition of claim 10, wherein said pharmaceutical composition comprises said modified antibody or an antigen-binding fragment thereof at a concentration in a range of from 10 mg/mL to 150 mg/mL.

12. The pharmaceutical composition of claim 10, wherein said pharmaceutical composition is formulated to be administered to a subject via intravenous injection (IV), intramuscular injection (IM), subcutaneous (SC) injection, or a combination thereof.

13. The pharmaceutical composition of claim 10, wherein said pharmaceutical composition is formulated for treatment of a person being one of:
a) a symptomatic, non-hospitalized adult with COVID-19 caused by SARS-CoV-2 infection; or
b) an hospitalized adult inpatient requiring supportive management of complications of severe infection of said SARS-CoV-2 selected from pneumonia, hypoxemic respiratory failure/ARDS, sepsis and septic shock, cardiomyopathy and arrhythmia, acute kidney injury, and complications from prolonged hospitalization including secondary bacterial and fungal infections, thromboembolism, gastrointestinal bleeding, critical illness polyneuropathy/myopathy, or a combination thereof.

14. The pharmaceutical composition of claim 10, wherein said pharmaceutical composition comprises a first modified antibody or an antigen-binding fragment thereof comprising:
   a HCDR1 comprising the sequence of SEQ ID NO: 105, a HCDR2 comprising the sequence of SEQ ID NO: 106, a HCDR3 comprising the sequence of SEQ ID NO: 107, a LCDR1 comprising the sequence of SEQ ID NO: 108, a LCDR2 comprising the sequence of SEQ ID NO: 109, and a LCDR3 comprising the sequence of SEQ ID NO: 110; and
   a second modified antibody or an antigen-binding fragment thereof, comprising a HCDR1 comprising the sequence of SEQ ID NO: 136, a HCDR2 comprising the sequence of SEQ ID NO: 137, a HCDR3 comprising the sequence of SEQ ID NO: 138, a LCDR1 comprising the sequence of SEQ ID NO: 139, a LCDR2 comprising the sequence of SEQ ID NO: 140, and a LCDR3 comprising the sequence of SEQ ID NO: 141.

15. The pharmaceutical composition of claim 13, wherein said person is a person 60 years and older.

\* \* \* \* \*

SEQUENCE LISTING

<160> NUMBER OF SEQ ID NOS: 437

<210> SEQ ID NO 1
<211> LENGTH: 8
<212> TYPE: PRT
<213> ORGANISM: Homo sapiens
<220> FEATURE:
<221> NAME/KEY: P2A-1A8 HCDR1
<222> LOCATION: (1)..(8)

<400> SEQUENCE: 1

Gly Phe Ala Phe Asp Asp Tyr Ala
1               5

<210> SEQ ID NO 2
<211> LENGTH: 8
<212> TYPE: PRT
<213> ORGANISM: Homo sapiens
<220> FEATURE:
<221> NAME/KEY: P2A-1A8 HCDR2
<222> LOCATION: (1)..(8)

```
<400> SEQUENCE: 2

Ser Thr Trp Asn Ser Gly Thr Ile
1               5

<210> SEQ ID NO 3
<211> LENGTH: 23
<212> TYPE: PRT
<213> ORGANISM: Homo sapiens
<220> FEATURE:
<221> NAME/KEY: P2A-1A8 HCDR3
<222> LOCATION: (1)..(23)

<400> SEQUENCE: 3

Ala Lys Leu Gly Gly Tyr Ser Asp Tyr Asp Tyr Pro Arg Pro Gly Asp
1               5                   10                  15

His Tyr Tyr Gly Leu Asp Val
            20

<210> SEQ ID NO 4
<211> LENGTH: 9
<212> TYPE: PRT
<213> ORGANISM: Homo sapiens
<220> FEATURE:
<221> NAME/KEY: P2A-1A8 LCDR1
<222> LOCATION: (1)..(9)

<400> SEQUENCE: 4

Ser Ser Asp Val Gly Ser Tyr Asn Leu
1               5

<210> SEQ ID NO 5
<211> LENGTH: 4
<212> TYPE: PRT
<213> ORGANISM: Homo sapiens
<220> FEATURE:
<221> NAME/KEY: P2A-1A8 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 5

Asp Val Asn Xaa
1

<210> SEQ ID NO 6
<211> LENGTH: 10
<212> TYPE: PRT
<213> ORGANISM: Homo sapiens
<220> FEATURE:
<221> NAME/KEY: P2A-1A8 LCDR3
<222> LOCATION: (1)..(10)

<400> SEQUENCE: 6

Arg Ser Tyr Thr Asp Ser Asn Thr Tyr Val
1               5                   10

<210> SEQ ID NO 7
<211> LENGTH: 130
<212> TYPE: PRT
<213> ORGANISM: Homo sapiens
<220> FEATURE:
<221> NAME/KEY: P2A-1A8 VH
<222> LOCATION: (1)..(130)

<400> SEQUENCE: 7
```

Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Ala Phe Asp Asp Tyr
                20                  25                  30

Ala Met His Trp Val Arg Gln Ala Pro Gly Lys Gly Leu Glu Trp Val
            35                  40                  45

Ser Gly Ser Thr Trp Asn Ser Gly Thr Ile Ala Tyr Ala Asp Ser Val
50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Thr Glu Asp Thr Ala Leu Tyr Tyr Cys
                85                  90                  95

Ala Lys Leu Gly Gly Tyr Ser Asp Tyr Asp Tyr Pro Arg Pro Gly Asp
            100                 105                 110

His Tyr Tyr Gly Leu Asp Val Trp Gly Gln Gly Thr Thr Val Thr Val
        115                 120                 125

Ser Ser
    130

<210> SEQ ID NO 8
<211> LENGTH: 110
<212> TYPE: PRT
<213> ORGANISM: Homo sapiens
<220> FEATURE:
<221> NAME/KEY: P2A-1A8 VL
<222> LOCATION: (1)..(110)

<400> SEQUENCE: 8

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Leu Val Ser Trp Tyr Gln Gln His Pro Gly Lys Val Pro Lys Leu
            35                  40                  45

Leu Ile Tyr Asp Val Asn Lys Arg Pro Ser Gly Ile Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Arg Ser Tyr Thr Asp Ser
                85                  90                  95

Asn Thr Tyr Val Phe Gly Thr Gly Thr Lys Val Thr Val Leu
            100                 105                 110

<210> SEQ ID NO 9
<211> LENGTH: 390
<212> TYPE: DNA
<213> ORGANISM: Homo sapiens
<220> FEATURE:
<221> NAME/KEY: P2A-1A8 VHnu
<222> LOCATION: (1)..(390)

<400> SEQUENCE: 9
gaagtgcagc tggtggagtc tgggggagac ttggtacagc ctggcaggtc cctgagactc      60
tcctgcgcag cctctggatt cgcctttgat gattatgcca tgcactgggt ccggcaagct     120
ccagggaagg gcctggagtg gtctcaggt agtacttgga atagtgggac catagcctat     180
gcggactctg tgaagggccg attcaccatc tccagagaca cgccaagaa gtccctgtat     240

```
ctgcaaatga acagtctgag aactgaggac acggccttat attactgtgc aaagttgggg      300
ggctacagtg actacgatta cccgaggccg ggagaccact attacggttt ggacgtctgg      360
ggccaaggga ccacggtcac cgtctcctca                                        390
```

<210> SEQ ID NO 10
<211> LENGTH: 330
<212> TYPE: DNA
<213> ORGANISM: Homo sapiens
<220> FEATURE:
<221> NAME/KEY: P2A-1A8 VLnu
<222> LOCATION: (1)..(330)

<400> SEQUENCE: 10

```
cagtctgccc tgactcagcc tgcctccgtg tctgggtctc ctggacagtc gatcaccatc       60
tcctgcactg gaaccagcag tgatgttggg agttataacc ttgtctcctg gtaccaacag      120
cacccaggca agtccccaa actcttgatt tatgatgtca ataagcggcc ctcagggatt       180
tccaatcgct ctctctggct caagtctggc aacacggcct ccctgaccat ctctgggctc      240
caggctgagg acgaggctga ttattactgc agatcatata cagacagcaa cacttatgtc      300
ttcggaactg ggaccaaggt caccgtccta                                        330
```

<210> SEQ ID NO 11
<211> LENGTH: 8
<212> TYPE: PRT
<213> ORGANISM: Homo sapiens
<220> FEATURE:
<221> NAME/KEY: P2A-1A9/P2B-2G11 HCDR1
<222> LOCATION: (1)..(8)

<400> SEQUENCE: 11

Gly Phe Thr Phe Asp Asp Tyr Ala
1               5

<210> SEQ ID NO 12
<211> LENGTH: 8
<212> TYPE: PRT
<213> ORGANISM: Homo sapiens
<220> FEATURE:
<221> NAME/KEY: P2A-1A9/P2B-2G11 HCDR2
<222> LOCATION: (1)..(8)

<400> SEQUENCE: 12

Ile Ser Trp Asn Gly Gly Ile Ile
1               5

<210> SEQ ID NO 13
<211> LENGTH: 17
<212> TYPE: PRT
<213> ORGANISM: Homo sapiens
<220> FEATURE:
<221> NAME/KEY: P2A-1A9/P2B-2G11 HCDR3
<222> LOCATION: (1)..(17)

<400> SEQUENCE: 13

Ala Lys Val Ala Gly Arg Gly Asp Tyr Asp Tyr Tyr Gly Met Asp
1               5                   10                  15

Val

<210> SEQ ID NO 14
<211> LENGTH: 9
<212> TYPE: PRT
<213> ORGANISM: Homo sapiens
<220> FEATURE:

```
<221> NAME/KEY: P2A-1A9/P2B-2G11 LCDR1
<222> LOCATION: (1)..(9)

<400> SEQUENCE: 14

Ser Ser Asn Ile Gly Ala Gly Tyr Asp
1               5

<210> SEQ ID NO 15
<211> LENGTH: 4
<212> TYPE: PRT
<213> ORGANISM: Homo sapiens
<220> FEATURE:
<221> NAME/KEY: P2A-1A9/P2B-2G11 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 15

Gly Asn Asn Xaa
1

<210> SEQ ID NO 16
<211> LENGTH: 11
<212> TYPE: PRT
<213> ORGANISM: Homo sapiens
<220> FEATURE:
<221> NAME/KEY: P2A-1A9/P2B-2G11 LCDR3
<222> LOCATION: (1)..(11)

<400> SEQUENCE: 16

Gln Ser Tyr Asp Ser Ser Leu Ser Gly Ser Val
1               5                   10

<210> SEQ ID NO 17
<211> LENGTH: 124
<212> TYPE: PRT
<213> ORGANISM: Homo sapiens
<220> FEATURE:
<221> NAME/KEY: P2A-1A9 VH
<222> LOCATION: (1)..(124)

<400> SEQUENCE: 17

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Asn Gly Gly Ile Ile Tyr Ala Asp Ser Val
    50                  55                  60

Lys Gly Arg Phe Thr Ile Ser Arg Asp Asn Ala Lys Thr Ser Leu Tyr
65                  70                  75                  80

Leu Gln Met Asn Ser Leu Arg Ala Glu Asp Thr Ala Leu Tyr Tyr Cys
                85                  90                  95

Ala Lys Val Ala Gly Arg Gly Asp Tyr Asp Tyr Tyr Tyr Gly Met Asp
            100                 105                 110

Val Trp Gly Gln Gly Thr Thr Val Thr Val Ser Ser
        115                 120

<210> SEQ ID NO 18
<211> LENGTH: 111
<212> TYPE: PRT
```

<213> ORGANISM: Homo sapiens
<220> FEATURE:
<221> NAME/KEY: P2A-1A9 VL
<222> LOCATION: (1)..(111)

<400> SEQUENCE: 18

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110

<210> SEQ ID NO 19
<211> LENGTH: 372
<212> TYPE: DNA
<213> ORGANISM: Homo sapiens
<220> FEATURE:
<221> NAME/KEY: P2A-1A9 VHnu
<222> LOCATION: (1)..(372)

<400> SEQUENCE: 19

```
gaagtgcagc tggtggagtc tgggggaggc ttggtacagc ctggcaggtc cctgagactc        60
tcctgtgcag cctctggatt cacctttgat gattatgcca tgcactgggt ccggcaagtt       120
ccagggaagg gcctggagtg ggtctcaggt attagttgga atggtggtat cataggctac       180
gcggactctg tgaagggccg attcaccatc tccagagaca acgccaagac ttccctgtat       240
ctgcaaatga acagtctgag agctgaggac acggccttgt attactgtgc aaaagtcgcg       300
ggaagggggg attacgacta ttactatggt atggacgtct ggggccaagg gaccacggtc       360
accgtctcct ca                                                           372
```

<210> SEQ ID NO 20
<211> LENGTH: 333
<212> TYPE: DNA
<213> ORGANISM: Homo sapiens
<220> FEATURE:
<221> NAME/KEY: P2A-1A9 VLnu
<222> LOCATION: (1)..(333)

<400> SEQUENCE: 20

```
cagtctgtgc tgacgcagcc gccctcagtg tctggggccc cagggcagag ggtcaccatc        60
tcctgcactg ggagcagctc caacatcggg gcaggttatg atgtacactg gtaccagcaa       120
cttccaggaa cagcccccaa actcctcatc tatggtaaca acaatcgccc ctcaggggtc       180
cctgaccgat tctctggctc caagtctggc acctcagcct ccctggccat cactgggctc       240
caggctgagg atgaggctga ttattactgc cagtcctatg acagcagcct gagtggttcg       300
gtattcggcg gagggaccaa gctgaccgtc cta                                    333
```

<210> SEQ ID NO 21
<211> LENGTH: 8

```
<212> TYPE: PRT
<213> ORGANISM: Homo sapiens
<220> FEATURE:
<221> NAME/KEY: P2A-1A10 HCDR1
<222> LOCATION: (1)..(8)

<400> SEQUENCE: 21

Gly Tyr Thr Phe Thr Gly Tyr Tyr
1               5

<210> SEQ ID NO 22
<211> LENGTH: 8
<212> TYPE: PRT
<213> ORGANISM: Homo sapiens
<220> FEATURE:
<221> NAME/KEY: P2A-1A10 HCDR2
<222> LOCATION: (1)..(8)

<400> SEQUENCE: 22

Ile Asn Pro Asn Ser Gly Gly Thr
1               5

<210> SEQ ID NO 23
<211> LENGTH: 19
<212> TYPE: PRT
<213> ORGANISM: Homo sapiens
<220> FEATURE:
<221> NAME/KEY: P2A-1A10 HCDR3
<222> LOCATION: (1)..(19)

<400> SEQUENCE: 23

Ala Arg Val Pro Tyr Cys Ser Ser Thr Ser Cys His Arg Asp Trp Tyr
1               5                   10                  15

Phe Asp Leu

<210> SEQ ID NO 24
<211> LENGTH: 12
<212> TYPE: PRT
<213> ORGANISM: Homo sapiens
<220> FEATURE:
<221> NAME/KEY: P2A-1A10 LCDR1
<222> LOCATION: (1)..(12)

<400> SEQUENCE: 24

Gln Ser Leu Leu Asp Ser Asp Asp Gly Asn Thr Tyr
1               5                   10

<210> SEQ ID NO 25
<211> LENGTH: 4
<212> TYPE: PRT
<213> ORGANISM: Homo sapiens
<220> FEATURE:
<221> NAME/KEY: P2A-1A10 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 25

Thr Leu Ser Xaa
1

<210> SEQ ID NO 26
<211> LENGTH: 9
<212> TYPE: PRT
<213> ORGANISM: Homo sapiens
<220> FEATURE:
```

<221> NAME/KEY: P2A-1A10 LCDR3
<222> LOCATION: (1)..(9)

<400> SEQUENCE: 26

Met Gln Arg Ile Glu Phe Pro Leu Thr
1               5

<210> SEQ ID NO 27
<211> LENGTH: 126
<212> TYPE: PRT
<213> ORGANISM: Homo sapiens
<220> FEATURE:
<221> NAME/KEY: P2A-1A10 VH
<222> LOCATION: (1)..(126)

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Val Pro Tyr Cys Ser Ser Thr Ser Cys His Arg Asp Trp Tyr
            100                 105                 110

Phe Asp Leu Trp Gly Arg Gly Thr Leu Val Thr Val Ser Ser
        115                 120                 125

<210> SEQ ID NO 28
<211> LENGTH: 113
<212> TYPE: PRT
<213> ORGANISM: Homo sapiens
<220> FEATURE:
<221> NAME/KEY: P2A-1A10 VL
<222> LOCATION: (1)..(113)

<400> SEQUENCE: 28

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
                20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Leu Thr Phe Gly Gly Gly Thr Lys Val Glu Ile
            100                 105                 110

Lys

<210> SEQ ID NO 29

```
<211> LENGTH: 378
<212> TYPE: DNA
<213> ORGANISM: Homo sapiens
<220> FEATURE:
<221> NAME/KEY: P2A-1A10 VHnu
<222> LOCATION: (1)..(378)

<400> SEQUENCE: 29
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggacgg atcaaccta acagtggtgg cacaaactat      180
gcacagaagt tcagggcag ggtcaccatg accaggaca cgtccatcag cacagcctac      240
atggagctga gcaggctgag atctgacgac acggccgtgt attactgtgc gagagtcccc      300
tattgtagta gtaccagctg ccatcgggac tggtacttcg atctctgggg ccgtggcacc      360
ctggtcactg tctcctca                                                   378

<210> SEQ ID NO 30
<211> LENGTH: 339
<212> TYPE: DNA
<213> ORGANISM: Homo sapiens
<220> FEATURE:
<221> NAME/KEY: P2A-1A10 VLnu
<222> LOCATION: (1)..(339)

<400> SEQUENCE: 30
gatattgtga tgacccagac tccactctcc ctgcccgtca cccctggaga gccggcctcc      60
atctcctgca ggtctagtca gagcctcttg gatagtgatg atggaaacac ctatttggac     120
tggtacctgc agaagccagg gcagtctcca cagctcctga tctatacgct ttcctatcgg     180
gcctctggag tcccagacag gttcagtggc agtgggtcag gcactgattt cacactgaaa      240
atcagcaggg tggaggctga ggatgttgga gtttattact gcatgcaacg tatagagttt      300
ccgctcactt tcggcggagg gaccaaggtg gagatcaaa                             339

<210> SEQ ID NO 31
<211> LENGTH: 8
<212> TYPE: PRT
<213> ORGANISM: Homo sapiens
<220> FEATURE:
<221> NAME/KEY: P2A-1B3 HCDR1
<222> LOCATION: (1)..(8)

<400> SEQUENCE: 31

Gly Phe Ser Phe Asn Arg Tyr Ser
1               5

<210> SEQ ID NO 32
<211> LENGTH: 8
<212> TYPE: PRT
<213> ORGANISM: Homo sapiens
<220> FEATURE:
<221> NAME/KEY: P2A-1B3 HCDR2
<222> LOCATION: (1)..(8)

<400> SEQUENCE: 32

Ile Ser Ala Ser Gly Asn Thr Ile
1               5

<210> SEQ ID NO 33
<211> LENGTH: 16
<212> TYPE: PRT
<213> ORGANISM: Homo sapiens
```

```
<220> FEATURE:
<221> NAME/KEY: P2A-1B3 HCDR3
<222> LOCATION: (1)..(16)

<400> SEQUENCE: 33

Ala Arg Pro Ala Met Val Arg Glu Gly Thr Tyr Asn Trp Phe Asp Pro
1               5                   10                  15

<210> SEQ ID NO 34
<211> LENGTH: 7
<212> TYPE: PRT
<213> ORGANISM: Homo sapiens
<220> FEATURE:
<221> NAME/KEY: P2A-1B3 LCDR1
<222> LOCATION: (1)..(7)

<400> SEQUENCE: 34

Gln Ser Val Ser Asn Asp Tyr
1               5

<210> SEQ ID NO 35
<211> LENGTH: 4
<212> TYPE: PRT
<213> ORGANISM: Homo sapiens
<220> FEATURE:
<221> NAME/KEY: P2A-1B3 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 35

Tyr Ala Ser Xaa
1

<210> SEQ ID NO 36
<211> LENGTH: 10
<212> TYPE: PRT
<213> ORGANISM: Homo sapiens
<220> FEATURE:
<221> NAME/KEY: P2A-1B3 LCDR3
<222> LOCATION: (1)..(10)

<400> SEQUENCE: 36

Gln Gln Tyr Gly Asp Ser Pro Pro Ile Thr
1               5                   10

<210> SEQ ID NO 37
<211> LENGTH: 123
<212> TYPE: PRT
<213> ORGANISM: Homo sapiens
<220> FEATURE:
<221> NAME/KEY: P2A-1B3 VH
<222> LOCATION: (1)..(123)

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Ser Phe Asn Arg Tyr
                20                  25                  30

Ser Met Asn Trp Leu Arg Gln Thr Pro Arg Lys Gly Leu Glu Trp Leu
            35                  40                  45

Ser Tyr Ile Ser Ala Ser Gly Asn Thr Ile Tyr Ala Asp Ser Val
        50                  55                  60

Arg Gly Arg Phe Thr Thr Ser Arg Asp Asn Ala Lys Asn Thr Leu Tyr
```

```
                65                  70                  75                  80
Leu Gln Met Asn Ser Leu Arg Asp Asp Thr Ala Val Tyr Phe Cys
                        85                  90                  95

Ala Arg Pro Ala Met Val Arg Glu Gly Thr Tyr Asn Trp Phe Asp Pro
                100                 105                 110

Trp Gly Gln Gly Thr Leu Val Thr Val Ser Ser
            115                 120
```

<210> SEQ ID NO 38
<211> LENGTH: 109
<212> TYPE: PRT
<213> ORGANISM: Homo sapiens
<220> FEATURE:
<221> NAME/KEY: P2A-1B3 VL
<222> LOCATION: (1)..(109)

<400> SEQUENCE: 38

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Asp
                20                  25                  30

Tyr Leu Ala Trp Tyr Gln Gln Lys Pro Gly Gln Ala Pro Arg Leu Leu
            35                  40                  45

Ile Tyr Tyr Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Gly Asp Ser Ala Val Tyr Tyr Cys Gln Gln Tyr Gly Asp Ser Pro
                85                  90                  95

Pro Ile Thr Phe Gly Gln Gly Thr Arg Leu Glu Ile Lys
            100                 105
```

<210> SEQ ID NO 39
<211> LENGTH: 369
<212> TYPE: DNA
<213> ORGANISM: Homo sapiens
<220> FEATURE:
<221> NAME/KEY: P2A-1B3 VHnu
<222> LOCATION: (1)..(369)

<400> SEQUENCE: 39

```
gaggtgcagc tggtggagtc tgggggaggc ttggtacagc ctgggggtc cctcagactc      60
tcctgtgtcg cctctggatt ctccttcaat cgatatagta tgaattggct ccgccagact    120
ccacggaagg ggctggagtg gctttcatac atcagtgcca gtggaaacac catatactac    180
gctgactctg tgaggggccg attcaccacc tccagagaca atgccaagaa cacactgtat    240
ctgcaaatga acagcctgcg agacgacgac acggctgtct atttctgtgc gcgacccgct    300
atggttcggg aggggaccta caactggttc gaccctggg ccagggaac cctggtcacc     360
gtctcctca                                                             369
```

<210> SEQ ID NO 40
<211> LENGTH: 327
<212> TYPE: DNA
<213> ORGANISM: Homo sapiens
<220> FEATURE:
<221> NAME/KEY: P2A-1B3 VLnu
<222> LOCATION: (1)..(327)

<400> SEQUENCE: 40

-continued

```
gaaattgtgt tgacgcagtc tccaggcacc ctgtctttgt ctccagggga aagagccacc    60
ctctcctgca gggccagtca gagtgttagc aacgactact tagcctggta ccagcagaaa   120
cctggccagg ctcccaggct cctcatctac tatgcatcca gcagggccac tggcatccca   180
gacaggttca gtggcagtgg gtctgggaca gacttcactc tcaccatcag cagactggag   240
cctggagatt ctgcagtgta ttactgtcag cagtatggtg actcacctcc gatcaccttc   300
ggccaaggga cacgactgga gattaaa                                        327
```

```
<210> SEQ ID NO 41
<211> LENGTH: 9
<212> TYPE: PRT
<213> ORGANISM: Homo sapiens
<220> FEATURE:
<221> NAME/KEY: P2B-2F6 HCDR1
<222> LOCATION: (1)..(9)

<400> SEQUENCE: 41

Gly Tyr Ser Ile Ser Ser Gly Tyr Tyr
1               5

<210> SEQ ID NO 42
<211> LENGTH: 7
<212> TYPE: PRT
<213> ORGANISM: Homo sapiens
<220> FEATURE:
<221> NAME/KEY: P2B-2F6 HCDR2
<222> LOCATION: (1)..(7)

<400> SEQUENCE: 42

Ile Tyr His Ser Gly Ser Thr
1               5

<210> SEQ ID NO 43
<211> LENGTH: 20
<212> TYPE: PRT
<213> ORGANISM: Homo sapiens
<220> FEATURE:
<221> NAME/KEY: P2B-2F6 HCDR3
<222> LOCATION: (1)..(20)

<400> SEQUENCE: 43

Ala Arg Ala Val Val Gly Ile Val Val Val Pro Ala Ala Gly Arg Arg
1               5                   10                  15

Ala Phe Asp Ile
            20

<210> SEQ ID NO 44
<211> LENGTH: 9
<212> TYPE: PRT
<213> ORGANISM: Homo sapiens
<220> FEATURE:
<221> NAME/KEY: P2B-2F6 LCDR1
<222> LOCATION: (1)..(9)

<400> SEQUENCE: 44

Ser Ser Asp Val Gly Gly Tyr Asn Tyr
1               5

<210> SEQ ID NO 45
<211> LENGTH: 4
<212> TYPE: PRT
<213> ORGANISM: Homo sapiens
<220> FEATURE:
<221> NAME/KEY: P2B-2F6 LCDR2
<222> LOCATION: (1)..(3)
```

```
<220> FEATURE:
<221> NAME/KEY: misc_feature
<222> LOCATION: (4)..(4)
<223> OTHER INFORMATION: Xaa is absent.

<400> SEQUENCE: 45

Glu Val Ser Xaa
1

<210> SEQ ID NO 46
<211> LENGTH: 10
<212> TYPE: PRT
<213> ORGANISM: Homo sapiens
<220> FEATURE:
<221> NAME/KEY: P2B-2F6 LCDR3
<222> LOCATION: (1)..(10)

<400> SEQUENCE: 46

Ser Ser Tyr Ala Gly Ser Asn Asn Leu Val
1               5                   10

<210> SEQ ID NO 47
<211> LENGTH: 127
<212> TYPE: PRT
<213> ORGANISM: Homo sapiens
<220> FEATURE:
<221> NAME/KEY: P2B-2F6 VH
<222> LOCATION: (1)..(127)

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Ser Ile Tyr His Ser Gly Ser Thr Tyr Tyr Asn Pro Ser Leu
        50                  55                  60

Lys Thr Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Val Val Gly Ile Val Val Pro Ala Ala Gly Arg Arg
            100                 105                 110

Ala Phe Asp Ile Trp Gly Gln Gly Thr Met Val Thr Val Ser Ser
        115                 120                 125

<210> SEQ ID NO 48
<211> LENGTH: 110
<212> TYPE: PRT
<213> ORGANISM: Homo sapiens
<220> FEATURE:
<221> NAME/KEY: P2B-2F6 VL
<222> LOCATION: (1)..(110)

<400> SEQUENCE: 48

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45
```

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu
            100                 105                 110

<210> SEQ ID NO 49
<211> LENGTH: 381
<212> TYPE: DNA
<213> ORGANISM: Homo sapiens
<220> FEATURE:
<221> NAME/KEY: P2B-2F6 VHnu
<222> LOCATION: (1)..(381)

<400> SEQUENCE: 49

```
caggtgcagc tgcaggagtc gggcccagga ctggtgaagc cttcggagac cctgtccctc      60
acctgcactg tctctggtta ctccatcagc agtggttact actgggctgg atccggcag     120
cccccaggga aggggctgga gtggattggg agtatctatc atagtgggag cacctactac    180
aacccgtccc tcaagactcg agtcaccata tcagtagaca cgtccaagaa ccagttctcc    240
ctgaagctga gctctgtgac cgccgcagac acggccgtct attactgtgc gagagcggtg    300
gtagggattg tagtagtacc agctgccggt cgtcgggctt ttgatatctg gggccaaggg    360
acaatggtca ccgtctcctc a                                              381
```

<210> SEQ ID NO 50
<211> LENGTH: 330
<212> TYPE: DNA
<213> ORGANISM: Homo sapiens
<220> FEATURE:
<221> NAME/KEY: P2B-2F6 VLnu
<222> LOCATION: (1)..(330)

<400> SEQUENCE: 50

```
cagtctgccc tgactcagcc tccctccgcg tccgggtctc ctggacagtc agtcaccatc      60
tcctgcactg gaaccagcag tgacgttggt ggttataact atgtctcctg gtaccaacag    120
cacccaggca aagcccccaa actcatgatt tatgaggtca gtaagcggcc ctcaggggtc    180
cctgatcgct tctctggctc caagtctggc aacacggcct ccctgaccgt ctctgggctc    240
caggctgagg atgaggctga ttattactgc agctcatatg caggcagcaa caatttggtg    300
ttcggcggag ggaccaagct gaccgtccta                                     330
```

<210> SEQ ID NO 51
<211> LENGTH: 8
<212> TYPE: PRT
<213> ORGANISM: Homo sapiens
<220> FEATURE:
<221> NAME/KEY: P2B-2G4 HCDR1
<222> LOCATION: (1)..(8)

<400> SEQUENCE: 51

Gly Phe Thr Phe Ser Ser Tyr Gly
1               5

<210> SEQ ID NO 52
<211> LENGTH: 8
<212> TYPE: PRT
<213> ORGANISM: Homo sapiens

```
<220> FEATURE:
<221> NAME/KEY: P2B-2G4 HCDR2
<222> LOCATION: (1)..(8)

<400> SEQUENCE: 52

Ile Trp Tyr Asp Gly Ser Asn Lys
1               5

<210> SEQ ID NO 53
<211> LENGTH: 11
<212> TYPE: PRT
<213> ORGANISM: Homo sapiens
<220> FEATURE:
<221> NAME/KEY: P2B-2G4 HCDR3
<222> LOCATION: (1)..(11)

<400> SEQUENCE: 53

Ala Arg Gly Ala Ala Met Val Trp Leu Asp Tyr
1               5                   10

<210> SEQ ID NO 54
<211> LENGTH: 9
<212> TYPE: PRT
<213> ORGANISM: Homo sapiens
<220> FEATURE:
<221> NAME/KEY: P2B-2G4 LCDR1
<222> LOCATION: (1)..(9)

<400> SEQUENCE: 54

Ser Ser Asp Val Gly Gly Tyr Asn Tyr
1               5

<210> SEQ ID NO 55
<211> LENGTH: 4
<212> TYPE: PRT
<213> ORGANISM: Homo sapiens
<220> FEATURE:
<221> NAME/KEY: P2B-2G4 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 55

Asp Val Ser Xaa
1

<210> SEQ ID NO 56
<211> LENGTH: 11
<212> TYPE: PRT
<213> ORGANISM: Homo sapiens
<220> FEATURE:
<221> NAME/KEY: P2B-2G4 LCDR3
<222> LOCATION: (1)..(11)

<400> SEQUENCE: 56

Cys Ser Tyr Ala Gly Ser Tyr Thr Phe Val Val
1               5                   10

<210> SEQ ID NO 57
<211> LENGTH: 118
<212> TYPE: PRT
<213> ORGANISM: Homo sapiens
<220> FEATURE:
<221> NAME/KEY: P2B-2G4 VH
<222> LOCATION: (1)..(118)

<400> SEQUENCE: 57
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Ala Met Val Trp Leu Asp Tyr Trp Gly Gln Gly Thr
            100                 105                 110

Leu Val Thr Val Ser Ser
            115

<210> SEQ ID NO 58
<211> LENGTH: 111
<212> TYPE: PRT
<213> ORGANISM: Homo sapiens
<220> FEATURE:
<221> NAME/KEY: P2B-2G4 VL
<222> LOCATION: (1)..(111)

<400> SEQUENCE: 58

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe Val Val Phe Gly Gly Gly Thr Lys Leu Thr Val Leu
            100                 105                 110

<210> SEQ ID NO 59
<211> LENGTH: 354
<212> TYPE: DNA
<213> ORGANISM: Homo sapiens
<220> FEATURE:
<221> NAME/KEY: P2B-2G4 VHnu
<222> LOCATION: (1)..(354)

<400> SEQUENCE: 59
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagaggggca     300
gctatggttt ggcttgacta ctggggccag ggaaccctgg tcaccgtctc ctca           354

<210> SEQ ID NO 60
<211> LENGTH: 333
<212> TYPE: DNA
<213> ORGANISM: Homo sapiens
<220> FEATURE:
<221> NAME/KEY: P2B-2G4 VLnu
<222> LOCATION: (1)..(333)

<400> SEQUENCE: 60

```
cagtctgccc tgactcagcc tcgctcagtg tccgggtctc ctggacagtc agtcaccatc      60
tcctgcactg gaaccagcag tgatgttggt ggttataact atgtctcctg gtaccaacag     120
cacccaggca agcccccaa actcatgatt tatgatgtca gtaagcggcc ctcaggggtc      180
cctgatcgct tctctggctc caagtctggc aacacggcct ccctgaccat ctctgggctc     240
caggctgagg atgaggctga ttattactgc tgctcatatg caggcagcta cactttcgtg     300
gtattcggcg gagggaccaa gctgaccgtc cta                                   333
```

<210> SEQ ID NO 61
<211> LENGTH: 124
<212> TYPE: PRT
<213> ORGANISM: Homo sapiens
<220> FEATURE:
<221> NAME/KEY: P2B-2G11 VH
<222> LOCATION: (1)..(124)

<400> SEQUENCE: 61

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Gly Gly Ile Ile Gly Tyr Ala Asp Ser Val
    50                  55                  60

Lys Gly Arg Phe Thr Ile Ser Arg Asp Asn Ala Lys Thr Ser Leu Tyr
65                  70                  75                  80

Leu Gln Met Asn Ser Leu Lys Pro Glu Asp Thr Ala Leu Tyr Tyr Cys
                85                  90                  95

Ala Lys Val Ala Gly Arg Gly Asp Tyr Asp Tyr Tyr Gly Met Asp
            100                 105                 110

Val Trp Gly Gln Gly Thr Thr Val Thr Val Ser Ser
        115                 120

<210> SEQ ID NO 62
<211> LENGTH: 111
<212> TYPE: PRT
<213> ORGANISM: Homo sapiens
<220> FEATURE:
<221> NAME/KEY: P2B-2G11 VL
<222> LOCATION: (1)..(111)

<400> SEQUENCE: 62

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

```
Leu Ile Tyr Gly Asn Asn Arg Pro Ser Gly Val Pro Asp Arg Phe
         50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Val Phe Gly Gly Gly Thr Lys Leu Thr Val Leu
            100                 105                 110

<210> SEQ ID NO 63
<211> LENGTH: 372
<212> TYPE: DNA
<213> ORGANISM: Homo sapiens
<220> FEATURE:
<221> NAME/KEY: P2B-2G11 VHnu
<222> LOCATION: (1)..(372)

<400> SEQUENCE: 63
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga atggtggtat cataggctat      180
gcggactctg tgaagggccg attcaccatc tccagagaca cgccaagac ttccctgtat      240 ctgcaaatga acagtctgaa acctgaggac acggccttgt attactgtgc aaaagtcgcg     300
ggaagggggg attacgacta ctactacggt atggacgtct ggggccaagg gaccacggtc     360
accgtctcct ca                                                         372

<210> SEQ ID NO 64
<211> LENGTH: 333
<212> TYPE: DNA
<213> ORGANISM: Homo sapiens
<220> FEATURE:
<221> NAME/KEY: P2B-2G11 VLnu
<222> LOCATION: (1)..(333)

<400> SEQUENCE: 64
cagtctgtgc tgacgcagcc gccctcagtg tctggggccc cagggcagag ggtcaccatc      60
tcctgcactg ggagcagctc caacatcggg gcaggttatg atgtacactg gtaccagcaa     120
cttccaggaa cagcccccaa actcctcatc tatgggaaca acaatcggcc ctcaggggtc     180
cctgaccgat tctctggctc caagtctggc acctcagcct ccctggccat cactgggctc     240
caggctgagg atgaggctga ttattactgc cagtcctatg acagcagcct gagtggttcg     300
gtattcggcg gagggaccaa gctgaccgtc cta                                  333

<210> SEQ ID NO 65
<211> LENGTH: 8
<212> TYPE: PRT
<213> ORGANISM: Homo sapiens
<220> FEATURE:
<221> NAME/KEY: P2C-1A3 HCDR1
<222> LOCATION: (1)..(8)

<400> SEQUENCE: 65

Gly Phe Thr Phe Ser Asp Tyr Tyr
 1                5

<210> SEQ ID NO 66
<211> LENGTH: 8
<212> TYPE: PRT
<213> ORGANISM: Homo sapiens
```

```
<220> FEATURE:
<221> NAME/KEY: P2C-1A3 HCDR2
<222> LOCATION: (1)..(8)

<400> SEQUENCE: 66

Ile Ser Ser Ser Gly Ser Thr Ile
1               5

<210> SEQ ID NO 67
<211> LENGTH: 12
<212> TYPE: PRT
<213> ORGANISM: Homo sapiens
<220> FEATURE:
<221> NAME/KEY: P2C-1A3 HCDR3
<222> LOCATION: (1)..(12)

<400> SEQUENCE: 67

Ala Arg Asp Phe Ser His Gln Gln Leu Val Pro Ser
1               5                   10

<210> SEQ ID NO 68
<211> LENGTH: 6
<212> TYPE: PRT
<213> ORGANISM: Homo sapiens
<220> FEATURE:
<221> NAME/KEY: P2C-1A3 LCDR1
<222> LOCATION: (1)..(6)

<400> SEQUENCE: 68

Gln Gly Ile Ser Ser Tyr
1               5

<210> SEQ ID NO 69
<211> LENGTH: 4
<212> TYPE: PRT
<213> ORGANISM: Homo sapiens
<220> FEATURE:
<221> NAME/KEY: P2C-1A3 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 69

Ala Ala Ser Xaa
1

<210> SEQ ID NO 70
<211> LENGTH: 9
<212> TYPE: PRT
<213> ORGANISM: Homo sapiens
<220> FEATURE:
<221> NAME/KEY: P2C-1A3 LCDR3
<222> LOCATION: (1)..(9)

<400> SEQUENCE: 70

Gln Gln Leu Asn Ser Tyr Pro Leu Thr
1               5

<210> SEQ ID NO 71
<211> LENGTH: 119
<212> TYPE: PRT
<213> ORGANISM: Homo sapiens
<220> FEATURE:
<221> NAME/KEY: P2C-1A3 VH
<222> LOCATION: (1)..(119)

<400> SEQUENCE: 71
```

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ser His Gln Gln Leu Val Pro Ser Trp Gly Gln Gly
            100                 105                 110

Thr Leu Val Thr Val Ser Ser
            115
```

<210> SEQ ID NO 72
<211> LENGTH: 107
<212> TYPE: PRT
<213> ORGANISM: Homo sapiens
<220> FEATURE:
<221> NAME/KEY: P2C-1A3 VL
<222> LOCATION: (1)..(107)

<400> SEQUENCE: 72

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105
```

<210> SEQ ID NO 73
<211> LENGTH: 357
<212> TYPE: DNA
<213> ORGANISM: Homo sapiens
<220> FEATURE:
<221> NAME/KEY: P2C-1A3 VHnu
<222> LOCATION: (1)..(357)

<400> SEQUENCE: 73

| | |
|---|---:|
| caggtgcagc tggtggagtc tgggggaggc ttggtcaagc ctggagggtc cctgagactc | 60 |
| tcctgtgcag cctctggatt caccttcagt gactactaca tgagctggat ccgccaggct | 120 |
| ccagggaagg ggctggagtg ggtttcatac attagtagta gtggtagtac catatactac | 180 |
| gcagactctg tgaagggccg attcaccatc tccagggaca acgccaagaa ctcactgtat | 240 |
| ctgcaaatga acagcctgag agccgaggac acggctgtgt attactgtgc gagagatttt | 300 |
| tctcatcagc agctggtacc ttcctggggc cagggaaccc tggtcaccgt ctcctca | 357 |

<210> SEQ ID NO 74
<211> LENGTH: 321
<212> TYPE: DNA
<213> ORGANISM: Homo sapiens
<220> FEATURE:
<221> NAME/KEY: P2C-1A3 VLnu
<222> LOCATION: (1)..(321)

<400> SEQUENCE: 74

```
gacatccagt tgacccagtc tccatccttc ctgtctgcat ctgtaggaga cagagtcacc    60
atcacttgcc gggccagtca gggcattagc agttatttag cctggtatca gcaaaaacca   120
gggaaagccc ctaagctcct gatctatgct gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatagtt acccgctcac tttcggcgga   300
gggaccaagg tggagatcaa a                                              321
```

<210> SEQ ID NO 75
<211> LENGTH: 8
<212> TYPE: PRT
<213> ORGANISM: Homo sapiens
<220> FEATURE:
<221> NAME/KEY: P2C-1C8 HCDR1
<222> LOCATION: (1)..(8)

<400> SEQUENCE: 75

Gly Phe Thr Phe Arg Ser Tyr Gly
1               5

<210> SEQ ID NO 76
<211> LENGTH: 8
<212> TYPE: PRT
<213> ORGANISM: Homo sapiens
<220> FEATURE:
<221> NAME/KEY: P2C-1C8 HCDR2
<222> LOCATION: (1)..(8)

<400> SEQUENCE: 76

Ile Trp Tyr Asp Gly Ser Asn Lys
1               5

<210> SEQ ID NO 77
<211> LENGTH: 13
<212> TYPE: PRT
<213> ORGANISM: Homo sapiens
<220> FEATURE:
<221> NAME/KEY: P2C-1C8 HCDR3
<222> LOCATION: (1)..(13)

<400> SEQUENCE: 77

Ala Arg Asp Ile Glu Ile Val Val Val Asn Ile Asp Tyr
1               5                   10

<210> SEQ ID NO 78
<211> LENGTH: 11
<212> TYPE: PRT
<213> ORGANISM: Homo sapiens
<220> FEATURE:
<221> NAME/KEY: P2C-1C8 LCDR1
<222> LOCATION: (1)..(11)

<400> SEQUENCE: 78

Gln Ser Leu Val Tyr Ser Asp Gly Asn Thr Tyr
1               5                   10

<210> SEQ ID NO 79
<211> LENGTH: 4
<212> TYPE: PRT
<213> ORGANISM: Homo sapiens
<220> FEATURE:
<221> NAME/KEY: P2C-1C8 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 79

Lys Val Ser Xaa
1

<210> SEQ ID NO 80
<211> LENGTH: 9
<212> TYPE: PRT
<213> ORGANISM: Homo sapiens
<220> FEATURE:
<221> NAME/KEY: P2C-1C8 LCDR3
<222> LOCATION: (1)..(9)

<400> SEQUENCE: 80

Met Gln Gly Thr His Trp Pro Tyr Thr
1               5

<210> SEQ ID NO 81
<211> LENGTH: 120
<212> TYPE: PRT
<213> ORGANISM: Homo sapiens
<220> FEATURE:
<221> NAME/KEY: P2C-1C8 VH
<222> LOCATION: (1)..(120)

<400> SEQUENCE: 81

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Glu Ile Val Val Asn Ile Asp Tyr Trp Gly Gln
            100                 105                 110

Gly Thr Leu Val Thr Val Ser Ser
        115                 120

<210> SEQ ID NO 82
<211> LENGTH: 112
<212> TYPE: PRT
<213> ORGANISM: Homo sapiens
<220> FEATURE:
<221> NAME/KEY: P2C-1C8 VL
<222> LOCATION: (1)..(112)

<400> SEQUENCE: 82

-continued

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Ile Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110
```

<210> SEQ ID NO 83
<211> LENGTH: 360
<212> TYPE: DNA
<213> ORGANISM: Homo sapiens
<220> FEATURE:
<221> NAME/KEY: P2C-1C8 VHnu
<222> LOCATION: (1)..(360)

<400> SEQUENCE: 83

```
caggtgcagc tggtggagtc tgggggaggc gtggtccagc ctggggaggtc cctgagactc    60
tcctgtgcag cgtctggatt caccttcagg agctatggca tgcactgggt ccgccaggct   120
ccaggcaagg ggctggagtg ggtggcagtt atctggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagatata   300
gagatagtag tggtaaatat tgactactgg ggccagggaa ccctggtcac cgtctcctca   360
```

<210> SEQ ID NO 84
<211> LENGTH: 336
<212> TYPE: DNA
<213> ORGANISM: Homo sapiens
<220> FEATURE:
<221> NAME/KEY: P2C-1C8 VLnu
<222> LOCATION: (1)..(336)

<400> SEQUENCE: 84

```
gatgttgtga tgactcagtc tccactctcc ctgcccgtca cccttggaca gccggcctcc    60
atctcctgca ggtctagtca aagcctcgta tacagtgatg aaacacccta cttgaattgg   120
tttcagcaga ggccaggcca atctccaagg cgcctaattt ataaggtttc tatctgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
tacactttg ccaggggac caagctggag atcaaa                                336
```

<210> SEQ ID NO 85
<211> LENGTH: 8
<212> TYPE: PRT
<213> ORGANISM: Homo sapiens
<220> FEATURE:
<221> NAME/KEY: P2C-1C10 HCDR1
<222> LOCATION: (1)..(8)

<400> SEQUENCE: 85

Gly Gly Thr Phe Ser Ser Tyr Ala

```
1               5

<210> SEQ ID NO 86
<211> LENGTH: 8
<212> TYPE: PRT
<213> ORGANISM: Homo sapiens
<220> FEATURE:
<221> NAME/KEY: P2C-1C10 HCDR2
<222> LOCATION: (1)..(8)

<400> SEQUENCE: 86

Ile Ile Pro Ile Phe Gly Thr Ala
1               5

<210> SEQ ID NO 87
<211> LENGTH: 11
<212> TYPE: PRT
<213> ORGANISM: Homo sapiens
<220> FEATURE:
<221> NAME/KEY: P2C-1C10 HCDR3
<222> LOCATION: (1)..(11)

<400> SEQUENCE: 87

Ala Arg Val Val Thr Gly Tyr Tyr Phe Asp Tyr
1               5                   10

<210> SEQ ID NO 88
<211> LENGTH: 6
<212> TYPE: PRT
<213> ORGANISM: Homo sapiens
<220> FEATURE:
<221> NAME/KEY: P2C-1C10 LCDR1
<222> LOCATION: (1)..(6)

<400> SEQUENCE: 88

Gln Ser Val Ser Ser Tyr
1               5

<210> SEQ ID NO 89
<211> LENGTH: 4
<212> TYPE: PRT
<213> ORGANISM: Homo sapiens
<220> FEATURE:
<221> NAME/KEY: P2C-1C10 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 89

Asp Ala Ser Xaa
1

<210> SEQ ID NO 90
<211> LENGTH: 8
<212> TYPE: PRT
<213> ORGANISM: Homo sapiens
<220> FEATURE:
<221> NAME/KEY: P2C-1C10 LCDR3
<222> LOCATION: (1)..(8)

<400> SEQUENCE: 90

Gln Gln Arg Ser Asn Trp Pro Ser
1               5

<210> SEQ ID NO 91
<211> LENGTH: 118
```

```
<212> TYPE: PRT
<213> ORGANISM: Homo sapiens
<220> FEATURE:
<221> NAME/KEY: P2C-1C10 VH
<222> LOCATION: (1)..(118)

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ile Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Val Thr Gly Tyr Tyr Phe Asp Tyr Trp Gly Gln Gly Thr
            100                 105                 110

Leu Val Thr Val Ser Ser
        115

<210> SEQ ID NO 92
<211> LENGTH: 106
<212> TYPE: PRT
<213> ORGANISM: Homo sapiens
<220> FEATURE:
<221> NAME/KEY: P2C-1C10 VL
<222> LOCATION: (1)..(106)

<400> SEQUENCE: 92

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ser
                85                  90                  95

Phe Gly Gln Gly Thr Lys Leu Glu Ile Lys
            100                 105

<210> SEQ ID NO 93
<211> LENGTH: 354
<212> TYPE: DNA
<213> ORGANISM: Homo sapiens
<220> FEATURE:
<221> NAME/KEY: P2C-1C10 VHnu
<222> LOCATION: (1)..(354)

<400> SEQUENCE: 93
caggtgcagc tggtgcagtc tggggctgag gtgaagaagc ctgggtcctc ggtgaaggtc      60
tcctgcaagg cttctggagg caccttcagc agctatgcta tcatctgggt gcgacaggcc    120
```

```
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagagtggta     300
acggggtact actttgacta ctggggccag ggaaccctgg tcaccgtctc ctca           354
```

<210> SEQ ID NO 94
<211> LENGTH: 318
<212> TYPE: DNA
<213> ORGANISM: Homo sapiens
<220> FEATURE:
<221> NAME/KEY: P2C-1C10 VLnu
<222> LOCATION: (1)..(318)

<400> SEQUENCE: 94

```
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggccttcttt tggccagggg     300
accaagctgg agatcaaa                                                   318
```

<210> SEQ ID NO 95
<211> LENGTH: 8
<212> TYPE: PRT
<213> ORGANISM: Homo sapiens
<220> FEATURE:
<221> NAME/KEY: P2C-1D5 HCDR1
<222> LOCATION: (1)..(8)

<400> SEQUENCE: 95

Gly Phe Thr Phe Ser Ser Phe Ala
1               5

<210> SEQ ID NO 96
<211> LENGTH: 8
<212> TYPE: PRT
<213> ORGANISM: Homo sapiens
<220> FEATURE:
<221> NAME/KEY: P2C-1D5 HCDR2
<222> LOCATION: (1)..(8)

<400> SEQUENCE: 96

Ile Ser Gly Ser Gly Gly Ser Thr
1               5

<210> SEQ ID NO 97
<211> LENGTH: 14
<212> TYPE: PRT
<213> ORGANISM: Homo sapiens
<220> FEATURE:
<221> NAME/KEY: P2C-1D5 HCDR3
<222> LOCATION: (1)..(14)

<400> SEQUENCE: 97

Ala Lys Asp Pro Asp Gly Ser Gly Ser Trp Tyr Phe Asp Tyr
1               5                   10

<210> SEQ ID NO 98
<211> LENGTH: 6
<212> TYPE: PRT
<213> ORGANISM: Homo sapiens
<220> FEATURE:

<221> NAME/KEY: P2C-1D5 LCDR1
<222> LOCATION: (1)..(6)

<400> SEQUENCE: 98

Asn Ile Gly Ser Lys Ser
1               5

<210> SEQ ID NO 99
<211> LENGTH: 4
<212> TYPE: PRT
<213> ORGANISM: Homo sapiens
<220> FEATURE:
<221> NAME/KEY: P2C-1D5 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 99

Tyr Asp Ser Xaa
1

<210> SEQ ID NO 100
<211> LENGTH: 11
<212> TYPE: PRT
<213> ORGANISM: Homo sapiens
<220> FEATURE:
<221> NAME/KEY: P2C-1D5 LCDR3
<222> LOCATION: (1)..(11)

<400> SEQUENCE: 100

Gln Val Trp Asp Ser Ser Ser Asp His His Val
1               5                   10

<210> SEQ ID NO 101
<211> LENGTH: 121
<212> TYPE: PRT
<213> ORGANISM: Homo sapiens
<220> FEATURE:
<221> NAME/KEY: P2C-1D5 VH
<222> LOCATION: (1)..(121)

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Asp Gly Ser Gly Ser Trp Tyr Phe Asp Tyr Trp Gly
            100                 105                 110

Gln Gly Thr Leu Val Thr Val Ser Ser
        115                 120

<210> SEQ ID NO 102
<211> LENGTH: 108
<212> TYPE: PRT

```
<213> ORGANISM: Homo sapiens
<220> FEATURE:
<221> NAME/KEY: P2C-1D5 VL
<222> LOCATION: (1)..(108)

<400> SEQUENCE: 102

Ser Tyr Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

His Val Phe Gly Thr Gly Thr Lys Val Thr Val Leu
            100                 105

<210> SEQ ID NO 103
<211> LENGTH: 363
<212> TYPE: DNA
<213> ORGANISM: Homo sapiens
<220> FEATURE:
<221> NAME/KEY: P2C-1D5 VHnu
<222> LOCATION: (1)..(363)

<400> SEQUENCE: 103
gaggtgcagc tggtggagtc tgggggaggc ttggtacagc ctggggggtc cctgagactc       60
tcctgtgcag cctctggatt cacctttagc agctttgcca tgagctgggt ccgccaggct      120
ccagggaagg gctggagtg gtctcagct attagtggta gtggtggtag cacatactac        180
gcagactccg tgaagggccg gttcaccatc tccagagaca attccaagaa cacgctgtat      240
ttgcaaatga acagcctgag agccgaggac acggccgtat attactgtgc gaaagatccg      300
gatggttcgg ggagttggta ctttgactac tggggccagg gaaccctggt caccgtctcc      360
tca                                                                    363

<210> SEQ ID NO 104
<211> LENGTH: 324
<212> TYPE: DNA
<213> ORGANISM: Homo sapiens
<220> FEATURE:
<221> NAME/KEY: P2C-1D5 VLnu
<222> LOCATION: (1)..(324)

<400> SEQUENCE: 104
tcctatgtgc tgactcagcc accctcagtg tcagtggccc caggaaagac ggccaggatt       60
acctgtgggg gaaacaacat tggaagtaaa agtgtgcact ggtaccagca gaagccaggc      120
caggcccctg tgctggtcat ctattatgat agcgaccggc cctcagggat ccctgagcga      180
ttctctggct ccaactctgg gaacaccgcc accctgacca tcagcagggt cgaagccggg      240
gatgaggccg actattactg tcaggtgtgg gatagtagta gtgatcatca tgtcttcgga      300
actgggacca aggtcaccgt ccta                                             324

<210> SEQ ID NO 105
<211> LENGTH: 8
```

```
<212> TYPE: PRT
<213> ORGANISM: Homo sapiens
<220> FEATURE:
<221> NAME/KEY: P2C-1F11 HCDR1
<222> LOCATION: (1)..(8)

<400> SEQUENCE: 105

Gly Ile Thr Val Ser Ser Asn Tyr
1               5

<210> SEQ ID NO 106
<211> LENGTH: 7
<212> TYPE: PRT
<213> ORGANISM: Homo sapiens
<220> FEATURE:
<221> NAME/KEY: P2C-1F11 HCDR2
<222> LOCATION: (1)..(7)

<400> SEQUENCE: 106

Ile Tyr Ser Gly Gly Ser Thr
1               5

<210> SEQ ID NO 107
<211> LENGTH: 11
<212> TYPE: PRT
<213> ORGANISM: Homo sapiens
<220> FEATURE:
<221> NAME/KEY: P2C-1F11 HCDR3
<222> LOCATION: (1)..(11)

<400> SEQUENCE: 107

Ala Arg Asp Leu Val Val Tyr Gly Met Asp Val
1               5                   10

<210> SEQ ID NO 108
<211> LENGTH: 7
<212> TYPE: PRT
<213> ORGANISM: Homo sapiens
<220> FEATURE:
<221> NAME/KEY: P2C-1F11 LCDR1
<222> LOCATION: (1)..(7)

<400> SEQUENCE: 108

Gln Ser Val Ser Ser Ser Tyr
1               5

<210> SEQ ID NO 109
<211> LENGTH: 4
<212> TYPE: PRT
<213> ORGANISM: Homo sapiens
<220> FEATURE:
<221> NAME/KEY: P2C-1F11 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 109

Gly Ala Ser Xaa
1

<210> SEQ ID NO 110
<211> LENGTH: 8
<212> TYPE: PRT
<213> ORGANISM: Homo sapiens
<220> FEATURE:
<221> NAME/KEY: P2C-1F11 LCDR3
<222> LOCATION: (1)..(8)
```

```
<400> SEQUENCE: 110

Gln Gln Tyr Gly Ser Ser Pro Thr
1               5

<210> SEQ ID NO 111
<211> LENGTH: 117
<212> TYPE: PRT
<213> ORGANISM: Homo sapiens
<220> FEATURE:
<221> NAME/KEY: P2C-1F11 VH
<222> LOCATION: (1)..(117)

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Val Ser Ser Asn
            20                  25                  30

Tyr Met Asn Trp Val Arg Gln Ala Pro Gly Lys Gly Leu Glu Trp Val
        35                  40                  45

Ser Leu Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr His Cys Ala
                85                  90                  95

Arg Asp Leu Val Val Tyr Gly Met Asp Val Trp Gly Gln Gly Thr Thr
            100                 105                 110

Val Thr Val Ser Ser
        115

<210> SEQ ID NO 112
<211> LENGTH: 107
<212> TYPE: PRT
<213> ORGANISM: Homo sapiens
<220> FEATURE:
<221> NAME/KEY: P2C-1F11 VL
<222> LOCATION: (1)..(107)

<400> SEQUENCE: 112

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gln Gly Thr Lys Leu Glu Ile Lys
            100                 105

<210> SEQ ID NO 113
<211> LENGTH: 351
<212> TYPE: DNA
<213> ORGANISM: Homo sapiens
<220> FEATURE:
```

<221> NAME/KEY: P2C-1F11 VHnu
<222> LOCATION: (1)..(351)

<400> SEQUENCE: 113

```
gaggtgcagc tggtggagtc tgggggaggc ttggtccagc ctgggggtc cctgagactc      60
tcctgtgcag cctctggaat caccgtcagt agcaactaca tgaactgggt ccgccaggct    120
ccagggaagg gctggagtg gtctcactt atttatagcg gtggtagcac atactacgca      180
gactccgtga aggcagatt caccatctcc agagacaatt ccaagaacac gttgtatctt     240
caaatgaaca gcctgagagc cgaggacacg gctgtgtatc actgtgcgag agatctggtg    300
gtatacggta tggacgtctg gggccaaggg accacggtca ccgtctcctc a             351
```

<210> SEQ ID NO 114
<211> LENGTH: 321
<212> TYPE: DNA
<213> ORGANISM: Homo sapiens
<220> FEATURE:
<221> NAME/KEY: P2C-1F11 VLnu
<222> LOCATION: (1)..(321)

<400> SEQUENCE: 114

```
gaaattgtgt tgacgcagtc tccaggcacc ctgtctttgt ctccagggga agagccacc      60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacccac ttttggccag    300
gggaccaagc tggagatcaa a                                              321
```

<210> SEQ ID NO 115
<211> LENGTH: 330
<212> TYPE: PRT
<213> ORGANISM: Homo sapiens
<220> FEATURE:
<221> NAME/KEY: Amino acid sequence of heavy chain constant region
<222> LOCATION: (1)..(330)

<400> SEQUENCE: 115

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

```
                145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 116
<211> LENGTH: 106
<212> TYPE: PRT
<213> ORGANISM: Homo sapiens
<220> FEATURE:
<221> NAME/KEY: Amino acid sequence of lambda light chain constant
      region
<222> LOCATION: (1)..(106)

<400> SEQUENCE: 116

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 117
<211> LENGTH: 107
<212> TYPE: PRT
<213> ORGANISM: Homo sapiens
<220> FEATURE:
<221> NAME/KEY: Amino acid sequence of appa light chain constant region
<222> LOCATION: (1)..(107)

<400> SEQUENCE: 117
```

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 118
<211> LENGTH: 990
<212> TYPE: DNA
<213> ORGANISM: Homo sapiens
<220> FEATURE:
<221> NAME/KEY: Nucleic acid sequence of heavy chain constant region
<222> LOCATION: (1)..(990)

<400> SEQUENCE: 118
gcgtcgacca agggcccatc ggtcttcccc ctggcaccct cctccaagag cacctctggg      60
ggcacagcgg ccctgggctg cctggtcaag gactacttcc ccgaacccgt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990

<210> SEQ ID NO 119
<211> LENGTH: 318
<212> TYPE: DNA
<213> ORGANISM: Homo sapiens
<220> FEATURE:
<221> NAME/KEY: Nucleic acid sequence of lambda light chain constant
       region
<222> LOCATION: (1)..(318)

<400> SEQUENCE: 119
ggtcagccca aggctgcccc ctcggtcact ctgttcccac cctcgagtga ggagcttcaa      60

```
gccaacaagg ccacactggt gtgtctcata agtgacttct acccgggagc cgtgacagtg    120
gcctggaagg cagatagcag ccccgtcaag gcgggagtgg agaccaccac accctccaaa    180
caaagcaaca acaagtacgc ggccagcagc tacctgagcc tgacgcctga gcagtggaag    240
tcccacagaa gctacagctg ccaggtcacg catgaaggga gcaccgtgga gaagacagtg    300
gcccctacag aatgttca                                                  318

<210> SEQ ID NO 120
<211> LENGTH: 321
<212> TYPE: DNA
<213> ORGANISM: Homo sapiens
<220> FEATURE:
<221> NAME/KEY: Nucleic acid sequence of kappa light chain constant
      region
<222> LOCATION: (1)..(321)

<400> SEQUENCE: 120
cgtacggtgg ctgcaccatc tgtcttcatc ttcccgccat ctgatgagca gttgaaatct     60
ggaactgcct ctgttgtgtg cctgctgaat aacttctacc ccagagaagc caaagtgcag    120
tggaaggtgg acaacgccct gcagagcgga aacagccagg aaagcgtgac agagcaggat    180
tccaaggatt ccacatacag cctgagcagc acactgacac tgtccaaggc cgactacgag    240
aagcacaagg tgtacgcctg cgaagtgaca caccagggac tgtcctcccc tgtgacaaag    300
agcttcaaca gaggagaatg c                                              321

<210> SEQ ID NO 121
<211> LENGTH: 1211
<212> TYPE: PRT
<213> ORGANISM: Artificial Sequence
<220> FEATURE:
<223> OTHER INFORMATION: Amino acid sequence of the extracellular domain
      of S protein of SARS-CoV-2

<400> SEQUENCE: 121

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175
```

```
Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
```

```
                595                 600                 605
Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
                675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
                755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
                915                 920                 925

Ser Ala Ile Gly Lys Ile Gln Asp Ser Leu Ser Ser Thr Ala Ser Ala
                930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
                995                 1000                1005

Thr Gln Gln Leu Ile Arg Ala Ala Glu Ile Arg Ala Ser Ala Asn
            1010                1015                1020
```

```
Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys
    1205                1210

<210> SEQ ID NO 122
<211> LENGTH: 1195
<212> TYPE: PRT
<213> ORGANISM: Artificial Sequence
<220> FEATURE:
<223> OTHER INFORMATION: Amino acid sequence of the extracellular domain
      of S protein of SARS-CoV

<400> SEQUENCE: 122

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
            35                  40                  45

Ser Asp Thr Leu Tyr Leu Thr Gln Asp Leu Phe Leu Pro Phe Tyr Ser
        50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
```

```
            145                 150                 155                 160
        Phe Glu Tyr Ile Ser Asp Ala Phe Ser Leu Asp Val Ser Glu Lys Ser
                        165                 170                 175
        Gly Asn Phe Lys His Leu Arg Glu Phe Val Phe Lys Asn Lys Asp Gly
                        180                 185                 190
        Phe Leu Tyr Val Tyr Lys Gly Tyr Gln Pro Ile Asp Val Val Arg Asp
                        195                 200                 205
        Leu Pro Ser Gly Phe Asn Thr Leu Lys Pro Ile Phe Lys Leu Pro Leu
        210                 215                 220
        Gly Ile Asn Ile Thr Asn Phe Arg Ala Ile Leu Thr Ala Phe Ser Pro
        225                 230                 235                 240
        Ala Gln Asp Ile Trp Gly Thr Ser Ala Ala Tyr Phe Val Gly Tyr
                        245                 250                 255
        Leu Lys Pro Thr Thr Phe Met Leu Lys Tyr Asp Glu Asn Gly Thr Ile
                        260                 265                 270
        Thr Asp Ala Val Asp Cys Ser Gln Asn Pro Leu Ala Glu Leu Lys Cys
                        275                 280                 285
        Ser Val Lys Ser Phe Glu Ile Asp Lys Gly Ile Tyr Gln Thr Ser Asn
                        290                 295                 300
        Phe Arg Val Val Pro Ser Gly Asp Val Val Arg Phe Pro Asn Ile Thr
        305                 310                 315                 320
        Asn Leu Cys Pro Phe Gly Glu Val Phe Asn Ala Thr Lys Phe Pro Ser
                        325                 330                 335
        Val Tyr Ala Trp Glu Arg Lys Lys Ile Ser Asn Cys Val Ala Asp Tyr
                        340                 345                 350
        Ser Val Leu Tyr Asn Ser Thr Phe Phe Ser Thr Phe Lys Cys Tyr Gly
                        355                 360                 365
        Val Ser Ala Thr Lys Leu Asn Asp Leu Cys Phe Ser Asn Val Tyr Ala
                        370                 375                 380
        Asp Ser Phe Val Val Lys Gly Asp Asp Val Arg Gln Ile Ala Pro Gly
        385                 390                 395                 400
        Gln Thr Gly Val Ile Ala Asp Tyr Asn Tyr Lys Leu Pro Asp Asp Phe
                        405                 410                 415
        Met Gly Cys Val Leu Ala Trp Asn Thr Arg Asn Ile Asp Ala Thr Ser
                        420                 425                 430
        Thr Gly Asn Tyr Asn Tyr Lys Tyr Arg Tyr Leu Arg His Gly Lys Leu
                        435                 440                 445
        Arg Pro Phe Glu Arg Asp Ile Ser Asn Val Pro Phe Ser Pro Asp Gly
        450                 455                 460
        Lys Pro Cys Thr Pro Pro Ala Leu Asn Cys Tyr Trp Pro Leu Asn Asp
        465                 470                 475                 480
        Tyr Gly Phe Tyr Thr Thr Thr Gly Ile Gly Tyr Gln Pro Tyr Arg Val
                        485                 490                 495
        Val Val Leu Ser Phe Glu Leu Leu Asn Ala Pro Ala Thr Val Cys Gly
                        500                 505                 510
        Pro Lys Leu Ser Thr Asp Leu Ile Lys Asn Gln Cys Val Asn Phe Asn
        515                 520                 525
        Phe Asn Gly Leu Thr Gly Thr Gly Val Leu Thr Pro Ser Ser Lys Arg
                        530                 535                 540
        Phe Gln Pro Phe Gln Gln Phe Gly Arg Asp Val Ser Asp Phe Thr Asp
        545                 550                 555                 560
        Ser Val Arg Asp Pro Lys Thr Ser Glu Ile Leu Asp Ile Ser Pro Cys
                        565                 570                 575
```

-continued

```
Ala Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
            595                 600                 605

Ala Ile His Ala Asp Gln Leu Thr Pro Ala Trp Arg Ile Tyr Ser Thr
610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
            645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
            725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
            770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
            930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990
```

Gln Leu Ile Arg Ala Ala Glu Ile Arg Ala Ser Ala Asn Leu Ala Ala
            995                 1000                1005

Thr Lys Met Ser Glu Cys Val Leu Gly Gln Ser Lys Arg Val Asp
    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro
    1190                1195

<210> SEQ ID NO 123
<211> LENGTH: 1290
<212> TYPE: PRT
<213> ORGANISM: Artificial Sequence
<220> FEATURE:
<223> OTHER INFORMATION: Amino acid sequence of the extracellular domain
      of S protein of MERS-CoV

<400> SEQUENCE: 123

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

```
Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
            165                 170                 175

Gly Thr Leu Leu Arg Ala Phe Tyr Cys Ile Leu Glu Pro Arg Ser Gly
        180                 185                 190

Asn His Cys Pro Ala Gly Asn Ser Tyr Thr Ser Phe Ala Thr Tyr His
    195                 200                 205

Thr Pro Ala Thr Asp Cys Ser Asp Gly Asn Tyr Asn Arg Asn Ala Ser
210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
        260                 265                 270

Leu Tyr Gly Gly Asn Met Phe Gln Phe Ala Thr Leu Pro Val Tyr Asp
    275                 280                 285

Thr Ile Lys Tyr Tyr Ser Ile Ile Pro His Ser Ile Arg Ser Ile Gln
290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
        340                 345                 350

Ser Phe Asp Val Glu Ser Gly Val Tyr Ser Val Ser Ser Phe Glu Ala
    355                 360                 365

Lys Pro Ser Gly Ser Val Val Glu Gln Ala Glu Gly Val Glu Cys Asp
370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
        420                 425                 430

Ile Ala Ser Asn Cys Tyr Ser Ser Leu Ile Leu Asp Tyr Phe Ser Tyr
    435                 440                 445

Pro Leu Ser Met Lys Ser Asp Leu Ser Val Ser Ser Ala Gly Pro Ile
450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
        500                 505                 510

Glu Val Pro Gln Leu Val Asn Ala Asn Gln Tyr Ser Pro Cys Val Ser
    515                 520                 525

Ile Val Pro Ser Thr Val Trp Glu Asp Gly Asp Tyr Tyr Arg Lys Gln
530                 535                 540

Leu Ser Pro Leu Glu Gly Gly Gly Trp Leu Val Ala Ser Gly Ser Thr
545                 550                 555                 560
```

```
Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
            610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
            645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
            675                 680                 685

Tyr Ser Arg Ser Thr Arg Ser Met Leu Lys Arg Arg Asp Ser Thr Tyr
            690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
            725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
            755                 760                 765

Gln Val Asp Gln Leu Asn Ser Ser Tyr Phe Lys Leu Ser Ile Pro Thr
            770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
            805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
            835                 840                 845

Leu Phe Ala Ser Val Lys Ser Ser Gln Ser Ser Pro Ile Ile Pro Gly
            850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
            885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
            915                 920                 925

Val Ala Gly Tyr Lys Val Leu Pro Pro Leu Met Asp Val Asn Met Glu
930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
            965                 970                 975

Phe Tyr Arg Leu Asn Gly Val Gly Ile Thr Gln Gln Val Leu Ser Glu
```

```
                980             985             990
Asn Gln Lys Leu Ile Ala Asn Lys Phe Asn Gln Ala Leu Gly Ala Met
            995                 1000                1005

Gln Thr Gly Phe Thr Thr Thr Asn Glu Ala Phe Gln Lys Val Gln
    1010                1015                1020

Asp Ala Val Asn Asn Asn Ala Gln Ala Leu Ser Lys Leu Ala Ser
    1025                1030                1035

Glu Leu Ser Asn Thr Phe Gly Ala Ile Ser Ala Ser Ile Gly Asp
    1040                1045                1050

Ile Ile Gln Arg Leu Asp Val Leu Glu Gln Asp Ala Gln Ile Asp
    1055                1060                1065

Arg Leu Ile Asn Gly Arg Leu Thr Thr Leu Asn Ala Phe Val Ala
    1070                1075                1080

Gln Gln Leu Val Arg Ser Glu Ser Ala Ala Leu Ser Ala Gln Leu
    1085                1090                1095

Ala Lys Asp Lys Val Asn Glu Cys Val Lys Ala Gln Ser Lys Arg
    1100                1105                1110

Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro Gln Val Thr Tyr Gln Asn Ile Ser Thr Asn Leu
    1205                1210                1215

Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr
    1280                1285                1290

<210> SEQ ID NO 124
<211> LENGTH: 222
<212> TYPE: PRT
<213> ORGANISM: Artificial Sequence
<220> FEATURE:
<223> OTHER INFORMATION: Amino acid sequence of the spike protein RBD of
      SARS-CoV

<400> SEQUENCE: 124

Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30
```

```
Tyr Ala Trp Glu Arg Lys Lys Ile Ser Asn Cys Val Ala Asp Tyr Ser
            35                  40                  45

Val Leu Tyr Asn Ser Thr Phe Phe Ser Thr Phe Lys Cys Tyr Gly Val
 50                  55                  60

Ser Ala Thr Lys Leu Asn Asp Leu Cys Phe Ser Asn Val Tyr Ala Asp
 65                  70                  75                  80

Ser Phe Val Val Lys Gly Asp Asp Val Arg Gln Ile Ala Pro Gly Gln
                 85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
            115                 120                 125

Gly Asn Tyr Asn Tyr Lys Tyr Arg Tyr Leu Arg His Gly Lys Leu Arg
            130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
                165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
            195                 200                 205

Lys Leu Ser Thr Asp Leu Ile Lys Asn Gln Cys Val Asn Phe
            210                 215                 220

<210> SEQ ID NO 125
<211> LENGTH: 666
<212> TYPE: DNA
<213> ORGANISM: Artificial Sequence
<220> FEATURE:
<223> OTHER INFORMATION: Nucleic acid sequence of the spike protein RBD
      of SARS-CoV

<400> SEQUENCE: 125
cgggtggtgc ccagcggcga cgtggtgcgg ttccccaaca tcaccaacct gtgcccttc      60 ggcgaggtgt tcaacgccac caagttcccc agcgtgtacg cctgggagcg gaagaagatc    120
agcaactgcg tggccgacta cagcgtgctg tacaacagca ccttcttcag caccttcaag    180
tgctacggcg tgagcgccac caagctgaac gacctgtgct tcagcaacgt gtacgccgac    240
agcttcgtgg tgaagggcga cgacgtgcgg cagatcgccc ccggccagac cggcgtgatc    300
gccgactaca actacaagct gcccgacgac ttcatgggct gcgtgctggc ctggaacacc    360
cggaacatcg acgccaccag caccggcaac tacaactaca gtaccggta cctgcggcac     420 ggcaagctgc ggcccttcga gcgggacatc agcaacgtgc cttcagccc cgacggcaag     480 ccctgcaccc ccccgccct gaactgctac tggcccctga cgactacgg cttctacacc      540 actaccggca tcggctacca gcctaccgg gtggtggtgc tgagcttcga gctgctgaac     600
gcccccgcca ccgtgtgcgg ccccaagctg agcaccgacc tgatcaagaa ccagtgcgtg    660
aacttc                                                              666

<210> SEQ ID NO 126
<211> LENGTH: 208
<212> TYPE: PRT
<213> ORGANISM: Artificial Sequence
<220> FEATURE:
<223> OTHER INFORMATION: Amino acid sequence of the spike protein RBD of
      MERS-CoV
```

<400> SEQUENCE: 126

Val Glu Cys Asp Phe Ser Pro Leu Leu Ser Gly Thr Pro Pro Gln Val
1               5                   10                  15

Tyr Asn Phe Lys Arg Leu Val Phe Thr Asn Cys Asn Tyr Asn Leu Thr
            20                  25                  30

Lys Leu Leu Ser Leu Phe Ser Val Asn Asp Phe Thr Cys Ser Gln Ile
        35                  40                  45

Ser Pro Ala Ala Ile Ala Ser Asn Cys Tyr Ser Ser Leu Ile Leu Asp
    50                  55                  60

Tyr Phe Ser Tyr Pro Leu Ser Met Lys Ser Asp Leu Ser Val Ser Ser
65                  70                  75                  80

Ala Gly Pro Ile Ser Gln Phe Asn Tyr Lys Gln Ser Phe Ser Asn Pro
                85                  90                  95

Thr Cys Leu Ile Leu Ala Thr Val Pro His Asn Leu Thr Thr Ile Thr
            100                 105                 110

Lys Pro Leu Lys Tyr Ser Tyr Ile Asn Lys Cys Ser Arg Leu Leu Ser
        115                 120                 125

Asp Asp Arg Thr Glu Val Pro Gln Leu Val Asn Ala Asn Gln Tyr Ser
    130                 135                 140

Pro Cys Val Ser Ile Val Pro Ser Thr Val Trp Glu Asp Gly Asp Tyr
145                 150                 155                 160

Tyr Arg Lys Gln Leu Ser Pro Leu Glu Gly Gly Gly Trp Leu Val Ala
                165                 170                 175

Ser Gly Ser Thr Val Ala Met Thr Glu Gln Leu Gln Met Gly Phe Gly
            180                 185                 190

Ile Thr Val Gln Tyr Gly Thr Asp Thr Asn Ser Val Cys Pro Lys Leu
        195                 200                 205

<210> SEQ ID NO 127
<211> LENGTH: 624
<212> TYPE: DNA
<213> ORGANISM: Artificial Sequence
<220> FEATURE:
<223> OTHER INFORMATION: Nucleic acid sequence of the spike protein RBD
      of MERS-CoV

<400> SEQUENCE: 127
gtggagtgtg acttcagccc actgctgtct ggcacacctc cacaggtcta caacttcaag      60
agactggtgt tcaccaactg taactacaac ctgaccaaac tgctgtccct gttctctgtg     120
aatgacttca cttgtagcca gattagccct gctgccattg ccagcaactg ttactcctcc     180
ctgattctgg actacttctc ctacccactg agtatgaagt ctgacctgtc tgtgtcctct     240
gctggaccaa tcagccagtt caactacaag cagtccttca gcaacccaac ttgtctgatt     300
ctggctacag tgccacacaa cctgaccacc atcaccaagc cactgaaata ctcctacatc     360
aacaagtgta gcagactgct gtctgatgac aggacagagg tgccacaact agtgaatgcc     420
aaccaataca gcccatgtgt gagcattgtg ccaagcacag tgggagga tggagactac      480 tacaggaagc aacttagccc attggaggga ggaggctggc tggtggcatc tggcagcaca     540
gtggctatga cagaacaact ccaaatgggc tttggcatca cagtccaata tggcacagac     600
accaactctg tgtgtccaaa attg                                             624

<210> SEQ ID NO 128
<211> LENGTH: 223
<212> TYPE: PRT

<213> ORGANISM: Artificial Sequence
<220> FEATURE:
<223> OTHER INFORMATION: Amino acid sequence of the spike protein RBD of SARS-CoV-2

<400> SEQUENCE: 128

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220
```

<210> SEQ ID NO 129
<211> LENGTH: 669
<212> TYPE: DNA
<213> ORGANISM: Artificial Sequence
<220> FEATURE:
<223> OTHER INFORMATION: Nucleic acid sequence of the spike protein RBD of SARS-CoV-2

<400> SEQUENCE: 129

```
cgcgtgcagc ccaccgagag catcgtgcgc ttccccaaca tcaccaacct gtgccccttc     60
ggcgaggtgt tcaacgccac ccgcttcgcc agcgtgtacg cctggaaccg caagcgcatc    120
agcaactgcg tggccgacta cagcgtgctg tacaacagcg ccagcttcag caccttcaag    180
tgctacggcg tgagccccac caagctgaac gacctgtgct tcaccaacgt gtacgccgac    240
agcttcgtga tccgcggcga cgaggtgcgc cagatcgccc ccggccagac cggcaagatc    300
gccgactaca actacaagct gcccgacgac ttcaccggct gcgtgatcgc ctggaacagc    360
aacaacctgg acagcaaggt gggcggcaac tacaactacc tgtaccgcct gttccgcaag    420
agcaacctga agcccttcga gcgcgacatc agcaccgaga tctaccaggc cggcagcacc    480
ccctgcaacg gcgtggaggg cttcaactgc tacttccccc tgcagagcta cggcttccag    540
cccaccaacg gcgtgggcta ccagccctac cgcgtggtgg tgctgagctt cgagctgctg    600
```

```
cacgccccccg ccaccgtgtg cggccccaag aagagcacca acctggtgaa gaacaagtgc    660
gtgaacttc                                                             669
```

<210> SEQ ID NO 130
<211> LENGTH: 19
<212> TYPE: PRT
<213> ORGANISM: Artificial Sequence
<220> FEATURE:
<223> OTHER INFORMATION: Signal peptide

<400> SEQUENCE: 130

```
Met Gly Trp Ser Cys Ile Ile Leu Phe Leu Val Ala Thr Ala Thr Gly
1               5                   10                  15

Val His Ser
```

<210> SEQ ID NO 131
<211> LENGTH: 19
<212> TYPE: PRT
<213> ORGANISM: Artificial Sequence
<220> FEATURE:
<223> OTHER INFORMATION: Signal peptide

<400> SEQUENCE: 131

```
Met Gly Trp Ser Cys Ile Ile Leu Phe Leu Val Ala Thr Ala Thr Gly
1               5                   10                  15

Ser Trp Ala
```

<210> SEQ ID NO 132
<211> LENGTH: 6
<212> TYPE: PRT
<213> ORGANISM: Artificial Sequence
<220> FEATURE:
<223> OTHER INFORMATION: 6XHis Tag

<400> SEQUENCE: 132

```
His His His His His His
1               5
```

<210> SEQ ID NO 133
<211> LENGTH: 10
<212> TYPE: PRT
<213> ORGANISM: Artificial Sequence
<220> FEATURE:
<223> OTHER INFORMATION: Tag

<400> SEQUENCE: 133

```
Met Ser Tyr Tyr His His His His His His
1               5                   10
```

<210> SEQ ID NO 134
<211> LENGTH: 1281
<212> TYPE: PRT
<213> ORGANISM: Artificial Sequence
<220> FEATURE:
<223> OTHER INFORMATION: Amino acid sequence of full length S protein of
      SARS-CoV-2

<400> SEQUENCE: 134

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
```

```
            35                  40                  45
His Ser Thr Gln Asp Leu Phe Leu Pro Phe Phe Ser Asn Val Thr Trp
 50                  55                  60
Phe His Ala Ile His Val Ser Gly Thr Asn Gly Thr Lys Arg Phe Asp
 65                  70                  75                  80
Asn Pro Val Leu Pro Phe Asn Asp Gly Val Tyr Phe Ala Ser Thr Glu
                 85                  90                  95
Lys Ser Asn Ile Ile Arg Gly Trp Ile Phe Gly Thr Thr Leu Asp Ser
                100                 105                 110
Lys Thr Gln Ser Leu Leu Ile Val Asn Asn Ala Thr Asn Val Val Ile
                115                 120                 125
Lys Val Cys Glu Phe Gln Phe Cys Asn Asp Pro Phe Leu Gly Val Tyr
        130                 135                 140
Tyr His Lys Asn Asn Lys Ser Trp Met Glu Ser Glu Phe Arg Val Tyr
145                 150                 155                 160
Ser Ser Ala Asn Asn Cys Thr Phe Glu Tyr Val Ser Gln Pro Phe Leu
                165                 170                 175
Met Asp Leu Glu Gly Lys Gln Gly Asn Phe Lys Asn Leu Arg Glu Phe
        180                 185                 190
Val Phe Lys Asn Ile Asp Gly Tyr Phe Lys Ile Tyr Ser Lys His Thr
        195                 200                 205
Pro Ile Asn Leu Val Arg Asp Leu Pro Gln Gly Phe Ser Ala Leu Glu
210                 215                 220
Pro Leu Val Asp Leu Pro Ile Gly Ile Asn Ile Thr Arg Phe Gln Thr
225                 230                 235                 240
Leu Leu Ala Leu His Arg Ser Tyr Leu Thr Pro Gly Asp Ser Ser Ser
                245                 250                 255
Gly Trp Thr Ala Gly Ala Ala Ala Tyr Tyr Val Gly Tyr Leu Gln Pro
                260                 265                 270
Arg Thr Phe Leu Leu Lys Tyr Asn Glu Asn Gly Thr Ile Thr Asp Ala
        275                 280                 285
Val Asp Cys Ala Leu Asp Pro Leu Ser Glu Thr Lys Cys Thr Leu Lys
        290                 295                 300
Ser Phe Thr Val Glu Lys Gly Ile Tyr Gln Thr Ser Asn Phe Arg Val
305                 310                 315                 320
Gln Pro Thr Glu Ser Ile Val Arg Phe Pro Asn Ile Thr Asn Leu Cys
                325                 330                 335
Pro Phe Gly Glu Val Phe Asn Ala Thr Arg Phe Ala Ser Val Tyr Ala
        340                 345                 350
Trp Asn Arg Lys Arg Ile Ser Asn Cys Val Ala Asp Tyr Ser Val Leu
        355                 360                 365
Tyr Asn Ser Ala Ser Phe Ser Thr Phe Lys Cys Tyr Gly Val Ser Pro
        370                 375                 380
Thr Lys Leu Asn Asp Leu Cys Phe Thr Asn Val Tyr Ala Asp Ser Phe
385                 390                 395                 400
Val Ile Arg Gly Asp Glu Val Arg Gln Ile Ala Pro Gly Gln Thr Gly
                405                 410                 415
Lys Ile Ala Asp Tyr Asn Tyr Lys Leu Pro Asp Asp Phe Thr Gly Cys
        420                 425                 430
Val Ile Ala Trp Asn Ser Asn Asn Leu Asp Ser Lys Val Gly Gly Asn
        435                 440                 445
Tyr Asn Tyr Leu Tyr Arg Leu Phe Arg Lys Ser Asn Leu Lys Pro Phe
450                 455                 460
```

```
Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880
```

```
Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
        980                 985                 990

Ile Asp Arg Leu Ile Thr Gly Arg Leu Gln Ser Leu Gln Thr Tyr Val
    995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr Trp Ser His Pro Gln
    1265                1270                1275

Phe Glu Lys
```

1280

<210> SEQ ID NO 135
<211> LENGTH: 3846
<212> TYPE: DNA
<213> ORGANISM: Artificial Sequence
<220> FEATURE:
<223> OTHER INFORMATION: Nucleic acid sequence of full length S protein of SARS-CoV-2

<400> SEQUENCE: 135
atgttcgtgt tcctggtgct gctgcctctg gtgagcagcc agtgcgtgaa tctgaccacc 60
agaacccagc tgcctcctgc ctacaccaat agcttcacca gaggagttta ttatcccgat 120
aaggtgttca gaagtagtgt attacatagt acccaggacc tgttcctacc tttcttcagt 180
aacgtgacct ggttccacgc catccacgtg agcggcacca atggcaccaa gagattcgac 240
aatcctgtgc tgcctttcaa tgacggcgtg tacttcgcca gcaccgagaa gagcaatatc 300
atcagaggct ggatcttcgg caccaccttg gattccaaga ctcagagcct gctgattgta 360
aacaacgcta caaatgtggt gatcaaggtg tgcgagttcc agttctgcaa tgaccctttc 420
ctgggtgttt attatcataa gaacaacaag agctggatgg agagcgagtt ccgcgtatat 480
tcgtcggcta ataattgcac cttcgagtac gtgagccagc ctttcctgat ggacctggag 540
ggcaagcagg gcaatttcaa gaatctgaga gagttcgtgt tcaagaatat cgacggctac 600
ttcaagatct acagcaagca cacacccatt aatctggtga gagacctgcc tcagggcttc 660
agcgccctgg agcctctggt ggacctgcct atcggcatca atatcaccag attccagacc 720
ctgctggccc tgcacagatc atatcttaca ccaggcgatt cgtcaagcgg ttggaccgct 780
ggagctgcgg catattacgt gggctacctg cagcctagaa ccttcctgct gaagtacaat 840
gagaatggta cgataaccga cgcagttgat tgtgccctgg accctctgag cgagaccaag 900
tgcaccctga agagcttcac cgtggagaag ggcatctacc agaccagcaa tttcagagtg 960
cagcctaccg agagcatcgt gagattccct aatatcacca atctgtgccc tttcggcgag 1020
gtgttcaatg ccaccagatt cgccagcgtg tacgcatgga accgcaagcg gataagcaat 1080
tgcgtggccg actacagcgt gctgtacaat agcgccagct tcagcacctt caaatgttat 1140
ggtgtttcgc caacaaagct gaatgacctg tgcttcacca atgtgtacgc cgacagcttc 1200
gtgatcagag gcgacgaggt gagacagatc gcgccagggc agaccggcaa gatcgccgac 1260
tacaattaca agctgcctga cgacttcacc ggctgcgtga tcgcgtggaa ctctaacaat 1320
ctagattcga aagttggagg caattacaat tacctgtaca gactgttcag aaagagcaat 1380
ctgaagcctt tcgagagaga catcagcacc gagatctacc aggccggcag cacaccgtgt 1440
aatggcgtgg agggcttcaa ttgctacttc cctctgcaga gctacggctt ccagcctacc 1500
aatggcgtgg gctaccagcc ttacagagtg gtggtgctga gcttcgagct gctgcacgct 1560
cccgctaccg tgtgcggccc taagaagagc accaatctgg tgaagaataa gtgcgtgaat 1620
ttcaatttca atggtctaac tggaacgggc gtgctgaccg agagcaataa gaagtttctt 1680
ccctttcaac aattcggcag agacatcgcc gacaccacag atgctgtaag agaccctcag 1740
accctggaga tcctggacat cactccgtgt agcttcggcg gcgtgagcgt gatcacaccg 1800
ggtaccaata ccagcaatca ggtggccgtg ctgtaccagg acgtgaattg caccgaggtg 1860
cctgtggcca tccacgccga ccagctgact cccacttgga gggtatattc cacgggaagc 1920
aatgtgttcc agaccagagc cggctgcctg atcggcgccg agcacgtgaa taatagctac 1980

-continued

```
gagtgcgaca tccctatcgg cgccggcatc tgcgccagct accagaccca gaccaatagc    2040
cctagaagag ccagaagcgt ggccagccag agcatcatcg cctacaccat gagcctgggc    2100
gccgagaata gcgtggccta cagcaataat agcatcgcca tccctaccaa tttcaccatc    2160
agcgtgacca ccgaaatatt accagtctcc atgaccaaga ccagcgtgga ctgcaccatg    2220
tacatctgcg gcgacagcac cgagtgcagc aatctgctgc tgcagtacgg cagcttctgc    2280
acccagctga atagagccct gaccggcatc gccgtggagc aggacaagaa tacccaggag    2340
gtgttcgccc aggtgaagca gatctacaag actccgccga tcaaggactt cggcggcttc    2400
aatttcagcc aaatactccc agatccaagc aagcctagca agaggagctt catcgaggac    2460
ctgctgttca ataaggtgac cctggccgac gccggcttca tcaagcagta cggcgactgc    2520
ctaggtgata ttgcggcaag agacctgatc tgcgcccaga gtttaacgg tttgacagta    2580 ctacctcctc tgctgaccga cgagatgata gcacaatata cgtcggcatt gctcgctggc    2640
acgatcacat cgggctggac tttcggcgcc ggagcagcgt tgcaaatccc tttcgccatg    2700
cagatggcct acagattcaa tggcatcggc gtgacccaga atgtgctgta cgagaatcag    2760
aagctgatcg ccaatcagtt caatagcgca tcggcaagaa tccaggacag cctgagcagc    2820
accgccagcg ccctgggcaa gctgcaggac gtggtgaatc agaatgccca ggccctgaat    2880
accctggtga agcagctgag cagcaatttc ggcgccatca gtagtgtact caacgatatc    2940
ctgagcagac tggacaaggt ggaggccgag gtgcaaattg atcgtcttat tactggcaga    3000
ctgcagagcc tgcagaccta cgtgacccag cagctgatca gagccgccga gatcagagcc    3060
agcgccaatc tggccgccac caagatgagc gagtgcgtgc tgggccagag caagagagtg    3120
gacttctgcg gcaagggcta ccacctgatg agcttccctc agagcgctcc acatggcgtg    3180
gtgttcctgc acgtgaccta cgtgcctgcc aggagaagaa atttcaccac cgcacccgca    3240
atctgccacg acggcaaggc ccacttccct agagagggcg tgttcgtgag caatggcacc    3300
cactggttcg tgacccagag aaatttctac gagcctcaga tcatcaccac cgacaatacc    3360
ttcgtgagcg gcaattgcga cgtggtgatc gggatagtca ataatactgt ctacgaccct    3420
ctgcagcctg agctggacag cttcaaggag gagctggaca gtacttcaa gaatcacacc    3480 agccctgacg tggacctcgg tgatatttcg ggaatcaatg ccagcgtggt gaatatccag    3540
aaggaaattg atcggctcaa cgaagtggcc aagaatctga atgagagcct gatcgacctg    3600
caggagctgg gcaagtacga gcagtacatc aagtggcctt ggtacatctg gctgggcttc    3660
atcgccggcc tgatcgccat cgtgatggtg accatcatgc tgtgctgcat gacctcctgt    3720
tgttcctgtt tgaaagggtg ttgttcgtgt gggtcctgct gcaagttcga cgaggacgac    3780
agcgagcctg tgctgaaggg cgtgaagctg cactacacct ggagccaccc tcagttcgag    3840
aagtga                                                               3846
```

<210> SEQ ID NO 136
<211> LENGTH: 8
<212> TYPE: PRT
<213> ORGANISM: Homo sapiens
<220> FEATURE:
<221> NAME/KEY: P2B-1G5 HCDR1
<222> LOCATION: (1)..(8)

<400> SEQUENCE: 136

Gly Tyr Thr Phe Thr Thr Tyr Val
1               5

```
<210> SEQ ID NO 137
<211> LENGTH: 8
<212> TYPE: PRT
<213> ORGANISM: Homo sapiens
<220> FEATURE:
<221> NAME/KEY: P2B-1G5 HCDR2
<222> LOCATION: (1)..(8)

<400> SEQUENCE: 137

Ile Asn Thr Asn Thr Gly Asn Pro
1               5

<210> SEQ ID NO 138
<211> LENGTH: 12
<212> TYPE: PRT
<213> ORGANISM: Homo sapiens
<220> FEATURE:
<221> NAME/KEY: P2B-1G5 HCDR3
<222> LOCATION: (1)..(12)

<400> SEQUENCE: 138

Ser Cys Glu Ile Thr Thr Leu Gly Gly Met Asp Val
1               5                   10

<210> SEQ ID NO 139
<211> LENGTH: 6
<212> TYPE: PRT
<213> ORGANISM: Homo sapiens
<220> FEATURE:
<221> NAME/KEY: P2B-1G5 LCDR1
<222> LOCATION: (1)..(6)

<400> SEQUENCE: 139

Asn Ile Gly Ser Lys Ser
1               5

<210> SEQ ID NO 140
<211> LENGTH: 4
<212> TYPE: PRT
<213> ORGANISM: Homo sapiens
<220> FEATURE:
<221> NAME/KEY: P2B-1G5 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 140

Tyr Asp Ser Xaa
1

<210> SEQ ID NO 141
<211> LENGTH: 11
<212> TYPE: PRT
<213> ORGANISM: Homo sapiens
<220> FEATURE:
<221> NAME/KEY: P2B-1G5 LCDR3
<222> LOCATION: (1)..(11)

<400> SEQUENCE: 141

Gln Val Trp Asp Ser Ile Ser Asp His Arg Val
1               5                   10

<210> SEQ ID NO 142
<211> LENGTH: 119
<212> TYPE: PRT
<213> ORGANISM: Homo sapiens
<220> FEATURE:
```

<221> NAME/KEY: P2B-1G5 VH
<222> LOCATION: (1)..(119)

<400> SEQUENCE: 142

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Val Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Ser
65                  70                  75                  80

Leu Gln Ile Ser Ser Leu Lys Ala Glu Asp Thr Ala Val Tyr Tyr Cys
                85                  90                  95

Ser Cys Glu Ile Thr Thr Leu Gly Gly Met Asp Val Trp Gly Gln Gly
            100                 105                 110

Thr Thr Val Thr Val Ser Ser
        115

<210> SEQ ID NO 143
<211> LENGTH: 108
<212> TYPE: PRT
<213> ORGANISM: Homo sapiens
<220> FEATURE:
<221> NAME/KEY: P2B-1G5 VL
<222> LOCATION: (1)..(108)

<400> SEQUENCE: 143

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Ser Ile Ser Asp His
                85                  90                  95

Arg Val Phe Gly Gly Gly Thr Lys Leu Thr Val Leu
            100                 105

<210> SEQ ID NO 144
<211> LENGTH: 357
<212> TYPE: DNA
<213> ORGANISM: Homo sapiens
<220> FEATURE:
<221> NAME/KEY: P2B-1G5 VHnu
<222> LOCATION: (1)..(357)

<400> SEQUENCE: 144
caggtgcagc tggtgcaatc tgggtctgag ttgaagaagc ctggggcctc agtgaaggtt      60
tcctgcaagg cttctggata caccttcact acctatgtta tgaattgggt gcgacaggcc     120
cctggacaag ggcttgagtg gatgggatgg atcaacacca acactgggaa cccaacgtat     180
gcccagggct tcacaggacg gtttgtcttc tccttggaca cctctgtcag cacggcatct     240

-continued ctgcagatca gcagcctaaa ggctgaggac actgccgtgt attactgttc gtgtgaaata    300
accaccttgg gcggtatgga cgtctggggc caagggacca cggtcaccgt ctcctca    357

<210> SEQ ID NO 145
<211> LENGTH: 324
<212> TYPE: DNA
<213> ORGANISM: Homo sapiens
<220> FEATURE:
<221> NAME/KEY: P2B-1G5 VLnu
<222> LOCATION: (1)..(324)

<400> SEQUENCE: 145
tcctatgtgc tgactcagcc accctcagtg tcagtggccc caggaaagac ggccaggatt    60
acctgtgggg gaaacaacat tggaagtaaa agtgtgcact ggtaccagca gaagccaggc    120
caggcccctg tgctggtcat ctattatgat agcgaccggc cctcagggat ccctgagcga    180
ttctctggct ccaactctgg gaacacggcc accctgacca tcagcggggt cgaagccggg    240
gatgaggccg actattactg tcaggtgtgg gatagtatta gtgatcatcg ggtgttcggc    300
ggagggacca agctgaccgt ccta    324

<210> SEQ ID NO 146
<211> LENGTH: 8
<212> TYPE: PRT
<213> ORGANISM: Homo sapiens
<220> FEATURE:
<221> NAME/KEY: P2B-1A1 HCDR1
<222> LOCATION: (1)..(8)

<400> SEQUENCE: 146

Gly Gly Ser Ile Ser Ser Tyr Tyr
1               5

<210> SEQ ID NO 147
<211> LENGTH: 7
<212> TYPE: PRT
<213> ORGANISM: Homo sapiens
<220> FEATURE:
<221> NAME/KEY: P2B-1A1 HCDR2
<222> LOCATION: (1)..(7)

<400> SEQUENCE: 147

Ile Tyr Tyr Ser Gly Ser Thr
1               5

<210> SEQ ID NO 148
<211> LENGTH: 14
<212> TYPE: PRT
<213> ORGANISM: Homo sapiens
<220> FEATURE:
<221> NAME/KEY: P2B-1A1 HCDR3
<222> LOCATION: (1)..(14)

<400> SEQUENCE: 148

Ala Arg Leu Glu Arg Asp Trp Pro Leu Asp Ala Phe Asp Ile
1               5                   10

<210> SEQ ID NO 149
<211> LENGTH: 9
<212> TYPE: PRT
<213> ORGANISM: Homo sapiens
<220> FEATURE:
<221> NAME/KEY: P2B-1A1 LCDR1
<222> LOCATION: (1)..(9)

```
<400> SEQUENCE: 149

Ser Ser Asp Val Gly Gly Tyr Asn Tyr
1               5

<210> SEQ ID NO 150
<211> LENGTH: 4
<212> TYPE: PRT
<213> ORGANISM: Homo sapiens
<220> FEATURE:
<221> NAME/KEY: P2B-1A1 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 150

Asp Val Ser Xaa
1

<210> SEQ ID NO 151
<211> LENGTH: 10
<212> TYPE: PRT
<213> ORGANISM: Homo sapiens
<220> FEATURE:
<221> NAME/KEY: P2B-1A1 LCDR3
<222> LOCATION: (1)..(10)

<400> SEQUENCE: 151

Ser Ser Tyr Thr Ser Asn Asn Thr Phe Ala
1               5                   10

<210> SEQ ID NO 152
<211> LENGTH: 120
<212> TYPE: PRT
<213> ORGANISM: Homo sapiens
<220> FEATURE:
<221> NAME/KEY: P2B-1A1 VH
<222> LOCATION: (1)..(120)

<400> SEQUENCE: 152

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Leu Glu Arg Asp Trp Pro Leu Asp Ala Phe Asp Ile Trp Gly Gln
            100                 105                 110

Gly Thr Met Val Thr Val Ser Ser
        115                 120

<210> SEQ ID NO 153
<211> LENGTH: 110
<212> TYPE: PRT
<213> ORGANISM: Homo sapiens
<220> FEATURE:
<221> NAME/KEY: P2B-1A1 VL
```

<220> LOCATION: (1)..(110)

<400> SEQUENCE: 153

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Phe
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Asn
                85                  90                  95

Asn Thr Phe Ala Phe Gly Gly Gly Thr Lys Leu Thr Val Leu
            100                 105                 110

<210> SEQ ID NO 154
<211> LENGTH: 360
<212> TYPE: DNA
<213> ORGANISM: Homo sapiens
<220> FEATURE:
<221> NAME/KEY: P2B-1A1 VHnu
<222> LOCATION: (1)..(360)

<400> SEQUENCE: 154
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaac     180
ccctccctca agagtcgagt caccatatca gtagacacgt ccaagaagca gttctccctg     240
aagctgagct ctgtgaccgc tgcggacacg gccgtgtatt actgtgcgag gctcgaacga     300
gactggccac ttgatgcttt tgatatctgg ggccaaggga caatggtcac cgtctcctca     360

<210> SEQ ID NO 155
<211> LENGTH: 330
<212> TYPE: DNA
<213> ORGANISM: Homo sapiens
<220> FEATURE:
<221> NAME/KEY: P2B-1A1 VLnu
<222> LOCATION: (1)..(330)

<400> SEQUENCE: 155
cagtctgccc tgactcagcc tgcctccgtg tctgggtctc ctggacagtc gatcaccatc      60
tcctgcactg gaaccagcag tgacgttggt ggttataact atgtctcctg gtaccaacag     120
cacccaggca agcccccaa attcatgatt tatgatgtca gtaagcggcc ctcaggggtt     180
tctaatcgct tctctggctc caagtctggc aacacggcct ccctgaccat ctctgggctc     240
caggctgagg acgaggctga ttattactgc agctcatata caagcaacaa cactttcgcg     300
ttcggcggag ggaccaagct gaccgtccta                                      330

<210> SEQ ID NO 156
<211> LENGTH: 8
<212> TYPE: PRT
<213> ORGANISM: Homo sapiens
<220> FEATURE:
<221> NAME/KEY: P2C-1D7 HCDR1
<222> LOCATION: (1)..(8)

```
<400> SEQUENCE: 156

Gly Phe Thr Val Ser Ser Asn Tyr
1               5

<210> SEQ ID NO 157
<211> LENGTH: 7
<212> TYPE: PRT
<213> ORGANISM: Homo sapiens
<220> FEATURE:
<221> NAME/KEY: P2C-1D7 HCDR2
<222> LOCATION: (1)..(7)

<400> SEQUENCE: 157

Ile Tyr Ser Gly Gly Ser Thr
1               5

<210> SEQ ID NO 158
<211> LENGTH: 12
<212> TYPE: PRT
<213> ORGANISM: Homo sapiens
<220> FEATURE:
<221> NAME/KEY: P2C-1D7 HCDR3
<222> LOCATION: (1)..(12)

<400> SEQUENCE: 158

Ala Arg Glu Leu Tyr Glu Val Gly Ala Thr Asp Tyr
1               5                   10

<210> SEQ ID NO 159
<211> LENGTH: 11
<212> TYPE: PRT
<213> ORGANISM: Homo sapiens
<220> FEATURE:
<221> NAME/KEY: P2C-1D7 LCDR1
<222> LOCATION: (1)..(11)

<400> SEQUENCE: 159

Gln Ser Leu Val Tyr Ser Asp Gly Asn Thr Tyr
1               5                   10

<210> SEQ ID NO 160
<211> LENGTH: 4
<212> TYPE: PRT
<213> ORGANISM: Homo sapiens
<220> FEATURE:
<221> NAME/KEY: P2C-1D7 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 160

Lys Val Ser Xaa
1

<210> SEQ ID NO 161
<211> LENGTH: 9
<212> TYPE: PRT
<213> ORGANISM: Homo sapiens
<220> FEATURE:
<221> NAME/KEY: P2C-1D7 LCDR3
<222> LOCATION: (1)..(9)

<400> SEQUENCE: 161

Met Gln Arg Tyr Thr Leu Ala Gly Val
1               5
```

<210> SEQ ID NO 162
<211> LENGTH: 118
<212> TYPE: PRT
<213> ORGANISM: Homo sapiens
<220> FEATURE:
<221> NAME/KEY: P2C-1D7 VH
<222> LOCATION: (1)..(118)

<400> SEQUENCE: 162

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Leu Tyr Glu Val Gly Ala Thr Asp Tyr Trp Gly Gln Gly Thr
            100                 105                 110

Leu Val Thr Val Ser Ser
        115

<210> SEQ ID NO 163
<211> LENGTH: 112
<212> TYPE: PRT
<213> ORGANISM: Homo sapiens
<220> FEATURE:
<221> NAME/KEY: P2C-1D7 VL
<222> LOCATION: (1)..(112)

<400> SEQUENCE: 163

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Arg
                85                  90                  95

Tyr Thr Leu Ala Gly Val Phe Gly Pro Gly Thr Lys Val Asp Ile Lys
            100                 105                 110

<210> SEQ ID NO 164
<211> LENGTH: 354
<212> TYPE: DNA
<213> ORGANISM: Homo sapiens
<220> FEATURE:
<221> NAME/KEY: P2C-1D7 VHnu
<222> LOCATION: (1)..(354)

<400> SEQUENCE: 164

```
gaggtgcagc tggtggagtc tggaggaggc ttgatccagc ctggggggtc cctgagactc      60
tcctgtgcag cctctgggtt caccgtcagt agcaactaca tgagctgggt ccgccaggct     120
ccagggaagg ggctggagtg ggtctcagtt atttatagcg gtggtagcac atactacgca     180
gactccgtga agggccgatt caccatctcc agagacaatt ccaagaacac gctgtatctt     240
caaatgaaca gcctgagagc cgaggacacg gccgtgtatt actgtgcgag agaattgtac     300
gaagtgggag ctacggacta ctggggccag ggaaccctgg tcaccgtctc ctca           354
```

<210> SEQ ID NO 165
<211> LENGTH: 336
<212> TYPE: DNA
<213> ORGANISM: Homo sapiens
<220> FEATURE:
<221> NAME/KEY: P2C-1D7 VLnu
<222> LOCATION: (1)..(336)

<400> SEQUENCE: 165

```
gatgttgtga tgactcagtc tccactctcc ctgcccgtca cccttggaca gccggcctcc      60
atctcctgca ggtctagtca aagcctcgta tacagtgatg aaacaccta cttgaattgg     120 tttcagcaga ggccaggcca atctccaagg cgcctaattt ataaggtttc taactgggac     180
tctggggtcc cagacagatt cagcggcagt gggtcaggca ctgatttcac actgaaaatc     240
agcagggtgg aggctgagga tgttggggtt tattactgca tgcaacggta cacactggcc     300
ggcgttttcg gccctgggac caaagtggat atcaaa                              336
```

<210> SEQ ID NO 166
<211> LENGTH: 8
<212> TYPE: PRT
<213> ORGANISM: Homo sapiens
<220> FEATURE:
<221> NAME/KEY: P2B-1A10 HCDR1
<222> LOCATION: (1)..(8)

<400> SEQUENCE: 166

Gly Phe Thr Val Ser Ser Asn Tyr
1               5

<210> SEQ ID NO 167
<211> LENGTH: 7
<212> TYPE: PRT
<213> ORGANISM: Homo sapiens
<220> FEATURE:
<221> NAME/KEY: P2B-1A10 HCDR2
<222> LOCATION: (1)..(7)

<400> SEQUENCE: 167

Ile Tyr Ser Gly Gly Ser Thr
1               5

<210> SEQ ID NO 168
<211> LENGTH: 15
<212> TYPE: PRT
<213> ORGANISM: Homo sapiens
<220> FEATURE:
<221> NAME/KEY: P2B-1A10 HCDR3
<222> LOCATION: (1)..(15)

<400> SEQUENCE: 168

Ala Arg Glu Gly Pro Lys Ser Ile Thr Gly Thr Ala Phe Asp Ile
1               5                   10                  15

<210> SEQ ID NO 169

```
<211> LENGTH: 6
<212> TYPE: PRT
<213> ORGANISM: Homo sapiens
<220> FEATURE:
<221> NAME/KEY: P2B-1A10 LCDR1
<222> LOCATION: (1)..(6)

<400> SEQUENCE: 169

Gln Asp Ile Ser Asn Tyr
1               5

<210> SEQ ID NO 170
<211> LENGTH: 4
<212> TYPE: PRT
<213> ORGANISM: Homo sapiens
<220> FEATURE:
<221> NAME/KEY: P2B-1A10 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 170

Asp Ala Ser Xaa
1

<210> SEQ ID NO 171
<211> LENGTH: 10
<212> TYPE: PRT
<213> ORGANISM: Homo sapiens
<220> FEATURE:
<221> NAME/KEY: P2B-1A10 LCDR3
<222> LOCATION: (1)..(10)

<400> SEQUENCE: 171

Gln Gln Tyr Asp Asn Leu Pro Met Tyr Thr
1               5                   10

<210> SEQ ID NO 172
<211> LENGTH: 121
<212> TYPE: PRT
<213> ORGANISM: Homo sapiens
<220> FEATURE:
<221> NAME/KEY: P2B-1A10 VH
<222> LOCATION: (1)..(121)

<400> SEQUENCE: 172

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Gly Pro Lys Ser Ile Thr Gly Thr Ala Phe Asp Ile Trp Gly
            100                 105                 110

Gln Gly Thr Ile Val Thr Val Ser Ser
        115                 120
```

<210> SEQ ID NO 173
<211> LENGTH: 108
<212> TYPE: PRT
<213> ORGANISM: Homo sapiens
<220> FEATURE:
<221> NAME/KEY: P2B-1A10 VL
<222> LOCATION: (1)..(108)

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Phe Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Met
                85                  90                  95

Tyr Thr Phe Gly Gln Gly Thr Lys Leu Glu Ile Lys
            100                 105

<210> SEQ ID NO 174
<211> LENGTH: 363
<212> TYPE: DNA
<213> ORGANISM: Homo sapiens
<220> FEATURE:
<221> NAME/KEY: P2B-1A10 VHnu
<222> LOCATION: (1)..(363)

<400> SEQUENCE: 174
gaggtgcagc tggtggagtc tggaggaggc ttgatccagc ctgggggtc cctgagactc      60 tcctgtgcag cctctgggtt caccgtcagt agcaactaca tgagctgggt ccgccaggct     120
ccagggaagg gctggagtg gtctcagtt atttatagcg gtggtagcac atactacgca       180
gactccgtga agggccgatt caccatctcc agagacaatt ccaagaacac gctgtatctt     240
caaatgaaca gcctgagagc cgaggacacg gccgtttatt actgtgcgag agagggccca     300
aagtctatta cagggacggc ttttgatatc tggggccaag gacaattgt caccgtctcc     360 tca                                                                   363

<210> SEQ ID NO 175
<211> LENGTH: 324
<212> TYPE: DNA
<213> ORGANISM: Homo sapiens
<220> FEATURE:
<221> NAME/KEY: P2B-1A10 VLnu
<222> LOCATION: (1)..(324)

<400> SEQUENCE: 175
gacatccaga tgacccagtc tccatcctcc ctgtctgcat ctgtaggaga cagagtcacc      60
atcacttgcc aggcgagtca ggacattagc aactatttta attggtatca gcagaaacca    120
gggaaagccc ctaagctcct gatctacgat gcatccaatt tggaaacagg ggtcccatca    180
aggttcagtg gaagtggatc tgggacagat tttactttca ccatcagcag cctgcagcct    240
gaagatattg caacatatta ctgtcaacag tatgataatc tccccatgta cactttggc    300 caggggacca agctggagat caaa                                            324

```
<210> SEQ ID NO 176
<211> LENGTH: 10
<212> TYPE: PRT
<213> ORGANISM: Homo sapiens
<220> FEATURE:
<221> NAME/KEY: P2B-1D9 HCDR1
<222> LOCATION: (1)..(10)

<400> SEQUENCE: 176

Gly Phe Ser Leu Ser Thr Ser Gly Val Gly
1               5                   10

<210> SEQ ID NO 177
<211> LENGTH: 7
<212> TYPE: PRT
<213> ORGANISM: Homo sapiens
<220> FEATURE:
<221> NAME/KEY: P2B-1D9 HCDR2
<222> LOCATION: (1)..(7)

<400> SEQUENCE: 177

Ile Tyr Trp Asp Asp Asp Lys
1               5

<210> SEQ ID NO 178
<211> LENGTH: 16
<212> TYPE: PRT
<213> ORGANISM: Homo sapiens
<220> FEATURE:
<221> NAME/KEY: P2B-1D9 HCDR3
<222> LOCATION: (1)..(16)

<400> SEQUENCE: 178

Ala His Thr Arg Ile Leu Tyr Tyr Gly Ser Gly Ser Tyr Tyr Asp Tyr
1               5                   10                  15

<210> SEQ ID NO 179
<211> LENGTH: 8
<212> TYPE: PRT
<213> ORGANISM: Homo sapiens
<220> FEATURE:
<221> NAME/KEY: P2B-1D9 LCDR1
<222> LOCATION: (1)..(8)

<400> SEQUENCE: 179

Ser Ser Asn Ile Gly Ser Asn Tyr
1               5

<210> SEQ ID NO 180
<211> LENGTH: 4
<212> TYPE: PRT
<213> ORGANISM: Homo sapiens
<220> FEATURE:
<221> NAME/KEY: P2B-1D9 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 180

Ser Asn Asn Xaa
1

<210> SEQ ID NO 181
<211> LENGTH: 11
<212> TYPE: PRT
```

```
<213> ORGANISM: Homo sapiens
<220> FEATURE:
<221> NAME/KEY: P2B-1D9 LCDR3
<222> LOCATION: (1)..(11)

<400> SEQUENCE: 181

Ala Ala Trp Asp Asp Ser Leu Ser Gly Val Val
1               5                   10

<210> SEQ ID NO 182
<211> LENGTH: 124
<212> TYPE: PRT
<213> ORGANISM: Homo sapiens
<220> FEATURE:
<221> NAME/KEY: P2B-1D9 VH
<222> LOCATION: (1)..(124)

<400> SEQUENCE: 182

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Lys Tyr Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Thr Arg Ile Leu Tyr Tyr Gly Ser Gly Ser Tyr Tyr Asp
            100                 105                 110

Tyr Trp Gly Gln Gly Thr Leu Val Thr Val Ser Ser
        115                 120

<210> SEQ ID NO 183
<211> LENGTH: 110
<212> TYPE: PRT
<213> ORGANISM: Homo sapiens
<220> FEATURE:
<221> NAME/KEY: P2B-1D9 VL
<222> LOCATION: (1)..(110)

<400> SEQUENCE: 183

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Leu
                85                  90                  95

Ser Gly Val Val Phe Gly Gly Gly Thr Lys Leu Thr Val Leu
        100                 105                 110

<210> SEQ ID NO 184
```

```
<211> LENGTH: 372
<212> TYPE: DNA
<213> ORGANISM: Homo sapiens
<220> FEATURE:
<221> NAME/KEY: P2B-1D9 VHnu
<222> LOCATION: (1)..(372)

<400> SEQUENCE: 184
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcactcattt attgggatga tgataaatac     180
tacagcccat ctctgaagag caggctcacc atcaccaagg acacctccaa aaaccaggtg     240
gtccttacaa tgaccaacat ggaccctgtg acacagcca catattactg tgcacacact     300
cgcatcttat actatggttc ggggagttat tatgactact ggggccaggg aaccctggtc     360
accgtctcct ca                                                         372

<210> SEQ ID NO 185
<211> LENGTH: 330
<212> TYPE: DNA
<213> ORGANISM: Homo sapiens
<220> FEATURE:
<221> NAME/KEY: P2B-1D9 VLnu
<222> LOCATION: (1)..(330)

<400> SEQUENCE: 185
cagtctgtgc tgactcagcc accctcagcg tctgggaccc ccgggcagag ggtcaccatc      60
tcttgttctg gaagcagctc caacatcgga agtaattatg tatactggta ccagcagctc     120
ccaggaacgg cccccaaact cctcatctat agtaataatc agcggccctc aggggtccct     180
gaccgattct ctggctccaa gtctggcacc tcagcctccc tggccatcag tgggctccgg     240
tccgaggatg aggctgatta ttactgtgca gcatgggatg acagcctgag tggtgtggta     300
ttcggcggag ggaccaagct gaccgtccta                                      330

<210> SEQ ID NO 186
<211> LENGTH: 10
<212> TYPE: PRT
<213> ORGANISM: Homo sapiens
<220> FEATURE:
<221> NAME/KEY: P2B-1E4 HCDR1
<222> LOCATION: (1)..(10)

<400> SEQUENCE: 186

Gly Phe Ser Leu Ser Thr Ser Gly Val Gly
1               5                   10

<210> SEQ ID NO 187
<211> LENGTH: 7
<212> TYPE: PRT
<213> ORGANISM: Homo sapiens
<220> FEATURE:
<221> NAME/KEY: P2B-1E4 HCDR2
<222> LOCATION: (1)..(7)

<400> SEQUENCE: 187

Ile Tyr Trp Asp Asp Asp Lys
1               5

<210> SEQ ID NO 188
<211> LENGTH: 11
<212> TYPE: PRT
<213> ORGANISM: Homo sapiens
```

```
<220> FEATURE:
<221> NAME/KEY: P2B-1E4 HCDR3
<222> LOCATION: (1)..(11)

<400> SEQUENCE: 188

Ala His Gln Ile Val Ala Thr Ile Ile Asp Tyr
1               5                   10

<210> SEQ ID NO 189
<211> LENGTH: 9
<212> TYPE: PRT
<213> ORGANISM: Homo sapiens
<220> FEATURE:
<221> NAME/KEY: P2B-1E4 LCDR1
<222> LOCATION: (1)..(9)

<400> SEQUENCE: 189

Ser Ser Asp Val Gly Gly Tyr Asn Tyr
1               5

<210> SEQ ID NO 190
<211> LENGTH: 4
<212> TYPE: PRT
<213> ORGANISM: Homo sapiens
<220> FEATURE:
<221> NAME/KEY: P2B-1E4 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 190

Asp Val Ser Xaa
1

<210> SEQ ID NO 191
<211> LENGTH: 9
<212> TYPE: PRT
<213> ORGANISM: Homo sapiens
<220> FEATURE:
<221> NAME/KEY: P2B-1E4 LCDR3
<222> LOCATION: (1)..(9)

<400> SEQUENCE: 191

Ser Ser Tyr Thr Ser Ser Ser Val Val
1               5

<210> SEQ ID NO 192
<211> LENGTH: 119
<212> TYPE: PRT
<213> ORGANISM: Homo sapiens
<220> FEATURE:
<221> NAME/KEY: P2B-1E4 VH
<222> LOCATION: (1)..(119)

<400> SEQUENCE: 192

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
```

```
                65                  70                  75                  80
Val Leu Thr Met Thr Asn Met Asp Pro Val Asp Thr Ala Thr Tyr Tyr
                        85                  90                  95

Cys Ala His Gln Ile Val Ala Thr Ile Ile Asp Tyr Trp Gly Gln Gly
            100                 105                 110

Thr Leu Val Thr Val Ser Ser
        115

<210> SEQ ID NO 193
<211> LENGTH: 109
<212> TYPE: PRT
<213> ORGANISM: Homo sapiens
<220> FEATURE:
<221> NAME/KEY: P2B-1E4 VL
<222> LOCATION: (1)..(109)

<400> SEQUENCE: 193

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Val Val Phe Gly Gly Gly Thr Lys Leu Thr Val Leu
            100                 105

<210> SEQ ID NO 194
<211> LENGTH: 357
<212> TYPE: DNA
<213> ORGANISM: Homo sapiens
<220> FEATURE:
<221> NAME/KEY: P2B-1E4 VHnu
<222> LOCATION: (1)..(357)

<400> SEQUENCE: 194
cagatcacct tgaaggagtc tggtcctacg ctggtgaaac ccacacagac cctcacgctg      60
acctgcacct ctctgggtt ctcactcagc actagtggag tgggtgtggg ctggatccgt     120
cagcccccag gaaaggccct ggagtggctt gcactcattt attgggatga tgataagcgc     180
tacagcccat ctctgaagag caggctcacc atcaccaagg acacctccaa aaaccaggtg     240
gtccttacaa tgaccaacat ggaccctgtg gacacagcca catattactg tgcacaccaa     300
atagtggcta cgattattga ctactggggc cagggaaccc tggtcaccgt ctcctca       357

<210> SEQ ID NO 195
<211> LENGTH: 327
<212> TYPE: DNA
<213> ORGANISM: Homo sapiens
<220> FEATURE:
<221> NAME/KEY: P2B-1E4 VLnu
<222> LOCATION: (1)..(327)

<400> SEQUENCE: 195
cagtctgccc tgactcagcc tgcctccgtg tctgggtctc ctggacagtc gatcaccatc      60
```

```
tcctgcactg gaaccagcag tgacgttggt ggttataact atgtctcctg gtaccaacag    120
cacccaggca agccccccaa actcatgatt tatgatgtca gtaagcggcc ctcagggggtt    180 tctaatcgct tctctggctc caagtctggc aacacggcct ccctgaccat ctctgggctc    240
caggctgagg acgaggctga ttattactgc agctcatata caagcagcag cgtggtattc    300
ggcggaggga ccaagctgac cgtccta                                        327
```

<210> SEQ ID NO 196
<211> LENGTH: 8
<212> TYPE: PRT
<213> ORGANISM: Homo sapiens
<220> FEATURE:
<221> NAME/KEY: P2B-1G1 HCDR1
<222> LOCATION: (1)..(8)

<400> SEQUENCE: 196

Gly Phe Thr Val Ser Ser Asn Tyr
1               5

<210> SEQ ID NO 197
<211> LENGTH: 7
<212> TYPE: PRT
<213> ORGANISM: Homo sapiens
<220> FEATURE:
<221> NAME/KEY: P2B-1G1 HCDR2
<222> LOCATION: (1)..(7)

<400> SEQUENCE: 197

Ile Tyr Ser Gly Gly Ser Thr
1               5

<210> SEQ ID NO 198
<211> LENGTH: 11
<212> TYPE: PRT
<213> ORGANISM: Homo sapiens
<220> FEATURE:
<221> NAME/KEY: P2B-1G1 HCDR3
<222> LOCATION: (1)..(11)

<400> SEQUENCE: 198

Ala Arg Asp Tyr Gly Asp Tyr Trp Phe Asp Pro
1               5                   10

<210> SEQ ID NO 199
<211> LENGTH: 7
<212> TYPE: PRT
<213> ORGANISM: Homo sapiens
<220> FEATURE:
<221> NAME/KEY: P2B-1G1 LCDR1
<222> LOCATION: (1)..(7)

<400> SEQUENCE: 199

Gln Ser Val Ser Ser Ser Tyr
1               5

<210> SEQ ID NO 200
<211> LENGTH: 4
<212> TYPE: PRT
<213> ORGANISM: Homo sapiens
<220> FEATURE:
<221> NAME/KEY: P2B-1G1 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

```
<400> SEQUENCE: 200

Gly Ala Ser Xaa
1

<210> SEQ ID NO 201
<211> LENGTH: 9
<212> TYPE: PRT
<213> ORGANISM: Homo sapiens
<220> FEATURE:
<221> NAME/KEY: P2B-1G1 LCDR3
<222> LOCATION: (1)..(9)

<400> SEQUENCE: 201

Gln Gln Tyr Gly Ser Ser Pro Arg Thr
1               5

<210> SEQ ID NO 202
<211> LENGTH: 117
<212> TYPE: PRT
<213> ORGANISM: Homo sapiens
<220> FEATURE:
<221> NAME/KEY: P2B-1G1 VH
<222> LOCATION: (1)..(117)

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Tyr Gly Asp Tyr Trp Phe Asp Pro Trp Gly Gln Gly Thr Leu
            100                 105                 110

Val Thr Val Ser Ser
        115

<210> SEQ ID NO 203
<211> LENGTH: 108
<212> TYPE: PRT
<213> ORGANISM: Homo sapiens
<220> FEATURE:
<221> NAME/KEY: P2B-1G1 VL
<222> LOCATION: (1)..(108)

<400> SEQUENCE: 203

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln Gln Tyr Gly Ser Ser Pro
            85                  90                  95

Arg Thr Phe Gly Gln Gly Thr Lys Leu Glu Ile Lys
            100                 105

<210> SEQ ID NO 204
<211> LENGTH: 351
<212> TYPE: DNA
<213> ORGANISM: Homo sapiens
<220> FEATURE:
<221> NAME/KEY: P2B-1G1 VHnu
<222> LOCATION: (1)..(351)

<400> SEQUENCE: 204
gaggtgcagc tggtggagtc tgggggaggc ttggtccagc ctgggggtc cctgagactc      60 tcctgtgcag cctctggatt caccgtcagt agcaactaca tgagctgggt ccgccaggct     120
ccagggaagg gctggagtg gtctcagtt atttatagcg gtggtagcac atactacgca      180
gactccgtga agggcagatt caccatctcc agagacaatt ccaagaacac gctgtatctt    240
caaatgaaca gcctgagagc cgaggacacg gctgtgtatt actgtgcgag agactacggt    300
gactactggt tcgaccctg gggccaggga accctggtca ccgtctcctc a              351

<210> SEQ ID NO 205
<211> LENGTH: 324
<212> TYPE: DNA
<213> ORGANISM: Homo sapiens
<220> FEATURE:
<221> NAME/KEY: P2B-1G1 VLnu
<222> LOCATION: (1)..(324)

<400> SEQUENCE: 205
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccgag acttttggc    300 cagggggacca agctggagat caaa                                          324

<210> SEQ ID NO 206
<211> LENGTH: 8
<212> TYPE: PRT
<213> ORGANISM: Homo sapiens
<220> FEATURE:
<221> NAME/KEY: P4A-2D9 HCDR1
<222> LOCATION: (1)..(8)

<400> SEQUENCE: 206

Gly Phe Thr Phe Ser Ser Tyr Gly
1               5

<210> SEQ ID NO 207
<211> LENGTH: 8
<212> TYPE: PRT
<213> ORGANISM: Homo sapiens
<220> FEATURE:
<221> NAME/KEY: P4A-2D9 HCDR2
<222> LOCATION: (1)..(8)

<400> SEQUENCE: 207

Ile Ser Asp Asp Gly Ser Asn Gln

```
<210> SEQ ID NO 208
<211> LENGTH: 21
<212> TYPE: PRT
<213> ORGANISM: Homo sapiens
<220> FEATURE:
<221> NAME/KEY: P4A-2D9 HCDR3
<222> LOCATION: (1)..(21)

<400> SEQUENCE: 208

Ala Lys Arg Gly Gly Tyr Cys Ser Thr Thr Ser Cys Leu Val Arg Trp
1               5                   10                  15

Val Tyr Phe Asp Tyr
            20

<210> SEQ ID NO 209
<211> LENGTH: 6
<212> TYPE: PRT
<213> ORGANISM: Homo sapiens
<220> FEATURE:
<221> NAME/KEY: P4A-2D9 LCDR1
<222> LOCATION: (1)..(6)

<400> SEQUENCE: 209

Gln Phe Ile Ser Ser Tyr
1               5

<210> SEQ ID NO 210
<211> LENGTH: 4
<212> TYPE: PRT
<213> ORGANISM: Homo sapiens
<220> FEATURE:
<221> NAME/KEY: P4A-2D9 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 210

Ala Thr Ser Xaa
1

<210> SEQ ID NO 211
<211> LENGTH: 8
<212> TYPE: PRT
<213> ORGANISM: Homo sapiens
<220> FEATURE:
<221> NAME/KEY: P4A-2D9 LCDR3
<222> LOCATION: (1)..(8)

<400> SEQUENCE: 211

Gln Gln Ser Tyr Asn Thr Leu Thr
1               5

<210> SEQ ID NO 212
<211> LENGTH: 128
<212> TYPE: PRT
<213> ORGANISM: Homo sapiens
<220> FEATURE:
<221> NAME/KEY: P4A-2D9 VH
<222> LOCATION: (1)..(128)

<400> SEQUENCE: 212

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30
Gly Met His Trp Val Arg Gln Ser Pro Gly Lys Gly Leu Glu Trp Val
        35                  40                  45
Ala Val Ile Ser Asp Asp Gly Ser Asn Gln Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Glu Ile Asn Ser Leu Arg Val Glu Asp Thr Ala Val Tyr Tyr Cys
                85                  90                  95
Ala Lys Arg Gly Gly Tyr Cys Ser Thr Thr Ser Cys Leu Val Arg Trp
            100                 105                 110
Val Tyr Phe Asp Tyr Trp Gly Gln Gly Thr Leu Val Thr Val Ser Ser
        115                 120                 125
```

<210> SEQ ID NO 213
<211> LENGTH: 106
<212> TYPE: PRT
<213> ORGANISM: Homo sapiens
<220> FEATURE:
<221> NAME/KEY: P4A-2D9 VL
<222> LOCATION: (1)..(106)

<400> SEQUENCE: 213

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Phe Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Thr Ser Ile Leu Gln Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Asn Thr Leu Thr
                85                  90                  95
Phe Gly Pro Gly Thr Lys Val Asp Ile Lys
            100                 105
```

<210> SEQ ID NO 214
<211> LENGTH: 384
<212> TYPE: DNA
<213> ORGANISM: Homo sapiens
<220> FEATURE:
<221> NAME/KEY: P4A-2D9 VHnu
<222> LOCATION: (1)..(384)

<400> SEQUENCE: 214

```
caggtgcagc tggtggagtc tgggggaggc gtggtccagc ctggggaggtc cctgagactc      60
tcctgtgcag cctctggatt caccttcagt agctatggca tgcactgggt ccgccagtct     120
ccaggcaagg gctggagtg gtggcagtt atatcagatg atggaagtaa tcaatactat        180
gcagactccg tgaagggccg attcaccatc tccagagaca attccaagaa cacgctgtat     240
ctggaaatca acagcctgag agttgaggac acggctgtgt attactgtgc gaaagggggc     300
ggatattgta gtactaccag ctgcctcgtt aggtgggtct actttgacta ctggggccag     360
ggaaccctgg tcaccgtctc ctca                                            384
```

<210> SEQ ID NO 215
<211> LENGTH: 318
<212> TYPE: DNA
<213> ORGANISM: Homo sapiens
<220> FEATURE:
<221> NAME/KEY: P4A-2D9 VLnu
<222> LOCATION: (1)..(318)

<400> SEQUENCE: 215

```
gacatccaga tgacccagtc tccatcctcc ctgtctgcat ctgtaggaga cagagtcacc    60
atcacttgcc gggcaagtca gttcattagc agctacttaa attggtatca gcagaaacca   120
gggaaagccc ctaagctcct gatctatgct acatccattt tgcaaactgg ggtcccatca   180
aggttcagtg gcagtggatc tgggacagat ttcactctca ccatcagcag tctgcaacct   240
gaagattttg caacttacta ctgtcaacag agttacaata cccttacttt cggccctggg   300
accaaagtcg atatcaaa                                                 318
```

<210> SEQ ID NO 216
<211> LENGTH: 10
<212> TYPE: PRT
<213> ORGANISM: Homo sapiens
<220> FEATURE:
<221> NAME/KEY: P5A-2G7 HCDR1
<222> LOCATION: (1)..(10)

<400> SEQUENCE: 216

Gly Asp Ser Val Ser Ser Gly Ser Tyr Tyr
1               5                   10

<210> SEQ ID NO 217
<211> LENGTH: 7
<212> TYPE: PRT
<213> ORGANISM: Homo sapiens
<220> FEATURE:
<221> NAME/KEY: P5A-2G7 HCDR2
<222> LOCATION: (1)..(7)

<400> SEQUENCE: 217

Ile Tyr Tyr Ser Gly Ser Thr
1               5

<210> SEQ ID NO 218
<211> LENGTH: 20
<212> TYPE: PRT
<213> ORGANISM: Homo sapiens
<220> FEATURE:
<221> NAME/KEY: P5A-2G7 HCDR3
<222> LOCATION: (1)..(20)

<400> SEQUENCE: 218

Ala Arg Glu Arg Cys Tyr Tyr Gly Ser Gly Arg Ala Pro Arg Cys Val
1               5                   10                  15
Trp Phe Asp Pro
            20

<210> SEQ ID NO 219
<211> LENGTH: 9
<212> TYPE: PRT
<213> ORGANISM: Homo sapiens
<220> FEATURE:
<221> NAME/KEY: P5A-2G7 LCDR1
<222> LOCATION: (1)..(9)

<400> SEQUENCE: 219

Ser Ser Asp Val Gly Gly Tyr Asn Tyr

```
1               5
```

<210> SEQ ID NO 220
<211> LENGTH: 4
<212> TYPE: PRT
<213> ORGANISM: Homo sapiens
<220> FEATURE:
<221> NAME/KEY: P5A-2G7 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 220

Asp Val Ser Xaa
1

<210> SEQ ID NO 221
<211> LENGTH: 11
<212> TYPE: PRT
<213> ORGANISM: Homo sapiens
<220> FEATURE:
<221> NAME/KEY: P5A-2G7 LCDR3
<222> LOCATION: (1)..(11)

<400> SEQUENCE: 221

```
Ser Ser Tyr Thr Ser Ser Ser Thr Leu Val Val
1               5                   10
```

<210> SEQ ID NO 222
<211> LENGTH: 128
<212> TYPE: PRT
<213> ORGANISM: Homo sapiens
<220> FEATURE:
<221> NAME/KEY: P5A-2G7 VH
<222> LOCATION: (1)..(128)

<400> SEQUENCE: 222

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Arg Cys Tyr Tyr Gly Ser Gly Arg Ala Pro Arg Cys
            100                 105                 110

Val Trp Phe Asp Pro Trp Gly Gln Gly Thr Leu Val Thr Val Ser Ser
        115                 120                 125
```

<210> SEQ ID NO 223
<211> LENGTH: 111
<212> TYPE: PRT
<213> ORGANISM: Homo sapiens
<220> FEATURE:
<221> NAME/KEY: P5A-2G7 VL
<222> LOCATION: (1)..(111)

<400> SEQUENCE: 223

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Ser
            85                  90                  95

Ser Thr Leu Val Val Phe Gly Gly Gly Thr Lys Leu Thr Val Leu
            100                 105                 110

<210> SEQ ID NO 224
<211> LENGTH: 384
<212> TYPE: DNA
<213> ORGANISM: Homo sapiens
<220> FEATURE:
<221> NAME/KEY: P5A-2G7 VHnu
<222> LOCATION: (1)..(384)

<400> SEQUENCE: 224
caggtgcagc tgcaggagtc gggcccagga ctggtgaagc cttcggagac cctgtccctc        60
acctgcactg tctctggtga ctccgtcagc agtggtagtt actactggag ctggatccgg       120
cagcccccag ggaagggact ggagtggatt gggtatatct attacagtgg gagcaccaac       180
tacaacccct ccctcaagag tcgagtcacc atatcagtag acacgtccaa gaaccagttc       240
tccctgaagc tgagctctgt gaccgctgcg gacacggccg tgtattactg tgcgagagag       300
cgatgttact atggttcagg gagagccccc cgttgtgtct ggttcgaccc ctggggccag       360
ggaaccctgg tcaccgtctc ctca                                              384

<210> SEQ ID NO 225
<211> LENGTH: 333
<212> TYPE: DNA
<213> ORGANISM: Homo sapiens
<220> FEATURE:
<221> NAME/KEY: P5A-2G7 VLnu
<222> LOCATION: (1)..(333)

<400> SEQUENCE: 225
cagtctgccc tgactcagcc tgcctccgtg tctgggtctc ctggacagtc gatcaccatc        60
tcctgcactg gaaccagcag tgacgttggt ggttataact atgtctcctg gtaccaacaa       120
cacccaggca aagcccccaa actcatgatt tatgatgtca gtaatcggcc ctcaggggtt       180
tctaatcgct tctctggctc caagtctggc aacacggcct ccctgaccat ctctgggctc       240
caggctgagg acgaggctga ttattactgc agctcatata caagcagcag cactctcgtg       300
gtattcggcg gagggaccaa gctgaccgtc cta                                    333

<210> SEQ ID NO 226
<211> LENGTH: 8
<212> TYPE: PRT
<213> ORGANISM: Homo sapiens
<220> FEATURE:
<221> NAME/KEY: P5A-3C8 HCDR1
<222> LOCATION: (1)..(8)

```
<400> SEQUENCE: 226

Gly Phe Thr Val Ser Ser Asn Tyr
1               5

<210> SEQ ID NO 227
<211> LENGTH: 7
<212> TYPE: PRT
<213> ORGANISM: Homo sapiens
<220> FEATURE:
<221> NAME/KEY: P5A-3C8 HCDR2
<222> LOCATION: (1)..(7)

<400> SEQUENCE: 227

Ile Tyr Ser Gly Gly Ser Thr
1               5

<210> SEQ ID NO 228
<211> LENGTH: 11
<212> TYPE: PRT
<213> ORGANISM: Homo sapiens
<220> FEATURE:
<221> NAME/KEY: P5A-3C8 HCDR3
<222> LOCATION: (1)..(11)

<400> SEQUENCE: 228

Ala Arg Asp Leu Gln Glu His Gly Met Asp Val
1               5                   10

<210> SEQ ID NO 229
<211> LENGTH: 6
<212> TYPE: PRT
<213> ORGANISM: Homo sapiens
<220> FEATURE:
<221> NAME/KEY: P5A-3C8 LCDR1
<222> LOCATION: (1)..(6)

<400> SEQUENCE: 229

Gln Gly Ile Ser Ser Tyr
1               5

<210> SEQ ID NO 230
<211> LENGTH: 4
<212> TYPE: PRT
<213> ORGANISM: Homo sapiens
<220> FEATURE:
<221> NAME/KEY: P5A-3C8 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 230

Ala Ala Ser Xaa
1

<210> SEQ ID NO 231
<211> LENGTH: 11
<212> TYPE: PRT
<213> ORGANISM: Homo sapiens
<220> FEATURE:
<221> NAME/KEY: P5A-3C8 LCDR3
<222> LOCATION: (1)..(11)

<400> SEQUENCE: 231

Gln His Leu Asn Ser Tyr Pro Pro Gly Tyr Thr
1               5                   10
```

```
<210> SEQ ID NO 232
<211> LENGTH: 117
<212> TYPE: PRT
<213> ORGANISM: Homo sapiens
<220> FEATURE:
<221> NAME/KEY: P5A-3C8 VH
<222> LOCATION: (1)..(117)

<400> SEQUENCE: 232
```

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Leu Gln Glu His Gly Met Asp Val Trp Gly Gln Gly Thr Thr
            100                 105                 110

Val Thr Val Ser Ser
        115

```
<210> SEQ ID NO 233
<211> LENGTH: 109
<212> TYPE: PRT
<213> ORGANISM: Homo sapiens
<220> FEATURE:
<221> NAME/KEY: P5A-3C8 VL
<222> LOCATION: (1)..(109)

<400> SEQUENCE: 233
```

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Leu Asn Ser Tyr Pro Pro
                85                  90                  95

Gly Tyr Thr Phe Gly Gln Gly Thr Lys Leu Glu Ile Lys
            100                 105

```
<210> SEQ ID NO 234
<211> LENGTH: 351
<212> TYPE: DNA
<213> ORGANISM: Homo sapiens
<220> FEATURE:
<221> NAME/KEY: P5A-3C8 VHnu
<222> LOCATION: (1)..(351)

<400> SEQUENCE: 234
gaggtgcagc tggtggagtc tgaggaggc ttgatccagc ctggggggtc cctgagactc        60
```

```
tcctgtgcag cctctgggtt caccgtcagt agcaactaca tgagctgggt ccgccaggct    120
ccagggaagg ggctggaatg ggtctcattt atttatagcg gtggtagtac atactacgca    180
gactccgtga agggccgatt caccatctcc agagacaatt ccaagaacac gctgtatctt    240
caaatgaaca gcctgagagc cgaggacacg gccgtgtatt actgtgcgag agatctacag    300
gaacacggta tggacgtctg gggccaaggg accacggtca ccgtctcctc a             351

<210> SEQ ID NO 235
<211> LENGTH: 327
<212> TYPE: DNA
<213> ORGANISM: Homo sapiens
<220> FEATURE:
<221> NAME/KEY: P5A-3C8 VLnu
<222> LOCATION: (1)..(327)

<400> SEQUENCE: 235
gacatccagt tgacccagtc tccatcctcc ctgtctgcat ctgtaggaga cagagtcacc     60
atcacttgcc gggccagtca gggcattagc agttatttag cctggtatca gcaaaaacca    120
gggaaagccc ctaagctcct gatctatgct gcatccactt tgcaaagtgg ggtcccatca    180
aggttcagcg gcagtggatc tgggacagat ttcactctca ccatcagcag cctgcagcct    240
gaagattttg caacttatta ctgtcaacac cttaatagtt accctccggg gtacactttt    300
ggccagggga ccaagctgga gatcaaa                                         327

<210> SEQ ID NO 236
<211> LENGTH: 8
<212> TYPE: PRT
<213> ORGANISM: Homo sapiens
<220> FEATURE:
<221> NAME/KEY: P5A-1D2 HCDR1
<222> LOCATION: (1)..(8)

<400> SEQUENCE: 236

Gly Phe Ile Val Ser Ser Asn Tyr
1               5

<210> SEQ ID NO 237
<211> LENGTH: 7
<212> TYPE: PRT
<213> ORGANISM: Homo sapiens
<220> FEATURE:
<221> NAME/KEY: P5A-1D2 HCDR2
<222> LOCATION: (1)..(7)

<400> SEQUENCE: 237

Ile Tyr Ser Gly Gly Ser Thr
1               5

<210> SEQ ID NO 238
<211> LENGTH: 15
<212> TYPE: PRT
<213> ORGANISM: Homo sapiens
<220> FEATURE:
<221> NAME/KEY: P5A-1D2 HCDR3
<222> LOCATION: (1)..(15)

<400> SEQUENCE: 238

Ala Arg Ala Leu Gln Val Gly Ala Thr Ser Asp Tyr Phe Asp Tyr
1               5                   10                  15

<210> SEQ ID NO 239
<211> LENGTH: 9
```

```
<212> TYPE: PRT
<213> ORGANISM: Homo sapiens
<220> FEATURE:
<221> NAME/KEY: P5A-1D2 LCDR1
<222> LOCATION: (1)..(9)

<400> SEQUENCE: 239

Ser Ser Asn Ile Gly Ala Gly Tyr Asp
1               5

<210> SEQ ID NO 240
<211> LENGTH: 4
<212> TYPE: PRT
<213> ORGANISM: Homo sapiens
<220> FEATURE:
<221> NAME/KEY: P5A-1D2 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 240

Gly Asn Ser Xaa
1

<210> SEQ ID NO 241
<211> LENGTH: 11
<212> TYPE: PRT
<213> ORGANISM: Homo sapiens
<220> FEATURE:
<221> NAME/KEY: P5A-1D2 LCDR3
<222> LOCATION: (1)..(11)

<400> SEQUENCE: 241

Gln Ser Cys Asp Ser Ser Leu Ser Val Val Val
1               5                   10

<210> SEQ ID NO 242
<211> LENGTH: 121
<212> TYPE: PRT
<213> ORGANISM: Homo sapiens
<220> FEATURE:
<221> NAME/KEY: P5A-1D2 VH
<222> LOCATION: (1)..(121)

<400> SEQUENCE: 242

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Ser Asn
            20                  25                  30

Tyr Met Ser Trp Val Arg Gln Ala Pro Gly Lys Gly Leu Glu Trp Val
        35                  40                  45

Ser Ile Ile Tyr Ser Gly Gly Ser Thr Tyr Tyr Ala Asp Ser Val Lys
    50                  55                  60

Gly Arg Phe Thr Ile Ser Arg Asp Asn Ser Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Leu Gln Val Gly Ala Thr Ser Asp Tyr Phe Asp Tyr Trp Gly
            100                 105                 110

Gln Gly Thr Leu Val Thr Val Ser Ser
        115                 120
```

<210> SEQ ID NO 243
<211> LENGTH: 111
<212> TYPE: PRT
<213> ORGANISM: Homo sapiens
<220> FEATURE:
<221> NAME/KEY: P5A-1D2 VL
<222> LOCATION: (1)..(111)

<400> SEQUENCE: 243

```
Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65              70                  75                  80

Gln Ala Glu Asp Glu Thr Asp Tyr Tyr Cys Gln Ser Cys Asp Ser Ser
                85                  90                  95

Leu Ser Val Val Val Phe Gly Gly Gly Thr Lys Leu Thr Val Leu
            100                 105                 110
```

<210> SEQ ID NO 244
<211> LENGTH: 363
<212> TYPE: DNA
<213> ORGANISM: Homo sapiens
<220> FEATURE:
<221> NAME/KEY: P5A-1D2 VHnu
<222> LOCATION: (1)..(363)

<400> SEQUENCE: 244

```
gaggtgcagc tggtggagtc tggaggaggc ttgatccagc ctggggggtc cctgagactc      60
tcctgtgcag cctctgggtt catcgtcagt agcaactaca tgagctgggt ccgccaggct     120
ccagggaagg gctggagtg gtctcaatt atttatagcg gtggtagcac atactacgca       180
gactccgtga aggccgatt caccatctcc agagacaatt ccaacaacac gctgtatctt      240
caaatgaaca gcctgagagc cgaggacacg gccgtatatt actgtgcgag agccctccag      300
gtgggagcta cttcggacta ctttgactac tggggccagg gaaccctggt caccgtctcc     360
tca                                                                   363
```

<210> SEQ ID NO 245
<211> LENGTH: 333
<212> TYPE: DNA
<213> ORGANISM: Homo sapiens
<220> FEATURE:
<221> NAME/KEY: P5A-1D2 VLnu
<222> LOCATION: (1)..(333)

<400> SEQUENCE: 245

```
cagtctgtgc tgacgcagcc gccctcagtg tctggggccc cagggcagag ggtcaccatc      60
tcctgcactg ggagcagctc caacatcggg gcaggttatg atgtacactg gtaccagcaa     120
cttccaggaa cagcccccaa actcctcatc tatggtaaca gcaatcggcc ctcaggggtc     180
cctgaccgat tctctggctc caagtctggc acctcagcct ccctggccat cactgggctc     240
caggctgaag atgagactga ttattactgc cagtcctgtg acagcagcct gagtgttgtg     300
gtattcggcg gagggaccaa gctgaccgtc cta                                   333
```

<210> SEQ ID NO 246
<211> LENGTH: 8
<212> TYPE: PRT
<213> ORGANISM: Homo sapiens
<220> FEATURE:
<221> NAME/KEY: P5A-2F11 HCDR1
<222> LOCATION: (1)..(8)

<400> SEQUENCE: 246

Gly Tyr Thr Phe Thr Ser Tyr Asp
1               5

<210> SEQ ID NO 247
<211> LENGTH: 8
<212> TYPE: PRT
<213> ORGANISM: Homo sapiens
<220> FEATURE:
<221> NAME/KEY: P5A-2F11 HCDR2
<222> LOCATION: (1)..(8)

<400> SEQUENCE: 247

Met Asn Pro Asn Ser Gly Asn Thr
1               5

<210> SEQ ID NO 248
<211> LENGTH: 15
<212> TYPE: PRT
<213> ORGANISM: Homo sapiens
<220> FEATURE:
<221> NAME/KEY: P5A-2F11 HCDR3
<222> LOCATION: (1)..(15)

<400> SEQUENCE: 248

Ala Arg Tyr Ile Val Val Val Pro Ala Ala Lys Gly Phe Asp Pro
1               5                   10                  15

<210> SEQ ID NO 249
<211> LENGTH: 12
<212> TYPE: PRT
<213> ORGANISM: Homo sapiens
<220> FEATURE:
<221> NAME/KEY: P5A-2F11 LCDR1
<222> LOCATION: (1)..(12)

<400> SEQUENCE: 249

Gln Ser Val Leu Tyr Ser Ser Asn Asn Lys Asn Tyr
1               5                   10

<210> SEQ ID NO 250
<211> LENGTH: 4
<212> TYPE: PRT
<213> ORGANISM: Homo sapiens
<220> FEATURE:
<221> NAME/KEY: P5A-2F11 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 250

Trp Ala Ser Xaa
1

<210> SEQ ID NO 251
<211> LENGTH: 9
<212> TYPE: PRT
<213> ORGANISM: Homo sapiens

```
<220> FEATURE:
<221> NAME/KEY: P5A-2F11 LCDR3
<222> LOCATION: (1)..(9)

<400> SEQUENCE: 251

Gln Gln Tyr Tyr Ser Thr Pro Leu Thr
1               5

<210> SEQ ID NO 252
<211> LENGTH: 122
<212> TYPE: PRT
<213> ORGANISM: Homo sapiens
<220> FEATURE:
<221> NAME/KEY: P5A-2F11 VH
<222> LOCATION: (1)..(122)

<400> SEQUENCE: 252

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Ile Val Val Pro Ala Ala Lys Gly Phe Asp Pro Trp
            100                 105                 110

Gly Gln Gly Thr Leu Val Thr Val Ser Ser
        115                 120

<210> SEQ ID NO 253
<211> LENGTH: 113
<212> TYPE: PRT
<213> ORGANISM: Homo sapiens
<220> FEATURE:
<221> NAME/KEY: P5A-2F11 VL
<222> LOCATION: (1)..(113)

<400> SEQUENCE: 253

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys
```

```
<210> SEQ ID NO 254
<211> LENGTH: 366
<212> TYPE: DNA
<213> ORGANISM: Homo sapiens
<220> FEATURE:
<221> NAME/KEY: P5A-2F11 VHnu
<222> LOCATION: (1)..(366)

<400> SEQUENCE: 254
caggtgcagc tggtgcagtc tggggctgag gtgaagaagc ctggggcctc agtgaaggtc    60
tcctgcaagg cttctggata caccttcacc agttatgata tcaactgggt gcgacaggcc   120
actggacaag ggcttgagtg gatgggatgg atgaaccca acagtggtaa cacaggctat   180
gcacagaagt tccagggcag agtcaccatg accaggaaca cctccataag cacagcctac   240
atggagctga gcagcctgag atctgaggac acggccgtgt attactgtgc gagatatatt   300
gtagtagtac cagctgcaaa agggttcgac ccctggggcc agggaaccct ggtcaccgtc   360
tcctca                                                              366

<210> SEQ ID NO 255
<211> LENGTH: 339
<212> TYPE: DNA
<213> ORGANISM: Homo sapiens
<220> FEATURE:
<221> NAME/KEY: P5A-2F11 VLnu
<222> LOCATION: (1)..(339)

<400> SEQUENCE: 255
gacatcgtga tgacccagtc tccagactcc ctggctgtgt ctctgggcga gagggccacc    60
atcaactgca gtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
cctctcactt tcggcggagg gaccaaggtg gagatcaaa                           339

<210> SEQ ID NO 256
<211> LENGTH: 8
<212> TYPE: PRT
<213> ORGANISM: Homo sapiens
<220> FEATURE:
<221> NAME/KEY: P5A-2E1 HCDR1
<222> LOCATION: (1)..(8)

<400> SEQUENCE: 256

Gly Tyr Ser Phe Thr Ser Tyr Trp
1               5

<210> SEQ ID NO 257
<211> LENGTH: 8
<212> TYPE: PRT
<213> ORGANISM: Homo sapiens
<220> FEATURE:
<221> NAME/KEY: P5A-2E1 HCDR2
<222> LOCATION: (1)..(8)

<400> SEQUENCE: 257

Ile Tyr Pro Gly Asp Ser Asp Thr
1               5

<210> SEQ ID NO 258
<211> LENGTH: 12
<212> TYPE: PRT
```

```
<213> ORGANISM: Homo sapiens
<220> FEATURE:
<221> NAME/KEY: P5A-2E1 HCDR3
<222> LOCATION: (1)..(12)

<400> SEQUENCE: 258

Ala Gln Thr Ser Val Thr Arg Asn Trp Phe Asp Pro
1               5                   10

<210> SEQ ID NO 259
<211> LENGTH: 6
<212> TYPE: PRT
<213> ORGANISM: Homo sapiens
<220> FEATURE:
<221> NAME/KEY: P5A-2E1 LCDR1
<222> LOCATION: (1)..(6)

<400> SEQUENCE: 259

Asn Ile Gly Ser Lys Ser
1               5

<210> SEQ ID NO 260
<211> LENGTH: 4
<212> TYPE: PRT
<213> ORGANISM: Homo sapiens
<220> FEATURE:
<221> NAME/KEY: P5A-2E1 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 260

Tyr Asp Ser Xaa
1

<210> SEQ ID NO 261
<211> LENGTH: 11
<212> TYPE: PRT
<213> ORGANISM: Homo sapiens
<220> FEATURE:
<221> NAME/KEY: P5A-2E1 LCDR3
<222> LOCATION: (1)..(11)

<400> SEQUENCE: 261

Gln Val Trp Asp Ser Ser Asp His Val Val
1               5                   10

<210> SEQ ID NO 262
<211> LENGTH: 119
<212> TYPE: PRT
<213> ORGANISM: Homo sapiens
<220> FEATURE:
<221> NAME/KEY: P5A-2E1 VH
<222> LOCATION: (1)..(119)

<400> SEQUENCE: 262

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60
```

```
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Gln Thr Ser Val Thr Arg Asn Trp Phe Asp Pro Trp Gly Gln Gly
            100                 105                 110

Thr Leu Val Thr Val Ser Ser
            115

<210> SEQ ID NO 263
<211> LENGTH: 108
<212> TYPE: PRT
<213> ORGANISM: Homo sapiens
<220> FEATURE:
<221> NAME/KEY: P5A-2E1 VL
<222> LOCATION: (1)..(108)

<400> SEQUENCE: 263

Ser Tyr Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Ile Tyr
         35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Lys Leu Thr Val Leu
            100                 105

<210> SEQ ID NO 264
<211> LENGTH: 357
<212> TYPE: DNA
<213> ORGANISM: Homo sapiens
<220> FEATURE:
<221> NAME/KEY: P5A-2E1 VHnu
<222> LOCATION: (1)..(357)

<400> SEQUENCE: 264
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcagc accgcctac      240 ctgcagtgga gcagcctgaa ggcctcggac accgccatgt attactgtgc cagacgtca      300 gtgactcgca actggttcga ccctgggggc cagggaaccc tggtcaccgt ctcctca       357

<210> SEQ ID NO 265
<211> LENGTH: 324
<212> TYPE: DNA
<213> ORGANISM: Homo sapiens
<220> FEATURE:
<221> NAME/KEY: P5A-2E1 VLnu
<222> LOCATION: (1)..(324)

<400> SEQUENCE: 265
tcctatgtgc tgactcagcc accctcagtg tcagtggccc caggaaagac ggccaggatt      60
```

```
acctgtgggg gaaacaacat tggaagtaaa agtgtgcact ggtaccagca gaagccaggc    120
caggcccctg tgctggtcat ctattatgat agcgaccggc cctcaggat ccctgagcga    180 ttctctggct ccaactctgg gaacacggcc accctgacca tcagcagggt cgaagccggg    240
gatgaggccg actattactg tcaggtgtgg gatagtagta gtgatcatgt ggtattcggc    300
ggagggacca agctgaccgt ccta                                            324
```

<210> SEQ ID NO 266
<211> LENGTH: 8
<212> TYPE: PRT
<213> ORGANISM: Homo sapiens
<220> FEATURE:
<221> NAME/KEY: P5A-1C8 HCDR1
<222> LOCATION: (1)..(8)

<400> SEQUENCE: 266

Gly Tyr Thr Phe Thr Ser Tyr Tyr
1               5

<210> SEQ ID NO 267
<211> LENGTH: 8
<212> TYPE: PRT
<213> ORGANISM: Homo sapiens
<220> FEATURE:
<221> NAME/KEY: P5A-1C8 HCDR2
<222> LOCATION: (1)..(8)

<400> SEQUENCE: 267

Ile Asn Pro Ser Gly Gly Ser Thr
1               5

<210> SEQ ID NO 268
<211> LENGTH: 22
<212> TYPE: PRT
<213> ORGANISM: Homo sapiens
<220> FEATURE:
<221> NAME/KEY: P5A-1C8 HCDR3
<222> LOCATION: (1)..(22)

<400> SEQUENCE: 268

Ala Arg Ser Ala Arg Asp Tyr Tyr Asp Ser Ser Gly Tyr Tyr Tyr Arg
1               5                   10                  15

Ala Glu Tyr Phe Gln His
            20

<210> SEQ ID NO 269
<211> LENGTH: 6
<212> TYPE: PRT
<213> ORGANISM: Homo sapiens
<220> FEATURE:
<221> NAME/KEY: P5A-1C8 LCDR1
<222> LOCATION: (1)..(6)

<400> SEQUENCE: 269

Gln Asp Ile Ser Asn Tyr
1               5

<210> SEQ ID NO 270
<211> LENGTH: 4
<212> TYPE: PRT
<213> ORGANISM: Homo sapiens
<220> FEATURE:
<221> NAME/KEY: P5A-1C8 LCDR2
<222> LOCATION: (1)..(3)
<220> FEATURE:

<221> NAME/KEY: misc_feature
<222> LOCATION: (4)..(4)
<223> OTHER INFORMATION: Xaa is absent.

<400> SEQUENCE: 270

Asp Ala Ser Xaa
1

<210> SEQ ID NO 271
<211> LENGTH: 10
<212> TYPE: PRT
<213> ORGANISM: Homo sapiens
<220> FEATURE:
<221> NAME/KEY: P5A-1C8 LCDR3
<222> LOCATION: (1)..(10)

<400> SEQUENCE: 271

Gln Gln Tyr Asp Asn Leu Pro Ser Ile Thr
1               5                   10

<210> SEQ ID NO 272
<211> LENGTH: 129
<212> TYPE: PRT
<213> ORGANISM: Homo sapiens
<220> FEATURE:
<221> NAME/KEY: P5A-1C8 VH
<222> LOCATION: (1)..(129)

<400> SEQUENCE: 272

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Ala Arg Asp Tyr Tyr Asp Ser Ser Gly Tyr Tyr Tyr Arg
            100                 105                 110

Ala Glu Tyr Phe Gln His Trp Gly Gln Gly Thr Leu Val Thr Val Ser
        115                 120                 125

Ser

<210> SEQ ID NO 273
<211> LENGTH: 108
<212> TYPE: PRT
<213> ORGANISM: Homo sapiens
<220> FEATURE:
<221> NAME/KEY: misc_feature
<222> LOCATION: (1)..(108)
<223> OTHER INFORMATION: P5A-1C8 VL

<400> SEQUENCE: 273

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile

```
              35                  40                  45
Tyr Asp Ala Ser Asn Leu Glu Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Ser
                 85                  90                  95

Ile Thr Phe Gly Gln Gly Thr Arg Leu Glu Ile Lys
            100                 105
```

```
<210> SEQ ID NO 274
<211> LENGTH: 387
<212> TYPE: DNA
<213> ORGANISM: Homo sapiens
<220> FEATURE:
<221> NAME/KEY: P5A-1C8 VHnu
<222> LOCATION: (1)..(387)

<400> SEQUENCE: 274
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaaccta gtggtggtag cacaagctac       180
gcacagaagt tccagggcag agtcaccatg accagggaca cgtccacgag cacagtctac     240
atggagctga gcagcctgag atctgaggac acggccgtgt attactgtgc gaggtcggcc     300
cgggattact atgatagtag tggttattac taccgcgctg aatacttcca gcactggggc     360
cagggcaccc tggtcaccgt ctcctca                                          387
```

```
<210> SEQ ID NO 275
<211> LENGTH: 324
<212> TYPE: DNA
<213> ORGANISM: Homo sapiens
<220> FEATURE:
<221> NAME/KEY: P5A-1C8 VLnu
<222> LOCATION: (1)..(324)

<400> SEQUENCE: 275
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtggatc tgggacagat tttactttca ccatcagcag cctgcagcct     240
gaagatattg caacatatta ctgtcaacag tatgataatc tcccctctat caccttcggc     300
caagggacac gactggagat taaa                                             324
```

```
<210> SEQ ID NO 276
<211> LENGTH: 8
<212> TYPE: PRT
<213> ORGANISM: Homo sapiens
<220> FEATURE:
<221> NAME/KEY: P1A-1C10 HCDR1
<222> LOCATION: (1)..(8)

<400> SEQUENCE: 276

Gly Gly Thr Ser Ser Phe Tyr Asp
 1               5
```

```
<210> SEQ ID NO 277
<211> LENGTH: 8
```

```
<212> TYPE: PRT
<213> ORGANISM: Homo sapiens
<220> FEATURE:
<221> NAME/KEY: P1A-1C10 HCDR2
<222> LOCATION: (1)..(8)

<400> SEQUENCE: 277

Ile Ile Pro Arg Leu Asp Ile Ala
1               5

<210> SEQ ID NO 278
<211> LENGTH: 16
<212> TYPE: PRT
<213> ORGANISM: Homo sapiens
<220> FEATURE:
<221> NAME/KEY: P1A-1C10 HCDR3
<222> LOCATION: (1)..(16)

<400> SEQUENCE: 278

Ala Arg Gly Arg Pro Gly Ser Glu Trp Ala Tyr Gly Pro Phe Asp Leu
1               5                   10                  15

<210> SEQ ID NO 279
<211> LENGTH: 6
<212> TYPE: PRT
<213> ORGANISM: Homo sapiens
<220> FEATURE:
<221> NAME/KEY: P1A-1C10 KCDR1
<222> LOCATION: (1)..(6)

<400> SEQUENCE: 279

Gln Ser Ser Arg Ala Trp
1               5

<210> SEQ ID NO 280
<211> LENGTH: 4
<212> TYPE: PRT
<213> ORGANISM: Homo sapiens
<220> FEATURE:
<221> NAME/KEY: P1A-1C10 KCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 280

Lys Ala Ser Xaa
1

<210> SEQ ID NO 281
<211> LENGTH: 9
<212> TYPE: PRT
<213> ORGANISM: Homo sapiens
<220> FEATURE:
<221> NAME/KEY: P1A-1C10 KCDR3
<222> LOCATION: (1)..(9)

<400> SEQUENCE: 281

His Gln Tyr Asn Ser Ser Pro Phe Thr
1               5

<210> SEQ ID NO 282
<211> LENGTH: 123
<212> TYPE: PRT
<213> ORGANISM: Homo sapiens
<220> FEATURE:
<221> NAME/KEY: P1A-1C10 VH
<222> LOCATION: (1)..(123)
```

<400> SEQUENCE: 282

Gln Val Gln Leu Val Gln Ser Gly Ala Glu Val Lys Asn Pro Gly Ser
1               5                   10                  15

Ser Val Lys Val Ser Cys Lys Ala Gly Gly Thr Ser Ser Phe Tyr
            20                  25                  30

Asp Ile Asn Trp Val Arg Gln Ala Pro Gly Gln Gly Leu Glu Trp Ile
        35                  40                  45

Gly Lys Ile Ile Pro Arg Leu Asp Ile Ala Asp Tyr Ala Gln Lys Ser
    50                  55                  60

Gln Gly Arg Val Thr Ile Thr Ala Asp Lys Ser Thr Ser Thr Val Tyr
65                  70                  75                  80

Leu Glu Leu Ser Ser Leu Lys Ser Asp Asp Thr Ala Val Tyr Phe Cys
                85                  90                  95

Ala Arg Gly Arg Pro Gly Ser Glu Trp Ala Tyr Gly Pro Phe Asp Leu
            100                 105                 110

Trp Gly Gln Gly Thr Leu Val Thr Val Ser Ser
            115                 120

<210> SEQ ID NO 283
<211> LENGTH: 107
<212> TYPE: PRT
<213> ORGANISM: Homo sapiens
<220> FEATURE:
<221> NAME/KEY: P1A-1C10 VL
<222> LOCATION: (1)..(107)

<400> SEQUENCE: 283

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ser Arg Ala Trp
            20                  25                  30

Leu Ala Trp Tyr Gln Gln Lys Pro Gly Lys Ala Pro Lys Leu Leu Ile
        35                  40                  45

Ser Lys Ala Ser Ser Leu Glu Ser Gly Val Pro Ser Arg Phe Ser Gly
    50                  55                  60

Ser Gly Tyr Gly Thr Glu Phe Thr Leu Thr Ile Ser Ser Leu Gln Pro
65                  70                  75                  80

Asp Asp Ser Ala Thr Tyr Tyr Cys His Gln Tyr Asn Ser Ser Pro Phe
                85                  90                  95

Thr Phe Gly Pro Gly Thr Lys Val Gln Ile Lys
            100                 105

<210> SEQ ID NO 284
<211> LENGTH: 369
<212> TYPE: DNA
<213> ORGANISM: Homo sapiens
<220> FEATURE:
<221> NAME/KEY: P1A-1C10 VHnu
<222> LOCATION: (1)..(369)

<400> SEQUENCE: 284
caggtgcagc tggtgcagtc tggggctgag gtgaagaacc cggggtcctc ggtgaaggtc    60
tcctgtaagg ctggtggagg cacctccagt ttctatgata tcaactgggt gcgacaggcc   120
cctggacaag gcttgagtg gataggaaaa atcatccta ggcttgatat agcagactac    180
gcacagaagt cccagggcag agtcacgatt accgcggaca atccacgag tacagtatac     240 ttggaattga gcagcctgaa gtcagacgac acggccgtgt atttctgtgc gagaggtcgg   300
ccgggttcgg agtgggcgta tgcccattt gacctctggg gccagggaac cctggtcacc    360
gtctcctca                                                           369

<210> SEQ ID NO 285
<211> LENGTH: 321
<212> TYPE: DNA
<213> ORGANISM: Homo sapiens
<220> FEATURE:
<221> NAME/KEY: P1A-1C10 Vlnu
<222> LOCATION: (1)..(321)

<400> SEQUENCE: 285
gacatccaga tgacccagtc tccttccacc ctgtctgcat ctgtaggaga cagagtcacc    60
atcacttgcc gggccagtca gagttctagg gcctggttgg cctggtatca gcagaaacca   120
gggaaagccc ctaaactcct gatctctaag gcgtctagtt tagaaagtgg ggtcccatca   180
aggttcagcg gcagtggata tgggacagaa ttcactctca ccatcagcag cctgcagcct   240
gatgattctg caacttatta ctgccaccag tataacagta gcccattcac tttcggccct   300
gggaccaaag tgcagatcaa a                                             321

<210> SEQ ID NO 286
<211> LENGTH: 8
<212> TYPE: PRT
<213> ORGANISM: Homo sapiens
<220> FEATURE:
<221> NAME/KEY: P4A-1H6 HCDR1
<222> LOCATION: (1)..(8)

<400> SEQUENCE: 286

Gly Phe Thr Phe Ser Ser Tyr Gly
1               5

<210> SEQ ID NO 287
<211> LENGTH: 8
<212> TYPE: PRT
<213> ORGANISM: Homo sapiens
<220> FEATURE:
<221> NAME/KEY: P4A-1H6 HCDR2
<222> LOCATION: (1)..(8)

<400> SEQUENCE: 287

Ile Ser Asp Asp Gly Ser Asn Gln
1               5

<210> SEQ ID NO 288
<211> LENGTH: 21
<212> TYPE: PRT
<213> ORGANISM: Homo sapiens
<220> FEATURE:
<221> NAME/KEY: P4A-1H6 HCDR3
<222> LOCATION: (1)..(21)

<400> SEQUENCE: 288

Ala Lys Arg Gly Gly Tyr Cys Ser Thr Thr Ser Cys Leu Leu Arg Trp
1               5                   10                  15
Val Tyr Phe Asp Phe
            20

<210> SEQ ID NO 289
<211> LENGTH: 6
<212> TYPE: PRT
<213> ORGANISM: Homo sapiens
<220> FEATURE:

```
<221> NAME/KEY: P4A-1H6 LCDR1
<222> LOCATION: (1)..(6)

<400> SEQUENCE: 289

Gln Ser Ile Ser Ser Tyr
1               5

<210> SEQ ID NO 290
<211> LENGTH: 4
<212> TYPE: PRT
<213> ORGANISM: Homo sapiens
<220> FEATURE:
<221> NAME/KEY: P4A-1H6 LCDR2
<222> LOCATION: (1)..(3)
<220> FEATURE:
<221> NAME/KEY: misc_feature
<222> LOCATION: (4)..(4)
<223> OTHER INFORMATION: Xaa is absent

<400> SEQUENCE: 290

Ala Ala Ser Xaa
1

<210> SEQ ID NO 291
<211> LENGTH: 8
<212> TYPE: PRT
<213> ORGANISM: Homo sapiens
<220> FEATURE:
<221> NAME/KEY: P4A-1H6 LCDR3
<222> LOCATION: (1)..(8)

<400> SEQUENCE: 291

Gln Gln Ser Tyr Asn Thr Pro Thr
1               5

<210> SEQ ID NO 292
<211> LENGTH: 128
<212> TYPE: PRT
<213> ORGANISM: Homo sapiens
<220> FEATURE:
<221> NAME/KEY: P4A-1H6 VH
<222> LOCATION: (1)..(128)

<400> SEQUENCE: 292

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ser Pro Gly Lys Gly Leu Glu Trp Val
        35                  40                  45

Ala Val Ile Ser Asp Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Arg Gly Gly Tyr Cys Ser Thr Thr Ser Cys Leu Leu Arg Trp
            100                 105                 110

Val Tyr Phe Asp Phe Trp Gly Gln Gly Thr Leu Ala Thr Val Ser Ser
        115                 120                 125

<210> SEQ ID NO 293
<211> LENGTH: 106
<212> TYPE: PRT
```

<213> ORGANISM: Homo sapiens
<220> FEATURE:
<221> NAME/KEY: P4A-1H6 VL
<222> LOCATION: (1)..(106)

<400> SEQUENCE: 293

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu His Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Thr
                85                  90                  95

Phe Gly Pro Gly Thr Lys Val Asp Ile Lys
            100                 105

<210> SEQ ID NO 294
<211> LENGTH: 384
<212> TYPE: DNA
<213> ORGANISM: Homo sapiens
<220> FEATURE:
<221> NAME/KEY: P4A-1H6 VHnu
<222> LOCATION: (1)..(384)

<400> SEQUENCE: 294
caggtgcagc tggtggagtc tggggggaggc gtggtccagc ctgggaggtc cctgagactc     60
tcctgtgcag cctctggatt caccttcagt agctatggca tgcactgggt ccgccagtct    120
ccaggcaagg ggctggagtg ggtggcagtt atatcagatg atggaagtaa tcaatactat    180
gcagactccg tgaagggccg attcaccatc tccagagaca attccaagaa cacgctgtat    240
ctgcaaatga acagcctgag agttgaggac acggctgtgt attactgtgc gaaaggggc    300
ggatattgta gtactaccag ctgcctcctt aggtgggtct actttgactt ctggggccag    360
ggaaccctgg ccaccgtctc ctca                                           384

<210> SEQ ID NO 295
<211> LENGTH: 318
<212> TYPE: DNA
<213> ORGANISM: Homo sapiens
<220> FEATURE:
<221> NAME/KEY: P4A-1H6 Vlnu
<222> LOCATION: (1)..(318)

<400> SEQUENCE: 295
gacatccaga tgacccagtc tccatcctcc ctgtctgcat ctgtaggaga cagagtcacc     60
atcacttgcc gggcaagtca gagcattagc agctatttac attggtatca gcaaaaacca    120
gggaaagccc ctaacctcct gatctatgct gcatccagtt tgcaaagtgg ggtcccatca    180
aggttcagtg gcagtggatc tgggacagat ttcactctca ccatcagcag tctgcaacct    240
gaagactttg caacttacta ctgtcaacag agttacaata cccctacttt cggccctggg    300
accaaagtgg atatcaaa                                                  318

<210> SEQ ID NO 296
<211> LENGTH: 8

```
<212> TYPE: PRT
<213> ORGANISM: Homo sapiens
<220> FEATURE:
<221> NAME/KEY: P4B-1F4 HCDR1
<222> LOCATION: (1)..(8)

<400> SEQUENCE: 296

Gly Phe Thr Phe Ser Ser Tyr Gly
1               5

<210> SEQ ID NO 297
<211> LENGTH: 8
<212> TYPE: PRT
<213> ORGANISM: Homo sapiens
<220> FEATURE:
<221> NAME/KEY: P4B-1F4 HCDR2
<222> LOCATION: (1)..(8)

<400> SEQUENCE: 297

Ile Ser Tyr Asp Gly Ser Asn Lys
1               5

<210> SEQ ID NO 298
<211> LENGTH: 22
<212> TYPE: PRT
<213> ORGANISM: Homo sapiens
<220> FEATURE:
<221> NAME/KEY: P4B-1F4 HCDR3
<222> LOCATION: (1)..(22)

<400> SEQUENCE: 298

Ala Lys Gly Pro Arg Tyr Ser Ser Ser Trp Tyr Ile Ser Leu Tyr Tyr
1               5                   10                  15

Tyr Tyr Gly Met Asp Val
            20

<210> SEQ ID NO 299
<211> LENGTH: 11
<212> TYPE: PRT
<213> ORGANISM: Homo sapiens
<220> FEATURE:
<221> NAME/KEY: P4B-1F4 LCDR1
<222> LOCATION: (1)..(11)

<400> SEQUENCE: 299

Gln Ser Leu Val Tyr Ser Asp Gly Asn Thr Tyr
1               5                   10

<210> SEQ ID NO 300
<211> LENGTH: 4
<212> TYPE: PRT
<213> ORGANISM: Homo sapiens
<220> FEATURE:
<221> NAME/KEY: P4B-1F4 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 300

Lys Val Ser Xaa
1

<210> SEQ ID NO 301
<211> LENGTH: 10
<212> TYPE: PRT
<213> ORGANISM: Homo sapiens
```

```
<220> FEATURE:
<221> NAME/KEY: P4B-1F4 LCDR3
<222> LOCATION: (1)..(10)

<400> SEQUENCE: 301

Met Gln Ala Thr His Trp Pro Leu Tyr Thr
1               5                   10

<210> SEQ ID NO 302
<211> LENGTH: 129
<212> TYPE: PRT
<213> ORGANISM: Homo sapiens
<220> FEATURE:
<221> NAME/KEY: P4B-1F4 VH
<222> LOCATION: (1)..(129)

<400> SEQUENCE: 302

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Tyr Cys
                85                  90                  95

Ala Lys Gly Pro Arg Tyr Ser Ser Ser Trp Tyr Ile Ser Leu Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 303
<211> LENGTH: 113
<212> TYPE: PRT
<213> ORGANISM: Homo sapiens
<220> FEATURE:
<221> NAME/KEY: P4B-1F4 VL
<222> LOCATION: (1)..(113)

<400> SEQUENCE: 303

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Trp Pro Leu Tyr Thr Phe Gly Gln Gly Thr Lys Leu Glu Ile
            100                 105                 110

Lys
```

<210> SEQ ID NO 304
<211> LENGTH: 387
<212> TYPE: DNA
<213> ORGANISM: Homo sapiens
<220> FEATURE:
<221> NAME/KEY: P4B-1F4 VHnu
<222> LOCATION: (1)..(387)

<400> SEQUENCE: 304

```
caggtgcagc tggtggagtc tgggggaggc gtggtccagc ctggagggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatca acagcctgag agctgaggac acggctgtgt attactgtgc gaaagggcct     300
cggtatagca gcagctggta cataagcctt tactactact acggtatgga cgtctggggc     360
caagggacca cggtcaccgt ctcctca                                          387
```

<210> SEQ ID NO 305
<211> LENGTH: 339
<212> TYPE: DNA
<213> ORGANISM: Homo sapiens
<220> FEATURE:
<221> NAME/KEY: P4B-1F4 Vlnu
<222> LOCATION: (1)..(339)

<400> SEQUENCE: 305

```
gatgttgtga tgactcagtc tccactctcc ctgcccgtca cccttggaca gccggcctcc      60
atctcctgca ggtctagtca aagcctcgta tacagtgatg gaaacaccta cttgaattgg     120
tttcagcaga ggccaggcca atctccaagg cgcctaattt ataaggtttc taaccgggac     180
tctggggtcc cagacagatt cagcggcagt gggtcaggca ctgatttcac actgaaaatc     240
agcagggtgg aggctgagga tgttggggtt tattactgca tgcaagctac acactggccc     300
ctgtacactt ttggccaggg gaccaagctg gagatcaaa                            339
```

<210> SEQ ID NO 306
<211> LENGTH: 8
<212> TYPE: PRT
<213> ORGANISM: Homo sapiens
<220> FEATURE:
<221> NAME/KEY: P5A-1B6 HCDR1
<222> LOCATION: (1)..(8)

<400> SEQUENCE: 306

Gly Phe Thr Phe Ser Ser Tyr Ala
1               5

<210> SEQ ID NO 307
<211> LENGTH: 8
<212> TYPE: PRT
<213> ORGANISM: Homo sapiens
<220> FEATURE:
<221> NAME/KEY: P5A-1B6 HCDR2
<222> LOCATION: (1)..(8)

<400> SEQUENCE: 307

Ile Ser Tyr Asp Gly Ser Asn Lys
1               5

<210> SEQ ID NO 308

-continued

```
<211> LENGTH: 20
<212> TYPE: PRT
<213> ORGANISM: Homo sapiens
<220> FEATURE:
<221> NAME/KEY: P5A-1B6 HCDR3
<222> LOCATION: (1)..(20)

<400> SEQUENCE: 308

Ala Arg Asp Gly Gln Ala Ile Thr Met Val Gln Gly Val Ile Gly Pro
1               5                   10                  15

Pro Phe Asp Tyr
            20

<210> SEQ ID NO 309
<211> LENGTH: 6
<212> TYPE: PRT
<213> ORGANISM: Homo sapiens
<220> FEATURE:
<221> NAME/KEY: P5A-1B6 LCDR1
<222> LOCATION: (1)..(6)

<400> SEQUENCE: 309

Gln Asp Ile Ser Asn Tyr
1               5

<210> SEQ ID NO 310
<211> LENGTH: 4
<212> TYPE: PRT
<213> ORGANISM: Homo sapiens
<220> FEATURE:
<221> NAME/KEY: P5A-1B6 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 310

Asp Ala Ser Xaa
1

<210> SEQ ID NO 311
<211> LENGTH: 9
<212> TYPE: PRT
<213> ORGANISM: Homo sapiens
<220> FEATURE:
<221> NAME/KEY: P5A-1B6 LCDR3
<222> LOCATION: (1)..(9)

<400> SEQUENCE: 311

Gln Gln Tyr Asp Asn Leu Pro Tyr Thr
1               5

<210> SEQ ID NO 312
<211> LENGTH: 127
<212> TYPE: PRT
<213> ORGANISM: Homo sapiens
<220> FEATURE:
<221> NAME/KEY: P5A-1B6 VH
<222> LOCATION: (1)..(127)

<400> SEQUENCE: 312

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
```

```
                35                  40                  45
Ala Val Ile Ser Tyr Asp Gly Ser Asn Lys Tyr Tyr Ala Asp Ser Val
                50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asp Gly Gln Ala Ile Thr Met Val Gln Gly Val Ile Gly Pro
            100                 105                 110
Pro Phe Asp Tyr Trp Gly Gln Gly Thr Leu Val Thr Val Ser Ser
        115                 120                 125
```

<210> SEQ ID NO 313
<211> LENGTH: 107
<212> TYPE: PRT
<213> ORGANISM: Homo sapiens
<220> FEATURE:
<221> NAME/KEY: P5A-1B6 VL
<222> LOCATION: (1)..(107)

<400> SEQUENCE: 313

```
Asp Ile Gln Met Thr Gln Ser Pro Ser Ser Leu Ser Ala Ser Val Gly
 1               5                  10                  15
Asp Arg Val Thr Ile Thr Cys Gln Ala Ser Gln Asp Ile Ser Asn Tyr
             20                  25                  30
Leu Asn Trp Tyr Gln Gln Lys Pro Gly Lys Ala Pro Lys Leu Leu Ile
         35                  40                  45
Tyr Asp Ala Ser Asn Leu Glu Thr Gly Val Pro Ser Arg Phe Ser Gly
     50                  55                  60
Ser Gly Ser Gly Thr Asp Phe Thr Phe Thr Ile Ser Ser Leu Gln Pro
 65                  70                  75                  80
Glu Asp Ile Ala Thr Tyr Tyr Cys Gln Gln Tyr Asp Asn Leu Pro Tyr
                 85                  90                  95
Thr Phe Gly Gln Gly Thr Lys Leu Glu Ile Lys
            100                 105
```

<210> SEQ ID NO 314
<211> LENGTH: 381
<212> TYPE: DNA
<213> ORGANISM: Homo sapiens
<220> FEATURE:
<221> NAME/KEY: P5A-1B6 VHnu
<222> LOCATION: (1)..(381)

<400> SEQUENCE: 314

```
caggtgcagc tggtggagtc tgggggaggc gtggtccagc ctggggaggtc cctgagactc      60
tcctgtgcag cctctggatt caccttcagt agctatgcta tgcactgggt ccgccaggct     120
ccaggcaagg ggctggagtg gtggcagtt atatcatatg atggaagtaa taaatactac     180
gcagactccg tgaagggccg attcaccatc tccagagaca attccaagaa cacgctgtat     240
ctgcaaatga acagcctgag agctgaggac acggctgtgt attactgtgc gagagatgga     300
caggctatta ctatggttca ggagttatc ggcccaccct ttgactactg gggccaggga     360
accctggtca ccgtctcctc a                                               381
```

<210> SEQ ID NO 315
<211> LENGTH: 321
<212> TYPE: DNA
<213> ORGANISM: Homo sapiens

```
<220> FEATURE:
<221> NAME/KEY: P5A-1B6 Vlnu
<222> LOCATION: (1)..(321)

<400> SEQUENCE: 315
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg ggtcccatca   180
aggttcagtg gaagtggatc tgggacagat tttactttca ccatcagcag cctgcagcct   240
gaagatattg caacatatta ctgtcaacag tatgataatc tcccgtacac ttttggccag   300
gggaccaagc tggagatcaa a                                             321

<210> SEQ ID NO 316
<211> LENGTH: 8
<212> TYPE: PRT
<213> ORGANISM: Homo sapiens
<220> FEATURE:
<221> NAME/KEY: P5A-1B8 HCDR1
<222> LOCATION: (1)..(8)

<400> SEQUENCE: 316

Gly Phe Thr Val Ser Ser Asn Tyr
1               5

<210> SEQ ID NO 317
<211> LENGTH: 7
<212> TYPE: PRT
<213> ORGANISM: Homo sapiens
<220> FEATURE:
<221> NAME/KEY: P5A-1B8 HCDR2
<222> LOCATION: (1)..(7)

<400> SEQUENCE: 317

Ile Tyr Pro Gly Gly Ser Thr
1               5

<210> SEQ ID NO 318
<211> LENGTH: 9
<212> TYPE: PRT
<213> ORGANISM: Homo sapiens
<220> FEATURE:
<221> NAME/KEY: P5A-1B8 HCDR3
<222> LOCATION: (1)..(9)

<400> SEQUENCE: 318

Ala Arg Glu Thr Leu Ala Phe Asp Tyr
1               5

<210> SEQ ID NO 319
<211> LENGTH: 6
<212> TYPE: PRT
<213> ORGANISM: Homo sapiens
<220> FEATURE:
<221> NAME/KEY: P5A-1B8 LCDR1
<222> LOCATION: (1)..(6)

<400> SEQUENCE: 319

Gln Gly Ile Ser Ser Tyr
1               5

<210> SEQ ID NO 320
<211> LENGTH: 4
<212> TYPE: PRT
<213> ORGANISM: Homo sapiens
```

```
<220> FEATURE:
<221> NAME/KEY: P5A-1B8 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 320

Ala Ala Ser Xaa
1

<210> SEQ ID NO 321
<211> LENGTH: 9
<212> TYPE: PRT
<213> ORGANISM: Homo sapiens
<220> FEATURE:
<221> NAME/KEY: P5A-1B8 LCDR3
<222> LOCATION: (1)..(9)

<400> SEQUENCE: 321

Gln Gln Leu Asn Ser Tyr Pro Pro Ala
1               5

<210> SEQ ID NO 322
<211> LENGTH: 115
<212> TYPE: PRT
<213> ORGANISM: Homo sapiens
<220> FEATURE:
<221> NAME/KEY: P5A-1B8 VH
<222> LOCATION: (1)..(115)

<400> SEQUENCE: 322

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Pro Gly Gly Ser Thr Phe Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Thr Leu Ala Phe Asp Tyr Trp Gly Gln Gly Thr Leu Val Thr
            100                 105                 110

Val Ser Ser
        115

<210> SEQ ID NO 323
<211> LENGTH: 107
<212> TYPE: PRT
<213> ORGANISM: Homo sapiens
<220> FEATURE:
<221> NAME/KEY: P5A-1B8 VL
<222> LOCATION: (1)..(107)

<400> SEQUENCE: 323

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30
```

```
Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Pro
                 85                  90                  95

Ala Phe Gly Gly Gly Thr Lys Val Glu Ile Lys
            100                 105
```

<210> SEQ ID NO 324
<211> LENGTH: 345
<212> TYPE: DNA
<213> ORGANISM: Homo sapiens
<220> FEATURE:
<221> NAME/KEY: P5A-1B8 VHnu
<222> LOCATION: (1)..(345)

<400> SEQUENCE: 324

```
gaggtgcagc tggtggagtc tgaggaggc ttgatccagc ctgggggtc cctgagactc      60 tcctgtgcag cctctgggtt caccgtcagt agcaactaca tgagctgggt ccgccaggct    120
ccagggaagg gctggagtg gtctcagtt atttatcccg gtggtagcac attctacgca     180
gactccgtga agggccgatt caccatctcc agagacaatt ccaagaacac cctgtatctt    240
caaatgaaca gcctgagagc cgaggacacg gccgtgtatt actgtgcgag agagaccccta  300 gcctttgact actggggcca gggaaccctg gtcaccgtct cctca                    345
```

<210> SEQ ID NO 325
<211> LENGTH: 321
<212> TYPE: DNA
<213> ORGANISM: Homo sapiens
<220> FEATURE:
<221> NAME/KEY: P5A-1B8 Vlnu
<222> LOCATION: (1)..(321)

<400> SEQUENCE: 325

```
gacatccagt tgacccagtc tccatccttc ctgtctgcat ctgtaggaga cagagtcacc     60
atcacttgcc gggccagtca gggcattagc agttatttag cctggtatca gcaaaaacca   120
gggaaagccc ctaagctcct gatctatgct gcatccactt tgcaaagtgg ggtcccatca    180
aggttcagcg gcagtggatc tgggacagaa ttcactctca caatcagcag cctgcagcct    240
gaagattttg caacttatta ctgtcaacag cttaatagtt accctccagc tttcggcgga    300
gggaccaagg tggagatcaa a                                              321
```

<210> SEQ ID NO 326
<211> LENGTH: 8
<212> TYPE: PRT
<213> ORGANISM: Homo sapiens
<220> FEATURE:
<221> NAME/KEY: P5A-1B9 HCDR1
<222> LOCATION: (1)..(8)

<400> SEQUENCE: 326

```
Gly Gly Ser Ile Ser Ser Tyr Tyr
 1               5
```

<210> SEQ ID NO 327
<211> LENGTH: 7
<212> TYPE: PRT

<213> ORGANISM: Homo sapiens
<220> FEATURE:
<221> NAME/KEY: P5A-1B9 HCDR2
<222> LOCATION: (1)..(7)

<400> SEQUENCE: 327

Ile Ser Tyr Ser Gly Ser Thr
1               5

<210> SEQ ID NO 328
<211> LENGTH: 22
<212> TYPE: PRT
<213> ORGANISM: Homo sapiens
<220> FEATURE:
<221> NAME/KEY: P5A-1B9 HCDR3
<222> LOCATION: (1)..(22)

<400> SEQUENCE: 328

Ala Ser Asn Gly Gln Tyr Tyr Asp Ile Leu Thr Gly Gln Pro Pro Asp
1               5                   10                  15

Tyr Trp Tyr Phe Asp Leu
            20

<210> SEQ ID NO 329
<211> LENGTH: 12
<212> TYPE: PRT
<213> ORGANISM: Homo sapiens
<220> FEATURE:
<221> NAME/KEY: P5A-1B9 LCDR1
<222> LOCATION: (1)..(12)

<400> SEQUENCE: 329

Gln Ser Val Leu Tyr Ser Ser Asn Asn Lys Asn Tyr
1               5                   10

<210> SEQ ID NO 330
<211> LENGTH: 4
<212> TYPE: PRT
<213> ORGANISM: Homo sapiens
<220> FEATURE:
<221> NAME/KEY: P5A-1B9 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 330

Trp Ala Ser Xaa
1

<210> SEQ ID NO 331
<211> LENGTH: 9
<212> TYPE: PRT
<213> ORGANISM: Homo sapiens
<220> FEATURE:
<221> NAME/KEY: P5A-1B9 LCDR3
<222> LOCATION: (1)..(9)

<400> SEQUENCE: 331

Gln Gln Tyr Tyr Ser Thr Pro Leu Thr
1               5

<210> SEQ ID NO 332
<211> LENGTH: 128
<212> TYPE: PRT
<213> ORGANISM: Homo sapiens
<220> FEATURE:

```
<221> NAME/KEY: P5A-1B9 VH
<222> LOCATION: (1)..(128)

<400> SEQUENCE: 332

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Ser Tyr Ser Gly Ser Thr Asn Tyr Asn Pro Ser Leu Lys
    50                  55                  60

Ser Arg Val Thr Ile Ser Leu Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Asn Gly Gln Tyr Tyr Asp Ile Leu Thr Gly Gln Pro Pro Asp Tyr
            100                 105                 110

Trp Tyr Phe Asp Leu Trp Gly Arg Gly Thr Leu Val Thr Val Ser Ser
        115                 120                 125

<210> SEQ ID NO 333
<211> LENGTH: 113
<212> TYPE: PRT
<213> ORGANISM: Homo sapiens
<220> FEATURE:
<221> NAME/KEY: P5A-1B9 VL
<222> LOCATION: (1)..(113)

<400> SEQUENCE: 333

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys

<210> SEQ ID NO 334
<211> LENGTH: 384
<212> TYPE: DNA
<213> ORGANISM: Homo sapiens
<220> FEATURE:
<221> NAME/KEY: P5A-1B9 VHnu
<222> LOCATION: (1)..(384)

<400> SEQUENCE: 334
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctcttaca gtgggagcac caactacaac     180
```

```
ccctccctca agagtcgagt caccatatca ctagacacgt ccaagaacca gttctccctg    240
aagctgagct ctgtgaccgc tgcggacacg gccgtgtatt actgtgcgag caacggccag    300
tattacgata ttttgactgg tcaacctcct gactactggt acttcgatct ctggggccgt    360
ggcaccctgg tcactgtctc ctca                                            384
```

<210> SEQ ID NO 335
<211> LENGTH: 339
<212> TYPE: DNA
<213> ORGANISM: Homo sapiens
<220> FEATURE:
<221> NAME/KEY: P5A-1B9 Vlnu
<222> LOCATION: (1)..(339)

<400> SEQUENCE: 335

```
gacatcgtga tgacccagtc tccagactcc ctggctgtgt ctctgggcga gagggccacc    60
atcaactgca gtccagcca gagtgtttta tacagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
ccgctcactt tcggcggagg gaccaaggtg gagatcaaa                            339
```

<210> SEQ ID NO 336
<211> LENGTH: 8
<212> TYPE: PRT
<213> ORGANISM: Homo sapiens
<220> FEATURE:
<221> NAME/KEY: P5A-1D1 HCDR1
<222> LOCATION: (1)..(8)

<400> SEQUENCE: 336

Gly Leu Thr Val Ser Ser Asn Tyr
1               5

<210> SEQ ID NO 337
<211> LENGTH: 7
<212> TYPE: PRT
<213> ORGANISM: Homo sapiens
<220> FEATURE:
<221> NAME/KEY: P5A-1D1 HCDR2
<222> LOCATION: (1)..(7)

<400> SEQUENCE: 337

Ile Tyr Ser Gly Gly Ser Thr
1               5

<210> SEQ ID NO 338
<211> LENGTH: 11
<212> TYPE: PRT
<213> ORGANISM: Homo sapiens
<220> FEATURE:
<221> NAME/KEY: P5A-1D1 HCDR3
<222> LOCATION: (1)..(11)

<400> SEQUENCE: 338

Ala Arg Asp Leu Tyr Tyr Tyr Gly Met Asp Val
1               5                   10

<210> SEQ ID NO 339
<211> LENGTH: 6
<212> TYPE: PRT
<213> ORGANISM: Homo sapiens

```
<220> FEATURE:
<221> NAME/KEY: P5A-1D1 LCDR1
<222> LOCATION: (1)..(6)

<400> SEQUENCE: 339

Gln Gly Ile Ser Ser Tyr
1               5

<210> SEQ ID NO 340
<211> LENGTH: 4
<212> TYPE: PRT
<213> ORGANISM: Homo sapiens
<220> FEATURE:
<221> NAME/KEY: P5A-1D1 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 340

Ala Ala Ser Xaa
1

<210> SEQ ID NO 341
<211> LENGTH: 8
<212> TYPE: PRT
<213> ORGANISM: Homo sapiens
<220> FEATURE:
<221> NAME/KEY: P5A-1D1 LCDR3
<222> LOCATION: (1)..(8)

<400> SEQUENCE: 341

Gln Gln Leu Asn Ser Tyr Pro Thr
1               5

<210> SEQ ID NO 342
<211> LENGTH: 117
<212> TYPE: PRT
<213> ORGANISM: Homo sapiens
<220> FEATURE:
<221> NAME/KEY: P5A-1D1 VH
<222> LOCATION: (1)..(117)

<400> SEQUENCE: 342

Glu Val Gln Leu Val Glu Ser Gly Gly Leu Ile Gln Pro Gly Gly
1               5                   10                  15

Ser Leu Arg Leu Ser Cys Ala Ala Ser Gly Leu Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Leu Tyr Tyr Tyr Gly Met Asp Val Trp Gly Gln Gly Thr Thr
            100                 105                 110

Val Thr Val Ser Thr
            115

<210> SEQ ID NO 343
<211> LENGTH: 106
```

```
<212> TYPE: PRT
<213> ORGANISM: Homo sapiens
<220> FEATURE:
<221> NAME/KEY: P5A-1D1 VL
<222> LOCATION: (1)..(106)

<400> SEQUENCE: 343

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Thr
                85                  90                  95

Phe Gly Gln Gly Thr Arg Leu Glu Ile Lys
            100                 105

<210> SEQ ID NO 344
<211> LENGTH: 351
<212> TYPE: DNA
<213> ORGANISM: Homo sapiens
<220> FEATURE:
<221> NAME/KEY: P5A-1D1 VHnu
<222> LOCATION: (1)..(351)

<400> SEQUENCE: 344
gaggtgcagc tggtggagtc tggaggaggc ttgatccagc ctgggggtc cctgagactc      60 tcctgtgcag cctctgggct caccgtcagt agcaactaca tgagctgggt ccgccaggct    120
ccagggaagg ggctggagtg ggtctcagtt atttatagcg gtggtagcac atactacgca    180
gactccgtga agggccgatt caccatctcc agagacaatt ccaagaacac gctgtatctt    240
caaatgaaca gcctgagagc cgaggacacg gccgtgtatt actgtgcgag agatttgtac    300
tactacggta tggacgtctg gggccaaggg accacggtca ccgtctccac a             351

<210> SEQ ID NO 345
<211> LENGTH: 318
<212> TYPE: DNA
<213> ORGANISM: Homo sapiens
<220> FEATURE:
<221> NAME/KEY: P5A-1D1 Vlnu
<222> LOCATION: (1)..(318)

<400> SEQUENCE: 345
gacatccagt tgacccagtc tccatccttc ctgtctgcat ctgtaggaga cagagtcacc      60
atcacttgcc gggccagtca gggcattagc agttatttag cctggtatca gcaaaaacca    120
gggaaagccc ctaagctcct gatctatgct gcatccactt tgcaaagtgg ggtcccatca    180
aggttcagcg gcagtggatc tgggacagat ttcactctca ccatcagcag cctgcagcct    240
gaagattttg caacttatta ctgtcaacag cttaatagtt accctacctt cggccaaggg    300
acacgactgg agattaaa                                                  318

<210> SEQ ID NO 346
<211> LENGTH: 8
<212> TYPE: PRT
```

```
<213> ORGANISM: Homo sapiens
<220> FEATURE:
<221> NAME/KEY: P5A-1D10 HCDR1
<222> LOCATION: (1)..(8)

<400> SEQUENCE: 346

Gln Phe Thr Phe Ser Asp Tyr Ser
1               5

<210> SEQ ID NO 347
<211> LENGTH: 8
<212> TYPE: PRT
<213> ORGANISM: Homo sapiens
<220> FEATURE:
<221> NAME/KEY: P5A-1D10 HCDR2
<222> LOCATION: (1)..(8)

<400> SEQUENCE: 347

Ile Ser Gln Ser Gly Ser Thr Ile
1               5

<210> SEQ ID NO 348
<211> LENGTH: 21
<212> TYPE: PRT
<213> ORGANISM: Homo sapiens
<220> FEATURE:
<221> NAME/KEY: P5A-1D10 HCDR3
<222> LOCATION: (1)..(21)

<400> SEQUENCE: 348

Ala Arg Gly Val Ser Pro Ser Tyr Val Trp Gly Ser Tyr Arg Ser Leu
1               5                   10                  15

Tyr His Phe Asp Tyr
            20

<210> SEQ ID NO 349
<211> LENGTH: 9
<212> TYPE: PRT
<213> ORGANISM: Homo sapiens
<220> FEATURE:
<221> NAME/KEY: P5A-1D10 LCDR1
<222> LOCATION: (1)..(9)

<400> SEQUENCE: 349

Ser Ser Asp Val Gly Gly Tyr Asn Tyr
1               5

<210> SEQ ID NO 350
<211> LENGTH: 4
<212> TYPE: PRT
<213> ORGANISM: Homo sapiens
<220> FEATURE:
<221> NAME/KEY: P5A-1D10 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 350

Asp Val Ser Xaa
1

<210> SEQ ID NO 351
<211> LENGTH: 11
<212> TYPE: PRT
<213> ORGANISM: Homo sapiens
<220> FEATURE:
```

<221> NAME/KEY: P5A-1D10 LCDR3
<222> LOCATION: (1)..(11)

<400> SEQUENCE: 351

Ser Ser Phe Thr Ser Ser Thr Thr Val Val Val
1               5                   10

<210> SEQ ID NO 352
<211> LENGTH: 128
<212> TYPE: PRT
<213> ORGANISM: Homo sapiens
<220> FEATURE:
<221> NAME/KEY: P5A-1D10 VH
<222> LOCATION: (1)..(128)

<400> SEQUENCE: 352

Gln Val Gln Leu Val Glu Ser Gly Gly Gly Leu Val Lys Pro Gly Gly
1               5                   10                  15

Ser Leu Arg Leu Ser Cys Ala Ala Ser Gln Phe Thr Phe Ser Asp Tyr
                20                  25                  30

Ser Met Thr Trp Ile Arg Gln Ala Pro Gly Lys Gly Leu Glu Trp Val
            35                  40                  45

Ser Tyr Ile Ser Gln Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Val Ser Pro Ser Tyr Val Trp Gly Ser Tyr Arg Ser Leu
            100                 105                 110

Tyr His Phe Asp Tyr Trp Gly Gln Gly Thr Leu Val Thr Val Ser Ser
        115                 120                 125

<210> SEQ ID NO 353
<211> LENGTH: 111
<212> TYPE: PRT
<213> ORGANISM: Homo sapiens
<220> FEATURE:
<221> NAME/KEY: P5A-1D10 VL
<222> LOCATION: (1)..(111)

<400> SEQUENCE: 353

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Ala Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Ser Ser
                85                  90                  95

Thr Thr Val Val Val Phe Gly Gly Gly Thr Lys Leu Thr Val Leu
            100                 105                 110

<210> SEQ ID NO 354
<211> LENGTH: 384
<212> TYPE: DNA

```
<213> ORGANISM: Homo sapiens
<220> FEATURE:
<221> NAME/KEY: P5A-1D10 VHnu
<222> LOCATION: (1)..(384)

<400> SEQUENCE: 354
caggtgcagc tggtggagtc tgggggaggc ttggtcaagc ctggagggtc cctgagactc      60
tcctgtgcag cctctcaatt caccttcagt gactactcca tgacctggat ccgccaggct     120
ccagggaagg ggctggagtg ggtttcatac attagtcaaa gtggtagtac catatactac     180
gcagactctg tgaagggccg attcaccatc tccagggaca acgccaagaa ctcactgtat     240
ctgcaaatga acagcctgag agccgaggac acggccgtgt attactgtgc gagaggtgtc     300
agcccatcct acgtttgggg gagttatcgt tccttgtacc actttgacta ctggggccag     360
ggaaccctgg tcaccgtctc ctca                                            384

<210> SEQ ID NO 355
<211> LENGTH: 333
<212> TYPE: DNA
<213> ORGANISM: Homo sapiens
<220> FEATURE:
<221> NAME/KEY: P5A-1D10 Vlnu
<222> LOCATION: (1)..(333)

<400> SEQUENCE: 355
cagtctgccc tgactcagcc tgcctccgtg tctgggtctc ctggacagtc gatcaccatc      60
tcctgcactg gaaccagcag tgacgttggt ggttataact atgtctcctg gtaccaacaa     120
cacccaggca aagcccccaa actcatgatt tatgatgtca gtaatcggcc ctcagggggtt    180 tctaatcgct tctctgcctc caagtctggc aacacggcct ccctgaccat ctctgggctc     240
caggctgagg acgaggctga ttattactgc agctcattta caagcagcac cactgtcgtg    300
gtattcggcg gagggaccaa gctgaccgtc cta                                   333

<210> SEQ ID NO 356
<211> LENGTH: 8
<212> TYPE: PRT
<213> ORGANISM: Homo sapiens
<220> FEATURE:
<221> NAME/KEY: P5A-2D11 HCDR1
<222> LOCATION: (1)..(8)

<400> SEQUENCE: 356

Gly Tyr Ser Phe Thr Ser Tyr Trp
1               5

<210> SEQ ID NO 357
<211> LENGTH: 8
<212> TYPE: PRT
<213> ORGANISM: Homo sapiens
<220> FEATURE:
<221> NAME/KEY: P5A-2D11 HCDR2
<222> LOCATION: (1)..(8)

<400> SEQUENCE: 357

Ile Tyr Pro Gly Asp Ser Asp Thr
1               5

<210> SEQ ID NO 358
<211> LENGTH: 13
<212> TYPE: PRT
<213> ORGANISM: Homo sapiens
<220> FEATURE:
<221> NAME/KEY: P5A-2D11 HCDR3
```

```
<222> LOCATION: (1)..(13)

<400> SEQUENCE: 358

Ala Arg Arg Asp Ser Thr Tyr Gly Gly Asn Thr Asp Tyr
1               5                   10

<210> SEQ ID NO 359
<211> LENGTH: 8
<212> TYPE: PRT
<213> ORGANISM: Homo sapiens
<220> FEATURE:
<221> NAME/KEY: P5A-2D11 LCDR1
<222> LOCATION: (1)..(8)

<400> SEQUENCE: 359

Ser Ser Asn Ile Gly Ser Asn Thr
1               5

<210> SEQ ID NO 360
<211> LENGTH: 4
<212> TYPE: PRT
<213> ORGANISM: Homo sapiens
<220> FEATURE:
<221> NAME/KEY: P5A-2D11 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 360

Ser Asn Asn Xaa
1

<210> SEQ ID NO 361
<211> LENGTH: 11
<212> TYPE: PRT
<213> ORGANISM: Homo sapiens
<220> FEATURE:
<221> NAME/KEY: P5A-2D11 LCDR3
<222> LOCATION: (1)..(11)

<400> SEQUENCE: 361

Ala Ala Trp Asp Asp Ser Leu Asn Gly Val Val
1               5                   10

<210> SEQ ID NO 362
<211> LENGTH: 120
<212> TYPE: PRT
<213> ORGANISM: Homo sapiens
<220> FEATURE:
<221> NAME/KEY: P5A-2D11 VH
<222> LOCATION: (1)..(120)

<400> SEQUENCE: 362

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Arg Asp Ser Thr Tyr Gly Gly Asn Thr Asp Tyr Trp Gly Gln
            100                 105                 110

Gly Thr Leu Val Thr Val Ser Ser
        115                 120

<210> SEQ ID NO 363
<211> LENGTH: 110
<212> TYPE: PRT
<213> ORGANISM: Homo sapiens
<220> FEATURE:
<221> NAME/KEY: P5A-2D11 VL
<222> LOCATION: (1)..(110)

<400> SEQUENCE: 363

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 364
<211> LENGTH: 360
<212> TYPE: DNA
<213> ORGANISM: Homo sapiens
<220> FEATURE:
<221> NAME/KEY: P5A-2D11 VHnu
<222> LOCATION: (1)..(360)

<400> SEQUENCE: 364
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac     240 ctgcagtgga gcagcctgaa ggcctcggac accgccatgt attactgtgc gagacgggat     300
tcgacctacg gtggtaacac tgactactgg ggccaggaa ccctggtcac cgtctcctca      360

<210> SEQ ID NO 365
<211> LENGTH: 330
<212> TYPE: DNA
<213> ORGANISM: Homo sapiens
<220> FEATURE:
<221> NAME/KEY: P5A-2D11 Vlnu
<222> LOCATION: (1)..(330)

<400> SEQUENCE: 365
cagtctgtgc tgactcagcc accctcagcg tctgggaccc ccgggcagag ggtcaccatc      60
tcttgttctg gaagcagctc caacatcgga agtaatactg taaactggta ccagcagctc     120
```

```
ccaggaacgg ccccaaaact cctcatctat agtaataatc agcggccctc agggtccct      180 gaccgattct ctggctccaa gtctggcacc tcagcctccc tggccatcag tgggctccag      240
tctgaggatg aggctgatta ttactgtgca gcatgggatg acagcctgaa tggtgtggta      300
ttcggcggag ggaccaagct gaccgtccta                                       330
```

<210> SEQ ID NO 366
<211> LENGTH: 8
<212> TYPE: PRT
<213> ORGANISM: Homo sapiens
<220> FEATURE:
<221> NAME/KEY: P5A-2G9 HCDR1
<222> LOCATION: (1)..(8)

<400> SEQUENCE: 366

Gly Phe Thr Phe Ser Ser Tyr Gly
1               5

<210> SEQ ID NO 367
<211> LENGTH: 8
<212> TYPE: PRT
<213> ORGANISM: Homo sapiens
<220> FEATURE:
<221> NAME/KEY: P5A-2G9 HCDR2
<222> LOCATION: (1)..(8)

<400> SEQUENCE: 367

Ile Trp Tyr Asp Gly Ser Asn Lys
1               5

<210> SEQ ID NO 368
<211> LENGTH: 12
<212> TYPE: PRT
<213> ORGANISM: Homo sapiens
<220> FEATURE:
<221> NAME/KEY: P5A-2G9 HCDR3
<222> LOCATION: (1)..(12)

<400> SEQUENCE: 368

Ala Arg Trp Phe His Thr Gly Gly Tyr Phe Asp Tyr
1               5                   10

<210> SEQ ID NO 369
<211> LENGTH: 9
<212> TYPE: PRT
<213> ORGANISM: Homo sapiens
<220> FEATURE:
<221> NAME/KEY: P5A-2G9 LCDR1
<222> LOCATION: (1)..(9)

<400> SEQUENCE: 369

Ser Asp Ile Asn Val Ser Ser Tyr Asn
1               5

<210> SEQ ID NO 370
<211> LENGTH: 7
<212> TYPE: PRT
<213> ORGANISM: Homo sapiens
<220> FEATURE:
<221> NAME/KEY: P5A-2G9 LCDR2
<222> LOCATION: (1)..(7)

<400> SEQUENCE: 370

Tyr Tyr Ser Asp Ser Asp Lys
1               5

```
<210> SEQ ID NO 371
<211> LENGTH: 10
<212> TYPE: PRT
<213> ORGANISM: Homo sapiens
<220> FEATURE:
<221> NAME/KEY: P5A-2G9 LCDR3
<222> LOCATION: (1)..(10)

<400> SEQUENCE: 371

Met Ile Trp Pro Ser Asn Ala Leu Tyr Val
1               5                   10

<210> SEQ ID NO 372
<211> LENGTH: 119
<212> TYPE: PRT
<213> ORGANISM: Homo sapiens
<220> FEATURE:
<221> NAME/KEY: P5A-2G9 VH
<222> LOCATION: (1)..(119)

<400> SEQUENCE: 372

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Phe His Thr Gly Gly Tyr Phe Asp Tyr Trp Gly Gln Gly
            100                 105                 110

Thr Leu Val Thr Val Ser Ser
        115

<210> SEQ ID NO 373
<211> LENGTH: 116
<212> TYPE: PRT
<213> ORGANISM: Homo sapiens
<220> FEATURE:
<221> NAME/KEY: P5A-2G9 VL
<222> LOCATION: (1)..(116)

<400> SEQUENCE: 373

Gln Pro Val Leu Thr Gln Pro Pro Ser Ser Ala Ser Pro Gly Glu
1               5                   10                  15

Ser Ala Arg Leu Thr Cys Thr Leu Pro Ser Asp Ile Asn Val Ser Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Asp Lys Gly Gln Gly Ser Gly Val
    50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

Met Ile Trp Pro Ser Asn Ala Leu Tyr Val Phe Gly Thr Gly Thr Lys
            100                 105                 110
```

Val Thr Val Leu
        115

<210> SEQ ID NO 374
<211> LENGTH: 357
<212> TYPE: DNA
<213> ORGANISM: Homo sapiens
<220> FEATURE:
<221> NAME/KEY: P5A-2G9 VHnu
<222> LOCATION: (1)..(357)

<400> SEQUENCE: 374
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagatggttc     300
cacacggggg ggtactttga ctactggggc cagggaaccc tggtcaccgt ctcctca       357

<210> SEQ ID NO 375
<211> LENGTH: 348
<212> TYPE: DNA
<213> ORGANISM: Homo sapiens
<220> FEATURE:
<221> NAME/KEY: P5A-2G9 Vlnu
<222> LOCATION: (1)..(348)

<400> SEQUENCE: 375
cagcctgtgc tgactcagcc accttcctcc tccgcatctc ctggagaatc cgccagactc      60
acctgcacct tgcccagtga catcaatgtt agtagctaca acatatactg gtaccagcag     120
aagccaggga gcctcccag gtatctcctg tactactact cagactcaga taagggccag     180
ggctctggag tccccagccg cttctctgga tccaaagatg cttcagccaa tacagggatt     240
ttactcatct ccgggctcca gtctgaggat gaggctgact attactgtat gatttggcca     300
agcaatgctc tttatgtctt cggaactggg accaaggtca ccgtccta                 348

<210> SEQ ID NO 376
<211> LENGTH: 8
<212> TYPE: PRT
<213> ORGANISM: Homo sapiens
<220> FEATURE:
<221> NAME/KEY: P5A-2H3 HCDR1
<222> LOCATION: (1)..(8)

<400> SEQUENCE: 376

Gly Tyr Ser Phe Thr Ser Tyr Trp
1               5

<210> SEQ ID NO 377
<211> LENGTH: 8
<212> TYPE: PRT
<213> ORGANISM: Homo sapiens
<220> FEATURE:
<221> NAME/KEY: P5A-2H3 HCDR2
<222> LOCATION: (1)..(8)

<400> SEQUENCE: 377

Ile Tyr Pro Gly Asp Ser Asp Thr
1               5

```
<210> SEQ ID NO 378
<211> LENGTH: 13
<212> TYPE: PRT
<213> ORGANISM: Homo sapiens
<220> FEATURE:
<221> NAME/KEY: P5A-2H3 HCDR3
<222> LOCATION: (1)..(13)

<400> SEQUENCE: 378

Ala Arg Arg Asp Ser Thr Tyr Gly Gly Asn Thr Asp Tyr
1               5                   10

<210> SEQ ID NO 379
<211> LENGTH: 8
<212> TYPE: PRT
<213> ORGANISM: Homo sapiens
<220> FEATURE:
<221> NAME/KEY: P5A-2H3 LCDR1
<222> LOCATION: (1)..(8)

<400> SEQUENCE: 379

Ser Ser Asn Ile Gly Ser Asn Thr
1               5

<210> SEQ ID NO 380
<211> LENGTH: 4
<212> TYPE: PRT
<213> ORGANISM: Homo sapiens
<220> FEATURE:
<221> NAME/KEY: P5A-2H3 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 380

Ser Asn Asn Xaa
1

<210> SEQ ID NO 381
<211> LENGTH: 11
<212> TYPE: PRT
<213> ORGANISM: Homo sapiens
<220> FEATURE:
<221> NAME/KEY: P5A-2H3 LCDR3
<222> LOCATION: (1)..(11)

<400> SEQUENCE: 381

Ala Ala Trp Asp Asp Ser Leu Asn Gly Val Val
1               5                   10

<210> SEQ ID NO 382
<211> LENGTH: 120
<212> TYPE: PRT
<213> ORGANISM: Homo sapiens
<220> FEATURE:
<221> NAME/KEY: P5A-2H3 VH
<222> LOCATION: (1)..(120)

<400> SEQUENCE: 382

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45
```

Gly Ile Ile Tyr Pro Gly Asp Ser Asp Thr Arg Tyr Ser Pro Ser Phe
    50                  55                  60

Gln Gly Gln Val Thr Ile Ser Ala Glu Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Asp Ser Thr Tyr Gly Gly Asn Thr Asp Tyr Trp Gly Gln
            100                 105                 110

Gly Thr Leu Val Thr Val Ser Ser
            115                 120

<210> SEQ ID NO 383
<211> LENGTH: 110
<212> TYPE: PRT
<213> ORGANISM: Homo sapiens
<220> FEATURE:
<221> NAME/KEY: P5A-2H3 VL
<222> LOCATION: (1)..(110)

<400> SEQUENCE: 383

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
                35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 384
<211> LENGTH: 360
<212> TYPE: DNA
<213> ORGANISM: Homo sapiens
<220> FEATURE:
<221> NAME/KEY: P5A-2H3 VHnu
<222> LOCATION: (1)..(360)

<400> SEQUENCE: 384
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaga gtccatcag caccgcctac      240 ctgcagtgga gcagcctgaa ggcctcggac accgccatgt attactgtgc gagacgggat     300
tcgacctacg gtggtaacac tgactactgg ggccagggaa ccctggtcac cgtctcctca     360

<210> SEQ ID NO 385
<211> LENGTH: 330
<212> TYPE: DNA
<213> ORGANISM: Homo sapiens
<220> FEATURE:
<221> NAME/KEY: P5A-2H3 Vlnu
<222> LOCATION: (1)..(330)

-continued

<400> SEQUENCE: 385

```
cagtctgtgc tgactcagcc accctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc agggggtccct  180 gaccgattct ctggctccaa gtctggcacc tcagcctccc tggccatcag tgggctccag   240
tctgaggatg aggctgatta ttactgtgca gcatgggatg acagcctgaa tggtgtggta   300
ttcggcggag ggaccaagct gaccgtccta                                    330
```

<210> SEQ ID NO 386
<211> LENGTH: 8
<212> TYPE: PRT
<213> ORGANISM: Homo sapiens
<220> FEATURE:
<221> NAME/KEY: P5A-3A1 HCDR1
<222> LOCATION: (1)..(8)

<400> SEQUENCE: 386

Gly Phe Thr Val Ser Ser Asn Tyr
1               5

<210> SEQ ID NO 387
<211> LENGTH: 7
<212> TYPE: PRT
<213> ORGANISM: Homo sapiens
<220> FEATURE:
<221> NAME/KEY: P5A-3A1 HCDR2
<222> LOCATION: (1)..(7)

<400> SEQUENCE: 387

Ile Tyr Ser Gly Gly Ser Thr
1               5

<210> SEQ ID NO 388
<211> LENGTH: 11
<212> TYPE: PRT
<213> ORGANISM: Homo sapiens
<220> FEATURE:
<221> NAME/KEY: P5A-3A1 HCDR3
<222> LOCATION: (1)..(11)

<400> SEQUENCE: 388

Ala Arg Asp Tyr Gly Asp Phe Tyr Phe Asp Tyr
1               5                   10

<210> SEQ ID NO 389
<211> LENGTH: 7
<212> TYPE: PRT
<213> ORGANISM: Homo sapiens
<220> FEATURE:
<221> NAME/KEY: P5A-3A1 LCDR1
<222> LOCATION: (1)..(7)

<400> SEQUENCE: 389

Gln Ser Val Ser Ser Ser Tyr
1               5

<210> SEQ ID NO 390
<211> LENGTH: 4
<212> TYPE: PRT
<213> ORGANISM: Homo sapiens
<220> FEATURE:
<221> NAME/KEY: P5A-3A1 LCDR2
<222> LOCATION: (1)..(3)
<220> FEATURE:

<221> NAME/KEY: misc_feature
<222> LOCATION: (4)..(4)
<223> OTHER INFORMATION: Xaa is absent.

<400> SEQUENCE: 390

Gly Ala Ser Xaa
1

<210> SEQ ID NO 391
<211> LENGTH: 9
<212> TYPE: PRT
<213> ORGANISM: Homo sapiens
<220> FEATURE:
<221> NAME/KEY: P5A-3A1 LCDR3
<222> LOCATION: (1)..(9)

<400> SEQUENCE: 391

Gln Gln Tyr Gly Ser Ser Pro Arg Thr
1               5

<210> SEQ ID NO 392
<211> LENGTH: 117
<212> TYPE: PRT
<213> ORGANISM: Homo sapiens
<220> FEATURE:
<221> NAME/KEY: P5A-3A1 VH
<222> LOCATION: (1)..(117)

<400> SEQUENCE: 392

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Tyr Gly Asp Phe Tyr Phe Asp Tyr Trp Gly Gln Gly Thr Leu
            100                 105                 110

Val Thr Val Ser Ser
        115

<210> SEQ ID NO 393
<211> LENGTH: 108
<212> TYPE: PRT
<213> ORGANISM: Homo sapiens
<220> FEATURE:
<221> NAME/KEY: P5A-3A1 VL
<222> LOCATION: (1)..(108)

<400> SEQUENCE: 393

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser

```
                50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Arg Thr Phe Gly Gln Gly Thr Lys Leu Glu Ile Lys
            100                 105
```

```
<210> SEQ ID NO 394
<211> LENGTH: 351
<212> TYPE: DNA
<213> ORGANISM: Homo sapiens
<220> FEATURE:
<221> NAME/KEY: P5A-3A1 VHnu
<222> LOCATION: (1)..(351)

<400> SEQUENCE: 394
gaggtgcagc tggtggagtc tggaggaggc ttgatccagc ctgggggtc cctgagactc      60 tcctgtgcag cctctgggtt caccgtcagt agcaactaca tgagctgggt ccgccaggct    120
ccagggaagg gctggagtg gtctcagtt atttatagcg gtggtagcac atactacgca      180
gactccgtga agggccgatt caccatctcc agagacaatt ccaagaacac gctgtatctt    240
caaatgaaca gcctgagagc cgaggacacg gccgtgtatt actgtgcgag agactacggt    300 gactttact tgactactg gggccaggga accctggtca ccgtctcctc a                351
```

```
<210> SEQ ID NO 395
<211> LENGTH: 324
<212> TYPE: DNA
<213> ORGANISM: Homo sapiens
<220> FEATURE:
<221> NAME/KEY: P5A-3A1 Vlnu
<222> LOCATION: (1)..(324)

<400> SEQUENCE: 395
gaaattgtgt tgacgcagtc tccaggcacc ctgtctttgt ctccagggga aagagccacc     60
ctctcctgca gggccagtca gagtgttagc agcagctact tagcctggta ccagcagaaa   120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacctcg cacttttggc    300
caggggacca agctggagat caaa                                            324
```

```
<210> SEQ ID NO 396
<211> LENGTH: 8
<212> TYPE: PRT
<213> ORGANISM: Homo sapiens
<220> FEATURE:
<221> NAME/KEY: P5A-3A6 HCDR1
<222> LOCATION: (1)..(8)

<400> SEQUENCE: 396

Gly Phe Thr Phe Asp Asp Tyr Ala
 1               5
```

```
<210> SEQ ID NO 397
<211> LENGTH: 8
<212> TYPE: PRT
<213> ORGANISM: Homo sapiens
<220> FEATURE:
<221> NAME/KEY: P5A-3A6 HCDR2
<222> LOCATION: (1)..(8)
```

<400> SEQUENCE: 397

Ile Ser Trp Asn Ser Gly Thr Ile
1               5

<210> SEQ ID NO 398
<211> LENGTH: 27
<212> TYPE: PRT
<213> ORGANISM: Homo sapiens
<220> FEATURE:
<221> NAME/KEY: P5A-3A6 HCDR3
<222> LOCATION: (1)..(27)

<400> SEQUENCE: 398

Ala Gly Gly Gly Thr Met Val Arg Gly Val Ile Ala Gly Gly Gly Thr
1               5                   10                  15

His Pro Val Asp Asp Tyr Tyr Gly Met Asp Val
            20                  25

<210> SEQ ID NO 399
<211> LENGTH: 9
<212> TYPE: PRT
<213> ORGANISM: Homo sapiens
<220> FEATURE:
<221> NAME/KEY: P5A-3A6 LCDR1
<222> LOCATION: (1)..(9)

<400> SEQUENCE: 399

Ser Ser Asp Val Gly Gly Tyr Asn Tyr
1               5

<210> SEQ ID NO 400
<211> LENGTH: 4
<212> TYPE: PRT
<213> ORGANISM: Homo sapiens
<220> FEATURE:
<221> NAME/KEY: P5A-3A6 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 400

Asp Val Ser Xaa
1

<210> SEQ ID NO 401
<211> LENGTH: 10
<212> TYPE: PRT
<213> ORGANISM: Homo sapiens
<220> FEATURE:
<221> NAME/KEY: P5A-3A6 LCDR3
<222> LOCATION: (1)..(10)

<400> SEQUENCE: 401

Ser Ser Tyr Thr Ser Ser Ser Thr Val Val
1               5                   10

<210> SEQ ID NO 402
<211> LENGTH: 134
<212> TYPE: PRT
<213> ORGANISM: Homo sapiens
<220> FEATURE:
<221> NAME/KEY: P5A-3A6 VH
<222> LOCATION: (1)..(134)

<400> SEQUENCE: 402

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Ile Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Gly Gly Gly Thr Met Val Arg Gly Val Ile Ala Gly Gly Thr
            100                 105                 110

His Pro Val Asp Asp Tyr Tyr Gly Met Asp Val Trp Gly Gln Gly Thr
        115                 120                 125

Thr Val Thr Val Ser Ser
        130

<210> SEQ ID NO 403
<211> LENGTH: 110
<212> TYPE: PRT
<213> ORGANISM: Homo sapiens
<220> FEATURE:
<221> NAME/KEY: P5A-3A6 VL
<222> LOCATION: (1)..(110)

<400> SEQUENCE: 403

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Gly Gly Thr Lys Leu Thr Val Leu
            100                 105                 110

<210> SEQ ID NO 404
<211> LENGTH: 402
<212> TYPE: DNA
<213> ORGANISM: Homo sapiens
<220> FEATURE:
<221> NAME/KEY: P5A-3A6 VHnu
<222> LOCATION: (1)..(402)

<400> SEQUENCE: 404
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg gtctcaggt attagttgga atagtggtac cataggctat   180
gcggactctg tgaagggccg attcatcatc tccagagaca acgccaagaa ctccctgtat   240

```
ctgcaaatga acagtctgag agctgaggac acggccttgt attactgtgc agggggtggt    300
actatggttc ggggagttat tgccggaggg ggaactcatc cggtggatga ctactacggt    360
atggacgtct ggggccaagg gaccacggtc accgtctcct ca                       402
```

<210> SEQ ID NO 405
<211> LENGTH: 330
<212> TYPE: DNA
<213> ORGANISM: Homo sapiens
<220> FEATURE:
<221> NAME/KEY: P5A-3A6 Vlnu
<222> LOCATION: (1)..(330)

<400> SEQUENCE: 405

```
cagtctgccc tgactcagcc tgcctccgtg tctgggtctc ctggacagtc gatcaccatc    60
tcctgcactg gaaccagcag tgacgttggt ggttataact atgtctcctg gtaccaacaa   120
cacccaggca agcccccaa actcatgatt tatgatgtca gtaatcggcc ctcaggggtt    180
tctaatcgct tctctggctc caagtctggc aacacggcct ccctgaccat ctctgggctc   240
caggctgagg acgaggctga ttattactgc agctcatata caagcagcag cactgtggta   300
ttcggcggag ggaccaagct gaccgtccta                                    330
```

<210> SEQ ID NO 406
<211> LENGTH: 8
<212> TYPE: PRT
<213> ORGANISM: Homo sapiens
<220> FEATURE:
<221> NAME/KEY: P5A-3B4 HCDR1
<222> LOCATION: (1)..(8)

<400> SEQUENCE: 406

Gly Tyr Ser Phe Thr Ser Tyr Trp
1               5

<210> SEQ ID NO 407
<211> LENGTH: 8
<212> TYPE: PRT
<213> ORGANISM: Homo sapiens
<220> FEATURE:
<221> NAME/KEY: P5A-3B4 HCDR2
<222> LOCATION: (1)..(8)

<400> SEQUENCE: 407

Ile Tyr Pro Gly Asp Ser Asp Thr
1               5

<210> SEQ ID NO 408
<211> LENGTH: 13
<212> TYPE: PRT
<213> ORGANISM: Homo sapiens
<220> FEATURE:
<221> NAME/KEY: P5A-3B4 HCDR3
<222> LOCATION: (1)..(13)

<400> SEQUENCE: 408

Ala Arg Arg Asp Ser Thr Tyr Gly Gly Asn Thr Asp Tyr
1               5                   10

<210> SEQ ID NO 409
<211> LENGTH: 8
<212> TYPE: PRT
<213> ORGANISM: Homo sapiens
<220> FEATURE:
<221> NAME/KEY: P5A-3B4 LCDR1
<222> LOCATION: (1)..(8)

<400> SEQUENCE: 409

Ser Ser Asn Ile Gly Ser Asn Thr
1               5

<210> SEQ ID NO 410
<211> LENGTH: 4
<212> TYPE: PRT
<213> ORGANISM: Homo sapiens
<220> FEATURE:
<221> NAME/KEY: P5A-3B4 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 410

Ser Asn Asn Xaa
1

<210> SEQ ID NO 411
<211> LENGTH: 11
<212> TYPE: PRT
<213> ORGANISM: Homo sapiens
<220> FEATURE:
<221> NAME/KEY: P5A-3B4 LCDR3
<222> LOCATION: (1)..(11)

<400> SEQUENCE: 411

Ala Ala Trp Asp Asp Ser Leu Asn Gly Val Val
1               5                   10

<210> SEQ ID NO 412
<211> LENGTH: 120
<212> TYPE: PRT
<213> ORGANISM: Homo sapiens
<220> FEATURE:
<221> NAME/KEY: P5A-3B4 VH
<222> LOCATION: (1)..(120)

<400> SEQUENCE: 412

Glu Val Gln Leu Val Gln Ser Gly Ala Glu Val Lys Glu Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Asp Ser Thr Tyr Gly Gly Asn Thr Asp Tyr Trp Gly Gln
            100                 105                 110

Gly Thr Leu Val Thr Val Ser Ser
        115                 120

<210> SEQ ID NO 413
<211> LENGTH: 110
<212> TYPE: PRT
<213> ORGANISM: Homo sapiens
<220> FEATURE:

<221> NAME/KEY: P5A-3B4 VL
<222> LOCATION: (1)..(110)

<400> SEQUENCE: 413

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 414
<211> LENGTH: 360
<212> TYPE: DNA
<213> ORGANISM: Homo sapiens
<220> FEATURE:
<221> NAME/KEY: P5A-3B4 VHnu
<222> LOCATION: (1)..(360)

<400> SEQUENCE: 414
gaggtgcagc tggtgcagtc tggagcagag gtgaaagagc cggggagtc tctgaagatc      60 tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac    240 ctgcagtgga gcagcctgaa ggcctcggac accgccatgt attactgtgc gagacgggat    300
tcgacctacg gtggtaacac tgactactgg ggccagggaa ccctggtcac cgtctcctca    360

<210> SEQ ID NO 415
<211> LENGTH: 330
<212> TYPE: DNA
<213> ORGANISM: Homo sapiens
<220> FEATURE:
<221> NAME/KEY: P5A-3B4 Vlnu
<222> LOCATION: (1)..(330)

<400> SEQUENCE: 415
cagtctgtgc tgactcagcc accctcagcg tctgggaccc ccgggcagag ggtcaccatc      60
tcttgttctg gaagcagctc caacatcgga agtaatactg taaactggta ccagcagctc    120
ccaggaacgg cccccaaact cctcatctat agtaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tggtgtggta    300
ttcggcggag ggaccaagct gaccgtccta                                     330

<210> SEQ ID NO 416
<211> LENGTH: 10
<212> TYPE: PRT
<213> ORGANISM: Homo sapiens
<220> FEATURE:
<221> NAME/KEY: P5A-3C12 HCDR1

<222> LOCATION: (1)..(10)

<400> SEQUENCE: 416

Gly Phe Ser Leu Ser Thr Ser Gly Val Gly
1               5                   10

<210> SEQ ID NO 417
<211> LENGTH: 7
<212> TYPE: PRT
<213> ORGANISM: Homo sapiens
<220> FEATURE:
<221> NAME/KEY: P5A-3C12 HCDR2
<222> LOCATION: (1)..(7)

<400> SEQUENCE: 417

Ile Tyr Trp Asp Asp Asp Lys
1               5

<210> SEQ ID NO 418
<211> LENGTH: 19
<212> TYPE: PRT
<213> ORGANISM: Homo sapiens
<220> FEATURE:
<221> NAME/KEY: P5A-3C12 HCDR3
<222> LOCATION: (1)..(19)

<400> SEQUENCE: 418

Ala His Ser Leu Phe Leu Thr Val Gly Tyr Ser Ser Ser Trp Ser Pro
1               5                   10                  15
Phe Asp Tyr

<210> SEQ ID NO 419
<211> LENGTH: 12
<212> TYPE: PRT
<213> ORGANISM: Homo sapiens
<220> FEATURE:
<221> NAME/KEY: P5A-3C12 LCDR1
<222> LOCATION: (1)..(12)

<400> SEQUENCE: 419

Gln Ser Val Leu Tyr Ser Ser Asn Asn Lys Asn Tyr
1               5                   10

<210> SEQ ID NO 420
<211> LENGTH: 4
<212> TYPE: PRT
<213> ORGANISM: Homo sapiens
<220> FEATURE:
<221> NAME/KEY: P5A-3C12 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 420

Trp Ala Ser Xaa
1

<210> SEQ ID NO 421
<211> LENGTH: 9
<212> TYPE: PRT
<213> ORGANISM: Homo sapiens
<220> FEATURE:
<221> NAME/KEY: P5A-3C12 LCDR3
<222> LOCATION: (1)..(9)

<400> SEQUENCE: 421

```
Gln Gln Tyr Tyr Ser Thr Pro His Thr
1               5

<210> SEQ ID NO 422
<211> LENGTH: 127
<212> TYPE: PRT
<213> ORGANISM: Homo sapiens
<220> FEATURE:
<221> NAME/KEY: P5A-3C12 VH
<222> LOCATION: (1)..(127)

<400> SEQUENCE: 422

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Leu Phe Leu Thr Val Gly Tyr Ser Ser Ser Trp Ser
            100                 105                 110

Pro Phe Asp Tyr Trp Gly Gln Gly Thr Leu Val Thr Val Ser Ser
        115                 120                 125

<210> SEQ ID NO 423
<211> LENGTH: 113
<212> TYPE: PRT
<213> ORGANISM: Homo sapiens
<220> FEATURE:
<221> NAME/KEY: P5A-3C12 VL
<222> LOCATION: (1)..(113)

<400> SEQUENCE: 423

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro His Thr Phe Gly Gln Gly Thr Lys Leu Glu Ile
            100                 105                 110

Lys

<210> SEQ ID NO 424
<211> LENGTH: 381
<212> TYPE: DNA
<213> ORGANISM: Homo sapiens
<220> FEATURE:
```

<221> NAME/KEY: P5A-3C12 VHnu
<222> LOCATION: (1)..(381)

<400> SEQUENCE: 424

```
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcactcattt attgggatga tgataagcgc    180
tacagcccat ctctgaagag caggctcacc atcaccaagg acacctccaa aaaccaggtg     240
gtccttacaa tgaccaacat ggaccctgtg gacacagcca catattactg tgcacacagt     300
ttgtttctca cggtagggta tagcagcagc tggtcccctt ttgactactg gggccaggga     360
accctggtca ccgtctcctc a                                                381
```

<210> SEQ ID NO 425
<211> LENGTH: 339
<212> TYPE: DNA
<213> ORGANISM: Homo sapiens
<220> FEATURE:
<221> NAME/KEY: P5A-3C12 Vlnu
<222> LOCATION: (1)..(339)

<400> SEQUENCE: 425

```
gacatcgtga tgacccagtc tccagactcc ctggctgtgt ctctgggcga gagggccacc      60
atcaactgca gtccagcca gagtgtttta tacagctcca acaataagaa ctacttagct      120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
cctcacactt ttggccaggg gaccaagctg gagatcaaa                             339
```

<210> SEQ ID NO 426
<211> LENGTH: 8
<212> TYPE: PRT
<213> ORGANISM: Homo sapiens
<220> FEATURE:
<221> NAME/KEY: P22A-1D1 HCDR1
<222> LOCATION: (1)..(8)

<400> SEQUENCE: 426

Gly Phe Thr Val Ser Ser Asn Tyr
1               5

<210> SEQ ID NO 427
<211> LENGTH: 7
<212> TYPE: PRT
<213> ORGANISM: Homo sapiens
<220> FEATURE:
<221> NAME/KEY: P22A-1D1 HCDR2
<222> LOCATION: (1)..(7)

<400> SEQUENCE: 427

Ile Tyr Ser Gly Gly Ser Thr
1               5

<210> SEQ ID NO 428
<211> LENGTH: 11
<212> TYPE: PRT
<213> ORGANISM: Homo sapiens
<220> FEATURE:
<221> NAME/KEY: P22A-1D1 HCDR3
<222> LOCATION: (1)..(11)

```
<400> SEQUENCE: 428

Ala Arg Asp Arg Asp Tyr Tyr Gly Met Asp Val
1               5                   10

<210> SEQ ID NO 429
<211> LENGTH: 6
<212> TYPE: PRT
<213> ORGANISM: Homo sapiens
<220> FEATURE:
<221> NAME/KEY: P22A-1D1 LCDR1
<222> LOCATION: (1)..(6)

<400> SEQUENCE: 429

Gln Gly Ile Ser Ser Tyr
1               5

<210> SEQ ID NO 430
<211> LENGTH: 4
<212> TYPE: PRT
<213> ORGANISM: Homo sapiens
<220> FEATURE:
<221> NAME/KEY: P22A-1D1 LCDR2
<222> LOCATION: (1)..(3)
<220> FEATURE:
<221> NAME/KEY: misc_feature
<222> LOCATION: (4)..(4)
<223> OTHER INFORMATION: Xaa is absent.

<400> SEQUENCE: 430

Ala Ala Ser Xaa
1

<210> SEQ ID NO 431
<211> LENGTH: 8
<212> TYPE: PRT
<213> ORGANISM: Homo sapiens
<220> FEATURE:
<221> NAME/KEY: P22A-1D1 LCDR3
<222> LOCATION: (1)..(8)

<400> SEQUENCE: 431

Leu His Leu Asn Ser Tyr Arg Thr
1               5

<210> SEQ ID NO 432
<211> LENGTH: 117
<212> TYPE: PRT
<213> ORGANISM: Homo sapiens
<220> FEATURE:
<221> NAME/KEY: P22A-1D1 VH
<222> LOCATION: (1)..(117)

<400> SEQUENCE: 432

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

Arg Asp Arg Asp Tyr Tyr Gly Met Asp Val Trp Gly Gln Gly Thr Thr
            100                 105                 110

Val Thr Val Ser Ser
        115

<210> SEQ ID NO 433
<211> LENGTH: 106
<212> TYPE: PRT
<213> ORGANISM: Homo sapiens
<220> FEATURE:
<221> NAME/KEY: P22A-1D1 VL
<222> LOCATION: (1)..(106)

<400> SEQUENCE: 433

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu His Leu Asn Ser Tyr Arg Thr
                85                  90                  95

Phe Gly Leu Gly Thr Lys Val Glu Ile Lys
            100                 105

<210> SEQ ID NO 434
<211> LENGTH: 351
<212> TYPE: DNA
<213> ORGANISM: Homo sapiens
<220> FEATURE:
<221> NAME/KEY: P22A-1D1 VHnu
<222> LOCATION: (1)..(351)

<400> SEQUENCE: 434
gaggtgcagc tggtggagtc tggaggaggc ttgatccagc ctgggggtc cctgagactc      60 tcctgtgcag cctctgggtt caccgtcagt agcaactaca tgagctgggt ccgccaggct     120
ccagggaagg gctggagtg gtctcagtt atttatagcg gtggtagcac atactacgca      180
gactccgtga agggccgatt caccatctcc agagacaatt ccaagaacac gctgtatctt     240
caaatgaaca gcctgagagc cgaggacacg gccgtgtatt actgtgcgag agatcgagac     300
tactacggta tggacgtctg gggccaaggg accacggtca ccgtctcctc a             351

<210> SEQ ID NO 435
<211> LENGTH: 318
<212> TYPE: DNA
<213> ORGANISM: Homo sapiens
<220> FEATURE:
<221> NAME/KEY: P22A-1D1 Vlnu
<222> LOCATION: (1)..(318)

<400> SEQUENCE: 435
gacatccagt tgacccagtc tccatccttc ctgtctgcat ctgtaggaga cagagtcacc      60
atcacttgcc gggccagtca gggcattagc agttatttag cctggtatca gcaaaaacca    120
gggaaagccc ctaagctcct gatctatgct gcatccactt tgcaaagtgg ggtcccatca    180

-continued

```
aggtttagcg gcagtggatc tgggacagaa ttcactctca caatcagcag cctgcagcct    240
gaagattttg caacttatta ctgtctacac cttaatagtt acaggacgtt cggcctaggg    300
accaaggtgg aaatcaaa                                                  318
```

```
<210> SEQ ID NO 436
<211> LENGTH: 97
<212> TYPE: PRT
<213> ORGANISM: Homo sapiens

<400> SEQUENCE: 436
```

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

```
<210> SEQ ID NO 437
<211> LENGTH: 97
<212> TYPE: PRT
<213> ORGANISM: Homo sapiens

<400> SEQUENCE: 437
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr His Cys Ala
                85                  90                  95

Arg